US012781281B2

(12) United States Patent
Shalek et al.

(10) Patent No.: US 12,781,281 B2
(45) Date of Patent: Nov. 3, 2026

(54) METHODS FOR IDENTIFYING AND MODULATING IMMUNE PHENOTYPES

(71) Applicants: MASSACHUSETTS INSTITUTE OF TECHNOLOGY, Cambridge, MA (US); THE REGENTS OF THE UNIVERSITY OF CALIFORNIA, Oakland, CA (US); THE GENERAL HOSPITAL CORPORATION, Boston, MA (US)

(72) Inventors: Alexander K. Shalek, Cambridge, MA (US); Kellie E. Kolb, Cambridge, MA (US); Michael B. Cole, Oakland, CA (US); Nir Yosef, Oakland, CA (US); Enrique Martin Gayo, Boston, MA (US); Zhengyu Ouyang, Boston, MA (US); Xu Yu, Boston, MA (US)

(73) Assignees: Massachusetts Institute of Technology, Cambridge, MA (US); The Regents of the University of California, Oakland, CA (US); The General Hospital Corporation, Boston, MA (US)

( * ) Notice: Subject to any disclaimer, the term of this patent is extended or adjusted under 35 U.S.C. 154(b) by 1934 days.

(21) Appl. No.: 16/078,884

(22) PCT Filed: Feb. 22, 2017

(86) PCT No.: PCT/US2017/018963

§ 371 (c)(1),
(2) Date: Aug. 22, 2018

(87) PCT Pub. No.: WO2017/147196

PCT Pub. Date: Aug. 31, 2017

(65) Prior Publication Data

US 2019/0144942 A1 May 16, 2019

Related U.S. Application Data

(60) Provisional application No. 62/298,349, filed on Feb. 22, 2016.

(51) Int. Cl.
*C12Q 1/6881* (2018.01)
*A61K 35/15* (2025.01)
*G01N 33/50* (2006.01)

(52) U.S. Cl.
CPC ............ *C12Q 1/6881* (2013.01); *A61K 35/15* (2013.01); *G01N 33/5047* (2013.01); *C12Q 2600/158* (2013.01)

(58) Field of Classification Search
None
See application file for complete search history.

(56) References Cited

U.S. PATENT DOCUMENTS 7,708,949 B2 5/2010 Stone et al.
RE41,780 E 9/2010 Anderson et al.

(Continued)

FOREIGN PATENT DOCUMENTS

EP 2047910 A2 4/2009
EP 2764103 A2 8/2014

(Continued)

OTHER PUBLICATIONS

Schinnerling, K., García-González, P. and Aguillón, J.C., 2015. Gene expression profiling of human monocyte-derived dendritic cells-searching for molecular regulators of tolerogenicity. Frontiers in immunology, 6, 528, pp. 1-10. (Year: 2015).*

(Continued)

*Primary Examiner* — G. Steven Vanni
*Assistant Examiner* — Meredith Abbott Vassell
(74) *Attorney, Agent, or Firm* — F. Brent Nix, Esq.; Johnson, Marcou, Isaacs & Nix, LLC; Ming Zhang

(57) ABSTRACT

The present invention provides tools and methods for the systematic analysis of genetic interactions in immune cells.

(Continued)

The present invention provides tools and methods for modulating immune cell phenotypes and compositions, combinatorial probing of cellular circuits, for dissecting cellular circuitry, for delineating molecular pathways, and/or for identifying relevant targets for therapeutics development.

14 Claims, 140 Drawing Sheets

(56) References Cited

U.S. PATENT DOCUMENTS

| | | | |
|---|---|---|---|
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 2005/0172476 | A1 | 8/2005 | Stone et al. |
| 2008/0003142 | A1 | 1/2008 | Link et al. |
| 2008/0014589 | A1 | 1/2008 | Link et al. |
| 2010/0002241 | A1 | 1/2010 | Hirose |
| 2010/0137163 | A1 | 6/2010 | Link et al. |
| 2010/0172803 | A1 | 7/2010 | Stone et al. |
| 2012/0219947 | A1 | 8/2012 | Yurkovetsky et al. |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0248702 | A1 | 9/2014 | Zhang et al. |
| 2014/0256046 | A1 | 9/2014 | Zhang et al. |
| 2014/0273231 | A1 | 9/2014 | Zhang et al. |
| 2014/0273232 | A1 | 9/2014 | Zhang et al. |
| 2014/0273234 | A1 | 9/2014 | Zhang et al. |
| 2014/0287938 | A1 | 9/2014 | Zhang et al. |
| 2014/0310830 | A1 | 10/2014 | Zhang et al. |

FOREIGN PATENT DOCUMENTS

| | | | |
|---|---|---|---|
| EP | 2771468 | A1 | 9/2014 |
| EP | 2784162 | A1 | 10/2014 |
| WO | 2004002627 | A2 | 1/2004 |
| WO | 2007089541 | A2 | 8/2007 |
| WO | 2011049603 | A1 | 4/2011 |
| WO | 2014018423 | A2 | 1/2014 |
| WO | 2014093595 | A1 | 6/2014 |
| WO | 2014093622 | A2 | 6/2014 |
| WO | 2014093635 | A1 | 6/2014 |
| WO | 2014093655 | A2 | 6/2014 |
| WO | 2014093661 | A2 | 6/2014 |
| WO | 2014093694 | A1 | 6/2014 |
| WO | 2014093701 | A1 | 6/2014 |
| WO | 2014093709 | A1 | 6/2014 |
| WO | 2014093712 | A1 | 6/2014 |
| WO | 2014093718 | A1 | 6/2014 |
| WO | 2014145631 | A1 | 9/2014 |
| WO | 2014204723 | A1 | 12/2014 |
| WO | 2014204724 | A1 | 12/2014 |
| WO | 2014204725 | A1 | 12/2014 |
| WO | 2014204726 | A1 | 12/2014 |
| WO | 2014204727 | A1 | 12/2014 |
| WO | 2014204728 | A1 | 12/2014 |
| WO | 2014204729 | A1 | 12/2014 |
| WO | 2016049024 | A2 | 3/2016 |
| WO | 2016049163 | A2 | 3/2016 |
| WO | 2016049258 | A2 | 3/2016 |

OTHER PUBLICATIONS

Parnas, O., Jovanovic, M., Eisenhaure, T.M., Herbst, R.H., Dixit, A., Ye, C.J., Przybylski, D., Platt, R.J., Tirosh, I., Sanjana, N.E. and Shalem, O., 2015. A genome-wide CRISPR screen in primary immune cells to dissect regulatory networks. Cell, 162(3), pp. 675-686. (Year: 2015).*

Bashirova et al., 2014. LILRB2 interaction with HLA class I correlates with control of HIV-1 infection. PLoS genetics, 10(3), p. e1004196; with supp. figure 1 attached, 11 pages total. (Year: 2014).*

Terhorst et al., 2015. Dynamics and transcriptomics of skin dendritic cells and macrophages in an imiquimod-induced, biphasic mouse model of psoriasis. The Journal of Immunology, 195(10), pp. 4953-4961; with supp. figs. 1-3 attached 13 pages total. (Year: 2015).*

Whittall et al., 2011. Immunogenic and tolerogenic signatures in human immunodeficiency virus (HIV)-infected controllers compared with progressors and a conversion strategy of virus control. Clinical & Experimental Immunology, 166(2), pp. 208-217. (Year: 2011).*

Dai, B., Yang, L., Yang, H., Hu, B., Baltimore, D. and Wang, P., 2009. HIV-1 Gag-specific immunity induced by a lentivector-based vaccine directed to dendritic cells. Proceedings of the National Academy of Sciences, 106(48), pp. 20382-20387. (Year: 2009).*

Appel, S., Mirakaj, V., Bringmann, A., Weck, M.M., Grünebach, F. and Brossart, P., 2005. PPAR-γ agonists inhibit toll-like receptor-mediated activation of dendritic cells via the MAP kinase and NF-κB pathways. Blood, 106(12), pp. 3888-3894. (Year: 2005).*

García et al., 2013. A dendritic cell-based vaccine elicits T cell responses associated with control of HIV-1 replication. Science translational medicine, 5(166), pp. 1-8. (Year: 2013).*

De Haes, et al.., 2010. Polyelectrolyte capsules-containing HIV-1 p24 and poly I: C modulate dendritic cells to stimulate HIV-1-specific immune responses. Molecular Therapy, 18(7), pp. 1408-1416. (Year: 2010).*

Porichis, F. and Kaufmann, D.E., 2012. Role of PD-1 in HIV pathogenesis and as target for therapy. Current HIV/AIDS Reports, 9, pp. 81-90. (Year: 2012).*

E. Ackerman, M. and Alter, G., 2013. Opportunities to exploit non-neutralizing HIV-specific antibody activity. Current HIV research, 11(5), pp. 365-377. (Year: 2013).*

Massachusetts Institute of Technology, "Communication pursuant to Article 94(3) EPC for EP 17709268.1", Mar. 24, 2021, 4 pages.

Massachusetts Institute of Technology, "Communication pursuant to Article 94(3) EPC for EP 17709268.1", Jul. 8, 2020, 4 pages.

International Search Report and Written Opinion for PCT International Application No. PCT/US2017/018963, Jul. 28, 2017, 22.

Haining, et al., "Integrating Genomic Signatures for Immunologic Discovery", Immunity, vol. 32, No. 2, Feb. 1, 2010, 152-161.

Ilicic, et al., "Classification of Low Quality Cells from Single-Cell RNA-Seq Data", Genome Biology, vol. 17, No. 1, Feb. 17, 2016, 15.

Martin-Gayo, et al., "Potent Cell-Instrinsic Immune Responses in Dendritic Cells Facilitate HIV-1-Specific T Cell Immunity in HIV-1 Elite Controllers", PLOS Pathogens, vol. 11, No. 6, Jun. 11, 2015, 22.

Tan, et al., "Gene Signatures Related to B-Cell Proliferation Predict Influenza Vaccine-Induced Antibody Response", European Journal of Immunology, vol. 44, No. 1, Nov. 29, 2013, 285-295.

Vigneault, et al., "Transcriptional Profiling of CD4 T Cells Identifies Distinct Subgroups of HIV-1 Elite Controllers", Journal of Virology, vol. 85, No. 6, Mar. 15, 2011, 3015-3019.

Zimmer, et al., "A Regulatory Dendritic Cell Signature Correlates with the Clinical Efficacy of Allergen-Specific Sublingual

(56) References Cited

OTHER PUBLICATIONS

Immunotherapy", Journal of Allergy and Clinical Immunology, vol. 129, No. 4, Feb. 15, 2012, 1020-1030.
Alter, et al., "HIV-1 Adaptation to NK Cell Mediated Immune Pressure", Nature, vol. 476, No. 7358, 2011, 96-100.
Amit, et al., "Unbiased Reconstruction of a Mammalian Transcriptional Network Mediating the Differential Response to Pathogens", Science, vol. 326, No. 5950, Oct. 9, 2009, 257-263.
Bendall, et al., "Single-Cell Mass Cytometry of Differential Immune and Drug Responses Across a Human Hematopoietic Continuum", Science, 332(6030), May 6, 2011, pp. 687-696.
Blankson, "Effector Mechanisms in HIV-1 Infected Elite Controllers: Highly Active Immune Responses?", Antiviral research, vol. 85, No. 1, Jan. 2010, 295-302.
Casanova, et al., "Human Genetic Basis of Interindividual Variability in the Course of Infection", Proceedings of the National Academy of Sciences of the United States of America, vol. 112, No. 51, Dec. 22, 2015, 118-127.
Chen, et al., "CD4+ T Cells from Elite Controllers Resist HIV-1 Infection by Selective Upregulation of P21", The Journal of Clinical Investigation, vol. 121, No. 4, Apr. 2011, 1549-1560.
Chevrier, et al., "Systematic Discovery of TLR Signaling Components Delineates Viral-Sensing Circuits", Cell, vol. 147, No. 4, Nov. 11, 2011, 853-867.
Cohen, et al., "Dynamic Proteomics of Individual Cancer Cells in Response to a Drug", Science, 322, 2008, pp. 1511-1516.
Dalerba, et al., "Single-Cell Dissection of Transcriptional Heterogeneity in Human Colon Tumors", Nature Biotechnology, vol. 29, No. 12, Nov. 13, 2011, 1120-1127.
Feinerman, et al., "Single-cell quantification of IL-2 response by effector and regulatory T cells reveals critical plasticity in immune response", Mol Syst Biol., 2010, 16 pages.
Gao, et al., "AIDS Restriction HLA Allotypes Target Distinct Intervals of FIIV-1 Pathogenesis", Nature Medicine, vol. 11, 2005, 1290-1292.
Habjan, et al., "Cytoplasmic Sensing of Viral Nucleic Acids", Current Opinion in Virology, vol. 11, Apr. 2015, 31-37.
Hersperger, et al., "Increased HIV-specific CD8+ T-cell cytotoxic potential in HIV elite controllers is associated with T-bet expression", Blood, 117(14), Apr. 2011, pp. 3799-3808.
Huang, et al., "Leukocyte Immunoglobulin-Like Receptors Maintain Unique Antigen-Presenting Properties of Circulating Myeloid Dendritic Cells in HIV-1-Infected Elite Controllers", Journal of Virology, vol. 84, No. 18, Sep. 2010, 9463-9471.
Kiepiela, et al., "Dominant Influence of HLA-B In Mediating the Potential Co-Evolution of HIV and HLA", Nature, vol. 432, Dec. 9, 2004, 769-774.
Liu, et al., "Homozygous Defect in HIV-1 Coreceptor Accounts for Resistance of Some Multiply-Exposed Individuals to HIV-1 Infection", Cell, vol. 86, Aug. 9, 1996, 367-377.
Loo, et al., "Immune Signaling by RIG-I-Like Receptors", Immunity, vol. 34, No. 5, May 27, 2011, 680-692.
Ma, et al., "The cGAS-STING Defense Pathway and Its Counteraction by Viruses", Cell Host Microbe, vol. 19, No. 2, Feb. 2016, 150-158.
Manel, et al., "A Cryptic Sensor for HIV-1 Activates Antiviral Innate Immunity in Dendritic Cells", Nature, vol. 467, No. 7312, Sep. 9, 2010, 214-217.
Martin-Gayo, et al., "A Reproducibility-Based Computational Framework Identifies an Inducible, Enhanced Antiviral State in Dendritic Cells from HIV-1 Elite Controllers", Genome Biology, 19(10), 2018, 21 pages.
Odorizzi, et al., "Genetic Absence of PD-1 Promotes Accumulation of Terminally Differentiated Exhausted CD8+ T Cells", The Journal of experimental medicine, vol. 212, Jun. 1, 2015, 1125-1137.
Patel, et al., "Single-cell RNA-seq highlights intratumoral heterogeneity in primary glioblastoma", Science, 344(6190), Jun. 2014, pp. 1396-1401.
Saez-Cirion, et al., "HIV Controllers Exhibit Potent CD8 T Cell Capacity to Suppress HIV Infection Ex Vivo and Peculiar Cytotoxic T Lymphocyte Activation Phenotype", Proceedings of the National Academy of Sciences of the United States of America, vol. 104, No. 16, Apr. 17, 2007, 6776-6781.
Sharma, et al., "A chromatin-mediated reversible drug-tolerant state in cancer cell subpopulations", Cell, 141, 2010, pp. 69-80.
Van Der Poel, et al., "Functional Characteristics of the High affinity IgG receptor, FcgammaRI", Journal of immunology 186,, 2011, pp. 2699-2704.
Yan, et al., "The Cytosolic Exonuclease TREX1 Inhibits the Innate Immune Response to HIV-1", Nature Immunology, vol. 11, Nov. 2010, 1005-1013.
Yosef, et al., "Dynamic regulatory network controlling TH17 cell differentiation", Nature, 496(7446), 2013, pp. 461-468.
Massachusetts Institute of Technology, "Communication pursuant to Article 94(3) EPC for EP 17709268.1", Sep. 16, 2019, 6 pages.
Shalek, et al., "Single-Cell RNA-seq Reveals Dynamic Paracrine Control of Cellular Variation", Nature, 510, Jun. 2014, pp. 363-369.
Shalek, et al., "Single-Cell Transcriptomes Reveals Biomodality in Expression and Splicing in Immune Cells", Nature, 198(7453), May 19, 2013, pp. 236-240.

* cited by examiner

B

VEx–B vs VEx–C

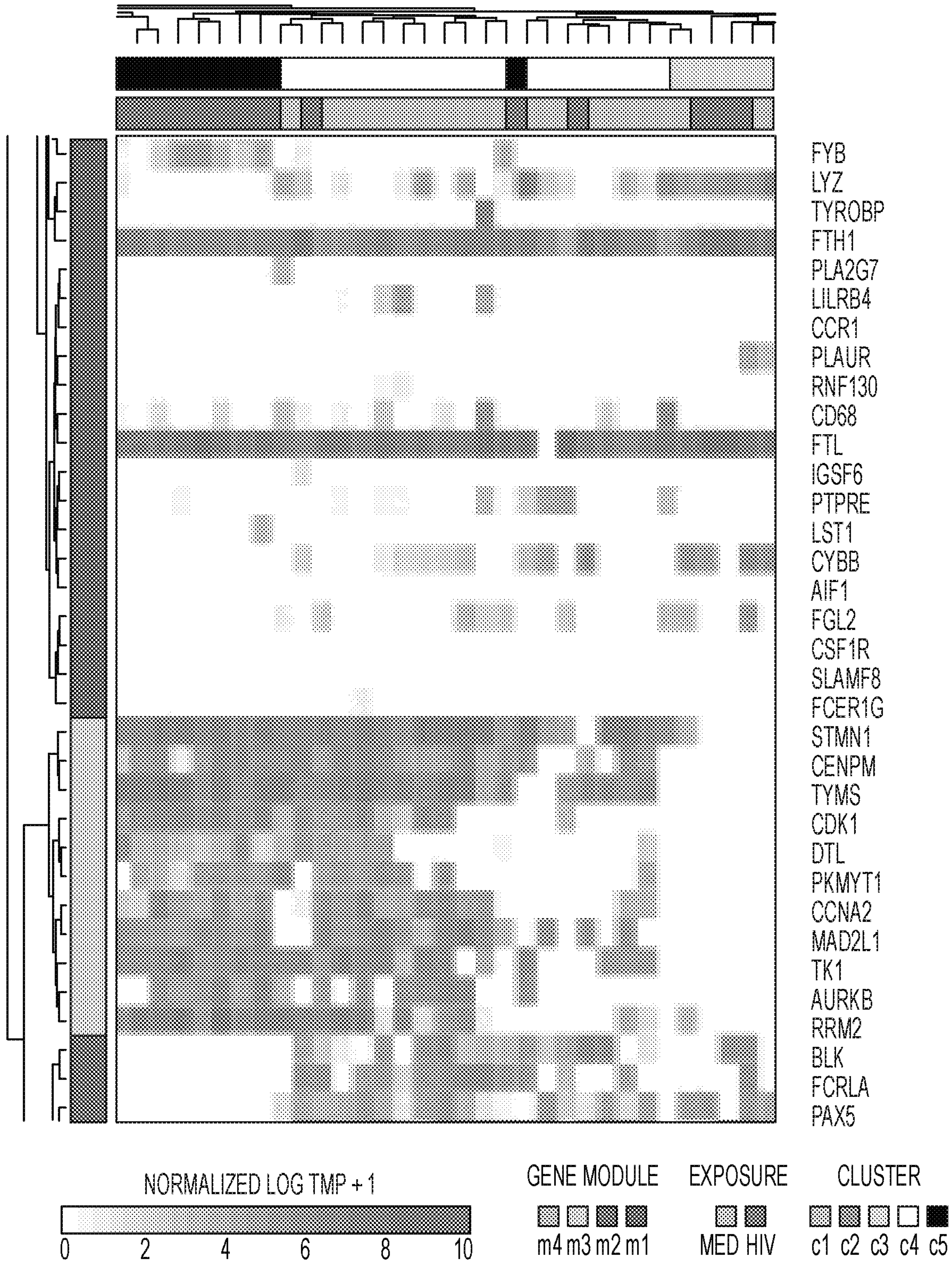
FIG. 15AAA

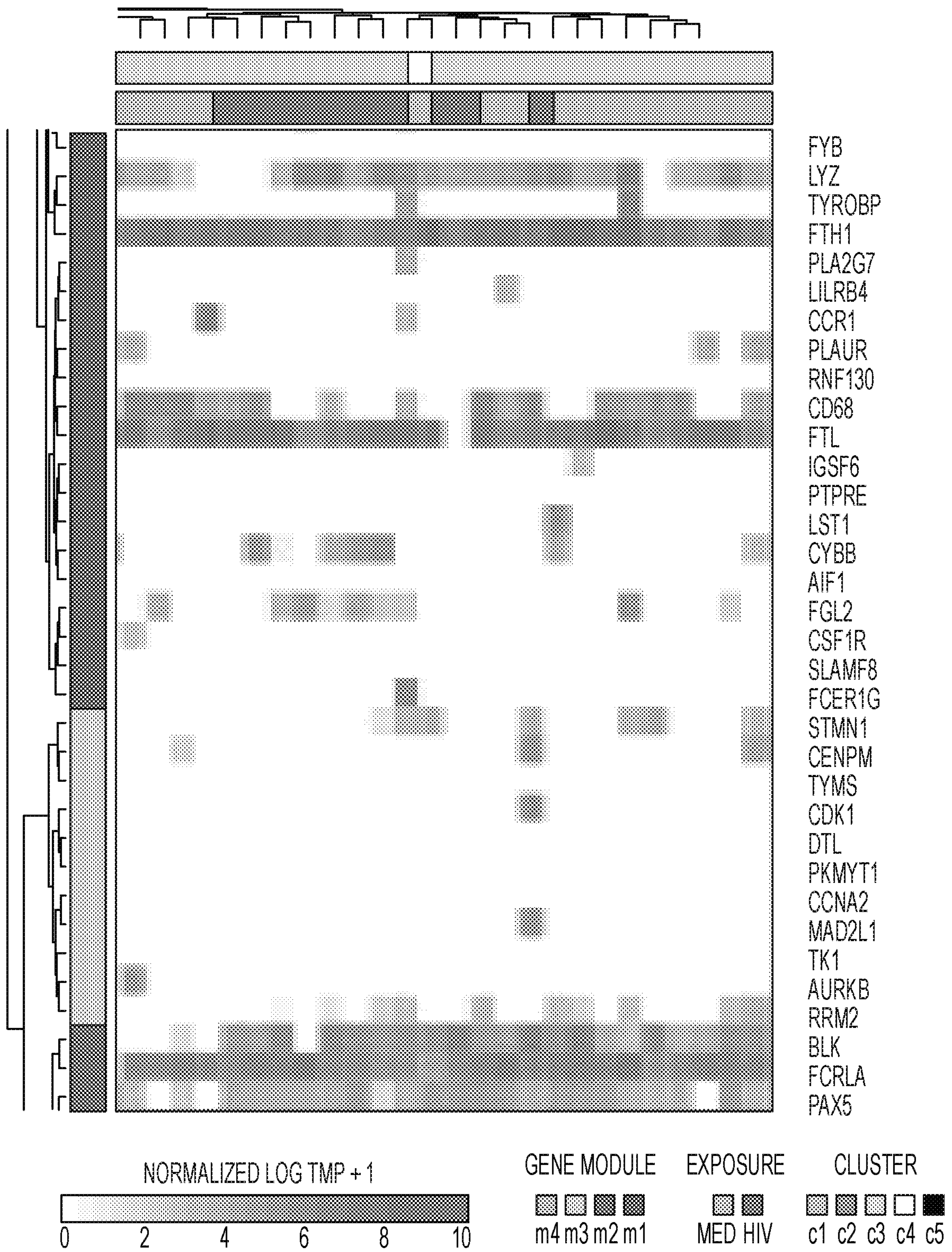
FIG. 15BBB

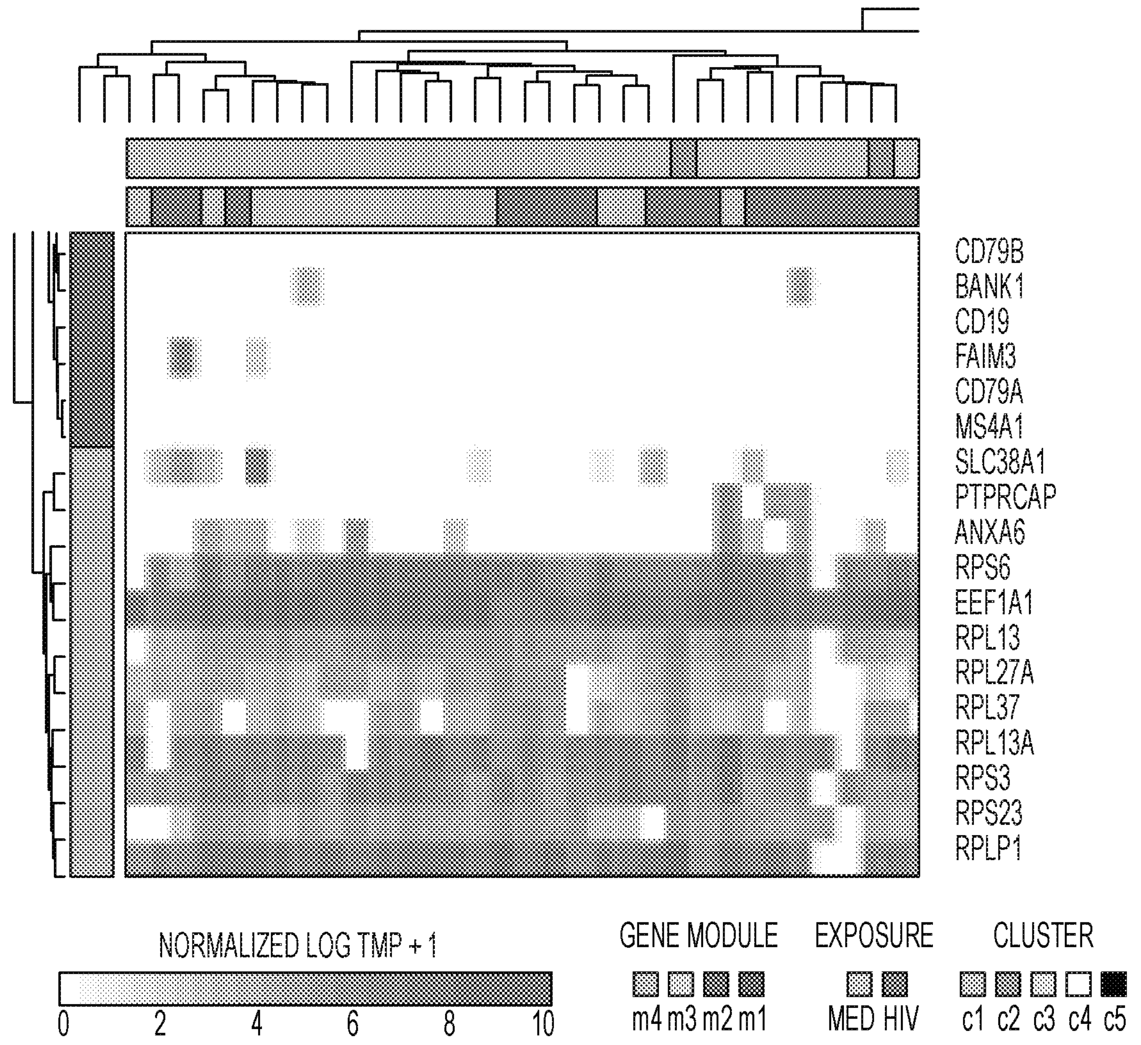
FIG. 15CCC

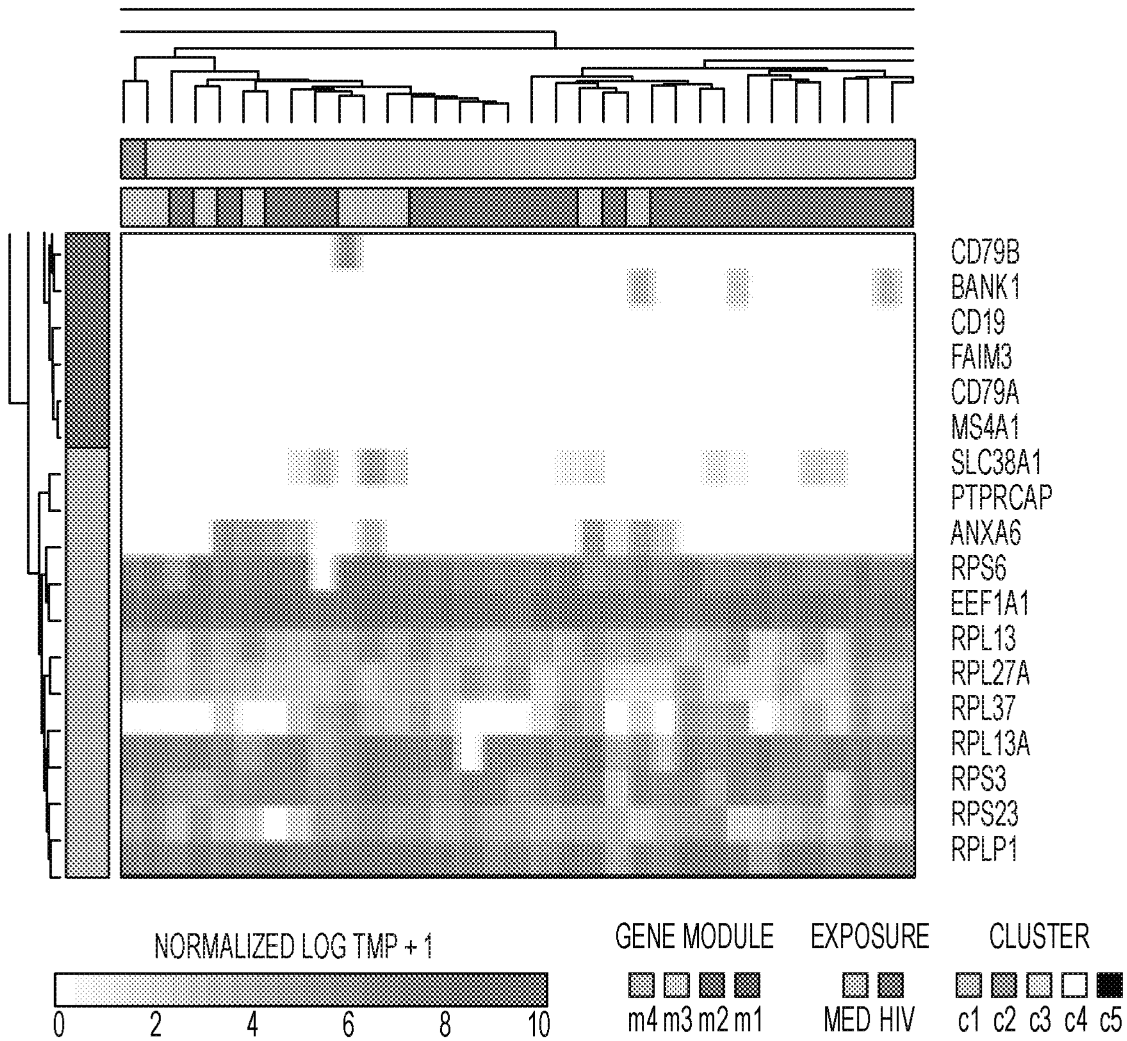
FIG. 15DDD

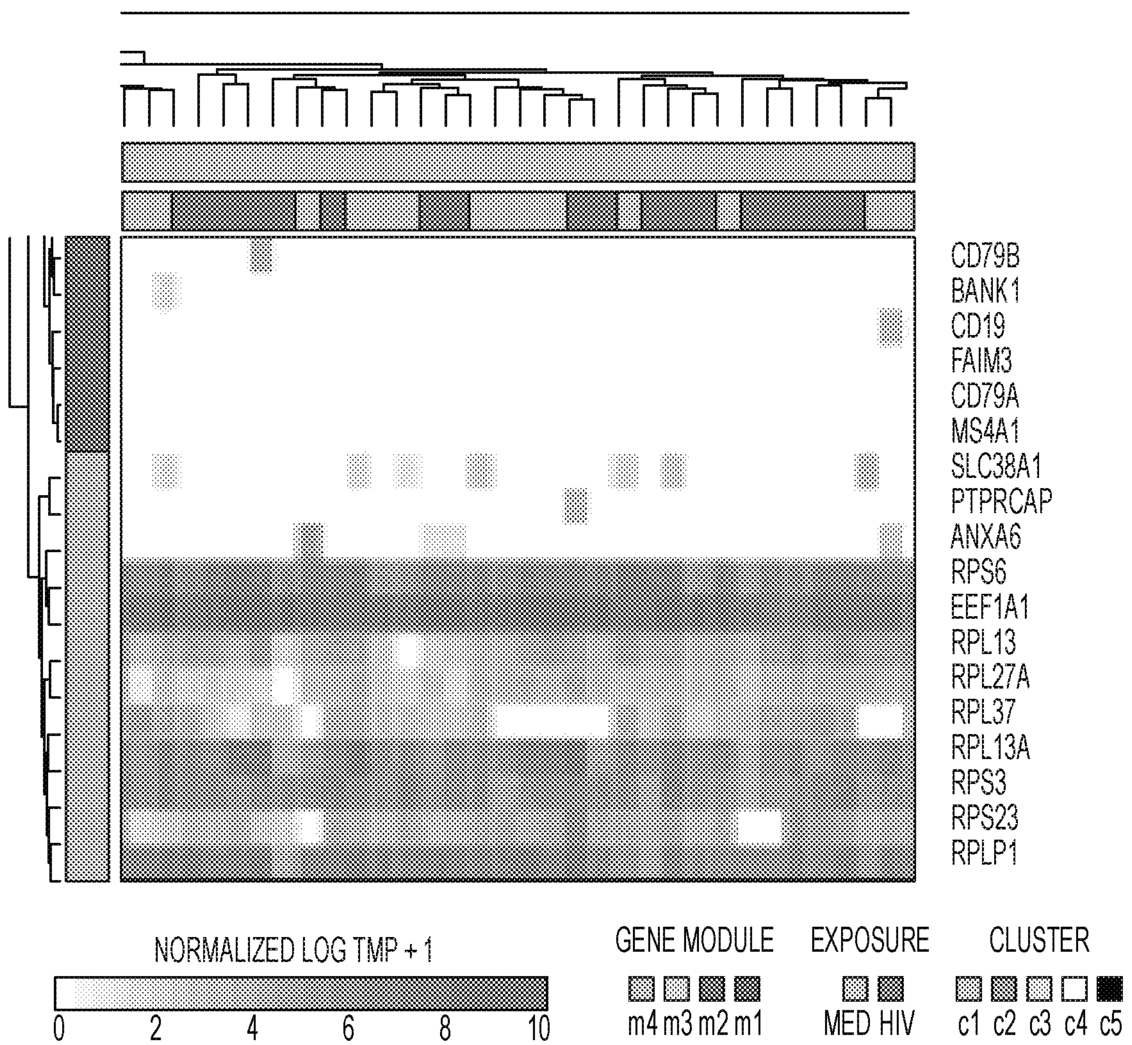
FIG. 15EEE

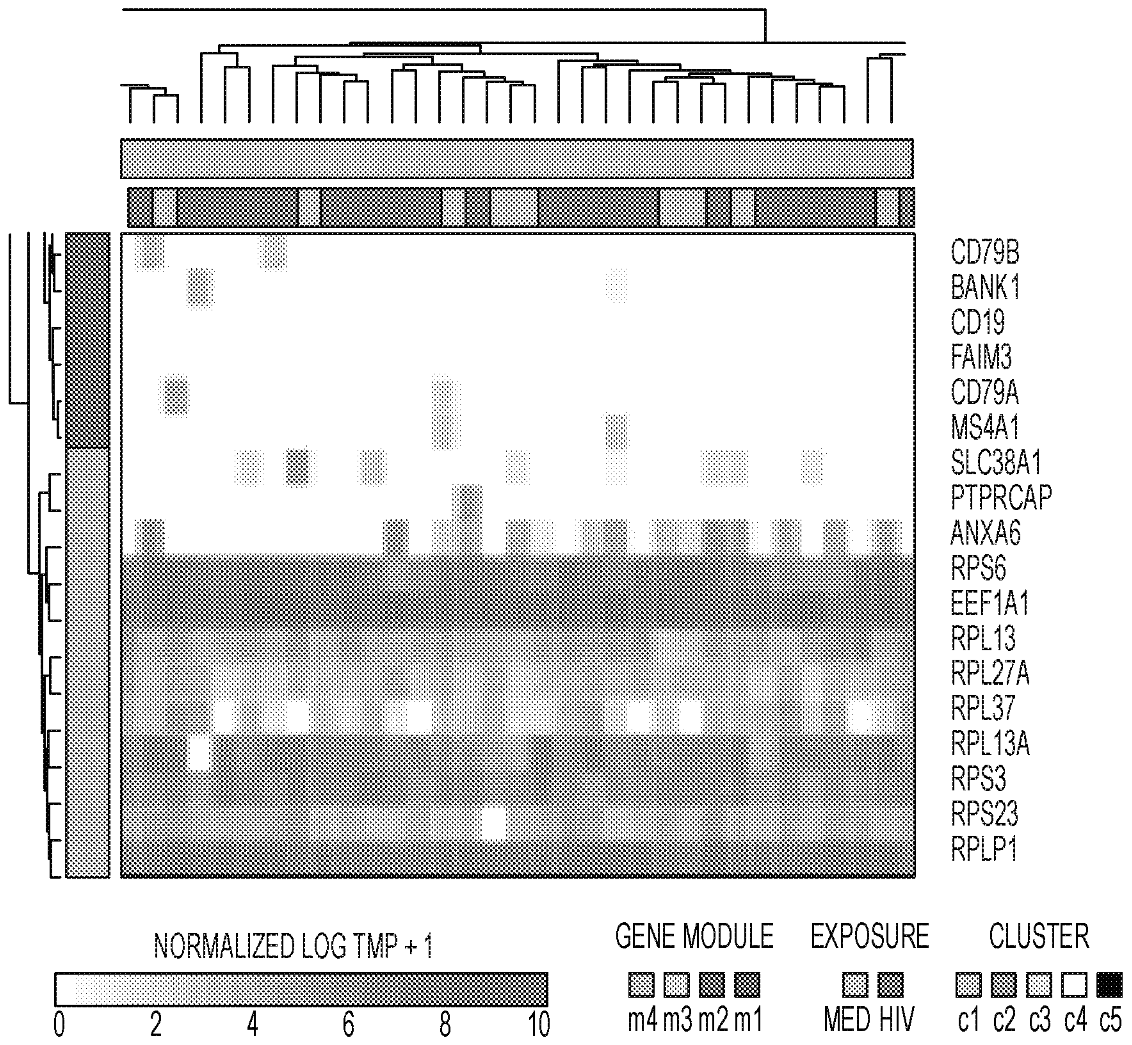
FIG. 15FFF

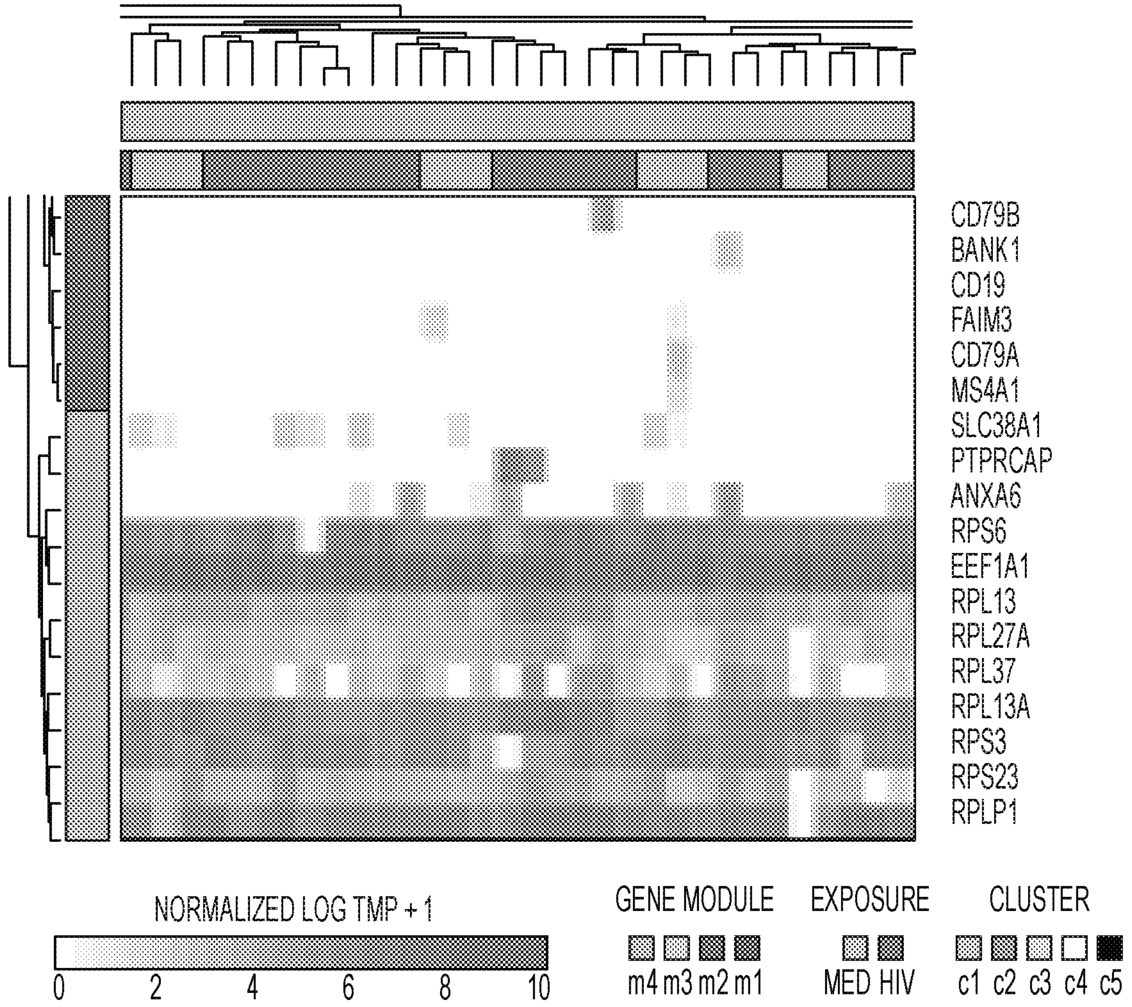
FIG. 15GGG

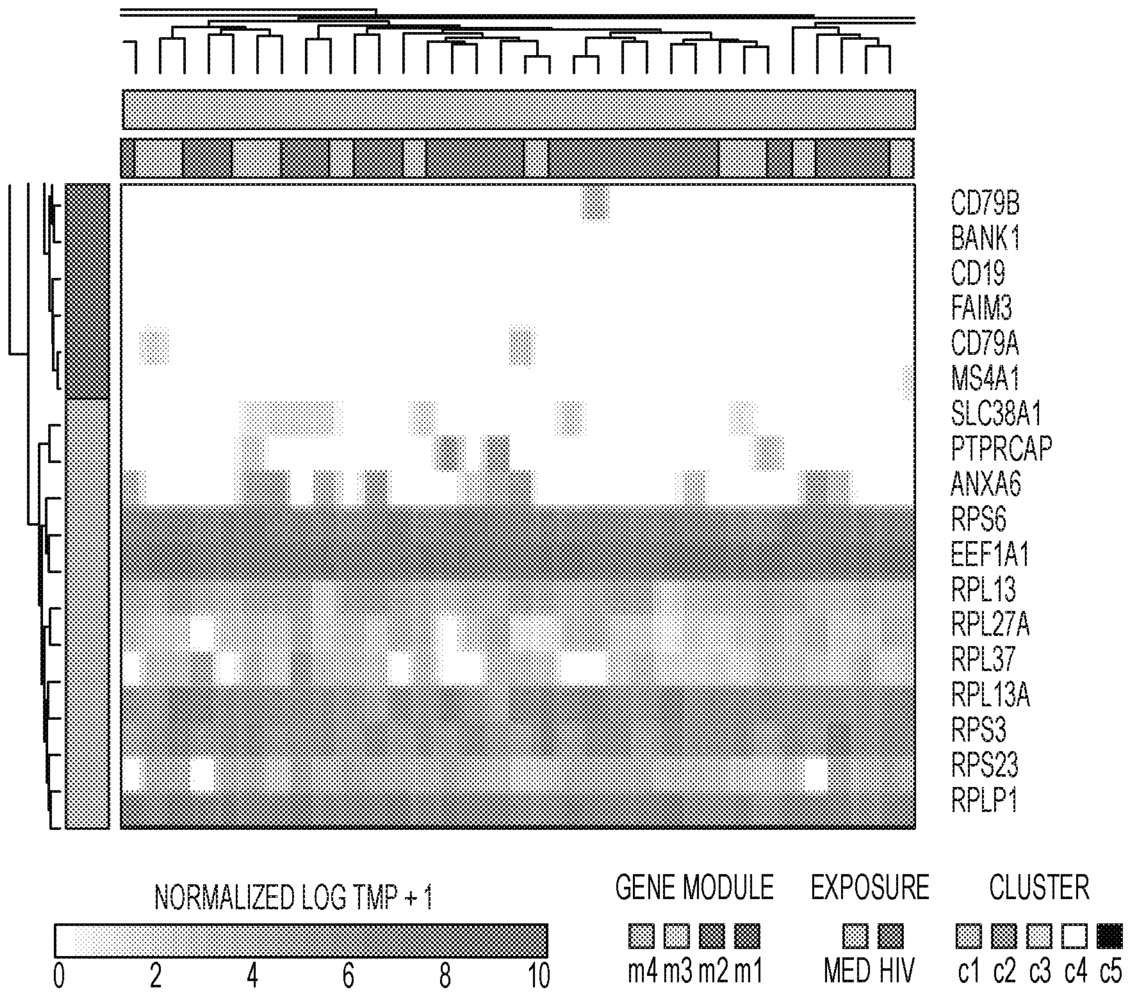
FIG. 15HHH

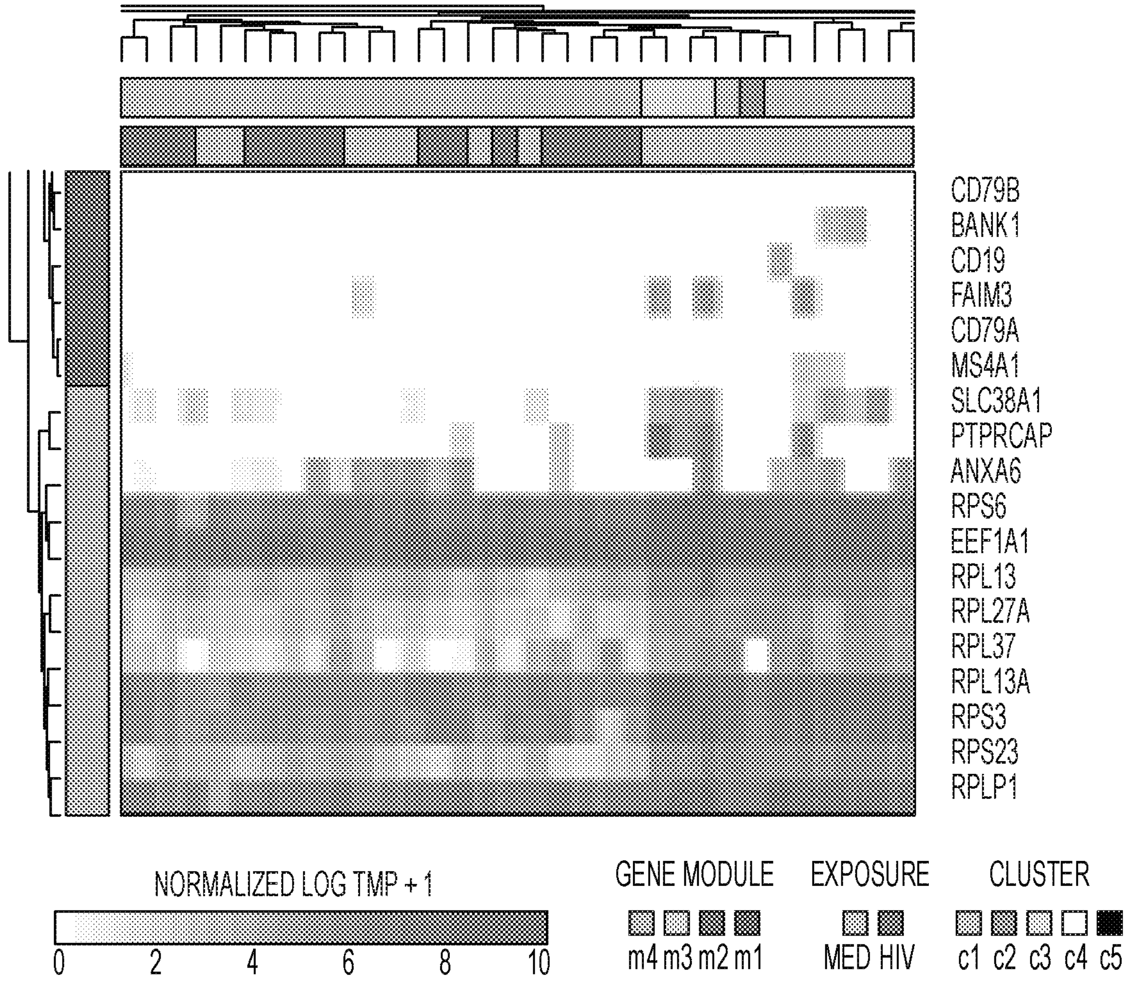
FIG. 15III

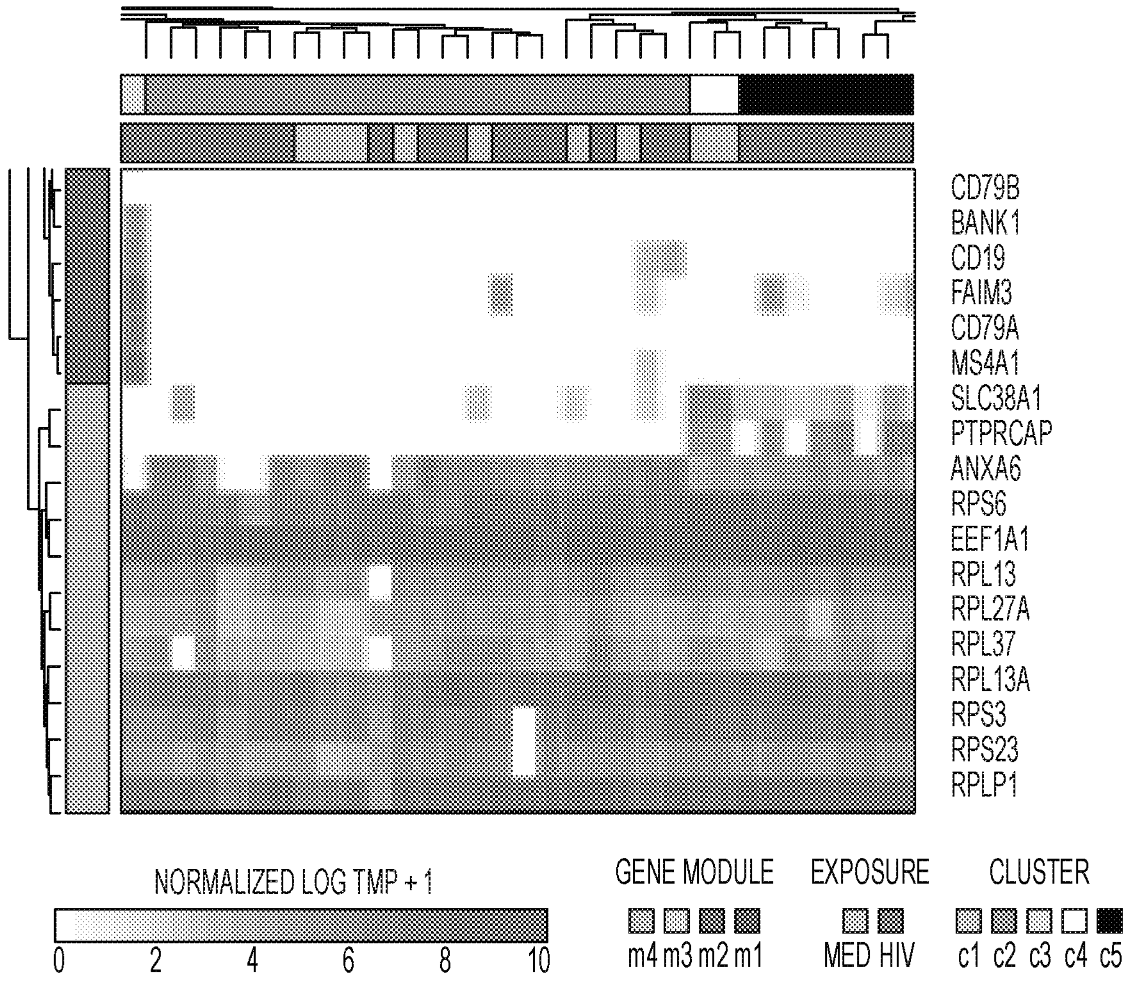
FIG. 15JJJ

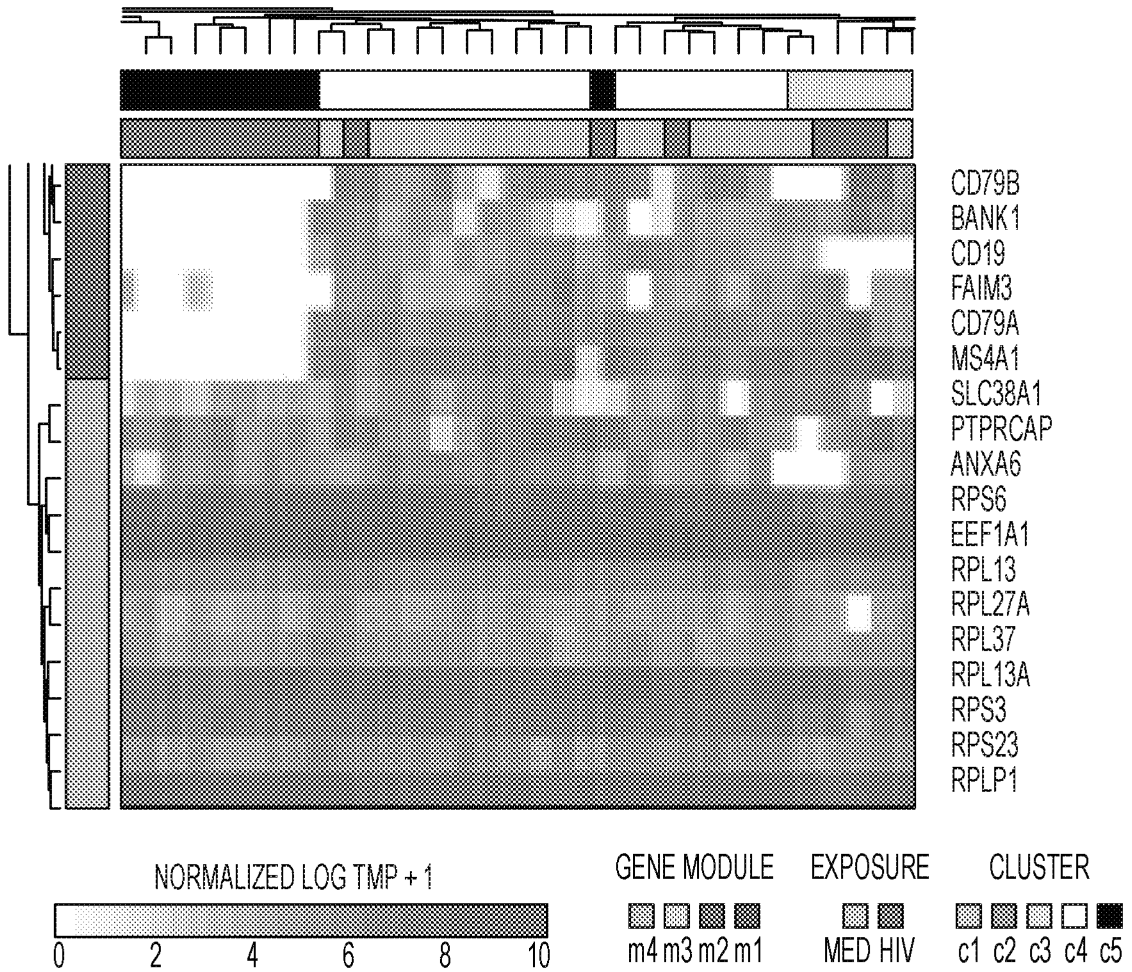
FIG. 15KKK

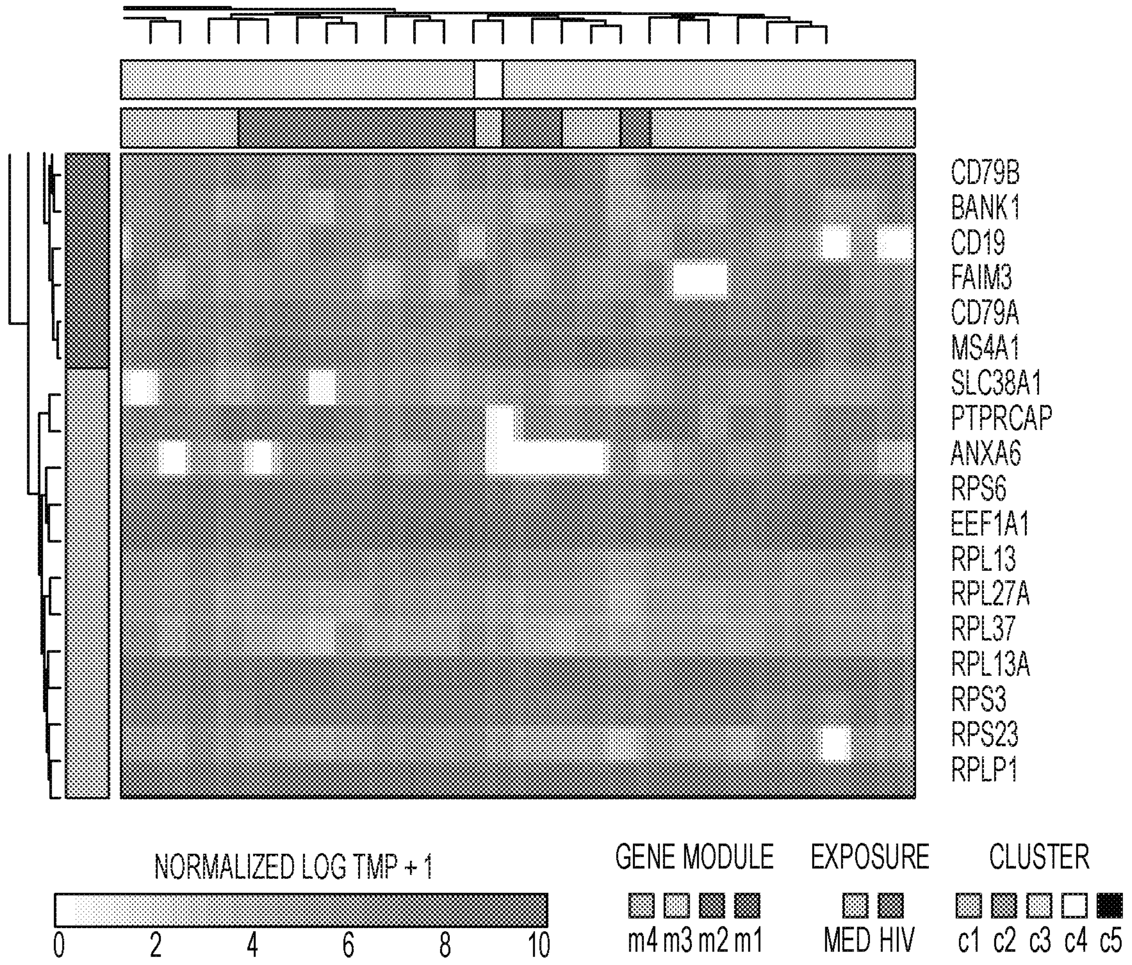
FIG. 15LLL

METHODS FOR IDENTIFYING AND MODULATING IMMUNE PHENOTYPES

INCORPORATION BY REFERENCE

This application is a U.S. National Stage of International Application No. PCT/US2017/018963, filed Feb. 22, 2017, published in English under PCT Article 21(2), which claims benefit of and priority to U.S. provisional patent application 62/298,349 filed Feb. 22, 2016, incorporated herein by reference.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant numbers AI078799, AI098484 and HL126554 awarded by the National Institutes of Health. The government has certain rights in the invention.

FIELD OF THE INVENTION

The present invention provides methods and tools for analyzing (epi)genetic and/or protein signatures of immune cells as well as (epi)genetic and/or protein signatures characteristic of immune cell phenotypes or immune cell behaviors or responses. The present invention relates to molecular profiling at the single cell level as well as cell population level. Applications include dissection of cell circuitry and delineation of functional or molecular pathways, as well as modulation of phenotypes, including modulation of immune cell population composition. The present invention is also relevant for therapeutics target discovery.

BACKGROUND OF THE INVENTION

Systems-level responses in the body represent the combined and coordinated behaviors of a highly diverse ensemble of cells. In the immune system, many specialized cells must work together to defend against myriad pathogenic threats, maintain long-term memory, and establish tolerance (Germain 2012). Moreover, the interplay between these cells must establish checks and balances to protect against autoimmunity or immunodeficiency (Littman and Rudensky 2010, Yosef, Shalek et al. 2013). Measuring these phenomena in bulk, however, blends and potentially masks the unique contributions of individual cells, particularly when their behaviors are heterogeneous or driven by rare cell types/states.

To overcome this issue, to date, analyses of immune cells have primarily relied on first dividing the system into distinct subpopulations from the "top-down," typically based on the expression of cellular markers, and subsequently characterizing each bin independently. This strategy has cataloged the major cell types of the mammalian immune system, established more nuanced functional divisions (Shay and Kang 2013), and uncovered that balanced composition is essential for proper function. Illustratively, overproduction of a subset of T helper cells (proinflammatory Th17) (Yosef, Shalek et al. 2013), or an imbalance in the relative proportions of DC subtypes (Nakahara, Uchi et al. 2010), can lead to autoimmune disease; similarly, in cancer, the density and diversity of tumor-infiltrating lymphocytes (TILs) has been shown to be predictive of tumor recurrence and clinical outcome (Galon, Costes et al. 2006). Yet, while informative, these "top-down" approaches depend on pre-selected markers, biasing experimental design. Recent work has shown that even seemingly identical cells can exhibit significant and functionally important heterogeneities (S. C. Bendall et al., Single-Cell Mass Cytometry of Differential Immune and Drug Responses Across a Human Hematopoietic Continuum. *Science* 332, 677-678 (2011); A. A. Cohen et al., Dynamic Proteomics of Individual Cancer Cells in Response to a Drug. *Science* 322, 1511-1516 (2008); A. K. Shalek et al., Single-cell transcriptomics reveals bimodality in expression and splicing in immune cells. *Nature* 498, 236-240 (2013); A. K. Shalek et al., Single-cell RNA-seq reveals dynamic paracrine control of cellular variation. *Nature* 510, 363-369 (2014); N. Yosef et al., Dynamic regulatory network controlling TH17 cell differentiation. *Nature* 496, 461-468 (2013); O. Feinerman et al., Single-cell quantification of IL-2 response by effector and regulatory T cells reveals critical plasticity in immune response. *Molecular Systems Biology* 6, 1-16 (2010)). Moreover, recent molecular studies have shown that even "identical" cells can substantially differ in gene expression, protein levels and phenotypic output (Cohen, Geva-Zatorsky et al. 2008, Raj and Van Oudenaarden 2009, Feinerman, Jentsch et al. 2010, Sharma, Lee et al. 2010, S. C. Bendall et al. 2011, Dalerba, Kalisky et al. 2011), with important functional consequences (Cohen, Geva-Zatorsky et al. 2008, Feinerman, Jentsch et al. 2010, Sharma, Lee et al. 2010), highlighting the shortcomings of "top-down" schemes.

A complementary approach is to examine a system from the "bottom-up," profiling its component cells individually. For example, in order to uncover salient variables in an immune response, one approach is to explore deviations that fundamentally alter human immunity (J. L. Casanova, Human genetic basis of interindividual variability in the course of infection. *Proceedings of the National Academy of Sciences of the U.S. of America* 112, E7118-7127 (2015)). Until recently, single-cell-based approaches, such as fluorescence activated cell sorting (FACS) or immunofluorescence, had been technically limited to probing a few preselected RNAs or proteins (Cohen, Geva-Zatorsky et al. 2008, Raj and Van Oudenaarden 2009, Sharma, Lee et al. 2010, Bendall, Simonds et al. 2011, Dalerba, Kalisky et al. 2011), hindering Applicants' ability to uncover novel factors. The recent emergence of single cell genomic approaches, and especially single-cell RNA-Seq (scRNA-seq), opens a new path for unbiased molecular profiling of individual immune cells from which Applicants can identify cell states and their associated signatures.

For example, analysis of T-cell lines from persons resistant to HIV-1 infection linked genetic variation in CCR5 to reduced risk (R. Liu et al., Homozygous defect in HIV-1 coreceptor accounts for resistance of some multiply-exposed individuals to HIV-1 infection. *Cell* 86, 367-377 (1996)). Similarly, studies of elite controllers (ECs)—a rare (~0.5%) subset of HIV-1 infected individuals whose immune systems naturally suppress viral replication without combination antiretroviral therapy (cART) (J. N. Blankson, Effector mechanisms in HIV-1 infected elite controllers: highly active immune responses? *Antiviral research* 85, 295-302 (2010); A. Saez-Cirion et al., HIV controllers exhibit potent CD8 T cell capacity to suppress HIV infection ex vivo and peculiar cytotoxic T lymphocyte activation phenotype. *Proceedings of the National Academy of Sciences of the U.S. of America* 104, 6776-6781 (2007))—have highlighted the importance of specific HLA-B variants and enhanced cytotoxic CD8$^{+}$ T cell responses (X. Gao et al., AIDS restriction HLA allotypes target distinct intervals of HIV-1 pathogenesis. *Nature medicine* 11, 1290-1292 (2005); P. Kiepiela et al., Dominant influence of HLA-B in mediating the potential co-evolution of HIV and HLA. *Nature* 432, 769-775 (2004)). Yet, these findings are not fully sufficient to explain viral control, implicating additional cellular components and interactions in coordinating an effective host defense. Indeed, further work in ECs has demonstrated improved crosstalk between the innate and adaptive immune systems (J. Huang et al., Leukocyte immunoglobulin-like receptors maintain unique antigen-presenting properties of circulating myeloid dendritic cells in HIV-1-infected elite controllers. *Journal of virology* 84, 9463-9471 (2010); E. Martin-Gayo et al., Potent Cell-Intrinsic Immune Responses in Dendritic Cells Facilitate HIV-1-Specific T Cell Immunity in HIV-1 Elite Controllers. *PLoS pathogens* 11, e1004930 (2015); G. Alter et al., HIV-1 adaptation to NK-cell-mediated immune pressure. *Nature* 476, 96-100 (2011)).

Illustratively, in Applicants' own work, using scRNA-Seq of 18 'identical' dendritic cells (DCs) exposed to lipopolysaccharide (LPS), Applicants discovered extensive bimodality in the DC response at multiple levels, including in the expression of key immune response genes and the splicing of RNA, which Applicants independently validated by RNA-FISH of 25 selected transcripts. By examining the co-variation between different genes across just 18 single cells, Applicants were able to decipher two distinct cell states and an interferon-driven antiviral circuit that Applicants subsequently validated in murine knockout models. Applicants then developed a high-throughput workflow for profiling many individual cells across different experimental conditions and used it to prepare scRNA-Seq libraries from over 1,800 BMDCs stimulated with three pathogenic components (Shalek, Satija et al. 2014). Here, Applicants identified a rare (~1%) subpopulation of precocious responders that expresses a core module of antiviral genes very early; this same module becomes active in all cells at later time points. By stimulating cells individually in sealed microfluidic chambers and analyzing DCs from knockout mice, Applicants showed that these precocious cells propagate and coordinate this response through interferon-mediated paracrine signaling. Surprisingly, the precocious cells are also essential for suppressing an early-induced inflammatory gene module. Taken together, these findings demonstrate the power and promise of single cell genomics, and highlight the importance of cell type/state, the microenvironment and inter-cellular communication in establishing and coordinating complex dynamic responses at the ensemble/system level.

These and related studies (Cohen, Geva-Zatorsky et al. 2008, Feinerman, Jentsch et al. 2010, Sharma, Lee et al. 2010, Bendall, Simonds et al. 2011, Dalerba, Kalisky et al. 2011) open fundamental questions for investigation: (1) How many cell types/states actually exist? (2) What cellular factors/intracellular circuits differentiate them? (3) How does the cellular microenvironment—including the spatiotemporal pattern of intercellular signals (autocrine & paracrine) received—alter and inform the molecular computations each cell type/state makes? (4) What information is transmitted via direct cellular communication (e.g., physical contact) and how is it integrated and weighed during cellular decision-making? (5) If rare cellular responses in seemingly "identical" cells and intercellular communication can drive collective decision-making, how can one discover them de novo? Might some diseases or favorable immune responses one assumes to be driven by faults or benefits in intracellular circuitry, respectively, actually be due to intercellular signaling or cellular composition (or some combination thereof)?

Appropriate immune responses require complex interactions between diverse collections of cells. Over the past several decades, substantial strides have been made in cataloging the cell types and interactions that drive these behaviors. Yet, recent studies (S. C. Bendall, et al. Science (2011); A. A. Cohen, et al. Science (2008); A. K. Shalek, et al. Nature (2013) A. K. Shalek, et al. Nature (2014); N. Yosef, et al. Nature (2013); O. Feinerman, et al. MSB (2010)) have revealed that even "identical" cells—e.g., "homogeneous" dendritic cells (DCs) responding to a single pathogenic component—can exhibit functionally important differences and that population-averaged responses can mask critical, informative cellular dynamics and their drivers (intracellular circuits) (A. P. Patel, et al. Science (2014)). Notably, current cell classification schemes and understanding of how ensemble dynamics are structured fail to explain this observed functional heterogeneity. Identifying the basic immune cell subsets and their molecular drivers can enable understanding and therapeutically manipulation of immune system response to stimuli, both good (e.g., commensal bacteria) and bad (e.g., viruses). Single cell genomic approaches, especially single-cell RNA-Seq (scRNA-seq), facilitates unbiased molecular profiling of individual immune cells, from which Applicants can identify cell states and their associated signatures.

Developing a deep understanding of the inter- and intracellular circuits that drive collective systems-level behaviors in health and disease will require experimental strategies that can both resolve the activity of individual cells. Clearly, advancements to further unravel complex immune system heterogeneity, in particular to establish cellular networks and cell interactions, aiming at improving diagnostic or therapeutic efforts are needed.

Citation or identification of any document in this application is not an admission that such document is available as prior art to the present invention.

SUMMARY OF THE INVENTION

In the present invention, it is demonstrated that Applicants can leverage single cell genomic approaches to identify and understand the cellular and molecular behaviors that inform ensemble phenotypes. This allows one to view the ensemble behavior as a sum of individual behaviors. As such, a desired outcome and/or response can be understood as arising from an alteration in the relative or absolute ratios of different cellular behaviors, either due to those behaviors themselves or their interactions. Thus, achieving a preferred response comes down to identifying the net change in phenotype that underscores this behavior via genetic and/or genomic profiling (e.g., bulk RNA differences between elite controllers and progressors), identifying the responses of individual cells via matches profiling (looking at the single cell states), uncovering and validating the drivers of those behaviors by comparing observed changes to reference databases (adjuvants, genes, chemicals), and utilizing this information diagnostically, therapeutically or prophylactically. In some instances, previously obtained single cell and reference data can be used to inform the analysis and modulation of ensemble profile data.

The following further underscores some of the intricacies involved when studying disease, including host-pathogen interactions, as well as host-specific diversity associated with particular cell types, or cell type subpopulations. Human cells have the ability to respond to pathogens, such as HIV and other viral infections, by cell-intrinsic immune responses that lead to secretion of, among others, type I IFN and upregulation of a wide panel of IFN-stimulated genes with antiviral effector functions. Conventional dendritic cells might contribute to spontaneous control of HIV-1 infection in HIV controllers. Elite controllers (EC) represent a small group of HIV infected individuals capable of controlling HIV-1 replication in the absence of treatment. Indeed, a spontaneous "functional cure" of HIV-1 naturally occurs in 0.3-0.5% of all infected people, known as elite controllers (ECs) (A. Saez-Cirion et al., HIV controllers exhibit potent CD8 T cell capacity to suppress HIV infection ex vivo and peculiar cytotoxic T lymphocyte activation phenotype. Proceedings of the National Academy of Sciences of the U.S. of America 104, 6776-6781 (2007)); Despite two decades of research, the mechanisms by which ECs naturally maintain undetectable levels of HIV virus without antiretroviral intervention remain unclear. For example, genome-wide association studies have proposed genetic variability in the HLA-B locus, such as the HLA-B*57 and B*27 alleles, which are more frequent in ECs and are associated with immune control of HIV-1 infection, and enhanced CD8 T cell immunity as contributors to the spontaneous immunological control of HIV-1 (Saez-Cirion et al 2007; Hersperger A R et al 2001). However, these studies fail to explain control in the large proportion of ECs who do not carry these alleles. Additional work has shown antiviral responses unique to ECs in both direct targets of HIV and cells involved in innate and adaptive immunity (G. Alter et al., HIV-1 adaptation to NK-cell-mediated immune pressure. *Nature* 476, 96-100 (2011); Huang J et al 2010, E. Martin-Gayo et al., Potent Cell-Intrinsic Immune Responses in Dendritic Cells Facilitate HIV-1-Specific T Cell Immunity in HIV-1 Elite Controllers. *PLoS pathogens* 11, e1004930 (2015)). Illustratively, applicants recently reported enhanced cell-intrinsic immune responses against HIV-1 in primary conventional dendritic cells (cDC) from ECs and observed that these cDCs had improved induction of antigen-specific CD4 and CD8 T cell responses in vitro (Martin-Gayo E et al 2015). However, the molecular mechanisms driving efficient cell-intrinsic immunity in EC cDCs are unknown, as is whether this efficacy is a property of all EC cDCs or just a subset of DCs unique to ECs.

Here, to further unravel complex immune system heterogeneity, in particular to establish cellular networks and cell interactions, aiming at improving diagnostic or therapeutic efforts, Applicants profiled cDCs from an EC at rest or exposed to pseudo-typed HIV-1 virus using single-cell RNA-Seq (scRNA-Seq), a recently developed approach that enables unbiased identification of the cell types, states, circuits, and molecular drivers normally convolved in a complex ensemble behavior. Here, Applicants applied scRNA-Seq to identify a highly functional subpopulation of elite controller dendritic cells responding to viral infection. Applicants developed and validated a computational infrastructure for identifying intracellular nodes and selecting immunomodulators that preferentially rebalance immune subset composition. Using identified immunomodulators, such as TLR3 ligands, such as poly I:C, Applicants induced a larger population of the functional subset of dendritic cells in normal donors, such as characterized by (surface) expression of CD64 and PD-L1, or high (surface) expression of CD64 and PD-L1, or increased (surface) expression of CD64 and PD-L1 (e.g. as compared to dendritic cells not belonging to the functional subset).

Unexpectedly, virus exposed cDCs separated into three distinct response groups, characterized by substantial differences in transcriptional programs associated with cellular activation and antiviral response. These clusters—influenced but not defined by viral interactions—revealed a new, highly functional group of cDCs, characterized by strong expression of innate immune activation genes and phenotypically distinguished by high surface expression of CD64 and PD-L1. Importantly, this group of cDCs has superior antigen presentation and T cell activation capabilities in vitro, and, although preferentially enriched in ECs, is common to all individuals. Using a combination of computational and experimental approaches to rationally uncover and test putative immunomodulators that can alter the relative abundances of these cDC groups, Applicants show that one can selectively adjuvant or inhibit this cDC subgroup in healthy individuals and ECs, respectively. With respect to EC, the study reveals functional heterogeneity in EC cDC responses and identifies transcriptional signatures associated with immune control of HIV-1 in cDCs; more generally, it demonstrates that immune system composition informs function and details new methodologies for identifying and rationally rebalancing salient components to realize, therapeutically or prophylactically, a desired response.

It has been established herein that these findings are not per se and only relevant for or characteristic of cDCs in control of HIV infection, but instead can be extrapolated to different types of immune cells, different types of pathological conditions, and/or different types of phenotypes or phenotypical behaviors, both at single cell levels as well as cell population level.

The present invention hereto generally relates to immune cell gene or protein signatures, as well as other genetic or epigenetic signatures, including methods for defining and utilizing immune cell gene signatures, both at single cell and population levels. Such gene cell signatures may be used to identify and define particular immune cell populations, more advantageously particular immune cell subpopulations as well as particular immune cell (sub)population cellular states or immune phenotypes. The present invention also relates to particular immune cell (sub)populations characterized by specific gene, protein, as well as other genetic or epigenetic signatures. Such (sub)populations may be associated with a particular immune phenotype. The invention further relates to methods for manipulating particular immune cells or immune cell (sub)populations based on the identified gene signatures, including modification of overall immune cell population composition, as well as screening methods to modulate immune phenotypes (including modulation of immune cell population compositions, such as for instance to redirect phenotypic behaviour) or to identify modulators of immune phenotypes. Diagnostic as well as therapeutic methods also form part of the present invention, and which are at least partly based on the particular gene signatures according to the invention, for instance modulation of immune cells or immune cell (sub)populations in order to induce or repress particular gene signatures, such as preferably particular gene signatures associated with a particular immune phenotype. Such allows for instance screening for immunomodulators which are capable of changing, be it inducing or repressing certain immune phenotypes.

The invention comprehends, and the invention provides each aspect as discussed herein. In an aspect of the invention, the application provides a method of identifying an immune cell gene signature, protein signature, and/or other genetic or epigenetic signature associated with a specific immune responder phenotype, comprising: comparing single cell or cell population RNA and/or protein expression profiles and/or other genetic or epigenetic profiles of a biological sample of said specific immune responder phenotype with single cell or cell population RNA and/or protein expression profiles and/or other genetic or epigenetic profiles of a biological sample of a different immune responder phenotype; determining differentially expressed RNAs and/or proteins and/or differential other genetic or epigenetic elements; determining an immune cell gene signature, protein signature, and/or other genetic or epigenetic signature associated with a specific immune responder phenotype as one or more of said differentially expressed RNAs and/or proteins or other differential genetic or epigenetic elements.

In a related aspect, the present application provides a method of identifying an immune cell gene signature, protein signature, and/or other genetic or epigenetic signature associated with an immune cell subpopulation associated with a specific immune responder phenotype, comprising: comparing single cell or cell population RNA and/or protein expression profiles and/or other genetic or epigenetic profiles of a biological sample of different immune cell subpopulations associated with said immune responder phenotype; determining differentially expressed RNAs and/or proteins and/or differential other genetic or epigenetic elements; determining an immune cell gene signature, protein signature, and/or other genetic or epigenetic signature associated with said subpopulation as one or more of said differentially expressed RNAs and/or proteins or other differential genetic or epigenetic element.

In a related aspect, the present application provides a method of identifying an immune cell subpopulation associated with a specific immune responder phenotype, comprising: identifying the gene signature, protein signature, and/or other genetic or epigenetic signature obtained according to the foregoing method in one or more immune cells from a biological sample. In a related aspect, the present application provides an immune cell subpopulation associated with a specific immune responder phenotype obtained according to the foregoing method In a related aspect, the present application provides a method of identifying a specific immune responder phenotype, comprising: identifying the gene signature, protein signature, and/or other genetic or epigenetic signature obtained according to the foregoing method in one or more immune cells from a biological sample. In an embodiment, wherein said gene signature, protein signature, and/or other genetic or epigenetic signature characterizes a specific immune cell state. In another embodiment, wherein said immune responder phenotype is characterized by an enhanced or improved immunological response to a pathological condition, or wherein said immune responder phenotype is characterized by an decreased or diminished immunological response to a pathological condition, and/or wherein said immune responder phenotype is characterized by a particular immunological state, such as breadth of neutralization, functionality of antigen presentation, etc. In a further embodiment wherein said pathological condition is an infection, an autoimmune disorder, allergy, a vaccine, or cancer. In an embodiment, wherein said immune cell is a leukocyte or a dendritic cell. In an embodiment, wherein the pathological condition is HIV infection.

In a related aspect, the present application provides an immune cell gene signature, protein signature, and/or other genetic or epigenetic signature associated with a specific immune responder phenotype obtained according to the foregoing method, such as a signature as defined in any of Tables 1 to 156.

In a related aspect, the present application provides a method of identifying an immunomodulant capable of driving a specific immune responder phenotype having a specific gene signature, protein signature, and/or other genetic or epigenetic signature, comprising: applying a candidate immunomodulant to an immune cell or a population of immune cells, wherein said immune cells preferably do not have said specific immune responder phenotype; identifying an immunomodulant capable of driving or inducing a specific immune responder phenotype if said specific gene signature, protein signature, and/or other genetic or epigenetic signature is detected in one or more of said immune cells. In an embodiment, an immunomodulant is obtained by the foregoing method.

In a related aspect, the present application provides a method of identifying an immunomodulant capable of suppressing a specific immune responder phenotype having a specific gene signature, protein signature, and/or other genetic or epigenetic signature, comprising: applying a candidate immunomodulant to an immune cell or a population of immune cells, wherein said immune cells preferably has said specific immune responder phenotype; identifying an immunomodulant capable of suppressing a specific immune responder phenotype if said specific gene signature, protein signature, and/or other genetic or epigenetic signature is reduced or repressed in one or more of said immune cells. In an embodiment, an immunomodulant is obtained by the foregoing method.

In a related aspect, the present application provides a method of identifying an immunomodulant capable of inducing a specific immune cell subpopulation associated with a specific immune responder phenotype, said immune cell subpopulation having a specific gene signature, protein signature, and/or other genetic or epigenetic signature, comprising: applying a candidate immunomodulant to an immune cell or a population of immune cells, wherein said immune cells optionally do not have said specific immune responder phenotype; identifying an immunomodulant capable of inducing a specific immune cell subpopulation associated with said immune responder phenotype if said specific gene signature, protein signature, and/or other genetic or epigenetic signature is detected in one or more of said immune cells. In an embodiment, an immunomodulant is obtained by the foregoing method.

In a related aspect, the present application provides a method of identifying an immunomodulant capable of suppressing a specific immune cell subpopulation associated with a specific immune responder phenotype, said immune cell subpopulation having a specific gene signature, protein signature, and/or other genetic or epigenetic signature, comprising: applying a candidate immunomodulant to an immune cell or a population of immune cells, wherein said immune cells optionally has said specific immune responder phenotype; identifying an immunomodulant capable of suppressing a specific immune cell subpopulation associated with said specific immune responder phenotype if said specific gene signature, protein signature, and/or other genetic or epigenetic signature is reduced or repressed in one or more of said immune cells. In an embodiment, an immunomodulant is obtained by the foregoing method.

In an embodiment, an immunomodulant is obtained by the foregoing method.

In a related aspect, the present application provides a method of modulating an immune responder phenotype, comprising: applying to an immune cell or a population of immune cells an immunomodulant capable of inducing or suppressing a gene signature, protein signature, and/or other genetic or epigenetic signature associated with a specific immune responder phenotype and/or associated with a subpopulation of immune cells associated with a specific immune responder phenotype.

In a related aspect, the present application provides a method for increasing or decreasing an immune cell subpopulation, comprising: applying to a population of immune cells an immunomodulant capable of inducing or suppressing a gene signature, protein signature, and/or other genetic or epigenetic signature associated with a specific immune responder phenotype, thereby increasing or decreasing an immune cell subpopulation characterized by said specific immune responder phenotype.

In a related aspect, the present application provides a method for increasing or decreasing an immune cell subpopulation, comprising applying an immunomodulant to an immune cell or immune cell population.

In a related aspect, the present application provides a method of identifying a pathway involved in or responsible for a specific immune responder phenotype or an immune cell subpopulation associated with a specific immune responder phenotype having a specific gene signature, protein signature, and/or other genetic or epigenetic signature, comprising: inducing or repressing a pathway in an immune cell or a population of immune cells; identifying a pathway involved in or responsible for a specific immune responder phenotype or an immune cell subpopulation associated with a specific immune responder phenotype if said specific gene signature, protein signature, and/or other genetic or epigenetic signature is detected in one or more of said immune cells. In an embodiment, the method wherein inducing or repressing said pathway in an immune cell or a population of immune cells comprises inducing or repressing expression or activity of one or more components of said pathway.

In a related aspect, the present application provides a method of modulating an immune responder phenotype, comprising: inducing or repressing a pathway involved in or responsible for inducing a gene signature, protein signature, and/or other genetic or epigenetic signature associated with a specific immune responder phenotype and/or an immune cell subpopulation associated with a specific immune responder phenotype.

In a related aspect, the present application provides a method of identifying a gene involved in or responsible for a specific immune responder phenotype or an immune cell subpopulation associated with a specific immune responder phenotype having a specific gene signature, protein signature, and/or other genetic or epigenetic signature, comprising: inducing or repressing a gene in an immune cell or a population of immune cells; identifying a gene involved in or responsible for a specific immune responder phenotype or an immune cell subpopulation associated with a specific immune responder phenotype if said specific gene signature, protein signature, and/or other genetic or epigenetic signature is detected in one or more of said immune cells.

In a related aspect, the present application provides a method of modulating an immune responder phenotype, comprising: inducing or repressing a gene involved in or responsible for inducing a gene signature, protein signature, and/or other genetic or epigenetic signature associated with a specific immune responder phenotype or an immune cell subpopulation associated with a specific immune responder phenotype.

In a related aspect, the present application provides a method of diagnosing or prognosing a specific pathological condition, comprising: comparing in a biological sample comprising one or more immune cell a single cell or cell (sub)population gene signature, protein signature, and/or other genetic or epigenetic signature with an immune cell gene signature, protein signature, and/or other genetic or epigenetic signature associated with a specific immune responder phenotype or an immune cell subpopulation associated with a specific immune responder phenotype; diagnosing or prognosing a specific pathological condition based on correspondence of said gene signature, protein signature, and/or other genetic or epigenetic signature with an immune cell gene signature, protein signature, and/or other genetic or epigenetic signature associated with a specific immune responder phenotype or an immune cell subpopulation associated with a specific immune responder phenotype.

In a related aspect, the present application provides a method of treating or preventing a specific pathological condition or prophylaxis of a specific pathological condition or being at risk for a pathological condition, comprising: administering to a subject, optionally said subject having said pathological condition: an immunomodulant capable of inducing an immune cell gene signature, protein signature, and/or other genetic or epigenetic signature associated with a specific immune responder phenotype or an immune cell subpopulation associated with a specific immune responder phenotype, wherein said immune responder phenotype or an immune cell subpopulation associated with a specific immune responder phenotype is characterized by an enhanced or improved immunological response to said pathological condition; or an immunomodulant capable of repressing an immune cell gene signature, protein signature, and/or other genetic or epigenetic signature associated with a specific immune responder phenotype or an immune cell subpopulation associated with a specific immune responder phenotype, wherein said immune responder phenotype or said immune cell subpopulation associated with a specific immune responder phenotype is characterized by a decreased or diminished immunological response to said pathological condition.

In a related aspect, the present application provides a method of treating or preventing a specific pathological condition or prophylaxis of a specific pathological condition or being at risk for a pathological condition, comprising: applying to one or more immune cell of a subject, optionally said subject having said pathological condition: an immunomodulant capable of inducing an immune cell gene signature, protein signature, and/or other genetic or epigenetic signature associated with a specific immune responder phenotype or an immune cell subpopulation associated with a specific immune responder phenotype, wherein said immune responder phenotype or said immune cell subpopulation associated with a specific immune responder phenotype is characterized by an enhanced or improved immunological response to said pathological condition; or an immunomodulant capable of repressing an immune cell gene signature, protein signature, and/or other genetic or epigenetic signature associated with a specific immune responder phenotype or an immune cell subpopulation associated with a specific immune responder phenotype, wherein said immune responder phenotype or said immune cell subpopulation associated with a specific immune responder phenotype is characterized by a decreased or diminished immunological response to said pathological condition; administering said one or more immune cell to said subject.

In a related aspect, the present application provides a method of monitoring treatment of a specific pathological condition, comprising, identifying an immune cell gene signature, protein signature, and/or other genetic or epigenetic signature associated with a specific immune responder phenotype or an immune cell subpopulation associated with a specific immune responder phenotype, optionally wherein said immune responder phenotype or an immune cell subpopulation associated with a specific immune responder phenotype is characterized by an enhanced or improved immunological response to said pathological condition, or wherein said immune responder phenotype or said immune cell subpopulation associated with a specific immune responder phenotype is characterized by a decreased or diminished immunological response to said pathological condition.

In a related aspect, the present application provides a method of determining the immune status of a subject, comprising: identifying an immune cell gene signature, protein signature, and/or other genetic or epigenetic signature associated with a specific immune responder phenotype or an immune cell subpopulation associated with a specific immune responder phenotype.

In a related aspect, the present application provides an isolated immune cell or immune cell (sub)population from a subject having a specific immune responder phenotype, wherein said immune cell or immune cell (sub)population is characterized by an immune cell gene signature, protein signature, and/or other genetic or epigenetic signature specifically associated with said immune responder phenotype or an immune cell subpopulation associated with a specific immune responder phenotype. The isolated immune cell or immune cell (sub)population wherein said immune cell gene signature, protein signature, and/or other genetic or epigenetic signature is not associated with a different immune responder phenotype or a different immune cell subpopulation associated with a specific immune responder phenotype.

The method according to any of the preceding statements wherein said immune cell gene signature, protein signature, and/or other genetic or epigenetic signature comprises one or more genes as defined in any of Tables 1 to 156.

The method according to any of the preceding statements, wherein said immune responder is an elite controller, a viremic controller, or a previous controller, or wherein said immune responder phenotype is as defined in any of Tables 1 to 156.

In a related aspect, the present application provides a method of identifying a differential signature gene or protein, a gene or protein signature or other genetic or epigenetic element associated with a specific immune responder phenotype as compared to a different or non-specific immune responder phenotype comprising: comparing single cell RNA and/or protein expression profiles or other genetic or epigenetic profiles of immune cells of a specific immune responder phenotype and a different or non-specific immune responder phenotype; or comparing population RNA and/or protein expression profiles or other genetic or epigenetic profiles of immune cells of a specific immune responder phenotype and a different or non-specific immune responder phenotype; optionally wherein said comparing is over a time course; optionally wherein said comparing is as to or in response to the particular pathological insult.

In an embodiment, the method or immune cell of any of the preceding statements wherein the immune cell comprises a leukocyte or an antigen presenting cell.

In an embodiment, the method or immune cell of any of the preceding statements wherein the immune cell comprises a B cell.

In an embodiment, the method or immune cell of any of the preceding statements wherein the immune cell comprises a T cell.

In an embodiment, the method or immune cell of any of the preceding statements wherein the immune cell comprises a monocyte.

In an embodiment, the method or immune cell of any of the preceding statements wherein the immune cell comprises a dendritic cell.

In an embodiment, the method of any of the preceding statements, wherein comparing is as to or in response to the particular pathogen, preferably a human or animal pathogen.

In an embodiment, the method of any of the preceding statements, wherein comparing is as to or in response to the particular pathogen and the particular pathogen comprises a bacterial, fungal, protozoal, parasitic, or viral pathogen. In an embodiment, the method wherein the viral pathogen comprises HIV.

In an embodiment, the method of any preceding statement wherein comparing obtains up-regulation of one or more of CD226, IL1R2, KIR2DS4, KIR3DL1, KIR3DL2, and said up-regulation indicates pathogen controller or elite controller immune cell.

In an embodiment, the method of any preceding statement wherein comparing obtains up-regulation of one or more of SPP1*, TNFAIP6*, CXCL10*, SPINK1, SLC39A8, IL24, MSC, EMP1*, FPR3, DHRS9, TPST1*, PPARG, IL1R2*, CD226, KIR3DL1, KIR2DS4, KIR3DL2, L1A*, or BCAR3, and said up-regulation indicates pathogen controller immune cell or elite controller immune cell.

In an embodiment, the application provides a method of any preceding statement wherein comparing obtains up-regulation of PD-L1 (CD274), and/or CD64 (FCGR1A) and said up-regulation indicates elite controller immune cell.

In an embodiment, the application provides a method or immune cell according to any of the preceding statements wherein said differential signature gene or said gene signature is one or more selected from CD226, IL1R2, KIR2DS4, KIR3DL1, KIR3DL2, preferably expression or upregulation thereof.

In an embodiment, the application provides a method or immune cell according to any of the preceding statements wherein said differential signature gene or protein or said gene or protein signature is one or more selected from SPP1*, TNFAIP6*, CXCL10*, SPINK1, SLC39A8, IL24, MSC, EMP1*, FPR3, DHRS9, TPST1*, PPARG, IL1R2*, CD226, KIR3DL1, KIR2DS4, KIR3DL2, IL1A*, or BCAR3, preferably expression or upregulation thereof.

In an embodiment, the application provides a method or immune cell according to any of the preceding statements wherein said differential signature gene or protein or said gene or protein signature is one or more selected from PD-L1, and/or CD64, preferably expression or upregulation thereof.

In an embodiment, the application provides a method or immune cell of any preceding statement wherein the immune cell comprises a mouse cell or a human immune cell or an immune cell in a model non-human organism, a model non-human mammal that expresses a Cas protein, a mouse that expresses a Cas protein, a cell in vivo or a cell ex vivo or a cell in vitro.

In an embodiment, the application provides a method or immune cell of any of the previous statements wherein the human immune cell comprises an immune cell of a patient having a particular pathological condition and comparing is as to or in response to the particular pathological condition.

In an embodiment, the application provides a method or immune cell of any of the previous statements wherein the human immune cell comprises an immune cell of a patient infected by the particular pathogen and comparing is as to or in response to the particular pathogen.

In an embodiment, the application provides a method or immune cell of any of the previous statements further comprising expanding a population of pathogen controller or elite controller immune cells or broad neutralizer immune cells.

In an embodiment, the application provides a method or immune cell of any of the preceding statements wherein the immune cell comprises elite controller immune cells.

In an embodiment, the application provides a method or immune cell of any of the preceding statements comprising introducing elite controller immune cells of the population into the patient.

In an embodiment, the application provides a method or immune cell of any of the previous statements further including administering to the patient an immune stimulator or adjuvant. In a further embodiment, the application provides a method or immune cell wherein the immune stimulator or adjuvant comprises TLR3 ligand, preferably poly I.C.

In a related aspect, the present application provides a method of constructing an immune cellular network or circuit associated a specific immune responder phenotype as compared to a different or non-specific immune responder phenotype, comprising: introducing perturbation(s) over a course of time to each cell in a population of the immune cells, measuring genomic, genetic, epigenetic, transcript, expression and/or phenotypic differences of each immune cell and coupling perturbation(s) with measured differences to infer intercellular and/or intracellular networks or circuits associated with the specific immune responder phenotype. In an embodiment, the application provides such a method wherein the perturbation(s) comprise at least 1, 2, 3, 4 or more single-order or combinatorial perturbations. In an embodiment, the application provides such a method wherein single-order or combinatorial perturbations comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 or massively parallel perturbations. In an embodiment, the method wherein perturbation(s) include contacting the immune cells with a particular pathogen.

In an embodiment, the application provides a method of any of the preceding statements wherein the immune cell comprises a leukocyte or an antigen presenting cell.

In an embodiment, the application provides a method of any of the preceding statements wherein the immune cell comprises a B cell.

In an embodiment, the application provides a method of any of the preceding statements wherein the immune cell comprises a T cell.

In an embodiment, the application provides a method of any of the preceding statements wherein the immune cell comprises a monocyte.

In an embodiment, the application provides a method of any of the preceding statements wherein the immune cell comprises a dendritic cell. In an embodiment, the method is a method wherein the particular pathogen comprises a bacterial, fungal, protozoal, parasitic, or viral pathogen. In an embodiment, the method is a method wherein the particular pathogen comprises a viral pathogen. In an embodiment, the method is a method wherein the viral pathogen comprises HIV. In an embodiment, the method is a method wherein perturbation(s) comprise one or more genetic perturbation and/or one or more epigenetic or epigenomic perturbation. In an embodiment, the application provides a method of any of the preceding statements wherein at least one perturbation is introduced with RNAi- or a CRISPR-Cas system. In an embodiment, of the method at least one perturbation is introduced via a chemical agent, an intracellular spatial relationship between two or more cells, an increase or decrease of temperature, addition or subtraction of energy, electromagnetic energy, or ultrasound. In an embodiment of the method the immune cell comprises the immune cell comprises a mouse cell or a human immune cell or an immune cell in a model non-human organism, a model non-human mammal that expresses a Cas protein, a mouse that expresses a Cas protein, a cell in vivo or a cell ex vivo or a cell in vitro. In an embodiment of the method measuring or measured differences comprises measuring or measured differences of DNA, RNA, protein or post translational modification; or measuring or measured differences of protein or post translational modification correlated to RNA and/or DNA level(s). In an embodiment of the method the method includes sequencing, and prior to sequencing: (a) perturbing and isolating a single cell with at least one labeling ligand specific for binding at one or more target RNA transcripts, or isolating a single cell with at least one labeling ligand specific for binding at one or more target RNA transcripts and perturbing the cell; and/or (b) lysing the cell under conditions wherein the labeling ligand binds to the target RNA transcript(s). In an embodiment of the method wherein step (a) comprises perturbing and isolating a single cell with at least one labeling ligand specific for binding at one or more target RNA transcripts. In an embodiment, the method wherein step (a) comprises isolating a single cell with at least one labeling ligand specific for binding at one or more target RNA transcripts or protein product thereof, and perturbing the cell. In an embodiment of the method perturbing or perturbation(s) comprise(s) genetic perturbing. In an embodiment of the method perturbing or perturbation(s) comprise(s) single-order perturbations. In an embodiment of the method perturbing or perturbation(s) comprise(s) combinatorial perturbations. In an embodiment, the perturbing or perturbation(s) comprises gene knock-down, gene knock-out, gene activation, gene inhibition, gene insertion, or regulatory element deletion. In an embodiment, the perturbing or perturbation(s) comprises genome-wide perturbation. In an embodiment, the perturbing or perturbation(s) comprises performing CRISPR-Cas-based perturbation. In an embodiment, the method perturbing or perturbation(s) comprises performing pooled single or combinatorial CRISPR-Cas-based perturbation with a genome-wide library of sgRNAs. In an embodiment, the perturbing or perturbation(s) comprises performing pooled combinatorial CRISPR-Cas-based perturbation with a genome-wide library of sgRNAs. In an embodiment of the method each sgRNA comprises a unique molecular identifier. In an embodiment, the each sgRNA is co-delivered with a reporter mRNA. In an embodiment of the method perturbing or perturbation(s) comprises subjecting the immune cell to an increase or decrease in temperature and/or a chemical agent; and/or a chemical agent and/or temperature increase or decrease across a gradient; and/or an immune stimulator or adjuvant; and/or a TLR3 ligand, for instance poly I:C.

In a related aspect, the application provides a method of any of the foregoing methods wherein the immune cell is in a microfluidic system.

In a related aspect, the application provides a method of any of the foregoing methods wherein the immune cell is in a droplet.

In an aspect, the application provides a method of constructing an immune cellular network or circuit associated a specific immune responder phenotype as compared to a different or non-specific immune responder phenotype wherein perturbing or perturbation(s) comprises transforming or transducing the immune cell or a population that includes and from which the immune cell is isolated with one or more genomic sequence-perturbation constructs that perturbs a genomic sequence in the immune cell. In an embodiment of the method perturbing or perturbation(s) comprises multiplex transformation with a plurality of genomic sequence-perturbation constructs.

In a related aspect, the present application provides a method of treating a patient in need thereof having a pathological condition comprising: (a) analyzing a gene signature, protein signature, and/or other genetic or epigenetic signature responsible for a particular immune responder phenotype in immune cells obtained from the patient; (b) treating the patient with an immunomodulatory, immune stimulator or adjuvant when the gene signature, protein signature, and/or other genetic or epigenetic signature is not detected, whereby the immunomodulatory, immune stimulator or adjuvant induced the gene signature, protein signature, and/or other genetic or epigenetic signature.

In a related aspect, the present application provides a method of treating a patient in need thereof having an infection comprising: (a) determining CD64 and/or PD-L1 expression in dendritic cells obtained from the patient; (b) treating the patient with an immune stimulator or adjuvant wherein the patient has $CD64^{Lo}$ and/or PD-L1− dendritic cells, whereby the immune stimulator or adjuvant shifts the proportion of dendritic cells towards $CD64^{+}$ and/or PD-L1+ dendritic cells. In an embodiment, the method wherein the immune stimulator or adjuvant is a TLR3 ligand.

In a related aspect, the present application provides a method of treating a patient in need thereof having an infection comprising: (a) determining the presence of an antipathogen gene signature, protein signature, and/or other genetic or epigenetic signature in immune cells obtained from the patient; (b) treating the patient with an immunomodulator, immune stimulator or adjuvant wherein the patient has immune cells not expressing an antipathogen gene signature, protein signature, and/or other genetic or epigenetic signature, whereby the immunomodulator, immune stimulator or adjuvant shifts the proportion of immune cells towards an antipathogen gene signature, protein signature, and/or other genetic or epigenetic signature. In an embodiment of the method the infection comprises a bacterial, fungal, protozoal, parasitic, or viral pathogen. In an embodiment of the method the infection comprises a viral infection. In an embodiment of the method the viral infection comprises HIV. In an embodiment of the method the immunomodulator, immune stimulator or adjuvant is a TLR3 ligand.

In a related aspect, the present application provides a method of treating a patient in need thereof having an infection comprising: (a) determining the presence of an antipathogen gene signature, protein signature, and/or other genetic or epigenetic signature in immune cells obtained from the patient; (b) treating the patient with immune cells having an antipathogen gene signature, protein signature, and/or other genetic or epigenetic signature. In an embodiment, the method is a method wherein determining the presence of an antipathogen gene signature, protein signature, and/or other genetic or epigenetic signature comprises determining CD64 and/or PD-L1 expression in dendritic cells obtained from the patient. In an embodiment of the method the patient has $CD64^{Lo}$ and/or PD-L1− dendritic cells, and treating the patient with dendritic cells having an antipathogen gene signature, protein signature, and/or other genetic or epigenetic signature comprises administering CD64+ and/or PD-L1+ dendritic cells. In an embodiment of the method the treating is of cells of a population that was expanded from a sample of cells of or from the patient. In an embodiment of the method the infection comprises a bacterial infection. In an embodiment of the method the infection comprises a viral infection. In an embodiment of the method the viral infection comprises HIV.

In an aspect of the invention, the present application provides an isolated population of immune cells from a specific immune responder phenotype, characterized by the signature as defined in any of Tables 1 to 156. In further particular embodiments, the isolated population of immune cells is a Cluster-1-like/$CD64^{Hi}$,$PD\text{-}L1^{Hi}$ cDC cell population.

In a related aspect, the present application provides a method for identifying an isolated cell population as characteristic for a specific immune responder phenotype, the method characterized by the steps of a) determining the gene and/or protein expression pattern and/or other genetic or epigenetic pattern of said isolated cell population and b) determining whether said expression pattern corresponds to a signature as defined in any of Tables 1 to 156.

In a related aspect, the present application provides a method of selecting cell population characteristic for a specific immune responder phenotype from a patient, said method comprising collecting a pool of immune cells from said patient and b) selecting said cell population based on a signature as defined in any of Tables 1 to 156.

In a related aspect, the present application provides a method for identifying an immunomodulant, said method comprising (a) obtaining a population of immune cells with an RNA and/or protein expression pattern and/or other genetic or epigenetic pattern which is different from a signature as defined in any of Tables 1 to 156 (b) treating said population of immune cells with a candidate immunomodulant and (c) determining whether the RNA and/or protein expression pattern and/or other genetic or epigenetic pattern of said immune cells evolves to a signature as defined in any of Tables 1 to 156.

In a related aspect, the present application provides a method for determining the immune status of a patient, said method comprising (a) isolating a population of immune cells from said patient and (b) determining the RNA and/or protein expression pattern and/or other genetic or epigenetic pattern of said isolated cell population as to whether or not said RNA and/or protein expression pattern and/or other genetic or epigenetic pattern corresponds to an RNA and/or protein expression pattern and/or other genetic or epigenetic pattern characteristic of a specific immune responder phenotype, said RNA and/or protein expression pattern and/or other genetic or epigenetic pattern being characterized respectively by a signature as defined in any of Tables 1 to 156.

In a related aspect, the present application provides a method for determining the suitability of a patient for treatment with an immunomodulator, said method comprising (a) isolating a population of immune cells from said patient and (b) determining the RNA and/or protein expression pattern and/or other genetic or epigenetic pattern of said isolated cell population as to whether or not said RNA and/or protein expression pattern and/or other genetic or epigenetic pattern corresponds to an RNA and/or protein expression pattern and/or other genetic or epigenetic pattern characteristic of a specific immune responder phenotype being characterized respectively by a signature as defined in any of Tables 1 to 156 and (c) determining the suitability of said patient for treatment with an immunomodulator based thereon.

In a related aspect, the present application provides a method of identifying a differential signature gene, a gene signature or other genetic or epigenetic element associated with a specific immune responder phenotype as compared to a different or non-specific immune responder phenotype comprising, comprising: comparing single cell RNA and/or protein expression profiles and/or other genetic or epigenetic profiles of immune cells of a specific immune responder phenotype and a different or non-specific immune responder phenotype; or comparing population RNA and/or protein expression profiles and/or other genetic or epigenetic profiles of immune cells of a specific immune responder phenotype and a different or non-specific immune responder phenotype; wherein said immune cells are selected based on their binding to or displaying of a pathogen protein. In an embodiment of the method said pathogen protein is a viral coat protein. In an embodiment of the method said viral protein is gp140.

In a related aspect, the present application provides a method for determining the immune status of a patient infected with a pathogen said method comprising (a) isolating an immune cell population from said patient (b) contacting said cells in vitro with said pathogen, (c) determining the single cell or cell population RNA and/or protein expression profiles and/or other genetic or epigenetic profiles of said immune cells and (d) determining the immune status of said patient based thereon. In an embodiment of the invention, the application provides a method wherein said method comprises determining the number of cells having an expression profile corresponding to either VexA, VexB and VexC cell profiles, characterized by a signature as defined in any of Tables 1 to 20.

In a related aspect, the present application provides a method for determining the suitability of a patient infected with a pathogen for treatment with an immunomodulator, said method comprising (a) isolating a population of immune cells from said patient and (b) contacting said cells in vitro with said pathogen, (c) determining the single cell or cell population RNA and/or protein expression profiles and/or other genetic or epigenetic profiles of said immune cells, based on the presence of cells having either a VexA, VexB or VexC profile and (d) determining the suitability of said patient for treatment with an immunomodulator based thereon.

In a related aspect, the present application provides a method for identifying an immunomodulant, said method comprising (a) obtaining a population of immune cells, (b) determining the single cell or cell population RNA and/or protein expression profiles and/or other genetic or epigenetic profiles of said immune cells (b) contacting said cells in vitro with said pathogen, (c) determining the single cell or cell population RNA and/or protein expression profiles and/or other genetic or epigenetic profiles of said immune cells and (d) determining whether said immunomodulant is capable of increasing the number of cells having an expression profile corresponding to the VexB profile.

In a related aspect, the present application provides a method for identifying an immunomodulant suitable for the treatment of a pathological condition comprising (a) identifying a differential signature gene, a gene signature or other genetic or epigenetic element associated with an immune responder phenotype, a responder immune cell or cell population, said method comprising comparing the RNA and/or protein expression profile of an immune cell or cell population from a patient afflicted with said pathological condition which is a responder patient to the RNA and/or protein expression profile and/or other genetic or epigenetic profile of a corresponding immune cell or cell population from a non-responder patient and (b) screening agents for their ability to induce said signature gene, a gene signature or other genetic or epigenetic element associated with an immune responder phenotype, a responder immune cell or cell population in a non-responder immune cell or cell population.

In an embodiment, the application provides a method according to any of the preceding statements wherein said immune responder phenotype is as defined in any of Tables 1 to 156.

In an embodiment, the application provides a method according to any of the preceding statements wherein said immune cell is selected from leukocytes or antigen presenting cells.

In an embodiment, the application provides a method according to any of the preceding statements wherein said immune cell is a B-cell.

In an embodiment, the application provides a method according to any of the preceding statements wherein said immune cell is a T-cell.

In an embodiment, the application provides a method according to any of the preceding statements wherein said immune cell is a dendritic cell.

In an embodiment, the application provides a method according to any of the preceding statements wherein said immune cell is a monocyte.

In a related aspect, the present application provides an (isolated) immune cell or immune cell population having a signature as defined in any of Tables 1 to 156. In further particular embodiments, the immune cell population is a cDC population characterized by a Cluster-1-like/CD64$^{Hi}$, PD-L1$^{Hi}$ signature In another aspect of the invention, the application provides a pharmaceutical composition comprising the (isolated) immune cell or immune cell population according to an (isolated) immune cell or immune cell population having a signature as defined above and/or the immunomodulant, immunostimulant, or adjuvant as defined in any of the previous statements. In an embodiment, the application provides the (isolated) immune cell or immune cell population or the pharmaceutical composition for use in therapy or prophylaxis. In an embodiment, the application provides an (isolated) immune cell or immune cell population or the pharmaceutical composition for use in treating or preventing infection, cancer, autoimmune disease, or allergy. In an embodiment, the application provides an (isolated) immune cell or immune cell population or the pharmaceutical composition for use in treating or preventing viral infection, preferably HIV. In an embodiment, the application provides a method for treating or preventing a pathological condition comprising administering to a subject in need thereof the (isolated) immune cell or immune cell population or the pharmaceutical composition. In an embodiment, the application provides a method wherein said pathological condition is selected from infection, cancer, autoimmune disease, or allergy. In an embodiment of the method said pathological condition is viral infection, preferably HIV.

In an embodiment, the application provides an immune cell, pharmaceutical composition, or method according to any of the preceding statements wherein said immune cell is selected from leukocytes or antigen presenting cells.

In an embodiment, the application provides an immune cell, pharmaceutical composition, or method according to any of the preceding statements wherein said immune cell is a B-cell.

In an embodiment of the immune cell, pharmaceutical composition, or method according to any of the preceding statements, said immune cell is a T-cell.

In an embodiment of the immune cell, pharmaceutical composition, or method according to any of the preceding statements said immune cell is a dendritic cell.

In an embodiment of the immune cell, pharmaceutical composition, or method according to any of the preceding statements said immune cell is a monocyte.

In a related aspect, the application provides a vaccine comprising the immune cell or pharmaceutical composition according to any of the preceding statements.

In a related aspect, the present application provides a vaccine comprising an immunomodulatory according to any of the previous statements. In an embodiment, the vaccine is characterized in that said immunomodulatory is capable of inducing or repressing a specific immune responder phenotype. In an embodiment, the vaccine further comprises an antigen. In an embodiment, the vaccine is characterized in that said antigen is an allergen, autoimmune antigen, tumor antigen, or pathogen antigen. In an embodiment, the vaccine is characterized in that said antigen is a viral antigen, preferably an HIV antigen.

In an aspect of the invention, the application provides the use of a gene signature, immune responder phenotype, immunomodulator, immune cell or immune cell (sub)population as defined in any of the previous statements for diagnosis or for determining the immune status.

In an aspect of the invention, the application provides the use of a gene signature, immune responder phenotype, immunomodulator, immune cell or immune cell (sub)population as defined in any of the previous statements in therapy.

In an aspect of the invention, the application provides the use of a gene signature, immune responder phenotype, immunomodulator, immune cell or immune cell (sub)population as defined in any of the previous statements for prognosis.

In an aspect of the invention, the application provides the use of a gene signature, immune responder phenotype, immunomodulator, immune cell or immune cell (sub)population as defined in any of the previous statements for monitoring treatment progression or efficiency.

In a related aspect, the present application provides a method for treating or preventing a pathological condition by inducing Vex-B DC phenotype in cDC of said patient.

In particular embodiments of these methods said patient is an immunocompromised patient.

In a related aspect, the application provides a method of inducing a population of $CD64^{HI}$, PD-$L1^{HI}$ dendritic cells (DCs) for treating HIV infection or suppressing HIV replication, comprising contacting PBMCs with an agent that activates one or more of the following pathways: TLR, IFNG, TLR3, STAT1, MAVS, and IRF1. In particular embodiments, the agent is a toll-like receptor 3 (TLR3) agonist, such as poly(I:C).

In a related aspect, the application provides a method from providing a population of $CD64^{Hi}$, PD-$L1^{HI}$ dendritic cells (DCs) for treating HIV infection or suppressing HIV replication, comprising contacting PBMCs with an agent that activates one or more of the following pathways: TLR, IFNG, TLR3, STAT1, MAVS, and IRF1, and selecting $CD64^{Hi}$, PD-$L1^{HI}$ cells therefrom.

In a related aspect, the application provides a method of identifying an agent for treating HIV infection or a method of identifying an agent for suppressing HIV replication, which comprises: incubating peripheral blood mononuclear cells (PBMCs) in the presence and in the absence of a test compound, measuring the proportion of cells that are $CD64^{Hi}$, PD-$L1^{HI}$ dendritic cells (DCs) compared to the proportion that are $CD64^{Lo}$, PD-$L1^{Lo}$ DCs, in the presence and in the absence of the test compound, and identifying the agent as treating HIV infection or suppressing HIV replication if the proportion of $CD64^{Hi}$, PD-$L1^{Hi}$ DCs is increased in the presence of the test compound.

In particular embodiments, the method comprises comparing expression of one or more of CD274, FCGR1A, FCGR3A, CLEC12A, SLAMF8, and ICAMI in the presence and absence of the test compound and identifying the agent as treating HIV infection or suppressing HIV replication if the level of one or more of CD274, FCGR1A, FCGR3A, CLEC12A, SLAMF8, and ICAMI1 is increased in the presence of the test compound.

In a related aspect, the application provides A method of inducing a population of $CD64^{Hi}$, PD-$L1^{Hi}$ dendritic cells (DCs) for treating HIV infection or suppressing HIV replication (or in a subject in need thereof), which comprises contacting PBMCs with an agent that activates TBK1.

In particular embodiments, of the methods provided above, cells of the population of $CD64^{Hi}$, PD-$L1^{HI}$ dendritic cells comprise one or more of the following markers differentially regulated as compared to conventional dendritic cells (cDCs): TNFSF10, TLR2, CSF1R, CD274 (PD-L1), TLR4, ENG, FCGR1A (CD64), SLC3A2, TNFRSF1A, CD4, CD63, SLAMF7, FCGR3A, ANPEP, ITGAX, CD68, ICAMI, PLAUR, C5AR1, SIGLEC9, LILRB3, LILRA6, LILRB2, LILRB1, LILRB4, SIRPB1, SIGLEC1, TLR8, LILRA3, CCR1, and CCR5.

In particular embodiments, cells of the population of $CD64^{Hi}$, PD-$L1^{HI}$ dendritic cells comprise one or more of the following markers upregulated as compared to conventional dendritic cells (cDCs): CD83, LAMP3, CD63, CD86, and CST7.

In particular embodiments, cells of the population of $CD64^{Hi}$, PD-$L1^{HI}$ dendritic cells, comprise one or more of the following markers upregulated as compared to cDCs: TNFSF10, CD274 (PD-L1), TLR2, TLR4, FCGR1A (CD64), TNFRSF1A, CD63, SLAMF7, FCGR3A, ITGAX, CD68, ICAM1, PLAUR, C5AR1, SIGLEC9, LILRB3, LILRA6, LILRB2, LILRB1, LILRB1, SIRPB1, SIGLEC1, TLR8, LILRA3, CCR1, and CCR5.

In particular embodiments, cells of the population of $CD64^{Hi}$, PD-$L1^{HI}$ dendritic cells, comprise one or more of the following markers upregulated as compared to cDCs: CD274, FCGR1A, FCGR3A, CLEC12A, SLAMF8, and ICAM1.

In particular embodiments, cells of the population of $CD64^{Hi}$, PD-$L1^{HI}$ dendritic cells comprise one or more of the following markers downregulated as compared to cDCs: CSF1R, SLC3A2, CD4, ANPEP.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1A:
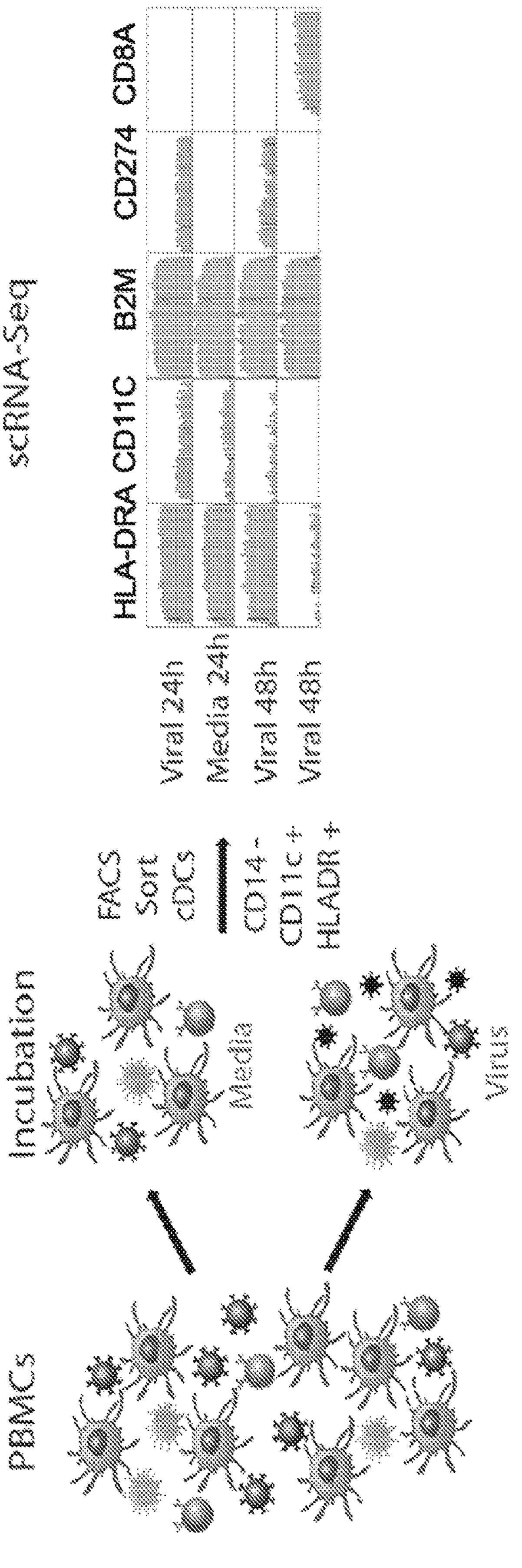
FIGS. 1A-1E illustrate a schematic of the experimental design. (1A) PBMCs are incubated in media alone or media and pseudo-typed human immunodeficiency virus for 24 or 48 hours. Single cells are isolated by FACS and immediately lysed. scRNA-Seq was performed on the single cell lysates. (1B) Weighted PCA plot of FACS sorted cells, 24 and 48 hours. Media cells are plotted in grey. Viral exposed cells (VEx) separate into three clusters, two distinct (A, purple; B, blue) and one akin to the media control (C, yellow). With the exception of late-emerging VExA, these populations are conserved from 24 to 48 hours. (1C) Hierarchical clustering and genes-by-cells heatmap of top loading factors associated with PC1 and PC2 from the wPCA shown in B. Two clusters, Vex-A and Vex-B, have disjoint sets of active genes. (1D and 1E) Differential expression analysis of each VEx subset vs. the media control. Barplot depicts the negative log base ten of enrichment P-values for significantly up- (green) or down- (red) regulated gene sets.
Figure 1B:
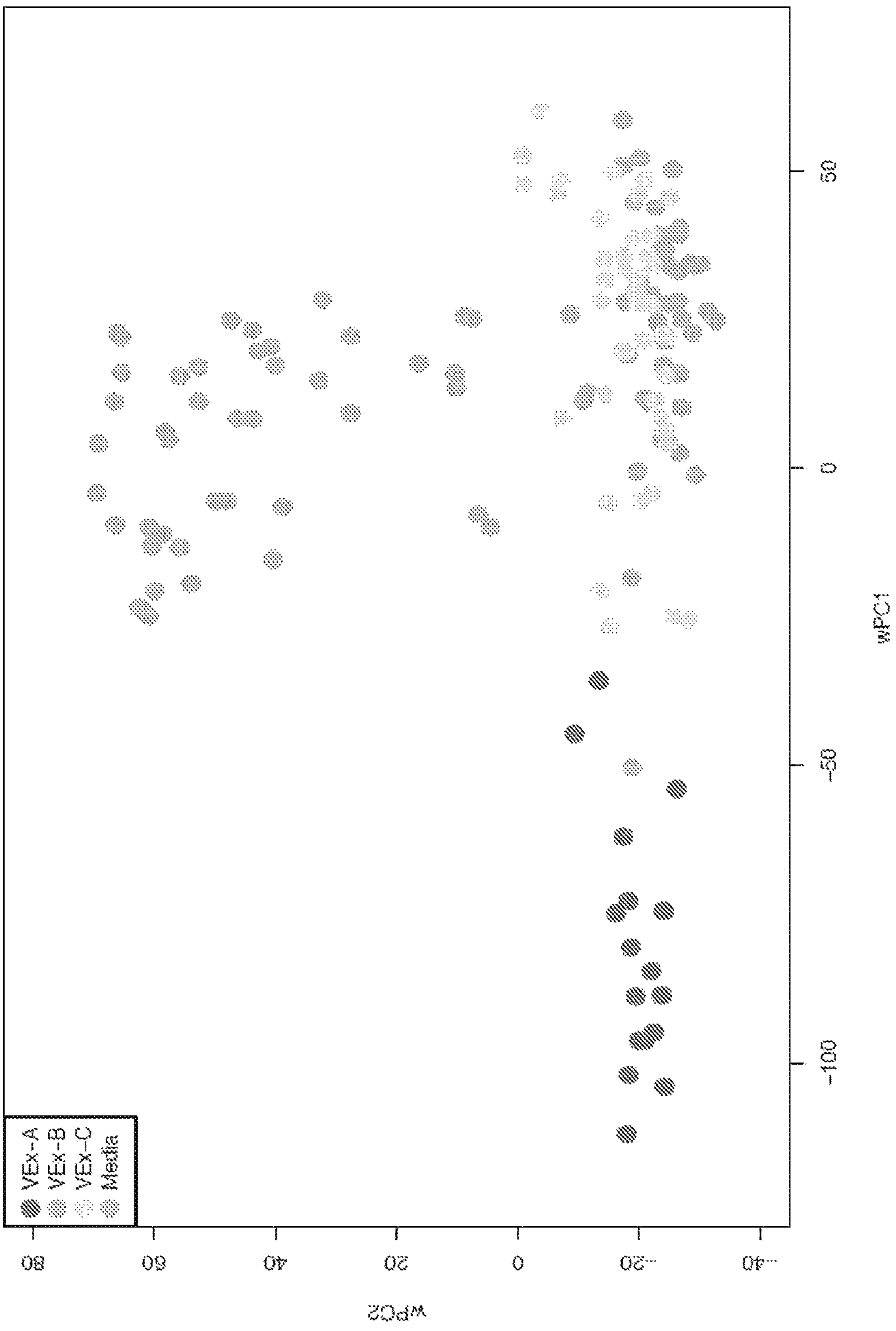
Figure 1C:
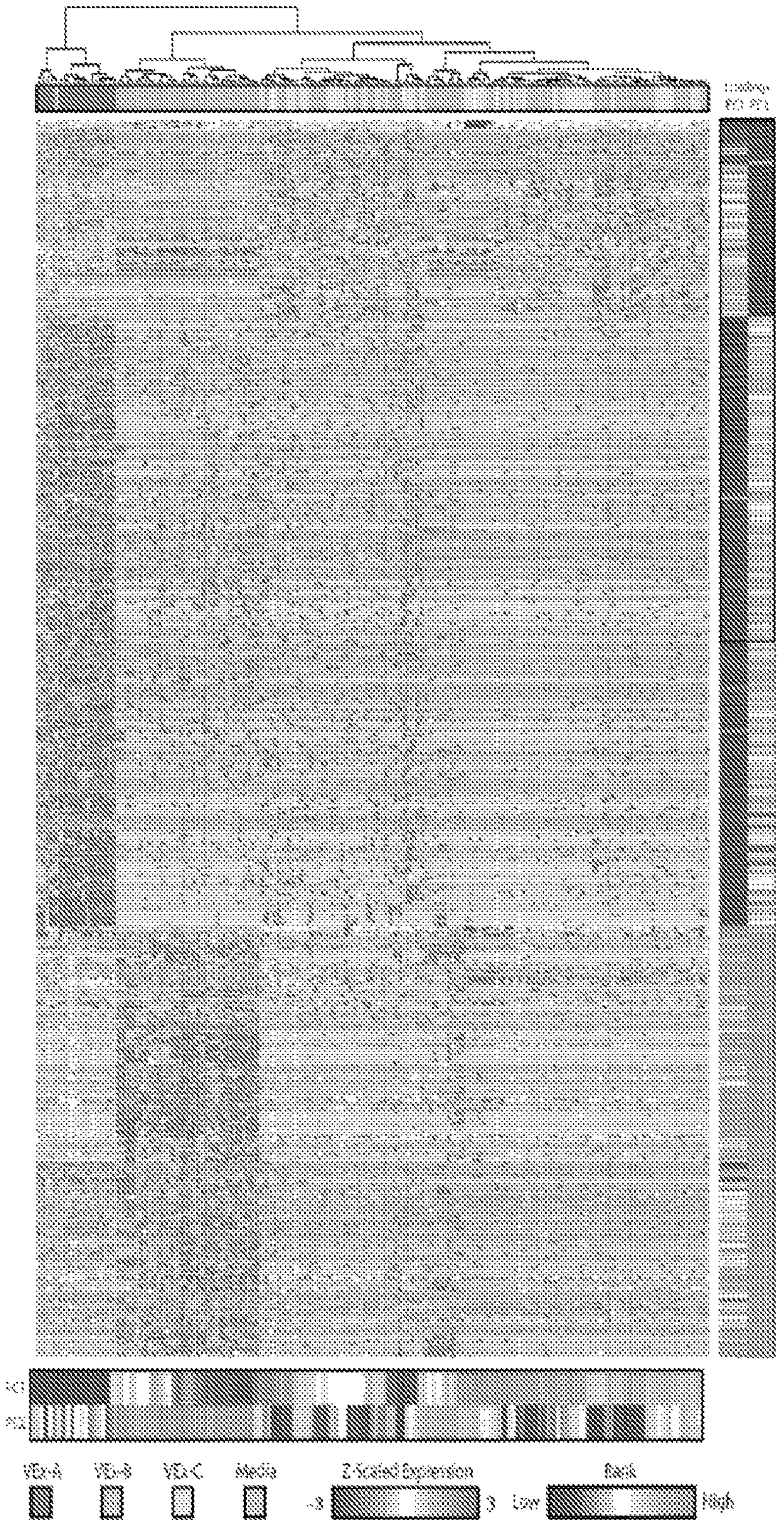
Figure 1D:
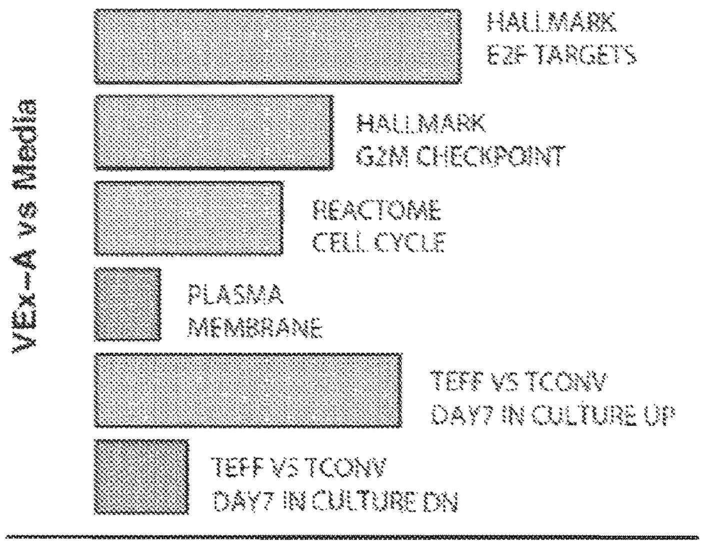
Figure 1E:
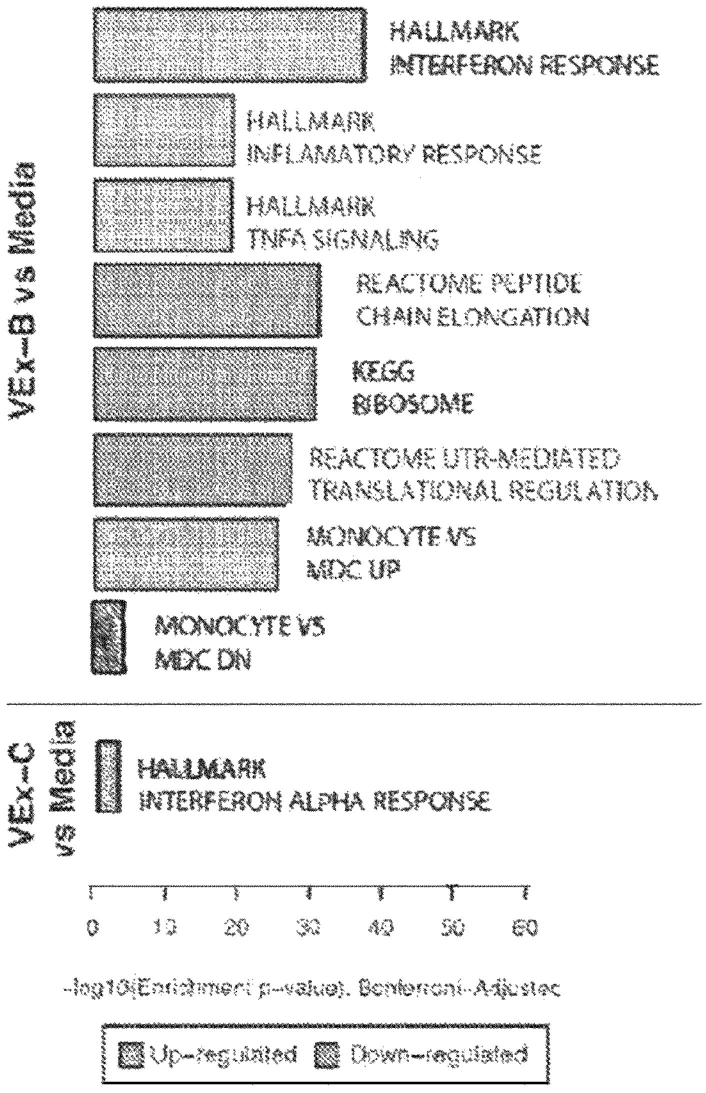

It is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims. Preferred features and embodiments of this invention are set forth herein, including by way of numbered statements. Each feature and embodiment of the invention so discussed herein may be combined with any other feature and/or embodiments unless clearly indicated to the contrary. In particular, any feature indicated as being preferred or advantageous may be combined with any other feature or features indicated as being preferred or advantageous. Aspects of the present invention include any one or any combination of one or more of the aspects, features or embodiments discussed herein, including as enumerated herein 1 to 74, with any other statement and/or embodiments. The present invention is discussed with respect to particular embodiments but the invention is not limited thereto but only by the claims. Any reference signs in the claims shall not be construed as limiting the scope. As also discussed herein, the term "comprising" does not exclude other elements or steps. The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of". "Consisting essentially of" permits inclusion of additional components not listed, provided that they do not materially affect the basic and novel properties of the invention. Singular terms, e.g., "a", "an", and "the" include both singular and plural referents unless the context clearly dictates otherwise. The recitation of numerical ranges by endpoints includes all numbers and fractions subsumed within the respective ranges, as well as the recited endpoints. The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed. Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. All references cited in the present specification are hereby incorporated by reference in their entirety. In particular, the teachings of all references herein specifically referred To are incorporated by reference. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination. Any drawings herewith form a part of this specification, and are provided as a way of illustration only of specific embodiments in which the invention may be practiced; but, it is to be understood that other embodiments may be utilized and structural or logical changes may be made without departing from the scope of the present invention. Accordingly, the herein detailed description is not to be taken in a limiting sense, and the scope of the present invention is defined by the appended claims.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainview, New York (1989); and Ausubel et al., Current Protocols in Molecular Biology (Supplement 47), John Wiley & Sons, New York (1999), Innis et al., PCR Protocols: A Guide to Methods and Applications, Academic Press: San Diego, 1990. General principles of microbiology are set forth, for example, in Davis, B. D. et al., Microbiology, 3rd edition, Harper & Row, publishers, Philadelphia, Pa. (1980), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein. Accordingly, the invention can be practiced without undue experimentation by way of the herein disclosure taken in conjunction with knowledge in the art.

The present invention provides tools and methods for the systematic analysis of genetic interactions in immune cells, in particular immune cell subpopulations, including higher order interactions.

The present invention provides tools and methods for combinatorial probing of cellular circuits, for dissecting cellular circuitry, for delineating molecular pathways, and/or for identifying relevant targets for therapeutics development.

The present invention in certain embodiments relates to analyzing genetic signatures of immune cells, such as molecular profiling at the single cell or cell (sub)population level, which immune cells are characterized by or characteristic of a particular immune responder phenotype. In an aspect, the invention relates to a method of identifying an immune cell gene signature, protein signature, and/or other genetic or epigenetic signature associated with a specific immune responder phenotype or an immune cell subpopulation associated with a specific immune responder phenotype, comprising: comparing single cell or cell population RNA and/or protein expression profiles and/or other genetic or epigenetic profiles of a biological sample of said specific immune responder phenotype with single cell or cell population RNA and/or protein expression profiles and/or other genetic or epigenetic profiles of a biological sample of a different immune responder phenotype or a different an immune cell subpopulation associated with said specific immune responder phenotype; determining differentially expressed RNAs and/or proteins and/or other genetic or epigenetic elements; determining an immune cell gene signature, protein signature, and/or other genetic or epigenetic signature associated with a specific immune responder phenotype or an immune cell subpopulation associated with a specific immune responder phenotype as one or more of said differentially expressed RNAs and/or proteins and/or other genetic or epigenetic elements.

Such method also in particular allows to identify particular immune cell subpopulations which are specifically associated with a particular immune responder phenotype, as well as to identify a particular immune responder phenotype, based on detection of such gene signatures, protein signature, and/or other genetic or epigenetic signature.

All methods according to various aspect and embodiments of the invention may involve analyzing gene signatures, protein signature, and/or other genetic or epigenetic signature or (immune cell) phenotypes based on single cell analyses or alternatively based on cell population analyses.

In related aspects, the invention relates to gene signatures, protein signature, and/or other genetic or epigenetic signature of immune cells associated with particular immune responder phenotypes, such as for instance particular immune cell subpopulations. The invention further relates to particular immune cell subpopulations, which may be identified based on the methods according to the invention as discussed herein; as well as methods to obtain such cell (sub)populations and screening methods to identify immunomodulators capable of inducing or suppressing particular immune cell (sub)populations, such as for instance to alter immune cell population composition. Methods as described herein allow for instance in certain aspects the specific (partial) induction or (partial) depletion of particular immune cell subpopulation, such as to alter for instance an immune responder phenotype, which may in certain embodiments be defined by particular immune cell (sub) population compositions (e.g. different immune cell subpopulations characterized by specific immune cell states).

The invention further relates to various uses of the gene signatures, protein signature, and/or other genetic or epigenetic signature as defined herein, as well as various uses of the immune cells or immune cell (sub)populations as defined herein. Particular advantageous uses include methods for identifying immunomodulators based on the gene signatures, protein signature, and/or other genetic or epigenetic signature as defined herein. In an aspect, the invention hereto provides for a method of identifying an immunomodulant capable of modulating, such as inducing or alternatively suppressing, a specific immune responder phenotype or a specific subpopulation of immune cells associated with a particular immune responder phenotype, and having a specific gene signature, protein signature, and/or other genetic or epigenetic signature, comprising: applying a candidate immunomodulant to an immune cell or a population of immune cells and identifying an immunomodulant capable of inducing or alternatively suppressing a specific immune responder phenotype if said specific gene signature, protein signature, and/or other genetic or epigenetic signature is induced or alternatively repressed in one or more of said immune cells. The invention further relates to immunomodulators capable of modulating, such as inducing or repressing, a particular immune responder phenotype or a specific gene signature, protein signature, and/or other genetic or epigenetic signature, as well as their use for modulating, such as inducing or repressing, a particular immune responder phenotype, or a particular gene signature, protein signature, and/or other genetic or epigenetic signature. Such modulation may include for instance specific induction or alternatively specific reduction of particular immune cells, or immune cell (sub)populations.

In further related aspects, the invention relates to diagnostic (including monitoring the immune status of a subject), prognostic (including monitoring treatment efficacy), prophylactic, or therapeutic methods. Diagnostic or prognostic methods according to the invention in particular may comprise detecting the gene signatures, protein signature, and/or other genetic or epigenetic signature as discussed herein. Therapeutic or prophylactic methods according to the invention in particular may comprise modulating the immune responder phenotype, and may include modulating the gene signature, protein signature, and/or other genetic or epigenetic signature of immune cells or immune cell (sub) populations. Such methods include both in vitro as well as in vivo modulation.

As used herein, the term “gene signature” may be used interchangeably with the term “signature gene”. These terms relate to one or more gene (or one or more particular splice variants thereof), the (increased) expression or activity of which or alternatively the decreased or absence of expression or activity of which is characteristic for a particular (multi)cellular phenotype, i.e. the occurrence of such particular (multi)cellular phenotype may be identified based on the presence or absence of such gene signature. The signature may thus be characteristic of a particular phenotype, but may also be characteristic of a particular immune cell subpopulation within a particular phenotype. Similarly, an "epigenetic signature" relates to one or more epigenetic element (or modification), the (increased) occurrence of which or alternatively the absence of which is characteristic for a particular (multi)cellular phenotype, i.e. the occurrence of such particular (multi)cellular phenotype may be identified based on the presence or absence of such epigenetic signature. As used herein a signature encompasses any gene or genes or epigenetic element(s) whose expression profile or whose occurrence is associated with a specific cell type, subtype, or cell state of a specific cell type or subtype within a population of cells. Increased or decreased expression or activity or prevalence may be compared between different phenotypes in order to characterize or identify specific phenotypes. A gene signature as used herein, may thus refer to any set of up- and down-regulated genes between two (multi)cellular states or phenotypes derived from a gene-expression profile. For example, a gene signature may comprise a list of genes differentially expressed in a distinction of interest; (e.g., high responders versus low responders; diseased state versus normal state; etc.). Similarly, an epigenetic signature as used herein, may thus refer to any set of induced or repressed epigenetic elements between two (multi)cellular states or phenotypes derived from an epigenetic profile. For example, an epigenetic signature may comprise a list of epigenetic elements differentially present in a distinction of interest; (e.g., high responders versus low responders; diseased state versus normal state; etc.). It is to be understood that also when referring to proteins (e.g. differentially expressed proteins), such may fall within the definition of "gene" signature, and may on certain occasions be referred to as "protein signature".

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. blood samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context (e.g. infection, cancer, autoimmune disease, allergy). Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states that occur in a subpopulation of immunological cells that are linked to particular pathological condition, or linked to a particular outcome or progression of a pathological condition, or linked to a particular response to treatment of a pathological condition.

The signature according to certain embodiments of the present invention may comprise or consist of one or more genes, proteins and/or epigenetic elements, such as for instance 1, 2, 3, 4, 5, 6, 7, 8, 9, 10 or more. It is to be understood that a signature according to the invention may for instance also include genes or proteins as well as epigenetic elements combined.

In certain embodiments, a signature is characterized as being specific for a particular immune responder phenotype or specific for a particular immune cell or immune cell (sub)population if it is only present, detected or detectable in that particular immune responder phenotype or specific for a particular immune cell or immune cell (sub)population. In this context, a signature consists of one or more differentially expressed genes/proteins or differential epigenetic elements when comparing different immune responder phenotypes or different immune cells or immune cell (sub) populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of immune cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

In one embodiment, the signatures are detected by immunofluorescence, by mass cytometry (CyTOF), FACS, ATAC-seq, in situ hybridization, etc. Other methods including absorbance assays and colorimetric assays are known in the art and may be used herein.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

Signatures may be functionally validated as being uniquely associated with a particular immune responder phenotype. Induction or suppression of a particular signature may consequentially associated with or causally drive a particular immune responder phenotype.

As used herein, the term "immune responder phenotype" may be used interchangeably with "immune response phenotype". These terms refer to an individual characterized by a specific immune response towards a pathological insult, or by a particular immunological state. By extension, these terms also refer to organs, tissues, cells, or cell (sub) populations of such individuals, including immune cells. By means of example, a specific immune response may constitute an improved or vigorous immune response or alternatively a poor immune response; a fast immune response or alternatively a slow immune response; an immune response characterized by for instance a specific cytokine profile or a specific sequence of succession of cytokine expression; etc. without limitation, for instance in the context of viral infection, such as for instance HIV infection, the immune responder phenotype may be an elite controller. Elite controller is a term applied to the rare group of HIV-positive individuals who maintain substantially undetectable viral loads in the absence of any treatment. Although genetic variability in the HLA locus and enhanced CD8 T cell immunity have been proposed to be some of the causes of the spontaneous immunological control of HIV-1 in this cohort, cellular and molecular mechanisms responsible for the elite controller phenotype are not fully understood. An elite controller may for instance be defined as having consecutive undetectable HIV-RNA measurements for more than six months or otherwise with at least 90% of measurements having less than 400 copies/ml over at least 10 years. Other immune responder phenotypes for instance include long term non progressors (LTNP), slow progressors, HIV controllers (HICs), viremic controllers, noncontrollers, and rapid progressors. A progressive controller has roughly about 100 copies of HIV while a viremic controller has full blown AIDS and declining health. Without wishing to be bound by any one particular theory, it is believed that someone who is a viremic controller was formerly an elite or progressive controller. The present invention thus relates to examining signatures for an elite controller, a progressive controller and a viremic individual. For a viremic controller and potentially a progressive controller, in certain embodiments it is desirable to modify the signatures of that individual by modulating, such as perturbing the system such that the signature resembles that of an elite controller. Other immune responder phenotypes for instance include phenotypes based on neutralizing antibody breadth, such as a phenotype characterized by broadly neutralizing antibodies. Broadly neutralizing antibodies are neutralizing antibodies (Nab), which are antibodies which defend a cell from an antigen or infectious body by inhibiting or neutralizing any effect it has biologically. Broadly neutralizing antibodies are neutralizing antibodies which for instance are capable of neutralizing multiple disease strains, such as multiple HIV strains.

An "immune cell" as used herein refers to any cell of the immune system, as well as includes antigen presenting cells or accessory cells, both of the innate or adaptive immune system. The immune cell as referred to herein may be a leukocyte, at any stage of differentiation or any activation stage. Immune cells include lymphocytes such as natural killer cells, T-cells (including e.g. thymocytes, Th or Tc; Th1, Th2, Th17, Thαβ, $CD4^+$, $CD8^+$, effector Th, memory Th, regulatory Th, CD4+/CD8+ thymocytes, CD4−/CD8− thymocytes, γδ T cells, etc) or B-cells (including e.g. pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including e.g. classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including e.g. Kupffer cells, stellate macrophages, M1 or M2 macrophages), (myeloid or lymphoid) dendritic cells (including e.g. Langerhans cells, conventional or myeloid dendritic cells, plasmacytoid dendritic cells, mDC-1, mDC-2, Mo-DC, HP-DC, veiled cells), granulocytes, polymorphonuclear cells, etc. In certain embodiments, the immune cell is a dendritic cells, B-cell, or monocyte (e.g. at any stage of differentiation or any activation stage).

In certain embodiments, the immune responder phenotype is characteristic of, associated with, or correlated with a particular (immune) response to a pathological condition.

A "pathological condition" as referred to herein includes any physiologically abnormal condition of an organism, which results in damage of or harm to the organism. A pathological condition as referred to herein is in particular associated with or causally related to an immunological response of the host organism, such as for instance an enhanced or improved immunological response or alternatively a decreased or reduced immunological response. The type of immunological response of an individual to a pathological condition may characterize the immune responder phenotype. The immunological response may be compared between individuals each of which being afflicted with the pathological condition, thereby allowing differentiation between or identification of different immune responder phenotypes, or alternatively may be compared between individuals afflicted with the pathological condition and individuals not afflicted with the pathological condition.

In certain embodiments, the pathological condition as referred to herein is an infection, autoimmune disease, allergy, or cancer. It is to be understood, that in aspects and embodiments wherein reference is made to prophylaxis, such means that the pathological condition referred to is to be prevented, such as for instance the prevention of infection, autoimmune disease, allergy, or cancer. More general, the pathological condition as referred to herein may include any pathological condition in which the immune system is involved and/or the immune system reacts abnormally or inappropriately, and may for instance also include graft versus host disease.

In certain embodiments, infection is due to bacteria, virus, protozoa, parasite, or fungus.

In certain embodiments, infection is a bacterial infection. In certain embodiments, the bacterial infection is infection due to *Bacillus* sp. (e.g. *Bacillus anthracis, Bacillus cereus*), *Bartonella* sp. (e.g. *Bartonella henselae, Bartonella quintana*), *Bordetella* sp. (e.g. *Bordetella pertussis*), *Borrelia* sp. (e.g. *Borrelia burgdorferi, Borrelia garinii, Borrelia afzelii, Borrelia recurrentis*), *Brucella* sp. (e.g. *Brucella abortus,*

*Brucella canis, Brucella melitensis, Brucella suis*), *Campylobacter* sp. (e.g. *Campylobacter jejuni*), , *Chlamydia* sp. (e.g. *Chlamydia pneumoniae, Chlamydia trachomatis*), , *Chlamydophila* sp. (e.g. *Chlamydophila psittaci*), *Clostridium* sp. (e.g. *Clostridium botulinum, Clostridium difficile, Clostridium perfringens, Clostridium tetani*), *Corynebacterium* sp. (e.g. *Corynebacterium diphtheria*), *Enterococcus* sp. (e.g. *Enterococcus faecalis, Enterococcus faecium*), *Escherichia* sp. (e.g. *Escherichia coli*), *Francisella* sp. (e.g. *Francisella tularensis*), *Haemophilus* sp. (e.g. *Haemophilus influenzae*), *Helicobacter* sp. (e.g. *Helicobacter pylori*), *Legionella* sp. (e.g. *Legionella pneumophila*), Leptospira sp. (e.g. *Leptospira interrogans, Leptospira santarosai, Leptospira weilii, Leptospira noguchii*), *Listeria* sp. (e.g. *Listeria monocytogenes*), *Mycobacterium* sp. (e.g. *Mycobacterium leprae, Mycobacterium tuberculosis, Mycobacterium ulcerans*), *Mycoplasma* sp. (e.g. *Mycoplasma pneumoniae*), *Neisseria* sp. (e.g. *Neisseria gonorrhoeae, Neisseria meningitides*), *Pseudomonas* sp. (e.g. *Pseudomonas aeruginosa*), *Rickettsia* sp. (e.g. *Rickettsia rickettsia*), *Salmonella* sp. (e.g. *Salmonella typhi, Salmonella typhimurium*), *Shigella* sp. (e.g. *Shigella sonnei*), *Staphylococcus* sp. (e.g. *Staphylococcus aureus, Staphylococcus epidermidis, Staphylococcus saprophyticus*), *Streptococcus* sp. (e.g. *Streptococcus agalactiae, Streptococcus pneumoniae, Streptococcus pyogenes*), *Treponema* sp. (e.g. *Treponema pallidum*), *Ureaplasma* sp. (e.g. *Ureaplasma urealyticum*), *Vibrio* sp. (e.g. *Vibrio cholerae*), or *Yersinia* sp. (e.g. *Yersinia pestis, Yersinia enterocolitica, Yersinia pseudotuberculosis*).

In certain embodiments, infection is a viral infection. In certain embodiments, the viral infection is infection due to Adenoviridae (e.g. Adenovirus), Herpesviridae (e.g. Herpes simplex, type 1, Herpes simplex, type 2, Varicella-zoster virus, Epstein-barr virus, Human cytomegalovirus, Human herpesvirus, type 8), Papillomaviridae (e.g. Human papillomavirus), Polyomaviridae (e.g. BK virus, JC virus), Poxviridae (e.g. Smallpox), Hepadnaviridae (e.g. Hepatitis B virus), Parvoviridae (e.g. Parvovirus B19), Astroviridae (e.g. Human astrovirus), Caliciviridae (e.g. Norwalk virus), Picornaviridae (e.g. coxsackievirus, hepatitis A virus, poliovirus, rhinovirus), Coronaviridae (e.g. Severe acute respiratory syndrome virus), Flaviviridae (e.g. Hepatitis C virus, yellow fever virus, dengue virus, West Nile virus, TBE virus), Togaviridae (e.g. Rubella virus), Hepeviridae (e.g. Hepatitis E virus), Retroviridae (e.g. Human immunodeficiency virus (HIV)), Orthomyxoviridae (e.g. Influenza virus), Arenaviridae (e.g. Lassa virus), Bunyaviridae (e.g. Crimean-Congo hemorrhagic fever virus, Hantaan virus), Filoviridae (e.g. Ebola virus, Marburg virus), Paramyxoviridae (e.g. Measles virus, Mumps virus, Parainfluenza virus, Respiratory syncytial virus), Rhabdoviridae (e.g. Rabies virus), Hepatitis D, or Reoviridae (e.g. Rotavirus, Orbivirus, Coltivirus, Banna virus).

In certain embodiments, infection is a protozoal or parasitic infection. In certain embodiments, the protozoan or parasitic infection is infection due to Euglenozoa (e.g. *Trypanosoma cruzi, Trypanosoma brucei, Leishmania* spp.), Heterolobosea (e.g. *Naegleria fowleri*), Diplomonadida (e.g. *Giardia intestinalis*), Amoebozoa (e.g. *Acanthamoeba castellanii, Balamuthia mandrillaris, Entamoeba histolytica*), *Blastocystis* (e.g. *Blastocystis hominis*), Apicomplexa (e.g. *Babesia microti, Cryptosporidium parvum, Cyclospora cayetanensis, Plasmodium* spp., *Toxoplasma gondii*), Roundworm infection (nematodiasis) (e.g. Filariasis (*Wuchereria bancrofti, Brugia malayi* infection), Onchocerciasis (*Onchocerca volvulus* infection), Soil-transmitted helminthiasis including ascariasis (*Ascaris lumbricoides* infection, trichuriasis (*Trichuris* infection), and hookworm infection (includes *Necatoriasis* and *Ancylostoma duodenale* infection), Trichostrongyliasis (*Trichostrongylus* spp. infection), Dracunculiasis (guinea worm infection)); Tapeworm infection (cestodiasis) (e.g. Echinococcosis (*Echinococcus* infection), Hymenolepiasis (*Hymenolepis* infection), Taeniasis/cysticercosis (*Taenia* infection), Coenurosis (*T. multiceps, T. serialis, T. glomerata* and *T. brauni* infection)); Trematode infection (trematodiasis) (e.g. Amphistomiasis (amphistomes infection), Clonorchiasis (*Clonorchis sinensis* infection), Fascioliasis (*Fasciola* infection), Fasciolopsiasis (*Fasciolopsis buski* infection), Opisthorchiasis (*Opisthorchis* infection), Paragonimiasis (*Paragonimus* infection), Schistosomiasis/bilharziasis (*Schistosoma* infection)); and Acanthocephala infection (e.g. *Moniliformis* infection).

In certain embodiments, infection is a fungal infection. In certain embodiments, the fungal infection is infection due to *Candida* species, such as *C. albicans; Cryptococcus* species, such as *C. neoformans, C. gattii; Aspergillus* species, such as *A. fumigatus* and *A. flavus; Pneumocystis* species, such as *P. carinii; Coccidioides* species such as *C. immitis; Trichophyton* species such as *T. verrucosum; Blastomyces* species such as *B. dermatitidis; Histoplasma* species such as *H. capsulatum; Paracoccidioides* species such as *P. brasiliensis; Mucoromycotina* sp.; *Sporothrix* sp, such as *S. schenckii*; and *Pythium* species such as *P. insidiosum.*

In certain embodiments autoimmune diseases are selected from Myocarditis, Postmyocardial infarction syndrome, Postpericardiotomy syndrome, Subacute bacterial endocarditis, Anti-Glomerular Basement Membrane nephritis, Interstitial cystitis, Lupus nephritis, Autoimmune hepatitis, Primary biliary cirrhosis, Primary sclerosing cholangitis, Antisynthetase syndrome, Alopecia Areata, Autoimmune Angioedema, Autoimmune progesterone dermatitis, Autoimmune urticaria, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, *Pityriasis lichenoides* et varioliformis acuta, Mucha-Habermann disease, Psoriasis, Systemic scleroderma, Vitiligo, Addison's disease, Autoimmune polyendocrine syndrome, Autoimmune polyendocrine syndrome type 2, Autoimmune polyendocrine syndrome type 3, Autoimmune pancreatitis, Diabetes mellitus type 1, Autoimmune thyroiditis, Ord's thyroiditis, Graves' disease, Autoimmune Oophoritis, Endometriosis, Autoimmune orchitis, Sjogren's syndrome, Autoimmune enteropathy, Celiac disease, Crohn's disease, Microscopic colitis, Ulcerative colitis, Antiphospholipid syndrome, Aplastic anemia, Autoimmune hemolytic anemia, Autoimmune lymphoproliferative syndrome, Autoimmune neutropenia, Autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, Thrombocytopenia, Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, Undifferentiated connective tissue disease, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis, Acute motor axonal neuropathy, Anti-N-Methyl-D-Aspartate Receptor Encephalitis, Balo concentric sclerosis, Bickerstaffs encephalitis, Chronic inflammatory demyelinating polyneuropathy, Guillain-Barre syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with *Streptococcus*, Progressive inflammatory neuropathy, Restless leg syndrome, Stiff person syndrome, Sydenham chorea, Transverse myelitis, Autoimmune retinopathy, Autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, Autoimmune inner ear disease, Meniere's disease, Anti-neutrophil cytoplasmic antibody-associated vasculitis, Behget's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, Polyarteritis nodosa, Polymyalgia rheumatica, Urticarial vasculitis, and Vasculitis.

In certain embodiments allergic diseases are selected from allergic rhinitis, drug allergy, latex allergy, insect sting/bite allergy, urticarial, contact dermatitis, allergic conjunctivitis, hay fever, food allergies, atopic dermatitis, allergic asthma, and anaphylaxis.

In certain embodiments cancer is selected from carcinoma, sarcoma, lymphoma, leukemia, germ cell tumors, blastoma. In certain embodiments cancer is selected from Acute lymphoblastic leukemia (ALL); Acute myeloid leukemia; Adrenocortical carcinoma; AIDS-related cancers; AIDS-related lymphoma; Anal cancer; Appendix cancer; Astrocytoma, childhood cerebellar or cerebral; Basal-cell carcinoma; Bile duct cancer, extrahepatic (see cholangiocarcinoma); Bladder cancer; Bone tumor, osteosarcoma/malignant fibrous histiocytoma; Brainstem glioma; Brain cancer; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt's lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/malignant glioma, childhood; Cervical cancer; Childhood cancers; Chondrosarcoma; Chronic lymphocytic leukemia; Chronic myelogenous leukemia; Chronic myeloproliferative disorders; Colon cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, childhood; Extragonadal germ cell tumor; Extrahepatic bile duct cancer; Eye cancer, intraocular melanoma; Eye cancer, retinoblastoma; Gallbladder cancer; Gastric (stomach) cancer; Gastrointestinal carcinoid tumor; Gastrointestinal stromal tumor (GIST); Germ cell tumor: extracranial, extragonadal, or ovarian; Gestational trophoblastic tumor; Glioma of the brain stem; Glioma, childhood cerebral astrocytoma; Glioma, childhood visual pathway and hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular melanoma; Islet cell carcinoma (endocrine pancreas); Kaposi sarcoma; Kidney cancer (renal cell cancer); Laryngeal cancer; Leukaemias; Leukaemia, acute lymphoblastic (also called acute lymphocytic leukaemia); Leukaemia, acute myeloid (also called acute myelogenous leukemia); Leukaemia, chronic lymphocytic (also called chronic lymphocytic leukemia); Leukemia, chronic myelogenous (also called chronic myeloid leukemia); Leukemia, hairy cell; Lip and oral cavity cancer; Liposarcoma; Liver cancer (primary); Lung cancer, non-small cell; Lung cancer, small cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, primary central nervous system; Macroglobulinemia, Waldenstrom; Male breast cancer; Malignant fibrous histiocytoma of bone/osteosarcoma; Medulloblastoma, childhood; Melanoma; Melanoma, intraocular (eye); Merkel cell cancer; Mesothelioma, adult malignant; Mesothelioma, childhood; Metastatic squamous neck cancer with occult primary; Mouth cancer; Multiple endocrine neoplasia syndrome, childhood; Multiple myeloma/plasma cell neoplasm; Mycosis fungoides; Myelodysplastic syndromes; Myelodysplastic/myeloproliferative diseases; Myelogenous leukemia, chronic; Myeloid leukemia, adult acute; Myeloid leukemia, childhood acute; Myeloma, multiple (cancer of the bone-marrow); Myeloproliferative disorders, chronic; Myxoma; Nasal cavity and paranasal sinus cancer; Nasopharyngeal carcinoma; Neuroblastoma; Non-Hodgkin lymphoma; Non-small cell lung cancer; Oligodendroglioma; Oral cancer; Oropharyngeal cancer; Osteosarcoma/malignant fibrous histiocytoma of bone; Ovarian cancer; Ovarian epithelial cancer (surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sezary syndrome; Skin cancer (non-melanoma); Skin cancer (melanoma); Skin carcinoma, Merkel cell; Small cell lung cancer; Small intestine cancer; Soft tissue sarcoma; Squamous cell carcinoma—see skin cancer (non-melanoma); Squamous neck cancer with occult primary, metastatic; Stomach cancer; Supratentorial primitive neuroectodermal tumor, childhood; T-Cell lymphoma, cutaneous—see Mycosis Fungoides and Sezary syndrome; Testicular cancer; Throat cancer; Thymoma, childhood; Thymoma and thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenstrom macroglobulinemia; Wilms tumor (kidney cancer), childhood.

In certain embodiments, the infectious disease is a prion. Prions are infectious pathogens that do not contain nucleic acids. These abnormally folded proteins are found characteristically in some diseases such as scrapie, bovine spongiform encephalopathy (mad cow disease) and Creutzfeldt-Jakob disease.

The immune cells as referred to herein according to the invention originate from an animal, including vertebrate and non-vertebrate animals, preferably vertebrate animals, such as without limitation including mammalians, reptiles, fish, birds, amphibians, preferably mammalians, such as without limitation primates, rodents, carnivores, artiodactyla, lagomorpha, etc. the cells may be human or non-human. The cells may be derived for instance from human, mouse, rat, rabbit.

Biological samples as used in the various methods or compositions as discussed herein preferably comprise immune cells. Such biological samples may for instance comprise lymphoid tissues, such as primary or secondary lymph tissues (e.g. lymph fluid, thymus, lymph nodes, spleen, bone marrow, tonsils, Peyer's patches, mucosa associated lymphoid tissue (MALT), appendix) or blood. Alternatively, the biological sample may be any tissue sample comprising immune cells.

According to certain aspects or embodiments of the invention, differential expression of protein or RNA is performed between samples, which may be differential expression of proteins or RNA based on single cell analyses. Such single cell based analyses may be performed by techniques as discussed herein (e.g. Drop-Seq).

In certain aspects and embodiments, the invention relates to immunomodulants, their use, and methods for identifying immunomodulants, as discussed herein. As used herein, the term immunomodulant may be used interchangeably with immunomodulator. An immunomodulant can basically be any class of agent, in particular biologically active agents, such as including, but not limited to small molecules, drugs, TLR agonists/antagonists, (epi)genetic perturbations, etc. As used herein, an immunomodulant refers preferably to a compound (or combination of compounds) which are capable of altering or affecting the functioning of the immune system, or of particular components of the immune system, such as one or more particular immune cells or cell types. An immunomodulant may alter for instance the cell state or phenotype of particular immune cells or immune cell (sub)populations. An immunomodulant may for instance increase or induce or alternatively decrease or ablate particular immune cells or immune cell (sub)populations, such that the entire immune cell population obtains a different functionality, such as for instance an improved immunological response towards a pathological conditions. Immunomodulants include any potential class of biologically active agent, such as for instance small molecules, drugs, TLR agonists, antagonists, genetic perturbations (e.g. knock-out, knock-down, or other types of (inactivating or otherwise modulating) mutations), etc. Methods for altering signatures, immune responder phenotypes, or immune cells such as immune cell (sub)populations may include contacting particular immune cells (or populations) with immunomodulatns as discussed herein, which may be in vitro or in vivo. If performed in vitro, the so-treated cells may after treatment be administered to an individual in need thereof. In certain embodiments, the immunomodulant may be provided in pharmaceutical compositions, and may for instance be included in a vaccine. Typically, a vaccine further comprises an antigen, wherein said antigen is preferably specific for a particular pathological condition and/or may further comprise immune cells (e.g. antigen presenting cells, optionally primer with antigen).

In certain aspects, the invention relates to the use of the immunomodulators as defined herein for inducing or augmenting a particular immune responder phenotype as defined herein. Such can be obtained and evaluated by inducing or increasing the gene signature associated with such phenotype. In certain aspects, the invention relates to the use of the immunomodulators as defined herein for reducing or depleting a particular immune responder phenotype as defined herein. Such can be obtained and evaluated by decreasing or repressing the gene signature associated with such phenotype. These methods may include increasing/decreasing the amount of cells having a particular gene signature or being associated with a particular immune responder phenotype, such as to shift or alter the relative amount or ration of cells having a particular gene signature or being associated with a particular immune responder phenotype within a total population of cells. Such methods may include altering a gene signature within any or a specific cell (sub)population.

The present invention also relates to compositions, such as pharmaceutical compositions, comprising the immune cells or immune cell (sub)populations as discussed herein and/or the immunomodulators as discussed herein, such as the immune cells or immune cell (sub)populations having particular signature as discussed herein, or the immune cells or immune cell (sub)populations associated with or characteristic of particular immune responder phenotypes as discussed herein. Such composition may for instance be a vaccine in certain embodiments.

As noted elsewhere, pharmaceutical compositions as taught herein comprise one or more pharmaceutically acceptable excipient.

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active substances is well known in the art. Such materials should be non-toxic and should not interfere with the activity of the cells or active components (e.g. immunomodulators).

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions comprising immunomodulators as discussed herein which are to be administered orally or topically will usually not comprise cells, although it may be envisioned for oral compositions to also comprise cells, for example when gastro-intestinal tract indications are treated. Each of the compounds as discussed herein (e.g. immune cells, immunomodulators) may be administered by the same route or may be administered by a different route. By means of example, and without limitation, the cells may be administered parenterally and the immunomodulator may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of its environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants. For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating said support with a liquid suspension containing said cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell populations can be administered in a manner that permits them to survive, grow, propagate and/or differentiate towards desired cell types (e.g. differentiation) or cell states. The cells or cell populations may be grafted to or may migrate to and engraft within the intended organ, such as, e.g., liver. Engraftment of the cells or cell populations in other places, tissues or organs such as liver, spleen, pancreas, kidney capsule, peritoneum or omentum may be envisaged.

In an embodiment the pharmaceutical cell preparation as defined above may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the desired cells and/or immunomodulants. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

In certain embodiments, the invention involves compositions as discussed herein, such as the pharmaceutical compositions as discussed herein.

In an embodiment, the invention relates to a composition as defined herein, such as a pharmaceutical composition, such as for instance a vaccine, comprising an immunomodulant as defined herein, such as an immunomodulant capable of increasing PD-L1 and/or CD63 expression (preferably in dendritic cells, such as cDC), such as for instance a TLR3 ligand, such as for instance poly I:C. In an embodiment, the invention relates to a composition as defined herein, such as a pharmaceutical composition, such as for instance a vaccine, comprising an immunomodulant as defined herein, such as an immunomodulant capable of increasing PD-L1 and/or CD63 expression (preferably in dendritic cells, such as cDC), such as for instance a TLR3 ligand, such as for instance poly I:C, and further comprising a pathogen, such as a virus, such as HIV (e.g. HIV-1), preferably an attenuated pathogen (i.e. a non-virulent pathogen), or a fragment of such pathogen, such as a genomic fragment of such pathogen, such as for instance HIV (e.g. HIV-1) genomic fragment (e.g. Gag (partially) encoding fragment). In an embodiment, the invention relates to a composition as defined herein, such as a pharmaceutical composition, such as for instance a vaccine, comprising an immunomodulant as defined herein, such as an immunomodulant capable of increasing PD-L1 and/or CD63 expression (preferably in dendritic cells, such as cDC), such as for instance a TLR3 ligand, such as for instance poly I:C, further comprising an immune cell, such as a dendritic cell, such as a cDC. In an embodiment, the invention relates to a composition as defined herein, such as a pharmaceutical composition, such as for instance a vaccine, comprising an immunomodulant as defined herein, such as an immunomodulant capable of increasing PD-L1 and/or CD63 expression (preferably in dendritic cells, such as cDC), such as for instance a TLR3 ligand, such as for instance poly I:C, and further comprising a pathogen, such as a virus, such as HIV (e.g. HIV-1), preferably an attenuated pathogen (i.e. a non-virulent pathogen), or a fragment of such pathogen, such as a genomic fragment of such pathogen, such as for instance HIV (e.g. HIV-1) genomic fragment (e.g. Gag (partially) encoding fragment), further comprising an immune cell, such as a dendritic cell, such as a cDC. In certain aspects, the invention relates to such compositions for therapeutic and/or prophylactic use, such as for therapeutic and/or prophylactic HIV (e.g. HIV-1) treatment. In certain aspects, the invention relates to therapeutic and/or prophylactic methods comprising administering such compositions, such as therapeutic and/or prophylactic HIV (e.g. HIV-1) treatment methods.

Tables 1 to 156 provide various signatures which can be used in embodiments according to the invention. One or more, such as 2, 3, 4, 5, 6, 7, 8, 9, 10, or more, or all of the genes/proteins listed in these tables, or alternatively epigenetically regulated expression thereof, may be used as signatures according to various embodiments of the invention. The signatures may comprise differentially expressed genes/proteins (or epigenetically regulated) which are preferably associated with a particular phenotype, particular cell type, or particular cell type population (optionally associated with a particular phenotype), optionally associated with or responsive to a particular pathological condition. Differential expression may be evaluated based on comparison with different phenotypes/cell (sub)types, such as including up- or downregulation. In certain embodiments, a subset of the signatures may be used, such as for instance corresponding to one or more, or including one or more cell surface exposed proteins (e.g. transmembrane proteins, or (extracellular) transmembrane associated proteins), which advantageously may aid for instance in cell sorting of the desired cell (sub)type/phenotype, etc. it will be understood that combinations of particular subsets may be made from the respective Tables of upregulated and downregulated genes (e.g. for a given phenotype or cell (sub)type or population). Accordingly, in certain embodiments, the invention relates to immune cells characterized by these signatures as well as the use of these signatures in the methods according to the invention as described herein. Gene/protein names in Tables 1-156 are as provided in refseq GRCh38.p2 GTF file.

TABLE 1

GZMB4, ZBED2, IL2RA0, TOP2A2, TYMS6, MCM23, MKI679, MTHFD16, GZMH3, FEN18, TMEM106C5, CISH, CDK18, DNAJC92, ZWINT6, PSAT18, TK18, CDCA55, TIGIT, ASF1B5, DTL, POLD12, NUSAP10, GPR1719, ACOT7, CD8B, CCL48, CCL45, NCAPD39, CDCA7, CCNA25, MSH2, RRP123, CENPF, TBL38, TPX24, SH2D1A6, TCF199, PTPN7, PPP5C9, CCL37, CCL36, CCL34, SCCPDH, NDC801, CDC453, NPRL2, DDX411, NCAPG7, SRM, UBE2C5, MCM109, BIRC50, PYCR18, WDHD14, SLC27A24, SLC38A51, RFC40, IPO118, POLA13, PPAT7, IPO46, LMNB21, SLC29A11, TIMELESS2, DHFR7, RAD516, GINS23, SLC7A56, UBE2T, ACD5, BUB1B4, VCAM1, CENPU7, IFNG3, DGCR147, FANCG3, BCAT17, NOC4L5, KIF21A3, RBBP89, TCF195, MAD2L17, CDC63, KIF236, PKMYT10, MRPL177, PWP24, ASUN8, EEF1E15, JAKMIP18, RFC53, RRS12, PAM6, CD3202, SLC1A4, CDC20, GZMA0, XCL2, RUSC1, LRWD17, QTRT17, DCAF128, ESCO28, HENMT1, UTP157, MELK3, CCNE26, MTX1, FBXO54, NDFIP20, EXO1, ZPR12, HMBS4, MRPL461, CCNF2, RRM2, NCAPG20, ICOS, CENPM9, CEP787, SH2D2A, SPAG52, PSMG17, THEMIS3, THEMIS7, CHAF1B9, CDKN35, EMC86, NLE19, CCDC1671, TTK4, POP77, LRR17, RECQL47, HELLS4, ZDHHC131, GMNN7, SAYSD12, CEP85, RAD54L, XCL1, TEX301, MANEA8, SDC45, RAD51AP13, PINX15, DSCC12, STARD3NL2, POLQ, DCLRE1B, FKBP116, CCDC51, QDPR8, PHF191, CEP1521, HIST1H1E6, TIMM214, TEX100, H2AFX5, PLK48, AURKB9, LAG38, SLCO4A16, ESPL19, NPM39, PSMC3IP8, NTHL15, DIAPH36, MTHFD1L4, DEPDC1B0, FAH5, FLYWCH24, RPL26L18, CDCA8, BOLA3, DDIAS4, KIFC14, CTU29, TMEM14A0, CMSS1, NUF2, MYL6B4, PRC12, PAQR49, SGOL2, SKA39, BUB1, PIP4K2B7, PIP4K2B5, UQCC26, ZNF3172, MTERF35, LAGE35, DLGAP59, POLE23, SESN2, LMTK24, OIP59, GPX7, PBK9, HDGFRP31, NT5DC2, DNA24, CDCA26, ORC1, SHCBP19, CCDC348, CCNB26, APITD1, E2F83, ANKRD542, MON1A, MRPL25, MIS18A8, KNSTRN5, PEMT3, GOT16, CENPW4, GGH1, KIF150, KIF15, MYBL28, ASB21, ASB22, CCDC772, GTSE15, SLC43A14, CCHCR14, MCM92, PTRH13, CDK74, APOO7, ATAD3A, MCAT8, MCM82, TMEM201, TNIP36, GPR686, LRRCC19, KIFC17, CHCHD68, KCNK54, RCE19, LTA3, LTA1, LTA2, WEE18, PUS77, KIF18A1, DCAF17, MAPK30, AURKA3, NUDT29, DONSON4, MTFR20, EMC99, POC1A, GPALPP16, BNIP15, TMEM185B, HPDL, IMMP1L4, NUFIP15, INO80C8, KHDC15, GEMIN50, PRADC1, RPL39L8, TADA1, UBQLN4, TROAP6, PRMT6, PARP3, MND12, SLC37A41, SLC37A48, APOBEC3H4, CCDC1529, HGH15, AKAP17A9, AKAP17A2, PRIMPOL6, SPIN46, CDPF11, B4GALT4, NCALD5, PMM15, MT1E7, GFI1, E2F19, KLHDC7B0, SMIM80, ACTR3C7, RPP219, RPP216, RPP217, SIK38, HRSP128, TNFSF4, CD388, ZNHIT20, SSBP45, ERLIN14, NME1-NME27, CHCHD4, CTTN4, TMEM991, ZNF7072, CDKN2A8, TRMT52, ADCK28, ENOSF17, RNLS5, KIAA01014, IFI27L18, IFI27L19, AP2A28, DUS4L3, SCRN26, ZNF186, CRTAM6, SLC39A85, N6AMT25, NENF, BBS76, BMP19, TNFRSF4, ERCC6L6, KIF247, MIER24, PROSER34, CDADC11, MT1X9, STXBP53, ALYREF1, GCSH1, TLCD17, UHRF11, UBE2Q1, UBE2S1, CISD31, CISD39, RHEBL16, ROGDI6, CKAP2L, CCND27, GSTZ17, SPC241, NCAPH, GINS13, TMTC46, PPP1R14B7, CDCA33, OSBPL39, MAGOHB1, ITM2A4, KLF100, MRPL122, E2F2, PGAP1, CDT15, MCM47, LMNA, DUT7, KIF110, SAP304, PCNA1, BCKDHB7, TNFRSF9, TSEN2, MCM75, CD2, SMARCAD12, CERCAM6, CD8A, EZH21, TUBB7, MCM32, MCM6, NME18, AMICA16, PRMT55, TSR15, CAD, TRAP16, KIF226, FANCI2, STRA134, LCK, RRM17, STMN1, ALG36, SYTL35, LAT3, CDK64, MRPL455, ALDH18A10, MRPS268, PAICS9, SLC43A31, MTMR25, CKS1B, CD96, CTPS1, HMGB21, CDCA45, TUBA1B0, BRIX12, SLC7A16, CHEK14, RUVBL22, TBRG47, DDX218, DDX491, CCDC865, WDR182, NDC1, CIRH1A1, NOP164, DKC12, HSPD1, CDK48, GPATCH4, GGCT5, EBP5, ACAT19, MSH6, SSRP16, IL2RB8, CAND15, WDR54, NOP148, PSD4, IPO57, KPNA29, IL324, EIF3C4, GEMIN43,

TABLE 1-continued

| |
|---|
| SLBP6, IFRD2, EBNA1BP2, GNL2, LDHA6, WDR746, TUBA1C3, ENO1, CD2260, RANBP19, NKG78, CASP35, NOB18, GMPS1, PPP2R5D1, RUVBL13, TUBG10, SLC25A195, PSMD14, MTFP19, CENPH2, AMD19, PIM15, TFDP13, GRPEL18, LAS1L3, DHX9, POLD22, DDX1, TTF2, GNL3, IMPDH2, TIMM236, TMPO9, MTHFD2, PFKP9, ADSS, EIF1AX0, LARP41, PSMD126, TRAF12, CUL19, SDHB, UTP181, HAT1, RBPJ0, TUBB5, TUBB9, TUBB0, TUBB1, TUBB5, TUBB2, NPM19, MRPL37, STOML25, TUBB4B6, SIGMAR12, MTCH26, EIF4A37, PA2G40, HSP90AB12, FPGS0, DHX30, VDAC13, MAT2A, EIF4G10, KLHDC32, HSPE1, STIP10, NOLC19, PSMA61, EED4, NOP569, SNRPD13, DDX39A2, HSP90AA11, SNRPC8, PSMC37, HSPA85, EXOSC88, CCT50, PSME20, DNMT19, LDHB9, TPI15, PGAM16, EIF5A4, NUDT219, APOBEC3G2, RAN8, PKM9, CBX32, CCT3, NONO2, SERBP1, PPIA0, NCL, SET6, GPI3, EIF4A19, GAPDH2, H2AFZ8, SRSF38, SLC25A56, HMGN2, CCT6A5, HNRNPM2, HNRNPF0, MAPK1IP1L7, ALDOA4, HNRNPA18, RPLP05, RPSA, PFN17, ACTG11, FKBP141, GABARAPL24, ZFP36L15, EMP28, AKAP97, KMT2E2, ITSN2, TSPAN31, HLA-DQA19, HLA-DQB14, ZNF8055, NPIPB97, MR1, CD79B3, IL160, CCDC1223, SNX25, S100A11, ZNF124, HLA-DRA0, HLA-DRA9, HLA-DRA3, RCSD1, CEBPZOS, HLA-DQA14, HLA-DQA13, ST6GAL16, HLA-DRA0, ATP6V1G11, OAS18, KIN7, LAPTM5, CPM6, N4BP2L22, HLA-DRB33, FILA-DRB31, SYK5, ARSA8, AHNAK3, CD52, HLA-DPA14, HLA-DPA10, HLA-DPA19, HLA-DPA16, HLA-DPA14, HEA-DPA13, RNF1417, ZFAND56, HLA-DRB13, HLA-DRB12, KIAA15510, CD372, PSAP6, LPIN38, B4GALT17, ATM1, HLA-DRB18, TBC1D5, PLEK, SERINC11, MIXL1, MEF2A3, PDE7A0, CTSS, TTN, LMBRD16, HLA-DPB15, FTH16, AFTPH, MTRNR2L103, EVI2A6, FCRLA, GM2A8, HLA-DMA8, HLA-DMA1, HLA-DMA7, HLA-DMA0, HLA-DMA8, HLA-DMA9, EVL8, RAPGEF66, UTRN1, POU2AF18, ZNF3025, EEA11, BANK13, HLA-DRB11, CHD25, HLA-DPB11, TPP15, FCRL3, DAPP15, FAIM3, TRIM389, CAT4, SWAP701, HLA-DRA3, HLA-DPB10, HLA-DPB15, RAPGEF14, PHKB6, ZNF6521, NBPF14, MS4A14, LRMP4, MTSS18, GLIPR12, ZEB2, EVI2B5, ASAH16, OGFRL10, ADRBK25, HIP1R9, GATAD2B6, BTN3A11, NBPF10, AMFR8, TP53I116, PDE11A, TFEB6, SLC12A83, HLA-DRB56, AXL0, ZFP361, LRRC37A20, METTL7A6, KLHL243, NUAK2, TTLL3, PIK3IP15, PNRC16, MPP66, TXNIP, NOTCH2NL, HIST1H2BK5, TLR107, APOOL7, CD683, HLA-DQB13, LAIR24, RASGRP29, PBXIP1, LYZ3, CXCL163, IFNGR10, SCPEP16, TNFSF13B8, PKIG0, SHOX7, KCNC37, RALGPS2, VNN26, MARCH18, FCRL5, FGR, RAB128, NOVA16, SPI14, ANXA4, MS4A71, BLK3, SNCA3, IRF2BPL5, RAB306, SHOX4, FCGR2B, LPAR50, CLECL12, CTBP21, GSTM2, JDP25, KIAA03557, RFN22, LILRB10, PAOX1, GSN8, PGAM25, TMIGD22, POU5F16, CTSZ8, NFAM12, PLEKHM15, PTGIR8, OTUD14, KLF26, CD1D, ZNF354B1, GSTT19, RNASE63, TMEM176A0, ITGAX0, PLXDC21, CHST20, MLXIP8, GLCCI12, LRRC181, ANGPTL1, RTKN, DAB29, BCL7A7, DST8, WDR815, SARM11, AVPI16, HIST1H2AC5, OSBPL73, FCGR2A, LILRB23, ZNF8210, NT5E5, ZNF4199, CLCF16, PITPNA7, PCDHGC31, KDM7A6, DTX13, ZNF6231, TXLNB2, A2M4, EPHB60, ZNF3411, CD92, PLTP4, GALNT48, TMCC34, GAB23, DHRS9, IGJ6, CYP27A1, CBX76, FAM65C2, PER3, WNT165, APBB35, RRAGB5, SYNPO1, RNF1306, CASD11, MYO1E7, ZNF1553, MS4A142, FMO5, TLE13, MTMR106, CNKSR25, TRIB2, LDLRAP1, RGMB0, SSPN0, MLXIP9, MARCKS5, ADGRE26, L3MBTL42, IKZF2, ABCA19, ABHD6, NPEPL19, ARHGAP121, SGSH0, TMEM2313, ST3GAL6, MYO18A7, IGSF61, NRP2, ZNF354A8, OXSM, NEGR1, ZNF385A4, DOCK51, LILRB23, PLA2G4B5, CTTNBP2NL, B3GNT2, BCAR3, CRLF28, CRLF21, DGKG9, SESN14, TMEM1641, PTPRO8, CHST154, DHX586, CTSO5, CTSO5, CACNA1A5, DENND5A0, TNFSF136, FCER1G, RASL11A2, RFFL5, DENND5B0, DNMBP8, KLF32, KIAA15987, SOX42, ARRDC22, EGLN1, PLXNA34, ANPEP3, CST38, CD1C, TTC21A, BTBD72, BTBD73, DSE0, ZNF3951, TBC1D21, ANKRD19, ZBP18, UNC93B17, HYLS13, HLA-DOB1, B3GNT7, RASSF44, TNFAIP24, CD200R1, CSF1R7, SLC7A78, ADRB20, SGK2239, MNDA, IFNGR26, SNX309, ZMAT11, UBL39, DPEP23, PTK24, TFE36, MALT14, LMF15, APP2, LILRB23, ZNF6082, ADAP26, SH3TC15, BMP2K7, CPNE57, SYT15, UBE2E2, CRIM1, MXD42, PTGS11, DUSP15, EPB41L4A1, TBC1D93, ALOX54, ALOX51, SIRPA3, LILRB18, IFNGR20, RGS1, LILRB16, HMOX12, LY968, BTN2A20, PLXNC16, GSAP9, IFIT21, NIPSNAP3B8, SETDB1, RNF144B7, HEPACAM8, CLEC4A6, IL74, SOX58, PCDH93, FCRL1, TIMP10, ADORA2A0, RASGEF1B6, HHEX3, CDK146, MAP3K12, SIGLEC61, LGALS15, FCRL2, RASGRP3, PHACTR15, TYROBP3, COBLL1, PLD42, CD1808, TGFBI0, LRRK27, ALDH25, HCK3. |

Table 1 in an embodiment provides a signature of dendritic cells (e.g. cDC), and represents differentially expressed genes in particular DC subpopulations, termed VEx-A ("virus exposed-A"), preferably associated with or derived from elite controller phenotype, preferably associated with HIV infection. Preferably differential expression is evaluated in infected cells, compared to non-infected cells.

TABLE 2

| |
|---|
| GZMB4, ZBED2, IL2RA0, TOP2A2, TYMS6, MCM23, MKI679, MTHFD16, GZMH3, FEN18, TMEM106C5, CISH, CDK18, DNAJC92, ZWINT6, PSATI8, TK18, CDCA55, TIGIT, ASF1B5, DTL, POLD12, NUSAP10, GPR1719, ACOT7, CD8B, CCL48, CCL45, NCAPD39, CDCA7, CCNA25, MSH2, RRP123, CENPF, TBL38, TPX24, SH2D1A6, TCF199, PTPN7, PPP5C9, CCL37, CCL36, CCL34, SCCPDH, NDC801, CDC453, NPRL2, |

TABLE 2-continued

DDX411, NCAPG7, SRM, UBE2C5, MCM109, BIRC50, PYCR18, WDHD14, SLC27A24, SLC38A51, RFC40, IPO118, POLA13, PPAT7, IPO46, LMNB21, SLC29A11, TIMELESS2, DHFR7, RAD516, GINS23, SLC7A56, UBE2T, ACD5, BUB1B4, VCAM1, CENPU7, IFNG3, DGCR147, FANCG3, BCAT17, NOC4L5, KIF21A3, RBBP89, TCF195, MAD2L17, CDC63, KIF236, PKMYT10, MRPL177, PWP24, ASUN8, EEF1E15, JAKMIP18, RFC53, RRS12, PAM6, CD3202, SLC1A4, CDC20, GZMA0, XCL2, RUSC1, LRWD17, QTRT17, DCAF128, ESCO28, HENMT1, UTP157, MELK3, CCNE26, MTX1, FBXO54, NDFIP20, EXO1, ZPR12, HMBS4, MRPT461, CCNF2, RRM2, NCAPG20, ICOS, CENPM9, CEP787, SH2D2A, SPAG52, PSMG17, THEMIS3, THEMIS7, CHAF1B9, CDKN35, EMC86, NLE19, CCDC1671, TTK4, POP77, LRR17, RECQL47, HELLS4, ZDHHC131, GMNN7, SAYSD12, CEP85, RAD54L, XCL1, TEX301, MANEA8, SDC45, RAD51AP13, PINX15, DSCC12, STARD3NL2, POLQ, DCLRE1B, FKBP116, CCDC51, QDPR8, PHF191, CEP1521, HIST1H1E6, TIMM214, TEX100, H2AFX5, PLK48, AURKB9, LAG38, SLCO4A16, ESPL19, NPM39, PSMC3IP8, NTHL15, DIAPH36, MTHFD1L4, DEPDC1B0, FAH5, FLYWCH24, RPL26L18, CDCA8, BOLA3, DDIAS4, KIFC14, CTU29, TMEM14A0, CMSS1, NUF2, MYL6B4, PRC12, PAQR49, SGOL2, SKA39, BUB1, PIP4K2B7, PIP4K2B5, UQCC26, ZNF3172, MTERF35, LAGE35, DLGAP59, POLE23, SESN2, LMTK24, OIP59, GPX7, PBK9, HDGFRP31, NT5DC2, DNA24, CDCA26, ORC1, SHCBP19, CCDC348, CCNB26, APITD1, E2F83, ANKRD542, MON1A, MRPL25, MIS18A8, KNSTRN5, PEMT3, GOT16, CENPW4, GGH1, KIF150, KIF15, MYBL28, ASB21, ASB22, CCDC772, GTSE15, SLC43A14, CCHCR14, MCM92, PTRH13, CDK74, APOO7, ATAD3A, MCAT8, MCM82, TMEM201, TNIP36, GPR686, LRRCC19, KIFC17, CHCHD68, KCNK54, RCE19, LTA3, LTA1, LTA2, WEE18, PUS77, KIF18A1, DCAF17, MAPK30, AURKA3, NUDT29, DONSON4, MTFR20, EMC99, POC1A, GPALPP16, BNIP15, TMEM185B, HPDL, IMMP1L4, NUFIP15, INO80C8, KHDC15, GEMIN50, PRADC1, RPL39L8, TADA1, UBQLN4, TROAP6, PRMT6, PARP3, MND12, SLC37A41, SLC37A48, APOBEC3H4, CCDC1529, HGH15, AKAP17A9, AKAP17A2, PRIMPOL6, SPIN46, CDPF11, B4GALT4, NCALD5, PMM15, MT1E7, GFI1, E2F19, KLHDC7B0, SMIM80, ACTR3C7, RPP219, RPP216, RPP217, SIK38, HRSP128, TNFSF4, CD388, ZNHIT20, SSBP45, ERLIN14, NME1-NME27, CHCHD4, CTTN4, TMEM991, ZNF7072, CDKN2A8, TRMT52, ADCK28, ENOSF17, RNLS5, KIAA01014, IFI27L18, IFI27L19, AP2A28, DUS4L3, SCRN26, ZNF186, CRTAM6, SLC39A85, N6AMT25, NENF, BBS76, BMP19, TNFRSF4, ERCC6L6, KIF247, MIER24, PROSER34, CDADC11, MT1X9, STXBP53, ALYREF1, GCSH1, TLCD17, UHRF11, UBE2Q1, UBE2S1, CISD31, CISD39, RHEBL16, ROGDI6, CKAP2L, CCND27, GSTZ17, SPC241, NCAPH, GINS13, TMTC46, PPP1R14B7, CDCA33, OSBPL39, MAGOHB1, ITM2A4, KLF100, MRPL122, E2F2, PGAP1, CDT15, MCM47, LMNA, DUT7, KTF110, SAP304, PCNA1, BCKDHB7, TNFRSF9, TSEN2, MCM75, CD2, SMARCAD12, CERCAM6, CD8A, EZH21, TUBB7, MCM32, MCM6, NME18, AMICA16, PRMT55, TSR15, CAD, TRAP16, KIF226, FANCI2, STRA134, LCK, RRM17, STMN1, ALG36, SYTL35, LAT3, CDK64, MRPL455, ALDH18A10, MRPS268, PAICS9, SLC43A31, MTMR25, CKS1B, CD96, CTPS1, HMGB21, CDCA45, TUBA1B0, BRIX12, SLC7A16, CHEK14, RUVBL22, TBRG47, DDX218, DDX491, CCDC865, WDR182, NDC1, CIRH1A1, NOP164, DKC12, HSPD1, CDK48, GPATCH4, GGCT5, EBP5, ACAT19, MSH6, SSRP16, IL2RB8, CAND15, WDR54, NOP148, PSD4, IPO57, KPNA29, IL324, EIF3C4, GEMIN43, SLBP6, IFRD2, EBNA1BP2, GNL2, LDHA6, WDR746, TUBA1C3, ENO1, CD2260, RANBP19, NKG78, CASP35, NOB18, GMPS1, PPP2R5D1, RUVBL13, TUBG10, SLC25A195, PSMD14, MTFP19, CENPH2, AMD19, PIM15, TFDP13, GRPEL18, LAS1L3, DHX9, POLD22, DDX1, TTF2, GNL3, IMPDH2, TIMM236, TMPO9, MTHFD2, PFKP9, ADSS, EIF1AX0, LARP41, PSMD126, TRAF12, CUL19, SDHB, LTP181, HAT1, RBPJ0, TUBB5, TUBB9, TUBB0, TUBB1, TUBB5, TUBB2, NPM19, MRPL37, STOML25, TUBB4B6, SIGMAR12, MTCH26, EIF4A37, PA2G40, HSP90AB12, FPGS0, DHX30, VDAC13, MAT2A, EIF4G10, KLHDC32, HSPE1, STIP10, NOLC19, PSMA61, EED4, NOP569, SNRPD13, DDX39A2, HSP90AA11, SNRPC8, PSMC37, HSPA85, EXOSC88, CCT50, PSME20, DNMT19, LDHB9, TPI15, PGAM16, EIF5A4, NUDT219, APOBEC3G2, RAN8, PKM9, CBX32, CCT3, NONO2, SERBP1, PPIA0, NCL, SET6, GPI3, EIF4A19, GAPDH2, H2AFZ8, SRSF38, SLC25A56, HMGN2, CCT6A5, FFNRNPM2, HNRNPF0, MAPK1IP1L7, ALDOA4, HNRNPA18, RPLP05, RPSA, PEN17, ACTG11.

Preferably GZMB4, ZBED2, IL2RA0, TOP2A2, TYMS6, MCM23, MKI679, MTHFD16, GZMH3, FEN18, TMEM106C5, CISH, CDK18, DNAJC92, ZWINT6, PSAT18, TK18, CDCA55, TIGIT, ASF1B5, DTE, POLD12, NUSAP10, GPR1719, ACOT7, CD8B, CCL48, CCL45, NCAPD39, CDCA7, CCNA25, MSH2, RRP123, CENPF, TBL38, TPX24, SH2D1A6, TCF199, PTPN7, PPP5C9, CCL37, CCL36, CCL34, SCCPDH, NDC801, CDC453, NPRL2, DDX411, NCAPG7, SRM, UBE2C5, MCM109, BIRC50, PYCR18, WDHD14, SLC27A24, SLC38A51, RFC40, IPO118, POLA13, PPAT7, IPO46, LMNB21, SLC29A11, TIMELESS2, DHFR7, RAD516, GINS23, SLC7A56, UBE2T, ACD5, BUB1B4, VCAM1, CENPU7, IFNG3, DGCR147, FANCG3, BCAT17, NOC4L5, KIF21A3, RBBP89, TCF195, MAD2L17, CDC63, KIF236, PKMYT10, ASUN8, EEF1E15, JAKMIP18, RFC53, RRS12, PAM6, CD3202, SLC1A4, CDC20, GZMA0, XCL2, RUSC1, LRWD17, QTRT17, DCAF128, ESCO28, HENMT1, UTP157, MELK3, CCNE26, MTX1, FBXO54, NDFIP20, EXO1, ZPR12, HMBS4, MRPL461, CCNF2, RRM2, NCAPG20, ICOS, CENPM9, CEP787, SH2D2A, SPAG52, PSMG17, THEMIS3, THEMIS7, CHAF1B9, CDKN35, EMC86, NLE19, CCDC1671, TTK4, POP77, LRR17, RECQL47, HELLS4, ZDHHC131, GMNN7, SAYSD12, CEP85, RAD54L, XCL1, TEX301, SDC45, RAD51AP13, PINX15, DSCC12, STARD3NL2, POLQ, DCLRE1B, FKBP116, CCDC51, QDPR8, PHF191, CEP1521, HIST1H1E6, TIMM214, TEX100, H2AFX5, PLK48, AURKB9, LAG38, SLCO4A16, ESPL19, NPM39, PSMC3IP8, NTHL15, DIAPH36, MTHFD1L4, DEPDC1B0, FAH5, FLYWCH24, RPL26L18, CDCA8, BOLA3, DDIAS4, KIFC14, CTU29, TMEM14A0, CMSS1, NUF2, MYL6B4, PRC12, PAQR49, SGOL2, SKA39, BUB1, PIP4K2B7, PIP4K2B5, UQCC26, ZNF3172, MTERF35, LAGE35, DLGAP59, POLE23, SESN2, LMTK24, OIP59, GPX7, PBK9, HDGFRP31, NT5DC2, DNA24, CDCA26, ORC1, SHCBP19, CCDC348, CCNB26, TABLE 2-continued APITD1, E2F83, ANKRD542, MON1A, MRPL25, MIS18A8, KNSTRN5, PEMT3, GOT16, CENPW4, GGH1, KIF150, KIFT5, MYBL28, CCDC772, GTSE15, SLC43A14, CCHCR14, MCM92, PTRH13, CDK74, APOO7, ATAD3A, MCM82, TMEM201, TNIP36, GPR686, LRRCC19, KIFC17, CHCHD68, KCNK54, RCE19, LTA3, LTA1, LTA2, WEE18, PUS77, KIF18A1, DCAF17, MAPK30, NUDT29, DONSON4, MTFR20, EMC99, POC1A, GPALPP16, BNIP15, TMEM185B, HPDL, IMMP1L4, NUFIP15, INO80C8, KHDC15, GEMIN50, PRADC1, RPL39L8, TADA1, UBQLN4, TROAP6, PARP3, MND12, SLC37A41, SLC37A48, APOBEC3H4, AKAP17A9, AKAP17A2, PRIMPOL6, SPIN46, CDPF11, B4GALT4, NCALD5, PMM15, MT1E7, GFI1, E2F19, KLHDC7B0, SMIM80, ACTR3C7, RPP219, RPP216, RPP217, TNFSF4, ZNHIT20, SSBP45, ERLIN14, NME1-NME27, CHCHD4, CTTN4, TMEM991, CDKN2A8, TRMT52, ADCK28, ENOSF17, RNLS5, KIAA01014, AP2A28, DUS4L3, SCRN26, ZNF186, CRTAM6, SLC39A85, NENF, BBS76, BMP19, TNFRSF4, ERCC6L6, KIF247, MIER24, PROSER34, CDADC11, MT1X9, STXBP53, ALYREF1, GCSH1, TLCD17, UHRF11, UBE2Q1, UBE2S1, CISD31, CISD39, RHEBL16, CKAP2L, CCND27, GSTZ17, SPC241, NCAPH, GINS13, TMTC46, PPP1R14B7, CDCA33, OSBPL39, MAGOHB1, ITM2A4, KLF100, MRPL122, E2F2, PGAP1, CDT15, MCM47, LMNA, DUT7, KIF110, SAP304, PCNA1, BCKDHB7, TNFRSF9, MCM75, CD2, SMARCAD12, CERCAM6, CD8A, EZH21, TUBB7, MCM32, MCM6, NME18, AMICA16, PRMT55, TSR15, CAD, TRAP16, KIF226, FANCI2, STRAI34, LCK, RRM17, STMN1, ALG36, SYTL35, LAT3, CDK64, MRPL455, ALDH18A10, MRPS268, PAICS9, SLC43A31, MTMR25, CKS1B, CD96, CTPS1, HMGB21, CDCA45, TUBA1B0, BRIX12, SLC7A16, RUVBL22, TBRG47, DDX218, DDX491, CCDC865, WDR182, NDC1, CIRH1A1, NOP164, DKC12, HSPD1, CDK48, GPATCH4, GGCT5, EBP5, ACAT19, MSH6, SSRP16, IL2RB8, CAND15, NOP148, PSD4, IPO57, KPNA29, IL324, EIF3C4, SLBP6, IFRD2, EBNA1BP2, GNL2, LDHA6, WDR746, TUBA1C3, ENO1, CD2260, RANBP19, NKG78, CASP35, NOB18, GMPS1, RUVBL13, TUBG10, SLC25A195, PSMD14, MTFP19, CENPH2, AMD19, GRPEL18, LAS1L3, DHX9, POLD22, DDX1, GNL3, IMPDH2, TIMM236, TMPO9, MTHFD2, PFKP9, ADSS, EIF1AX0, LARP41, PSMD126, CUL19, SDHB, UTP181, HAT1, RBPJ0, TUBB5, TUBB9, TUBB0, TUBB1, TUBB5, TUBB2, NPM19, STOML25, TUBB4B6, MTCH26, EIF4A37, PA2G40, HSP90AB12, FPGS0, DHX30, VDAC13, MAT2A, EIF4G10, KLHDC32, HSPE1, STIP10, PSMA61, EED4, NOP569, SNRPD13, DDX39A2, HSP90AA11, PSMC37, HSPA85, EXOSC88, CCT50, PSME20, DNMT19, LDHB9, TPI15, PGAM16, EIF5A4, APOBEC3G2, RAN8, PKM9, CBX32, CCT3, NONO2, SERBP1, PPIA0, NCL, SET6, GPI3, EIF4A19, GAPDH2, H2AFZ8, SRSF38, SLC25A56, HMGN2, CCT6A5, HNRNPM2, HNRNPF0, ALDOA4, HNRNPA18, RPLP05, RPSA, PFN17.

More preferably GZMB4, ZBED2, IL2RA0, TOP2A2, TYMS6, MCM23, MKI679, MTHFD16, GZMH3, FEN18, TMEM106C5, CISH, CDK18, DNAJC92, ZWINT6, PSAT18, TK18, CDCA55, TIGIT, ASF1B5, DTE, POLD12, NUSAP10, GPR1719, ACOT7, CD8B, CCL48, CCL45, NCAPD39, CDCA7, CCNA25, MSH2, RRP123, CENPF, TBL38, TPX24, SH2D1A6, TCF199, PTPN7, PPP5C9, CCL37, CCL36, CCL34, SCCPDH, NDC801, CDC453, NCAPG7, SRM, UBE2C5, MCM109, BIRC50, PYCR18, WDHD14, SLC27A24, SLC38A51, RFC40, POLA13, PPAT7, LMNB21, SLC29A11, TIMELESS2, DHFR7, RAD516, GINS23, SLC7A56, UBE2T, BUB1B4, VCAM1, CENPU7, IFNG3, FANCG3, BCAT17, KIF21A3, RBBP89, TCF195, MAD2L17, CDC63, KIF236, PKMYT10, ASUN8, EEF1E15, JAKMIP18, RRS12, PAM6, CD3202, SEC1A4, CDC20, XCL2, RUSC1, QTRT17, DCAF128, ESCO28, UTP157, MELK3, CCNE26, FBXO54, NDFIP20, EXO1, MRPL461, CCNF2, RRM2, NCAPG20, ICOS, CENPM9, SH2D2A, SPAG52, PSMG17, THEMIS3, THEMIS7, CHAF1B9, CDKN35, EMC86, TTK4, POP77, LRR17, RECQL47, ZDHHC131, GMNN7, SAYSD12, CEP85, RAD54L, XCL1, TEX301, SDC45, RAD51AP13, PINX15, DSCC12, STARD3NL2, POLQ, CCDC51, QDPR8, HIST1H1E6, H2AFX5, PLK48, AURKB9, LAG38, ESPL19, NPM39, PSMC3IP8, DIAPH36, MTHFD1L4, DEPDC1B0, FAH5, CDCA8, BOLA3, DDIAS4, KIFC14, TMEM14A0, CMSS1, NUF2, PRC12, PAQR49, SGOL2, SKA39, BUB1, UQCC26, MTERF35, LAGE35, DLGAP59, POLE23, LMTK24, OIP59, GPX7, PBK9, HDGFRP31, NT5DC2, DNA24, CDCA26, ORC1, SHCBP19, CCDC348, CCNB26, APITD1, E2F83, MRPL25, KNSTRN5, GOT16, CENPW4, GGH1, KIF150, KIF15, MYBL28, GTSE15, SLC43A14, MCM92, CDK74, APOO7, ATAD3A, TMEM201, TNIP36, GPR686, LRRCC19, KIFC17, CHCHD68, KCNK54, RCE19, LTA3, LTA1, LTA2, PUS77, KIF18A1, DCAF17, MAPK30, DONSON4, MTFR20, POC1A, GPALPP16, BNIP15, TMEM185B, HPDL, NUFIP15, INO80C8, KHDC15, RPL39L8, TADA1, UBQLN4, TROAP6, MND12, SLC37A41, SLC37A48, APOBEC3H4, PRIMPOL6, SPIN46, B4GALT4, NCALD5, PMM15, MT1E7, GFI1, E2F19, SMIM80, ACTR3C7, RPP219, RPP216, RPP217, TNFSF4, ZNHIT20, NME1-NME27, CHCHD4, CTTN4, TMEM991, CDKN2A8, ADCK28, ENOSF17, RNLS5, KIAA01014, AP2A28, DUS4L3, SCRN26, ZNF186, CRTAM6, SLC39A85, BBS76, TNFRSF4, ERCC6L6, KIF247, PROSER34, CDADC11, ALYREF1, GCSH1, TLCD17, UHRF11, UBE2Q1, UBE2S1, RHEBL16, CCND27, SPC241, GINS13, TMTC46, PPP1R14B7, OSBPL39, MAGOHB1, ITM2A4, MRPL122, MCM47, LMNA, DUT7, PCNA1, TNFRSF9, MCM75, CD2, SMARCAD12, CD8A, EZH21, TUBB7, MCM32, MCM6, NME18, AMICA16, PRMT55, TSR15, CAD, TRAP16, KIF226, FANCI2, STRA134, LCK, RRM17, STMN1, ALG36, SYTL35, LAT3, CDK64, MRPL455, MRPS268, PAICS9, SLC43A31, MTMR25, CKS1B, CD96, HMGB21, CDCA45, TUBA1B0, BRIX12, SLC7A16, DDX218, DDX491, CCDC865, WDR182, CIRH1A1, NOP164, DKC12, HSPD1, CDK48, EBP5, ACAT19, MSH6, SSRP16, IL2RB8, CAND15, IPO57, KPNA29, IL324, EIF3C4, IFRD2, EBNA1BP2, LDHA6, TUBA1C3, ENO1, CD2260, RANBP19, NKG78, CASP35, PSMD14, DHX9, POLD22, DDX1, GNL3, IMPDH2, TMPO9, MTHFD2, EIF1AX0, PSMD126, HAT1, RBPJ0, TUBB5, TUBB9, TUBB0, TUBB1, TUBB5, TUBB2, NPM19, TUBB4B6, EIF4A37, PA2G40, HSP90AB12, MAT2A, EIF4G10, HSPE1, STIP10, PSMA61, NOP569, SNRPD13, TABLE 2-continued

| |
|---|
| DDX39A2, HSP90AA11, HSPA85, PSME20, LDHB9, TPI15, PGAM16, EIF5A4, RAN8, PKM9, CCT3, NONO2, SERBP1, PPIA0, NCL, SET6, GPI3, ELF4A19, GAPDH2, SRSF38, SLC25A56, HMGN2, RPLP05, RPSA. |

TABLE 3

| |
|---|
| GZMB4, ZBED2, IL2RA0, TOP2A2, TYMS6, MCM23, MKI679, MTHFD16, GZMH3, FEN18, TMEM106C5, CISH, CDK18, DNAJC92, ZWINT6, PSAT18, TK18, CDCA55, TIGIT, ASF1B5, DTL, POLD12, NUSAP10, GPR1719, ACOT7, CD8B, CCL48, CCL45, NCAPD39, CDCA7, CCNA25, MSH2, RRP123, CENPF, TBL38, TPX24, SH2D1A6, TCF199, PTPN7, PPP5C9, CCL37, CCL36, CCL34, SCCPDH, NDC801, CDC453, NPRL2, DDX411, NCAPG7, SRM, UBE2C5, MCM109, BIRC50, PYCR18, WDHD14, SLC27A24, SLC38A51, RFC40, IPO118, POLA13, PPAT7, IPO46, LMNB21, SLC29A11, TIMELESS2, DHFR7, RAD516, GINS23, SLC7A56, UBE2T, ACD5, BUB1B4, VCAM1, CENPU7, IFNG3, DGCR147, FANCG3, BCAT17, NOC4L5, KIF21A3, RBBP89, TCF195, MAD2L17, CDC63, KIF236, PKMYT10, MRPL177, PWP24, ASUN8, EEF1E15, JAKMIP18, RFC53, RRS12, PAM6, CD3202, SLC1A4, CDC20, GZMA0, XCL2, RUSC1, LRWD17, QTRT17, DCAF128, ESCO28, HENMT1, UTP157, MELK3, CCNE26, MTX1, FBXO54, NDFIP20, EXO1, ZPR12, HMBS4, MRPL461, CCNF2, RRM2, NCAPG20, ICOS, CENPM9, CEP787, SH2D2A, SPAG52, PSMG17, THEMIS3, THEMIS7, CHAF1B9, CDKN35, EMC86, NLE19, CCDC1671, TTK4, POP77, LRR17, RECQL47, HELLS4, ZDHHC131, GMNN7, SAYSD12, CEP85, RAD54L, XCL1, TEX301, MANEA8, SDC45, RAD51AP13, PINX15, DSCC12, STARD3NL2, POLQ, DCLRE1B, FKBP116, CCDC51, QDPR8, PHF191, CEP1521, HIST1H1E6. |
| Preferably GZMB4, ZBED2, IL2RA0, TOP2A2, TYMS6, MCM23, MKI679, MTHFD16, GZMH3, FEN18, TMEM106C5, CISH, CDK18, DNAJC92, ZWINT6, PSAT18, TK18, CDCA55, TIGIT, ASF1B5, DTL, POLD12, NUSAP10, GPR1719, ACOT7, CD8B, CCL48, CCL45, NCAPD39, CDCA7, CCNA25, MSH2, RRP123, CENPF, TBL38, TPX24, SH2D1A6, TCF199, PTPN7, PPP5C9, CCL37, CCL36, CCL34, SCCPDH, NDC801, CDC453, NPRL2, DDX411, NCAPG7, SRM, UBE2C5, MCM109, BIRC50, PYCR18, WDHD14, SLC27A24, SLC38A51, RFC40, IPO118, POLA13, PPAT7, IPO46, LMNB21, SLC29A11, TIMELESS2, DHFR7, RAD516, GINS23, SLC7A56, UBE2T, ACD5, BUB1B4, VCAM1, CENPU7, IFNG3, DGCR147, FANCG3, BCAT17, NOC4L5, KIF21A3, RBBP89, TCF195, MAD2L17, CDC63, KIF236, PKMYT10, ASUN8, EEF1E15, JAKMIP18, RFC53, RRS12, PAM6, CD3202, SLC1A4, CDC20, GZMA0, XCL2, RUSC1, LRWD17, QTRT17, DCAF128, ESCO28, HENMT1, UTP157, MELK3, CCNE26, MTX1, FBXO54, NDFIP20, EXO1, ZPR12, HMBS4, MRPL461, CCNF2, RRM2, NCAPG20, ICOS, CENPM9, CEP787, SH2D2A, SPAG52, PSMG17, THEMIS3, THEMIS7, CHAF1B9, CDKN35, EMC86, NLE19, CCDC1671, TTK4, POP77, LRR17, RECQL47, HELLS4, ZDHHC131, GMNN7, SAYSD12, CEP85, RAD54L, XCL1, TEX301, SDC45, RAD51AP13, PINX15, DSCC12, STARD3NL2, POLQ, DCLRE1B, FKBP116, CCDC51, QDPR8, PHF191, CEP1521, HIST1H1E6. |
| More preferably GZMB, ZBED2, IL2RA, TOP2A, TYMS, MCM2, MKI67, MTHFD1, GZMH, FEN1, TMEM106C, CISH, CDK18, DNAJC9, ZWINT, PSAT1, TK1, CDCA5, TIGIT, ASF1B, DTL, POLD1, NUSAP1, GPR171, ACOT7, CD8B, CCL4, NCAPD3, CDCA7, CCBA2, NSH2, RRP12, CENPF, TBAL3, TPX2, SH2D1A, TCF19, PTPN7, PPP5C, CCL3, SCCPDH, NDC80, CDC45, NCAPG, SRM, UBE2C, MCM10, FIRC5, PYCR1, WDHD1, SLC27A2, SLC38A5, RFC40, POLA1, PPAT, LMNB2, SLC29A1, TIMELESS, DHFR, RAD51, GINS23, SLC7A5, UBE2T, BUB1B, VCAM1, CENPU, IFNG, FANCG, BCAT1, KIF21A, RBBP8, TCF19, MAD2L1, CDC6, KIF23, PKMYT1, ASUN, EEF1E1, JAKMIP1, RRS1, PAM, CD320, SLC1A4, CDC20, XCL2, RUSC1, QTRT1, DCAF12, ESCO2, UTP15, MELK, CCNE2, FBXO5, NDFIP2, EXO1, MRPL46, CCNF, RRM2, NCAPG2, ICOS, CENPM, SH2D2A, SPAG5, PSMG1, THEMIS, CHAF1B, CDKN3, EMC8, TTK, POP7, LRR1, RECQL4, ZDHHC13, GMCC, SAYSD1, CEP85, RAD54L, SCL1, TEX30, SDC4, RAD51AP1, PINX1, DSCC1, STARD3NL, POLQ, CCDC51, QDPR, and HIST1H1E. |

Tables 2 and 3 in an embodiment provides a signature of dendritic cells (e.g. cDC), and represents upregulated genes in particular DC subpopulations, termed VEx-A, preferably associated with or derived from elite controller phenotype, preferably associated with HIV infection. Preferably upregulation is evaluated in infected cells, compared to non-infected cells.

TABLE 4

| |
|---|
| FKBP141, GABARAPL24, ZFP36L15, EMP28, AKAP97, KMT2E2, ITSN2, TSPAN31, HLA-DQA19, HLA-DQB14, ZNF8055, NPIPB97, MR1, CD79B3, IL160, CCDC1223, SNX25, S100A11, ZNF124, HLA-DRA0, HLA-DRA9, HLA-DRA3, RCSD1, CEBPZOS, HLA-DQA14, HLA-DQA13, ST6GAL16, HLA-DRA0, ATP6V1G11, OAS18, KIN7, LAPTM5, CPM6, N4BP2L22, HLA-DRB33, HLA-DRB31, SYK5, ARSA8, AHNAK3, CD52, HLA-DPA14, HLA-DPA10, HLA-DPA19, HLA-DPA16, HLA-DPA14, HLA-DPA13, RNF1417, ZFAND56, HLA-DRB13, HLA-DRB12, KIAA15510, CD372, PSAP6, LPIN38, B4GALT17, ATM1, HLA-DRB18, TBC1D5, PLEK, SERINC11, MIXL1, MEF2A3, |

TABLE 4-continued

PDE7A0, CTSS, TTN, LMBRD16, HLA-DPB15, FTH16, AFTPH, MTRNR2L103, EVI2A6, FCRLA, GM2A8, HLA-DMA8, HLA-DMA1, HLA-DMA7, HLA-DMA0, HLA-DMA8, HLA-DMA9, EVL8, RAPGEF66, UTRN1, POU2AF18, ZNF3025, EEA11, BANK13, HLA-DRB11, CHD25, HLA-DPB11, TPP15, FCRL3, DAPP15, FAIM3, TRIM389, CAT4, SWAP701, HLA-DRA3, HLA-DPB10, HLA-DPB15, RAPGEF14, PHKB6, ZNF6521, NBPF14, MS4A14, LRMP4, MTSS18, GLTPR12, ZEB2, EVI2B5, ASAH16, OGFRL10, ADRBK25, HIP1R9, GATAD2B6, BTN3A11, NBPF10, AMFR8, TP53I116, PDE11A, TFEB6, SLC12A83, HLA-DRB56, AXL0, ZFP361, LRRC37A20, METTL7A6, KLHL243, NUAK2, TTLL3, PIK3IP15, PNRC16, MPP66, TXNIP, NOTCH2NL, HIST1H2BK5, TLR107, APOOL7, CD683, HLA-DQB13, LAIR24, RASGRP29, PBXIP1, LYZ3, CXCL163, IFNGR10, SCPEP16, TNFSF13B8, PKIG0, SHOX7, KCNC37, RALGPS2, VNN26, MARCH18, FCRL5, FGR, RAB128, NOVA16, SPI14, ANXA4, MS4A71, BLK3, SNCA3, IRF2BPL5, RAB306, SHOX4, FCGR2B, LPAR50, CLECL12, CTBP21, GSTM2, JDP25, KIAA03557, RIN22, LILRB10, PAOX1, GSN8, PGAM25, TMIGD22, POU5F16, CTSZ8, NFAM12, PLEKHM15, PTGIR8, OTUD14, KLF26, CD1D, ZNF354B1, GSTT19, RNASE63, TMEM176A0, ITGAX0, PLXDC21, CHST20, MLXIP8, GLCCI12, LRRC181, ANGPTL1, RTKN, DAB29, BCL7A7, DST8, WDR815, SARM11, AVPI16, HIST1H2AC5, OSBPL73, FCGR2A, LILRB23, ZNF8210, NT5E5, ZNF4199, CLCF16, PITPNA7, PCDHGC31, KDM7A6, DTX13, ZNF6231, TXLNB2, A2M4, EPHB60, ZNF3411, CD92, PLTP4, GALNT48, TMCC34, GAB23, DHRS9, IGJ6, CYP27A1, CBX76, FAM65C2, PER3, WNT165, APBB35, RRAGB5, SYNPO1, RNF1306, CASD11, MYO1E7, ZNF1553, MS4A142, FMO5, TLE13, MTMR106, CNKSR25, TRIB2, LDLRAP1, RGMB0, SSPN0, MLXIP9, MARCKS5, ADGRE26, L3MBTL42, IKZF2, ABCA19, ABHD6, NPEPL19, ARHGAP121, SGSH0, TMEM2313, ST3GAL6, MYO18A7, IGSF61, NRP2, ZNF354A8, OXSM, NEGR1, ZNF385A4, DOCK51, LILRB23, PLA2G4B5, CTTNBP2NL, B3GNT2, BCAR3, CRLF28, CRLF21, DGKG9, SESN14, TMEM1641, PTPRO8, CHST154, DHX586, CTSO5, CTSO5, CACNA1A5, DENND5A0, TNFSF136, FCER1G, RASL11A2, RFFL5, DENND5B0, DNMBP8, KLF32, KIAA15987, SOX42, ARRDC22, EGLN1, PLXNA34, ANPEP3, CST38, CD1C, TTC21A, BTBD72, BTBD73, DSE0, ZNF3951, TBC1D21, ANKRD19, ZBP18, UNC93B17, HYLS13, HLA-DOB1, B3GNT7, RASSF44, TNFAIP24, CD200R1, CSF1R7, SLC7A78, ADRB20, SGK2239, MNDA, IFNGR26, SNX309, ZMAT11, UBL39, DPEP23, PTK24, TFE36, MALT14, LMF15, APP2, LILRB23, ZNF6082, ADAP26, SH3TC15, BMP2K7, CPNE57, SYT15, UBE2E2, CRIM1, MXD42, PTGS11, DUSP15, EPB41L4A1, TBC1D93, ALOX54, ALOX51, SIRPA3, LILRB18, IFNGR20, RGS1, LILRB16, HMOX12, LY968, BTN2A20, PLXNC16, GSAP9, IFIT21, NIPSNAP3B8, SETDB1, RNF144B7, HEPACAM8, CLEC4A6, IL74, SOX58, PCDH93, FCRL1, TIMP10, ADORA2A0, RASGEF1B6, HHEX3, CDK146, MAP3K12, SIGLEC61, LGALS15, FCRL2, RASGRP3, PHACTR15, TYROBP3, COBLL1, PLD42, CD1808, TGFBI0, LRRK27, ALDH25, HCK3.

Preferably GABARAPL24, ZFP36L15, AKAP97, KMT2E2, ITSN2, TSPAN31, HLA-DQA19, HLA-DQB14, ZNF8055, NPIPB97, MR1, IL160, CCDC1223, SNX25, S100A11, ZNF124, HLA-DRA0, HLA-DRA9, HLA-DRA3, RCSD1, CEBPZOS, HLA-DQA14, HLA-DQA13, ST6GAL16, HLA-DRA0, ATP6V1G11, OAS18, KIN7, LAPTM5, CPM6, N4BP2L22, HLA-DRB33, HLA-DRB31, SYK5, ARSA8, AHNAK3, CD52, HLA-DPA14, HLA-DPA10, HLA-DPA19, HLA-DPA16, HLA-DPA14, HLA-DPA13, RNF1417, ZFAND56, HLA-DRB13, HLA-DRB12, KIAA15510, CD372, PSAP6, LPIN38, B4GALT17, ATM1, HLA-DRB18, TBC1D5, PLEK, SERINC11, MIXL1, MEF2A3, PDE7A0, CTSS, TTN, LMBRD16, HLA-DPB15, FTH16, AFTPH, EVI2A6, FCRLA, GM2A8, HLA-DMA8, HLA-DMA1, HLA-DMA7, HLA-DMA0, HLA-DMA8, HLA-DMA9, EVL8, RAPGEF66, POU2AF18, ZNF3025, EEA11, BANK13, HLA-DRB11, CHD25, HLA-DPB11, TPP15, FCRL3, DAPP15, FAIM3, TRIM389, CAT4, SWAP701, HLA-DRA3, HLA-DPB10, HLA-DPB15, RAPGEF14, PHKB6, ZNF6521, NBPF14, MS4A14, LRMP4, MTSS18, GLIPR12, ZEB2, EVI2B5, ASAH16, OGFRL10, ADRBK25, GATAD2B6, BTN3A11, NBPF10, AMFR8, TP53I116, PDE11A, TFEB6, SLC12A83, HLA-DRB56, AXL0, ZFP361, METTL7A6, KLHL243, NUAK2, TTLL3, PIK3IP15, PNRC16, MPP66, TXNIP, NOTCH2NL, HIST1H2BK5, TLR107, APOOL7, CD683, HLA-DQB13, LAIR24, RASGRP29, PBXIP1, LYZ3, CXCL163, SCPEP16, TNFSF13B8, SHOX7, KCNC37, RALGPS2, VNN26, MARCH18, FGR, RAB128, NOVA16, SPI14, ANXA4, MS4A71, BLK3, SNCA3, IRF2BPL5, RAB306, SHOX4, FCGR2B, LPAR50, CLECL12, CTBP21, GSTM2, JDP25, KIAA03557, RIN22, LILRB10, PAOX1, GSN8, PGAM25, TMIGD22, POU5F16, CTSZ8, NFAM12, PLEKHM15, PTGIR8, OTUD14, KLF26, CD1D, ZNF354B1, GSTT19, RNASE63, TMEM176A0, ITGAX0, PLXDC21, CHST20, MLXIP8, ANGPTL1, RTKN, DAB29, BCL7A7, DST8, WDR815, SARM11, AVPI16, HIST1H2AC5, OSBPL73, FCGR2A, LILRB23, ZNF8210, NT5E5, ZNF4199, CLCF16, PITPNA7, PCDHGC31, DTX13, ZNF6231, TXLNB2, EPHB60, ZNF3411, CD92, PLTP4, GALNT48, GAB23, DHRS9, IGJ6, CYP27A1, CBX76, FAM65C2, PER3, WNT165, APBB35, RRAGB5, SYNPO1, RNF1306, CASD11, MYO1E7, ZNF1553, MS4A142, FMO5, TLE13, MTMR106, CNKSR25, TRIB2, LDLRAP1, RGMB0, SSPN0, MLXIP9, MARCKS5, ADGRE26, L3MBTL42, IKZF2, ABCA19, ABHD6, NPEPL19, ARHGAP121, SGSH0, TMEM2313, ST3GAL6, MYO18A7, IGSF61, NRP2, ZNF354A8, OXSM, NEGR1, ZNF385A4, DOCK51, LILRB23, PLA2G4B5, CTTNBP2NL, BCAR3, CRLF28, CRLF21, DGKG9, SESN14, TMEM1641, CHST154, DHX586, CTSO5, CTSO5, CACNA1A5, DENND5A0, TNFSF136, FCER1G, RASL11A2, RFFL5, DENND5B0, DNMBP8, KLF32, KIAA15987, SOX42, ARRDC22, EGLN1, PLXNA34, ANPEP3, CST38, CD1C, TTC21A, BTBD72, BTBD73, DSE0, ZNF3951, TBC1D21, ANKRD19, ZBP18, UNC93B17, HYLS13, HLA-DOB1, B3GNT7, RASSF44, TNFAIP24, CD200R1, CSF1R7, SLC7A78, ADRB20, SGK2239, MNDA, IFNGR26, SNX309, ZMAT11, DPEP23, PTK24, TFE36, MALT14, LMF15, APP2, LILRB23, ZNF6082, ADAP26, SH3TC15, BMP2K7, CPNE57, SYT15, UBE2E2, CRLM1, MXD42, PTGS11, DUSP15, EPB41L4A1, TBC1D93, ALOX54, ALOX51, SIRPA3, LILRB18, IFNGR20, RGS1, LILRB16, HMOX12, LY968, BTN2A20, PLXNC16, GSAP9, TABLE 4-continued

| |
|---|
| IFIT21, NIPSNAP3B8, SETDB1, RNF144B7, HEPACAM8, CLEC4A6, IL74, SOX58, PCDH93, FCRL1, TIMP10, ADORA2A0, RASGEF1B6, HHEX3, CDK146, MAP3K12, SIGLEC61, LGALS15, FCRL2, RASGRP3, PHACTR15, TYROBP3, COBLL1, CD1808, TGFBI0, LRRK27, ALDH25, HCK3. |
| More preferably IL160, SNX25, S100A11, HLA-DRA0, HLA-DRA9, HLA-DRA3, CEBPZOS, HLA-DRA0, ATP6V1G11, KIN7, LAPTM5, N4BP2L22, HLA-DRB33, HLA-DRB31, SYK5, ARSA8, AHNAK3, CD52, HLA-DPA14, HLA-DPA10, HLA-DPA19, HLA-DPA16, HLA-DPA14, HLA-DPA13, RNF1417, ZFAND56, HLA-DRB13, HLA-DRB12, KIAA15510, CD372, PSAP6, LPIN38, B4GALT17, HLA-DRB18, PLEK, PDE7A0, CTSS, TTN, LMBRD16, HLA-DPB15, FTH16, AFTPH, FCRLA, HLA-DMA8, HLA-DMA1, HLA-DMA7, HLA-DMA0, HLA-DMA8, HLA-DMA9, EVL8, RAPGEF66, ZNF3025, EEA11, BANK13, HLA-DRB11, CHD25, HLA-DPB11, TPP15, FCRL3, FAIM3, TRIM389, CAT4, SWAP701, HLA-DRA3, HLA-DPB10, HLA-DPB15, RAPGEF14, NBPF14, MS4A14, MTSS18, GLIPR12, ZEB2, EVI2B5, ASAH16, OGFRL10, ADRBK25, GATAD2B6, BTN3A11, NBPF10, AMFR8, PDE11A, AXL0, ZFP361, METTL7A6, NUAK2, MPP66, TXNIP, HIST1H2BK5, TLR107, APOOL7, CD683, LAIR24, LYZ3, CXCL163, SCPEP16, TNFSF13B8, SHOX7, RALGPS2, FGR, RAB128, NOVA16, SPI14, ANXA4, MS4A71, IRF2BPL5, RAB306, SHOX4, FCGR2B, LPAR50, CLECL12, JDP25, RIN22, LILRB10, PAOX1, TMIGD22, POU5F16, CTSZ8, PLEKHM15, PTGIR8, OTUD14, RNASE63, TMEM176A0, ITGAX0, CHST20, MLXIP8, ANGPTL1, RTKN, DAB29, BCL7A7, DST8, AVPI16, FCGR2A, LILRB23, ZNF8210, NT5E5, CLCF16, PITPNA7, PCDHGC31, DTX13, ZNF6231, TXLNB2, CD92, PLTP4, GALNT48, DHRS9, IGJ6, CBX76, FAM65C2, WNT165, SYNPO1, RNF1306, ZNF1553, MS4A142, FMO5, TLE13, MTMR106, CNKSR25, SSPN0, ADGRE26, L3MBTL42, IKZF2, ABCA19, ABHD6, NPEPL19, ARHGAP121, SGSH0, TMEM2313, MYO18A7, IGSF61, NRP2, ZNF385A4, DOCK51, LILRB23, PLA2G4B5, CTTNBP2NL, CRLF21 DGKG9, SESN14, TMEM1641, CHST154, DHX586, CTSO5, CTSO5, TNFSF136, FCER1G, DENND5B0, DNMBP8, KLF32, KIAA15987, ARRDC22, EGLN1, PLXNA34, ANPEP3, CST38, TTC21A, ZNF3951, TBC1D21, ANKRD19, ZBP18, HYLS13, HLA-DOB1, B3GNT7, RASSF44, CD200R1, CSF1R7, SLC7A78, ADRB20, SNX309, ZMAT11, TFE36, MALT14, LMF15, APP2, LILRB23, ZNF6082, ADAP26, CPNE57, SYT15, UBE2E2, PTGS11, DUSP15, EPB41L4A1, ALOX54, ALOX51, SIRPA3, IFNGR20, RGS1, LILRB16, HMOX12, LY968, BTN2A20, PLXNC16, NIPSNAP3B8, SETDB1, RNF144B7, HEPACAM8, CLEC4A6, IL74, SOX58, PCDH93, TIMP10, ADORA2A0, RASGEF1B6, HHEX3, CDK146, MAP3K12, FCRL2, RASGRP3, PHACTR15, TYROBP3, COBLL1, CD1808, TGFBI0, LRRK27, ALDH25. |

TABLE 5

| |
|---|
| UBL39, DPEP23, PTK24, TFE36, MALT14, LMF15, APP2, LILRB23, ZNF6082, ADAP26, SH3TC15, BMP2K7, CPNE57, SYT15, UBE2E2, CRIM1, MXD42, PTGS11, DUSP15, EPB41L4A1, TBC1D93, ALOX54, ALOX51, SIRPA3, LILRB18, IFNGR20, RGS1, LILRB16, HMOX12, LY968, BTN2A20, PLXNC16, GSAP9, IFIT21, NIPSNAP3B8, SETDB1, RNF144B7, HEPACAM8, CLEC4A6, IL74, SOX58, PCDH93, FCRL1, TIMP10, ADORA2A0, RASGEF1B6, HHEX3, CDK146, MAP3K12, SIGLEC61, LGALS15, FCRL2, RASGRP3, PHACTR15, TYROBP3, COBLL1, PLD42, CD1808, TGFBI0, LRRK27, ALDH25, HCK3. |
| Preferably DPEP23, PTK24, TFE36, MALT14, LMF15, APP2, LILRB23, ZNF6082, ADAP26, SH3TC15, BMP2K7, CPNE57, SYT15, UBE2E2, CRIM1, MXD42, PTGS11, DUSP15, EPB41L4A1, TBC1D93, ALOX54, ALOX51, SIRPA3, LILRB18, IFNGR20, RGS1, LILRB16, HMOX12, LY968, BTN2A20, PLXNC16, GSAP9, IFIT21, NIPSNAP3B8, SETDB1, RNFT44B7, HEPACAM8, CLEC4A6, IL74, SOX58, PCDH93, FCRL1, TIMP10, ADORA2A0, RASGEF1B6, HHEX3, CDK146, MAP3K12, SIGLEC61, LGALS15, FCRL2, RASGRP3, PHACTR15, TYROBP3, COBLL1, CD1808, TGFBI0, LRRK27, ALDH25, HCK3. |
| More preferably TFE36, MALT14, LMF15, APP2, LILRB23, ZNF6082, ADAP26, CPNE57, SYT15, UBE2E2, PTGS11, DUSP15, EPB41L4A1, ALOX54, ALOX51, SIRPA3, IFNGR20, RGS1, LILRB16, HMOX12, LY968, BTN2A20, PLXNC16, NIPSNAP3B8, SETDB1, RNF144B7, HEPACAM8, CLEC4A6, IL74, SOX58, PCDH93, TIMP10, ADORA2A0, RASGEF1B6, HHEX3, CDK146, MAP3K12, FCRL2, RASGRP3, PHACTR15, TYROBP3, COBLL1, CD1808, TGFBI0, LRRK27, ALDH25. |

Tables 4 and 5 in an embodiment provides a signature of dendritic cells (e.g. cDC), and represents downregulated genes in particular DC subpopulations, termed VEx-A, preferably associated with or derived from elite controller phenotype, preferably associated with HIV infection. Preferably downregulation is evaluated in infected cells, compared to non-infected cells.

TABLE 6

| |
|---|
| CXCL10, CXCL9, CD274, IFITM3, IL4I1, FCGR3A, SLAMF8, ANKRD22, GIMAP4, IL1RN, RGL1, CCR5, CXCL11, DUSP6, ATF3, HCAR3, SERPING1, RAB20, ETV7, FCGR1A, INHBA, CCRL2, C3AR1, CCL2, LILRB4, HK3, C1QB, IRG1, P2RY6, ITGAM, TLR4, TNFRSF1A, LILRA3, LILRB4, CD38, MAFB, SIGLEC1, PTGER2, DOCK4, |

TABLE 6-continued

HCAR2, DMXL2, SECTM1, NPL, EDN1, MSR1, PARP10, LILRA6, C1QC, TLR8, FCN1, ACP2, SUCNR1, FNIP2, LACC1, MOB3C, HAPLN3, FLVCR2, NOD2, MSRB1, TIPARP, FCGR1B, LIMK2, TSC22D1, BATF2, LHFPL2, CCL3, CCL3, CCL3, ZPR1, HERC5, OASL, MITF, SLC1A4, PDCD1LG2, LILRA3, TNFAIP6, TLR2, LILRA3, MTMR6, ACVR2A, CDKN2AIP, ATP13A3, XPNPEP1, KCTD12, LTBR, LGALS2, HLX, SIGLEC9, TMEM51, LILRA3, SORT1, TNF, TNF, TNF, TNF, TNF, TNF, TNF, PPARGC1B, RCE1, LILRA2, SDSL, LGALS3BP, GIMAP6, LILRA6, STEAP4, HEBP1, KCNJ2, CLEC12A, CCL4, CCL4, ELAVL4, EMC8, SOCS3, AIF1, AIF1, AIF1, AIF1, WDR7, SLC1A3, FAM105A, VASH1, SLC16A6, RNF24, AIF1, AIF1, CD300LF, MCTP1, CD276, IL3RA, IL3RA, ADAMTSL4, P2RY14, ZNF654, ARHGEF10L, CD33, LST1, GUCY1A3, SAMD4A, SLC12A7, ZNF438, TIMELESS, PLXND1, OGFR, RNMTL1, LILRA6, SPHK1, APOBEC3B, SLC15A3, CARD9, SOCS1, EMILIN2, SAYSD1, GPR68, CEBPB, CREB5, BATF3, SLC6A12, SRXN1, FCRL6, AQP9, SLC26A11, TCF7L2, SORBS3, ERLIN1, FAM20A, ASCL2, CCL3L1, ZNF317, ENPP2, BST1, CFB, CFB, CFB, CFB, TIFAB, LILRB4, LMTK2, CISH, FBXO30, FAM20C, MRPL2, PLBD1, EEPD1, AMER1, BRI3, VPS9D1, SIK3, AKT1S1, LILRB3, LILRA6, LATS2, STARD8, SLC25A16, LAGE3, SELM, B3GALT4, DCAF17, NEURL3, APOBR, MGST1, MRPL46, METRNL, POP7, CTLA4, PTRH1, MON1A, CRAT, ZMYND15, ZNF707, ZNF707, LILRA1, CPEB3, PDE4A, EXOC6B, MTERF3, DRAM1, SNAPC5, AP4M1, LST1, USP31, CFD, CFD, METRNL, SLC27A3, SLC27A3, CISD3, CISD3, SNF8, PINX1, MED16, PRADC1, MLLT4, GBP5, APOBEC3A, BNIP1, FAM26F, NUFIP1, BAG3, SNX10, CYP1B1, EGR2, MYL5, INAFM1, LILRB3, SMTNL1, KLF10, PLAUR, ICAM1, LST1, LST1, LST1, LST1, LST1, LST1, RSAD2, ATP1B1, RNF19B, FGL2, FFAR2, CYBB, JAKMIP2, CCR1, GBP1, IDO1, TMEM176B, SLC31A2, P2RX7, IFI44L, PLXNB2, PLSCR1, RIN2, FCER1G, TNFSF10, CDKN1A, SQRDL, GLUL, MYOF, IFIT3, LAP3, APOL3, NINJ1, SIRPB1, PIM1, PILRA, CTSL, CENPJ, TFEC, PTPRE, SLAMF7, GK, POU5F1, IFIT2, SMAP2, GBP4, RAPGEF2, MRAS, ATF5, RIPK2, LILRB2, SLC25A13, KDM6B, IGSF6, KMO, CUL1, EPB41L3, GCH1, LILRB2, DARS2, HSD3B7, TNFAIP2, SPG20, STX11, SERTAD1, VMO1, GIMAP8, ATP6V1B2, PPP1R15A, FRG1, FRG1, SLC8A1, UBE2D1, RCBTB2, NCF2, PLXDC2, EPG5, CLEC7A, CD80, RBM47, FCGR2A, UBE2Z, WARS, CD226, ALAS1, SRC, VAMP5, PAK1, FYB, SOD2, LYZ, SERPINA1, IFIH1, CSF2RB, GCLC, SMCO4, ARHGAP10, CTSB, RALB, PLOD3, GABARAPL1, LILRB2, SLC43A3, ENG, TOM1, TYMP, MTHFD2, LILRB2, LRRC25, RHEB, SLC7A7, RAB35, TMEM176A, FKBP15, CXCL16, LGALS3, STAT1 ADPRHL2, KIAA0368, PSTPIP2, DYNLT1, FAR1, PGD, PIM3, BCL2A1, NAMPT, CECR1, GNS, CASP1, DDX21, JAK2, IRF1, NSFL1C, SAT1, GIMAP5, EPSTI1, SCO2, LCP2, TYROBP, RASGEF1B, GTF2B, DENND1B, EAF1, NFE2L2, ATG3, ADGRE2, IFI6, FBXO6, RARRES3, ACSL1, NCF1, RAB24, SEC14L1, TNS3, PTAFR, TRAFD1, IFITM1, DNAJC7, MS4A7, MIIP, MGAT1, AATF, AATF, LPCAT2, NCF4, ATP1B3, LYN, CD68, GBP2, STAT2, CTSS, EIF2S1, IRF7, TXN, YWHAG, NMI, JUNB, SDCBP, RNH1, RNH1, IFI30, PSME2, CCDC47, TMEM30A, FKBP5, UBE2L6, APOL2, MT2A, CD40, APOL4, MDM2, STOM, SPPL2A, DTX3L, GLIPR2, OAS3, PTTG1IP, CTSD, DEK, PRDX1, NUP62, APOL6, TAP1, TAP1, TAP1, TAP1, TAP1, TAP1, LILRB2, NBN, TANK, CNDP2, CTSC, S100A11, TRIM22, STAT3, UBC, ITGAX, IRP2, RNF213, ZNFX1, KLF6, ANXA5, PSAP, SNX27, H3F3B, ATP6V0B, TNFSF13B, XAF1, TMSB10, ANXA2, PARP14, ENO1, LAPTM5, RPL15, RPL4, RPL28, RPL6, TPT1, RPL18, PTMA, EEF1B2, HLA-DQB1, RPL35A, RPS20, RPS16, RPL19, LPIN3, RPL24, RPS15A, RPS24, RPL26, RPS19, TRIM38, DDX17, RPS13, NME2, RPL36A, RPS10, RPS7, RPS17, RPS17, RPS14, GNB2L1, RPL11, RPL17, RPL9, RPL37A, RPS23, APOBEC3F, RPS27A, RPS4Y1, RPL14, RPS9, RPS9, RPS9, RPS9, RPS9, RPS9, RPS9, RPS9, RPL38, HLA-DQA1, HLA-DQA1, RPS2, RPL7, ITSN2, RPL30, RPL18A, TTC3, RPL27, RPS27, RPLP2, TSPYL1, BTN3A2, TOMM7, RPL37, RPL31, RPS8, RPS11, RPS3, CPNE1, OGT, PIK3CD, RPS29, RPL41, RPL5, PDK3, APOBEC3C, CNN2, GSTP1, RPL34, ERP29, SASH3, RCSD1, RPL39, RPL27A, PARP1, MCM5, RPS21, HMGB1, RPL10A, RPL32, RPLP0, ARHGAP25, FDFT1, AKNA, EIF4B, RPS4X, RPS3A, ZNF302, POU2AF1, RAC2, LIMD2, TNFRSF1B, RPS5, RPL7A, RPL7A, RPLP1, RPS6, RABGAP1L, PEBP1, ARHGD1B, RPS18, RPS18, RPS18, RPS18, RPS18, CASP2, RAB12, RPL13, FAM96A, CD48, RPL21, RPS25, RPS25, RPSA, SYK, RPL12, RSRP1, ATM, CCL5, CIB1, EEF1G, CCDC69, RPL29, RPS12, SP140, PNN, LMBRD1, RPL3, LRRC37A, SRPK2, ARL17A, BPTF, SPIB, CD37, TNRC6B, IFNLR1, KIAA1551, CD52, RPL13A, ARHGAP15, AMFR, PIKFYVE, ANP32E, CBX5, HMBOX1, SNRPD2, APOOL, SHOX, RPL23A, BLNK, HMGN3, FOXP1, INPP5F, POU2F2, CCR7, TCF4, TRAF3IP3, PXK, SWAP70, CRIP1, ITGB7, NUAK2, IKZF3, GGA2, ECHDC2, ARHGAP24, QARS, RASGRP3, SLC12A8, WDFY4, TP53I11, PSIP1, ADD1, AP1G2, GPR183, SNRPN, EZH1, CBLB, MTSS1, RBM4B, LDHB, SNURF, PHACTR1, EZR, TFEB, SETBP1, SREBF2, GLIPR1, CD82, TCF3, MYO9A, ADAM19, MAST3, ZBTB20, MFNG, ZCCHC11, SMC6, CLEC2D, HIST1H1C, CLECL1, CXCR4, PRR3, PRR3, PRR3, PRR3, IL16, NOVA1, FAM65B, GTF2IRD2, MEF2C, RGL2, RGL2, RGL2, RGL2, RGL2, P2RY10, TTN, PIK3C2B, CAT, IGLL1, SLC38A1, ANKRD1, GALNT1, MPRIP, CORO1A, AFF3, KIAA0355, FAM173A, EPB41, TSPAN3, GSTM2, TCP11L2, CENPK, CAMKMT, WDR59, SNX25, TMEM55B, GCHFR, AGK, RAD51B, EML2, ADARB1, MOSPD3, NUTM2B, ZNF708, PASK, RCAN3, PGAM2, NEXN, GFOD1, HLA-DPA1, PRMT9, TXLNG, HLA-DPA1, TADA2A, KLF2, PYHIN1, ITPR3, RNF141, GAMT, ZBTB37, RNASE6, ZNF439, BBS1, LCLAT1, SNED1, ATF7IP2, CLSTN1, ZNF141, LTBP4, CFAP36, ANGPTL1, RTKN, FAM43A, ALKBH2, GECCI1, CCNG2, P4HTM, CLSTN3, MTA3, MSI2, ENO2, TRAF4, FBXW4, HIST1H2BD, ARL4D, PIK3R1, ITM2A, RAD51C, PGM1, FAM46C, BCL7A, BAD, DPH1, MAFIP, MMD, CCBL1, SH3YL1, RUFY2, RASSF7, RAB39B, TMEM14E, FAM98B, SIT1, CTPS1, NFS1, TRAT1, PPAPDC2, BTBD2, GSTM1, SLC2A1, ARHGAP35, PLTP, DFNA5, ACSS1, SIDT1, SPICE1, OSBPL7, SERGEF, ALDH18A1, TFDP1, DTX1, ATAD2, ATP11B, MYLIP, EFNA4, PCDHGC3, SMAD3, RHOBTB2, FUCA1, MLLT3, ZNF821, MRS2, KLHL3, ZNF66, ZNF700, NT5E, EHD3, HLTF, ZNF813, ACOT2, SERPINH1, CRYZ, TEX9, ZNF287, SHMT1, EPHB6, MBIP, IGJ, SLC26A6,

TABLE 6-continued

| |
|---|
| ZNF581, CLPTM1L, FANCC, PLEKHG1, HDDC2, GZMM, ZNF436, PPOX, CBX7, CHTF18, UNG, FMO5, ZFP3, RAB37, CDC7, FAM65C, ALDOC, ZAP70, SPOCK2, GRAP2, TLE1, ADCY3, WNT16, SYNPO, ZMYND11, ABHD5, CD3E, LBHD1, ZNF138, FUT11, CNKSR2, ZBTB14, THBS3, RNF8, CASD1, JADE3, ZADH2, MTMR10, CD70, CD2, SSPN, CD247, SERF1B, PHC1, EHMT2, FAM78A, RSAD1, TBCD, METTL4, PECR, PAFAH1B3, ANO9, RRAS2, LDLRAP1, TRIB2, SARS2, TMEM231, TER10, FBXO41, ZNF510, RAMP1, HOPX, KIF3B, RCC1, LFNG, LAT, SLC10A7, KIZ, YPEL3, IKZF2, BICD1, RGMB, SURF1, SURF1, REPIN1, AASDH, GSTM4, SKAP1, MAP4K2, FAN1, ZEB1, FLNB, OXCT1, DENND5B, DHRS3, LANCE1, ZNF33B, FAM20B, ZNF518B, ABCD2, DUSP18, ST20, SLC35B4, ATHL1, ACO1, TESPA1, ANKRD33B, CFL2, TOX, NIPSNAP1, RIC3, PLA2G4B, ZNF564, SGSM2, ZNF549, GLMN, GRAP, PRKAB2, DGKG, TM7SF3, PJA1, RASL11A, WBSCR16, CDC14A, DDHD2, CACNA1A, CHST12, FBXO10, CDCA7L, MCM6, KIAA0391, MLH3, STRBP, MDM1, TSEN54, PGAP2, CD27, ACAD11, IL2RB, CHIC1, ZNF507, B3GNT7, LEO1, FAM3C, WDSUB1, DNMBP, SPATA20, RANBP6, OSBPL10, MACROD2, NOL4L, MZF1, KLF8, CARD11, NEDD9, ANK3, BACH2, HN1L, KIF21B, ASNSD1, FAM102A, SACS, PDE4D, PLXNA3, TMEM156, ETS1, ITK, TTC21A, CNR2, DUSP12, EML3, ELP6, CD200R1, TBC1D10A, FOXO1, ABCD4, GOLGA8A, ZNF395, MARCH3, DNHD1, ZNF608, LCK, SGK223, KIAA0226L, DPEP2, ORMDL3, PRF1, ZBTB32, UBL3, ATP2B4, PNOC, DENND4C, ZDHHC21, PCMTD2, CD3D, PTK2, RASGRP2, SYT1, CPNE5, GNG7, BCL11B, ASXL1, FAM179B, CERKL, WDR34, MKNK2, KLF12, TGFBR2, ATP8A1, VPS13A, LRBA, DUS2, ST6GALNAC4, RASGRP1, SYNE1, SUN1, NLRP1, BIN1, VAV2, SLC25A38, TRPT1, ST6GALNAC6, LPCAT1, SLC9A3R1, SEMA4B, ATG4C, EIF4EBP1, SLAMF1, ITPR1, SYTL1, DGKA, USP48, ARHGEF18, NIPSNAP3B, LPAR5, SLC4A7, PCDH9, LY86, SCAPER, STAP1, USP9Y, HMGXB3, IFT57, SEMA7A, GEMIN7, MBNL3, CKAP2, FCRL1, NBEAL2, CLEC17A, SLAMF6, BCL9L, MPP6, CCDC141, ITM2C, INTS1, PFKFB3, SPTBN1, ATP2A3, RHOH, NUP210, NKG7, SOX5, AGL, DNAJC4, AGAP1, ALOX5AP, CHD3, BCAS4, PCED1B, PRRC2B, TMC8, HHEX, TLR9, DEF6, SIGLEC6, PTPN22, PBXIP1, CD99, CD99, ANKRD36, SPPL2B, NFATC2, ANKRD36C, VNN2, SYNE2, CST7, SH2D3C, EBF1, FCRL2, RALGPS2, LY9, PKIG, CALHM2, BTLA, HIP1R, WDR6, CXCR3, FCRL5, ABHD14B, TBC1D10C, CXCR5, AKR1B1, TPD52, ICAM3, SIPA1L3, ID3, P2RX5, ESYT1, ADAM28, PPP1R16B, TNFRSF13B, PLD4, RAB30, COBLL1, CD22, S1PR1, BCL11A, BLK, PDLIM1, FCGR2B, MAP4K1, PRKACB, PAX5, EMB, SHMT2, SEL1L3, CYFIP2, ADD3, ABLIM1, SLC44A2, LRMP, FLOT2, ANXA6, TMEM154, CD19, PTPRCAP, FAIM3, CD79B, IGLL5, BANK1, LBH, ST6GAL1, FCRLA, CD79A, FCRL3, MS4A1. |

Table 6 in an embodiment provides a signature of dendritic cells (e.g. cDC), and represents differentially expressed genes in particular DC subpopulations, termed VEx-B ("virus exposed-B"), preferably associated with or derived from elite controller phenotype, preferably associated with HIV infection. Preferably differential expression is evaluated in infected cells, compared to non-infected cells.

TABLE 7

| |
|---|
| CXCL10, CXCL9, CD274, IFITM3, IL4I1, FCGR3A, SLAMF8, ANKRD22, GIMAP4, IL1RN, RGL1, CCR5, CXCL11, DUSP6, ATF3, HCAR3, SERPING1, RAB20, ETV7, FCGR1A, INHBA, CCRL2, C3AR1, CCL2, LILRB4, HK3, C1QB, IRG1, P2RY6, ITGAM, TLR4, TNFRSF1A, LILRA3, LILRB4, CD38, MAFB, SIGLEC1, PTGER2, DOCK4, HCAR2, DMXL2, SECTM1, NPL, EDN1, MSR1, PARP10, LILRA6, C1QC, TLR8, FCN1, ACP2, SUCNR1, FNIP2, LACC1, MOB3C, HAPLN3, FLVCR2, NOD2, MSRB1, TIPARP, FCGR1B, LIMK2, TSC22D1, BATF2, LHFPL2, CCL3, CCL3, CCL3, ZPR1, HERC5, OASL, MITF, SLC1A4, PDCD1LG2, LILRA3, TNFAIP6, TLR2, LILRA3, MTMR6, ACVR2A, CDKN2AIP, ATP13A3, XPNPEP1, KCTD12, LTBR, LGALS2, HLX, SIGLEC9, TMEM51, LILRA3, SORT1, TNF, TNF, TNF, TNF, TNF, TNF, TNF, PPARGC1B, RCE1, LILRA2, SDSL, LGALS3BP, GIMAP6, LILRA6, STEAP4, HEBP1, KCNJ2, CLEC12A, CCL4, CCL4, ELAVL4, EMC8, SOCS3, AIF1, AIF1, AIF1, AIF1, WDR7, SLC1A3, FAM105A, VASH1, SLC16A6, RNF24, AIF1, AIF1, CD300LF, MCTP1, CD276, IL3RA, IL3RA, ADAMTSL4, P2RY14, ZNF654, ARHGEF10L, CD33, LST1, GUCY1A3, SAMD4A, SLC12A7, ZNF438, TIMELESS, PLXND1, OGFR, RNMTL1, LILRA6, SPHK1, APOBEC3B, SLC15A3, CARD9, SOCS1, EMILIN2, SAYSD1, GPR68, CEBPB, CREB5, BATF3, SLC6A12, SRXN1, FCRL6, AQP9, SLC26A11, TCF7L2, SORBS3, ERLIN1, FAM20A, ASCL2, CCL3L1, ZNF317, ENPP2, BST1, CFB, CFB, CFB, CFB, TIFAB, LILRB4, LMTK2, CISH, FBXO30, FAM20C, MRPL2, PLBD1, EEPD1, AMER1, BRI3, VPS9D1, SIK3, AKTIS1, LILRB3, LILRA6, LATS2, STARD8, SLC25A16, LAGE3, SELM, B3GALT4, DCAF17, NEURL3, APOBR, MGST1, MRPL46, METRNL, POP7, CTLA4, PTRH1, MON1A, CRAT, ZMYND15, ZNF707, ZNF707, LILRA1, CPEB3, PDE4A, EXOC6B, MTERF3, DRAM1, SNAPC5, AP4M1, LST1, USP31, CFD, CFD, METRNL, SLC27A3, SLC27A3, CISD3, CISD3, SNF8, PINX1, MED16, PRADC1, MLLT4, GBP5, APOBEC3A, BNIP1, FAM26F, NUFIP1, BAG3, SNX10, CYP1B1, EGR2, MYL5, INAFM1, LILRB3, SMTNL1, KLF10, PLAUR, ICAM1, LST1, LST1, LST1, LST1, LST1, LST1, RSAD2, ATP1B1, RNF19B, FGL2, FFAR2, CYBB, JAKMIP2, CCR1, GBP1, IDO1, TMEM176B, SLC31A2, P2RX7, IFI44L, PLXNB2, PLSCR1, RIN2, FCER1G, TNFSF10, CDKN1A, SQRDL, GLUL, MYOF, IFIT3, LAP3, APOL3, NINJ1, SIRPB1, PIM1, PILRA, CTSL, CENPJ, TFEC, PTPRE, SLAMF7, GK, POU5F1, IFIT2, SMAP2, GBP4, RAPGEF2, MRAS, ATF5, RIPK2, LILRB2, |

TABLE 7-continued

| |
|---|
| SLC25A13, KDM6B, IGSF6, KMO, CUL1, EPB41L3, GCH1, LILRB2, DARS2, HSD3B7, TNFAIP2, SPG20, STX11, SERTAD1, VMO1, GIMAP8, ATP6V1B2, PPP1R15A, FRG1, FRG1, SLC8A1, UBE2D1, RCBTB2, NCF2, PLXDC2, EPG5, CLEC7A, CD80, RBM47, FCGR2A, UBE2Z, WARS, CD226, ALAS1, SRC, VAMP5, PAK1, FYB, SOD2, LYZ, SERPINA1, IFIH1, CSF2RB, GCLC, SMCO4, ARHGAP10, CTSB, RALB, PLOD3, GABARAPL1, LILRB2, SLC43A3, ENG, TOM1, TYMP, MTHFD2, LILRB2, LRRC25, RHEB, SLC7A7, RAB35, TMEM176A, FKBP15, CXCL16, LGALS3, STAT1, ADPRHL2, KIAA0368, PSTPIP2, DYNLT1, FAR1, PGD, PIM3, BCL2A1, NAMPT, CECR1, GNS, CASP1, DDX21, JAK2, IRF1, NSFL1C, SAT1, GIMAP5, EPSTI1, SCO2, LCP2, TYROBP, RASGEF1B, GTF2B, DENND1B, EAF1, NFE2L2, ATG3, ADGRE2, IFI6, FBXO6, RARRES3, ACSL1, NCF1, RAB24, SEC14L1, TNS3, PTAFR, TRAFD1, IFITM1, DNAJC7, MS4A7, MIIP, MGAT1, AATF, AATF, LPCAT2, NCF4, ATP1B3, LYN, CD68, GBP2, STAT2, CTSS, ETF2S1, IRF7, TXN, YWHAG, NMI, JUNB, SDCBP, RNH1, RNH1, IFI30, PSME2, CCDC47, TMEM30A, FKBP5, UBE2L6, APOL2, MT2A, CD40, APOL4, MDM2, STOM, SPPL2A, DTX3L, GLIPR2, OAS3, PTTG1IP, CTSD, DEK, PRDX1, NUP62, APOL6, TAP1, TAP1, TAP1, TAP1, TAP1, TAP1, LILRB2, NBN, TANK, CNDP2, CTSC, S100A11, TRIM22, STAT3, UBC, ITGAX, IRF2, RNF213, ZNFX1, KLF6, ANXA5, PSAP, SNX27, H3F3B, ATP6V0B, TNFSF13B, XAF1, TMSB10, ANXA2, PARP14, ENO1. Preferably CXCL10, CXCL9, CD274, IFITM3, IL4I1, FCGR3A, SLAMF8, ANKRD22, GIMAP4, IL1RN, RGL1, CCR5, CXCL11, DUSP6, ATF3, HCAR3, SERPFNG1, RAB20, ETV7, FCGR1A, INHBA, CCRL2, C3AR1, CCL2, LILRB4, HK3, C1QB, IRG1, P2RY6, ITGAM, TLR4, TNFRSF1A, LILRA3, LILRB4, CD38, MAFB, SIGLEC1, PTGER2, DOCK4, HCAR2, DMXL2, SECTM1, NPL, EDN1, MSR1, PARP10, LILRA6, C1QC, TLR8, FCN1, ACP2, SUCNR1, FNIP2, LACC1, MOB3C, HAPLN3, FLVCR2, NOD2, MSRB1, TIPARP, FCGR1B, LIMK2, TSC22D1, BATF2, CCL3, CCL3, CCL3, ZPR1, OASL, MITF, SLC1A4, PDCD1LG2, LILRA3, TNFAIP6, TLR2, LILRA3, MTMR6, ACVR2A, CDKN2AIP, ATP13A3, XPNPEP1, KCTD12, LTBR, LGALS2, HLX, SIGLEC9, TMEM51, LILRA3, SORT1, TNF, TNF, TNF, TNF, TNF, TNF, TNF, PPARGC1B, RCE1, LILRA2, SDSL, LGALS3BP, GIMAP6, LILRA6, STEAP4, HEBP1, KCNJ2, CCL4, CCL4, ELAVL4, EMC8, SOCS3, AIF1, AIF1, AIF1, AIF1, SLC1A3, FAM105A, VASH1, SLC16A6, AIF1, AIF1, CD300LF, MCTP1, ADAMTSL4, P2RY14, ZNF654, ARHGEF10L, CD33, LST1, SAMD4A, SLC12A7, ZNF438, RNMTL1, LILRA6, SPHK1, APOBEC3B, CARD9, SOCS1, EMILIN2, SAYSD1, GPR68, CEBPB, BATF3, SRXN1, FCRL6, AQP9, TCF7L2, ERLIN1, FAM20A, ASCL2, CCL3L1, ZNF317, ENPP2, BST1, CFB, CFB, CFB, CFB, TIFAB, LILRB4, LMTK2, CISH, FBXO30, PLBD1, AMER1, BRI3, SIK3, AKT1S1, LILRB3, LILRA6, STARD8, SLC25A16, DCAF17, NEURL3, APOBR, MGST1, MRPL46, METRNL, PTRH1, CPEB3, MTERF3, DRAM1, LST1, USP31, METRNL, SLC27A3, SLC27A3, CISD3, CISD3, SNF8, PINX1, MED16, MLLT4, GBP5, APOBEC3A, BNIP1, FAM26F, NUFIP1, SNX10, CYP1B1, EGR2, MYL5, INAFM1, LILRB3, SMTNL1, KLF10, PLAUR, ICAM1, LST1, LST1, LST1, LST1, LST1, LST1, RSAD2, ATP1B1, FGL2, FFAR2, CYBB, CCR1, GBP1, IDO1, TMEM176B, SLC31A2, P2RX7, IFI44L, PLXNB2, PLSCR1, RIN2, FCER1G, TNFSF10, CDKN1A, SQRDL, GLUL, MYOF, IFIT3, LAP3, APOL3, NINJ1, SIRPB1, PIM1, PILRA, CTSL, TFEC, PTPRE, SLAMF7, GK, IFIT2, SMAP2, GBP4, RAPGEF2, RIPK2, LILRB2, SLC25A13, KDM6B, IGSF6, KMO, CUL1, EPB41L3, GCH1, LILRB2, DARS2, HSD3B7, TNFAIP2, SPG20, STX11, SERTAD1, VMO1, GIMAP8, ATP6V1B2, PPP1R15A, SLC8A1, UBE2D1, RCBTB2, NCF2, PLXDC2, EPG5, CLEC7A, CD80, RBM47, UBE2Z, WARS, CD226, ALAS1, SRC, VAMP5, PAK1, FYB, SOD2, LYZ, IFIH1, CSF2RB, GCLC, SMCO4, ARHGAP10, CTSB, RALB, PLOD3, GABARAPL1, LILRB2, SLC43A3, TOM1, TYMP, MTHFD2, LILRB2, LRRC25, RHEB, SLC7A7, CXCL16, LGALS3, STAT1, PSTPIP2, FAR1, PGD, PIM3, BCL2A1, NAMPT, CECR1, GNS, DDX21, JAK2, IRF1, SAT1, GIMAP5, EPSTI1, LCP2, TYROBP, RASGEF1B, EAF1, NFE2L2, ATG3, ADGRE2, IFI6, FBXO6, ACSL1, NCF1, TNS3, PTAFR, TRAFD1, IFITM1, DNAJC7, MS4A7, MGAT1, LPCAT2, NCF4, ATP1B3, LYN, CD68, GBP2, STAT2, CTSS, EIF2S1, IRF7, TXN, NMI, JUNB, SDCBP, RNH1, RNH1, IFI30, PSME2, UBE2L6, APOL2, CD40, APOL4, STOM, SPPL2A, DTX3L, OAS3, DEK, PRDX1, APOL6, TAP1, TAP1, TAP1, TAP1, TAP1, TAP1, CNDP2, CTSC, S100A11, TRIM22, UBC, RNF213, KLF6, ANXA5, PSAP, H3F3B, XAF1, TMSB10, ANXA2, PARP14. |

TABLE 8

| |
|---|
| CXCL10, CXCL9, CD274, IFITM3, IL4I1, FCGR3A, SLAMF8, ANKRD22, GIMAP4, IL1RN, RGL1, CCR5, CXCL11, DUSP6, ATF3, HCAR3, SERPING1, RAB20, ETV7, FCGR1A, INHBA, CCRL2, C3AR1, CCL2, LILRB4, HK3, C1QB, IRG1, P2RY6, ITGAM, TLR4, TNFRSF1A, LILRA3, LILRB4, CD38, MAFB, SIGLEC1, PTGER2, DOCK4, HCAR2, DMXL2, SECTM1, NPL, EDN1, MSR1, PARP10, LILRA6, C1QC, TLR8, FCN1, ACP2, SUCNR1, FNIP2, LACC1, MOB3C, HAPLN3, FLVCR2, NOD2, MSRB1, TIPARP, FCGR1B, LIMK2, TSC22D1, BATF2, LHFPL2, CCL3, CCL3, CCL3, ZPR1, HERC5, OASL, MITF, SLC1A4, PDCD1LG2, LILRA3, TNFAIP6, TLR2, LILRA3, MTMR6, ACVR2A, CDKN2AIP, ATP13A3, XPNPEP1, KCTD12, LTBR, LGALS2, HLX, SIGLEC9, TMEM51, LILRA3, SORT1, TNF, TNF, TNF, TNF, TNF, TNF, TNF, PPARGC1B, RCE1, LILRA2, SDSL, LGALS3BP, GIMAP6, LILRA6, STEAP4, HEBP1, KCNJ2, CLEC12A, CCL4, CCL4, ELAVL4, EMC8, SOCS3, AIF1, AIF1, AIF1, AIF1, WDR7, SLC1A3, FAM105A, VASH1, SLC16A6, RNF24, AIF1, AIF1, CD300LF, MCTP1, CD276, IL3RA, IL3RA, ADAMTSL4, P2RY14, ZNF654, ARHGEF10L, CD33, LST1, GUCY1A3, SAMD4A, SLC12A7, ZNF438, TIMELESS, PLXND1, OGFR, RNMTL1, LILRA6, SPHK1. |

TABLE 8-continued

| |
|---|
| Preferably CXCL10, CXCL9, CD274, IFITM3, IL4I1, FCGR3A, SLAMF8, ANKRD22, GIMAP4, IL1RN, RGL1, CCR5, CXCL11, DUSP6, ATF3, HCAR3, SERPING1, RAB20, ETV7, FCGR1A, INHBA, CCRL2, C3AR1, CCL2, LILRB4, HK3, C1QB, IRG1, P2RY6, ITGAM, TLR4, TNFRSF1A, LILRA3, LILRB4, CD38, MAFB, SIGLEC1, PTGER2, DOCK4, HCAR2, DMXL2, SECTM1, NPL, EDN1, MSR1, PARP10, LILRA6, C1QC, TLR8, FCN1, ACP2, SUCNR1, FNIP2, LACC1, MOB3C, HAPLN3, FLVCR2, NOD2, MSRB1, TIPARP, FCGR1B, LIMK2, TSC22D1, BATF2, CCL3, CCL3, CCL3, ZPR1, OASL, MITF, SLC1A4, PDCD1LG2, LILRA3, TNFAIP6, TLR2, LILRA3, MTMR6, ACVR2A, CDKN2AIP, ATP13A3, XPNPEP1, KCTD12, LTBR, LGALS2, HLX, SIGLEC9, TMEM51, LILRA3, SORT1, TNF, TNF, TNF, TNF, TNF, TNF, TNF, PPARGC1B, RCE1, LILRA2, SDSL, LGALS3BP, GIMAP6, LILRA6, STEAP4, HEBP1, KCNJ2, CCL4, CCL4, ELAVL4, EMC8, SOCS3, AIF1, AIF1, AIF1, AIF1, SLC1A3, FAM105A, VASH1, SLC16A6, AIF1, AIF1, CD300LF, MCTP1, ADAMTSL4, P2RY14, ZNF654, ARHGEF10L, CD33, LST1, SAMD4A, SLC12A7, ZNF438, RNMTL1, LILRA6, SPHK1. |

Tables 7 and 8 in an embodiment provides a signature of dendritic cells (e.g. cDC), and represents upregulated genes in particular DC subpopulations, termed VEx-B, preferably associated with or derived from elite controller phenotype, preferably associated with HIV infection. Preferably upregulation is evaluated in infected cells, compared to non-infected cells.

TABLE 9

| |
|---|
| LAPTM5, RPL15, RPL4, RPL28, RPL6, TPT1, RPL18, PTMA, EEF1B2, HLA-DQB1, RPL35A, RPS20, RPS16, RPL19, LPIN3, RPL24, RPS15A, RPS24, RPL26, RPS19, TRIM38, DDX17, RPS13, NME2, RPL36A, RPS10, RPS7, RPS17, RPS17, RPS14, GNB2L1, RPL11, RPL17, RPL9, RPL37A, RPS23, APOBEC3F, RPS27A, RPS4Y1, RPL14, RPS9, RPS9, RPS9, RPS9, RPS9, RPS9, RPS9, RPL38, HLA-DQA1, HLA-DQA1, RPS2, RPL7, ITSN2, RPL30, RPL18A, TTC3, RPL27, RPS27, RPLP2, TSPYL1, BTN3A2, TOMM7, RPL37, RPL31, RPS8, RPS11, RPS3, CPNE1, OGT, PIK3CD, RPS29, RPL41, RPL5, PDK3, APOBEC3C, CNN2, GSTP1, RPL34, ERP29, SASH3, RCSD1, RPL39, RPL27A, PARP1, MCM5, RPS21, HMGB1, RPL10A, RPL32, RPLP0, ARHGAP25, FDFT1, AKNA, EIF4B, RPS4X, RPS3A, ZNF302, POU2AF1, RAC2, LIMD2, TNFRSF1B, RPS5, RPL7A, RPL7A, RPLP1, RPS6, RABGAP1L, PEBP1, ARHGDIB, RPS18, RPS18, RPS18, RPS18, RPS18, CASP2, RAB12, RPL13, FAM96A, CD48, RPL21, RPS25, RPS25, RPSA, SYK, RPL12, RSRP1, ATM, CCL5, CIB1, EEF1G, CCDC69, RPL29, RPS12, SP140, PNN, LMBRD1, RPL3, LRRC37A, SRPK2, ARL17A, BPTF, SPIB, CD37, TNRC6B, IFNLR1, KIAA1551, CD52, RPL13A, ARHGAP15, AMFR, PIKFYVE, ANP32E, CBX5, HMBOX1, SNRPD2, APOOL, SHOX, RPL23A, BLNK, HMGN3, FOXP1, INPP5F, POU2F2, CCR7, TCF4, TRAF3IP3, PXK, SWAP70, CRIP1, ITGB7, NUAK2, IKZF3, GGA2, ECHDC2, ARHGAP24, QARS, RASGRP3, SLC12A8, WDFY4, TP53I11, PSIP1, ADD1, AP1G2, GPR183, SNRPN, EZH1, CBLB, MTSS1, RBM4B, LDHB, SNURF, PHACTR1, EZR, TFEB, SETBP1, SREBF2, GLIPR1, CD82, TCF3, MYO9A, ADAM19, MAST3, ZBTB20, MFNG, ZCCHC11, SMC6, CLEC2D, HIST1H1C, CLECL1, CXCR4, PRR3, PRR3, PRR3, PRR3, IL16, NOVA1, FAM65B, GTF2IRD2, MEF2C, RGL2, RGL2, RGL2, RGL2, RGL2, P2RY10, TTN, PIK3C2B, CAT, IGLL1, SLC38A1, ANKRD1, GALNT1, MPRIP, CORO1A, AFF3, KIAA0355, FAM173A, EPB41, TSPAN3, GSTM2, TCP11L2, CENPK, CAMKMT, WDR59, SNX25, TMEM55B, GCHFR, AGK, RAD51B, EML2, ADARB1, MOSPD3, NUTM2B, ZNF708, PASK, RCAN3, PGAM2, NEXN, GFOD1, HLA-DPA1, PRMT9, TXLNG, HLA-DPA1, TADA2A, KLF2, PYHIN1, ITPR3, RNF141, GAMT, ZBTB37, RNASE6, ZNF439, BBS1, LCLAT1, SNED1, ATF7IP2, CLSTN1, ZNF141, LTRP4, CFAP36, ANGPTL1, RTKN, FAM43A, ALKBH2, GLCCI1, CCNG2, P4HTM, CLSTN3, MTA3, MSI2, ENO2, TRAF4, FBXW4, HIST1H2BD, ARL4D, PIK3R1, ITM2A, RAD51C, PGM1, FAM46C, BCL7A, BAD, DPH1, MAFIP, MMD, CCBL1, SH3YL1, RUFY2, RASSF7, RAB39B, TMEM14E, FAM98B, SIT1, CTPS1, NFS1, TRAT1, PPAPDC2, BTBD2, GSTM1, SLC2A1, ARHGAP35, PLTP, DFNA5, ACSS1, SIDT1, SPICE1, OSBPL7, SERGEF, ALDH18A1, TFDP1, DTX1, ATAD2, ATP11B, MYLIP, EFNA4, PCDHGC3, SMAD3, RHOBTB2, FUCA1, MLLT3, ZNF821, MRS2, KLHL3, ZNF66, ZNF700, NT5E, EHD3, HLTF, ZNF813, ACOT2, SERPINH1, CRYZ, TEX9, ZNF287, SHMT1, EPHB6, MBIP, IGJ, SLC26A6, ZNF581, CLPTM1L, FANCC, PLEKHG1, HDDC2, GZMM, ZNF436, PPOX, CBX7, CHTF18, UNG, FMO5, ZFP3, RAB37, CDC7, FAM65C, ALDOC, ZAP70, SPOCK2, GRAP2, TLE1, ADCY3, WNT16, SYNPO, ZMYND11, ABHD5, CD3E, LBHD1, ZNF138, FUT11, CNKSR2, ZBTB14, THBS3, RNF8, CASD1, JADE3, ZADH2, MTMR10, CD70, CD2, SSPN, CD247, SERF1B, PHC1, EHMT2, FAM78A, RSAD1, TBCD, METTL4, PECR, PAFAH1B3, ANO9, RRAS2, LDLRAP1, TRIB2, SARS2, TMEM231, TLR10, FBXO41, ZNF510, RAMP1, HOPX, KIF3B, RCC1, LFNG, LAT, SLC10A7, KIZ, YPEL3, IKZF2, BICD1, RGMB, SURF1, SURF1, REPIN1, AASDH, GSTM4, SKAP1, MAP4K2, FAN1, ZEB1, FLNB, OXCT1, DENND5B, DHRS3, LANCL1, ZNF33B, FAM20B, ZNF518B, ABCD2, DUSP18, ST20, SLC35B4, ATHL1, ACO1, TESPA1, ANKRD33B, CFL2, TOX, NIPSNAP1, RIC3, PLA2G4B, ZNF564, SGSM2, ZNF549, GLMN, GRAP, PRKAB2, DGKG, TM7SF3, PJA1, RASL11A, WBSCR16, CDC14A, DDHD2, CACNA1A, CHST12, FBXO10, CDCA7L, MCM6, KIAA0391, MLH3, STRBP, MDM1, TSEN54, PGAP2, CD27, ACAD11, IL2RB, CHIC1, ZNF507, B3GNT7, LEO1, FAM3C, WDSUB1, DNMBP, SPATA20, RANBP6, OSBPL10, MACROD2, NOL4L, MZF1, KLF8, CARD11, NEDD9, ANK3, |

TABLE 9-continued

| |
|---|
| BACH2, HN1L, KTF21B, ASNSD1, FAM102A, SACS, PDE4D, PLXNA3, TMEM156, ETS1, ITK, TTC21A, CNR2, DUSP12, EML3, ELP6, CD200R1, TBC1D10A, FOXO1, ABCD4, GOLGA8A, ZNF395, MARCH3, DNHD1, ZNF608, LCK, SGK223, KIAA0226L, DPEP2, ORMDL3, PRF1, ZBTB32, UBL3, ATP2B4, PNOC, DENND4C, ZDHHC21, PCMTD2, CD3D, PTK2, RASGRP2, SYT1, CPNE5, GNG7, BCL11B, ASXL1, FAM179B, CERKL, WDR34, MKNK2, KLF12, TGFBR2, ATP8A1, VPS13A, LRBA, DUS2, ST6GALNAC4, RASGRP1, SYNE1, SUN1, NLRP1, BIN1, VAV2, SLC25A38, TRPT1, ST6GALNAC6, LPCAT1, SLC9A3R1, SEMA4B, ATG4C, EIE4EBP1, SLAMF1, ITPR1, SYTL1, DGKA, USP48, ARHGEF18, NIPSNAP3B, LPAR5, SLC4A7, PCDH9, LY86, SCAPER, STAP1, USP9Y, HMGXB3, IFT57, SEMA7A, GEMIN7, MBNL3, CKAP2, FCRL1, NBEAL2, CLEC17A, SLAMF6, BCL9L, MPP6, CCDC141, ITM2C, INTS1, PFKFB3, SPTBN1, ATP2A3, RHOH, NUP210, NKG7, SOX5, AGL, DNAJC4, ACAP1, ALOX5AP, CHD3, BCAS4, PCED1B, PRRC2B, TMC8, HHEX, TLR9, DEF6, SIGLEC6, PTPN22, PBXIP1, CD99, CD99, ANKRD36, SPPL2B, NFATC2, ANKRD36C, VNN2, SYNH2, CST7, SH2D3C, EBF1, FCRL2, RALGPS2, LY9, PKIG, CALHM2, BTLA, HIP1R, WDR6, CXCR3, FCRL5, ABHD14B, TBC1D10C, CXCR5, AKR1B1, TPD52, ICAM3, SIPA1L3, ID3, P2RX5, ESYT1, ADAM28, PPP1R16B, TNFRSF13B, PLD4, RAB30, COBLL1, CD22, S1PR1, BCL11A, BLK, PDLIM1, FCGR2B, MAP4K1, PRKACB, PAX5, EMB, SHMT2, SEL1L3, CYFIP2, ADD3, ABLIM1, SLC44A2, LRMP, FLOT2, ANXA6, TMEM154, CD19, PTPRCAP, FAIM3, CD79B, IGLL5, BANK1, LBH, ST6GAL1, FCRLA, CD79A, FCRL3, MS4A1. |
| Preferably RPL15, RPL4, PTMA, RPS20, RPS16, RPL19, RPL24, RPS15A, RPS24, RPL26, RPS19, DDX17, RPS13, RPL36A, RPS10, RPS7, RPS17, RPS14, GNB2L1, RPL11, RPL17, RPL9, RPL37A, RPS23, RPS27A, RPL14, RPS9, RPS9, RPS9, RPS9, RPS9, RPS9, RPS9, RPL38, HLA-DQA1, HLA-DQA1, RPS2, RPL7, RPL30, RPL18A, RPL27, RPS27, RPLP2, BTN3A2, TOMM7, RPL37, RPL31, RPS8, RPS11, RPS3, PIK3CD, RPS29, RPL41, RPL5, APOBEC3C, CNN2, GSTP1, RPL34, RCSD1, RPL39, RPL27A, RPS21, HMGB1, RPL10A, RPL32, RPLP0, FDFT1, AKNA, EIF4B, RPS4X, RPS3A, RAC2, LIMD2, TNFRSF1B, RPS5, RPL7A, RPL7A, RPLP1, RPS6, PEBP1, ARHGDIB, RPS18, RPS18, RPS18, RPS18, RPS18, CASP2, RAB12 RPE13, FAM96A, CD48, RPL21, RPS25, RPS25, RPSA, SYK, RPL12, RSRP1, ATM, CCL5, CIB1, EEF1G, RPL29, RPS12, PNN, LMBRD1, RPL3, SRPK2, ARL17A, BPTF, SPIB, CD37, TNRC6B, IFNLR1, KIAA1551, CD52, RPL13A, AMFR, ANP32E, CBX5, HMBOX1, SNRPD2, APOOL, SHOX, RPL23A, FOXP1, POU2F2, CCR7, TCF4, PXK, SWAP70, CRIP1, ITGB7, NUAK2, IKZF3, GGA2, QARS, RASGRP3, SLC12A8, WDFY4, TP53I11, ADD1, AP1G2, GPR183, CBLB, MTSS1, LDHB, PHACTR1, EZR, TFEB, SETBP1, SREBF2, GLIPR1, CD82, ADAM19, MAST3, ZBTB20, MFNG, ZCCHC11, SMC6, CLEC2D, HIST1H1C, CLECL1, CXCR4, IL16, NOVA1, FAM65B, GTF2IRD2, MEF2C, RGL2, RGL2, RGL2, RGL2, RGL2, P2RY10, TTN, CAT, IGLL1, SLC38A1, GALNT1, MPRIP, CORO1A, AFF3, KIAA0355, EPB41, TSPAN3, GSTM2, TCP11L2, CENPK, WDR59, SNX25, TMEM55B, GCHFR, AGK, EML2, ADARB1, NUTM2B, PASK, RCAN3, PGAM2, NEXN, GFOD1, PRMT9, TXLNG, PYHIN1, ITPR3, RNF141, ZBTB37, RNASE6, ZNF439, BBS1, LCLAT1, SNED1, ATF7IP2, CLSTN1, ZNF141, LTBP4, ANGPTL1, RTKN, ALKBH2, GLCCI1, CCNG2, P4HTM, CLSTN3, MTA3, MSI2, ENO2, HIST1H2BD, ARL4D, PIK3R1, RAD51C, PGM1, FAM46C, BCL7A, BAD, DPH1, MAFIP, MMD, CCBL1, TMEM14E, FAM98B, SIT1, CTPS1, NFS1, TRAT1, PPAPDC2, BTBD2, GSTM1, SLC2A1, ARHGAP35, PLTP, DFNA5, ACSS1, SPICE1, OSBPL7, SERGEF, ALDH18A1, TFDP1, DTX1, ATAD2, MYLIP, EFNA4, PCDHGC3, FUCA1, MLLT3, ZNF821, MRS2, KLHL3, ZNF66, ZNF700, NT5E, EHD3, SERPINH1, CRYZ, TEX9, ZNF287, SHMT1, EPHB6, MBIP, IGJ, PLEKHG1, HDDC2, GZMM, ZNF436, PPOX, CBX7, FMO5, ZFP3, RAB37, CDC7, FAM65C, ALDOC, SPOCK2, GRAP2, TLE1, ADCY3, WNT16, CD3E, LBHD1, ZNF138, FUT11, CNKSR2, ZBTB14, RNF8, CASD1, JADE3, CD70, CD2, SSPN, CD247, FAM78A, RSAD1, TBCD, METTL4, PECR, PAFAH1B3, ANO9, RRAS2, LDLRAP1, TRIB2, SARS2, TMEM231, TER10, FBXO41, RAMP1, HOPX, RCC1, LENG, LAT, SLC10A7, YPEL3, IKZF2, BICD1, RGMB, AASDH, GSTM4, SKAP1, OXCT1, DENND5B, DHRS3, LANCL1, ZNF33B, FAM20B, ZNF518B, SLC35B4, ATHL1, ACO1, TESPA1, ANKRD33B, CFL2, TOX, NIPSNAP1, RIC3, PLA2G4B, SGSM2, ZNF549, GLMN, GRAP, PRKAB2, DGKG, CDC14A, DDHD2, CACNA1A, CHST12, FBXO10, CDCA7L, MCM6, STRBP, TSEN54, PGAP2, CD27, ACAD11, IL2RB, CHIC1, ZNF507, B3GNT7, WDSUB1, DNMBP, SPATA20, RANBP6, OSBPL10, MACROD2, NOL4L, MZF1, KLF8, CARD11, NEDD9, ANK3, BACH2, HN1L, KTF21B, SACS, PDE4D, PLXNA3, TMEM156, ETS1, ITK, TTC21A, CNR2, EML3, ELP6, CD200R1, TBC1D10A, ABCD4, GOLGA8A, ZNF395, MARCH3, DNHD1, ZNF608, LCK, SGK223, KIAA0226L, ORMDL3, PRF1, ZBTB32, UBL3, ATP2B4, PNOC, ZDHHC21, PCMTD2, CD3D, PTK2, RASGRP2, SYT1, CPNE5, GNG7, BCL11B, FAM179B, CERKL, WDR34, MKNK2, KLF12, ATP8A1, VPS13A, LRBA, DUS2, ST6GALNAC4, RASGRP1, SYNE1, SUN1, NLRP1, BIN1, VAV2, SLC25A38, TRPT1, ST6GALNAC6, LPCAT1, SLC9A3R1, SEMA4B, EIF4EBP1, SLAMF1, ITPR1, SYTL1, DGKA, USP48, ARHGEF18, NIPSNAP3B, LPAR5, SLC4A7, PCDH9, LY86, SCAPER, STAP1, USP9Y, HMGXB3, IFT57, SEMA7A, GEMIN7, MBNL3, CKAP2, FCRL1, NBEAL2, CLEC17A, SLAMF6, BCL9L, MPP6, CCDC141, ITM2C, INTS1, PFKFB3, SPTBN1, ATP2A3, RHOH, NUP210, NKG7, SOX5, AGL, DNAJC4, AGAP1, ALOX5AP, CHD3, BCAS4, PCED1B, PRRC2B, TMC8, HHEX, TLR9, DEF6, SIGLEC6, PTPN22, PBXIP1, CD99, CD99, ANKRD36, SPPL2B, NFATC2, ANKRD36C, VNN2, SYNE2, CST7, SH2D3C, EBF1, FCRL2, RALGPS2, LY9, PKIG, CALHM2, BTLA, HIP1R, WDR6, CXCR3, FCRL5, ABHD14B, TBC1D10C, CXCR5, AKR1B1, TPD52, ICAM3, SIPA1L3, ID3, P2RX5, ESYT1, ADAM28, PPP1R16B, TNFRSF13B, PLD4, RAB30, |

TABLE 9-continued

| |
|---|
| COBLL1, CD22, SIPR1, BCL11A, BLK, PDLIM1, FCGR2B, MAP4K1, PRKACB, PAX5, EMB, SHMT2, SEL1L3, CYFIP2, ADD3, ABLIM1, SLC44A2, LRMP, FLOT2, ANXA6, TMEM154, CD19, PTPRCAP, FAIM3, CD79B, IGLL5, BANK1, LBH, ST6GAL1, FCRLA, CD79A, FCRL3, MS4A1. |

TABLE 10

| |
|---|
| SGK223, KIAA0226L, DPEP2, ORMDL3, PRF1, ZBTB32, UBL3, ATP2B4, PNOC, DENND4C, ZDHHC21, PCMTD2, CD3D, PTK2, RASGRP2, SYT1, CPNE5, GNG7, BCL11B, ASXL1, FAM179B, CERKL, WDR34, MKNK2, KLF12, TGFBR2, ATP8A1, VPS13A, LRBA, DUS2, ST6GALNAC4, RASGRP1, SYNE1, SUN1, NLRP1, BIN1, VAV2, SLC25A38, TRPT1, ST6GALNAC6, LPCAT1, SLC9A3R1, SEMA4B, ATG4C, EIF4EBP1, SLAMF1, ITPR1, SYTL1, DGKA, USP48, ARHGEF18, NIPSNAP3B, LPAR5, SLC4A7, PCDH9, LY86, SCAPER, STAP1, USP9Y, HMGXB3, IFT57, SEMA7A, GEMIN7, MBNL3, CKAP2, FCRL1, NBEAL2, CLEC17A, SLAMF6, BCL9L, MPP6, CCDC141, ITM2C, INTS1, PFKFB3, SPTBN1, ATP2A3, RHOH, NUP210, NKG7, SOX5, AGL, DNAJC4, ACAP1, ALOX5AP, CHD3, BCAS4, PCED1B, PRRC2B, TMC8, HHEX, TLR9, DEF6, SIGLEC6, PTPN22, PBXIP1, CD99, CD99, ANKRD36, SPPL2B, NFATC2, ANKRD36C, VNN2, SYNE2, CST7, SH2D3C, EBF1, FCRL2, RALGPS2, LY9, PKIG, CALHM2, BTLA, HIP1R, WDR6, CXCR3, FCRL5, ABHD14B, TBC1D10C, CXCR5, AKR1B1, TPD52, ICAM3, SIPA1L3, ID3, P2RX5, ESYT1, ADAM28, PPP1R16B, TNFRSF13B, PLD4, RAB30, COBLL1, CD22, S1PR1, BCL11A, BLK, PDLIM1, FCGR2B, MAP4K1, PRKACB, PAX5, EMB, SHMT2, SEL1L3, CYFIP2, ADD3, ABLIM1, SLC44A2, LRMP, FLOT2, ANXA6, TMEM154, CD19, PTPRCAP, FAIM3, CD79B, IGLL5, BANK1, LBH, ST6GAL1, FCRLA, CD79A, FCRL3, MS4A1. |
| Preferably SGK223, KIAA0226L, ORMDL3, PRF1, ZBTB32, UBL3, ATP2B4, PNOC, ZDHHC21, PCMTD2, CD3D, PTK2, RASGRP2, SYT1, CPNE5, GNG7, BCL11B, FAM179B, CERKL, WDR34, MKNK2, KLF12, ATP8A1, VPS13A, LRBA, DUS2, ST6GALNAC4, RASGRP1, SYNE1, SUN1, NLRP1, BIN1, VAV2, SLC25A38, TRPT1, ST6GALNAC6, LPCAT1, SLC9A3R1, SEMA4B, EIF4EBP1, SLAMF1, ITPR1, SYTL1, DGKA, USP48, ARHGEF18, NIPSNAP3B, LPAR5, SLC4A7, PCDH9, LY86, SCAPER, STAP1, USP9Y, HMGXB3, IFT57, SEMA7A, GEMIN7, MBNL3, CKAP2, FCRL1, NBEAL2, CLEC17A, SLAMF6, BCL9L, MPP6, CCDC141, ITM2C, INTS1, PFKFB3, SPTBN1, ATP2A3, RHOH, NUP210, NKG7, SOX5, AGL, DNAJC4, AGAP1, ALOX5AP, CHD3, BCAS4, PCED1B, PRRC2B, TMC8, HHEX, TLR9, DEF6, SIGLEC6, PTPN22, PBXIP1, CD99, CD99, ANKRD36, SPPL2B, NFATC2, ANKRD36C, VNN2, SYNE2, CST7, SH2D3C, EBF1, FCRL2, RALGPS2, LY9, PKIG, CALHM2, BTLA, HIP1R, WDR6, CXCR3, FCRL5, ABHD14B, TBC1D10C, CXCR5, AKR1B1, TPD52, ICAM3, SIPA1L3, ID3, P2RX5, ESYT1, ADAM28, PPP1R16B, TNFRSF13B, PLD4, RAB30, COBLL1, CD22, S1PR1, BCL11A, BLK, PDLIM1, FCGR2B, MAP4K1, PRKACB, PAX5, EMB, SHMT2, SEL1L3, CYFIP2, ADD3, ABLIM1, SLC44A2, LRMP, FLOT2, ANXA6, TMEM154, CD19, PTPRCAP, FAIM3, CD79B, IGLL5, BANK1, LBH, ST6GAL1, FCRLA, CD79A, FCRL3, MS4A1. |

Tables 9 and 10 in an embodiment provides a signature of dendritic cells (e.g. cDC), and represents downregulated genes in particular DC subpopulations, termed VEx-B, preferably associated with or derived from elite controller phenotype, preferably associated with HIV infection. Preferably downregulation is evaluated in infected cells, compared to non-infected cells.

TABLE 11

| |
|---|
| MTHFD1, SOCS1, TCL1A, MED26, CXCL10, CD38, FEN1, MIER2, EMC8, PRMT6, KCTD6, SAYSD1, WEE1, MRPL46, GPX7, POU5F1, WWOX, PPM1N, GPALPP1, IFI44L, NAP1L6, IFIT5, IFITM1, GBP4, IFIT3, GBP5, IFI44, SC5D, ISG15, EPSTI1, IRF1, TRIM22, WARS, UBE2L6, APOL2, ISG20, LAP3, IFI6, STAT2, APOL6, DTX3L, RNF213, STAT1, XAF1, PARP14, PSME1, OGFRL1, CAT, APOOL, HEATR5A, LAIR2, CSNK2B, ARRB1, IFT46, PSMG4, TRIM69, POLR3F, NDRG1, TRIM41, RIN2, HYOU1, HYOU1, TMEM62, FAM89B, ZNF699, KBTBD2, HSPE1-MOB4, ENDOV, TUBG2, TADA2A, DHX35, FGGY, KCTD2, COG7, ZAR1, DIAPH2, CRLS1, GNAT2, EI24, PRPS1, ZNF354B, ZFYVE19, TRIM69, RXRA, RNF166, CCDC43, DAB2, TBC1D22B, TXLNB, P4HTM, SLC35B3, ICT1, WDR53, CCBL1, MYO19, KTI12, MMD, MYO19, METTL18, WDR81, FAM73B, CMC1, AIMP2, ZFAND1, A2M, TFDP1, LILRB2, PCDHGC3, ZKSCAN5, TP53RK, DUSP10, TOR2A, CD9, ZBTB41, TMEM254, PCED1A, GMEB2, ZNF821, BDH2, CYP27A1, PCYT1A, WDR81, USF2, KCTD5, ZNF397, PPP1R3E, MED22, MED22, SHMT1, ZNF287, COPG2, SLC26A6, GZMM, ZNF436, ALDOC, ZAP70, RNF130, ZNF786, TEX9, PER3, PAK1IP1, RRAGB, ITGA5, KLF9, DHX37, ABHD5, BSCL2, ZMYND11, HCCS, VPS52, VPS52, CD3E, H2AFJ, JADE3, RRAS2, TK2, LAT, INTS12, FOSL2, GPATCH1, RGMB, NOL6, PIK3CB, ABCD3, IQGAP2, LARS2, SEPHS1, PDE3B, TUBG1, AGRN, NUP37, MVB12A, MYOF, SRBD1, METTL10, LANCL1, CTTNBP2NL, |

TABLE 11-continued

| |
|---|
| IGSF6, CLN3, PLA2G4B, CYFIP1, COG4, GIMAP8, AMICA1, TPRA1, FAN1, POP1, TBXAS1, USP20, DOCK5, ZBED4, SIL1, DAPK1, CDK2AP1, TOR1B, BRD1, MLH3, MAPKAPK3, GLMN, SCYL2, MED21, CRLF2, YIF1B, PDE4D, KIAA1598, RFFL, TNFSF13, PGAP2, PI4K2A, CD4, BTRC, COPS4, ANPEP, WBSCR16, PLXNA3, MTERF1, FCER1G, SEMA4A, ANKRD1, PPTC7, NIPSNAP3A, TBC1D2, GIMAP5, ITK, PDE6D, ZNF441, PITRM1, NFXL1, FES, S100A4, ARHGAP18, CSF1R, ELP6, TRIP4, ANXA1, DHCR24, MED23, ADAP2, PRF1, GIMAP7, THOC5, FURIN, RNF169, MALT1, VPS11, VPS11, COPS7A, USP40, AKAP10, SNX18, SIRPA, ABHD12, AQR, TTLL4, ATG4C, FYB, COA3, TIMP1, ASAP1, DLD, AP3D1, SAMHD1, TGFBI, LGALS3. |

Table 11 in an embodiment provides a signature of dendritic cells (e.g. cDC), and represents differentially expressed genes in particular DC subpopulations, termed VEx-C ("virus exposed-C"), preferably associated with or derived from elite controller phenotype, preferably associated with HIV infection. Preferably differential expression is evaluated in infected cells, compared to non-infected cells.

TABLE 12

| |
|---|
| MTHFD1, SOCS1, TCL1A, MED26, CXCL10, CD38, FEN1, MIER2, EMC8, PRMT6, KCTD6, SAYSD1, WEE1, MRPL46, GPX7, POU5F1, WWOX, PPM1N, GPALPP1, IFI44L, NAP1L6, IFIT5, IFITM1, GBP4, IFIT3, GBP5, IFI44, SC5D, ISG15, EPSTI1, IRF1, TRIM22, WARS, UBE2L6, APOL2, ISG20, LAP3, IFI6, STAT2, APOL6, DTX3L, RNF213, STAT1, XAF1, PARP14, PSME1. |
| Preferably MTHFD1, SOCS1, MED26, CXCL10, EMC8, KCTD6, MRPL46, GPX7, WWOX, PPM1N, IFI44L, IFITM1, GBP4, IRF1, TRIM22, WARS, UBE2L6, ISG20, DTX3L, RNF213. |
| More preferably MTHFD1, SOCS1, CXCL10, EMC8, GPX7, WWOX, IFI44L, IFITM1, GBP4, IRF1, TRIM22, WARS, UBE2L6, ISG20, DTX3L, RNF213. |
| Most preferably MTHFD1, SOCS1, EMC8, IFI44L, IFITM1, GBP4, IRF1, WARS, ISG20, DTX3L, RNF213. |

TABLE 13

| |
|---|
| MTHFD1, SOCS1, TCL1A, MED26. |
| Preferably MTHFD1, SOCS1, TCL1A. |
| More preferably MTHFD1, SOCS1. |

Tables 12 and 13 in an embodiment provides a signature of dendritic cells (e.g. cDC), and represents upregulated genes in particular DC subpopulations, termed VEx-C, preferably associated with or derived from elite controller phenotype, preferably associated with HIV infection. Preferably upregulation is evaluated in infected cells, compared to non-infected cells.

TABLE 14

| |
|---|
| OGFRL1, CAT, APOOL, HEATR5A, LAIR2, CSNK2B, ARRB1, IFT46, PSMG4, TRIM69, POLR3F, NDRG1, TRIM41, RIN2, HYOU1, HYOU1, TMEM62, FAM89B, ZNF699, KBTBD2, HSPE1-MOB4, ENDOV, TUBG2, TADA2A, DHX35, FGGY, KCTD2, COG7, ZAR1, DIAPH2, CRLS1, GNAT2, EI24, PRPS1, ZNF354B, ZFYVE19, TRIM69, RXRA, RNF166, CCDC43, DAB2, TBC1D22B, TXLNB, P4HTM, SLC35B3, ICT1, WDR53, CCBL1, MYO19, KTI12, MMD, MYO19, METTL18, WDR81, FAM73B, CMC1, AIMP2, ZFAND1, A2M, TFDP1, LILRB2, PCDHGC3, ZKSCAN5, TP53RK, DUSP10, TOR2A, CD9, ZBTB41, TMEM254, PCED1A, GMEB2, ZNF821, BDH2, CYP27A1, PCYT1A, WDR81, USF2, KCTD5, ZNF397, PPP1R3E, MED22, MED22, SHMT1, ZNF287, COPG2, SLC26A6, GZMM, ZNF436, ALDOC, ZAP70, RNF130, ZNF786, TEX9, PER3, PAK1IP1, RRAGB, ITGA5, KLF9, DHX37, ABHD5, BSCL2, ZMYND11, HCCS, VPS52, VPS52, CD3E, H2AFJ, JADE3, RRAS2, TK2, LAT, INTS12, FOSL2, GPATCH1, RGMB, NOL6, PIK3CB, ABCD3, IQGAP2, LARS2, SEPHS1, PDE3B, TUBG1, AGRN, NUP37, MVB12A, MYOF, SRBD1, METTL10, LANCL1, CTTNBP2NL, IGSF6, CLN3, PLA2G4B, CYFIP1, COG4, GIMAP8, AMICA1, TPRA1, FAN1, POP1, TBXAS1, USP20, DOCK5, ZBED4, SIL1, DAPK1, CDK2AP1, TOR1B, BRD1, MLH3, MAPKAPK3, GLMN, SCYL2, MED21, CRLF2, YIF1B, PDE4D, KIAA1598, RFFL, TNFSF13, PGAP2, PI4K2A, CD4, BTRC, COPS4, ANPEP, WBSCR16, PLXNA3, MTERF1, FCER1G, SEMA4A, ANKRD1, PPTC7, NIPSNAP3A, TBC1D2, GIMAP5, ITK, PDE6D, ZNF441, PITRM1, NFXL1, FES, S100A4, ARHGAP18, CSF1R, ELP6, TRIP4, ANXA1, DHCR24, MED23, ADAP2, PRF1, GIMAP7, THOC5, FURIN, RNF169, MALT1, VPS11, VPS11, COPS7A, USP40, AKAP10, SNX18, SIRPA, ABHD12, AQR, TTLL4, ATG4C, FYB, COA3, TIMP1, ASAP1, DLD, AP3D1, SAMHD1, TGFBI, LGALS3. |

TABLE 14-continued

| |
|---|
| Preferably LAIR2, PSMG4, TRIM69, NDRG1, TRIM41, TMEM62, KBTBD2, ENDOV, TUBG2, KCTD2, CRLS1, TRIM69, DAB2, TBC1D22B, WDR53, CCBL1, MYO19, KTI12, MMD, MYO19, METTL18, CMC1, AIMP2, ZFAND1, LILRB2, TP53RK, DUSP10, TOR2A, BDH2, PPP1R3E, MED22, MED22, SHMT1, ZNF287, SLC26A6, GZMM, ZNF436, RNF130, ZNF786, TEX9, PER3, PAK1IP1, RRAGB, ITGA5, KLF9, ZMYND11, HCCS, VPS52, VPS52, CD3E, H2AFJ, JADE3, FOSL2, RGMB, NOL6, ABCD3, IQGAP2, PDE3B, TUBG1, AGRN, NUP37, IGSF6, CLN3, PLA2G4B, CYFIP1, GIMAP8, AMICA1, TPRA1, TBXAS1, USP20, DOCK5, ZBED4, SIL1, CDK2AP1, TOR1B, BRD1, SCYL2, PDE4D, KIAA1598, RFFL, PGAP2, PI4K2A, CD4, BTRC, COPS4, ANPEP, PLXNA3, MTERF1, PPTC7, NIPSNAP3A, TBC1D2, GIMAP5, NFXL1, CSF1R, ELP6, ANXA1, MED23, PRF1, FURIN, RNF169, MALT1, USP40, AKAP10, SIRPA, TTLL4, FYB, TIMP1, AP3D1, SAMHD1, TGFBI, LGALS3. |
| More preferably LAIR2, TRIM41, KBTBD2, ENDOV, KCTD2, CRLS1, TRIM69, DAB2, CCBL1, MYO19, KTI12, MMD, MYO19, METTL18, ZFAND1, TP53RK, DUSP10, TOR2A, BDH2, ZNF287, GZMM, ZNF436, TEX9, PER3, PAK1IP1, KLF9, VPS52, VPS52, CD3E, H2AFJ, JADE3, RGMB, NOL6, PDE3B, NUP37, CLN3, PLA2G4B, CYFIP1, GIMAP8, AMICA1, TPRA1, USP20, DOCK5, ZBED4, SIL1, TOR1B, BRD1, SCYL2, KIAA1598, RFFL, PI4K2A, CD4, COPS4, ANPEP, PLXNA3, MTERF1, NIPSNAP3A, TBC1D2, GIMAP5, NFXL1, ELP6, ANXA1, MED23, PRF1, RNF169, USP40, FYB, TIMP1, SAMHD1, TGFBI, LGALS3. |
| Most preferably ENDOV, KCTD2, CRLS1, CCBL1, MYO19, MMD, MYO19, METTL18, ZFAND1, DUSP10, TOR2A, BDH2, ZNF287, GZMM, ZNF436, TEX9, PER3, PAK1IP1, KLF9, CD3E, H2AFJ, JADE3, RGMB, NOL6, PDE3B, NUP37, PLA2G4B, CYFIP1, AMICA1, TPRA1, USP20, DOCK5, ZBED4, SIL1, BRD1, RFFL, PI4K2A, CD4, ANPEP, MTERF1, TBC1D2, GIMAP5, ELP6, ANXA1, MED23, PRF1, RNF169, USP40, FYB, SAMHD1. |

TABLE 15

| |
|---|
| ADAP2, PRF1, GIMAP7, THOC5, FURIN, RNF169, MALT1, VPS11, VPS11, COPS7A, USP40, AKAP10, SNX18, SIRPA, ABHD12, AQR, TTLL4, ATG4C, FYB, COA3, TIMP1, ASAP1, DLD, AP3D1, SAMHD1, TGFBI, LGALS3. |
| Preferably MED23, PRF1, FURIN, RNF169, MALT1, USP40, AKAP10, SIRPA, TTLL4, FYB, TTMP1, AP3D1, SAMHD1, TGFBI, LGALS3. |
| More preferably MED23, PRF1, RNF169, USP40, FYB, TIMP1, SAMHD1, TGFBI, LGALS3. |
| Most preferably MED23, PRF1, RNF169, USP40, FYB, SAMHD1. |

Tables 14 and 15 in an embodiment provides a signature of dendritic cells (e.g. cDC), and represents downregulated genes in particular DC subpopulations, termed VEx-C, preferably associated with or derived from elite controller phenotype, preferably associated with HIV infection. Preferably downregulation is evaluated in infected cells, compared to non-infected cells.

TABLE 16

| |
|---|
| CXCL10, CXCL9, NCF2, FAM26F, IFIT2, TYROBP, IL4I1, CYP1B1, FCER1G, IFITM3, SLC31A2, FCGR3A, ANKRD22, SLAMF8, RASGEF1B, CCR1, CSF1R, IL1RN, RGL1, TMEM176B, TNFAIP2, ATF3, VMO1, DUSP6, CTSL, CXCL11, LILRB2, IGSF6, PLAUR, HCAR3, HCK, RASSF4, TFEC, SERPING1, RAB20, SLC7A7, PLA2G7, FCGR1A, P2RX7, SIRPA, HMOX1, SERPINA1, LILRB4, TOM1, INHBA, CCL2, C3AR1, LILRB3, HK3, CCRL2, C1QB, LILRB2, LILRB1, RNF144B, PILRA, TGFBI, LILRB1, PRKCD, RNF130, IRG1, ITGAM, TLR4, P2RY6, SRC, SMCO4, MAFB, LILRB4, LILRA3, ANPEP, DMXL2, SPG20, ARHGAP10, SIGLEC1, NPL, CST3, ADAP2, UBD, DOCK4, LILRA6, FPR3, HCAR2, EDN1, A2M, IFNGR2, FCGR2A, C1QC, SECTM1, GSAP, RREB1, MYO1E, TIMP1, LRRK2, LRRC25, RIN2, MSR1, SIRPB1, TLR8, DUSP1, FCN1, SGK1, SUCNR1, DAPK1, LACC1, EPB41L3, TNS3, FLVCR2, BLVRB, GABARAPL1, FBP1, MOB3C, NOD2, SLC41A2, IL13RA1, DHX58, FCGR1B, ADGRE2, TSC22D1, SPI1, PLXDC2, FNIP2, IFNGR2, TDRD6, LHFPL2, PLOD3, BATF2, MITF, PELI1, UBE2E2, PDCD1LG2, GCLC, LILRB2, CSF2RA, HSD3B7, TNFAIP6, LILRA3, LILRA3, LILRB2, ZNF385A, LTBR, TMEM176A, DOCK5, IL15, NRP2, RAPGEF2, MRAS, HLX, TICAM2, MNDA, PLXNC1, KCTD12, SIGLEC9, TMEM51, ACVR2A, TLR2, ATP10D, LILRB1, ZMAT1, LGALS2, SORT1, LILRA6, IFIT1, MAP3K1, SDSL, MS4A14, NFAM1, LILRA3, H1F0, LILRA2, KCNJ2, BTN2A2, ALDH2, CTNND1, STEAP4, TBC1D2, TIAM1, CTTNBP2NL, ATF5, AIF1, AIF1, AIF1, AIF1, CLEC12A, RNF24, LY96, ANTXR2, CLCN7, RXRA, SLC16A6, AIF1, AIF1, KIAA1598, ELAVL4, MXD1, IRAK3, SLC8A1, VASH1, SOCS3, LST1, LST1, LST1, LST1, LST1, LST1, DLGAP4, ATP1B1, CD300LF, ZC3H10, C5AR1, SERPINA1, ADAMTSL4, CD300E, CD276, DENND1A, IL3RA, IL3RA, SLC1A3, ARHGEF10L, SGSH, ZNF438, PTPRO, GUCY1A3, P2RY14, LST1, ADORA2A, SAMD4A, SULF2, ERN1, CD33, MARCKS, BHLHE41, MCTP1, UNC93B1, SLC12A7, B4GALT7, |

TABLE 16-continued

| |
|---|
| RAB13, OGFR, AHRR, FFAR2, LILRA6, PLBD2, KDM7A, TDRD7, RFWD2, PVRL2, FCRL6, GAB2, SLC15A3, ARRB1, VPS37C, RAB39A, CREB5, SLCO3A1, EMP1, DAB2, SH2B2, ME1, CARD9, CLIC2, SETDB1, AQP9, CYBB, TNFAIP8L2, RGS12, CMPK2, SLC6A12, LILRA1, LRP1, BEST1, LILRA1, SLC26A11, ITGAX, DSE, NLRC4, MOB3B, LILRA1, FMNL2, TCF7L2, IRAK2, FCGR3B, ASCL2, SORBS3, RAPH1, ABCA1, BST1, CFB, CFB, CFB, CFB, PLBD1, DAGLA, SETD7, ENPP2, PTGIR, PSEN2, NAV1, TIFAB, PER1, FAM20A, LILRB4, SLC39A13, TFE3, MFSD2A, CTBP2, LILRB3, LILRA6, FAM20C, AKT1S1, OTUD1, BRI3, HNMT, LATS2, PLA2G4A, CD99L2, CA2, CD9, SUV420H1, APP, SIGLEC7, ICOSLG, CD300C, ST3GAL6, CEBPB, BCL2L14, BCL2L14, ASPHD2, TNFSF13, CD274, CLEC4E, LIMS3L, ZNF350, CLEC4A, RCOR1, FOS, INSL6, TBC1D8, PITPNA, ACPP, CD1D, APOBR, ZNF155, MFSD7, LILRA1, PHF1, STARD8, NPEPL1, NEURL3, ZMYND15, RNF217, C1QA, B3GALT4, B3GALT4, B3GALT4, B3GALT4, ZCWPW1, CTSO, CTSO, IDO1, PRAM1, RBM47, CHST15, TTYH2, LYZ, DST, ZNF516, CFD, CFD, MS4A7, FGL2, PELI2, ZNRF2, TP53I3, MLXIP, SLC27A3, SLC27A3, CXCL16, METRNL, CARS2, ADRB2, TMEM150A, IFIT3, DHRS9, MLLT4, PGBD2, RSAD2, PLEKHM1, MYOF, PTPRE, SIK1, TMEM164, HLA-DRB4, KYNU, DIAPH2, CD68, GSN, CSTA, TMEM116, CSF2RB, NR1D2, MYL5, ICAM1, NCF4, IL18BP, HLA-DRB4, ETV7, KIAA0930, THEMIS2, DRAM1, TNFSF13B, GABBR1, GABBR1, GABBR1, GABBR1, KMO, GLUL, CECR1, CREG1, SOD2, TLR1, TNFRSF1A, RIPK2, CLEC7A, CTSB, RNF19B, TXNIP, NADK, PTGER2, TYMP, ABHD12, SSFA2, PPP1R15A, LAIR2, GIMAP8, CTSS, SAT1, VAMP5, SLC2A6, FBXL5, NPC2, LGALS3, GK, TNF, TNF, TNF, TNF, TNF, TNF, TNF, CASP1, LILRB2, GBP1, P2RX4, SNX10, CUX1, GBP5, GBP3, CD38, ZFP36, EPSTI1, MGLL, N4BP2L1, NPPA, TBC1D23, DPYD, IL6ST, KDM1B, ANXA4, FGR, GAS7, APOL3, RAB24, PTPN12, IFNGR1, FUCA2, SLC2A6, UBE2D1, HELZ2, APOBEC3A, PSTPIP2, THAP1, SNX20, CDKN1A, PSAP, CREBRF, SCPEP1, JAK2, FTH1, RARRES3, RNFT1, CCPG1, OAS3, GALNS, CSF2RA, SDCBP, IFI30, S100A11, ADPRH, ZEB2, GIMAP4, LAP3, TLDC2, LPCAT2, DDX58, ALDH3B1, GNS, TICAM1, ATG7, SCARB2, GCH1, PAK1, UBE2Z, FNDC3B, IQSEC1, LYN, APOL4, RICTOR, H6PD, PTAFR, SLAMF7, GRINA, CD40, SAMHD1, CTSD, SERINC1, SCYL2, CORO1B, GBP4, ATP6V1B2, SNX14, SLC25A25, CASP10, PLEK, HIST1H2BK, S100A4, ASAH1, SLC16A3, IRF7, LIPA, MKNK1, ITPRIPL2, PARP12, TMEM140, AP5B1, STX11, FYB, OAS1, ALPK1, SLC37A2, NCF1, FAM156A, HAVCR2, LCP2, FKBP5, APOL6, MGAT1, EGR2, NPC1, TRAFD1, STAT2, TNFSF10, NFE2L2, NBPF10, ARHGEF2, FBXO6, IL6R, SMAP2, MPEG1, RAP2B, TXN, RTN4, GLRX, CNTLN, ZFAND5, TPP1, ADAM17, CPM, LGALS9, RALB, YTHDF3, RAPGEF1, NINJ1, PDLIM5, FGD4, EPG5, ATP6V1A, IRF2, CD63, TMEM127, ARRB2, SAMD9L, SPG21, SH3BP2, HLA-DRA, PTPN2, ATG3, GPX1, KLF6, INSIG1, CCR5, EAF1, XAF1, PGD, HLA-DPA1, HLA-DPA1, HLA-DPA1, HLA-DPA1, HLA-DPA1, HLA-DPA1, ALAS1, HLA-DPB1, HLA-DPB1, LACTB, S100A6, FTL, RIOK3, CD83, PLEKHO1, PML, ABL2, PEA15, HLA-DRB3, HLA-DRB3, STAT1, EVI2B, GNB4, PLSCR1, HLA-DRB1, SQRDL, CIR1, TMED5, PTTG1IP, CSTB, SQSTM1, NBN, LIMS1, LEPROT, IRF1, GABARAP, DOCK8, IFI6, HLA-DMA, HLA-DMA, HLA-DMA, HLA-DMA, HLA-DMA, HLA-DMA, APOL2, HLA-DRB1, PARP14, COQ10B, BRD2, ZYX, MR1, ANXA5, VPS13C, ZNFX1, SLU7, RPS6KA1, RPS6KA1, GBP2, HLA-DRB1, HLA-DRB1, ANXA2, LAPTM4A, ATP6V1G1, JUNB, RNF213, CD44, DTX3L, TAP1, TAP1, TAP1, TAP1, TAP1, TAP1, ITGB2, RNH1, RNH1, TMSB10, HLA-DPB1, RNASEK, MX1, PSMB9, PSMB9, PSMB9, ACTG1, RPL11, RPL28, PABPC1, RPS14, NONO, EIF5A, RPL6, NCL, PARK7, RPL18, RPS19, HNRNPA2B1, EEF2, RPL37A, RPS13, UBB, SET, RPL26, ENO1, RPL15, GPI, RPS15, RPS16, RPL10, TPI1, PHB2, EIF4B, RPL27, RPLP2, HSP90AA1, HMGN2, SLC25A5, RPS27A, RPS11, SUMO1, RPS10, RPL32, RPL31, SNRPE, TFRC, HSPE1, EEF1B2, RPS24, RPL14, SOD1, RPL27A, RPL19, STRAP, PA2G4, CD48, H2AFZ, RPL18A, RPS23, RPL17, PNN, ATP5G3, SERBP1, RPL8, PRMT1, FDFT1, NOP56, CCT2, C1QBP, HNRNPM, RPS21, RPL36A, PTMA, JAK3, EIF3C, CASP2, FUBP1, ANP32B, RPL12, RPL4, CCT3, PPIA, ELOVL5, NOLC1, AHCY, RPL41, RPS8, RPL7, MRPL12, NUDT21, CBX5, RBBP7, RANBP1, RPL21, RPS18, RPS18, RPS18, RPS18, RPS18, RPL29, KIF2A, RAC2, HSPA8, MAP2K3, ARPC5L, ENSA, RPS3A, RPL13, TUBA1C, RPS25, RPS25, FIBP, GNB2L1, CRIP1, SFXN1, MCM5, APOBEC3C, RPS12, RPS2, RPL5, HBS1L, RPL7A, RPL7A, RPS4X, HNRNPA1, SNRPD2, IKZF3, RPL10A, NIPAL3, EBNA1BP2, TUBA4A, SLC25A39, NME2, RPS3, GAPDH, CCND3, GTF3A, DHX30, PEBP1, EZR, RAN, RPLP1, STIP1, EEF1G, CD82, HACD3, CCL5, PDCD4, NOP16, RPA1, CDK4, RPS6, RPS5, RPL13A, PPP2R5D, SFI1, DKC1, PARP1, SMC4, FBL, FBL, IARS, IRF4, PAICS, TUBA1B, TUBB, TUBB, TUBB, TUBB, TUBB, TUBB, IL32, SSRP1, HMGB1, RPL23A, RRM1, ACAT1, ANP32E, SKA2, AAAS, CRTAM, WHSC1, ECE1, HPRT1, IMPDH2, PGAM1, RPL3, SCP2, PCNA, MRPS26, CLEC2D, TTF2, HSP90AB1, PRMT5, IPO5, PCNT, SLBP, YARS, HSPD1, FANCG, APOBEC3G, TRAF3IP3, CUEDC2, PHB, AKR7A2, FANCD2, NASP, SAMM50, RPLP0, CSRP1, CISH, GARS, QARS, TECR, EEF1E1, FBXO21, NME1, RPSA, TSEN15, FKBP11, SIGMAR1, LIG1, LDHA, NPM1, BRD3, HDAC3, ABCF2, RUVBL2, CCND2, OSBPL3, CLSPN, AARS, PRKCH, CDK6, TSPAN3, SPATC1L, SPATC1L, P2RY10, TMPO, TESC, FANCI, MTHFD1, DUT, SLC38A1, SNX25, SAP30, HMGB2, DNAJC9, HIST1H1D, SQLE, TUBB, BHLHE40, EBP, MT1F, FYN, CD96, MPRIP, NLGN4Y, ADGRG1, PRKAB2, GFOD1, ZNF836, KIF11, PFAS, KIAA0101, MFNG, GALNT3, POLR3G, GSTZ1, TNFRSF9, FAM117A, TUBB, UTS2, LDHB, ASRGL1, PNOC, PLEKHF1, TCTEX1D2, SLC37A3, FUT11, ZNF518B, MLLT3, RLTPR, NLRX1, SERF1B, CDK8, PPAPDC2, ADARB1, TMEM55B, SETD8, CLDN15, PRR3, ALYREF, ANO9, TXNDC5, LMBRD2, TMEM9, CRYL1, PPAP2A, FNDC9, P4HTM, STRBP, BLK, TNFRSF13B, VWA5A, MT1X, TULP3, PRR3, PRR3, PRR3, PHOSPHO2, PFKM, SEC61A2, ZNF324, MTA3, ZNF700, ERCC6L, ZNF718, ERCC2, CORO1A, MLLT11, SURF1, SURF1, CD24, STK35, VNN2, SLA2, FAM159A, CDK5, AGL, PKIG, METTL4, HEG1, TNFAIP1, KAT2A, ZKSCAN4, HHLA3, IFI27L1, IFI27L1, LIME1, IL18R1, EBF1, UBE3D, UBAP1L, ZNF287, KATNAL2, ZNF708, IPO13, N6AMT2, |

TABLE 16-continued

| |
|---|
| FASLG, LY9, ZNF428, CREB3L4, LXN, EOMES, FKRP, ZNF138, ARHGAP35, PECR, CNTROB, SEMA4B, MTMR1, FAM111B, SIAH2, COPG2, ABHD14A, TXLNG, SMYD2, LRRC61, PHTF1, SRF, ST6GALNAC6, PDCD2L, RAB33A, FGFBP2, ZNF121, ATP11B, SDHAF3, AUNIP, FEZ1, CENPQ, ZNF66, RCAN3, NELL2, AKAP1, DERL3, DERL3, PEX5, BTLA, LIMA1, USP30, CD244, WDSUB1, MAGEH1, CERK, P2RX5, FAHD2B, BRMS1L, KIAA0226L, TMPRSS3, ZNF33B, COQ7, ZNF398, FAM216A, DENND6B, LTBP4, ZNRD1, ZNRD1, ZNRD1, ZNRD1, ZNRD1, ZNRD1, TCAF1, LYSMD1, NUDT8, EHMT2, RRAS2, E2F1, VAV2, ZGRF1, MMACHC, NCALD, CFAP36, ATG10, GFI1, ISYNA1, ZNF507, ZNF444, TCTN1, RPL39L, NEIL2, PPOX, HGH1, NET1, B4GALT4, E2F7, FAM98B, NCAPH, CCDC64, PI4K2B, ARHGAP19-SLIT1, PIK3R1, ZBTB14, PARP3, ZBTB2, BCL9L, DPH1, APOBEC3H, URGCP, ABLIM1, CCNB1, TROAP, PSMG4, CLPTM1L, RAD51B, PRKAR1B, GSTM4, BAD, SLC39A14, MND1, ATP8A1, ALDOC, MMD, PDK1, IMMP2L, CCDC152, ACOT2, FUCA1, POC1A, HIST1H1C, KEF18A, RANBP6, BDH1, RPS26, APBB1, HPDL, FAM78A, TBCD, FKTN, ACO1, NUDT2, CCDC141, BICD1, KLHL22, MTFR2, RAD17, PLEKHG1, MSI2, FAM53C, SIT1, IGSF8, CPOX, LTA, LTA, LTA, SERGEF, CENPP, HIP1R, TMEM216, TNRC6C, MAPK3, MCM8, SPDL1, LRRCC1, PRMT9, MRM1, KIFC1, CHCHD6, KCNK5, NVL, INVS, RIC3, FAM20B, MBIP, MNAT1, IMMP1L, EHMT2, NBEAL2, TPD52, TADA2A, RNF8, CDT1, HDHD3, RASSF7, ALOX5AP, ACAD11, CHAF1A, CD7, CLSTN1, GTSE1, SLC2A1, WRN, WEE1, ATXN7L2, CRACR2A, CCHCR1, TMUB1, BACH2, AGAP2, CEP128, TSEN2, PXN, TRIP13, GAMT, CCDC77, GGH, XYLT2, SLC43A1, PGAP2, CHD3, SPATA20, KIF15, KIF15, MYBL2, ATG2B, ATP2B4, GOLPH3L, MMAB, TMEM154, SCD, KNSTRN, PNKD, HINT2, FADS1, FAM173A, TNIP3, E2F8, PEMT, PRIM2, CDCA3, ASB2, ASB2, TMEM223, DUS2, APITD1, TGFBR3, CCDC34, KIAA1524, MED30, ANKRD39, CCNB2, CDC7, CDCA2, PBK, PLCG1, NT5DC2, MBNL3, DNA2, GINS3, PTTG1, AGK, RNF126, SAAL1, HDGFRP3, SLC4A7, SHCBP1, NFS1, ITGB3BP, NLRP1, CCDC14, TBCD, OIP5, LANCL2, HMGXB3, EML3, ALKBH2, ANKRD33B, MKNK2, DLGAP5, CENPK, GPX7, TM7SF3, SUV39H1, CSPP1, TRPT1, KIF21B, ADCY3, PCED1B, CARD11, LRP8, TESPA1, CLP1, HJURP, SARS2, PIP4K2B, PIP4K2B, BCL11B, HADH, ANKRD32, PAQR4, BUB1, BCS1L, PRKCQ, POLE2, POMGNT1, SHMT1, NTAN1, NTAN1, TRAF4, SGOL2, FOXM1, PRC1, NUF2, STMN1, TMEM218, TMEM261, ANKRD54, MYL6B, MIPEP, SLC25A4, DDIAS, BIN1, CENPO, ITPR3, PDE4D, CMSS1, CD70, FAH, SKA3, KIFC1, FLYWCH2, KIF3B, DEPDC1B, MTHFD1L, PHF19, BOLA3, PSMC3IP, GRAP2, TMEM14A, PCMTD2, MPHOSPH9, H2AFX, SLCO4A1, ASNSD1, VPS13A, AURKB, LAG3, NPM3, JMJD4, MYO19, GSTM1, MANEA, POLR3H, CD3G, SYNE1, CEP152, QDPR, KLF12, ORC1, RSAD1, SLC9B2, NEDD9, SLC35B4, CDK2, GLMN, CKAP2L, PLK4, POLQ, CASC5, TFB2M, CCDC51, RAD51C, ANKRD36, DSCC1, MRS2, USP48, ASXL1, GIT1, PELO, OCIAD2, RAD54L, FIGNL1, CISD1, SLC16A1, SLC16A1, LRMP, MYO19, BAG2, XCL1, SUN1, CKAP2, ZMYND11, POLR2I, GMNN, TBC1D10C, DSN1, HDDC2, LANCL1, UBASH3A, SLAMF6, RECQL4, TMC8, TRUB2, SACS, KLRG1, NLE1, ZDHHC13, SPTBN1, CENPH, CDKN3, ABHD5, BCAS4, TTK, SMARCAD1, PRPSAP1, CLEC17A, ELP6, CCNF, HELLS, PAFAH1B3, INPP4B, SH2D2A, IFT57, NCAPG2, CD99, CD99, ICOS, THEMIS, THEMIS, DEF6, KRI1, UCK2, KIF20B, LCLAT1, SPAG5, CHAF1B, EXO1, SLC5A3, REXO2, SEL1L3, CDC6, BLM, ESCO2, S1PR1, NDFIP2, RFC3, CHEK1, TSEN54, EML2, CCNE2, IL12RB2, ETS1, CENPM, SCAPER, NIPSNAP1, CD22, KLRK1, HN1L, LRWD1, RITA1, GOLGA8A, NFATC2, CRYZ, DHCR7, RUSC1, PASK, MYCBP, CD5, DGKA, RNASEH2A, ATP2A3, SKAP1, XCL2, EIF4EBP1, ZAP70, RAD51, TRAT1, CDC20, CD320, KNTC1, FASN, LEO1, SNRNP25, MELK, KIF23, TMEM97, GZMA, CD247, JAKMIP1, GZMM, NCAPD2, ICAM3, LRBA, VRK1, WARS2, INTS1, LMAN1, CHTF18, KIF21A, RHOH, TCF19, COQ4, ATAD5, MAD2L1, ASNS, POLR1E, PARP2, RCC1, ITPR1, ANKRD36C, PRRC2B, DGCR14, NDC1, ORMDL3, SLC25A38, PGM1, CD3E, TOX, PKMYT1, TFDP1, MTFP1, IFNG, BUB1B, WDR54, TTI2, RFC4, SLC7A5, ACTN1, UBE2T, SEMA7A, ENO2, RPS6KB2, ATP6V0E2, UBE2C, CD6, VCAM1, FTSJ1, CCDC86, BCAT1, SLC29A1, DHFR, CENPU, THOC3, POLA1, IPO4, ACAP1, MCM10, SRM, GINS2, RGS16, PPAT, LMNB2, OXCT1, PHGDH, NPRL2, TPGS2, CDCA7L, DTYMK, WDHD1, SLC27A2, PRDX2, SLC38A5, TACC3, NCAPG, BIRC5, PYCR1, ADD3, SLC9A3R1, NDC80, DHRS3, CDC45, BANK1, ULK3, SCCPDH, TNFRSF18, CST7, SLC7A1, P2RY8, P2RY8, PDLIM1, PPP1R16B, HMGCR, RUVBL1, GEMIN4, TPX2, TCF19, SH2D1A, BARD1, CENPF, CTPS1, ITK, WDR34, HOPX, MAP4K1, ZBTB32, BCL11A, ATAD2, ADH5, GNG2, CCNA2, PRKACB, DHCR24, SLC35B2, NCAPD3, FCRLA, EMB, CDCA7, ALDH18A1, MSH2, UNG, RACGAP1, CD3D, SYNE2, GPR171, ACOT7, PTPN7, AKR1B1, RRM2, CD8B, CD79B, CDCA4, PSD4, NUP210, KIF22, ASF1B, WDR6, CXCR3, ST6GAL1, DTL, CDCA5, TK1, ZWINT, CAD, FCRL3, PSAT1, NUSAP1, ESYT1, UHRF1, TIGIT, CDK1, DDIT4, ADGRG5, PAX5, LAT, TMEM106C, IL2RB, PTPRCAP, FEN1, MCM4, POLD2, CD19, PRF1, GZMH, ITM2A, CYFIP2, AMICA1, CD2, MKI67, LBH, CXCR5, CD79A, CD8A, ANXA6, MCM2, MCM6, SHMT2, LCK, TYMS, TOP2A, MCM3, NKG7, MS4A1, IL2RA, MCM7, ZBED2, GZMB. |

Table 16 in an embodiment provides a signature of dendritic cells (e.g. cDC), and represents differentially expressed genes in particular DC subpopulations, termed VEx-B, preferably associated with or derived from elite controller phenotype, preferably associated with HIV infection. Preferably differential expression is evaluated compared to VEx-A cells.

TABLE 17

CXCL10, CXCL9, NCF2, FAM26F, IFIT2, TYROBP, IL4I1, CYP1B1, FCER1G, IFITM3, SLC31A2, FCGR3A, ANKRD22, SLAMF8, RASGEF1B, CCR1, CSF1R, IL1RN, RGL1, TMEM176B, TNFAIP2, ATF3, VMO1, DUSP6, CTSL, CXCL11, LILRB2, IGSF6, PLAUR, HCAR3, HCK, RASSF4, TFEC, SERPING1, RAB20, SLC7A7, PLA2G7, FCGR1A, P2RX7, SIRPA, HMOX1, SERPINA1, LILRB4, TOM1, INHBA, CCL2, C3AR1, LILRB3, HK3, CCRL2, C1QB, LILRB2, LILRB1, RNF144B, PILRA, TGFBI, LILRB1, PRKCD, RNF130, IRG1, ITGAM, TLR4, P2RY6, SRC, SMCO4, MAFB, LILRB4, LILRA3, ANPEP, DMXL2, SPG20, ARHGAP10, SIGLEC1, NPL, CST3, ADAP2, UBD, DOCK4, LILRA6, FPR3, HCAR2, EDN1, A2M, IFNGR2, FCGR2A, C1QC, SECTM1, GSAP, RREB1, MYO1E, TIMP1, LRRK2, LRRC25, RIN2, MSR1, SIRPB1, TLR8, DUSP1, FCN1, SGK1, SUCNR1, DAPK1, LACC1, EPB41L3, TNS3, FLVCR2, BLVRB, GABARAPL1, FBP1, MOB3C, NOD2, SLC41A2, IL13RA1, DHX58, FCGR1B, ADGRE2, TSC22D1, SPI1, PLXDC2, FNIP2, IFNGR2, TDRD6, LHFPL2, PLOD3, BATF2, MITF, PELI1, UBE2E2, PDCD1LG2, GCLC, LILRB2, CSF2RA, HSD3B7, TNFAIP6, LILRA3, LILRA3, LILRB2, ZNF385A, LTBR, TMEM176A, DOCK5, IL15, NRP2, RAPGEF2, MRAS, HLX, TICAM2, MNDA, PLXNC1, KCTD12, SIGLEC9, TMEM51, ACVR2A, TLR2, ATP10D, LILRB1, ZMAT1, LGALS2, SORT1, LILRA6, IFIT1, MAP3K1, SDSL, MS4A14, NFAM1, LILRA3, H1F0, LILRA2, KCNJ2, BTN2A2, ALDH2, CTNND1, STEAP4, TBC1D2, TIAM1, CTTNBP2NL, ATF5, AIF1, AIF1, AIF1, AIF1, CLEC12A, RNF24, LY96, ANTXR2, CLCN7, RXRA, SLC16A6, AIF1, AIF1, KIAA1598, ELAVL4, MXD1, IRAK3, SLC8A1, VASH1, SOCS3, LST1, LST1, LST1, LST1, LST1, LST1, DLGAP4, ATP1B1, CD300LF, ZC3H10, C5AR1, SERPINA1, ADAMTSL4, CD300E, CD276, DENND1A, IL3RA, IL3RA, SLC1A3, ARHGEF10L, SGSH, ZNF438, PTPRO, GUCY1A3, P2RY14, LST1, ADORA2A, SAMD4A, SULF2, ERN1, CD33, MARCKS, BHLHE41, MCTP1, UNC93B1, SLC12A7, B4GALT7, RAB13, OGFR, AHRR, FFAR2, LILRA6, PLBD2, KDM7A, TDRD7, RFWD2, PVRL2, FCRL6, GAB2, SLC15A3, ARRB1, VPS37C, RAB39A, CREB5, SLCO3A1, EMP1, DAB2, SH2B2, ME1, CARD9, CLIC2, SETDB1, AQP9, CYBB, TNFAIP8L2, RGS12, CMPK2, SLC6A12, LILRA1, LRP1, BEST1, LILRA1, SLC26A11, ITGAX, DSE, NLRC4, MOB3B, LILRA1, FMNL2, TCF7L2, IRAK2, FCGR3B, ASCL2, SORBS3, RAPH1, ABCA1, BST1, CFB, CFB, CFB, CFB, PLBD1, DAGLA, SETD7, ENPP2, PTGIR, PSEN2, NAV1, TIFAB, PER1, FAM20A, LILRB4, SLC39A13, TFE3, MFSD2A, CTBP2, LILRB3, LILRA6, FAM20C, AKT1S1, OTUD1, BRI3, HNMT, LATS2, PLA2G4A, CD99L2, CA2, CD9, SUV420H1, APP, SIGLEC7, ICOSLG, CD300C, ST3GAL6, CEBPB, BCL2L14, BCL2L14, ASPHD2, TNFSF13, CD274, CLEC4E, LIMS3L, ZNF350, CLEC4A, RCOR1, FOS, INSL6, TBC1D8, PITPNA, ACPP, CD1D, APOBR, ZNF155, MFSD7, LILRA1, PHF1, STARD8, NPEPL1, NEURL3, ZMYND15, RNF217, C1QA, B3GALT4, B3GALT4, B3GALT4, B3GALT4, ZCWPW1, CTSO, CTSO, IDO1, PRAM1, RBM47, CHST15, TTYH2, LYZ, DST, ZNF516, CFD, CFD, MS4A7, FGL2, PELI2, ZNRF2, TP53I3, MLXIP, SLC27A3, SLC27A3, CXCL16, METRNL, CARS2, ADRB2, TMEM150A, IFIT3, DHRS9, MLLT4, PGBD2, RSAD2, PLEKHM1, MYOF, PTPRE, SIK1, TMEM164, HLA-DRB4, KYNU, DIAPH2, CD68, GSN, CSTA, TMEM116, CSF2RB, NR1D2, MYL5, ICAM1, NCF4, IL18BP, HLA-DRB4, ETV7, KIAA0930, THEMIS2, DRAM1, TNFSF13B, GABBR1, GABBR1, GABBR1, GABBR1, KMO, GLUL, CECR1, CREG1, SOD2, TLR1, TNFRSF1A, RIPK2, CLEC7A, CTSB, RNF19B, TXNIP, NADK, PTGER2, TYMP, ABHD12, SSFA2, PPP1R15A, LAIR2, GIMAP8, CTSS, SAT1, VAMP5, SLC2A6, FBXL5, NPC2, LGALS3, GK, TNF, TNF, TNF, TNF, TNF, TNF, TNF, CASP1, LILRB2, GBP1, P2RX4, SNX10, CUX1, GBP5, GBP3, CD38, ZFP36, EPSTI1, MGLL, N4BP2L1, NPPA, TBC1D23, DPYD, IL6ST, KDM1B, ANXA4, FGR, GAS7, APOL3, RAB24, PTPN12, IFNGR1, FUCA2, SLC2A6, UBE2D1, HELZ2, APOBEC3A, PSTPIP2, THAP1, SNX20, CDKN1A, PSAP, CREBRF, SCPEP1, JAK2, FTH1, RARRES3, RNFT1, CCPG1, OAS3, GALNS, CSF2RA, SDCBP, IFI30, S100A11, ADPRH, ZEB2, GIMAP4, LAP3, TLDC2, LPCAT2, DDX58, ALDH3B1, GNS, TICAM1, ATG7, SCARB2, GCH1, PAK1, UBE2Z, FNDC3B, IQSEC1, LYN, APOL4, RICTOR, H6PD, PTAFR, SLAMF7, GRINA, CD40, SAMHD1, CTSD, SERINC1, SCYL2, CORO1B, GBP4, ATP6V1B2, SNX14, SLC25A25, CASP10, PLEK, HIST1H2BK, S100A4, ASAH1, SLC16A3, IRF7, LIPA, MKNK1, ITPRIPL2, PARP12, TMEM140, AP5B1, STX11, FYB, OAS1, ALPK1, SLC37A2, NCF1, FAM156A, HAVCR2, LCP2, FKBP5, APOL6, MGAT1, EGR2, NPC1, TRAFD1, STAT2, TNFSF10, NFE2L2, NBPF10, ARHGEF2, FBXO6, IL6R, SMAP2, MPEG1, RAP2B, TXN, RTN4, GLRX, CNTLN, ZFAND5, TPP1, ADAM17, CPM, LGALS9, RALB, YTHDF3, RAPGEF1, NINJ1, PDLIM5, FGD4, EPG5, ATP6V1A, IRF2, CD63, TMEM127, ARRB2, SAMD9L, SPG21, SH3BP2, HLA-DRA, PTPN2, ATG3, GPX1, KLF6, INSIG1, CCR5, EAF1, XAF1, PGD, HLA-DPA1, HLA-DPA1, HLA-DPA1, HLA-DPA1, HLA-DPA1, HLA-DPA1, ALAS1, HLA-DPB1, HLA-DPB1, LACTB, S100A6, FTL, RIOK3, CD83, PLEKHO1, PML, ABL2, PEA15, HLA-DRB3, HLA-DRB3, STAT1, EVI2B, GNB4, PLSCR1, HLA-DRB1, SQRDL, CIR1, TMED5, PTTG1IP, CSTB, SQSTM1, NBN, LIMS1, LEPROT, IRF1, GABARAP, DOCK8, IFI6, HLA-DMA, HLA-DMA, HLA-DMA, HLA-DMA, HLA-DMA, HLA-DMA, APOL2, HLA-DRB1, PARP14, COQ10B, BRD2, ZYX, MR1, ANXA5, VPS13C, ZNFX1, SLU7, RPS6KA1, RPS6KA1, GBP2, HLA-DRB1, HLA-DRB1, ANXA2, LAPTM4A, ATP6V1G1, JUNB, RNF213, CD44, DTX3L, TAP1, TAP1, TAP1, TAP1, TAP1, TAP1, ITGB2, RNH1, RNH1, TMSB10, HLA-DPB1, RNASEK, MX1, PSMB9, PSMB9, PSMB9, Preferably CXCL10, CXCL9, NCF2, FAM26F, IFIT2, TYROBP, IL4I1, CYP1B1, FCER1G, IFITM3, SLC31A2, FCGR3A, ANKRD22, SLAMF8, RASGEF1B, CCR1, CSF1R, IL1RN, RGL1, TMEM176B, TNFAIP2, ATF3, VMO1, DUSP6, CTSL, CXCL11, LILRB2, IGSF6, PLAUR, HCAR3, HCK, RASSF4, TFEC, SERPING1, RAB20, SLC7A7, PLA2G7, FCGR1A, P2RX7, SIRPA, HMOX1, SERPINA1, LILRB4, TOM1, INHBA, CCL2, C3AR1, LILRB3, HK3, CCRL2, C1QB, LILRB2, LILRB1, RNF144B, PILRA, TGFBI, LILRB1, PRKCD, RNF130, IRG1, ITGAM, TLR4, P2RY6, SRC, SMCO4, MAFB, LILRB4, LILRA3, ANPEP, DMXL2, SPG20, ARHGAP10, SIGLEC1, NPL, CST3, ADAP2, UBD, DOCK4, LILRA6, FPR3, HCAR2, EDN1, A2M, IFNGR2, FCGR2A, C1QC, SECTM1, GSAP, RREB1, MYO1E, TIMP1, LRRK2, LRRC25, RIN2, MSR1, SIRPB1, TLR8, DUSP1, FCN1, SGK1, TABLE 17-continued

| |
|---|
| SUCNR1, DAPK1, LACC1, EPB41L3, TNS3, FLVCR2, BLVRB, GABARAPL1, FBP1, MOB3C, NOD2, SLC41A2, IL13RA1, DHX58, FCGR1B, ADGRE2, TSC22D1, SPI1, PLXDC2, FNIP2, IFNGR2, TDRD6, LHFPL2, PLOD3, BATF2, MITF, PELI1, UBE2E2, PDCD1LG2, GCLC, LILRB2, CSF2RA, HSD3B7, TNFAIP6, LILRA3, LILRA3, LILRB2, ZNF385A, LTBR, TMEM176A, DOCK5, IL15, NRP2, RAPGEF2, MRAS, HLX, TICAM2, MNDA, PLXNC1, KCTD12, SIGLEC9, TMEM51, ACVR2A, TLR2, ATP10D, LILRB1, ZMAT1, LGALS2, SORT1, LILRA6, MAP3K1, SDSL, MS4A14, NFAM1, LILRA3, H1F0, LILRA2, KCNJ2, BTN2A2, ALDH2, CTNND1, STEAP4, TBC1D2, TIAM1, CTTNBP2NL, ATF5, AIF1, AIF1, AIF1, AIF1, CLEC12A, RNF24, LY96, ANTXR2, CLCN7, RXRA, SLC16A6, AIF1, AIF1, KIAA1598, ELAVL4, MXD1, IRAK3, SLC8A1, VASH1, SOCS3, LST1, LST1, LST1, LST1, LST1, LST1, DLGAP4, ATP1B1, CD300LF, ZC3H10, C5AR1, SERPINA1, ADAMTSL4, CD300E, CD276, DENND1A, IL3RA, IL3RA, SLC1A3, ARHGEF10L, SGSH, ZNF438, PTPRO, GUCY1A3, P2RY14, LST1, ADORA2A, SAMD4A, SULF2, CD33, MARCKS, BHLHE41, MCTP1, UNC93B1, SLC12A7, RAB13, OGFR, AHRR, FFAR2, LILRA6, PLBD2, TDRD7, RFWD2, PVRL2, FCRL6, GAB2, SLC15A3, ARRB1, VPS37C, RAB39A, CREB5, SLCO3A1, EMP1, DAB2, SH2B2, ME1, CARD9, CLIC2, AQP9, CYBB, TNFAIP8L2, RGS12, CMPK2, SLC6A12, LILRA1, LRP1, BEST1, LILRA1, SLC26A11, ITGAX, DSE, NLRC4, MOB3B, LILRA1, FMNL2, TCF7L2, FCGR3B, ASCL2, SORBS3, RAPH1, ABCA1, BST1, CFB, CFB, CFB, CFB, PLBD1, DAGLA, ENPP2, PTGIR, PSEN2, NAV1, TIFAB, PER1, FAM20A, LILRB4, SLC39A13, TFE3, MFSD2A, CTBP2, LILRB3, LILRA6, FAM20C, AKT1S1, OTUD1, BRI3, HNMT, LATS2, PLA2G4A, CD99L2, CA2, APP, SIGLEC7, CD300C, ST3GAL6, CEBPB, BCL2L14, BCL2L14, ASPHD2, TNFSF13, CD274, CLEC4E, LIMS3L, ZNF350, CLEC4A, RCOR1, FOS, INSL6, TBC1D8, PITPNA, ACPP, CD1D, APOBR, ZNF155, MFSD7, LILRA1, PHF1, STARD8, NPEPL1, NEURL3, ZMYND15, RNF217, C1QA, B3GALT4, B3GALT4, B3GALT4, B3GALT4, ZCWPW1, CTSO, CTSO, IDO1, PRAM1, RBM47, CHST15, TTYH2, LYZ, DST, ZNF516, CFD, CFD, MS4A7, FGL2, PELI2, ZNRF2, TP53I3, MLXIP, SLC27A3, SLC27A3, CXCL16, METRNL, CARS2, ADRB2, TMEM150A, IFIT3, DHRS9, MLLT4, PGBD2, RSAD2, PLEKHM1, MYOF, PTPRE, HLA-DRB4, KYNU, CD68, GSN, CSF2RB, NR1D2, MYL5, ICAM1, NCF4, IL18BP, HLA-DRB4, ETV7, KIAA0930, THEMIS2, DRAM1, TNFSF13B, GABBR1, GABBR1, GABBR1, GABBR1, KMQ, GLUL, CECR1, CREG1, SOD2, TLR1, TNFRSF1A, RIPK2, CLEC7A, CTSB, RNF19B, TXNIP, NADK, PTGER2, TYMP, ABHD12, SSFA2, PPP1R15A, LAIR2, GIMAP8, CTSS, SAT1, VAMP5, SLC2A6, FBXL5, NPC2, LGALS3, GK, TNF, TNF, TNF, TNF, TNF, TNF, TNF, CASP1, LILRB2, GBP1, P2RX4, SNX10, CUX1, GBP5, GBP3, CD38, ZFP36, EPSTI1, MGLL, N4BP2L1, NPPA, TBC1D23, DPYD, IL6ST, KDM1B, ANXA4, FGR, GAS7, APOL3, RAB24, PTPN12, IFNGR1, FUCA2, SLC2A6, UBE2D1, HELZ2, APOBEC3A, PSTPIP2, SNX20, CDKN1A, PSAP, CREBRF, SCPEP1, JAK2, FTH1, CCPG1, OAS3, GALNS, CSF2RA, SDCBP, IFI30, S100A11, ADPRH, ZEB2, GIMAP4, LAP3, TLDC2, LPCAT2, DDX58, ALDH3B1, GNS, TICAM1, ATG7, SCARB2, GCH1, PAK1, UBE2Z, FNDC3B, IQSEC1, LYN, APOL4, RICTOR, H6PD, PTAFR, SLAMF7, GRINA, CD40, SAMHD1, CTSD, SERINC1, CORO1B, GBP4, ATP6V1B2, SNX14, SLC25A25, CASP10, PLEK, S100A4, ASAH1, SLC16A3, IRF7, LIPA, MKNK1, ITPRIPL2, PARP12, TMEM140, AP5B1, STX11, FYB, OAS1, ALPK1, SLC37A2, NCF1, FAM156A, HAVCR2, LCP2, FKBP5, APOL6, MGAT1, EGR2, NPC1, TRAFD1, STAT2, TNFSF10, NFE2L2, NBPF10, ARHGEF2, FBXO6, IL6R, SMAP2, MPEG1, RAP2B, TXN, RTN4, GLRX, CNTLN, ZFAND5, TPP1, ADAM17, CPM, LGALS9, RALB, YTHDF3, RAPGEF1, NINJ1, PDLIM5, EPG5, ATP6V1A, IRF2, CD63, ARRB2, SAMD9L, SPG21, SH3BP2, HLA-DRA, PTPN2, ATG3, GPX1, KLF6, CCR5, EAF1, XAF1, PGD, HLA-DPA1, HLA-DPA1, HLA-DPA1, HLA-DPA1, HLA-DPA1, HLA-DPA1, ALAS1, HLA-DPB1, HLA-DPB1, LACTB, S100A6, FTL, PLEKHO1, PML, ABL2, PEA15, HLA-DRB3, HLA-DRB3, STAT1, EVI2B, GNB4, PLSCR1, HLA-DRB1, SQRDL, CIR1, TMED5, PTTG1IP, CSTB, SQSTM1, NBN, LIMS1, LEPROT, IRF1, GABARAP, DOCK8, IFI6, APOL2, HLA-DRB1, PARP14, COQ10B, MR1, ANXA5, VPS13C, ZNFX1, RPS6KA1, RPS6KA1, GBP2, HLA-DRB1, HLA-DRB1, ANXA2, LAPTM4A, ATP6V1G1, JUNB, RNF213, CD44, DTX3L, TAP1, TAP1, TAP1, TAP1, TAP1, TAP1, HLA-DPB1, RNASEK, PSMB9, PSMB9, PSMB9. |

TABLE 18

| |
|---|
| CXCL10, CXCL9, NCF2, FAM26F, IFIT2, TYROBP, IL4I1, CYP1B1, FCER1G, IFITM3, SLC31A2, FCGR3A, ANKRD22, SLAMF8, RASGEF1B, CCR1, CSF1R, IL1RN, RGL1, TMEM176B, TNFAIP2, ATF3, VMO1, DUSP6, CTSL, CXCL11, LILRB2, IGSF6, PLAUR, HCAR3, HCK, RASSF4, TFEC, SERPING1, RAB20, SLC7A7, PLA2G7, FCGR1A, P2RX7, SIRPA, HMOX1, SERPINA1, LILRB4, TOM1, INHBA, CCL2, C3AR1, LILRB3, HK3, CCRL2, C1QB, LILRB2, LILRB1, RNF144B, PILRA, TGFB1, LILRB1, PRKCD, RNF130, IRG1, ITGAM, TLR4, P2RY6, SRC, SMCO4, MAFB, LILRB4, LILRA3, ANPEP, DMXL2, SPG20, ARHGAP10, SIGLEC1, NPL, CST3, ADAP2, UBD, DOCK4, LILRA6, FPR3, HCAR2, EDN1, A2M, IFNGR2, FCGR2A, C1QC, SECTM1, GSAP, RREB1, MYO1E, TIMP1, LRRK2, LRRC25, RIN2, MSR1, SIRPB1, TLR8, DUSP1, FCN1, SGK1, SUCNR1, DAPK1, LACC1, EPB41L3, TNS3, FLVCR2, BLVRB, GABARAPL1, FBP1, MOB3C, NOD2, SLC41A2, IL13RA1, DHX58, FCGR1B, ADGRE2, TSC22D1, SPI1, PLXDC2, FNIP2, IFNGR2, TDRD6, LHFPL2, PLOD3, BATF2, MITF, PELI1, UBE2E2, PDCD1LG2, GCLC, LILRB2, CSF2RA, HSD3B7, TNFAIP6, LILRA3, LILRA3, LILRB2, ZNF385A, LTBR, TMEM176A, DOCK5, IL15, NRP2, RAPGEF2, MRAS, HLX, TICAM2, MNDA, PLXNC1, KCTD12, SIGLEC9, TMEM51, ACVR2A, TLR2, ATP10D, LILRB1, ZMAT1, LGALS2, SORT1, LILRA6, IFIT1, MAP3K1, SDSL, MS4A14, NFAM1, LILRA3, H1F0, |

TABLE 18-continued

| |
|---|
| LILRA2, KCNJ2, BTN2A2, ALDH2, CTNND1, STEAP4, TBC1D2, TIAM1, CTTNBP2NL, ATF5, AIF1, AIF1, AIF1, AIF1, CLEC12A, RNF24, LY96, ANTXR2, CLCN7, RXRA, SLC16A6, AIF1, AIF1, KIAA1598, ELAVL4, MXD1, IRAK3, SLC8A1, VASH1, SOCS3, LST1, LST1, LST1, LST1, LSTI, LST1, DLGAP4, ATP1B1, CD300LF, ZC3H10, C5AR1, SERPINA1, ADAMTSL4, CD300E, CD276, DENND1A, IL3RA, IL3RA, SLC1A3, ARHGEF10L, SGSH, ZNF438, PTPRO, GUCY1A3, P2RY14, LST1, ADORA2A, SAMD4A, SULF2, ERN1, CD33, MARCKS, BHLHE41, MCTP1, UNC93B1, SLC12A7, B4GALT7, RAB13, OGFR, AHRR, FFAR2, |
| Preferably CXCL10, CXCL9, NCF2, FAM26F, IFIT2, TYROBP, IL4I1, CYP1B1, FCER1G, IFITM3, SLC31A2, FCGR3A, ANKRD22, SLAMF8, RASGEF1B, CCR1, CSF1R, IL1RN, RGL1, TMEM176B, TNFAIP2, ATF3, VMO1, DUSP6, CTSL, CXCL11, LILRB2, IGSF6, PLAUR, HCAR3, HCK, RASSF4, TFEC, SERPING1, RAB20, SLC7A7, PLA2G7, FCGR1A, P2RX7, SIRPA, HMOX1, SERPINA1, LILRB4, TOM1, INHBA, CCL2, C3AR1, LILRB3, HK3, CCRL2, C1QB, LILRB2, LILRB1, RNF144B, PILRA, TGFBI, LILRB1, PRKCD, RNF130, IRG1, ITGAM, TLR4, P2RY6, SRC, SMCO4, MAFB, LILRB4, LILRA3, ANPEP, DMXL2, SPG20, ARHGAP10, SIGLEC1, NPL, CST3, ADAP2, UBD, DOCK4, LILRA6, FPR3, HCAR2, EDN1, A2M, IFNGR2, FCGR2A, C1QC, SECTM1, GSAP, RREB1, MYO1E, TIMP1, LRRK2, LRRC25, RIN2, MSR1, SIRPB1, TLR8, DUSP1, FCN1, SGK1, SUCNR1, DAPK1, LACC1, EPB41L3, TNS3, FLVCR2, BLVRB, GABARAPL1, FBP1, MOB3C, NOD2, SLC41A2, IL13RA1, DHX58, FCGR1B, ADGRE2, TSC22D1, SPI1, PLXDC2, FNIP2, IFNGR2, TDRD6, LHFPL2, PLOD3, BATF2, MITF, PELI1, UBE2E2, PDCD1LG2, GCLC, LILRB2, CSF2RA, HSD3B7, TNFAIP6, LILRA3, LILRA3, LILRB2, ZNF385A, LTBR, TMEM176A, DOCK5, IL15, NRP2, RAPGEF2, MRAS, HLX, TICAM2, MNDA, PLXNC1, KCTD12, SIGLEC9, TMEM51, ACVR2A, TLR2, ATP10D, LILRB1, ZMAT1, LGALS2, SORT1, LILRA6, MAP3K1, SDSL, MS4A14, NFAM1, LILRA3, H1F0, LILRA2, KCNJ2, BTN2A2, ALDH2, CTNND1, STEAP4, TBC1D2, TIAM1, CTTNBP2NL, ATF5, AIF1, AIF1, AIF1, AIF1, CLEC12A, RNF24, LY96, ANTXR2, CLCN7, RXRA, SLC16A6, AIF1, AIF1, KIAA1598, ELAVL4, MXD1, IRAK3, SLC8A1, VASH1, SOCS3, LST1, LST1, LST1, LST1, LST1, LST1, DLGAP4, ATP1B1, CD300LF, ZC3H10, C5AR1, SERPINA1, ADAMTSL4, CD300E, CD276, DENND1A, IL3RA, IL3RA, SLC1A3, ARHGEF10L, SGSH, ZNF438, PTPRO, GUCY1A3, P2RY14, LST1, ADORA2A, SAMD4A, SULF2, CD33, MARCKS, BHLHE41, MCTP1, UNC93B1, SLC12A7, RAB13, OGFR, AHRR, FFAR2, LILRA6. |

Tables 17 and 18 in an embodiment provides a signature of dendritic cells (e.g. cDC), and represents upregulated genes in particular DC subpopulations, termed VEx-B, preferably associated with or derived from elite controller phenotype, preferably associated with HIV infection. Preferably upregulation is evaluated compared to VEx-A cells.

TABLE 19

| |
|---|
| ACTG1, RPL11, RPL28, PABPC1, RPS14, NONO, EIF5A, RPL6, NCL, PARK7, RPL18, RPS19, HNRNPA2B1, EEF2, RPL37A, RPS13, UBB, SET, RPL26, ENO1, RPL15, GPI, RPS15, RPS16, RPL10, TPI1, PHB2, EIF4B, RPL27, RPLP2, HSP90AA1, HMGN2, SLC25A5, RPS27A, RPS11, SUMO1, RPS10, RPL32, RPL31, SNRPE, TFRC, HSPE1, EEF1B2, RPS24, RPL14, SOD1, RPL27A, RPL19, STRAP, PA2G4, CD48, H2AFZ, RPL18A, RPS23, RPL17, PNN, ATP5G3, SERBP1, RPL8, PRMT1, FDFT1, NOP56, CCT2, C1QBP, HNRNPM, RPS21, RPL36A, PTMA, JAK3, EIF3C, CASP2, FUBP1, ANP32B, RPL12, RPL4, CCT3, PPIA, ELOVL5, NOLC1, AHCY, RPL41, RPS8, RPL7, MRPL12, NUDT21, CBX5, RBBP7, RANBP1, RPL21, RPS18, RPS18, RPS18, RPS18, RPS18, RPL29, KIF2A, RAC2, HSPA8, MAP2K3, ARPC5L, ENSA, RPS3A, RPL13, TUBA1C, RPS25, RPS25, FIBP, GNB2L1, CRIP1, SFXN1, MCM5, APOBEC3C, RPS12, RPS2, RPL5, HBS1L, RPL7A, RPL7A, RPS4X, HNRNPA1, SNRPD2, IKZF3, RPL10A, NIPAL3, EBNA1BP2, TUBA4A, SLC25A39, NME2, RPS3, GAPDH, CCND3, GTF3A, DHX30, PERP1, EZR, RAN, RPLP1, STIP1, EEF1G, CD82, HACD3, CCL5, PDCD4, NOP16, RPA1, CDK4, RPS6, RPS5, RPL13A, PPP2R5D, SFI1, DKC1, PARP1, SMC4, FBL, FBL, IARS, IRF4, PAICS, TUBA1B, TUBB, TUBB, TUBB, TUBB, TUBB, TUBB, IL32, SSRP1, HMGB1, RPL23A, RRM1, ACAT1, ANP32E, SKA2, AAAS, CRTAM, WHSC1, ECE1, HPRT1, IMPDH2, PGAM1, RPL3, SCP2, PCNA, MRPS26, CLEC2D, TTF2, HSP90AB1, PRMT5, IPO5, PCNT, SLBP, YARS, HSPD1, FANCG, APOBEC3G, TRAF3IP3, CUEDC2, PHB, AKR7A2, FANCD2, NASP, SAMM50, RPLP0, CSRP1, CISH, GARS, QARS, TECR, EEF1E1, FBXO21, NME1, RPSA, TSEN15, FKBP11, SIGMAR1, LIG1, LDHA, NPM1, BRD3, HDAC3, ABCF2, RUVBL2, CCND2, OSBPL3, CLSPN, AARS, PRKCH, CDK6, TSPAN3, SPATC1L, SPATC1L, P2RY10, TMPO, TESC, FANCI, MTHFD1, DUT, SLC38A1, SNX25, SAP30, HMGB2, DNAJC9, HIST1H1D, SQLE, TUBB, BHLHE40, EBP, MT1F, FYN, CD96, MPRIP, NLGN4Y, ADGRG1, PRKAB2, GFOD1, ZNF836, KIF11, PFAS, KIAA0101, MFNG, GALNT3, POLR3G, GSTZ1, TNFRSF9, FAM117A, TUBB, UTS2, LDHB, ASRGL1, PNOC, PLEKHF1, TCTEX1D2, SLC37A3, FUT11, ZNF518B, MLLT3, RLTPR, NLRX1, SERF1B, CDK8, PPAPDC2, ADARB1, TMEM55B, SETD8, CLDN15, PRR3, ALYREF, ANO9, TXNDC5, LMBRD2, TMEM9, CRYL1, PPAP2A, FNDC9, P4HTM, STRBP, BLK, TNFRSF13B, VWA5A, MT1X, TULP3, PRR3, PRR3, PRR3, PHOSPHO2, PFKM, SEC61A2, ZNF324, MTA3, ZNF700, ERCC6L, ZNF718, ERCC2, CORO1A, MLLT11, SURF1, SURF1, CD24, STK35, VNN2, SLA2, FAM159A, CDK5, AGL, PKIG, METTL4, HEG1, TNFAIP1, KAT2A, ZKSCAN4, HHLA3, IFI27L1, IFI27L1, LIME1, IL18R1, EBF1, UBE3D, UBAP1L, ZNF287, KATNAL2, ZNF708, IPO13, N6AMT2, |

TABLE 19-continued

| |
|---|
| FASLG, LY9, ZNF428, CREB3L4, LXN, EOMES, FKRP, ZNF138, ARHGAP35, PECR, CNTROB, SEMA4B, MTMR1, FAM111B, SIAH2, COPG2, ABHD14A, TXLNG, SMYD2, LRRC61, PHTF1, SRF, ST6GALNAC6, PDCD2L, RAB33A, FGFBP2, ZNF121, ATP11B, SDHAF3, AUNIP, FEZ1, CENPQ, ZNF66, RCAN3, NELL2, AKAP1, DERL3, DERL3, PEX5, BTLA, LIMA1, USP30, CD244, WDSUB1, MAGEH1, CERK, P2RX5, FAHD2B, BRMS1L, KIAA0226L, TMPRSS3, ZNF33B, COQ7, ZNF398, FAM216A, DENND6B, LTBP4, ZNRD1, ZNRD1, ZNRD1, ZNRD1, ZNRD1, ZNRD1, TCAF1, LYSMD1, NUDT8, EHMT2, RRAS2, E2F1, VAV2, ZGRF1, MMACHC, NCALD, CFAP36, ATG10, GFI1, ISYNA1, ZNF507, ZNF444, TCTN1, RPL39L, NEIL2, PPOX, HGH1, NET1, B4GALT4, E2F7, FAM98B, NCAPH, CCDC64, PI4K2B, ARHGAP19-SLIT1, PIK3R1, ZBTB14, PARP3, ZBTB2, BCL9L, DPH1, APOBEC3H, URGCP, ABLIM1, CCNB1, TROAP, PSMG4, CLPTM1L, RAD51B, PRKAR1B, GSTM4, BAD, SLC39A14, MND1, ATP8A1, ALDOC, MMD, PDK1, IMMP2L, CCDC152, ACOT2, FUCA1, POC1A, HIST1H1C, KIF18A, RANBP6, BDH1, RPS26, APBB1, HPDL, FAM78A, TBCD, FKTN, ACO1, NUDT2, CCDC141, BICD1, KLHL22, MTFR2, RAD17, PLEKHG1, MSI2, FAM53C, SIT1, IGSF8, CPOX, LTA, LTA, LTA, SERGEF, CENPP, HIP1R, TMEM216, TNRC6C, MAPK3, MCM8, SPDL1, LRRCC1, PRMT9, MRM1, KIFC1, CHCHD6, KCNK5, NVL, INVS, RIC3, FAM20B, MBIP, MNAT1, IMMP1L, EHMT2, NBEAL2, TPD52, TADA2A, RNF8, CDT1, HDHD3, RASSF7, ALOX5AP, ACAD11, CHAF1A, CD7, CLSTN1, GTSE1, SLC2A1, WRN, WEE1, ATXN7L2, CRACR2A, CCHCR1, TMUB1, BACH2, AGAP2, CEP128, TSEN2, PXN, TRIP13, GAMT, CCDC77, GGH, XYLT2, SLC43A1, PGAP2, CHD3, SPATA20, KIF15, KIF15, MYBL2, ATG2B, ATP2B4, GOLPH3L, MMAB, TMEM154, SCD, KNSTRN, PNKD, HINT2, FADS1, FAM173A, TNIP3, E2F8, PEMT, PRIM2, CDCA3, ASB2, ASB2, TMEM223, DUS2, APITD1, TGFBR3, CCDC34, KIAA1524, MED30, ANKRD39, CCNB2, CDC7, CDCA2, PBK, PLCG1, NT5DC2, MBNL3, DNA2, GINS3, PTTG1, AGK, RNF126, SAAL1, HDGFRP3, SLC4A7, SHCBP1, NFS1, ITGB3BP, NLRP1, CCDC14, TBCD, OIP5, LANCL2, HMGXB3, EML3, ALKBH2, ANKRD33B, MKNK2, DLGAP5, CENPK, GPX7, TM7SF3, SUV39H1, CSPP1, TRPT1, KIF21B, ADCY3, PCED1B, CARD11, LRP8, TESPA1, CLP1, HJURP, SARS2, PIP4K2B, PIP4K2B, BCL11B, HADH, ANKRD32, PAQR4, BUB1, BCS1L, PRKCQ, POLE2, POMGNT1, SHMT1, NTAN1, NTAN1, TRAF4, SGOL2, FOXM1, PRC1, NUF2, STMN1, TMEM218, TMEM261, ANKRD54, MYL6B, MIPEP, SLC25A4, DDIAS, BIN1, CENPO, ITPR3, PDE4D, CMSS1, CD70, FAH, SKA3, KIFC1, FLYWCH2, KIF3B, DEPDC1B, MTHFD1L, PHF19, BOLA3, PSMC3IP, GRAP2, TMEM14A, PCMTD2, MPHOSPH9, H2AFX, SLCO4A1, ASNSD1, VPS13A, AURKB, LAG3, NPM3, JMJD4, MYO19, GSTM1, MANEA, POLR3H, CD3G, SYNE1, CEP152, QDPR, KLF12, ORC1, RSAD1, SLC9B2, NEDD9, SLC35B4, CDK2, GLMN, CKAP2L, PLK4, POLQ, CASC5, TFB2M, CCDC51, RAD51C, ANKRD36, DSCC1, MRS2, USP48, ASXL1, GIT1, PELO, OCIAD2, RAD54L, FIGNL1, CISD1, SLC16A1, SLC16A1, LRMP, MYO19, BAG2, XCL1, SUN1, CKAP2, ZMYND11, POLR2I, GMNN, TBC1D10C, DSN1, HDDC2, LANCL1, UBASH3A, SLAMF6, RECQL4, TMC8, TRUB2, SACS, KLRG1, NLE1, ZDHHC13, SPTBN1, CENPH, CDKN3, ABHD5, BCAS4, TTK, SMARCAD1, PRPSAP1, CLEC17A, ELP6, CCNF, HELLS, PAFAH1B3, INPP4B, SH2D2A, IFT57, NCAPG2, CD99, CD99, ICOS, THEMIS, THEMIS, DEF6, KRI1, UCK2, KIF20B, LCLAT1, SPAG5, CHAF1B, EXO1, SLC5A3, REXO2, SEL1L3, CDC6, BLM, ESCO2, S1PR1, NDFIP2, RFC3, CHEK1, TSEN54, EML2, CCNE2, IL12RB2, ETS1, CENPM, SCAPER, NIPSNAP1, CD22, KLRK1, HN1L, LRWD1, RITA1, GOLGA8A, NFATC2, CRYZ, DHCR7, RUSC1, PASK, MYCBP, CD5, DGKA, RNASEH2A, ATP2A3, SKAP1, XCL2, EIF4EBP1, ZAP70, RAD51, TRAT1, CDC20, CD320, KNTC1, FASN, LEO1, SNRNP25, MELK, KIF23, TMEM97, GZMA, CD247, JAKMIP1, GZMM, NCAPD2, ICAM3, LRBA, VRK1, WARS2, INTS1, LMAN1, CHTF18, KIF21A, RHOH, TCF19, COQ4, ATAD5, MAD2L1, ASNS, POLR1E, PARP2, RCC1, ITPR1, ANKRD36C, PRRC2B, DGCR14, NDC1, ORMDL3, SLC25A38, PGM1, CD3E, TOX, PKMYT1, TFDP1, MTFP1, IFNG, BUB1B, WDR54, TTI2, RFC4, SLC7A5, ACTN1, UBE2T, SEMA7A, ENO2, RPS6KB2, ATP6V0E2, UBE2C, CD6, VCAM1, FTSJ1, CCDC86, BCAT1, SLC29A1, DHFR, CENPU, THOC3, POLA1, IPO4, ACAP1, MCM10, SRM, GINS2, RGS16, PPAT, LMNB2, OXCT1, PHGDH, NPRL2, TPGS2, CDCA7L, DTYMK, WDHD1, SLC27A2, PRDX2, SLC38A5, TACC3, NCAPG, BIRC5, PYCR1, ADD3, SLC9A3R1, NDC80, DHRS3, CDC45, BANK1, ULK3, SCCPDH, TNFRSF18, CST7, SLC7A1, P2RY8, P2RY8, PDLIM1, PPP1R16B, HMGCR, RUVBL1, GEMIN4, TPX2, TCF19, SH2D1A, BARD1, CENPF, CTPS1, ITK, WDR34, HOPX, MAP4K1, ZBTB32, BCL11A, ATAD2, ADH5, GNG2, CCNA2, PRKACB, DHCR24, SLC35B2, NCAPD3, FCRLA, EMB, CDCA7, ALDH18A1, MSH2, UNG, RACGAP1, CD3D, SYNE2, GPR171, ACOT7, PTPN7, AKR1B1, RRM2, CD8B, CD79B, CDCA4, PSD4, NUP210, KIF22, ASF1B, WDR6, CXCR3, ST6GAL1, DTL, CDCA5, TK1, ZWINT, CAD, FCRL3, PSAT1, NUSAP1, ESYT1, UHRF1, TIGIT, CDK1, DDIT4, ADGRG5, PAX5, LAT, TMEM106C, IL2RB, PTPRCAP, FEN1, MCM4, POLD2, CD19, PRF1, GZMH, ITM2A, CYFIP2, AMICA1, CD2, MKI67, LBH, CXCR5, CD79A, CD8A, ANXA6, MCM2, MCM6, SHMT2, LCK, TYMS, TOP2A, MCM3, NKG7, MS4A1, IL2RA, MCM7, ZBED2, GZMB. |
| Preferably ACTG1, PABPC1, RPS14, NONO, EIF5A, RPL6, PARK7, RPL18, RPS19, HNRNPA2B1, EEF2, RPL37A, RPS13, UBB, SET, RPL26, ENO1, RPL15, GPI, RPS15, RPS16, RPL10, TPI1, EIF4B, RPL27, RPLP2, HSP90AA1, HMGN2, SLC25A5, RPS27A, RPS11, RPS10, RPL32, RPL31, HSPE1, EEF1B2, RPS24, RPL14, SOD1, RPL27A, RPL19, CD48, H2AFZ, RPL18A, RPS23, RPL17, ATP5G3, SERBP1, RPL8, PRMT1, FDFT1, NOP56, CCT2, C1QBP, HNRNPM, RPS21, RPL36A, PTMA, JAK3, EIF3C, CASP2, FUBP1, ANP32B, RPL12, RPL4, CCT3, PPIA, ELOVL5, NOLC1, AHCY, RPL41, RPS8, RPL7, MRPL12, NUDT21, CBX5, RBBP7, RANBP1, RPL21, RPS18, RPS18, RPS18, RPS18, RPS18, RPL29, RAC2, HSPA8, ARPC5L, ENSA, RPS3A, RPL13, TUBA1C, RPS25, RPS25, GNB2L1, SFXN1, MCM5, APOBEC3C, RPS12, RPS2, RPL5, RPL7A, RPL7A, RPS4X, HNRNPA1, SNRPD2, IKZF3, RPL10A, EBNA1BP2, TUBA4A, SLC25A39, NME2, RPS3, GAPDH, CCND3, GTF3A, DHX30, PEBP1, EZR, RAN, RPLP1, STIP1, EEF1G, CD82, |

TABLE 19-continued

HACD3, CCL5, PDCD4, NOP16, RPA1, CDK4, RPS6, RPS5, RPL13A, SFI1, DKC1, PARP1, SMC4, FBL, FBL, IARS, IRF4, PAICS, TUBA1B, TUBB, TUBB, TUBB, TUBB, TUBB, TUBB, IL32, SSRP1, HMGB1, RPL23A, RRM1, ACAT1, ANP32E, CRTAM, WHSC1, ECE1, HPRT1, IMPDH2, PGAM1, RPL3, SCP2, PCNA, MRPS26, CLEC2D, TTF2, HSP90AB1, IPO5, PCNT, SLBP, YARS, HSPD1, APOBEC3G, TRAF3IP3, CUEDC2, PHB, AKR7A2, FANCD2, NASP, SAMM50, RPLP0, CISH, GARS, QARS, TECR, EEF1E1, NME1, RPSA, TSEN15, SIGMAR1, LIG1, LDHA, NPM1, BRD3, HDAC3, ABCF2, RUVBL2, CCND2, OSBPL3, CLSPN, AARS, PRKCH, CDK6, TSPAN3, SPATC1L, SPATC1L, P2RY10, TMPO, TESC, FANCI, MTHFD1, DUT, SLC38A1, SNX25, SAP30, HMGB2, DNAJC9, HIST1H1D, SQLE, TUBB, BHLHE40, EBP, MT1F, FYN, CD96, MPRIP, NLGN4Y, ADGRG1, PRKAB2, GFOD1, ZNF836, PFAS, KIAA0101, MFNG, GALNT3, POLR3G, GSTZ1, TNFRSF9, FAM117A, UTS2, LDHB, ASRGL1, PNOC, PLEKHF1, TCTEX1D2, SLC37A3, FUT11, MLLT3, RLTPR, NLRX1, SERF1B, CDK8, PPAPDC2, ADARB1, TMEM55B, SETD8, CLDN15, PRR3, ALYREF, ANO9, TXNDC5, TMEM9, CRYL1, PPAP2A, FNDC9, P4HTM, STRBP, BLK, TNFRSF13B, VWA5A, MT1X, PRR3, PRR3, PRR3, PHOSPHO2, PFKM, SEC61A2, ZNF324, MTA3, ZNF700, ERCC6L, ZNF718, ERCC2, CORO1A, CD24, STK35, VNN2, SLA2, FAM159A, CDK5, AGL, PKIG, HEG1, TNFAIP1, KAT2A, ZKSCAN4, HHLA3, IFI27L1, IFI27L1, LIME1, IL18R1, EBF1, UBE3D, UBAP1L, ZNF287, ZNF708, IPO13, N6AMT2, FASLG, LY9, ZNF428, CREB3L4, LXN, EOMES, ZNF138, ARHGAP35, PECR, CNTROB, SEMA4B, MTMR1, FAM111B, SIAH2, COPG2, ABHD14A, TXLNG, SMYD2, LRRC61, PHTF1, SRF, ST6GALNAC6, PDCD2L, RAB33A, FGFBP2, ATP11B, SDHAF3, AUNIP, FEZ1, CENPQ, ZNF66, RCAN3, NELL2, AKAP1, DERL3, DERL3, PEX5, BTLA, LIMA1, USP30, CD244, WDSUB1, MAGEH1, CERK, P2RX5, FAHD2B, BRMS1L, KIAA0226L, TMPRSS3, ZNF33B, COQ7, ZNF398, FAM216A, DENND6B, LTBP4, ZNRD1, ZNRD1, ZNRD1, ZNRD1, ZNRD1, ZNRD1, LYSMD1, NUDT8, EHMT2, RRAS2, E2F1, VAV2, MMACHC, NCALD, CFAP36, ATG10, GFI1, ZNF507, ZNF444, TCTN1, RPL39L, NEIL2, PPOX, HGH1, B4GALT4, E2F7, FAM98B, NCAPH, CCDC64, PI4K2B, ARHGAP19-SLIT1, PIK3R1, ZBTB14, PARP3, ZBTB2, BCL9L, DPH1, APOBEC3H, ABLIM1, CCNB1, TROAP, CLPTM1L, RAD51B, PRKAR1B, GSTM4, BAD, SLC39A14, MND1, ATP8A1, ALDOC, MMD, PDK1, IMMP2L, CCDC152, FUCA1, POC1A, HIST1H1C, KIF18A, RANBP6, BDH1, RPS26, APBB1, HPDL, FKTN, ACO1, NUDT2, CCDC141, BICD1, KLHL22, MTFR2, RAD17, PLEKHG1, MSI2, FAM53C, SIT1, IGSF8, CPOX, LTA, LTA, LTA, SERGEF, CENPP, HIP1R, TNRC6C, MAPK3, MCM8, SPDL1, LRRCC1, PRMT9, MRM1, KIFC1, CHCHD6, KCNK5, RIC3, FAM20B, MBIP, EHMT2, NBEAL2, TPD52, TADA2A, RNF8, CDT1, HDHD3, RASSF7, ALOX5AP, ACAD11, CHAF1A, CD7, CLSTN1, GTSE1, SLC2A1, WRN, WEE1, ATXN7L2, CRACR2A, CCHCR1, TMUB1, BACH2, AGAP2, CEP128, TSEN2, PXN, TRIP13, GAMT, CCDC77, GGH, XYLT2, SLC43A1, PGAP2, CHD3, SPATA20, KIF15, KIF15, MYBL2, ATG2B, ATP2B4, GOLPH3L, MMAB, TMEM154, SCD, HINT2, FADS1, FAM173A, TNIP3, E2F8, PEMT, PRIM2, CDCA3, ASB2, ASB2, DUS2, APITD1, TGFBR3, CCDC34, KIAA1524, MED30, ANKRD39, CCNB2, CDC7, CDCA2, PBK, PLCG1, NT5DC2, MBNL3, DNA2, GINS3, PTTG1, AGK, SAAL1, HDGFRP3, SLC4A7, SHCBP1, NFS1, ITGB3BP, NLRP1, CCDC14, TBCD, OIP5, LANCL2, HMGXB3, EML3, ALKBH2, ANKRD33B, MKNK2, DLGAP5, CENPK, GPX7, TM7SF3, SUV39H1, CSPP1, TRPT1, KIF21B, ADCY3, PCED1B, CARD11, LRP8, TESPA1, CLP1, HJURP, SARS2, PIP4K2B, PIP4K2B, BCL11B, HADH, ANKRD32, PAQR4, BUB1, BCS1L, PRKCQ, POLE2, POMGNT1, SHMT1, NTAN1, NTAN1, TRAF4, SGOL2, FOXM1, PRC1, NUF2, STMN1, TMEM218, TMEM261, ANKRD54, MYL6B, MIPEP, SLC25A4, DDIAS, BIN1, CENPO, ITPR3, PDE4D, CMSS1, CD70, FAH, SKA3, KIFC1, FLYWCH2, KIF3B, DEPDC1B, MTHFD1L, BOLA3, PSMC3IP, GRAP2, TMEM14A, MPHOSPH9, H2AFX, SLCO4A1, ASNSD1, VPS13A, AURKB, LAG3, NPM3, JMJD4, MYO19, GSTM1, MANEA, POLR3H, CD3G, SYNE1, CEP152, QDPR, KLF12, ORC1, RSAD1, SLC9B2, NEDD9, SLC35B4, CDK2, GLMN, CKAP2L, PLK4, POLQ, CASC5, TFB2M, CCDC51, RAD51C, ANKRD36, DSCC1, MRS2, USP48, ASXL1, GIT1, PELO, OCIAD2, RAD54L, FIGNL1, CISD1, SLC16A1, SLC16A1, LRMP, MYO19, BAG2, XCL1, SUN1, CKAP2, ZMYND11, POLR2I, GMNN, TBC1D10C, DSN1, HDDC2, LANCL1, UBASH3A, SLAMF6, RECQL4, TMC8, TRUB2, SACS, KLRG1, NLE1, ZDHHC13, SPTBN1, CENPH, CDKN3, ABHD5, BCAS4, TTK, SMARCAD1, PRPSAP1, CLEC17A, ELP6, CCNF, HELLS, PAFAH1B3, INPP4B, SH2D2A, IFT57, NCAPG2, CD99, CD99, ICOS, THEMIS, THEMIS, DEF6, KRI1, UCK2, KIF20B, LCLAT1, SPAG5, CHAF1B, EXO1, SLC5A3, REXO2, SEL1L3, CDC6, BLM, ESCO2, NDFIP2, RFC3, CHEK1, TSEN54, EML2, CCNE2, IL12RB2, ETS1, CENPM, SCAPER, NIPSNAP1, CD22, KLRK1, HNIL, LRWD1, RITA1, GOLGA8A, NFATC2, CRYZ, DHCR7, RUSC1, PASK, MYCBP, CD5, DGKA, RNASEH2A, ATP2A3, SKAP1, XCL2, EIF4EBP1, ZAP70, RAD51, TRAT1, CDC20, CD320, KNTC1, FASN, LEO1, SNRNP25, MELK, KIF23, TMEM97, GZMA, CD247, JAKMIP1, GZMM, ICAM3, LRBA, VRK1, WARS2, INTS1, LMAN1, CHTF18, KIF21A, RHOH, TCF19, COQ4, ATAD5, MAD2L1, ASNS, POLR1E, PARP2, RCC1, ITPR1, ANKRD36C, PRRC2B, DGCR14, NDC1, ORMDL3, SLC25A38, PGM1, CD3E, TOX, PKMYT1, TFDP1, MTFP1, IFNG, BUB1B, WDR54, TTI2, RFC4, SLC7A5, ACTN1, UBE2T, SEMA7A, ENO2, RPS6KB2, ATP6V0E2, UBE2C, CD6, VCAM1, FTSJ1, CCDC86, BCAT1, SLC29A1, DHFR, CENPU, THOC3, POLA1, IPO4, ACAP1, MCM10, SRM, GINS2, RGS16, PPAT, LMNB2, OXCT1, PHGDH, NPRL2, TPGS2, CDCA7L, DTYMK, WDHD1, SLC27A2, PRDX2, SLC38A5, TACC3, NCAPG, BIRC5, PYCR1, ADD3, SLC9A3R1, NDC80, DHRS3, CDC45, BANK1, ULK3, SCCPDH, TNFRSF18, CST7, SLC7A1, P2RY8, P2RY8, PDLIM1, PPP1R16B, HMGCR, RUVBL1, GEMIN4, TPX2, TCF19, SH2D1A, BARD1, CENPF, CTPS1, ITK, WDR34, HOPX, MAP4K1, ZBTB32, BCL11A, ATAD2, ADH5, GNG2, CCNA2, PRKACB, DHCR24, SLC35B2, NCAPD3, FCRLA, EMB, CDCA7, ALDH18A1, MSH2, UNG, RACGAP1, CD3D, SYNE2, GPR171, ACOT7, PTPN7, AKR1B1, RRM2, CD8B, CD79B, CDCA4, PSD4, NUP210, KIF22, ASF1B, WDR6, CXCR3, ST6GAL1, DTL, CDCA5, TK1, ZWINT, CAD, FCRL3, PSAT1,

TABLE 19-continued

| |
|---|
| NUSAP1, ESYT1, UHRF1, TIGIT, CDK1, DDIT4, ADGRG5, PAX5, LAT, TMEM106C, IL2RB, PTPRCAP, FEN1, MCM4, POLD2, CD19, PRF1, GZMH, ITM2A, CYFIP2, AMICA1, CD2, MKI67, LBH, CXCR5, CD79A, CD8A, ANXA6, MCM2, MCM6, SHMT2, LCK, TYMS, TOP2A, MCM3, NKG7, MS4A1, IL2RA, MCM7, ZBED2, GZMB. |

TABLE 20

| |
|---|
| JMJD4, MYO19, GSTM1, MANEA, POLR3H, CD3G, SYNE1, CEP152, QDPR, KLF12, ORC1, RSAD1, SLC9B2, NEDD9, SLC35B4, CDK2, GLMN, CKAP2L, PLK4, POLQ, CASC5, TFB2M, CCDC51, RAD51C, ANKRD36, DSCC1, MRS2, USP48, ASXL1, GIT1, PELO, OCIAD2, RAD54L, FIGNL1, CISD1, SLC16A1, SLC16A1, LRMP, MYO19, BAG2, XCL1, SUN1, CKAP2, ZMYND11, POLR2I, GMNN, TBC1D10C, DSN1, HDDC2, LANC1, UBASH3A, SLAMF6, RECQL4, TMC8, TRUB2, SACS, KLRG1, NLE1, ZDHHC13, SPTBN1, CENPH, CDKN3, ABHD5, BCAS4, TTK, SMARCAD1, PRPSAP1, CLEC17A, ELP6, CCNF, HELLS, PAFAH1B3, INPP4B, SH2D2A, IFT57, NCAPG2, CD99, CD99, ICOS, THEMIS, THEMIS, DEF6, KRI1, UCK2, KIF20B, LCLAT1, SPAG5, CHAF1B, EXO1, SLC5A3, REXO2, SEL1L3, CDC6, BLM, ESCO2, S1PR1, NDFIP2, RFC3, CHEK1, TSEN54, EML2, CCNE2, IL12RB2, ETS1, CENPM, SCAPER, NIPSNAP1, CD22, KLRK1, HN1L, LRWD1, RITA1, GOLGA8A, NFATC2, CRYZ, DHCR7, RUSC1, PASK, MYCBP, CD5, DGKA, RNASEH2A, ATP2A3, SKAP1, XCL2, EIF4EBP1, ZAP70, RAD51, TRAT1, CDC20, CD320, KNTC1, FASN, LEO1, SNRNP25, MELK, KIF23, TMEM97, GZMA, CD247, JAKMIP1, GZMM, NCAPD2, ICAM3, LRBA, VRK1, WARS2, INTS1, LMAN1, CHTF18, KIF21A, RHOH, TCF19, COQ4, ATAD5, MAD2L1, ASNS, POLR1E, PARP2, RCC1, ITPR1, ANKRD36C, PRRC2B, DGCR14, NDC1, ORMDL3, SLC25A38, PGM1, CD3E, TOX, PKMYT1, TFDP1, MTFP1, IFNG, BUB1B, WDR54, TTI2, RFC4, SLC7A5, ACTN1, UBE2T, SEMA7A, ENO2, RPS6KB2, ATP6V0E2, UBE2C, CD6, VCAM1, FTSJ1, CCDC86, BCAT1, SLC29A1, DHFR, CENPU, THOC3, POLA1, IPO4, ACAP1, MCM10, SRM, GINS2, RGS16, PPAT, LMNB2, OXCT1, PHGDH, NPRL2, TPGS2, CDCA7L, DTYMK, WDHD1, SLC27A2, PRDX2, SLC38A5, TACC3, NCAPG, BIRC5, PYCR1, ADD3, SLC9A3R1, NDC80, DHRS3, CDC45, BANK1, ULK3, SCCPDH, TNFRSF18, CST7, SLC7A1, P2RY8, P2RY8, PDLIM1, PPP1R16B, HMGCR, RUVBL1, GEMIN4, TPX2, TCF19, SH2D1A, BARD1, CENPF, CTPS1, ITK, WDR34, HOPX, MAP4K1, ZBTB32, BCL11A, ATAD2, ADH5, GNG2, CCNA2, PRKACB, DHCR24, SLC35B2, NCAPD3, FCRLA, EMB, CDCA7, ALDH18A1, MSH2, UNG, RACGAP1, CD3D, SYNE2, GPR171, ACOT7, PTPN7, AKR1B1, RRM2, CD8B, CD79B, CDCA4, PSD4, NUP210, KIF22, ASF1B, WDR6, CXCR3, ST6GAL1, DTL, CDCA5, TK1, ZWINT, CAD, FCRL3, PSAT1, NUSAP1, ESYT1, UHRF1, TIGIT, CDK1, DDIT4, ADGRG5, PAX5, LAT, TMEM106C, IL2RB, PTPRCAP, FEN1, MCM4, POLD2, CD19, PRF1, GZMH, ITM2A, CYFIP2, AMICA1, CD2, MKI67, LBH, CXCR5, CD79A, CD8A, ANXA6, MCM2, MCM6, SHMT2, LCK, TYMS, TOP2A, MCM3, NKG7, MS4A1, IL2RA, MCM7, ZBED2, GZMB. |
| Preferably JMJD4, MYO19, GSTM1, MANEA, POLR3H, CD3G, SYNE1, CEP152, QDPR, KLF12, ORC1, RSAD1, SLC9B2, NEDD9, SLC35B4, CDK2, GLMN, CKAP2L, PLK4, POLQ, CASC5, TFB2M, CCDC51, RAD51C, ANKRD36, DSCC1, MRS2, USP48, ASXL1, GIT1, PELO, OCIAD2, RAD54L, FIGNL1, CISD1, SLC16A1, SLC16A1, LRMP, MYO19, BAG2, XCL1, SUN1, CKAP2, ZMYND11, POLR2I, GMNN, TBC1D10C, DSN1, HDDC2, LANCL1, UBASH3A, SLAMF6, RECQL4, TMC8, TRUB2, SACS, KLRG1, NLE1, ZDHHC13, SPTBN1, CENPH, CDKN3, ABHD5, BCAS4, TTK, SMARCAD1, PRPSAP1, CLEC17A, ELP6, CCNF, HELLS, PAFAH1B3, INPP4B, SH2D2A, IFT57, NCAPG2, CD99, CD99, ICOS, THEMIS, THEMIS, DEF6, KRI1, UCK2, KIF20B, LCLAT1, SPAG5, CHAF1B, EXO1, SLC5A3, REXO2, SEL1L3, CDC6, BLM, ESCO2, NDFIP2, RFC3, CHEK1, TSEN54, EML2, CCNE2, IL12RB2, ETS1, CENPM, SCAPER, NIPSNAP1, CD22, KLRK1, HN1L, LRWD1, RITA1, GOLGA8A, NFATC2, CRYZ, DHCR7, RUSC1, PASK, MYCBP, CD5, DGKA, RNASEH2A, ATP2A3, SKAP1, XCL2, EIF4EBP1, ZAP70, RAD51, TRAT1, CDC20, CD320, KNTC1, FASN, LEO1, SNRNP25, MELK, KIF23, TMEM97, GZMA, CD247, JAKMIP1, GZMM, ICAM3, LRBA, VRK1, WARS2, INTS1, LMAN1, CHTF18, KIF21A, RHOH, TCF19, COQ4, ATAD5, MAD2L1, ASNS, POLR1E, PARP2, RCC1, ITPR1, ANKRD36C, PRRC2B, DGCR14, NDC1, ORMDL3, SLC25A38, PGM1, CD3E, TOX, PKMYT1, TFDP1, MTFP1, IFNG, BUB1B, WDR54, TTI2, RFC4, SLC7A5, ACTN1, UBE2T, SEMA7A, ENO2, RPS6KB2, ATP6V0E2, UBE2C, CD6, VCAM1, FTSJ1, CCDC86, BCAT1, SLC29A1, DHFR, CENPU, THOC3, POLA1, IPO4, ACAP1, MCM10, SRM, GINS2, RGS16, PPAT, LMNB2, OXCT1, PHGDH, NPRL2, TPGS2, CDCA7L, DTYMK, WDHD1, SLC27A2, PRDX2, SLC38A5, TACC3, NCAPG, BIRC5, PYCR1, ADD3, SLC9A3R1, NDC80, DHRS3, CDC45, BANK1, ULK3, SCCPDH, TNFRSF18, CST7, SLC7A1, P2RY8, P2RY8, PDLIM1, PPP1R16B, HMGCR, RUVBL1, GEMIN4, TPX2, TCF19, SH2D1A, BARD1, CENPF, CTPS1, ITK, WDR34, HOPX, MAP4K1, ZBTB32, BCL11A, ATAD2, ADH5, GNG2, CCNA2, PRKACB, DHCR24, SLC35B2, NCAPD3, FCRLA, EMB, CDCA7, ALDH18A1, MSH2, UNG, RACGAP1, CD3D, SYNE2, GPR171, ACOT7, PTPN7, AKR1B1, RRM2, CD8B, CD79B, CDCA4, PSD4, NUP210, KIF22, ASF1B, WDR6, CXCR3, ST6GAL1, DTL, CDCA5, TK1, ZWINT, CAD, FCRL3, PSAT1, NUSAP1, ESYT1, UHRF1, TIGIT, CDK1, DDIT4, ADGRG5, PAX5, LAT, TMEM106C, IL2RB, PTPRCAP, FEN1, MCM4, POLD2, CD19, PRF1, GZMH, ITM2A, CYFIP2, AMICA1, CD2, MKI67, LBH, CXCR5, CD79A, CD8A, ANXA6, MCM2, MCM6, SHMT2, LCK, TYMS, TOP2A, MCM3, NKG7, MS4A1, IL2RA, MCM7, ZBED2, GZMB. |

Tables 19 and 20 in an embodiment provides a signature of dendritic cells (e.g. cDC), and represents downregulated genes in particular DC subpopulations, termed VEx-B, preferably associated with or derived from elite controller phenotype, preferably associated with HIV infection. Preferably downregulation is evaluated compared to VEx-A cells.

TABLE 21

| |
|---|
| TTN, PCDH9, PRH2, FRMD6, NAP1L2, GABARAPL2, WNT10B, UNC5D, EIF2B2, NME6, XKR5, PLVAP, ACADS, TIAM1, TRMT61A, STXBP6, MYO6, KCTD9, LHFPL3, METTL7B, FABP2, MGAT4C, ZSWIM2, CAMK2D, CC2D1A, ATOH8, LPHN3, GJA1, COL25A1, CPA4, FAM83H, VASH2, CAB39L, STK33, DOPEY2, S100Z, PIGB, CCDC110, HECTD1, PIM1, TLE3, SPSB1, AKAP12, SLC38A7, EIF1AX, SLC15A4, DNAJC11, AACS, GATA3, SETDB2, RTTN, NANOS1, WDR24, TNFRSF11B, DLG5, CD160, CELSR1, RASGRP1, ESRRG, CDH9, TGFBR3, JAKMIP1, ST20, GLYR1, ST20-MTHFS, MTHFS, APBB1IP, FAM198B, SSPN, PPARGC1B, CDKL5, DOK1, POLR2C, MEF2C, TMEM155, SLCO1B1, NOL4, SLCO6A1, SIGLEC1, PTPRG, LYPD6, ZNF507, UCKL1, ANGPTL1, RAB2B, IER3, CCBL2, BIN1, KCNMB4, USP2, RBM39, SLAIN2, DCDC5, DCDC1, C9orf68, TMPRSS11A, TSC22D3, MFAP5, MUC16, SOWAHD, AKR1B10, LMOD2, SPDYE5, LETMD1, PPP1R35, SLC4A4, BDH1, PRR14L, MARS, CYBB, SDHC, EFCAB5, INO80E, ZFY, NEK9, CHM, GABPB1, CPEB4, CSF1R C9orf131 ZNF619, SH3RF1, AP1M1, TEX28, LPL, ARL6, PRG2, PTPN11, AAMP, SLC35E1, SLC43A3, FCRL5, LDHD, PRKAA2, NOC2L, PSG3, PSG1, ATG9B, TUBB4B, CHL1, KCNK5, SPATA7, ACVR1C, AEN, TP53BP1, TNIP3, ZNF786, CCDC141, NHSL2, MAPRE3, GLS, RFWD2, CBFA2T3, GPR85, N4BP3, GLIS3, SPHK2, C6orf130, XPC, SEMA4D, MATK, NCR1, NIPAL4, MYOZ2. |

Table 21 in an embodiment provides a signature of dendritic cells (e.g. cDC), and represents differentially expressed genes in particular DC subpopulations, preferably associated with or derived from high neutralizer phenotype, preferably associated with HIV infection. Preferably differential expression is evaluated compared to cells from non-high neutralizers.

TABLE 22

| |
|---|
| CD160, TTN, SIGLEC1, TGFBR3, ZFY, BIN1, IER3, FCRL5, MFAP5, GATA3, MATK, RASGRP1, PIM1, PCDH9, MYO6, AACS, JAKMIP1, BDH1, PPP1R35, KCTD9, AEN, NIPAL4, NCR1, CCDC141, CPA4, C9orf68, TUBB4B, ZNF507, POLR2C, SLC15A4, TP53BP1, GABPB1, CPEB4, NAP1L2, RBM39, N4BP3, TLE3, HECTD1, STXBP6, DLG5, TSC22D3, STK33, WNT10B, SLC35E1, NANOS1, FRMD6, CAMK2D, GLS, KCNK5, CCDC110, PRH2, RAB2B, TEX28, LHFPL3, TNFRSF11B, MGAT4C, SLC4A4, LYPD6, GPR85, PTPN11, GJA1, DCDC5, DCDC1, SEMA4D, SSPN, KCNMB4, TMPRSS11A, UNC5D, FABP2, CDH9, EIF1AX, SLCO6A1, CELSR1, LPHN3, NOL4, SLCO1B1, MYOZ2, C9orf131, PTPRG, TNIP3, VASH2, PRKAA2, ATOH8, USP2, ATG9B, TMEM155, LMOD2, ZSWIM2, SPSB1, COL25A1, CHL1, PSG3, PSG1, XKR5, ACVR1C, FAM83H, AKR1B10, ESRRG, ANGPTL1, MUC16, AKAP12, EFCAB5. |
| Preferably CD160, TTN, SIGLEC1, TGFBR3, ZFY, BIN1, IER3, FCRL5, MFAP5, GATA3, MATK. |

Table 22 in an embodiment provides a signature of dendritic cells (e.g. cDC), and represents upregulated genes in particular DC subpopulations, preferably associated with or derived from high neutralizer phenotype, preferably associated with HIV infection. Preferably upregulation is evaluated compared to cells from non-high neutralizers.

TABLE 23

| |
|---|
| NOC2L, LETMD1, SLAIN2, MARS, GLIS3, GLYR1, AP1M1, XPC, UCKL1, SDHC, APBB1IP, PRR14L, CC2D1A, DOPEY2, NEK9, SETDB2, GABARAPL2, CBFA2T3, CDKL5, AAMP, PRG2, SLC43A3, EIF2B2, PIGB, DNAJC11, MEF2C, DOK1, CCBL2, RFWD2, WDR24, ZNF619, C6orf130, TRMT61A, TIAM1, METTL7B, PLVAP, SPDYE5, CHM, ARL6, PPARGC1B, MAPRE3, CYBB, CAB39L, NME6, ACADS, INO80E, RTTN, ZNF786, ST20, ST20-MTHFS, MTHFS, SH3RF1, SPATA7, SOWAHD, S100Z, SPHK2, NHSL2, CSF1R, SLC38A7, LPL, FAM198B, LDHD. |
| Preferably SPATA7, SOWAHD, S100Z, SPHK2, NHSL2, CSF1R, SLC38A7, LPL, FAM198B, LDHD. |

Table 23 in an embodiment provides a signature of dendritic cells (e.g. cDC), and represents downregulated genes in particular DC subpopulations, preferably associated with or derived from high neutralizer phenotype, preferably associated with HIV infection. Preferably downregulation is evaluated compared to cells from non-high neutralizers.

TABLE 24

| |
|---|
| TMEM199, INO80E, SLC45A1, C21orf2, TRIM26, DOPEY2, PQLC2, IER3, C11orf1, SIGLEC1, ATP10A, SELRC1, STK33, C1orf159, C22orf40, LPAR5, SEC22A, UBXN8, RAB3C, RABGAP1, CNTROB, SERPINB6, SNX14, ARSB, TNFAIP8L1, FAM20A, HAT1, ZC3H6, CHMP7, KIAA0913, MOXD1, ZMAT2, STEAP4, RFESD, PSG3, PSG1, CDAN1, KDM5C, NOC2L, SYCP2, CA8, ZXDB, LDOC1L, TNRC6C, MFSD10, ASPH, GEMIN6, TMEM44, KCNRG, WARS2, HDAC10, LRRC45, LRRN1, CD7, NEK11, TAF9B, IRGM, C19orf40, LOC100130451, PHF16, RNF126, PPP1R16B, BPI, C12orf65, MYH9, GLUD2, C10orf26, NME6, PNISR, ANKRD5, GDPD3, MIB2, CDC42BPB, THOC5, ORMDL2, IMP4, FNDC9, RCAN3, LYSMD2, BARD1, REPS2, CAST, GATAD2A, ANGPTL1, LRP12, HK2, CCDC126, DDX56, LINGO3, TBCCD1, WDR45, N4BP2, PRAF2, SLC19A3, FAM134A, RALGAPA1, ASF1B, GBP4, TCERG1, GNRH1, PHKA1, GADD45B, HSD17B10, BIN1, CHP2, RASL11A, ASXL1, MAFK, GLT1D1, TREX2, UNC5D, C15orf54, GALR2, ANKAR, ACAT2, AACS. |

Table 24 in an embodiment provides a signature of dendritic cells (e.g. cDC), and represents differentially expressed genes in particular DC subpopulations, preferably associated with or derived from low neutralizer phenotype, preferably associated with HIV infection. Preferably differential expression is evaluated compared to cells from non-low neutralizers.

TABLE 25

| |
|---|
| C22orf40, LPAR5, INO80E, GEMIN6, C19orf40, RASL11A, PQLC2, SELRC1, ASF1B, CDAN1, WARS2, C1orf159, GBP4, FAM20A, CHMP7, TMEM199, SEC22A, NME6, DOPEY2, C12orf65, KCNRG, TNFAIP8L1, CCDC126, SLC45A1, C10orf26, LRP12, STEAP4, ORMDL2, CNTROB, KIAA0913, ATP10A, THOC5, TBCCD1, RABGAP1, LYSMD2, ZMAT2, BARD1, NEK11, BPI, HAT1, REPS2, SNX14, SNX14, IMP4, DDX56, TREX2, GLT1D1, ANKRD5, FNDC9, FAM134A, RAB3C, PHF16, ZC3H6, WDR45, PRAF2, PHKA1, GLUD2, SLC19A3, LINGO3, NOC2L, LRRN1. |
| Preferably C22orf40, LPAR5, INO80E, GEMIN6, C19orf40, RASL11A. |
| Or preferably INO80E, TMEM199, SLC45A1. |
| More preferably INO80E. |

Table 25 in an embodiment provides a signature of dendritic cells (e.g. cDC), and represents upregulated genes in particular DC subpopulations, preferably associated with or derived from low neutralizer phenotype, preferably associated with HIV infection. Preferably upregulation is evaluated compared to cells from non-low neutralizers.

TABLE 26

| |
|---|
| PSG3, PSG1, UNC5D, CAST, ANGPTL1, HSD17B10, GALR2, CHP2, MYH9, MFSD10, RALGAPA1, C15orf54, ACAT2, PNISR, IRGM, TCERG1, MOXD1, RFESD, SERPINB6, N4BP2, GATAD2A, STK33, CA8, TNRC6C, TMEM44, LDOC1L, KDM5C, TAF9B, HK2, LOC100130451, RNF126, ASXL1, MAFK, SYCP2, ZXDB, C21orf2, CDC42BPB, ARSB, ASPH, LRRC45, AACS, GDPD3, HDAC10, TRIM26, ANKAR, GNRH1, RCAN3, GADD45B, BIN1, C11orf1, UBXN8, CD7, PPP1R16B, MIB2, SIGLEC1, IER3. |
| Preferably RCAN3, GADD45B, BIN1, C11orf1, UBXN8, CD7, PPP1R16B, MIB2, SIGLEC1, IER3. |
| Or preferably C21orf2, TRIM26. |

Table 26 in an embodiment provides a signature of dendritic cells (e.g. cDC), and represents downregulated genes in particular DC subpopulations, preferably associated with or derived from low neutralizer phenotype, preferably associated with HIV infection. Preferably downregulation is evaluated compared to cells from non-low neutralizers.

TABLE 27

| |
|---|
| TUBE1, MOG, QPCTL, C20orf152, ZDHHC15, ALDH6A1, KLHL28, ZNF805, ABCA7, SOWAHD, PRSS3, FGF5, DIS3, NOG, PIF1, ENAH, SPG21, OSGEP, ADCY7, MANEAL, ADIPOQ, CCBE1, LIN28A, CNNM3, TMEM14C, HCFC1R1, GPR180, PAEP, LRRN4CL, |

TABLE 27-continued

| |
|---|
| ABLIM1, TMEM41B, C1orf123, PLEKHH3, DACT3, MFSD1, AKAP5, TMEM44, MTMR11, VCL, SPINT1, MYO6, IGBP1, AGXT2L2, DPH1, IRE1, ZNF490, ASCC2, RSPH3, TMEM130, POLQ, FAM18A, ABCB9, SYNJ2, NXN, WDR31, ATG4D, TRAF3, TRIM26, CBFA2T2, PIWIL2, SLC27A3, MFSD10, RUNDC1, ABCA1, HEXIM2, ADAMTS4, TMEM2, SAR1B, CRTAM, ACP5, ZNF432, CPEB4, NDFIP1, C9orf47, TMEM213, TRIP11, RNF41, KANSL2, MCF2L2, GALNTL1, IGSF6, FBLIM1, DENND1C, PARP3, NRD1, HOXA7, PARD6G, ITFG3, POGZ, MRPL11, ZNF543, ZC3H6, ZDBF2, GPNMB, STAC2, METTL7B, LOC100506688, C4orf27, PBX4, PLVAP, TMEM8A, G6PC3, C3orf37, FAM40B, C21orf62, TMEM170A, GANC, TMEM87A, TTYH1, OTUD7B, HIBADH, CPNE1, SPHK2, DECR1, SCFD2, NAGPA, MXRA7, AP2B1, ASTE1, RAF1, MFSD7, CDK8, SPAG17, PCDH11X, TBCCD1, MDM2, FRG1, RRN3, FLI1, DZANK1, NIP7, C16orf62, NNT, TRAF3IP1, CNTN4, SSTR2, PLEKHG4B, CPT1C, NHSL2, BDH1, FIG4, FAM175A, KIAA0226, ATP13A3, CLSPN, IGF1, CACNG8, C19orf33, CAPN3, RAD51B, COBLL1, PROM2, CWC25, DPM1, MRPS25, MOCOS, TAF8, NMNAT1, BRAT1, VPS45, SDHC, MYH7B, PRELP, FANCD2, CBFB, PLOD3, CCNK, AIFM3, LZTR1, HGSNAT, PRR19, EXPH5, MAGEB10, SPATA7, THUMPD1, ORC6, OTUD3, FBXO6, HLA-B, SRPK3, SLC19A3, LHX4, RPS6KL1, SCN11A, SLC38A10, SYTL1, SF3B4, C12orf65, PTPDC1, PDE4C, ZNF549, GAS6, C11orf1, LETMD1, DBF4, ECI2, LRP1, LDLRAP1, CDYL, TMEM173, RBBP5, NCSTN, TAF7, KLB, FUT9, PREX2, DSG3, RNF144A, FBXO10, ZBTB7B, ACN9, YWHAG, PYCR2, MAGT1, CD33, PLEKHJ1, HDLBP, PRAM1, NMRAL1, AHNAK2, DCDC5, DCDC1, TMTC2, PCYT1B, CD24, RNF126, VPS52, DOCK2, DGKZ, SIX4, UBA1, SLC28A2, STAC3, DUXA, WDR78, GPR161, DNAJC22, F2R, TMEM144, EPB41L4A, PPP2R5C, ZBTB6, NUDT5, C17orf75, LPXN, SMC4. |

Table 27 in an embodiment provides a signature of dendritic cells (e.g. cDC), and represents differentially expressed genes in particular DC subpopulations, preferably associated with or derived from non-neutralizer phenotype, preferably associated with HIV infection. Preferably differential expression is evaluated compared to cells from not non-neutralizers.

TABLE 28

| |
|---|
| C19orf33, HEXIM2, SOWAHD, PRSS3, NHSL2, IGSF6, GAS6, CAPN3, ALDH6A1, SPINT1, HCFC1R1, PARP3, STAC3, TMEM44, SPHK2, RAD51B, RSPH3, SCFD2, TMTC2, ACN9, C16orf62, LPXN, SLC27A3, VCL, HIBADH, LDLRAP1, C11orf1, VPS45, PLVAP, SPATA7, CD33, NMRAL1, ADCY7, SLC38A10, MFSD1, AGXT2L2, TRIM26, ZBTB7B, MFSD7, TMEM144, C1orf123, MRPL11, SPG21, CDK8, FLI1, G6PC3, ABCA7, HGSNAT, PRAM1, GANC, TMEM173, AIFM3, LZTR1, VPS52, C4orf27, OSGEP, C3orf37, AHNAK2, PYCR2, DECR1, CDYL, CPNE1, MTMR11, DGKZ, RNF126, TMEM14C, LRP1, TMEM8A, ECI2, FAM175A, YWHAG, SYTL1, FIG4, PLEKHJ1, AP2B1, NUDT5, NRD1, ITFG3, NAGPA, HDLBP, SDHC, MRPS25, BRAT1, NOG, NCSTN, CCNK, NDFIP1, NNT, MOCOS, UBA1, ASCC2, IGBP1, DENND1C, SPAG17, PLOD3, METTL7B, DOCK2, MFSD10, HOXA7, SF3B4, LHX4, PTPDC1, LETMD1, C9orf47. |
| Preferably C19orf33, HEXIM2, SOWAHD, PRSS3, NHSL2, IGSF6, GAS6, CAPN3, ALDH6A1, SPINT1, HCFC1R1, PARP3, STAC3, TMEM44, SPHK2, RAD51B, RSPH3, SCFD2, TMTC2, ACN9, C16orf62. |
| Or preferably SOWAHD, PRSS3, ALDH6A1, SPINT1, HCFC1R1, TMEM44, RSPH3, VCL, ADCY7, MFSD1, AGXT2L2, C1orf123, SPG21, ABCA7, OSGEP, MTMR11, TMEM14C, NOG, ASCC2, IGBP1. |
| More preferably SOWAHD, PRSS3, ALDH6A1, SPINT1, HCFC1R1, TMEM44, RSPH3. |

Table 28 in an embodiment provides a signature of dendritic cells (e.g. cDC), and represents upregulated genes in particular DC subpopulations, preferably associated with or derived from non-neutralizer phenotype, preferably associated with HIV infection. Preferably upregulation is evaluated compared to cells from not non-neutralizers.

TABLE 29

| |
|---|
| SRPK3, MAGT1, FUT9, CNTN4, PRELP, PLEKHG4B, RAF1, POGZ, POLQ, SLC19A3, CACNG8, FRG1, IGF1, DPM1, LIN28A, TAF7, ZDBF2, THUMPD1, MCF2L2, PARD6G, TMEM87A, PCYT1B, DCDC5, DCDC1, WDR78, KIAA0226, CBFB, ZC3H6, PPP2R5C, GALNTL1, GPR161, DIS3, RRN3, STAC2, ADIPOQ, RBBP5, SAR1B, SMC4, PREX2, FBXO6, SCN11A, ZNF549, NIP7, KLB, MDM2, EPB41L4A, ENAH, ATP13A3, SSTR2, OTUD3, DUXA, RNF41, ORC6, CPEB4, CLSPN, ZBTB6, FBXO10, TMEM170A, TRIP11, ZDHHC15, PROM2, KANSL2, FANCD2, TTYH1, EXPH5, ASTE1, TRAF3IP1, TAF8, IRF1, CWC25, MAGEB10, GPR180, OTUD7B, HLA-B, ZNF805, C12orf65, DSG3, FGF5, PBX4, C17orf75, FAM40B, TMEM41B, TMEM130, CPT1C, BDH1, TMEM213, RNF144A, DNAJC22, C21orf62, PAEP, CCBE1, ATG4D, SLC28A2, DPH1, MYO6, TBCCD1, |

TABLE 29-continued

| |
|---|
| DZANK1, TRAF3, LOC100506688, GPNMB, KLHL28, RUNDC1, CBFA2T2, ZNF432, PCDH11X, ADAMTS4, FAM18A, PLEKHH3, NXN, PDE4C, CNNM3, LRRN4CL, PRR19, SYNJ2, AKAP5, RPS6KL1, ACP5, QPCTL, NMNAT1, ZNF490, CD24, TMEM2, SIX4, MXRA7, COBLL1, ZNF543, ABCA1, DBF4, MOG, DACT3, ABCB9, MYH7B, F2R, CRTAM, ABLIM1, PIWIL2, C20orf152, TUBE1, WDR31, MANEAL, FBLIM1, PIF1. |
| Preferably TRAF3, LOC100506688, GPNMB, KLHL28, RUNDC1, CBFA2T2, ZNF432, PCDH11X, ADAMTS4, FAM18A, PLEKHH3, NXN, PDE4C, CNNM3, LRRN4CL, PRR19, SYNJ2, AKAP5, RPS6KL1, ACP5, QPCTL, NMNAT1, ZNF490, CD24, TMEM2, SIX4, MXRA7, COBLL1, ZNF543, ABCA1, DBF4, MOG, DACT3, ABCB9, MYH7B, F2R, CRTAM, ABLIM1, PIWIL2, C20orf152, TUBE1, WDR31, MANEAL, FBLIM1, PIF1. |
| Or preferably POLQ, LIN28A, DIS3, ADIPOQ, ENAH, ZDHHC15, IRF1, GPR180, ZNF805, FGF5, TMEM41B, TMEM130, PAEP, CCBE1, DPH1, MYO6, KLHL28, FAM18A, PLEKHH3, CNNM3, LRRN4CL, AKAP5, QPCTL, ZNF490, MOG, DACT3, ABCB9, ABLIM1, C20orf152, TUBE1, MANEAL, PIF1. |
| More preferably KLHL28, FAM18A, PLEKHH3, CNNM3, LRRN4CL, AKAP5, QPCTL, ZNF490, MOG, DACT3, ABCB9, ABLIM1, C20orf152, TUBE1, MANEAL, PIF1. |

Table 29 in an embodiment provides a signature of dendritic cells (e.g. cDC), and represents downregulated genes in particular DC subpopulations, preferably associated with or derived from non-neutralizer phenotype, preferably associated with HIV infection. Preferably downregulation is evaluated compared to cells from not non-neutralizers.

TABLE 30

| |
|---|
| GAS2L1, GPR34, RAD50, ANKRD33B, DTX1, RALY, CHML, C7orf31, PCDH9, EIF4E3, C8orf80, MPP6, JAKMIP1, LAX1, POU2AF1, FAIM3, CD80, SLCO4A1, EGR3, ZBTB32, CCL4, AMIGO2, LGALS3BP, FASTKD3, ACYP2, SOX4, CCDC112, FBXW2, LONRF2, ATAD3C, SOX5, KCTD18, CD320, F2R, SLC25A4, IL6, FCRL5, PDIK1L, HSDL2, SLC18A1, CEP44, ACO2, OTUB1, TMEM133, ZNF667, SLC6A20, WNT10B, SLC35G5, CSMD3, MRPL40, CBX5, RCAN2, SLC2A5, RPS6KL1, SCML4, IL28RA, KLRC3, KLRC2, CTSO, HADHA, N4BP3, NCR1, ANKRD39, KLRC4, UCN, ABAT, TNS3, TPM1, ACAD10, GFN1, QTRT1, PLK1S1, NUDCD3, SYTL5, C5orf25, TMX3, HHEX, ZFP57, NDUFAF4, FAM117B, AGPS, GIT2, FSTL1, ZNF572, SMARCE1, CLEC18A, CLEC18C, PUF60, PKD1L1, KIAA1210, GATS, NFIX, B4GALT3, ANKH, DCDC5, DCDC1, SLC1A3, FBXO40, C1orf190, BNC2, GGA1, SYNGR3, MCF2L2, PDZK1, MED27, LRP2BP, PIDD, NRCAM, TMEM120A, TUBB4A, SLC35E2, ULK3, UHRF1BP1, DOCK9, SLC35E2B, FSD1, CAMK2D, B9D1, MYBL2, DOT1L, ZNF257, WHSC1, SOX13, NXN, NDRG4, BMP8B, KLK1, TBX21, GTF2IRD2B, MOG, OTUD7B, SLC14A2, TPX2, C20orf72, ASPH, KIAA0101, TMEM181, MYO6, CERCAM, ENO2, KCNN4, RASGRP1, PLIN5, CD7, PTPRCAP, ECI1, ECHDC2, SH2D2A, GPR56, FCRLA, PVRIG, BLK, KLRD1, MS4A1, IGJ, CD160, KIR2DL4, KIR3DL2, KIR3DL1, KIR2DS4, XCL2, GZMB, CD79A, CCL4L2. |

Table 30 in an embodiment provides a signature of dendritic cells (e.g. cDC), and represents differentially expressed genes in particular DC subpopulations, preferably associated with or derived from elite controller phenotype, preferably associated with HIV infection. Preferably differential expression is evaluated compared to cells from non-elite controllers.

TABLE 31

| |
|---|
| GPR34, FASTKD3, UCN, ACYP2, SOX4, PDIK1L, ABAT, TNS3, CCDC112, TPM1, ACAD10, GIN1, HSDL2, QTRT1, PLK1S1, CTSO, NUDCD3, SYTL5, C5orf25, TMX3, HHEX, RAD50, ZFP57, SLC18A1, NDUFAF4, FAM117B, CEP44, AGPS, ACO2, GIT2, FSTL1, HADHA, OTUB1, TMEM133, FBXW2, ZNF572, SMARCE1, CLEC18A, CLEC18C, PUF60, PKD1L1. |
| Preferably GPR34, FASTKD3, UCN. |

Table 31 in an embodiment provides a signature of dendritic cells (e.g. cDC), and represents upregulated genes in particular DC subpopulations, preferably associated with or derived from elite controller phenotype, preferably associated with HIV infection. Preferably upregulation is evaluated compared to cells from non elite controllers.

TABLE 32

| |
|---|
| KIAA1210, LONRF2, GATS, NFIX, B4GALT3, ANKH, DCDC5, DCDC1, SLC1A3, ZNF667, SLC6A20, FBXO40, C1orf190, BNC2, ANKRD33B, GGA1, DTX1, RALY, SYNGR3, MCF2L2, WNT10B, PDZK1, ATAD3C, SLC35G5, CSMD3, MRPL40, MED27, CBX5, RCAN2, N4BP3, CHML, LRP2BP, PIDD, NRCAM, TMEM120A, TUBB4A, SLC2A5, SLC35E2, ULK3, UHRF1BP1, DOCK9, SLC35E2B, FSD1, CAMK2D, B9D1, MYBL2, DOT1L, ZNF257, WHSC1, SOX5, SOX13, NXN, NDRG4, BMP8B, KLK1, TBX21, GTF2IRD2B, SLC25A4, MOG, OTUD7B, C7orf31, KCTD18, SLC14A2, TPX2, C20orf72, ASPH, PCDH9, KIAA0101, EIF4E3, RPS6KL1, TMEM181, NCR1, C8orf80, MYO6, MPP6, CERCAM, AMIGO2, ENO2, KCNN4, RASGRP1, PLIN5, CD7, PTPRCAP, LGALS3BP, SCML4, GAS2L1, ECI1, JAKMIP1, ECHDC2, ANKRD39, IL28RA, LAX1, SH2D2A, IL6, POU2AF1, KLRC4, FAIM3, CD320, CD80, GPR56, FCRLA, SLCO4A1, |

TABLE 32-continued

| |
|---|
| F2R, PVRIG, BLK, FCRL5, KLRD1, EGR3, MS4A1, IGJ, CD160, ZBTB32, KIR2DL4, KIR3DL2, KIR3DL1, KIR2DS4, XCL2, GZMB, CD79A, CCL4L2, KLRC3, KLRC2, CCL4. |
| Preferably PLIN5, CD7, PTPRCAP, LGALS3BP, SCML4, GAS2L1, ECI1, JAKMIP1, ECHDC2, ANKRD39, IL28RA, LAX1, SH2D2A, IL6, POU2AF1, KLRC4, FAIM3, CD320, CD80, GPR56, FCRLA, SLCO4A1, F2R, PVRIG, BLK, FCRL5, KLRD1, EGR3, MS4A1, IGJ, CD160, ZBTB32, KIR2DL4, KIR3DL2, KIR3DL1, KIR2DS4, XCL2, GZMB, CD79A, CCL4L2, KLRC3, KLRC2, CCL4. |
| More preferably GAS2L1. |

Table 32 in an embodiment provides a signature of dendritic cells (e.g. cDC), and represents downregulated genes in particular DC subpopulations, preferably associated with or derived from elite controller phenotype, preferably associated with HIV infection. Preferably downregulation is evaluated compared to cells from non elite controllers.

TABLE 33

| |
|---|
| IFI27, KIR2DS2, KIR2DS1, KIR2DS3, KIR3DS1, USP18, C1QB, C1QC, IFIT2, AIM2, BATF2, ZNF684, SERPING1, LGALS3BP, IFIT3, RTP4, APOBEC3H, IFI6, S100A3, TMOD1, FKBP9, RDH5, PPIL1, STBD1, MX1, C1GALT1C1, LRIF1, LY6E, IL29, LAP3, C9orf125, SLC31A2, EXOC3L1, OAS3, LPCAT1, S100A5, PALLD, RFC5, GFRAL, LYG2, ASIP, PLN, TRIM22, PFDN6, CABIN1, C4BPB, MRPS11, TUBB4A, TSNAXIP1, LGALS9B, PARP9, ZNF782, CD5L, TXNDC9, RPL26L1, CDC25C, NLRC5, C8orf80, GPR89A, GPR89C, LRTM1, PSME2, CDH11, DPF3, C2orf28, TCL1B, MR1, COX7B, SPATA9, NLRP7, OTUD7A, QRICH2, PSME1, CASC1, ADAR, RFK, MFSD2B, BECN1, SLC2A10, GLDC, TNR, C15orf53, SPSB1, NLGN1, ERN2, EPAS1, RHOT2, SUPT6H, BEND3, ATF1, ELF2, MMAB, GABPA, TEX9, ZNF318, VPS53, TTBK2, ZNF443, ZNF703, FER, LARP1B, ADAM19, NOMO2, CADM1, ARHGAP24, RAB3A, KIFC2, S100A13. |

Table 33 in an embodiment provides a signature of dendritic cells (e.g. cDC), and represents differentially expressed genes in particular DC subpopulations, preferably associated with or derived from previous controller phenotype, preferably associated with HIV infection. Preferably differential expression is evaluated compared to cells from non-previous controllers.

TABLE 34

| |
|---|
| IFI27, KIR2DS2, KIR2DS1, KIR2DS3, KIR3DS1, USP18, C1QB, C1QC, IFIT2, AIM2, BATF2, ZNF684, SERPING1, LGALS3BP, IFIT3, RTP4, APOBEC3H, IFI6, S100A3, TMOD1, FKBP9, RDH5, PPIL1, STBD1, MX1, C1GALT1C1, LRIF1, LY6E, IL29, LAP3, C9orf125, SLC31A2, EXOC3L1, OAS3, LPCAT1, S100A5, PALLD, RFC5, GFRAL, LYG2, ASIP, PLN, TRIM22, PFDN6, CABIN1, C4BPB, MRPS11, TUBB4A, TSNAXIP1, LGALS9B, PARP9, ZNF782, CD5L, TXNDC9, RPL26L1, CDC25C, NLRC5, C8orf80, GPR89A, GPR89C, LRTM1, PSME2, CDH11, DPF3, C2orf28, TCL1B, MR1, COX7B, SPATA9, NLRP7, OTUD7A, QRICH2, PSME1, CASC1, ADAR, RFK, MFSD2B, BECN1, SLC2A10, GLDC, TNR, C15orf53, SPSB1, NLGN1, ERN2, EPAS1. |
| Preferably IFI27, KIR2DS2, KIR2DS1, KIR2DS3, KIR3DS1, USP18, C1QB, C1QC, IFIT2, AIM2, BATF2, ZNF684, SERPING1, LGALS3BP, IFIT3, RTP4, APOBEC3H, IFI6, S100A3, TMOD1, FKBP9, RDH5, PPIL1, STBD1, MX1, C1GALT1C1, LRIF1, LY6E, IL29, LAP3, C9orf125, SLC31A2, EXOC3L1, OAS3, LPCAT1, S100A5, PALLD, RFC5, GFRAL, LYG2, ASIP, PLN. |

Table 34 in an embodiment provides a signature of dendritic cells (e.g. cDC), and represents upregulated genes in particular DC subpopulations, preferably associated with or derived from previous controller phenotype, preferably associated with HIV infection. Preferably_upregulation is evaluated compared to cells from non previous controllers.

TABLE 35

| |
|---|
| RHOT2, SUPT6H, BEND3, ATF1, ELF2, MMAB, GABPA, TEX9, ZNF318, VPS53, TTBK2, ZNF443, ZNF703, FER, LARP1B, ADAM19, NOMO2, CADM1, ARHGAP24, RAB3A, KIFC2, S100A13. |

TABLE 35-continued

| |
|---|
| Preferably FER, LARP1B, ADAM19, NOMO2, CADM1, ARHGAP24, RAB3A, KIFC2, S100A13. |

Table 35 in an embodiment provides a signature of dendritic cells (e.g. cDC), and represents downregulated genes in particular DC subpopulations, preferably associated with or derived from previous controller phenotype, preferably associated with HIV infection. Preferably downregulation is evaluated compared to cells from non previous controllers.

TABLE 36

| |
|---|
| XCL2, ZBTB32, HIST1H3A, FCRL5, EGR3, CD80, KLRC4, ULBP2, RALGPS2, CD320, SEMA7A, LAX1, DMD, MPP6, POU2AF1, LY9, UAP1L1, ATP2A2, SYNJ2, CTH, ISYNA1, BCAR3, GPRC5D, IL6, C22orf29, RIMKLB, GAS2L1, NDRG4, NBPF15, PCDH9, C2orf27A, KCTD18, ZBTB6, BMP8B, TNFRSF13C, MYBL2, RRP12, ARID3A, SOX5, TGM5, ULK3, N4BP3, F12, ACSM2A, HPD, ZNF80, CMTM5, MGAT4A, SLC2A5, SLC35G5, FXYD7, CBX5, FSD1, RAP2A, IL12RB2, STX1A, FBXO2, ANKRD33B, CHML, ATAD3C, CCDC144NL, ZNF462, MYBPC2, SMNDC1, C1orf151-NBL1, NBL1, TMCC2, USP2, ILDR1, ENSA, GGA1, DTX1, RASD2, IGFBP4, SLC6A20, DLG3, GATS, KRT7, PM20D1, NFIX, WNT10A, OBSCN, ANK2, ADAMTS6, KIAA0284, MGAT3, COL5A2, GPR98, PRICKLE2, PGA3, PKD1L1, ITGB8, SMARCE1, ZNF572, CCDC96, EDA2R, HADHA, ATP6V0D1, HDAC2, LYPLA1, FAM48A, ZNF717, RAD50, NDUFB5, CCDC43, SYTL5, ZNF585B, VTA1, RBFA, SPIC, TXNDC9, PKP4, APH1B, LPPR4, TMX3, ZNF468, CTSO, RCSD1, NUDCD3, C1QL3, GIN1, PLK1S1, XYLB, ALDH3B1, ACTG2, ZNF573, TPM1, DUSP7, PTX4, OLFML2B, C6orf70, DLEU7, ACYP2, SPA17, GEMIN5, PYGL, P2RY12, ZNF623, TMEM186, HFE, MFSD3. |

Table 36 in an embodiment provides a signature of dendritic cells (e.g. cDC), and represents differentially expressed genes in particular DC subpopulations, preferably associated with or derived from viremic controller phenotype, preferably associated with HIV infection. Preferably differential expression is evaluated compared to cells from non-viremic controllers.

TABLE 37

| |
|---|
| XCL2, ZBTB32, HIST1H3A, FCRL5, EGR3, CD80, KLRC4, ULBP2, RALGPS2, CD320, SEMA7A, LAX1, DMD, MPP6, POU2AF1, LY9, UAP1L1, ATP2A2, SYNJ2, CTH, ISYNA1, BCAR3, GPRC5D, IL6, C22orf29, RIMKLB, GAS2L1, NDRG4, NBPF15, PCDH9, C2orf27A, KCTD18, ZBTB6, BMP8B, TNFRSF13C, MYBL2, RRP12, ARID3A, SOX5, TGM5, ULK3, N4BP3, F12, ACSM2A, HPD, ZNF80, CMTM5, MGAT4A, SLC2A5, SLC35G5, FXYD7, CBX5, FSD1, RAP2A, IL12RB2, STX1A, FBXO2, ANKRD33B, CHML, ATAD3C, CCDC144NL, ZNF462, MYBPC2, SMNDC1, C1orf151-NBL1, NBL1, TMCC2, USP2, ILDR1, ENSA, GGA1, DTX1, RASD2, IGFBP4, SLC6A20, DLG3, CATS, KRT7, PM20D1, NFIX, WNT10A, OBSCN, ANK2, ADAMTS6, KIAA0284, MGAT3, COL5A2, GPR98, PRICKLE2. |
| Preferably XCL2, ZBTB32, HIST1H3A, FCRL5, EGR3, CD80, KLRC4, ULBP2, RALGPS2, CD320, SEMA7A, LAX1, DMD, MPP6, POU2AF1, LY9. |

Table 37 in an embodiment provides a signature of dendritic cells (e.g. cDC), and represents upregulated genes in particular DC subpopulations, preferably associated with or derived from viremic controller phenotype, preferably associated with HIV infection. Preferably upregulation is evaluated compared to cells from non viremic controllers.

TABLE 38

| |
|---|
| PGA3, PKD1L1, ITGB8, SMARCE1, ZNF572, CCDC96, EDA2R, HADHA, ATP6V0D1, HDAC2, LYPLA1, FAM48A, ZNF717, RAD50, NDUFB5, CCDC43, SYTL5, ZNF585B, VTA1, RBFA, SPIC, TXNDC9, PKP4, APH1B, LPPR4, TMX3, ZNF468, CTSO, RCSD1, NUDCD3, C1QL3, GIN1, PLK1S1, XYLB, ALDH3B1, ACTG2 ZNF573, TPM1, DUSP7, PTX4, OLFML2B, C6ort70, DLEU7, ACYP2, SPA17, GEMIN5, PYGL, P2RY12, ZNF623, TMEM186, HFE, MFSD3. |
| Preferably PYGL, P2RY12, ZNF623, TMEM186, HFE, MFSD3. |

Table 38 in an embodiment provides a signature of dendritic cells (e.g. cDC), and represents downregulated genes in particular DC subpopulations, preferably associated with or derived from viremic controller phenotype, preferably associated with HIV infection. Preferably downregulation is evaluated compared to cells from non viremic controllers.

TABLE 39

| |
|---|
| RALGPS2, RGPD2, RGPD1, C10orf137, MIB2, EZH2, TAF1C, FAM98B, Nbla00487, ATAT1, NIPBL, STK11, ZBTB25, CUL5, TMEM41A, SRRT, C2orf69, GMNN, ZFC3H1, BRP44, RBM17, SMURF2, PROC, AMT, STK31, RGPD4, DUSP12, RBBP6, ISYNA1, CTTNBP2NL, P4HB, FAM105B, AXL, MOSPD1, TAPBP, HSF2, CCDC58, SEC31B, HCST, MAPK3, CLN3, STARD7, SEMA7A, MAP1LC3B, GPATCH3, HIRA, TRAF6, CCNF, CNST, SAR1A, PPM1D, CAMK2D, MSL2, DDX3X, ZNF430, DDX3Y, CAMTA1, SMPD4, ZNF586, NEIL3, NUDT21, C10orf118, ATAD2, THUMPD2, SPHK1, PMPCB, TRIM37, KPNA2, POLE3, ZXDB, ASB7, TWSG1, PIK3R1, MICAL3, ORAI1, RELA, SLC35A2, ARGLU1, YTHDC1, ACAP3, ZCCHC10, KIF18A, LAMB2, RENBP, C11orf68, APOBEC3F, APOBEC3G, GPX8, OLFML1, C11orf83, SLC37A2, MAN1C1, SGK3, C8orf44-SGK3, DBP, SARS, ZNF57, CNDP2, SNAI3, OGFOD1, LILRA6, LILRB3, LILRA3, IPO13, PRKAG1, FLVCR2, CBY1, ATG10, IL15, HRH2, HYAL4, PTX4, PREP, NDUFA8, MPDU1, MED7, L3MBTL2, MOSPD2, KMO, LIMCH1, FAIM, PTRH2, ACTL6A, TNS1, KSR1, WBSCR16, PIGU, NMI, CPSF2, NPHP4, NUP62, HM13, ZNF528, TEX261, TFE3, ERAL1, HIST1H2BJ, C6orf97, ICMT, MERTK, FBXW8, S100A11, KIAA1841, PTRH1, FMNL2, C6orf70, MED22, BAX, LACC1, C9orf103, SCRN1, |

TABLE 39-continued

| |
|---|
| CCDC115, GAPT, PRADC1, CHMP6, KIAA1609, TLR1, PUF60, POGLUT1, ZNF783, WDR81, TDRD7, RBM43, SP1, POC5, C20orf30, RAB3IP, RECQL, PEX10, SRFBP1, HJURP, PDE8B, PANK2, NLN, NME6, SPATA7, ADD2, ULK2, LPL, TNFRSF8, HOXA1, ATP10A, ZFYVE21, SDCCAG8, BAHD1, TIAM1, TSPAN31, MFSD6, SH3RF1, TCP10L, C21orf59, MED18, SCNN1D, ACAD9, MAP2K4, MYOF, MON1A, AP1M1, FNIP2, CASP6, TBC1D30, CASP5, SPTLC2. |

Table 39 in an embodiment provides a signature of dendritic cells (e.g. cDC), and represents genes/proteins in particular DC subpopulations, preferably of which the expression (or activity) level is positively or negatively correlated with the quantitative phenotype CD19+ CD3− CD38Int CD27Int Activated Memory-Germinal Center B cells, preferably associated with HIV infection.

TABLE 40

| |
|---|
| RALGPS2, RGPD2, RGPD1, C10orf137, MIB2, EZH2, TAF1C, FAM98B, Nbla00487, ATAT1, NIPBL, STK11, ZBTB25, CUL5, TMEM41A, SRRT, C2orf69, GMNN, ZFC3H1, BRP44, RBM17, SMURF2, PROC, AMT, STK31, RGPD4, DUSP12, RBBP6, ISYNA1, CTTNBP2NL, P4HB, FAM105B, AXL, MOSPD1, TAPBP, HSF2, CCDC58, SEC31B, HCST, MAPK3, CLN3, STARD7, SEMA7A, MAP1LC3B, GPATCH3, HIRA, TRAF6, CCNF, CNST, SAR1A, PPM1D, CAMK2D, MSL2, DDX3X, ZNF430, DDX3Y, CAMTA1, SMPD4, ZNF586, NEIL3, NUDT21, C10orf118, ATAD2, THUMPD2, SPHK1, PMPCB, TRIM37, KPNA2, POLE3, ZXDB, ASB7, TWSG1, PIK3R1, MICAL3, ORAI1, RELA, SLC35A2, ARGLU1, YTHDC1, ACAP3, ZCCHC10, KIF18A, LAMB2. |
| Preferably RALGPS2, RGPD2, RGPD1, C10orf137, MIB2, EZH2, TAF1C, FAM98B, Nbla00487, ATAT1, NIPBL, STK11, ZBTB25. |

Table 40 in an embodiment provides a signature of dendritic cells (e.g. cDC), and represents genes/proteins in particular DC subpopulations, preferably of which the expression (or activity) level is positively correlated with the quantitative phenotype CD19+ CD3− CD38Int CD27Int Activated Memory-Germinal Center B cells, preferably associated with HIV infection.

TABLE 41

| |
|---|
| RENBP, C11orf68, APOBEC3F, APOBEC3G, GPX8, OLFML1, C11orf83, SLC37A2, MAN1C1, SGK3, C8orf44-SGK3, DBP, SARS, ZNF57, CNDP2, SNAI3, OGFOD1, LILRA6, LILRB3, LILRA3, IPO13, PRKAG1, FLVCR2, CBY1, ATG10, IL15, HRH2, HYAL4, PTX4, PREP, NDUFA8, MPDU1, MED7, L3MBTL2, MOSPD2, KMO, LTMCH1, FAIM, PTRH2, ACTL6A, TNS1, KSR1, WBSCR16, PIGU, NMI, CPSF2, NPHP4, NUP62, HM13, ZNF528, TEX261, TFE3, ERAL1, HIST1H2BJ, C6orf97, ICMT, MERTK, FBXW8, S100A11, KIAA1841, PTRH1, FMNL2, C6orf70, MED22, BAX, LACC1, C9orf103, SCRN1, CCDC115, GAPT, PRADC1, CHMP6, KIAA1609, TLR1, PUF60, POGLUT1, ZNF783, WDR81, TDRD7, RBM43, SP1, POC5, C20orf30, RAB3IP, RECQL, PEX10, SRFBP1, HJURP, PDE8B, PANK2, NLN, NME6, SRATA7, ADD2, ULK2, LPL, TNFRSF8, HOXA1, ATP10A, ZFYVE21, SDCCAG8, BAHD1, TIAM1, TSPAN31, MFSD6, SH3RF1, TCP10L, C21orf59, MED18, SCNN1D, ACAD9, MAP2K4, MYOF, MON1A, AP1M1, FNIP2, CASP6, TBC1D30, CASP5, SPTLC2. |
| Preferably TSPAN31, MFSD6, SH3RF1, TCP10L, C21orf59, MED18, SCNN1D, ACAD9, MAP2K4, MYOF, MON1A, AP1M1, FNIP2, CASP6, TBC1D30, CASP5, SPTLC2. |

Table 41 in an embodiment provides a signature of dendritic cells (e.g. cDC), and represents genes/proteins in particular DC subpopulations, preferably of which the expression (or activity) level is negatively correlated with the quantitative phenotype CD19+ CD3− CD38Int CD27Int Activated Memory-Germinal Center B cells, preferably associated with HIV infection.

TABLE 42

| |
|---|
| DZIP3, PACSIN2, TSPAN13, ARHGAP10, SLC39A8, RABGAP1, FBXO46, CUL2, ADAMTSL3, TAB3, GPR114, JMJD5, TNFRSF19, CIRH1A, C11orf84, FZD6, RFFL, PDS5A, BAGE, BAGE5, BAGE2, PCDHB9, KCTD18, MINK1, EYS, LXN, RAD51D, SLAMF9, MRPL42, SHMT1, C6orf105, ARMCX3, DLST, MAP2K2, LRRC27, FBXL20, MTX1, TRAK2, MAVS, SLC38A5, ATAD2B, ATP1A4, CD9, RNASEH2C, ME2, ZNF41, |

TABLE 42-continued

| |
|---|
| PCBD2, PSPC1, MYH9, ZSWIM1, LPO, UBTF, SFXN4, APOL4, NLRX1, WASH1, ATIC, MAP3K4, EEF1E1, ANAPC1, C16orf74, C19orf43, RNF144A, TMEM63B, PGS1, SH2D3C, PROCA1, ZNF665, GCLM, DNAJC7, SLC25A16, ZNF638, RBM14-RBM4, RBM14, RBM4, RABL2A, NCAPD3, FAM160A2, ZNF785, ITIH4, IPMK, FTSJ1, DNAJC8, KATNA1, CH25H, GFPT1, FAT3, MAP1LC3B2, ZDHHC3, STAC2, MS4A2, KDM5C, PARD6A, DUXA, SAMD1, SGSM1, RFX3, SEMA4B, UFC1, FOPNL, PHC3, SPICE1, CHAC2, LTA4H, HSPA2, SPAG8. |

Table 42 in an embodiment provides a signature of dendritic cells (e.g. cDC), and represents genes/proteins in particular DC subpopulations, preferably of which the expression (or activity) level is positively or negatively correlated with the quantitative phenotype Age, preferably associated with HIV infection. Age is the age of the human subject at time of biological sample acquisition.

TABLE 43

| |
|---|
| PACSIN2, TSPAN13, ARHGAP10, SLC39A8, FBXO46, CUL2, TAB3, GPR114, JMJD5, CIRH1A, FZD6, RFFL, PDS5A, MINK1, LXN, RAD51D, SLAMF9, MRPL42, C6orf105, ARMCX3, DLST, MAP2K2, MTX1, TRAK2, SLC38A5, ATAD2B, CD9, RNASEH2C, ZNF41, PSPC1, MYH9, UBTF, SFXN4, ATIC, EEF1E1, ANAPC1, C16orf74, C19orf43, TMEM63B, PGS1, PROCA1, DNAJC7, SLC25A16, ZNF638, RBM14-RBM4, RBM14, RBM4, RABL2A, NCAPD3, FAM160A2, FTSJ1, DNAJC8, KATNA1, CH25H, MAP1LC3B2, KDM5C, PARD6A, SAMD1, RFX3, SEMA4B, UFC1, CHAC2, HSPA2, SPAG8. |

Table 43 in an embodiment provides a signature of dendritic cells (e.g. cDC), and represents genes/proteins in particular DC subpopulations, preferably of which the expression (or activity) level is positively correlated with the quantitative phenotype Age, preferably associated with HIV infection.

TABLE 44

| |
|---|
| LTA4H, SPICE1, PHC3, FOPNL, SGSM1, DUXA, MS4A2, STAC2, ZDHHC3, FAT3, GFPT1, IPMK, ZNF785, ITIH4, GCLM, ZNF665, SH2D3C, RNF144A, MAP3K4, WASH1, NLRX1, APOL4, LPO, ZSWIM1, PCBD2, ME2, ATP1A4, MAVS, FBXL20, LRRC27, SHMT1, EYS, KCTD18, PCDHB9, BAGE, BAGE5, BAGE2, C11orf84, TNFRSF19, ADAMTSL3, RABGAP1, DZIP3. |

Table 44 in an embodiment provides a signature of dendritic cells (e.g. cDC), and represents genes/proteins in particular DC subpopulations, preferably of which the expression (or activity) level is negatively correlated with the quantitative phenotype Age, preferably associated with HIV infection.

TABLE 45

| |
|---|
| UBE2D3, PAIP2, PLEKHA3, BEND3, CEP44, SAP18, DNAJC8, FAM53C, CHSY1, AMPD2, JMJD6, C20orf111, PNRC1, HNRNPA0, VAPA, DNAJC21, CLINT1, RABGEF1, EIF4A2, EIF1, RCL1, HDAC1, NAGS, ZNF394, TMTC1, SELK, VTI1A, ARF6, SKIL, PFN2, CHMP2B, ZBTB1, DNAJC3, LOC100507462, SLC16A5, HNRNPA1L2, RAB1A, ZNF28, PTGR2, TULP1, ERAL1, PGBD2, LRRC46, MRPS12, ESCO2, BTN2A2, ZCRB1, B9D2, NHLRC2, ADO, RAD54B, HINT3, PRICKLE1, LIMK1, WDHD1, SLC24A1, PRMT5, PRMT6, TMEM156, TLR6, IFI16, PIK3C2B, GCNT2, PRR14L, GBP3, MKI67, ZNF146, CD200R1, ANKZF1, TAMM41. |

Table 45 in an embodiment provides a signature of dendritic cells (e.g. cDC), and represents genes/proteins in particular DC subpopulations, preferably of which the expression (or activity) level is positively or negatively correlated with the quantitative phenotype CD4Count(Cells/mm3), preferably associated with HIV infection. Applicants counted the number of CD4 T lymphocytes per ml of blood present in each particular patient at time of sample acquisition.

TABLE 46

| |
|---|
| UBE2D3, PAIP2, PLEKHA3, BEND3, CEP44, SAP18, DNAJC8, FAM53C, CHSY1, AMPD2, JMJD6, C20orf111, PNRC1, HNRNPA0, VAPA, DNAJC21, CLINT1, RABGEF1, EIF4A2, EIF1, RCL1, HDAC1, NAGS, ZNF394, TMTC1, SELK, VTI1A, ARF6, SKIL, PFN2, CHMP2B, ZBTB1, DNAJC3, LOC100507462, SLC16A5, HNRNPA1L2, RAB1A. |
| Preferably UBE2D3. |

Table 46 in an embodiment provides a signature of dendritic cells (e.g. cDC), and represents genes/proteins in particular DC subpopulations, preferably of which the expression (or activity) level is positively correlated with the quantitative phenotype CD4Count(Cells/mm3), preferably associated with HIV infection.

TABLE 47

| |
|---|
| ZNF28, PTGR2, TULP1, ERAL1, PGBD2, LRRC46, MRPS12, ESCO2, BTN2A2, ZCRB1, B9D2, NHLRC2, ADO, RAD54B, HINT3, PRICKLE1, LIMK1, WDHD1, SLC24A1, PRMT5, PRMT6, TMEM156, TLR6, IFI16, PIK3C2B, GCNT2, PRR14L, GBP3, MKI67, ZNF146, CD200R1, ANKZF1, TAMM41. |

Table 47 in an embodiment provides a signature of dendritic cells (e.g. cDC), and represents genes/proteins in particular DC subpopulations, preferably of which the expression (or activity) level is negatively correlated with the quantitative phenotype CD4Count(Cells/mm3), preferably associated with HIV infection.

TABLE 48

| |
|---|
| HIST2H3D, LRR1, SDK2, LAMB2, CEP152, TCFL5, LOC100132247, RRAGA, RUFY4, LHFP, JUN, PDSS1, P2RY14, DNAJC24, ZFP161, MTRNR2L2, ZNF771, CCNG1, TMEM18, ATXN7, LIMD2, MARS2, WBSCR16, TMEM175, RET, CCDC125, CCDC82, C5orf44, SCYL2, KIAA0528, FANCF, ACADM, TIGD3, HS1BP3, SOWAHC, PDE8B, TGDS, DGUOK, MRPS15, PNMA1, NEK3, HAUS4, NUFIP2, ACER3, SLC44A4, ZNF143, DHX37, LTB, ARHGEF10, CD109, SLC10A3, PAFAH1B1, HIST1H3A, STX3. |

Table 48 in an embodiment provides a signature of dendritic cells (e.g. cDC), and represents genes/proteins in particular DC subpopulations, preferably of which the expression (or activity) level is positively or negatively correlated with the quantitative phenotype T follicular helper cell defined as CXCR5+CXCR3−PD1+, preferably associated with HIV infection.

TABLE 49

| |
|---|
| HIST2H3D, SDK2, LAMB2, CEP152, LOC10013224, RUFY4, LHFP, JUN, PDSS1, P2RY14, MTRNR2L2, CCNG1, ATXN7, CCDC125, C5orf44, MRPS15, NEK3, HAUS4, NUFIP2, ACER3, CD109, HIST1H3A, STX3. |

Table 49 in an embodiment provides a signature of dendritic cells (e.g. cDC), and represents genes/proteins in particular DC subpopulations, preferably of which the expression (or activity) level is positively correlated with the quantitative phenotype T follicular helper cell defined as CXCR5+CXCR3−PD1+, preferably associated with HIV infection.

TABLE 50

| |
|---|
| PAFAH1B1, SLC10A3, ARHGEF10, LTB, DHX37, ZNF143, SLC44A4, PNMA1, DGUOK, TGDS, PDE8B, SOWAHC, HS1BP3, TIGD3, ACADM, FANCF, KIAA0528, SCYL2, CCDC82, RET, TMEM175, WBSCR16, MARS2, LIMD2, TMEM18, ZNF771, ZFP161, DNAJC24, RRAGA, TCFL5, LRR1. |

Table 50 in an embodiment provides a signature of dendritic cells (e.g. cDC), and represents genes/proteins in particular DC subpopulations, preferably of which the expression (or activity) level is negatively correlated with the quantitative phenotype T follicular helper cell defined as CXCR5+CXCR3−PD1+, preferably associated with HIV infection.

TABLE 51

| |
|---|
| IPO5, WIPI1, FAM158A, SLC31A1, SORL1, AP2A2, SLC7A11, C3orf17, P2RX5, ZNF470, OSBPL2, LGALS4, SMURF2, SDK2, NANP, PIPOX, SLC3A1, APC, TMED8, MTHFR, SLC22A20, BRAF, FBXL18, ADCY4, NKTR, PIK3C2B, GIGYF1, DYNC1H1, STARD8, TMEM87A, STARD3, CCT6B, RHBDF2, EIF2C1, ACOT9, SFTPD, C3orf52, ECHDC1, SNX33, WDR18, STYXL1, SAE1, ATE1, PPRC1, SLC22A5, C2orf76, PLOD1, HDAC4, TOMM40, UBTD1, PRKCB, POLR2G, PSMB3, PHC1, CDK4, SELL, VCAN, MLKL, FTSJ1, TCF12, ARF3, SAP18, S100A9, BST1, ADSL, RASSF7, CASP5, COX16, SYNJ2BP-COX16, SYNJ2BP, MPP7, TCEA3, CDK19, AK2, TMCO4, KHK, TM6SF1, NDRG3, MRPL4, VPS25, STMN1, NSMCE4A, ACTR2, SNCA, TPM1, GALK1, CDC123, DIS3L2, PET112, DUT, NPHP4, FADS2, CDK6, MAN1A2, TPK1, TRIT1, ENHO, VPS11, MRPL24, CNPY4, ORC5, MAD1L1, C6orf97, XYLB, XPOT, CD36, ERI3, SLC38A6, LCP1, FAM129A, ECHS1, MRPL11, SERF2, GMPPA, FAM109A, MYBBP1A, NHP2, COMMD8, CCND3, NUDCD2, PARN, PROSC, RSU1, CPT1B, CD163, AAAS, PRPSAP2, ALG12, ENOPH1. |

Table 51 in an embodiment provides a signature of dendritic cells (e.g. cDC), and represents genes/proteins in particular DC subpopulations, preferably of which the expression (or activity) level is positively or negatively correlated with the quantitative phenotype T follicular helper cell defined as CXCR5+PD1+, preferably associated with HIV infection.

TABLE 52

| |
|---|
| IPO5, WIPI1, FAM158A, SLC31A1, SORL1, AP2A2, SLC7A11, C3orf17, P2RX5, ZNF470, OSBPL2, LGALS4, SMURF2, SDK2, NANP, PIPOX, SLC3A1, APC, TMED8, MTHFR, SLC22A20, BRAF, FBXL18, ADCY4, NKTR, PIK3C2B, GIGYF1, DYNC1H1, STARD8, TMEM87A, STARD3, CCT6B, RHBDF2, EIF2C1, ACOT9, SFTPD, C3orf52. |

Table 52 in an embodiment provides a signature of dendritic cells (e.g. cDC), and represents genes/proteins in particular DC subpopulations, preferably of which the expression (or activity) level is positively correlated with the quantitative phenotype T follicular helper cell defined as CXCR5+PD1+, preferably associated with HIV infection.

TABLE 53

| |
|---|
| ECHDC1, SNX33, WDR18, STYXL1, SAE1, ATE1, PPRC1, SLC22A5, C2orf76, PLOD1, HDAC4, TOMM40, UBTD1, PRKCB, POLR2G, PSMB3, PHC1, CDK4, SELL, VCAN, MLKL, FTSJ1, TCF12, ARF3, SAP18, S100A9, BST1, ADSL, RASSF7, CASP5, COX16, SYNJ2BP-COX16, SYNJ2BP, MPP7, TCEA3, CDK19, AK2, TMCO4, KHK, TM6SF1, NDRG3, MRPL4, VPS25, STMN1, NSMCE4A, ACTR2, SNCA, TPM1, GALK1, CDC123, DIS3L2, PET112, DUT, NPHP4, FADS2, CDK6, MAN1A2, TPK1, TRIT1, ENHO, VPS11, MRPL24, CNPY4, ORC5, MAD1L1, C6orf97, XYLB, XPOT, CD36, ERI3, SLC38A6, LCP1, FAM129A, ECHS1, MRPL11, SERF2, GMPPA, FAM109A, MYBBP1A, NHP2, COMMD8, CCND3, NUDCD2, PARN, PROSC, RSU1, CPT1B, CD163, AAAS, PRPSAP2, ALG12, ENOPH1. |

Table 53 in an embodiment provides a signature of dendritic cells (e.g. cDC), and represents genes/proteins in particular DC subpopulations, preferably of which the expression (or activity) level is negatively correlated with the quantitative phenotype T follicular helper cell defined as CXCR5+PD1+, preferably associated with HIV infection.

TABLE 54

| |
|---|
| MYO6, TTN, FBXO10, ZNF507, TP53BP1, FCRL5, ABLIM1, VASH2, FCRL1, PIF1, PBX4, GATA3, JAKMIP1, PCDH9, TMEM2, POU2AF1, TGFBR3, CD80, KANSL2, GLS, ASTE1, AXL, RASGRP1, NUPL1, DACT3, ZBTB32, KCTD9, CPEB4, DCDC5, DCDC1, MANEAL, SPSB1, PRH2, POLQ, CAMK2D, CD160, LAX1, SMC4, GOLGA8B, NAP1L2, FBXO32, DPM1, OTUD7B, PPM1D, BDH1, BCL9, CASP6, SYTL1, FAM118A, VPS45, CDKL5, GRSF1, HEXIM2, NME6, PAPSS1, CYFIP1, CPPED1, MAPRE3, MCTP1, C1orf123, FKBP1A, VTA1, SIGLEC9, NHSL2, SDHC, TRMT61A, FLI1, IARS2, CAT, IGSF6, C19orf33, TBXAS1, LAMP2, XPC, LPCAT2, CD4, ULK2, FAM82B, MTMR11, PPARGC1B, MERTK, SPATA7, FAM198B, NDFIP1, GABARAPL2, VCL, MFSD1, PANK2, WDR24, METTL7B, PYGL, TMTC2, TMEM14C, DOCK2, S100Z, SOWAHD, PLVAP, TIAM1. |

Table 54 in an embodiment provides a signature of dendritic cells (e.g. cDC), and represents genes/proteins in particular DC subpopulations, preferably of which the expression (or activity) level is positively or negatively correlated with the quantitative phenotype HIV-1-specific Neutralizing breadth defined by the proportions of HIV-1 strains tested (n=11) by the plasma of the study patients, NA Breadth, preferably associated with HIV infection.

TABLE 55

| |
|---|
| MYO6, TTN, FBXO10, ZNF507, TP53BP1, FCRL5, ABLIM1, VASH2, FCRL1, PIF1, PBX4, GATA3, JAKMIP1, PCDH9, TMEM2, POU2AF1, TGFBR3, CD80, KANSL2, GLS, ASTE1, AXL, RASGRP1, NUPL1, DACT3, ZBTB32, KCTD9, CPEB4, DCDC5, DCDC1, MANEAL, SPSB1, PRH2, POLQ, CAMK2D, CD160, LAX1, SMC4, GOLGA8B, NAP1L2, FBXO32, DPM1, OTUD7B, PPM1D, BDH1. |

Table 55 in an embodiment provides a signature of dendritic cells (e.g. cDC), and represents genes/proteins in particular DC subpopulations, preferably of which the expression (or activity) level is positively correlated with the quantitative phenotype HIV-1-specific Neutralizing breadth defined by the proportions of HIV-1 strains tested (n=11) by the plasma of the study patients, preferably associated with HIV infection.

TABLE 56

| |
|---|
| BCL9, CASP6, SYTL1, FAM118A, VPS45, CDKL5, GRSF1, HEXIM2, NME6, PAPSS1, CYFIP1, CPPED1, MAPRE3, MCTP1, C1orf123, FKBP1A, VTA1, SIGLEC9, NHSL2, SDHC, TRMT61A, FLI1, IARS2, CAT, IGSF6, C19orf33, TBXAS1, LAMP2, XPC, LPCAT2, CD4, ULK2, FAM82B, MTMR11, PPARGC1B, MERTK, SPATA7, FAM198B, NDFIP1, GABARAPL2, VCL, MFSD1, PANK2, WDR24, METTL7B, PYGL, TMTC2, TMEM14C, DOCK2, S100Z, SOWAHD, PLVAP, TIAM1. |
| Preferably TIAM1. |

Table 56 in an embodiment provides a signature of dendritic cells (e.g. cDC), and represents genes/proteins in particular DC subpopulations, preferably of which the expression (or activity) level is negatively correlated with the quantitative phenotype HIV-1-specific Neutralizing breadth defined by the proportions of HIV-1 strains tested (n=11) by the plasma of the study patients, preferably associated with HIV infection.

TABLE 57

| |
|---|
| CASP5, DDX3Y, PRADC1, TEX261, POC5, MON1A, NLGN3, SH3RF1, SIAH1, SPTLC2, TBC1D30, AXL, DGCR8, MAP2K4, UBE2F, POR, AP1M1, CLEC2B, RAB11FIP1, SPATA7, MED22, GNA13, TMEM41A, NLN, CTAGE5, SWI5, RINT1, C19orf25, TBRG4, CNDP2, CCDC58, PROC, PNO1, ATAD2, CPA4, PNMA3, AP1S3, BAK1, NT5E, RECQL, DENND4B, G3BP2, EBP, BRP44, METTL21D, LPCAT2, SMNDC1, CDK19, NAAA, SMYD5, HUS1, HRH2, CCDC75, FMNL2, ZNF562, PUS3, MCM3AP, PLIN4, SH3GL1, GPR183, SCRN1, ETV3, FLT3LG, STAM, GPHN, ZNF586, ABR, DNAJB9, S1PR4, CTDP1, UBL4A, CARS, VASP, PLVAP, CAMTA1, TAGLN, PPP1R32, IDH1, PIEZO1, G6PC3, ANKDD1A, HAUS1, EFR3A, PPM1D, ZNF324, HCST, CTTNBP2NL, RPL22L1, UTP15, SIGLEC10, RAB15, POU2F2, TRAF4, RPS6KB1, CAMKK2, C2orf69, DVL1, RAB9A, ALG14, RBBP6, LOC100507341, ST3GAL2, MRPL19, WDR1, THOC5, DYNLL1. |

Table 57 in an embodiment provides a signature of dendritic cells (e.g. cDC), and represents genes/proteins in particular DC subpopulations, preferably of which the expression (or activity) level is positively or negatively correlated with the quantitative phenotype CD3− CD19+ CD38Lo/−CD27− (NAlike) B cells preferably associated with HIV infection.

TABLE 58

| |
|---|
| CASP5, PRADC1, TEX261, POC5, MON1A, SH3RF1, SPTLC2, TBC1D30, DGCR8, MAP2K4, POR, AP1M1, SPATA7, MED22, NLN, SWI5, C19orf25, TBRG4, CNDP2, PNMA3, NT5E, RECQL, DENND4B, LPCAT2, CDK19, NAAA, SMYD5, HRH2, FMNL2, ZNF562, PUS3, MCM3AP, SCRN1, FLT3LG, ABR, S1PR4, UBL4A, CARS, VASP, PLVAP, TAGLN, IDH1, PIEZO1, G6PC3, HAUS1, EFR3A, SIGLEC10, POU2F2, CAMKK2, ALG14, ST3GAL2, MRPL19, WDR1, THOC5, DYNLL1. |

Table 58 in an embodiment provides a signature of dendritic cells (e.g. cDC), and represents genes/proteins in particular DC subpopulations, preferably of which the expression (or activity) level is positively correlated with the quantitative CD3− CD19+ CD38Lo/− CD27− (NAlike) B cell phenotype, preferably associated with HIV infection.

TABLE 59

| |
|---|
| LOC100507341, RBBP6, RAB9A, DVL1, C2orf69, RPS6KB1, TRAF4, RAB15, UTP15, RPL22L1, CTTNBP2NL, HCST, ZNF324, PPM1D, ANKDD1A, PPP1R32, CAMTA1, CTDP1, DNAJB9, ZNF586, GPHN, STAM, ETV3, GPR183, SH3GL1, PLIN4, CCDC75, HUS1, SMNDC1, METTL21D, BRP44, EBP, G3BP2, BAK1, AP1S3, CPA4, ATAD2, PNO1, PROC, CCDC58, RINT1, CTAGE5, TMEM41A, GNA13, RAB11FIP1, CLEC2B, UBE2F, AXL, SIAH1, NLGN3, DDX3Y. |

Table 59 in an embodiment provides a signature of dendritic cells (e.g. cDC), and represents genes/proteins in particular DC subpopulations, preferably of which the expression (or activity) level is negatively correlated with the quantitative phenotype CD3− CD19+ CD38Lo/− CD27− (NAlike), preferably associated with HIV infection.

TABLE 60

| |
|---|
| YES1, MYO6, DCDC5, DCDC1, EPB41L4A, POU2AF1, MYO3B, MDM2, C11orf84, TGFBR3, SRPK3, FGF5, PIF1, CSGALNACT1, ZNF571, ANKRD13C, OTUD7B, SLC4A4, FCRL2, RPL36AL, TP53BP1, FANCD2, RASA2, SUMO1, SNTA1, RNF144A, ABCA1, PRX4, TTYH1, KIAA2018, SOX6, ENPP4, MCF2L2, ELK4, SLC45A3, STARD9, MTRNR2L5, POLQ, PCDH9, CD160, TTN, MAGEB10, ZNF33B, SPTAN1, FCHSD1, ATG4D, WRAP73, PRH2, CERCAM, RAB2B, DOCK1, FCRL5, ZNF507, JAKMIP1, FAM179A, CD24, HPS3, TAGLN, BEND3, CD300E, MRE11A, NMRAL1, PIGV, GSDMD, ACOX3, TRAPPC12, NUDT13, AIG1, METTL7B, PCCA, CPSF2, NHSL2, INTS9, NUDT5, PRG2, SLC43A3, TREML2, SEC16B, NDFIP1, CYSLTR2, VPS41, COQ9, PRSS3, FAM104B, SLC38A7, HSBP1L1, FAM118A, FNIP2, SDS, HSDL2, MFSD7, PPP1R17, CLEC4G, FIG4, CARD9, SIPA1L2, STK38L, DAPK1, |

TABLE 60-continued

| |
|---|
| PRAM1, MS4A14, GABARAPL2, MTMR11, CYSLTR1, TMTC2, SIGLEC9, MPEG1, HNMT, SPATA7, KCTD17, VPS45, TLR1, MFSD1, CDYL, XYLT1, SPG21, TMEM144, KYNU, BCL9, TIAM1, SOWAHD. |

Table 60 in an embodiment provides a signature of dendritic cells (e.g. cDC), and represents genes/proteins in particular DC subpopulations, preferably of which the expression (or activity) level is positively or negatively correlated with the quantitative phenotype CD3− CD19+ CD38Hi CD27Hi Plasmablast-like (PB-like) B cells preferably associated with HIV infection.

TABLE 61

| |
|---|
| YES1, MYO6, DCDC5, DCDC1, EPB41L4A, POU2AF1, MYO3B, MDM2, C11orf84, TGFBR3, SRPK3, FGF5, PIF1, CSGALNACT1, ZNF571, ANKRD13C, OTUD7B, SLC4A4, FCRL2, RPL36AL, TP53BP1, FANCD2, RASA2, SUMO1, SNTA1, RNF144A, ABCA1, PBX4, TTYH1, KIAA2018, SOX6, ENPP4, MCF2L2, ELK4, SLC45A3, STARD9, MTRNR2L5, POLQ, PCDH9, CD160, TTN, MAGEB10, ZNF33B, SPTAN1, FCHSD1, ATG4D, WRAP73, PRH2, CERCAM, RAB2B DOCK1, FCRL5, ZNF507, JAKMIP1, FAM179A, CD24. |

Table 61 in an embodiment provides a signature of dendritic cells (e.g. cDC), and represents genes/proteins in particular DC subpopulations, preferably of which the expression (or activity) level is positively correlated with the quantitative CD3− CD19+ CD38Hi CD27Hi PB-like B cell, phenotype, preferably associated with HIV infection.

TABLE 62

| |
|---|
| HPS3, TAGLN, BEND3, CD300E, MRE11A, NMRAL1, PIGV, GSDMD, ACOX3, TRAPPC12, NUDT13, AIG1, METTL7B, PCCA, CPSF2, NHSL2, INTS9, NUDT5, PRG2, SLC43A3, TREML2, SEC16B, NDFIP1, CYSLTR2, VPS41, COQ9, PRSS3, FAM104B, SLC38A7, HSBP1L1, FAM118A, FNIP2, SDS, HSDL2, MFSD7, PPP1R17, CLEC4G, FIG4, CARD9, SIPA1L2, STK38L, DAPK1, PRAM1, MS4A14, GABARAPL2, MTMR11, CYSLTR1, TMTC2, SIGLEC9, MPEG1, HNMT, SPATA7, KCTD17, VPS45, TLR1, MFSD1, CDYL, XYLT1, SPG21, TMEM144, KYNU, BCL9, TIAM1, SOWAHD. |

Table 62 in an embodiment provides a signature of dendritic cells (e.g. cDC), and represents genes/proteins in particular DC subpopulations, preferably of which the expression (or activity) level is negatively correlated with the quantitative CD3− CD19+ CD38Hi CD27Hi PB-like B cell phenotype, preferably associated with HIV infection.

TABLE 63

| |
|---|
| TCF25, PION, TRRAP, CSF2RB, HYAL3, NAT6, XRCC3, ATP5L2, ENOX2, NHEJ1, FAM3A, WDR74, GALK2, IFT46, AHI1, NCAPH2, CLEC11A, REV3L, CR1, TAF1B, UBA7, FHL1, EXOC4, FAM208B, EP400, MTMR1, ZMAT1, CDK5RAP2, SAP30L, CD2AP, PKD1, TRIM52, CYP1A2, SYTL4, CEACAM5, IQCB1, POP7, NME6, TAF8, CRAMP1L, SYDE2, LPIN3, ZNF273, S1PR2, COPS3, MRPL36, COTL1, SLC6A14, ZNF71, ZNF506, CXorf56, CLDN4, MRPS23, CYP2B6, CPT1A, TNFAIP8L1, YPEL1, MRPL13, CCDC90A, CNOT7. |

Table 63 in an embodiment provides a signature of dendritic cells (e.g. cDC), and represents genes/proteins in particular DC subpopulations, preferably of which the expression (or activity) level is positively or negatively correlated with the quantitative CD3− CD19+ CD38-CD27+ resting memory B cell phenotype, preferably associated with HIV infection.

TABLE 64

| |
|---|
| TCF25, PION, TRRAP, CSF2RB, HYAL3, NAT6, XRCC3, ATP5L2, ENOX2, NHEJ1, FAM3A, WDR74, GALK2, IFT46, AHI1, NCAPH2, CLEC11A, REV3L, CR1, TAF1B, UBA7, FHL1, EXOC4, FAM208B, EP400, MTMR1, ZMAT1, CDK5RAP2, SAP30L, CD2AP, PKD1, TRIM52. |

Table 64 in an embodiment provides a signature of dendritic cells (e.g. cDC), and represents genes/proteins in particular DC subpopulations, preferably of which the expression (or activity) level is positively correlated with the quantitative CD3− CD19+ CD38− CD27+RestingMemory, B cell phenotype preferably associated with HIV infection.

TABLE 65

| |
|---|
| CYP1A2, SYTL4, CEACAM5, IQCB1, POP7, NME6, TAF8, CRAMP1L, SYDE2, LPIN3, ZNF273, S1PR2, COPS3, MRPL36, COTL1, SLC6A14, ZNF71, ZNF506, CXorf56, CLDN4, MRPS23, CYP2B6, CPT1A, TNFAIP8L1, YPEL1, MRPL13, CCDC90A, CNOT7. |

Table 65 in an embodiment provides a signature of dendritic cells (e.g. cDC), and represents genes/proteins in particular DC subpopulations, preferably of which the expression (or activity) level is negatively correlated with the quantitative CD3− CD19+ CD38− CD27+Resting-Memory, B cell phenotype, preferably associated with HIV infection.

TABLE 66

| |
|---|
| OLIG1, GRIN3A, CETP, TMEM99, AVPR2, OLFML2B, RFESD, TRPM8, CD300LG, LOC284385, ERI2, PRTG, SLC5A9, ANKRD22, SAC3D1, AGBL2, ANKRD35, ZNF573, ZNF285, ZFP112, CCDC34, AVIL, SEMA3A, ZNF425, PARS2, HECW2, ZNF491, BATF2, LY6G5C, TNNT3, CYP1A1, TXNDC5, MUTED, PDE2A, SEMA7A. |

Table 66 in an embodiment provides a signature of dendritic cells (e.g. cDC), and represents genes/proteins in particular DC subpopulations, preferably of which the expression (or activity) level is positively or negatively correlated with the quantitative phenotype TimePoint, preferably associated with HIV infection. Time point refers to a specific time point of sample collection after infection with HIV-1 or after in vitro culture.

TABLE 67

| |
|---|
| OLIG1, GRIN3A, CETP, TMEM99, AVPR2, OLFML2B, RFESD, TRPM8, CD300LG, LOC284385, ERI2, PRTG, SLC5A9, ANKRD22, SAC3D1, AGBL2, ANKRD35, ZNF573, ZNF285, ZFP112, CCDC34, AVIL, SEMA3A, ZNF425, PARS2, HECW2, ZNF491, BATF2, LY6G5C. |

Table 67 in an embodiment provides a signature of dendritic cells (e.g. cDC), and represents genes/proteins in particular DC subpopulations, preferably of which the expression (or activity) level is positively correlated with the quantitative phenotype TimePoint, preferably associated with HIV infection.

TABLE 68

| |
|---|
| TNNT3, CYP1A1, TXNDC5, MUTED, PDE2A, SEMA7A. |

Table 68 in an embodiment provides a signature of dendritic cells (e.g. cDC), and represents genes/proteins in particular DC subpopulations, preferably of which the expression (or activity) level is negatively correlated with the quantitative phenotype TimePoint, preferably associated with HIV infection.

TABLE 69

| |
|---|
| MOG, NAE1, LOC100287177, ZNF506, COX19, YPEL1, HIPK1, COPS3, ZNF626, CRCP, CEACAM5, TBC1D15, HLA-B, LYSMD3, AGFG2, CCHCR1, TIPRL, POLDIP2, NLGN3, WDR76, COG1, GPNMB, S1PR2, CYP1A2, GPAM, SCMH1, KLHL21, MKI67IP, C1orf55, DDX19B, DDX19A, C5orf32, NHEJ1, CARS, FAM214B, GTSF1, NT5E, INPP5E, EP400, TRIM25, CSF2RB, RBFA, ARAP1, CDCA3, TRIM52, FAM213B, RPGR, FILIP1L, PKD1, PION, AMACR, DHX16, POC5, ENOX2, PYGM, UGGT2, IFT46, TM7SF2. |

Table 69 in an embodiment provides a signature of dendritic cells (e.g. cDC), and represents genes/proteins in particular DC subpopulations, preferably of which the expression (or activity) level is positively or negatively correlated with the quantitative CD3− CD19+ CD38Hi CD27− B cell phenotype, preferably associated with HIV infection.

TABLE 70

| |
|---|
| MOG, NAE1, LOC100287177, ZNY506, COX19, YPEL1, HIPK1, COPS3, ZNF626, CRCP, CEACAM5, TBC1D15, HLA-B, LYSMD3, AGFG2, CCHCR1, TIPRL, POLDIP2, NLGN3, WDR76, COG1, GPNMB, S1PR2, CYP1A2, GPAM, SCMH1, KLHL21, MKI67IP, C1orf55, DDX19B, DDX19A, C5orf32. |
| Preferably MOG. |

Table 70 in an embodiment provides a signature of dendritic cells (e.g. cDC), and represents genes/proteins in particular DC subpopulations, preferably of which the expression (or activity) level is positively correlated with the quantitative CD3− CD19+ CD38Hi CD27− B cell phenotype, preferably associated with HIV infection.

TABLE 71

| |
|---|
| NHEJ1, CARS, FAM214B, GTSF1, NT5E, INPP5E, EP400, TRIM25, CSF2RB, RBFA, ARAP1, CDCA3, TRIM52, FAM213B, RPGR, FILIP1L, PKD1, PION, AMACR, DHX16, POC5, ENOX2, PYGM, UGGT2, IFT46, TM7SF2. |

Table 71 in an embodiment provides a signature of dendritic cells (e.g. cDC), and represents genes/proteins in particular DC subpopulations, preferably of which the expression (or activity) level is negatively correlated with the quantitative CD3− CD19+ CD38Hi CD27− B cell phenotype, preferably associated with HIV infection.

TABLE 72

| |
|---|
| MKI67, PLA2G16, TOX, ANKRD39, MT1X, AES, KIR2DL4, CTSW, RRM2, ECHDC2, CXXC5, KLRC3, KLRC2, PPAPDC1B, GZMA, NKG7, SH2D2A, GPR56, SCML4, CD160, MRPL40, PDGFD, CCL5, KIR3DL2, KIR3DL1, KIR2DS4, RBCK1, PTGR2, KLRD1, GNLY, TC2N, CHML, MOAP1, CD38, PRDM1, KIR2DL3, KIR2DL1, CENPF, LGALS3BP, MTHFD1L, PVRIG, CST7, CD3E, UGCG, CD99, IFNG, HCST, LOC100293516, KLF9, TYMS, C1orf174, IFI44, FOXRED2, TOP2A, NCR3, EFHD2, UROS, AMIGO2, SNRNP27, APOL6, NMUR1, MYL6B, LIME1, STARD9, CCL4, C10orf137, TARP, CLIC3, TGFBR3, LIMS3, PRF1, C17orf77, KLRC4-KLRK1, KLRK1, S1PR5, TBX21, KCTD9, IL2RB, PLEKHF1, SKAP1, ZNF282, AKR1B1, TOP1MT, PRSS23, WBSCR22, CPNE2, SRSF5, LBH, RAD17, DLG3, SAMD3, CUTA, BCL7C, HAPLN3, FSIP1, MT2A, SREBF1, ZNF831, KIR2DL2, DYNLT1, POLR2L, CYB5R1, MAD2L2, KLRC4, G0S2, CTIF, F2R, EIF4E3, FAM100B, SLC25A4, KIAA0564, CENPN, SSR4, CD3D, SBDS, PTGDR, NDUFB7, STMN1, NPLOC4, TMEM111, USP49, PTPRM, TMEM14A, ZNF284, USP46, CES4A, SEC22C, CASC5, ASPH, ENSA, SEC11C, CD22, PAFAH2, GTF3A, SUB1, C2orf88, LZTS2, PSME1, KLRG1, ACOT1, SDCBP, RBM27, KIAA1033, PRPF6, USP4, SCYL2, SLC38A6, TLR1, TIAF1, TMBIM1, TDP1, HDLBP, ELP4, RIN2, NOC2L, NARS, TCEANC2, SIXBP3, E4F1, RAD50, DPF2, ZCCHC6, ALKBH8, RPGR, CTNNA1, FAM164A, TMEM48, FUCA1, FNBP1L, SKIL, YARS2, SLC4A1AP, NUMB, RHOT2, TOP3B, ZFAT, CRLF3, PRG2, SLC43A3, RASSF2, CHURC1, CHURC1-FNTB, FNTB, UBL4A, SLC25A44, MRAS, CD300E, PIK3C3, RFWD2, ERCC5, BIVM, BIVM-ERCC5, ACAD10, FASTK, SPDYE5, SPTLC1, ZNF623, AP4M1, RNF146, SMAP2, ANGEL1, CD44, CLN5, HIPK3, RFX1, GEMIN5, COG1, BMPR1A, ZNF710, DST, BFAR, MDM1, CTSO, EI24, FUS, ZSWIM6, SEC23IP, DDX56, PAPSS2, KCTD15, TMEM106B, EXOSC10, FBXW2, PSEN1, DAPK1, ADSS, NUDCD3, SH3PXD2A, FAM120B, ABAT, ST7L. |

Table 72 in an embodiment provides a signature of dendritic cells (e.g. cDC), and represents genes/proteins in particular DC subpopulations, preferably of which the expression (or activity) level is positively or negatively correlated with the quantitative phenotype ViralLoad(Copies/ml), preferably associated with HIV infection. Viral load refers to the number of copies of HIV-1 RNA detected per ml of plasma analyzed for each particular patient. If the number falls below threshold of the technology applied, then the number was called at zero.

TABLE 73

| |
|---|
| MKI67, PLA2G16, TOX, ANKRD39, MT1X, AES, KIR2DL4, CTSW, RRM2, ECHDC2, CXXC5, KLRC3, KLRC2, PPAPDC1B, GZMA, NKG7, SH2D2A, GPR56, SCML4, CD160, MRPL40, PDGFD, CCL5, KIR3DL2, KIR3DL1, KIR2DS4, RBCK1, PTGR2, KLRD1, GNLY, TC2N, CHML, MOAP1, CD38, PRDM1, KIR2DL3, KIR2DL1, CENPF, LGALS3BP, |

TABLE 73-continued

| |
|---|
| MTHFD1L, PVRIG, CST7, CD3E, UGCG, CD99, IFNG, HCST, LOC100293516, KLF9, TYMS, C1orf174, IFI44, FOXRED2, TOP2A, NCR3, EFHD2, UROS, AMIGO2, SNRNP27, APOL6, NMUR1, MYL6B, LIME1, STARD9, CCL4, C10orf137, TARP, CLIC3, TGFBR3, LIMS3, PRF1, C17orf77, KLRC4-KLRK1, KLRK1, S1PR5, TBX21, KCTD9, IL2RB, PLEKHF1, SKAP1, ZNF282, AKR1B1, TOP1MT, PRSS23, WBSCR22, CPNE2, SRSF5, LBH, RAD17, DLG3, SAMD3, CUTA, BCL7C, HAPLN3, FSIP1, MT2A, SREBF1, ZNF831, KIR2DL2, DYNLT1, POLR2L, CYB5R1, MAD2L2, KLRC4, G0S2, CTIF, F2R, EIF4E3, FAM100B, SLC25A4, KIAA0564, CENPN, SSR4, CD3D, SBDS, PTGDR, NDUFB7, STMN1, NPLOC4, TMEM111, USP49, PTPRM, TMEM14A, ZNF284, USP46, CES4A, SEC22C, CASC5, ASPH, ENSA, SEC11C, CD22, PAFAH2, GTF3A, SUB1, C2orf88, LZTS2, PSME1, KLRG1, ACOT1. |
| Or preferably MKI67, PLA2G16, TOX, ANKRD39, MT1X, AES, KIR2DL4, CTSW, RRM2, ECHDC2, CXXC5, KLRC3, KLRC2, PPAPDC1B, GZMA, NKG7, SH2D2A, GPR56, SCML4, CD160, MRPL40, PDGFD, CCL5, KIR3DL2, KIR3DL1, KIR2DS4, RBCK1, PTGR2, KLRD1, GNLY, TC2N, CHML, MOAP1, CD38, PRDM1, KIR2DL3, KIR2DL1, CENPF, LGALS3BP, MTHFD1L, PVRIG, CST7, CD3E, UGCG, CD99, IFNG, HCST, LOC100293516, KLF9, TYMS, C1orf174, IFI44, FOXRED2, TOP2A, NCR3, EFHD2, UROS, AMIGO2, SNRNP27, APOL6, NMUR1, MYL6B, LIME1, STARD9, CCL4, C10orf137. |
| More preferably MKI67, PLA2G16, TOX. |

Table 73 in an embodiment provides a signature of dendritic cells (e.g. cDC), and represents genes/proteins in particular DC subpopulations, preferably of which the expression (or activity) level is positively correlated with the quantitative phenotype ViralLoad(Copies/ml), preferably associated with HIV infection.

TABLE 74

| |
|---|
| SDCBP, RBM27, KIAA1033, PRPF6, USP4, SCYL2, SLC38A6, TLR1, TIAF1, TMBIM1, TDP1, HDLBP, ELP4, RIN2, NOC2L, NARS, TCEANC2, SIXBP3, E4F1, RAD50, DPF2, ZCCHC6, ALKBH8, RPGR, CTNNA1, FAM164A, TMEM48, FUCA1, FNBP1L, SKIL, YARS2, SLC4A1AP, NUMB, RHOT2, TOP3B, ZFAT, CRLF3, PRG2, SLC43A3, RASSF2, CHURC1, CHURC1-FNTB, FNTB, UBL4A, SLC25A44, MRAS, CD300E, PIK3C3, RFWD2, ERCC5, BIVM, BIVM-ERCC5, ACAD10, FASTK, SPDYE5, SPTLC1, ZNF623, AP4M1, RNF146, SMAP2, ANGEL1, CD44, CLN5, HIPK3, RFX1, GEMIN5, COG1, BMPR1A, ZNF710, DST, BFAR, MDM1, CTSO, EI24, FUS, ZSWIM6, SEC23IP, DDX56, PAPSS2, KCTD15, TMEM106B, EXOSC10, FBXW2, PSEN1, DAPK1, ADSS, NUDCD3, SH3PXD2A, FAM120B, ABAT, ST7L. |
| Preferably CD300E, PIK3C3, RFWD2, ERCC5, BIVM, BIVM-ERCC5, ACAD10, FASTK, SPDYE5, SPTLC1, ZNF623, AP4M1, RNF146, SMAP2, ANGEL1, CD44, CLN5, HIPK3, RFX1, GEMIN5, COG1, BMPR1A, ZNF710, DST, BFAR, MDM1, CTSO, EI24, FUS, ZSWIM6, SEC23IP, DDX56, PAPSS2, KCTD15, TMEM106B, EXOSC10, FBXW2, PSEN1, DAPK1, ADSS, NUDCD3, SH3PXD2A, FAM120B, ABAT, ST7L. |

Table 74 in an embodiment provides a signature of dendritic cells (e.g. cDC), and represents genes/proteins in particular DC subpopulations, preferably of which the expression (or activity) level is negatively correlated with the quantitative phenotype ViralLoad(Copies/ml), preferably associated with HIV infection.

TABLE 75

| |
|---|
| CD79A, PF4V1, FGFBP2, HIST1H3A, ZAP70, KIR2DL2, KLRF1, SH2D2A, CLCF1, CD80, ZNF683, GPRC5C, P2RY1, GPR174, XCL2, CSF1, ODF3L1, IFITM1, MYOM2, STK17A, CD22, FCRL5, RBP4, DNASE1L3, PRL, CPNE5, IRF7, TNFRSF13B, XRCC3, ACE, MTMR1, LCN2, PELP1, FLT3LG, OAS3, SGMS1, THOC1, RHOF, SERPINI1, CACNB3, PIK3R4, GCLC, IL2RA, C6orf105, DDX47, RBM10, OTOF, POM121, CNN3, IL17RB, OTUB2, GPR153, GABRA5, GTF2A1L, STON1, STON1-GTF2A1L, MID2, BEND6, CCDC110, SRSF2, FHOD3, SAMD12, ZNF323, MUC4, SULF1, CELSR1, CD68, CFP, C22orf28, PSAP, GPR180, TMED7, TMED7-TICAM2, TICAM2, SPCS3, CTSD, C19orf79, CYB5R1, ASCC3, IER3IP1, GDE1, NCF2, HMG20A, NCF4, ACAD8, TMEM159, CPVL, EML2, STRADB, CRYBB1, LTA4H, EVI2A, UBXN2B, LSMD1, ENTPD5, GTF2E2, CRIPT, SPPL2B, DBNDD2, CRHBP, HPS6, BBS1, LTB4R, MUDENG, TMSB4Y, HIST1H4E, CLEC4D, CUTC, FOS, CACNA2D4, ASGR2, LIN7A, FAAH, WLS, C22orf40, C20orf196. |
| Preferably CD79A, PF4V1, FGFBP2, HIST1H3A, ZAP70, KIR2DL2, KLRF1, SH2D2A, CLCF1, CD80, ZNF683, GPRC5C, P2RY1. |

Table 75 in an embodiment provides a signature of monocytes (e.g. cDC), and represents differentially expressed genes in particular DC subpopulations, preferably associated with or derived from high neutralizer phenotype, preferably associated with HIV infection. Preferably differential expression is evaluated compared to cells from non-high neutralizers.

TABLE 76

| |
|---|
| CD79A, PF4V1, FGFBP2, HIST1H3A, ZAP70, KIR2DL2, KLRF1, SH2D2A, CLCF1, CD80, ZNF683, GPRC5C, P2RY1, GPR174, XCL2, CSF1, ODF3L1, IFITM1, MYOM2, STK17A, CD22, FCRL5, RBP4, DNASE1L3, PRL, CPNE5, IRF7, TNFRSF13B, XRCC3, ACE, MTMR1, LCN2, PELP1, FLT3LG, OAS3, SGMS1, THOC1, RHOF, SERPINI1, CACNB3, PIK3R4, GCLC, IL2RA, C6orf105, DDX47, RBM10, OTOF, POM121, CNN3, IL17RB, OTUB2, GPR153, GABRA5, GTF2A1L, STON1, STON1-GTF2A1L, MID2, BEND6, CCDC110, SRSF2, FHOD3, SAMD12, ZNF323, MUC4, SULF1, CELSR1. |

Table 76 in an embodiment provides a signature of monocytes (e.g. cDC), and represents upregulated genes in particular DC subpopulations, preferably associated with or derived from high neutralizer phenotype, preferably associated with HIV infection. Preferably upregulation is evaluated compared to cells from non-high neutralizers.

TABLE 77

| |
|---|
| CD68, CFP, C22orf28, PSAP, GPR180, TMED7, TMED7-TICAM2, TICAM2, SPCS3, CTSD, C19orf79, CYB5R1, ASCC3, IER3IP1, GDE1, NCF2, HMG20A, NCF4, ACAD8, TMEM159, CPVL, EML2, STRADB, CRYBB1, LTA4H, EVI2A, UBXN2B, LSMD1, ENTPD5, GTF2E2, CRIPT, SPPL2B, DBNDD2, CRHBP, HPS6, BBS1, LTB4R, MUDENG, TMSB4Y, HIST1H4E, CLEC4D, CUTC, FOS, CACNA2D4, ASGR2, LIN7A, FAAH, WLS, C22orf40, C20orf196. |
| Preferably C20orf196. |

Table 77 in an embodiment provides a signature of monocytes (e.g. cDC), and represents downregulated genes in particular DC subpopulations, preferably associated with or derived from high neutralizer phenotype, preferably associated with HIV infection. Preferably downregulation is evaluated compared to cells from non-high neutralizers.

TABLE 78

| |
|---|
| RPS4Y2, FAM98B, C2orf76, RAB28, TMEM191B, ZNF768, CRIPT, MAN1C1, ZNF771, PRSS3, BET1, ENTPD5, CRHBP, ASCC3, ZC3H12D, STARD3NL, GPKOW, ATF1, PRKAG1, EVI2A, RAB3C, MTUS1, CHCHD1, TPSAB1, TPRKB, ABP1, NCF4, E2F4, THG1L, SEC23A, NCBP2, IER3IP1, NAV1, LSM1, H1FNT, NXT2, TMED7, TMED7-TICAM2, TICAM2, LAMP2, KRT72, SSR1, AFAP1L1, OR51E1, NDFIP2, ZBTB41, ZNF502, PLAA, PLEKHG4, FANCM, DDX47, ASB3, GPR75-ASB3, RBM10, GCLC, C9orf25, C20orf194, VAV2, ZDHHC17, CD2AP, OSTalpha, SPATA5L1, RRNAD1, ZNF577, CD72, GADD45B, SH2D2A, PRR7, HIST1H3A. |
| Preferably FAM98B or ASCC3. |

Table 78 in an embodiment provides a signature of monocytes (e.g. cDC), and represents differentially expressed genes in particular DC subpopulations, preferably associated with or derived from low neutralizer phenotype, preferably associated with HIV infection. Preferably differential expression is evaluated compared to cells from non-low neutralizers.

TABLE 79

| |
|---|
| RPS4Y2, FAM98B, C2orf76, RAB28, TMEM191B, ZNF768, CRIPT, MAN1C1, ZNF771, PRSS3, BET1, ENTPD5, CRHBP, ASCC3, ZC3H12D, STARD3NL, GPKOW, ATF1, PRKAG1, EVI2A, RAB3C, MTUS1, CHCHD1, TPSAB1, TPRKB, ABP1, NCF4, E2F4, THG1L, SEC23A, NCBP2, IER3IP1, NAV1, LSM1, H1FNT, NXT2, TMED7, TMED7-TICAM2, TICAM2, LAMP2, KRT72, SSR1, AFAP1L1, OR51E1, NDFIP2. |
| Preferably RPS4Y2, FAM98B, C2orf76, RAB28. |
| More preferably FAM98B or ASCC3. |
| Most preferably FAM98B. |

Table 79 in an embodiment provides a signature of monocytes (e.g. cDC), and represents upregulated genes in particular DC subpopulations, preferably associated with or derived from low neutralizer phenotype, preferably associated with HIV infection. Preferably upregulation is evaluated compared to cells from non-low neutralizers.

TABLE 80

| |
|---|
| ZBTB41, ZNF502, PLAA, PLEKHG4, FANCM, DDX47, ASB3, GPR75-ASB3, RBM10, GCLC, C9orf25, C20orf194, VAV2, ZDHHC17, CD2AP, OSTalpha, SPATA5L1, RRNAD1, ZNF577, CD72, GADD45B, SH2D2A, PRR7, HIST1H3A. |
| Preferably CD72, GADD45B, SH2D2A, PRR7, HIST1H3A. |

Table 80 in an embodiment provides a signature of monocytes (e.g. cDC), and represents downregulated genes in particular DC subpopulations, preferably associated with or derived from low neutralizer phenotype, preferably associated with HIV infection. Preferably downregulation is evaluated compared to cells from non-low neutralizers.

TABLE 81

| |
|---|
| LIPT2, LIN7B, BPI, LIN7A, F2RL1, WLS, THAP9, HPS6, ZFP90, FADD, LYG1, CSTL1, UBXN2B, PRAM1, LEPREL2, GPR162, ZNF85, SERPINF2, C17orf90, ABHD4, CUTC, ADHFE1, LTA4H, GPNMB, NECAB2, CAMK2G, MRP63, ZNF22, KRBA1, PSTPIP1, TM2D1, CMTM4, ARHGAP9, YDJC, GLS2, MILR1, ANKRD42, C10orf131, PARN, ZBTB41, OPLAH, SHARPIN, UMPS, PDZD9, ANAPC16, ITGB2, HEBP1, CDC42BPA, POLR2J, PDZK1, PPP1R9A, NDFIP2, NOP58, NAPA, UBE2D2, RAI1, NEMF, PSTPIP2, CPNE9, MADD, KIF21A, FRY, ARFGAP3, WARS, URIAD1, RAD1, RGS12, PCDHGB3, PCDHGA6, PCDHGB7, PCDHGA9, PCDHGA2, PCDHGA10, PCDHGA7, PCDHGC4, PCDHGB2, PCDHGB6, PCDHGA11, PCDHGC3, PCDHGA3, PCDHGB1, PCDHGA8, PCDHGB5, PCDHGB4, PCDHGA5, PCDHGA4, PCDHGA12, PCDHGA1, PCDHGC5, C5, XRCC3, NCR1, FARP2, TMEM88, CD22, RWDD2A, KLRF1, HIST3H2A. |

Table 81 in an embodiment provides a signature of monocytes (e.g. cDC), and represents differentially expressed genes in particular DC subpopulations, preferably associated with or derived from non-neutralizer phenotype, preferably associated with HIV infection. Preferably differential expression is evaluated compared to cells from not non-neutralizers.

TABLE 82

| |
|---|
| LIPT2, LIN7B, BPI, LIN7A, F2RL1, WLS, THAP9, HPS6, ZFP90, FADD, LYG1, CSTL1, UBXN2B, PRAM1, LEPREL2, GPR162, ZNF85, SERPINF2, C17orf90, ABHD4, CUTC, ADHFE1, LTA4H, GPNMB, NECAB2, CAMK2G, MRP63, ZNF22, KRBA1, PSTPIP1, TM2D1, CMTM4, ARHGAP9, YDJC, GLS2, MILR1, ANKRD42, C10orf131, PARN, ZBTB41, OPLAH, SHARPIN, UMPS, PDZD9, ANAPC16, ITGB2, HEBP1, CDC42BPA, POLR2J, PDZK1. |
| Preferably LIPT2, LIN7B, BPI, LIN7A, F2RL1, WLS. |
| Or preferably LIN7B, ABHD4, TM2D1, ANKRD42. |
| More preferably LIN7B. |

Table 82 in an embodiment provides a signature of monocytes (e.g. cDC), and represents upregulated genes in particular DC subpopulations, preferably associated with or derived from non-neutralizer phenotype, preferably associated with HIV infection. Preferably upregulation is evaluated compared to cells from not non-neutralizers.

TABLE 83

| |
|---|
| PPP1R9A, NDFIP2, NOP58, NAPA, UBE2D2, RAI1, NEMF, PSTPIP2, CPNE9, MADD, KIF21A, FRY, ARFGAP3, WARS, UBIAD1, RAD1, RGS12, PCDHGB3, PCDHGA6, PCDHGB7, PCDHGA9, PCDHGA2, PCDHGA10, PCDHGA7, PCDHGC4, PCDHGB2, PCDHGB6, PCDHGA11, PCDHGC3, PCDHGA3, PCDHGB1, PCDHGA8, PCDHGB5, PCDHGB4, PCDHGA5, PCDHGA4, PCDHGA12, PCDHGA1, PCDHGC5, C5, XRCC3, NCR1, FARP2, TMEM88, CD22, RWDD2A, KLRF1, HIST3H2A. |
| Preferably NCR1, FARP2, TMEM88, CD22, RWDD2A, KLRF1, HIST3H2A. |

TABLE 83-continued

| |
|---|
| Or preferably UBIAD1, RAD1, PCDHGB3, PCDHGA6, PCDHGB7, PCDHGA9, PCDHGA2, PCDHGA10, PCDHGA7, PCDHGC4, PCDHGB2, PCDHGB6, PCDHGA11, PCDHGC3, PCDHGA3, PCDHGB1, PCDHGA8, PCDHGB5, PCDHGB4, PCDHGA5, PCDHGA4, PCDHGA12, PCDHGA1, PCDHGC5, CD22. |
| More preferably CD22. |

Table 83 in an embodiment provides a signature of monocytes (e.g. cDC), and represents downregulated genes in particular DC subpopulations, preferably associated with or derived from non-neutralizer phenotype, preferably associated with HIV infection. Preferably downregulation is evaluated compared to cells from not non-neutralizers.

TABLE 84

| |
|---|
| FCER1A, CD1A, C11orf67, HSD17B4, TNFRSF10C, CRYZ, KLHDC8B, ABCC5, CLTCL1, C12orf24, ZNF559, C16orf74, SNCA, MS4A6A, PADI4, C1GALT1C1, GCA, F13A1, RTN4IP1, ACN9, OCEL1, RTN1, FGL2, WLS, SIGLEC7, C16orf88, COL9A3, GLCE, C14orf80, NDRG2, HIBCH, PLBD1, F5, FAM164A, CEACAM4, AMICA1, ECI2, ZC4H2, KCTD12, NUDT6, CD163, CPNE8, VNN2, PRDX3, TNFRSF6B, FYB, SKAP2, SPINT1, FIG4, CPPED1, BPI, TMEM71, SCFD2, RHBDL2, DPYSL2, SERPINH1, ISOC1, S100A9, ECHDC1, ALAD, BCAT2, NINJ2, PYGL, CBX1, SAMHD1, FAHD2A, FAM104B, VCAN, PLOD1, KLHL22, ALG6, ANO10, DYX1C1, CCPG1, RBM45, ALDH6A1, CLEC4A, RENBP, RAB3D, TAMM41, MAP2K6, TACC3, TM6SF1, THYN1, CUTC, ALKBH3, MRPL12, CAT, COMMD8, WDR83, PIGN, FAM72B, TMEM150A, TTLL12, EMB, COMT, TBC1D9, TMEM128, NAALADL1, FAM105A, PRMT3, C6orf97, PLB1, PMVK, ZNF354A, LPL, MEGF9, S100A12, PAK1, CECR5, ALG3, CMTM1, CKLF, CKLF-CMTM1, PTPRC, NUAK2, C3orf23, PDHB, MRPL24, DPYD, TIAM1, RGS2, CWC27, CR1, SEZ6L, CASP6, SPTSSA, ENTPD1, ATF1, ACO1, BCKDHB, MRPL3, PHACTR2, SLC25A40, CD33, LAT2, VPS8, BRCC3, NKIRAS1, FAM96A, NUDT8, DAK, C10orf11, MRPS5, MYO7A, FANCF, RFC3, N4BP2L1, VCL, CLPB, SULT1A3, LY86, PCMTD1, PCMTD2, FAM82A1, BLVRB, GKAP1, PRPS1, CTPS2, TMBIM4, ERGIC2, KCNE3, TK2, NDUFB2, GLIPR2, FCHO1, CPNE3, LY75, CD302, LY75-CD302, CTSS, TXNDC17, EEF1E1, IL16, SCP2, ST20, ST20-MTHFS, MTHFS, ARHGAP24, DLAT, ZNF438, UGP2, GALNT7, C5orf51, ARHGAP9, ROPN1L, SPATA6, CSTL1, SCCPDH, ZMAT5, AP1S2, DDRGK1, CD300LF, RALBP1, RXRB, TNFSF13B, KCNE2, ANKRD34B, FCN1, FAM117B, PPT1, FAM63A, UBTF, ABCF2, L3MBTL2, ARHGEF6, TALDO1, YIF1B, CACYBP, TIMM44, PARN, THOC7, TBXAS1, C20orf177, G6PD, SPCS2, PARVG, MAPKAP1, RNF44, PPP1R7, ARL6IP5, RHBDD1, FCGR2A, ZNF33B, PAPSS1, AGTRAP, NAAA, RTN3, ITFG1, DGCR2, CPM, OSBPL11, LAS1L, REEP5, NCF2, CD4, CENPO, MGST1, RAP1GDS1, ARHGAP15, SH3BGRL, GPR180, SUCLG1, ALG12, ZNF185, GPS1, CYB5B, PLCB1, DDX18, DOCK8, ADAMTS5, SMARCA4, THG1L, FKBP1A, HNMT, PTPMT1, RNF13, LYPLA2, PGCP, LSM3, ZNF660, ALDH2, PRCP, OAZ2, ESD, PLEKHJ1, WDFY3, ALG9, SYK, SEPHS1, SDR39U1, ATP5E, EIF2B1, PAK2, RBM6, TMX4, CDK19, NCOA1, SPTLC2, RNF130, PTPN2, ERBB2IP, MRPL37, POGK, PDIA4, CAST, C7orf73, SPCS3, FGF13, TGFBI, C20orf30, PLLP, CAPZA2, ARPC1B, SHISA5, OAZ1, ARPC3, FGR, WDR83OS, PPP2R3B, SERBP1, NBN, DPY19L2, PPP1R14C, TMBIM6, OR51E1, RGS10, TMPRSS12, KIF2C, BEGAIN, ZNF592, PPM1F, GRB10, PMPCA, GPBP1L1, ZNF323, KCNK5, PBX4, ABR, SART1, SYNRG, KIAA0226, NLRC5, WARS, LTN1, NXF1, SUPT6H, FRS2, CYTH1, SV2A, PRDM2, TAF7, ZNFX1, ATP10B, NCAPH2, CERK, P2RX4, TNPO1, CEP70, KIF21A, YAF2, GATAD2A, MTRNR2L1, CCNE2, GFRAL, C3orf62, PCDHGB3, PCDHGA6, PCDHGB7, PCDHGA9, PCDHGA2, PCDHGA10, PCDHGA7, PCDHGC4, PCDHGB2, PCDHGB6, PCDHGA11, PCDHGC3, PCDHGA3, PCDHGB1, PCDHGA8, PCDHGB5, PCDHGB4, PCDHGA5, PCDHGA4, PCDHGA12, PCDHGA1, PCDHGC5, CDC25B, FAM199X, ALAS1, ELP2, SERHL2, C6orf106, INO80D, PDE7A, TRRAP, SP140, LRRC32, IL12RB1, TBC1D19, FBRS, ITGB7, ZNF773, SETD5, GGA2, RELA, SYNE2, C2orf65, KLRD1, GUCA1B, C1orf21, ST6GALNAC6, CYB561D1, IRF4, ORMDL3, ZNF707, SPATA12, PLEKHO2, SEC61A2, CSF1, SLC41A2, TMEM184B, SLFN12L, C20orf112, TIGIT, CHD7, ZNF295, LCAT, PATL2, MCOLN2, B4GALT5, CD22, IRF1, PRKCH, FARP2, ZNF335, POMZP3, SMAD3, MET, PYHIN1, GBP5, DUSP4, CD8B, SH2D1A, OPTN, CYP1A1, CD8A, HMGA1, ASB2, NKG7, IL24, CST7, ADAM28, HAPLN3, CD6, HCAR3, C12orf75, TARP, BIN1, TNFRSF12A, GPR56, IL6, TSPYL2, TIPARP, TNFAIP3, HIST3H2A, CCL4. |
| Preferably FCER1A, CD1A, CRYZ, KLHDC8B, ABCC5, ZNF559, C16orf74, SNCA, MS4A6A, F13A1, RTN4IP1, WLS, SIGLEC7, PLBD1, F5, ZC4H2, PRDX3, CPPED1, TMEM71, SCFD2, SERPINH1, ALAD, PYGL, VCAN, DYX1C1, CCPG1, CLEC4A, CUTC, MRPL12, CAT, EMB, COMT, FAM105A, C6orf97, ALG3, CMTM1, CKLF, CKLF-CMTM1, PTPRC, NUAK2, PHACTR2, DAK, LY75, CD302, LY75-CD302, CTSS, EEF1E1, SCP2, RALBP1, CACYBP, TEXAS1, FCGR2A, RTN3, REEP5, SH3BGRL, GPR180, GPS1, LSM3, PRCP, OAZ2, SUPT6H, MTRNR2L1, INO80D, TRRAP, ZNF773, C1orf21, CYB561D1, TIGIT, CD22, ZNF335, OPTN, HMGA1, NKG7, HAPLN3, CD6, C12orf75, BIN1, GPR56, CCL4. |
| More preferably SERPINH1, CLEC4A, CMTM1, CKLF, CKLF-CMTM1, CACYBP, OPTN. |
| Most preferably OPTN. |

Table 84 in an embodiment provides a signature of monocytes (e.g. cDC), and represents differentially expressed genes in particular DC subpopulations, preferably associated with or derived from elite controller phenotype, preferably associated with HIV infection. Preferably differential expression is evaluated compared to cells from non-elite controllers.

TABLE 85

| |
|---|
| FCER1A, CD1A, C11orf67, HSD17B4, TNFRSF10C, CRYZ, KLHDC8B, ABCC5, CLTCL1, C12orf24, ZNF559, C16orf74, SNCA, MS4A6A, PADI4, C1GALT1C1, GCA, F13A1, RTN4IP1, ACN9, OCEL1, RTN1, FGL2, WLS, SIGLEC7, C16orf88, COL9A3, GLCE, C14orf80, NDRG2, HIBCH, PLBD1, F5, FAM164A, CEACAM4, AMICA1, ECI2, ZC4H2, KCTD12, NUDT6, CD163, CPNE8, VNN2, PRDX3, TNFRSF6B, FYB, SKAP2, SPINT1, FIG4, CPPED1, BPI, TMEM71, SCFD2, RHBDL2, DPYSL2, SERPINH1, ISOC1, S100A9, ECHDC1, ALAD, BCAT2, NINJ2, PYGL, CBX1, SAMHD1, FAHD2A, FAM104B, VCAN, PLOD1, KLHL22, ALG6, ANO10, DYX1C1, CCPG1, RBM45, ALDH6A1, CLEC4A, RENBP, RAB3D, TAMM41, MAP2K6, TACC3, TM6SF1, THYN1, CUTC, ALKBH3, MRPL12, CAT, COMMD8, WDR83, PIGN, FAM72B, TMEM150A, TTLL12, EMB, COMT, TBC1D9, TMEM128, NAALADL1, FAM105A, PRMT3, C6orf97, PLB1, PMVK, ZNF354A, LPL, MEGF9, S100A12, PAK1, CECR5, ALG3, CMTM1, CKLF, CKLF-CMTM1, PTPRC, NUAK2, C3orf23, PDHB, MRPL24, DPYD, TIAM1, RGS2, CWC27, CR1, SEZ6L, CASP6, SPTSSA, ENTPD1, ATF1, ACO1, BCKDHB, MRPL3, PHACTR2, SLC25A40, CD33, LAT2, VPS8, BRCC3, NKIRAS1, FAM96A, NUDT8, DAK, C10orf11, MRPS5, MYO7A, FANCF, RFC3, N4BP2L1, VCL, CLPB, SULT1A3, LY86, PCMTD1, PCMTD2, FAM82A1, BLVRB, GKAP1, PRPS1, CTPS2, TMBIM4, ERGIC2, KCNE3, TK2, NDUFB2, GLIPR2, FCHO1, CPNE3, LY75, CD302, LY75-CD302, CTSS, TXNDC17, EEF1E1, IL16, SCP2, ST20, ST20-MTHFS, MTHFS, ARHGAP24, DLAT, ZNF438, UGP2, GALNT7, C5orf51, ARHGAP9, ROPN1L, SPATA6, CSTL1, SCCPDH, ZMAT5, AP1S2, DDRGK1, CD300LF, RALBP1, RXRB, TNFSF13B, KCNE2, ANKRD34B, FCN1, FAM117B, PPT1, FAM63A, UBTF, ABCF2, L3MBTL2, ARHGEF6, TALDO1, YIF1B, CACYBP, TIMM44, PARN, THOC7, TBXAS1, C20orf177, G6PD, SPCS2, PARVG, MAPKAP1, RNF44, PPP1R7, ARL6IP5, RHBDD1, FCGR2A, ZNF33B, PAPSS1, AGTRAP, NAAA, RTN3, ITFG1, DGCR2, CPM, OSBPL11, LAS1L, REEP5, NCF2, CD4, CENPO, MGST1, RAP1GDS1, ARHGAP15, SH3BGRL, GPR180, SUCLG1, ALG12, ZNF185, GPS1, CYB5B, PLCB1, DDX18, DOCK8, ADAMTS5, SMARCA4, THG1L, FKBP1A, HNMT, PTPMT1, RNF13, LYPLA2, PGCP, LSM3, ZNF660, ALDH2, PRCP, OAZ2, ESD, PLEKHJ1, WDFY3, ALG9, SYK, SEPHS1, SDR39U1, ATP5E, EIF2B1, PAK2, RBM6, TMX4, CDK19, NCOA1, SPTLC2, RNF130, PTPN2, ERBB2IP, MRPL37, POGK, PDIA4, CAST, C7orf73, SPCS3, FGF13, TGFBI, C20orf30, PLLP, CAPZA2, ARPC1B, SHISA5, OAZ1, ARPC3, FGR, WDR83OS, PPP2R3B, SERBP1, NBN, DPY19L2, PPP1R14C, TMBIM6, OR51E1. |
| Preferably FCER1A, CD1A, CRYZ, KLHDC8B, ABCC5, ZNF559, C16orf74, SNCA, MS4A6A, F13A1, RTN4IP1, WLS, SIGLEC7, PLBD1, F5, ZC4H2, PRDX3, CPPED1, TMEM71, SCFD2, SERPINH1, ALAD, PYGL, VCAN, DYX1C1, CCPG1, CLEC4A, CUTC, MRPL12, CAT, EMB, COMT, FAM105A, C6orf97, ALG3, CMTM1, CKLF, CKLF-CMTM1, PTPRC, NUAK2, PHACTR2, DAK, LY75, CD302, LY75-CD302, CTSS, EEF1E1, SCP2, RALBP1, CACYBP, TBXAS1, FCGR2A, RTN3, REEP5, SH3BGRL, GPR180, GPS1, LSM3, PRCP, OAZ2. More preferably SERPINH1, CLEC4A, CMTM1, CKLF, CKLF-CMTM1, CACYBP. |
| Or preferably FCER1A, CD1A, C11orf67, HSD17B4, TNFRSF10C, CRYZ, KLHDC8B, ABCC5, CLTCL1, C12orf24, ZNF559, C16orf74, SNCA, MS4A6A, PADI4, C1GALT1C1, GCA, F13A1, RTN4IP1, ACN9, OCEL1, RTN1, FGL2, WLS, SIGLEC7, C16orf88, COL9A3, GLCE, C14orf80, NDRG2, HIBCH, PLBD1, F5, FAM164A, CEACAM4, AMICA1, ECI2, ZC4H2, KCTD12, NUDT6, CD163, CPNE8, VNN2, PRDX3, TNFRSF6B, FYB, SKAP2, SPINT1. More preferably FCER1A, CD1A, CRYZ, KLHDC8B, ABCC5, ZNF559, C16orf74, SNCA, MS4A6A, F13A1, RTN4IP1, WLS, SIGLEC7, PLBD1, F5, ZC4H2, PRDX3. |

Table 85 in an embodiment provides a signature of monocytes (e.g. cDC), and represents upregulated genes in particular DC subpopulations, preferably associated with or derived from elite controller phenotype, preferably associated with HIV infection. Preferably upregulation is evaluated compared to cells from non elite controllers.

TABLE 86

| |
|---|
| RGS10, TMPRSS12, KIF2C, BEGAIN, ZNF592, PPM1F, GRB10, PMPCA, GPBP1L1, ZNF323, KCNK5, PBX4, ABR, SART1, SYNRG, KIAA0226, NLRC5, WARS, LTN1, NXF1, SUPT6H, FRS2, CYTH1, SV2A, PRDM2, TAF7, ZNFX1, ATP10B, NCAPH2, CERK, P2RX4, TNPO1, CEP70, KIF21A, YAF2, GATAD2A, MTRNR2L1, CCNE2, GFRAL, C3orf62, PCDHGB3, PCDHGA6, PCDHGB7, PCDHGA9, PCDHGA2, PCDHGA10, PCDHGA7, PCDHGC4, PCDHGB2, PCDHGB6, PCDHGA11, PCDHGC3, PCDHGA3, PCDHGB1, PCDHGA8, PCDHGB5, PCDHGB4, PCDHGA5, PCDHGA4, PCDHGA12, PCDHGA1, PCDHGC5, CDC25B, FAM199X, ALAS1, ELP2, SERHL2, C6orf106, INO80D, PDE7A, TRRAP, SP140, LRRC32, IL12RB1, TBC1D19, FBRS, ITGB7, ZNF773, SETD5, GGA2, RELA, SYNE2, C2orf65, KLRD1, GUCA1B, C1orf21, ST6GALNAC6, CYB561D1, IRF4, ORMDL3, ZNF707, SPATA12, PLEKHO2, SEC61A2, CSF1, SLC41A2, TMEM184B, SLFN12L, C20orf112, TIGIT, CHD7, ZNF295, LCAT, PATL2, MCOLN2, B4GALT5, CD22, IRF1, PRKCH, FARP2, ZNF335, POMZP3, SMAD3, |

TABLE 86-continued

| |
|---|
| MET, PYHIN1, GBP5, DUSP4, CD8B, SH2D1A, OPTN, CYP1A1, CD8A, HMGA1, ASB2, NKG7, IL24, CST7, ADAM28, HAPLN3, CD6, HCAR3, C12orf75, TARP, BIN1, TNFRSF12A, GPR56, IL6, TSPYL2, TIPARP, TNFAIP3, HIST3H2A, CCL4. |
| Preferably SUPT6H, MTRNR2L1, INO80D, TRRAP, ZNF773, C1orf21, CYB561D1, TIGIT, CD22, ZNF335, OPTN, HMGA1, NKG7, HAPLN3, CD6, C12orf75, BIN1, GPR56, CCL4. |
| More preferably OPTN. |
| Or preferably SMAD3, MET, PYHIN1, GBP5, DUSP4, CD8B, SH2D1A, OPTN, CYP1A1, CD8A, HMGA1, ASB2, NKG7, IL24, CST7, ADAM28, HAPLN3, CD6, HCAR3, C12orf75, TARP, BIN1, TNFRSF12A, GPR56, IL6, TSPYL2, TIPARP, TNFAIP3, HIST3H2A, CCL4. |
| More preferably OPTN, HMGA1, NKG7, HAPLN3, CD6, C12orf75, BIN1, GPR56, CCL4. |

Table 86 in an embodiment provides a signature of monocytes (e.g. cDC), and represents downregulated genes in particular DC subpopulations, preferably associated with or derived from elite controller phenotype, preferably associated with HIV infection. Preferably downregulation is evaluated compared to cells from non elite controllers.

TABLE 87

| |
|---|
| GNLY, PRSS23, GZMB, IFIT2, PYHIN1, SIGLEC11, IFIT3, MCTS1, PRF1, SPRYD4, PLEKHF1, SLAMF6, CXCL11, COQ3, MX1, LCK, MARCO, GPR56, MLYCD, XAF1, PHOSPHO1, SYCP2, GBP3, FANCL, LOC554223, UBASH3A, ZNF48, HLA-DOB, TAP2, DNAJC22, CRIPAK, TMEM181, ANXA9, SLC35B3, APOBEC3H, TMEM14A, ETV2, IL17RB, OR52N5, ALKBH6, UGT2B4, TRIM22, RBM41, MRPS9, GBP4, PTOV1, PANX1, PBK, TPMT, FAM129C, MTO1, TMEM209, KCNE4, KIF4A, POU5F1B, GPR83, ATXN3, MYO1A, SLC2A4, DCAF13, TPRG1, SCO1, LIAS, C3orf70, KIFC1, GBP7, TATDN3, PRELP, SNRPD1, ALG10B, WDTC1, RGS17, ST8SIA1, CAMK2N1, TBC1D9B, N4BP2L2, FAM59B, XK, OPALIN, SLC12A3, MAPK10, CDH12, GNB1, TKT, KIAA0368, ARHGEF1, PSMD2, CLK3, FARP1, AP2A2, CTDP1, MAD2L2, INF2, ARRB2, SDF4, TMEM127, DHX9, EIF5A, CKAP4, SH3BP1, PDXP, NFATC1, BACE1, ATP6V0C, UTS2D, AGMO, VPS18, PRKACA, HNRNPA0, TTLL4, ZNF219, PRUNE2, SELP, AMFR, ATP11B, ACOT1, FURIN, TGFB1, ERN1, RUSC2, CNTD1, LHFP, SOCS6, BRF2, TCEAL3. |
| Preferably ZNF48 or MCTS1. |
| More preferably MCTS1. |

Table 87 in an embodiment provides a signature of monocytes (e.g. cDC), and represents differentially expressed genes in particular DC subpopulations, preferably associated with or derived from previous controller phenotype, preferably associated with HIV infection. Preferably differential expression is evaluated compared to cells from non-previous controllers.

TABLE 88

| |
|---|
| GNLY, PRSS23, GZMB, IFIT2, PYHIN1, SIGLEC11, IFIT3, MCTS1, PRF1, SPRYD4, PLEKHF1, SLAMF6, CXCL11, COQ3, MX1, LCK, MARCO, GPR56, MLYCD, XAF1, PHOSPHO1, SYCP2, GBP3, FANCL, LOC554223, UBASH3A, ZNF48, HLA-DOB, TAP2, DNAJC22, CRIPAK, TMEM181, ANXA9, SLC35B3, APOBEC3H, TMEM14A, ETV2, IL17RB, OR52N5, ALKBH6, UGT2B4, TRIM22, RBM41, MRPS9, GBP4, PTOV1, PANX1, PBK, TPMT, FAM129C, MTO1, TMEM209, KCNE4, KIF4A, POU5F1B, GPR83, ATXN3, MYO1A, SLC2A4, DCAF13, TPRG1, SCO1, LIAS, C3orf70, KIFC1, GBP7, TATDN3, PRELP, SNRPD1, ALG10B, WDTC1, RGS17, ST8SIA1, CAMK2N1, TBC1D9B, N4BP2L2, FAM59B, XK, OPALIN, SLC12A3, MAPK10, CDH12. |
| Preferably ZNF48 or MCTS1. More preferably MCTS1. |
| Or preferably GNLY, PRSS23, GZMB, IFIT2, PYHIN1, SIGLEC11, IFIT3, MCTS1, PRF1, SPRYD4, PLEKHF1, SLAMF6, CXCL11, COQ3, MX1, LCK, MARCO, GPR56, MLYCD, XAF1, PHOSPHO1, SYCP2, GBP3, FANCL, LOC554223, UBASH3A, ZNF48, HLA-DOB, TAP2, DNAJC22, CRIPAK, TMEM181, ANXA9. More preferably ZNF48 or MCTS1. |
| Or preferably MCTS1, SPRYD4, ZNF48, ANXA9. |

Table 88 in an embodiment provides a signature of monocytes (e.g. cDC), and represents upregulated genes in particular DC subpopulations, preferably associated with or derived from previous controller phenotype, preferably associated with HIV infection. Preferably upregulation is evaluated compared to cells from non previous controllers.

TABLE 89

| |
|---|
| GNB1, TKT, KIAA0368, ARHGEF1, PSMD2, CLK3, FARP1, AP2A2, CTDP1, MAD2L2, INF2, ARRB2, SDF4, TMEM127, DHX9, EIF5A, CKAP4, SH3BP1, PDXP, NFATC1, BACE1, ATP6V0C, UTS2D, AGMO, VPS18, PRKACA, HNRNPA0, TTLL4, ZNF219, PRUNE2, SELP, AMFR, ATP11B, ACOT1, FURIN, |

TABLE 89-continued

| |
|---|
| TGFB1, ERN1, RUSC2, CNTD1, LHFP, SOCS6, BRF2, TCEAL3. Preferably SELP, AMFR, ATP11B, ACOT1, FURIN, TGFB1, ERN1, RUSC2, CNTD1, LHFP, SOCS6, BRF2, TCEAL3. |

Table 89 in an embodiment provides a signature of monocytes (e.g. cDC), and represents downregulated genes in particular DC subpopulations, preferably associated with or derived from previous controller phenotype, preferably associated with HIV infection. Preferably downregulation is evaluated compared to cells from non previous controllers.

TABLE 90

| |
|---|
| CCL4, EGR2, HIST3H2A, DHRS3, TNFRSF12A, TSPYL2, RHOH, IL24, HCAR3, CYP1A1, SDC2, BIN1, HMGA1, DUSP4, STX1A, ASB2, ADAM28, MET, C12orf75, LONRF1, BCL3, PVRL2, IL6, KRM38, CXCR5, CD6, POMZP3, FAM20C, SPRY2, ZNF295, SLC35E4, NEU4, GNA12, PLEKHO2, OVCA2, ZHX2, BIK, AKAP2, PALM2, PALM2-AKAP2, PPP1R16B, MAFG, VOPP1, CCL28, ACOT1, FCRL3, IRF1, FAM46C, RAPGEF1, VASH1, RELA, FAM168B, TGFB1, SEC61A2, LTBP4, AMFR, HNRPLL, ZDHHC18, CHD7, ELF4, CDC42EP4, IRF4, LRRC32, ZNF335, SCML1, SUV39H1, HAVCR1, FBRS, SPATA12, RBP4, CD22, TMEM184B, PPP3CC, PANX2, SLC7A1, GEM, ORMDL3, TBC1D12, C20orf112, ST3GAL1, ATP11B, ZNF773, SLC43A2, LUZP1, SGTA, TNPO1, CEP70, OPTN, CDK16, ALG2, SRA1, TPCN2, SYNJ1, CCNE2, C6orf106, SPPL2A, SIVA1, GATAD2A, SUPT5H, ILVBL, CAV1, POLDIP3, KDM5C, MZT2B, PLEC, SRCAP, FAM211B, MED23, EML4, TRRAP, MED13L, ELP2, FAM193A, SRRT, LY6K, TFE3, KIFC3, ANXA11, P2RX4, ZBTB7A, MVD, HMGXB4, KCND1, MTRNR2L1, ZNF24, DFNB31, RFWD3, GFRAL, SYN2, PLIN4, RNF10, AMD1, ATP6V0C, C12orf51, ZC3H18, DGKA, FEM1B, EIF5A, PRDM2, ARID2, U2AF1L4, LRRC59, KRAS, CYTH1, KDM2A, ATP1A1, SSFA2, PABPC4, MED22, WAPAL, TOR1AIP2, KIN, C1orf21, ANKRD11, DDA1, NXF1, TRPC4AP, TNFRSF1B, ABR, MKRN1, BTBD18, PLEKHG1, PCBP2, AFG3L2, PPM1F, PLEKHB2, DDX39A, GUK1, ZNF592, UHMK1, SENP6, SUPT6H, TGM4, CDC27, SDF4, KCNK5, DCAF4L1, SARTI, PI4KA, CNPPD1, GPBP1L1, SRRM2, TCIRG1, SEMA7A, MTMR3, SGIP1, FAM65A, P4HB, BEGAIN, LMOD2, ADRBK1, SNPH, GABRA5, MFSD10, STARD9, HNRNPH1, NLGN4Y, LCT, DENR, HDAC2, WDR83OS, SERBP1, FGR, CAST, SLC4A1AP, TGFBI, ARPC1B, C7orf73, SLC31A1, FAM54B, UQCR11, SHISA5, NFYC, SRP9, C20orf30, SP140L, TDRD6, ITM2B, C2orf63, NDUFS2, FCGR2A, RBM6, ERBB2IP, ATP5E, SERPINB6, SPTLC2, SNX14, OAZ2, UQCRQ, LSM3, SNRNP40, KCNE2, CEP104, ANAPC16, CYB5B, PRCP, WRAP73, UBA3, MRPL37, PLCB1, R3HDM2, RNF141, ATRX, PRKDC, SCN9A, PGA3, DNAJC25, GNG10, DNAJC25-GNG10, ZNF131, TAS2R5, TPMT, KHDC1, SYK, TBXAS1, SH3BGRL, SPCS2, SEPHS1, CASD1, ANXA9, ZNF48, PSMD10, PARVG, RALBP1, SLC46A1, REEP5, OSBPL11, DOCK8, APBB1IP, CPM, ENOPH1, LAS1L, HNRNPUL2, NAAA, PAPSS1, PHF17, RAB11A, RTN3, NSL1, SFT2D1, CACYBP, RHBDD1, PMS2, THOC7, CD4, ARHGAP15, ITFG1, BBIP1, UGP2, LILRA1, LILRA2, STAMBP, WWC2, C6orf97, TNFSF13B, IFT140, ZNF33B, TXNDC15, SPRYD4, RABEP2, FPGT, TNNI3K, FPGT-TNNI3K, HDAC8, CTSS, CTPS2, RNGTT, AP1S2, MRPL52, FAM63A, UMPS, SCO1, LRSAM1, PARN, ACER3, FAM200B, MRPS25, DTWD1, APAF1, MYO1A, MRPS5, LILRA6, LILRB3, LILRA3, FCN1, SPATA6, PCMTD2, C5orf51, TIMM44, C20orf72, NEFH, SCCPDH, CLNS1A, GPR180, FAM86B2, GALNT7, NUAK2, SFXN5, HSDL2, BTK, WDR67, SCP2, RBBP9, BLVRA, ANKRD44, TIGD7, DLAT, DAK, RNASEH2B, PHACTR2, RBM41, CR1, B3GNTL1, ANKZF1, NDUFB2, BRCC3, NUDT8, EEF1E1, VPS8, ALG3, WFDC8, TSNAX, TXNDC9, OSBPL1A, GIN1, MRPL12, ZNF438, MLKL, GLIPR2, IL16, DIMT1, SLC25A40, MAML3, DNAJC11, NHLRC1, PCMTD1, FAM117A, TBC1D9, LAT2, FAM96A, SULT1A3, TXNDC17, MAP2K6, PDCL3, MYCBP, FKBP4, DNAJC17, SLC43A1, AKAP7, MEIS1, VCAN, SERPINH1, EMB, PLB1, BLVRB, PMVK, CWC27, MEGF9, C3orf23, COMMD8, ERCC8, PTPRC, CLEC4D, OLFML2B, DYX1C1, CCPG1, APLF, CD33, PRMT5, DPYD, CLEC4A, DAPP1, POLR2H, CMTM1, CKLF, CKLF-CMTM1, TACC3, CASP6, TM6SF1, CAT, CUTC, ERGIC2, S100A12, GLRX, PARP16, C19orf59, PDHB, SPTSSA, PRMT3, DET1, TBCE, DDX23, FAM105A, ARHGAP24, CPPED1, SULT1A1, TMEM71, KLHL22, SCFD2, F5, FAM164A, C6orf203, HEATR3, ALAD, S100A8, ZFP36L2, CISD1, RHBDL2, C8orf55, SIGLEC15, SPINT1, PIN4, SKAP2, TMEM128, TTC4, ISOC1, NUDT6, VNN2, WLS, ALG6, ARL11, CBX1, ALDH6A1, FYB, C4orf43, THYN1, ZNF354A, NINJ2, KIF23, ATIC, PYGL, SELL, BPI, MRPS9, RAB39A, P2RY13, GPD1L, F13A1, SDCCAG3, RNF170, ALKBH3, MCTS1, C7orf58, FAHD2A, S100A9, PRDX3, CD200R1, COL9A3, HVCN1, AMICA1, COMMD10, KCTD12, SLC25A43, PLBD1, CEACAM4, CD163, CD1C, MTX2, BCAT2, RTN4IP1, FGL2, CPNE8, TCEAL1, C16orf88, NDRG2, SIGLEC7, C11orf82, MS4A6A, GCA, ACN9, CRYZ, TRIM7, C12orf24, C1GALT1C1, PADI4, ABCC5, GLCE, KLHDC8B, CMKLR1, C11orf67, CLTCL1, PGA4, ZNF559, MNDA, HSD17B4, CD1A, ACYP1, C3orf78. Preferably IL24, CYP1A1, POMZP3, PLEKHO2, IRF1, RELA, IRF4, LRRC32, ZNF773, CEP70, CCNE2, SUPT5H, TRRAP, RNF10, DCAF4L1, PGA3, ANXA9, REEP5, CACYBP, IFT140, ZNF33B, SCO1, MYO1A, FCN1, TIMM44, GPR180, SCP2, DLAT, EEF1E1, ZNF438, FAM96A, TXNDC17, PTPRC, OLFML2B, CLFC4A, CMTM1, CKLF, CKLF-CMTM1, CUTC, ERGIC2, FAM105A, C8orf55, TMEM128, ARL11, KIF23, PYGL, MRPS9, PRDX3, PLBD1, BCAT2, CPNE8, SIGLEC7, C1GALT1C1, GLCE, CMKLR1, ZNF559, HSD17B4, CD1A. |

Table 90 in an embodiment provides a signature of monocytes (e.g. cDC), and represents differentially expressed genes in particular DC subpopulations, preferably associated with or derived from viremic controller phenotype, preferably associated with HIV infection. Preferably differential expression is evaluated compared to cells from non-viremic controllers.

TABLE 91

| |
|---|
| CCL4, EGR2, HIST3H2A, DHRS3, TNFRSF12A, TSPYL2, RHOH, IL24, HCAR3, CYP1A1, SDC2, BIN1, HMGA1, DUSP4, STX1A, ASB2, ADAM28, MET, C12orf75, LONRF1, BCL3, PVRL2, IL6, RBM38, CXCR5, CD6, POMZP3, FAM20C, SPRY2, ZNF295, SLC35E4, NEU4, GNA12, PLEKHO2, OVCA2, ZHX2, BIK, AKAP2, PALM2, PALM2-AKAP2, PPP1R16B, MAFG, VOPP1, CCL28, ACOT1, FCRL3, IRF1, FAM46C, RAPGEF1, VASH1, RELA, FAM168B, TGFB1, SEC61A2, LTBP4, AMFR, HNRPLL, ZDHHC18, CHD7, ELF4, CDC42EP4, IRF4, LRRC32, ZNF335, SCML1, SUV39H1, HAVCR1, FBRS, SPATA12, RBP4, CD22, TMEM184B, PPP3CC, PANX2, SLC7A1, GEM, ORMDL3, TBC1D12, C20orf112, ST3GAL1, ATP11B, ZNF773, SLC43A2, LUZP1, SGTA, TNPO1, CEP70, OPTN, CDK16, ALG2, SRA1, TPCN2, SYNJ1, CCNE2, C6orf106, SPPL2A, SIVA1, GATAD2A, SUPT5H, ILVBL, CAV1, POLDIP3, KDM5C, MZT2B, PLEC, SRCAP, FAM211B, MED23, EML4, TRRAP, MED13L, ELP2, FAM193A, SRRT, LY6K, TFE3, KIFC3, ANXA11, P2RX4, ZBTB7A, MVD, HMGXB4, KCND1, MTRNR2L1, ZNF24, DFNB31, RFWD3, GFRAL, SYN2, PLIN4, RNF10, AMD1, ATP6V0C, C12orf51, ZC3H18, DGKA, FEM1B, EIF5A, PRDM2, ARID2, U2AF1L4, LRRC59, KRAS, CYTH1, KDM2A, ATP1A1, SSFA2, PABPC4, MED22, WAPAL, TOR1AIP2, KIN, C1orf21, ANKRD11, DDA1, NXF1, TRPC4AP, TNFRSF1B, ABR, MKRN1, BTBD18, PLEKHG1, PCBP2, AFG3L2, PPM1F, PLEKHB2, DDX39A, GUK1, ZNF592, UHMK1, SENP6, SUPT6H, TGM4, CDC27, SDF4, KCNK5, DCAF4L1, SART1, PI4KA, CNPPD1, GPBP1L1, SRRM2, TCIRG1, SEMA7A, MTMR3, SGIP1, FAM65A, P4HB, BEGAIN, LMOD2, ADRBK1, SNPH, GABRA5, MFSD10, STARD9, HNRNPH1, NLGN4Y.<br>Preferably IL24, CYP1A1, POMZP3, PLEKHO2, IRF1, RELA, IRF4, LRRC32, ZNF773, CEP70, CCNE2, SUPT5H, TRRAP, RNF10, DCAF4L1.<br>Or preferably CCL4, EGR2, HIST3H2A, DHRS3, TNFRSF12A, TSPYL2, RHOH, IL24, HCAR3, CYP1A1, SDC2, BIN1, HMGA1, DUSP4, STX1A, ASB2, ADAM28, MET, C12orf75, LONRF1, BCL3, PVRL2, IL6, RBM38, CXCR5, CD6, POMZP3, FAM20C, SPRY2, ZNF295, SLC35E4, NEU4. More preferably IL24, CYP1A1, POMZP3, PLEKHO2. |

Table 91 in an embodiment provides a signature of monocytes (e.g. cDC), and represents upregulated genes in particular DC subpopulations, preferably associated with or derived from viremic controller phenotype, preferably associated with HIV infection. Preferably upregulation is evaluated compared to cells from non viremic controllers.

TABLE 92

| |
|---|
| LCT, DENR, HDAC2, WDR83OS, SERBP1, FGR, CAST, SLC4A1AP, TGFBI, ARPC1B, C7orf73, SLC31A1, FAM54B, UQCR11, SHISA5, NFYC, SRP9, C20orf30, SP140L, TDRD6, ITM2B, C2orf63, NDUFS2, FCGR2A, RBM6, ERBB2IP, ATP5E, SERPINB6, SPTLC2, SNX14, OAZ2, UQCRQ, LSM3, SNRNP40, KCNE2, CEP104, ANAPC16, CYB5B, PRCP, WRAP73, UBA3, MRPL37, PLCB1, R3HDM2, RNF141, ATRX, PRKDC, SCN9A, PGA3, DNAJC25, GNG10, DNAJC25-GNG10, ZNF131, TAS2R5, TPMT, KHDC1, SYK, TBXAS1, SH3BGRL, SPCS2, SEPHS1, CASD1, ANXA9, ZNF48, PSMD10, PARVG, RALBP1, SLC46A1, REEP5, OSBPL11, DOCK8, APBB1IP, CPM, ENOPH1, LAS1L, HNRNPUL2, NAAA, PAPSS1, PHF17, RAB11A, RTN3, NSL1, SFT2D1, CACYBP, RHBDD1, PMS2, THOC7, CD4, ARHGAP15, ITFG1, BBIP1, UGP2, LILRA1, LILRA2, STAMBP, WWC2, C6orf97, TNFSF13B, IFT140, ZNF33B, TXNDC15, SPRYD4, RABEP2, FPGT, TNNI3K, FPGT-TNNI3K, HDAC8, CTSS, CTPS2, RNGTT, AP1S2, MRPL52, FAM63A, UMPS, SCO1, LRSAM1, PARN, ACER3, FAM200B, MRPS25, DTWD1, APAF1, MYO1A, MRPS5, LILRA6, LILRB3, LILRA3, FCN1, SPATA6, PCMTD2, C5orf51, TIMM44, C20orf72, NEFH, SCCPDH, CLNS1A, GPR180, FAM86B2, GALNT7, NUAK2, SFXN5, HSDL2, BTK, WDR67, SCP2, RBBP9, BLVRA, ANKRD44, TIGD7, DLAT, DAK, RNASEH2B, PHACTR2, RBM41, CR1, B3GNTL1, ANKZF1, NDUFB2, BRCC3, NUDT8, EEF1E1, VPS8, ALG3, WFDC8, TSNAX, TXNDC9, OSBPL1A, GIN1, MRPL12, ZNF438, MLKL, GLIPR2, IL16, DIMT1, SLC25A40, MAML3, DNAJC11, NHLRC1, PCMTD1, FAM117A, TBC1D9, LAT2, FAM96A, SULT1A3, TXNDC17, MAP2K6, PDCL3, MYCBP, FKBP4, DNAJC17, SLC43A1, AKAP7, MEIS1, VCAN, SERPINH1, EMB, PLB1, BLVRB, PMVK, CWC27, MEGF9, C3orf23, COMMD8, ERCC8, PTPRC, CLEC4D, OLFML2B, DYX1C1, CCPG1, APLF, CD33, PRMT5, DPYD, CLEC4A, DAPP1, POLR2H, CMTM1, CKLF, CKLF-CMTM1, TACC3, CASP6, TM6SF1, CAT, CUTC, ERGIC2, S100A12, GLRX, PARP16, C19orf59, PDHB, SPTSSA, PRMT3, DET1, TBCE, DDX23, FAM105A, ARHGAP24, CPPED1, SULT1A1, TMEM71, KLHL22, SCFD2, F5, FAM164A, C6orf203, HEATR3, ALAD, S100A8, ZFP36L2, CISD1, RHBDL2, C8orf55, SIGLEC15, SPINT1, PIN4, SKAP2, TMEM128, TTC4, ISOC1, NUDT6, VNN2, WLS, ALG6, ARL11, CBX1, ALDH6A1, FYB, C4orf43, THYN1, ZNF354A, NINJ2, KIF23, ATIC, PYGL, SELL, BPI, MRPS9, RAB39A, P2RY13, GPD1L, F13A1, SDCCAG3, RNF170, ALKBH3, MCTS1, C7orf58, FAHD2A, S100A9, PRDX3, CD200R1, COL9A3, HVCN1, AMICA1, COMMD10, |

TABLE 92-continued

| |
|---|
| KCTD12, SLC25A43, PLBD1, CEACAM4, CD163, CD1C, MTX2, BCAT2, RTN4IP1, FGL2, CPNE8, TCEAL1, C16orf88, NDRG2, SIGLEC7, C11orf82, MS4A6A, GCA, ACN9, CRYZ, TRIM7, C12orf24, C1GALT1C1, PADI4, ABCC5, GLCE, KLHDC8B, CMKLR1, C11orf67, CLTCL1, PGA4, ZNF559, MNDA, HSD17B4, CD1A, ACYP1, C3orf78. Preferably PGA3, ANXA9, REEP5, CACYBP, IFT140, ZNF33B, SCO1, MYO1A, FCN1, TIMM44, GPR180, SCP2, DLAT, EEF1E1, ZNF438, FAM96A, TXNDC17, PTPRC, OLFML2B, CLEC4A, CMTM1, CKLF, CKLF-CMTM1, CUTC, ERGIC2, FAM105A, C8orf55, TMEM128, ARL11, KIF23, PYGL, MRPS9, PRDX3, PLBD1, BCAT2, CPNE8, SIGLEC7, C1GALT1C1, GLCE, CMKLR1, ZNF559, HSD17B4, CD1A. More preferably ANXA9. |
| Or preferably RAB39A, P2RY13, GPD1L, F13A1, SDCCAG3, RNF170, ALKBH3, MCTS1, C7orf58, FAHD2A, S100A9, PRDX3, CD200R1, COL9A3, HVCNI, AMICA1, COMMD10, KCTD12, SLC25A43, PLBD1, CEACAM4, CD163, CD1C, MTX2, BCAT2, RTN4IP1, FGL2, CPNE8, TCEAL1, C16orf88, NDRG2, SIGLEC7, C11orf82, MS4A6A, GCA, ACN9, CRYZ, TRIM7, C12orf24, C1GALT1C1, PADI4, ABCC5, GLCE, KLHDC8B, CMKLR1, C11orf67, CLTCL1, PGA4, ZNF559, MNDA, HSD17B4, CD1A, ACYP1, C3orf78. More preferably ARL11, KIF23, PYGL, MRPS9, PRDX3, PLBD1, BCAT2, CPNE8, SIGLEC7, C1GALT1C1, GLCE, CMKLR1, ZNF559, HSD17B4, CD1A. |

Table 92 in an embodiment provides a signature of monocytes (e.g. cDC), and represents downregulated genes in particular DC subpopulations, preferably associated with or derived from viremic controller phenotype, preferably associated with HIV infection. Preferably downregulation is evaluated compared to cells from non viremic controllers.

TABLE 93

| |
|---|
| FLYWCH1, GRK5, LETMD1, PLEKHM3, C3orf67, TAZ, VGLL4, RPRD2, THOC1, RRAS2, ING2, KRT18, SEC61A2, IRF4, LTV1, RBM10, KIAA1737, ZBTB39, POM121, ZNF492, VRK3, OLFML2B, GPAT2, SNTB1, PGA4, ZNF506, IER3IP1, NAE1, IFT81, SNX33, PPP1R3D, SCO1, ATN1, TMEM40, TNRC6C, VSIG2, FSD1L, TNS3, PEF1, ENTPD5, MURC, SPIRE1, THAP5, SLC39A14, DIEXF, MS4A2, MAGEA10, ZCRB1. |

Table 93 in an embodiment provides a signature of monocytes (e.g. cDC), and represents genes/proteins in particular DC subpopulations, preferably of which the expression (or activity) level is positively or negatively correlated with the quantitative CD3− CD19+ CD38Int CD27 Int B cell Activated Memory-Germinal Center B cells phenotype, preferably associated with HIV infection.

TABLE 94

| |
|---|
| FLYWCH1, GRK5, LETMD1, PLEKHM3, C3orf67, TAZ, VGLL4, RPRD2, THOC1, RRAS2, ING2, KRT18, SEC61A2, IRF4, LTV1, RBM10, KIAA1737, ZBTB39, POM121, ZNF492. |

Table 94 in an embodiment provides a signature of monocytes (e.g. cDC), and represents genes/proteins in particular DC subpopulations, preferably of which the expression (or activity) level is positively correlated with the quantitative phenotype CD3− CD19+ CD38Int CD27 Int B cell Activated Memory-Germinal Center B cells, preferably associated with HIV infection.

TABLE 95

| |
|---|
| VRK3, OLFML2B, GPAT2, SNTB1, PGA4, ZNF506, IER3IP1, NAE1, IFT81, SNX33, PPP1R3D, SCO1, ATN1, TMEM40, TNRC6C, VSIG2, FSD1L, TNS3, PEF1, ENTPD5, MURC, SPIRE1, THAP5, SLC39A14, DIEXF, MS4A2, MAGEA10, ZCRB1. |

Table 95 in an embodiment provides a signature of monocytes (e.g. cDC), and represents genes/proteins in particular DC subpopulations, preferably of which the expression (or activity) level is negatively correlated with the quantitative phenotype CD3− CD19+ CD38Int CD27 Int B cell Activated Memory-Germinal Center B cells, preferably associated with HIV infection.

TABLE 96

| |
|---|
| TRAK2, STEAP4, DDI2, PPP1R11, HDLBP, TOM1L2, SMG9, FAM157A, MGAM, RACGAP1, BANP, UBAP2, MTF1, ZRANB2, NUMB, MIS12, OXSR1, SRSF1, CD164, CDC73, CSF2RA, RCBTB2, ARHGDIA, SEC61A1, SAFB, ACSL5, UXT, KIFC3, DMXL2, MGST1, GHITM, CCDC92, LPAR1, CFLAR, REXO2, NEB, ATP6AP1L, HLA-DPA1, ZNF667, ENAH, XAF1, VTI1B, B3GNT6, ENC1, RPS19, CBFA2T2, SHMT1, LIN28A, TPCN1, TMEM169, PML, C9orf91, TAF8, NCOA7, C9orf9, RAET1E, CEP104, SYVN1, RNPC3, PIPOX, B3GALT2, DZIP3, U2AF1L4, DPP9, WHAMM, TCEAL8, PGAM5, C20orf152, MAP3K9, IFITM3, ZBTB44, ZNF426, MOG, OAS3, PNPO, TTYH1, SLC6A11, SHROOM1, GPSM2, HDGFRP2, ZNF765, CCDC25, RPAIN, ST8SIA1, PPP1R32, CD300LG. |

Table 96 in an embodiment provides a signature of monocytes (e.g. cDC), and represents genes/proteins in particular DC subpopulations, preferably of which the expression (or activity) level is positively or negatively correlated with the quantitative phenotype Age, preferably associated with HIV infection. Age parameter refers to the age of patients included in the study cohort.

TABLE 97

| |
|---|
| TRAK2, STEAP4, DDI2, PPP1R11, HDLBP, TOM1L2, SMG9, FAM157A, MGAM, RACGAP1, BANP, UBAP2, MTF1, ZRANB2, NUMB, MIS12, OXSR1, SRSF1, CD164, CDC73, CSF2RA, RCBTB2, ARHGDIA, SEC61A1, SAFB, ACSL5, UXT, KIFC3, DMXL2, MGST1, GHITM, CCDC92, LPAR1, CFLAR, REXO2. |

Table 97 in an embodiment provides a signature of monocytes (e.g. cDC), and represents genes/proteins in particular DC subpopulations, preferably of which the expression (or activity) level is positively correlated with the quantitative phenotype Age, preferably associated with HIV infection.

TABLE 98

| |
|---|
| NEB, ATP6AP1L, HLA-DPA1, ZNF667, ENAH, XAF1, VT11B, B3GNT6, ENC1, RPS19, CBFA2T2, SHMT1, LIN28A, TPCN1, TMEM169, PML, C9orf91, TAF8, NCOA7, C9orf9, RAET1E, CEP104, SYVN1, RNPC3, PIPOX, B3GALT2, DZIP3, U2AF1L4, DPP9, WHAMM, TCEAL8, PGAM5, C20orf152, MAP3K9, IFITM3, ZBTB44, ZNF426, MOG, OAS3, PNPO, TTYH1, SLC6A11, SHROOM1, GPSM2, HDGFRP2, ZNF765, CCDC25, RPAIN, ST8SIA1, PPR1R32, CD300LG. |

Table 98 in an embodiment provides a signature of monocytes (e.g. cDC), and represents genes/proteins in particular DC subpopulations, preferably of which the expression (or activity) level is negatively correlated with the quantitative phenotype Age, preferably associated with HIV infection.

TABLE 99

| |
|---|
| LMF1, KCTD3, DYRK4, THRAP3, EFHA1, GLS2, MIF, ZFY, PAXIP1, BLK, AKR1D1, HECTD2, SLC39A4, PDCD4, ZFP62, PIGP, STK36, C20orf94, HIP1R, NAT9, ITGA6, VWA5B1, DAK, BYSL, UBE2CBP, SLC10A7, C19orf63, CRYZ, GBA2, DPY19L3, MPP1, FBXL15, LHFPL4, GNL1, SEMA3C, PIK3C2B, FXR2, TOLLIP, CGGBP1, CAMKK2. |

Table 99 in an embodiment provides a signature of monocytes (e.g. cDC), and represents genes/proteins in particular DC subpopulations, preferably of which the expression (or activity) level is positively or negatively correlated with the quantitative phenotype CD4Count(Cells/mm3), preferably associated with HIV infection.

TABLE 100

| |
|---|
| LMF1, KCTD3, DYRK4, THRAP3, EFHA1, GLS2, MIF, ZFY, PAXIP1, BLK, AKR1D1, HECTD2, SLC39A4, PDCD4, ZFP62, PIGP, STK36, C20orf94, HIP1R, NAT9, ITGA6, VWA5B1, DAK, BYSL, UBE2CBP, SLC10A7, C19orf63, CRYZ. |

Table 100 in an embodiment provides a signature of monocytes (e.g. cDC), and represents genes/proteins in particular DC subpopulations, preferably of which the expression (or activity) level is positively correlated with the quantitative phenotype CD4Count(Cells/mm3), preferably associated with HIV infection.

TABLE 101

| |
|---|
| GBA2, DPY19L3, MPP1, FBXL15, LHFPL4, GNL1, SEMA3C, PIK3C2B, FXR2, TOLLIP, CGGBP1, CAMKK2. |

Table 101 in an embodiment provides a signature of monocytes (e.g. cDC), and represents genes/proteins in particular DC subpopulations, preferably of which the expression (or activity) level is negatively correlated with the quantitative phenotype CD4Count(Cells/mm3), preferably associated with HIV infection.

TABLE 102

| |
|---|
| DEPDC5, PSMA3, KTN1, GPR1, CD99L2, ZC3H8, HORMAD1, MT1E, RAPGEF2, A4GALT, SELS, SESTD1, NDUFA2, MYO5C, PDE4B, RPL22L1, UQCRH, SIAH1, TMEM104, UIMC1, ASNS, PSMA2, ZNF836, ZCWPW1, KIAA1467, MORF4L2, LAMB3, RNF139, PSMA1, ING5, LRRC8B, NUB1, SEC13, DNPEP, VPS13A, ADCY9, PRKRIP1, LOC100289561, MAP1B, RSF1, ZNF302, ZNF577, COQ3, JAK3, HMG20A, ZBTB40, B9D2, ERAP2, ASTE1, NR2C2, MCTP2, ALOX12, MDN1, RAD50, MRPS17, EMR3, ZNF141, PUS3, NOL8, NPIPL3, IGJ, RET, ADCK5, DIEXF, ZNF75A, SPDYE2L. |

Table 102 in an embodiment provides a signature of monocytes (e.g. cDC), and represents genes/proteins in particular DC subpopulations, preferably of which the expression (or activity) level is positively or negatively correlated with the quantitative conventional T follicular helper cell phenotype defined as CXCR5+CXCR3−PD1+, preferably associated with HIV infection.

TABLE 103

| |
|---|
| DEPDC5, PSMA3, KTN1, GPR1, CD99L2, ZC3H8, HORMAD1, MT1E, RAPGEF2, A4GALT, SELS, SESTD1, NDUFA2, MYO5C, PDE4B, RPL22L1, UQCRH, SIAH1, TMEM104, UIMC1, ASNS, PSMA2, ZNF836, ZCWPW1, KIAA1467, MORF4L2, LAMB3, RNF139, PSMA1, ING5, LRRC8B, NUB1, SEC13, DNPEP, VPS13A, ADCY9, PRKRIP1, LOC100289561, MAP1B, RSF1. |

Table 103 in an embodiment provides a signature of monocytes (e.g. cDC), and represents genes/proteins in particular DC subpopulations, preferably of which the expression (or activity) level is positively correlated with the quantitative conventional T follicular helper cell phenotype defined as CXCR5+CXCR3−PDI+, preferably associated with HIV infection.

TABLE 104

| |
|---|
| ZNF302, ZNF577, COQ3, JAK3, HMG20A, ZBTB40, B9D2, ERAP2, ASTE1, NR2C2, MCTP2, ALOX12, MDN1, RAD50, MRPS17, EMR3, ZNF141, PUS3, NOL8, NPIPL3, IGJ, RET, ADCK5, DIEXF, ZNF75A, SPDYE2L. |

Table 104 in an embodiment provides a signature of monocytes (e.g. cDC), and represents genes/proteins in particular DC subpopulations, preferably of which the expression (or activity) level is negatively correlated with the quantitative conventional T follicular helper cell phenotype defined as CXCR5+CXCR3−PDI+, preferably associated with HIV infection.

TABLE 105

| |
|---|
| SUPT7L, ARFGAP1, AP2A2, TNPO1, CDR2, ABCA5, SMG1, NBPF24, CDCP1, SUSD5, SERAC1, SLC30A4, HPS3, RNF219, POLR3F, MLLT6, ITGA5, TMEM136, HIPK2, CLASP1, SLC7A11, TNFAIP6, CYB5D1, DOLK, MICALL1, TMEM184B, CCL4, ARID2, C17orf63, IL6R, DVL3, MED31, SYDE2, B4GALT6, ZEB2, BTN2A1, ZNF124, SMC4, LIMS3, BTBD1, NOX5, ZBTB4, ATP2A3, PAM16, CORO7-PAM16, CORO7, WDR91, ZNF154, ILVBL, PDE2A, BIN1, GOLGB1, ALDH1L1, EXOC3, EXOC5, ABLIM1, GMEB1, CDKN1B, AIF1, FAM92A1, PIEZO1, ZMYND8, SERPINA1, TTC27, EIF2B1, F13A1, COX7A2, AATF, CISD3, PLEKHJ1, TLN1, ERP29, NSMCE4A, CAMK1, TRAPPC12, DLG1, BIN2, RTN1, TRADD, LCP1, FKBP3, C1orf123, YIF1A, DPEP2, VMAC, TMEM173, FBXO44, SPOCK1, DYSF, FAM149B1, F5, COX16, SYNJ2BP-COX16, SYNJ2BP, C19orf24, PRR13, ALDH6A1, ADI1, SCFD2, BNIP3, FKBP4, ARPC4, ARPC4-TTLL3, TTLL3, DDO, LY6G5C, FAHD2A, EIF3B, MRPL34, RNF220, RAB8A, LILRA6, LILRB3, LILRA3, BRAT1, SH3KBP1, HDAC8, BTK, LPCAT2, GLIPR1, NPEPL1, UTP14A, ARHGDIB, HMBOX1, GNB1L, TNFRSF6B, PEPD, ZC4H2, SEMA6A, TOMM6, METAP1, C20orf197, TRIM34, TRIM6, TRIM6-TRIM34, DPCD, ACPP, ERLIN2, TBC1D9B, TBCE, FXN, NDUFA3, CPPED1, TBCB, UBLCP1, UBL7, TMEM141, ALAD, TSN, SNTB1, CYB5D2, DES, ROGDI, ESF1, AURKAIP1, JAK3, C6orf70, AAAS, PARK7, WLS, PTPN18, NLRP1, C10orf54, CECR5, CUTC, PCYT2, ZFP64, MSRB2, LYST, MSN, CRELD1, SCLT1, VASP, TMEM42, MYO7B, TSEN15, CARD9, IL13RA1, KCTD15, AGTRAP, C9orf139, SNRPC, MPND, FAM125A, STXBP2, CAPN3, SIGMAR1, MAP3K6, CERKL |

Table 105 in an embodiment provides a signature of monocytes (e.g. cDC), and represents genes/proteins in particular DC subpopulations, preferably of which the expression (or activity) level is positively or negatively correlated with the quantitative T follicular helper cell-like phenotype CXCR5+PD1+, preferably associated with HIV infection.

TABLE 106

| |
|---|
| SUPT7L, ARFGAP1, AP2A2, TNPO1, CDR2, ABCA5, SMG1, NBPF24, CDCP1, SUSD5, SERAC1, SLC30A4, HPS3, RNF219, POLR3F, MLLT6, ITGA5, TMEM136, HIPK2, CLASP1, SLC7A11, TNFAIP6, CYB5D1, DOLK, MICALL1, TMEM184B, CCL4, ARID2, C17orf63, IL6R, DVL3, MED31, SYDE2, B4GALT6, ZEB2, BTN2A1, ZNF124, SMC4 LIMS3, BTBD1, NOX5, ZBTB4, ATP2A3, PAM16, CORO7-PAM16, CORO7, WDR91, ZNF154, ILVBL, PDE2A, BIN1, GOLGB1, ALDH1L1, EXOC3, EXOC5, ABLIM1, GMEB1. |
| Preferably SUPT7L, ARFGAP1, AP2A2, TNPO1, CDR2, ABCA5, SMG1. |

Table 106 in an embodiment provides a signature of monocytes (e.g. cDC), and represents genes/proteins in particular DC subpopulations, preferably of which the expression (or activity) level is positively correlated with the quantitative T follicular helper cell-like phenotype CXCR5+ PD1+, preferably associated with HIV infection.

TABLE 107

| |
|---|
| CDKN1B, AIF1, FAM92A1, PIEZO1, ZMYND8, SERPINA1, TTC27, EIF2B1, F13A1, COX7A2, AATF, CISD3, PLEKHJ1, TLN1, ERP29, NSMCE4A, CAMK1, TRAPPC12, DLG1, BIN2, RTN1, TRADD, LCP1, FKBP3, C1orf123, YIF1A, DPEP2, VMAC, TMEM173, FBXO44, SPOCK1, DYSF, FAM149B1, F5, COX16, SYNJ2BP-COX16, SYNJ2BP, C19orf24, PRR13, ALDH6A1, ADI1, SCFD2, BNIP3, FKBP4, ARPC4, ARPC4-TTLL3, TTLL3, DDO, LY6G5C, FAHD2A, EIF3B, MRPL34, RNF220, RAB8A, LILRA6, LILRB3, LILRA3, BRAT1, SH3KBP1, HDAC8, BTK, LPCAT2, GLIPR1, NPEPL1, UTP14A, ARHGDIB, HMBOX1, GNB1L, TNFRSF6B, PEPD, ZC4H2, SEMA6A, TOMM6, METAP1, C20orf197, TRIM34, TRIM6, TRIM6-TRIM34, DPCD, ACPP, ERLIN2, TBC1D9B, TBCE, FXN, NDUFA3, CPPED1, TBCB, UBLCP1, UBL7, TMEM141, ALAD, TSN, SNTB1, CYB5D2, DES, ROGDI, ESF1, AURKAIP1, JAK3, C6orf70, AAAS, PARK7, WLS, PTPN18, NLRP1, C10orf54, CECR5, CUTC, PCYT2, ZFP64, MSRB2, LYST, MSN, CRELD1, SCLT1, VASP, TMEM42, MYO7B, TSEN15, CARD9, IL13RA1, KCTD15, AGTRAP, C9orf139, SNRPC, MPND, FAM125A, STXBP2, CAPN3, SIGMAR1, MAP3K6, CERKL |
| Preferably TMEM42, MYO7B, TSEN15, CARD9, IL13RA1, KCTD15, AGTRAP, C9orf139, SNRPC, MPND, FAM125A, STXBP2, CAPN3, SIGMAR1, MAP3K6, CERKL. |

Table 107 in an embodiment provides a signature of monocytes (e.g. cDC), and represents genes/proteins in particular DC subpopulations, preferably of which the expression (or activity) level is negatively correlated with the quantitative T follicular helper cell-like phenotype CXCR5+PD1+, preferably associated with HIV infection.

TABLE 108

| |
|---|
| CD22, FCRL5, CD79A, XRCC3, ACE, SH2D2A, CD80, PIK3R4, PELP1, TMEM194A, MS4A1, IRF7, SGMS1, MADD, EZR, NOP58, IL2RA, KIR2DL2, FLT3LG, CDC42SE1, CERK, C14orf21, CPNE5, SFT2D2, IRF9, GTF2A1L, STON1, STON1-GTF2A1L, MKLN1, DLC1, SLC5A3, NUMA1, KIAA1522, SART, PF4V1, IL21R, EARS2, MYOM2, C12orf75, RHOF, GPR174, IFITM1, PLEKHM3, CSF1, NEMF, FGFBP2, FARP2, NLRC5, NFKB1, XCL2, ERN1, ZAP70, MCOLN2, GPR68, GPNMB, COMT, BCKDHA, TMEM91, RNF170, TRIM34, TRIM6, TRIM6-TRIM34, CAMK2G, ZNF561, PLTP, GGT7, GRSF1, MRPS28, IDH3G, YDJC, ITM2B, TKT, CLEC4A, HMG20A, PARN, RAB3D, LIN7B, CACNB2, TFEB, SCRN2, C20orf30, FCN1, UPK3BL, C19orf79, DUS4L, CDC42BPA, PRICKLE3, ERP29, UMPS, AGTRAP, FBXL5, HEBP1, RPS19BP1, C20orf196, GDE1, NUDT6, IER3IP1, ABHD4, HPS6, ZFP90, LSMD1, PYGL, SLC25A43, HYAL4, RBP7, SULT1A2, RAB40C, CPVL, SHARPIN, BACE1, ARHGAP9, PRKCDBP, CYB5R1, CLEC4D, DRAM2, AP1S2, DBNDD2, CEP104, EIF4E3, LIN7A, SIGLEC12, RANGRF, ASGR2, FOS, LTA4H, RNF130, UBXN2B, CUTC, MILR1, WLS. |
| Preferably CD22. |

Table 108 in an embodiment provides a signature of monocytes (e.g. cDC), and represents genes/proteins in particular DC subpopulations, preferably of which the expression (or activity) level is positively or negatively correlated with the quantitative phenotype HIV-1-specific Neutralizing breadth defined by the proportions of HIV-1 strains tested (n=11) by the plasma of the study patients, preferably associated with HIV infection.

TABLE 109

| |
|---|
| CD22, FCRL5, CD79A, XRCC3, ACE, SH2D2A, CD80, PIK3R4, PELP1, TMEM194A, MS4A1, IRF7, SGMS1, MADD, EZR, NOP58, IL2RA, KIR2DL2, FLT3LG, CDC42SE1, CERK, C14orf21, CPNE5, SFT2D2, IRF9, GTF2A1L, STON1, STON1-GTF2A1L, MKLN1, DLC1, SLC5A3, NUMA1, KIAA1522, SART1, PF4V1, IL21R, EARS2, MYOM2, C12orf75, RHOF, CPR174, IFITM1, PLEKHM3, CSF1, NEMF, FGFBP2, FARP2, NLRC5, NFKB1, XCL2, ERN1, ZAP70, MCOLN2, GPR68. |
| Preferably CD22. |

Table 109 in an embodiment provides a signature of monocytes (e.g. cDC), and represents genes/proteins in particular DC subpopulations, preferably of which the expression (or activity) level is positively correlated with the quantitative phenotype HIV-1-specific Neutralizing breadth defined by the proportions of HIV-1 strains tested (n=11) by the plasma of the study patients, preferably associated with HIV infection.

TABLE 110

| |
|---|
| GPNMB, COMT, BCKDHA, TMEM91, RNF170, TRIM34, TRIM6, TRIM6-TRIM34, CAMK2G, ZNF561, PLTP, GGT7, GRSF1, MRPS28, IDH3G, YDJC, ITM2B, TKT, CLEC4A, HMG20A, PARN, RAB3D, LIN7B, CACNB2, TFEB, SCRN2, C20orf30, FCN1, UPK3BL, C19orf79, DUS4L, CDC42BPA, PRICKLE3, ERP29, UMPS, AGTRAP, FBXL5, HEBP1, RPS19BP1, C20orf196, GDE1, NUDT6, IER3IP1, ABHD4, HPS6, ZFP90, LSMD1, PYGL, SLC25A43, HYAL4, RBP7, SULT1A2, RAB40C, CPVL, SHARPIN, BACE1, ARHGAP9, PRKCDBP, CYB5R1, CLEC4D, DRAM2, AP1S2, DBNDD2, CEP104, EIF4E3, LIN7A, SIGLEC12, RANGRF, ASGR2, FOS, LTA4H, RNF130, UBXN2B, CUTC, MILR1, WLS. |

Table 110 in an embodiment provides a signature of monocytes (e.g. cDC), and represents genes/proteins in particular DC subpopulations, preferably of which the expression (or activity) level is negatively correlated with the quantitative phenotype HIV-1-specific Neutralizing breadth defined by the proportions of HIV-1 strains tested (n=11) by the plasma of the study patients, preferably associated with HIV infection.

TABLE 111

| |
|---|
| PRKDC, TMEM56, ERH, UBAC2, PGA4, AIM1, EIF4EBP3, CD40, GLG1, TNS3, CD38, CNOT7, MAP2K4, WDR73, THAP5, C11orf58, CTSB, AKR1B1, KIF9, CPVL, ADSL, TOR1B, TRAM2, SCO1, PVR, PNOC, HENMT1, SPTLC2, ACO1, VSIG2, FEZ2, HEATR2, MRPS9, SERINC3, C5orf30, ZNF253, CD58, LILRA4, MRPS27, WRB, SLC39A10, TMEM222, MRPS16, CD4, RAB11A, NFE2L3, AFF4, KIAA0226, SART1, WEE1, PIK3CG, ASB7, RUSC2, NRSN2, HIPK1, APPL2, TCTN1, NXF1, MAPK12, C4orf40, RCOR3, LETMD1, ACIN1, FLYWCH1, TNFRSF12A, LPAR2, SMPD1, PRKCG, MFN2, SETD1B, MADD, AKAP17A, FAM91A1, PHTF2, GRK5, LTA, HIST3H2A, FAM76B, KDM3B, VGLL4, SEC61A2, GRIPAP1. |

Table 111 in an embodiment provides a signature of monocytes (e.g. cDC), and represents genes/proteins in particular DC subpopulations, preferably of which the expression (or activity) level is positively or negatively correlated with the quantitative phenotype CD3− CD19+ CD38LO/− CD27− B cells (NAlike), preferably associated with HIV infection.

TABLE 112

| |
|---|
| PRKDC, TMEM56, ERH, UBAC2, PGA4, AIM1, EIF4EBP3, CD40, GLG1, TNS3, CD38, CNOT7, MAP2K4, WDR73, THAP5, C11orf58, CTSB, AKR1B1, KIF9, CPVL, ADSL, TOR1B, TRAM2, SCO1, PVR, PNOC, HENMT1, SPTLC2, ACO1, VSIG2, FEZ2, HEATR2, MRPS9, SERINC3, C5orf30, ZNF253, CD58, LILRA4, MRPS27, WRB, SLC39A10, TMEM222, MRPS16, CD4, RAB11A, NFE2L3. |
| Preferably PRKDC. |

Table 112 in an embodiment provides a signature of monocytes (e.g. cDC), and represents genes/proteins in particular DC subpopulations, preferably of which the expression (or activity) level is positively correlated with the quantitative phenotype CD3− CD19+ CD38LO/− CD27− B cells (NAlike), preferably associated with HIV infection.

TABLE 113

| |
|---|
| AFF4, KIAA0226, SART1, WEE1, PIK3CG, ASB7, RUSC2, NRSN2, HIPK1, APPL2, TCTN1, NXF1, MAPK12, C4orf40, RCOR3, LETMD1, ACIN1, FLYWCH1, TNFRSF12A, LPAR2, SMPD1, PRKCG, MFN2, SETD1B, MADD, AKAP17A, FAM91A1, PHTF2, GRK5, LTA, HIST3H2A, FAM76B, KDM3B, VGLL4, SEC61A2, GRIPAP1. |

Table 113 in an embodiment provides a signature of monocytes (e.g. cDC), and represents genes/proteins in particular DC subpopulations, preferably of which the expression (or activity) level is negatively correlated with the quantitative phenotype CD3− CD19+ CD38LO/− CD27− B cells (NAlike), preferably associated with HIV infection.

TABLE 114

| |
|---|
| CD22, GPR56, FAM109A, GZMB, MS4A1, SLAMF6, RHOC, IFITMI, C17orf56, CPNE5, MYOM2, NUMA1, CTSW, NLRC5, OAS3, NKG7, HAUS3, PF4V1, NCALD, NFX1, CUX1, ZNF683, MCOLN2, PRF1, CLYBL, FRY, SFT2D2, GTF3C1, LIMD1, RPRD2, NCKAP5L, C17orf100, C12orf75, COQ3, LCAT, CADM1, IGJ, SH2D2A, PTPRCAP, FCRL5, SYVN1, ACE, ST7, RHOF, SYNE2, SAMD3, PNPLA6, CD79B, ETV5, IFITM3, PLD4, XRCC3, GNLY, PRSS23, OAS2, IFNG, CCM2, HARBI1, GPR171, SKAP1, CCDC30, SLCO1A2, F2R, GATA3, TUBGCP6, C14ort21, IL21R, SPG7, PCDHGB3, PCDHGA6, PCDHGB7, PCDHGA9, PCDHGA2, PCDHGA10, PCDHGA7, PCDHGC4, PCDHGB2, PCDHGB6, PCDHGA11, PCDHGC3, PCDHGA3, PCDHGB1, PCDHGA8, PCDHGB5, PCDHGB4, PCDHGA5, PCDHGA4, PCDHGA12, PCDHGA1, PCDHGC5, CDC25B, PYHIN1, ZNF23, ARHGEF9, ACACB, IFI27, ECHDC2, RBM33, UBASH3B, CERK, SMARCE1, PCDH9, IFT88, FGFBP2, ZAP70, GALE, ACOT7, ADA, PSKH1, NUP107, PI4K2B, FDXR, ABI3, AK1, ARHGAP27, CD8A, IBTK, FBXO34, CHP, CPM, APBA3, HELQ, CTSK, EIF4E3, AGMO, HMGN3, MAML3, POLR2D, CALU, MILR1, HN1L, CANX, EIF1AY, PTEN, RALBP1, SPIRE1, BPI, ASAP1, KIAA0141, SSR2, SSPO, LHFPL2, LIMK2, WLS, CNIH, CKAP4, GPNMB, DMXL2, CSF2RA, SLC3A2, OS9, CRTAM, METTL9, GLRX2, UBXN2B, HEBP1, SPG21, UPK3BL, FBN2, YDJC, CLEC4D, PLA2G7, THAP9, FCN1, TPT1, HSD3B7, TM2D1, POGK, CLEC4G, RPS19BP1, SDF2, QPCT, C19orf79. |
| Preferably CD22. |

Table 114 in an embodiment provides a signature of monocytes (e.g. cDC), and represents genes/proteins in particular DC subpopulations, preferably of which the expression (or activity) level is positively or negatively correlated with the quantitative phenotype CD3− CD19− CD38Hi CD27Hi (PB-like), preferably associated with HIV infection.

TABLE 115

| |
|---|
| CD22, GPR56, FAM109A, GZMB, MS4A1, SLAMF6, RHOC, IFITM1, C17orf56, CPNE5, MYOM2, NUMA1, CTSW, NLRC5, OAS3, NKG7, HAUS3, PF4V1, NCALD, NFX1, CUX1, ZNF683, MCOLN2, PRF1, CLYBL, FRY, SFT2D2, GTF3C1, LIMD1, RPRD2, NCKAP5L, C17orf100, C12orf75, COQ3, LCAT, CADM1, IGJ, SH2D2A, PTPRCAP, FCRL5, SYVN1, ACE, ST7, RHOF, SYNE2, SAMD3, PNPLA6, CD79B, ETV5, IFITM3, PLD4, XRCC3, GNLY, PRSS23, OAS2, IFNG, CCM2, HARBI1, GPR171, SKAP1, CCDC30, SLCO1A2, F2R, GATA3, TUBGCP6, C14orf21, IL21R, SPG7, PCDHGB3, |

TABLE 115-continued

| |
|---|
| PCDHGA6, PCDHGB7, PCDHGA9, PCDHGA2, PCDHGA10, PCDHGA7, PCDHGC4, PCDHGB2, PCDHGB6, PCDHGA11, PCDHGC3, PCDHGA3, PCDHGB1, PCDHGA8, PCDHGB5, PCDHGB4, PCDHGA5, PCDHGA4, PCDHGA12, PCDHGA1, PCDHGC5, CDC25B, PYHIN1, ZNF23, ARHGEF9, ACACB, IFI27, ECHDC2, RBM33, UBASH3B, CERK, SMARCE1, PCDH9, IFT88, FGFBP2, ZAP70, GALE, ACOT7, ADA, PSKH1, NUP107, PI4K2B, FDXR, ABI3, AK1, ARHGAP27, CD8A, IBTK. |
| Preferably CD22, GPR56, FAM109A, GZMB, MS4A1, SLAMF6, RHOC, IFITM1, C17orf56, CPNE5, MYOM2, NUMA1, CTSW. |
| More preferably CD22. |

Table 115 in an embodiment provides a signature of monocytes (e.g. cDC), and represents genes/proteins in particular DC subpopulations, preferably of which the expression (or activity) level is positively correlated with the quantitative phenotype CD3− CD19− CD38Hi CD27Hi (PB-like), preferably associated with HIV infection.

TABLE 116

| |
|---|
| FBXO34, CHP, CPM, APBA3, HELQ, CTSK, EIF4E3, AGMO, HMGN3, MAML3, POLR2D, CALU, MILR1, HN1L, CANX, EIF1AY, PTEN, RALBP1, SPIRE1, BPI, ASAP1, KIAA0141, SSR2, SSPO, LHFPL2, LIMK2, WLS, CNIH, CKAP4, GPNMB, DMXL2, CSF2RA, SLC3A2, OS9, CRTAM, METTL9, GLRX2, UBXN2B, HEBP1, SPG21, UPK3BL, FBN2, YDJC, CLEC4D, PLA2G7, THAP9, FCN1, TPT1, HSD3B7, TM2D1, POGK, CLEC4G, RPS19BP1, SDF2, QPCT, C19orf79. |
| Preferably SDF2, QPCT, C19orf79. |

Table 116 in an embodiment provides a signature of monocytes (e.g. cDC), and represents genes/proteins in particular DC subpopulations, preferably of which the expression (or activity) level is negatively correlated with the quantitative phenotype CD3− CD19− CD38Hi CD27Hi (PB-like), preferably associated with HIV infection.

TABLE 117

| |
|---|
| LMLN, ZSWIM1, GNG7, AXL, RGNEF, VIM, NUBP2, TAGAP, CHRM3, MBD5, TAF13, SPIB, SRGAP3, PPP1R17, MTA2, YAE1D1, MRE11A, FAM124A, TRIO, CDKN2B, PGAM14, FANCB, EARS2, PPP1R18, TMEM106B, DLG4, PPP1R3D, LPAR1, GSDMB, SETD6, BRI3, C10orf25, SH3BGRL3, OSGEPL1, KRI1, REXO4, TMEM86B, DDX28, PEX12, TBPL1, ERO1L, TPST1, TBC1D2B, FXR2. |

Table 117 in an embodiment provides a signature of monocytes (e.g. cDC), and represents genes/proteins in particular DC subpopulations, preferably of which the expression (or activity) level is positively or negatively correlated with the quantitative phenotype CD3− CD19+ CD38− CD27+ B cells (RestingMemory), preferably associated with HIV infection.

TABLE 118

| |
|---|
| LMLN, ZSWIM1, GNG7, AXL, RGNEF, VIM, NUBP2, TAGAP, CHRM3, MBD5, TAF13, SPIB, SRGAP3, PPP1R17, MTA2, YAE1D1, MRE11A, FAM124A, TRIO, CDKN2B, PGAM4, FANCB, EARS2. |

Table 118 in an embodiment provides a signature of monocytes (e.g. cDC), and represents genes/proteins in particular DC subpopulations, preferably of which the expression (or activity) level is positively correlated with the quantitative phenotype CD3− CD 19+ CD38− CD27+ B cells (RestingMemory), preferably associated with HIV infection.

TABLE 119

| |
|---|
| PPP1R18, TMEM106B, DLG4, PPP1R3D, LPAR1, GSDMB, SETD6, BRI3, C10orf125, SH3BGRL3, OSGEPL1, KRI1, REXO4, TMEM86B, DDX28, PEX12, TBPL1, ERO1L, TPST1, TBC1D2B, FXR2. |

Table 119 in an embodiment provides a signature of monocytes (e.g. cDC), and represents genes/proteins in particular DC subpopulations, preferably of which the expression (or activity) level is negatively correlated with the quantitative phenotype CD3− CD19+ CD38− CD27+ B cells (RestingMemory), preferably associated with HIV infection.

TABLE 120

| |
|---|
| PCDH12, JAKMIP1, HIST2H3D, NEFH, BICD1, UBASH3A, THNSL1, TMEM177, TTC16, GRIN3A, NOS3, ZNF439, CCM2, TCL1A, PARS2, CLDN7, SPIN3, H2AFY2, PTCH1, DHFRL1, DHRS13, PFDN6, C22orf46, FAM72D, HIST1H2BC, C1orf35, GZMK, MRM1, C17orf100, BTLA, ERBB2, ZNF585B, FCRLA, PTGDS, EHHADH, SIRPG, RPP25, RIPK3, PTPN13, SLC2A3, RPL15, GPR97, TMEM66, HNRNPK, PRDX6, SLC2A14, BNIP2, RPS4Y1, KCTD20, TMBIM1, ZNF469, RNF130, SAT1, ZNF10, DUSP3, CNBP, SPRY2, SPCS3, TMED10, C5AR1, HAS1. |

Table 120 in an embodiment provides a signature of monocytes (e.g. cDC), and represents genes/proteins in particular DC subpopulations, preferably of which the expression (or activity) level is positively or negatively correlated with the quantitative phenotype TimePoint, preferably associated with HIV infection.

TABLE 121

| |
|---|
| PCDH12, JAKMIP1, HIST2H3D, NEFH, BICD1, UBASH3A, THNSL1, TMEM177, TTC16, GRIN3A, NOS3, ZNF439, CCM2, TCL1A, PARS2, CLDN7, SPIN3, H2AFY2, PTCH1, DHFRL1, DHRS13, PFDN6, C22orf46, FAM72D, HIST1H2BC, C1orf35, GZMK, MRM1, C17orf100, BTLA, ERBB2, ZNF585B, FCRLA, PTGDS, EHHADH, SIRPG, RPP25, RIPK3, PTPN13. |

Table 121 in an embodiment provides a signature of monocytes (e.g. cDC), and represents genes/proteins in particular DC subpopulations, preferably of which the expression (or activity) level is positively correlated with the quantitative phenotype TimePoint, preferably associated with HIV infection.

TABLE 122

| |
|---|
| SLC2A3, RPL15, GPR97, TMEM66, HNRNPK; PRDX6, SLC2A14, BNIP2, RPS4Y1, KCTD20, TMBIM1, ZNF469, RNF130, SAT1, ZNF10, DUSP3, CNBP, SPRY2, SPCS3, TMED10, C5AR1, HAS1. |

Table 122 in an embodiment provides a signature of monocytes (e.g. cDC), and represents genes/proteins in particular DC subpopulations, preferably of which the expression (or activity) level is negatively correlated with the quantitative phenotype TimePoint, preferably associated with HIV infection.

TABLE 123

| |
|---|
| SH3BGRL3, FXR2, TBPL1, CD6, TIMM9, ERO1L, KDM3B, PPP1R18, BCORL1, TBC1D2B, C14orf105, DMWD, PPP1R3D, MFN2, SMURF1, PLEKHO1, DCTD, FAM91A1, POMZP3, NCR1, TMEM180, ANKRD23, EPG5, SLC35D2, SLC10A7, PGAM4, HRSP12, MAP4K1, PTPRC, YAE1D1, GAR1, SLIT1, PPIAL4G, BLNK, CHRNE, MAPKBP1, PUS7, FAM86B1, NUBP2, TCTN3, LMLN, GTF2H4. |

Table 123 in an embodiment provides a signature of monocytes (e.g. cDC), and represents genes/proteins in particular DC subpopulations, preferably of which the expression (or activity) level is positively or negatively correlated with the quantitative phenotype CD3− CD19+ CD38Int CD27Int (Transitional), preferably associated with HIV infection.

TABLE 124

| |
|---|
| SH3BGRL3, FXR2, TBPL1, CD6, TIMM9, ERO1L, KDM3B, PPP1R18, BCORL1, TBC1D2B, C14orf105, DMWD, PPP1R3D, MFN2, SMURF1, PLEKHO1, DCTD, FAM91A1, POMZP3, NCR1, TMEM180, ANKRD23, EPG5, SLC35D2. |

Table 124 in an embodiment provides a signature of monocytes (e.g. cDC), and represents genes/proteins in particular DC subpopulations, preferably of which the expression (or activity) level is positively correlated with the quantitative phenotype CD3− CD19+ CD38Int CD27Int (Transitional), preferably associated with HIV infection.

TABLE 125

| |
|---|
| SLC10A7, PGAM4, HRSP12, MAP4K1, PTPRC, YAE1D1, GAR1, SLIT1, PPIAL4G, BLNK, CHRNE, MAPKBP1, PUS7, FAM86B1, NUBP2, TCTN3, LMLN, GTF2H4. |

Table 125 in an embodiment provides a signature of monocytes (e.g. cDC), and represents genes/proteins in particular DC subpopulations, preferably of which the expression (or activity) level is negatively correlated with the quantitative phenotype CD3− CD19+ CD38Int CD27Int (Transitional), preferably associated with HIV infection.

TABLE 126

| |
|---|
| ORMDL3, ALDH4A1, IRF7, CYC1, MTHFD1L, C16orf87, WBSCR22, CD81, IFITM3, ETV7, OPTN, SF3B2, CSF1, MON2, C9orf86, HOXA1, CRTC1, FAM199X, SUPT5H, PFDN2, ASB1, GAS6, PPIH, RPS10-NUDT3, NUDT3, RPS10, DVL1, CCDC141, RELA, TNFRSF12A, PXN, DENND3, ABHD4, METTL23, ERGIC2, SERP1, JRKL, ANTXR2, NFYC, PRICKLE3, IPO11, TMEM128, VNN2, KLHL22, EDEM3, TTC33, CCDC157, ACTR2, NDUFS2, FUCA1, C9orf102, CTAGE5, CTPS2, NDUFS1, ZNF630, KIAA0195, HCCS, PMM2, STXBP3, GPR180, C11orf58, ESD, NFE2L3, CCDC153, PYROXD2, NOP14, EEF1E1, RHBDL2, THRAP3. |

Table 126 in an embodiment provides a signature of monocytes (e.g. cDC), and represents genes/proteins in particular DC subpopulations, preferably of which the expression (or activity) level is positively or negatively correlated with the quantitative phenotype ViralLoad(Copies/ml), preferably associated with HIV infection.

TABLE 127

| |
|---|
| ORMDL3, ALDH4A1, IRF7, CYC1, MTHFD1L, C16orf87, WBSCR22, CD81, IFITM3, ETV7, OPTN, SF3B2, CSF1, MON2, C9orf86, HOXA1, CRTC1, FAM199X, SUPT5H, PFDN2, ASB1, GAS6, PPIH, RPS10-NUDT3, NUDT3, RPS10, DVL1, CCDC141, RELA, TNFRSF12A, PXN, DENND3. |

Table 127 in an embodiment provides a signature of monocytes (e.g. cDC), and represents genes/proteins in particular DC subpopulations, preferably of which the expression (or activity) level is positively correlated with the quantitative phenotype ViralLoad(Copies/ml), preferably associated with HIV infection.

TABLE 128

| |
|---|
| METTL23, ERGIC2, SERP1, JRKL, ANTXR2, NFYC, PRICKLE3, IPO11, TMEM128, VNN2, KLHL22, EDEM3, TTC33, CCDC157, ACTR2, NDUFS2, FUCA1, C9orf102, CTAGE5, CTPS2, NDUFS1, ZNF630, KIAA0195, HCCS, PMM2, STXBP3, GPR180, C11orf58, ESD, NFE2L3, CCDC153, PYROXD2, NOP14, EEF1E1, RHBDL2, THRAP3. |

Table 128 in an embodiment provides a signature of monocytes (e.g. cDC), and represents genes/proteins in particular DC subpopulations, preferably of which the expression (or activity) level is negatively correlated with the quantitative phenotype ViralLoad(Copies/ml), preferably associated with HIV infection.

Table 128 in an embodiment provides a signature of monocytes (e.g. cDC), and represents genes/proteins in particular DC subpopulations, preferably of which the expression (or activity) level is negatively correlated with the quantitative phenotype ViralLoad(Copies/ml), preferably associated with HIV infection.

TABLE 129

| |
|---|
| LMNA, HIST1H3A, SPATA2, NFKBIA, CCDC58, BCL2A1, MICA, EFHD2, POU6F2, TUBB6, GADD45B, TNNC2, DNAJA1, EHD4, SEC61A2, C7orf53, TUBB4B, MASTL, ZNF473, PATL1, EIF4A3, DVL1, TNIP2, AHI1, MICB, DLST, IER5, CHMP1B, TFE3, TTC30A, EIF1, INTS6, IRS2, PMFBP1, FKRP, ZFYVE20, RNF115, BRWD1, SLC9A8, CCDC144NL, THOC1, FARP2, PDRG1, ZSCAN18, CASC5, SHISA8, AMY2B, HNRNPA3, RFWD3, RXRB, XKR3, CADM2, FAM103A1, TARDBP, C22orf23, POLRMT, HDAC7, PLEKHM1, GATC, GORAB, TP53I13, STRN4, YLPM1, SEC14L3, HBS1L, MEF2A, GTF2A1L, STON1, STON1-GTF2A1L, ABP1, LENG8, LHFPL3, CLK3, SRSF10, GPATCH2, COL25A1, GSTA1, FSIP2, DCLK1, GABRG2, FRG2C, ADAR, GLI3, GIPC2, AATK, ZCCHC24, SET, CDH2, PODXL, PAQR4, ATP5L, EPB49, GIT2, CCNG1, PARL, EID1, GSS, POTEM, DROSHA, SNX14, HIST1H2BK, TMEM168, SHISA5, TFPI, NDUFB11, CALR, MRPS35, SPCS2, ECH1, HNRNPL, PSMB10, RRBP1, LDHB, DARS, CREB3, CDC42EP4, TMBIM4, HS1BP3, BCL11A, COL4A4, MUDENG, GLB1, SYVN1, ANP32A, PDCD5, C15orf29, ANKIB1, FRG1, TNFAIP8, KDELR3, RASA4, SUCLG1, TMCO1, ARHGEF6, CFDP1, FAM150B, CARD8, C19orf10, ANKS1A, ATP6AP1, TXLNA, PARVG, TUBB4A, USP53, ZBTB7B, ORC5, SUCLG2, TMEM40, EEFSEC, TNK1, NIPSNAP1, UNG, HS2ST1, MTHFD1, MPEG1, HINFP, SLC25A40, HADH, TRADD, ANO10, MAP2K5, VWA5A, AQP11, BBS7, TIMMDC1, ACADM, PAPSS1, F8A3, CDCA3, C2orf88, FAM195A, FUT10, SPINT1, GADD45A, SIRPB1, PPBP, LOC100130301, RWDD2B, MED11, HIST1H2BG, HBB. |
| Preferably LOC100130301 or MED11. |

Table 129 in an embodiment provides a signature of dendritic cells (e.g. cDC), and represents differentially expressed genes in particular DC subpopulations, preferably associated with or derived from high neutralizer phenotype, preferably associated with HIV infection. Preferably differential expression is evaluated compared to cells from non-high neutralizers

TABLE 130

| |
|---|
| LMNA, HIST1H3A, SPATA2, NFKBIA, CCDC58, BCL2A1, MICA, EFHD2, POU6F2, TUBB6, GADD45B, TNNC2, DNAJA1, EHD4, SEC61A2, C7orf53, TUBB4B, MASTL, ZNF473, PATL1, EIF4A3, DVL1, TNIP2, AHI1, MICB, DLST, IER5, CHMP1B, TFE3, TTC30A, EIF1, INTS6, IRS2, PMFBP1, FKRP, ZFYVE20, RNF115, BRWD1, SLC9A8, CCDC144NL, THOC1, FARP2, PDRG1, ZSCAN18, CASC5, SHISA8, AMY2B, HNRNPA3, RFWD3, RXRB, XKR3, CADM2, FAM103A1, TARDBP, C22orf23, POLRMT, HDAC7, PLEKHM1, GATC, GORAB, TP53I13, STRN4, YLPM1, SEC14L3, HBS1L, MEF2A, GTF2A1L, STON1, STON1-GTF2A1L, ABP1, LENG8, LHFPL3, CLK3, SRSF10, GPATCH2, COL25A1, GSTA1, FSIP2, DCLK1, GABRG2, FRG2C, ADAR, GLI3. |
| Preferably LMNA, HIST1H3A, SPATA2, NFKBIA, CCDC58, BCL2A1, MICA, EFHD2, POU6F2, TUBB6, GADD45B, TNNC2. |
| More preferably LMNA. |

Table 130 in an embodiment provides a signature of dendritic cells (e.g. cDC), and represents upregulated genes in particular DC subpopulations, preferably associated with or derived from high neutralizer phenotype, preferably associated with HIV infection. Preferably upregulation is evaluated compared to cells from non-high neutralizers.

TABLE 131

| |
|---|
| GIPC2, AATK, ZCCHC24, SET, CDH2, PODXL, PAQR4, ATP5L, EPB49, GIT2, CCNG1, PARL, EID1, GSS, POTEM, DROSHA, SNX14, HIST1H2BK, TMEM168, SHISA5, TFPI, NDUFB11, CALR, MRPS35, SPCS2, ECH1, HNRNPL, PSMB10, RRBP1, LDHB, DARS, CREB3, CDC42EP4, TMBIM4, HS1BP3, BCL11A, COL4A4, MUDENG, GLB1, SYVN1, ANP32A, PDCD5, C15orf29, ANKIB1, FRG1, TNFAIP8, KDELR3, RASA4, SUCLG1, TMCO1, ARHGEF6, CFDP1, FAM150B, CARD8, C19orf10, ANKS1A, ATP6AP1, TXLNA, |

TABLE 131-continued

| |
|---|
| PARVG, TUBB4A, USP53, ZBTB7B, ORC5, SUCLG2, TMEM40, EEFSEC, TNK1, NIPSNAP1, UNG, HS2ST1, MTHFD1, MPEG1, HINFP, SLC25A40, HADH, TRADD, ANO10, MAP2K5, VWA5A, AQP11, BBS7, TIMMDC1, ACADM, PAPSS1, F8A3, CDCA3, C2orf88, FAM195A, FUT10, SPINT1, GADD45A, SIRPB1, PPBP, LOC100130301, RWDD2B, MED11, HIST1H2BG, HBB. |
| Preferably PAPSS1, F8A3, CDCA3, C2orf88, FAM195A, FUT10, SPINT1, GADD45A, SIRPB1, PPBP, LOC100130301, RWDD2B, MED11, HIST1H2BG, HBB. |
| More preferably LOC100130301 or MED11. |

Table 131 in an embodiment provides a signature of dendritic cells (e.g. cDC), and represents downregulated genes in particular DC subpopulations, preferably associated with or derived from high neutralizer phenotype, preferably associated with HIV infection. Preferably downregulation is evaluated compared to cells from non-high neutralizers.

TABLE 132

| |
|---|
| FAM195A, TNK1, ESCO2, WDR83, KCNA3, TMEM170A, BRD2, TTC30A, PLEKHG2, RNF43. |

Table 132 in an embodiment provides a signature of dendritic cells (e.g. cDC), and represents differentially expressed genes in particular DC subpopulations, preferably associated with or derived from non-neutralizer phenotype, preferably associated with HIV infection. Preferably differential expression is evaluated compared to cells from not non-neutralizers.

TABLE 133

| |
|---|
| FAM195A, TNK1, ESCO2, WDR83, KCNA3. |
| Preferably FAM195A, TNK1, ESCO2, WDR83. |

Table 133 in an embodiment provides a signature of dendritic cells (e.g. cDC), and represents upregulated genes in particular DC subpopulations, preferably associated with or derived from non-neutralizer phenotype, preferably associated with HIV infection. Preferably upregulation is evaluated compared to cells from not non-neutralizers.

TABLE 134

| |
|---|
| TMEM170A, BRD2, TTC30A, PLEKHG2, RNF43. |
| Preferably PLEKHG2, RNF43. |

Table 134 in an embodiment provides a signature of dendritic cells (e.g. cDC), and represents downregulated genes in particular DC subpopulations, preferably associated with or derived from non-neutralizer phenotype, preferably associated with HIV infection. Preferably downregulation is evaluated compared to cells from not non-neutralizers.

TABLE 135

| |
|---|
| TUBB4A, NOA1, PRPS2, RANBP1, EID1, LAS1L, HADHA, ZCCHC6, TSPAN14, RP2, ZEB2, SSH2, GAS7, RAB12, C17orf107, DYNLT1. |
| Preferably EID1, LAS1L, HADHA, ZCCHC6, SSH2, RAB12. |

Table 135 in an embodiment provides a signature of dendritic cells (e.g. cDC), and represents differentially expressed genes in particular DC subpopulations, preferably associated with or derived from elite controller phenotype, preferably associated with HIV infection. Preferably differential expression is evaluated compared to cells from non-elite controllers.

TABLE 136

| |
|---|
| TUBB4A, NOA1, PRPS2, RANBP1, EID1, LAS1L, HADHA. |
| Preferably EID1, LAS1L, HADHA. |
| Or preferably TUBB4A. |

Table 136 in an embodiment provides a signature of dendritic cells (e.g. cDC), and represents upregulated genes in particular DC subpopulations, preferably associated with or derived from elite controller phenotype, preferably associated with HIV infection. Preferably upregulation is evaluated compared to cells from non elite controllers.

TABLE 137

| |
|---|
| ZCCHC6, TSPAN14, RP2, ZEB2, SSH2, GAS7, RAB12, C17orf107, DYNLT1. |
| Preferably ZCCHC6, SSH2, RAB12. |
| Or preferably RAB12, C17orf107, DYNLT1. More preferably RAB12. |

Table 137 in an embodiment provides a signature of dendritic cells (e.g. cDC), and represents downregulated genes in particular DC subpopulations, preferably associated with or derived from elite controller phenotype, preferably associated with HIV infection. Preferably downregulation is evaluated compared to cells from non elite controllers.

TABLE 138

| |
|---|
| UCHL1, CFHR4, CFH, SLC23A2. |

Table 138 in an embodiment provides a signature of dendritic cells (e.g. cDC), and represents differentially expressed genes in particular DC subpopulations, preferably associated with or derived from previous controller phenotype, preferably associated with HIV infection. Preferably differential expression is evaluated compared to cells from non-previous controllers.

TABLE 139

| |
|---|
| UCHL1, CFHR4, CFH. |
| Preferably UCHL1. |

Table 139 in an embodiment provides a signature of dendritic cells (e.g. cDC), and represents upregulated genes in particular DC subpopulations, preferably associated with or derived from previous controller phenotype, preferably associated with HIV infection. Preferably upregulation is evaluated compared to cells from non previous controllers.

TABLE 140

| |
|---|
| SLC23A2. |

Table 140 in an embodiment provides a signature of dendritic cells (e.g. cDC), and represents downregulated genes in particular DC subpopulations, preferably associated with or derived from previous controller phenotype, preferably associated with HIV infection. Preferably downregulation is evaluated compared to cells from non previous controllers.

TABLE 141

| |
|---|
| NR4A2, ZNF331, METRNL, ARL4D, TMEM212, ASTN2, MIPOL1, TBC1D8B, GPR137B, THBS1, C12orf50, RASGEF1B, SIK1, NCKAP5, MORC4, SOX5, REXO1L1, NR4A3, MAB21L3, OPHN1, DMD, BCL3, L2HGDH, IDI1, RGS2, TMEM45A, LPAR2, SPATA2L, ABCC9, ADAMTSL3, KIAA1328, NDRG4, C17orf107, ATP9B, NRIP3, ZNF295, MASTL, SLC9A4, DYNLT1, RAB12, FAM49A, GSG1, SHISA9, XKR9, MYO1C, ATXN1, GFOD1, WEE1, C12orf61, USP36, PRKAR2A, LCLAT1, ODF2L, KRT8, GCM1, SDC3, KLHL18, PELI3, CES3, ZFYVE20, ZNF483, SSH2, EIF1AD, REV1, PRDM2, GNL1, TMEM55B, UNC80, LRTOMT, PEAK1, FGFR1, ZSCAN18, LPIN3, COLQ, RASEF, PPIL6, MAP3K8, SLC25A14, ODF3L1, SYT11, POLN, RBM15, SAT1, AK1, ANKRD28, ITIH5, ZNF639, GAS7, NMNAT1, PUS10, FBXO42, DENND4A, TSPYL2, LOC100293516, PTPN1, C5orf34, MEF2A, CCNT1, GEN1, TP53BP1, ZNF627, TBC1D12, PLEKHA3, UPF2, ANKRD16, MCL1, KLHL29, SIPA1L1, RNF144A, GPR110, KSR1, HBP1, AP1S3, C1orf130, KAT6A, ZNFX1, PRKD3, EBF1, CSNK1E, PHF20, ZEB2, MYO9B, TMPPE, CLN8, GOSR1, KIAA1731, ANKRD12, TNNI1, ARSI, NUP214, ACOT9, TUBD1, CHRM3, ZNF850, MYLK3, PLEKHG1, HERC1, CCDC36, CNTNAP3, KIAA0355, CDYL, PPEF2, KIF1B, ANKRD42, CRAMP1L, AKAP13, DYNC1H1, PDE3B, NPHS1, ATP7A, TLK2, RPS6KL1, CTGF, GEMIN8, RP2, IKZF2, YLPM1, SLC19A3, ZFAND3, HIVEP1, MTSS1, KTI12, APH1A, SIN3A, CXorf38, HIP1R, SAMD4A, RFX7, C3orf19, SEC24B, PEA15, ASXL1, TNPO1, CIC, ITSN2, IFT57, EEF2K, TET2, UBXN7, ZNF184, ATG9A, NFIX, MON1B, SETD5, TMEM170A, RXRB, AFF4, CLASRP, FOXRED2, GDAP2, SLC7A14, KIAA1456, C6orf132, CAND2, ZNF687, RBMXL1, ZDHHC20, PCSK7, ZNF292, ETV5, RHOA, UBQLN1, ZCCHC6, MATN1, ZFC3H1, DEDD, NOTCH4, SF3B4, PRKX, PHACTR4, RAB11FIP4, SUPT6H, ABL2, FBXL2, WAC, SRSF11, ATF6, BRWD3, HNRNPA3, RAD23B, NAPG, C8orf33, USP35, ZNF655, UBR2, TAF1C, SLC9A5, FRMD6, TAOK1, SUGP2, PUM1, ZKSCAN1, KPNB1, PRTG, ULBP1, EFHC2, SEC24A, C3, IL12RB2, GFRA2, SLC2A10, PLEKHA6, CFHR4, CFH, STYK1, ATP6V1G1, HADHA, ACTR2, ATP6AP2, PDE8B, C5orf4, ENOPH1, CRYZL1, DONSON, ATP5O, CYBRD1, NSFL1C, HMGN1, LAS1L, AKAP3, PCBP1, PARL, GHITM, PLEKHG3, CTCF, HDAC2, EIF2S3, CHODL, C17orf49, TRIM44, ERP44, OLA1, ARPC3, VAMP8, F2RL1, YWHAB, ANKS1B, SSR1, TCEB2, PSMB10, ZNHIT1, OCIAD1, DDX49, SNRPD3, NUP93, SAMM50, BICD2, MYD88, LARP4, UBQLNL, RPS6KA4, CEBPD, CTSS, EIF2B1, NSUN5, NCAPD3, ARHGDIB, FAM203A, OR2W3, NARG2, RNF13, SARS2, FBXO17, FARSB, MEF2C, ZNF467, CCDC153, SH3BGRL, EIF3C, EIF3CL, EMB, PPID, OR2L13, ATF7IP2, APRT, BRD3, DHRS7, MRPL45, TNNT1, ACTR8, LRRC47, RANBP1, EID1, OGFOD2, TTC1, GNG5, TMSB10, DNAJC11, ATXN10, FDPS, TAF9B, ZNF781, ANP32A, TCP10L, C21orf59, CACYBP, CSNK2A1, ZFAND1, C7orf58, ETFB, LCMT1, L3MBTL2, NDUFS7, GIMAP8, AP1S2, C1QB, BCKDHA, TMEM91, TRIM35, HN1, TRAP1, PRPS2, CCT7, C16orf53, ARMCX5, TTYH2, DCAF13, ADSL, PDCL3, CHST12, LIMA1, ZNF470, TIMMDC1, CSRP2BP, SF3A3, HMG20B, ZNF792, NR1H3, MPHOSPH9, PCMTD2, SH2D3C, SNX18, ANAPC11, CRYZ, THNSL1, LEAP2, WIBG, PLD3, CCDC121, PECAM1, TPX2, IL7, PAK1IP1, SLC35F2, BBS10, BSCL2, GOT2, SMARCAL1, IMPACT, MGST2, PYCR2, C15orf61, HIST1H1C, TMEM109, ACP2, NOA1, LCP2, TUBB4A, TCEAL1, CES1, LTBP3, BPHL, NUF2, GATM, SLC25A4, MOCS2, MRPS5, CSTF3, LSMD1, ALDH3A2, PPP1R32, ANKMY2, CISD1, DERA, GCET2, FAM114A2, C12orf45, SLC2A5, NDUFS6, BIN2, ECHS1, POLA1, ELP3, RNASE6, DUT, FAM104B, FOLR3, SFXN4, ANKRD5, NT5E, HMGCL, LOC100130301, HSDL2, NUPL2, ZNF391, AHSA1, GCSH, POLR2H, CCR2, IFI35, ALDH1A1, ANXA1, INO80C, ZNF860, GGCT, FUT10, NDUFA8, PAPSS1, ATF1, TUBG1, C6orf115, MRPS34, RAD51C, LCK, AIMP2, TTLL1, HIST1H2AC, CSF1R, S100A4, YAE1D1, ARV1, TFPT, TNFRSF17, FAM177B, HRSP12, FDX1L, GGH. |
| Preferably LPAR2, NRIP3, RAB12, EID1, FDPS, NOA1, ATF1. More preferably LPAR2, RAB12, EID1, FDPS, ATF1. |

Table 141 in an embodiment provides a signature of dendritic cells (e.g. cDC), and represents differentially expressed genes in particular DC subpopulations, preferably associated with or derived from viremic controller phenotype, preferably associated with HIV infection. Preferably differential expression is evaluated compared to cells from non-viremic controllers.

TABLE 142

| |
|---|
| NR4A2, ZNF331, METRNL, ARL4D, TMEM212, ASTN2, MIPOL1, TBC1D8B, GPR137B, THBS1, C12orf50, RASGEF1B, SIK1, NCKAP5, MORC4, SOX5, REXO1L1, NR4A3, MAB21L3, OPHN1, DMD, BCL3, L2HGDH, IDI1, RGS2, TMEM45A, LPAR2, SPATA2L, ABCC9, ADAMTSL3, KIAA1328, NDRG4, C17orf107, ATP9B, NRIP3, ZNF295, MASTL, SLC9A4, DYNLT1, RAB12, FAM49A, GSG1, SHISA9, XKR9, MYO1C, ATXN1, GFOD1, WEE1, C12orf61, USP36, PRKAR2A, LCLAT1, ODF2L, KRT8, GCM1, SDC3, KLHL18, PELI3, CES3, ZFYVE20, ZNF483, SSH2, EIF1AD, REV1, PRDM2, GNL1, TMEM55B, |

TABLE 142-continued

| |
|---|
| UNC80, LRTOMT, PEAK1, FGFR1, ZSCAN18, LPIN3, COLQ, RASEF, PPIL6, MAP3K8, SLC25A14, ODF3L1, SYT11, POLN, RBM15, SAT1, AK1, ANKRD28, ITIH5, ZNF639, GAS7, NMNAT1, PUS10, FBXO42, DENND4A, TSPYL2, LOC100293516, PTPN1, C5orf34, MEF2A, CCNT1, GEN1, TP53BP1, ZNF627, TBC1D12, PLEKHA3, UPF2, ANKRD16, MCL1, KLHL29, SIPA1L1, RNF144A, GPR110, KSR1, HBP1, AP1S3, C1orf130, KAT6A, ZNFX1, PRKD3, EBF1, CSNK1E, PHF20, ZEB2, MYO9B, TMPPE, CLN8, GOSR1, KIAA1731, ANKRD12, TNNI1, ARSI, NUP214, ACOT9, TUBD1, CHRM3, ZNF850, MYLK3, PLEKHG1, HERC1, CCDC36, CNTNAP3, KIAA0355, CDYL, PPEF2, KIF1B, ANKRD42, CRAMP1L, AKAP13, DYNC1H1, PDE3B, NPHS1, ATP7A, TLK2, RPS6KL1, CTGF, GEMIN8, RP2, IKZF2, YLPM1, SLC19A3, ZFAND3, HIVEP1, MTSS1, KTI12, APH1A, SIN3A, CXorf38, HIP1R, SAMD4A, RFX7, C3orf19, SEC24B, PEA15, ASXL1, TNPO1, CIC, ITSN2, IFT57, EEF2K, TET2, UBXN7, ZNF184, ATG9A, NFIX, MON1B, SETD5, TMEM170A, RXRB, AFF4, CLASRP, FOXRED2, GDAP2, SLC7A14, KIAA1456, C6orf132, CAND2, ZNF687, RBMXL1, ZDHHC20, PCSK7, ZNF292, ETV5, RHOA, UBQLN1, ZCCHC6, MATN1, ZFC3H1, DEDD, NOTCH4, SF3B4, PRKX, PHACTR4, RAB11FIP4, SUPT6H, ABL2, FBXL2, WAC, SRSF11, ATF6, BRWD3, HNRNPA3, RAD23B, NAPG, C8orf33, USP35, ZNF655, UBR2, TAF1C, SLC9A5, FRMD6, TAOK1, SUGP2, PUM1, ZKSCAN1, KPNB1, PRTG, ULBP1, EFHC2, SEC24A, C3, IL12RB2. |
| Preferably NR4A2, ZNF331, METRNL, ARL4D, TMEM212, ASTN2, MIPOL1, TBC1D8B, GPR137B, THBS1, C12orf50, RASGEF1B, SIK1, NCKAP5, MORC4, SOX5, REXO1L1, NR4A3, MAB21L3, OPHN1, DMD, BCL3, L2HGDH, IDI1, RGS2, TMEM45A, LPAR2, SPATA2L, ABCC9, ADAMTSL3, KIAA1328, NDRG4, C17orf107, ATP9B, NRIP3, ZNF295, MASTL, SLC9A4, DYNLT1, RAB12. |
| More preferably LPAR2, NRIP3, RAB12. |
| Most preferably LPAR2, RAB12. |

derived from viremic controller phenotype, preferably associated with HIV infection. Preferably upregulation is evaluated compared to cells from non viremic controllers.

TABLE 143

| |
|---|
| GFRA2, SLC2A10, PLEKHA6, CFHR4, CFH, STYK1, ATP6V1G1, HADHA, ACTR2, ATP6AP2, PDE8B, C5orf4, ENOPH1, CRYZL1, DONSON, ATP5O, CYBRD1, NSFL1C, HMGN1, LAS1L, AKAP3, PCBP1, PARL, GHITM, PLEKHG3, CTCF, HDAC2, EIF2S3, CHODL, C17orf49, TRIM44, ERP44, OLA1, ARPC3, VAMP8, F2RL1, YWHAB, ANKS1B, SSR1, TCEB2, PSMB10, ZNHIT1, OCIAD1, DDX49, SNRPD3, NUP93, SAMM50, BICD2, MYD88, LARP4, UBQLNL, RPS6KA4, CEBPD, CTSS, EIF2B1, NSUN5, NCAPD3, ARHGDIB, FAM203A, OR2W3, NARG2, RNF13, SARS2, FBXO17, FARSB, MEF2C, ZNF467, CCDC153, SH3BGRL, EIF3C, EIF3CL, EMB, PPID, OR2L13, ATF7IP2, APRT, BRD3, DHRS7, MRPL45, TNNT1, ACTR8, LRRC47, RANBP1, EID1, OGFOD2, TTC1, GNG5, TMSB10, DNAJC11, ATXN10, FDPS, TAF9B, ZNF781, ANP32A, TCP10L, C21orf59, CACYBP, CSNK2A1, ZFAND1, C7orf58, ETFB, LCMT1, L3MBTL2, NDUFS7, GIMAP8, AP1S2, C1QB, BCKDHA, TMEM91, TRIM35, HN1, TRAP1, PRPS2, CCT7, C16orf53, ARMCX5, TTYH2, DCAF13, ADSL, PDCL3, CHST12, LIMA1, ZNF470, TIMMDC1, CSRP2BP, SF3A3, HMG20B, ZNF792, NR1H3, MPHOSPH9, PCMTD2, SH2D3C, SNX18, ANAPC11, CRYZ, THNSL1, LEAP2, WIBG, PLD3, CCDC121, PECAM1, TPX2, IL7, PAK1IP1, SLC35F2, BBS10, BSCL2, GOT2, SMARCAL1, IMPACT, MGST2, PYCR2, C15orf61, HIST1H1C, TMEM109, ACP2, NOA1, LCP2, TUBB4A, TCEAL1, CES1, LTBP3, BPHL, NUF2, GATM, SLC25A4, MOCS2, MRPS5, CSTF3, LSMD1, ALDH3A2, PPP1R32, ANKMY2, CISD1, DERA, GCET2, FAM114A2, C12orf45, SLC2A5, NDUFS6, BIN2, ECHS1, POLA1, ELP3, RNASE6, DUT, FAM104B, FOLR3, SFXN4, ANKRD5, NT5E, HMGCL, LOC100130301, HSDL2, NUPL2, ZNF391, AHSA1, GCSH, POLR2H, CCR2, IFI35, ALDH1A1, ANXA1, INO80C, ZNF860, GGCT, FUT10, NDUFA8, PAPSS1, ATF1, TUBG1, C6orf115, MRPS34, RAD51C, LCK, AIMP2, TTLL1, HIST1H2AC, CSF1R, S100A4, YAE1D1, ARV1, TFPT, TNFRSF17, FAM177B, HRSP12, FDX1L, GGH. |
| Preferably SLC2A5, NDUFS6, BIN2, ECHS1, POLA1, ELP3, RNASE6, DUT, FAM104B, FOLR3, SFXN4, ANKRD5, NT5E, HMGCL, LOC100130301, HSDL2, NUPL2, ZNF391, AHSA1, GCSH, POLR2H, CCR2, IFI35, ALDH1A1, ANXA1, INO80C, ZNF860, GGCT, FUT10, NDUFA8, PAPSS1, ATF1, TUBG1, C6orf115, MRPS34, RAD51C, LCK, AIMP2, TTLL1, HIST1H2AC, CSF1R, S100A4, YAE1D1, ARV1, TFPT, TNFRSF17, FAM177B, HRSP12, FDX1L, GGH. |
| More preferably EID1, FDPS, NOA1, ATF1. More preferably EID1, FDPS, ATF1. |
| Most preferably ATF1. |

Table 143 in an embodiment provides a signature of dendritic cells (e.g. cDC), and represents downregulated genes in particular DC subpopulations, preferably associated with or derived from viremic controller phenotype, preferably associated with HIV infection. Preferably downregulation is evaluated compared to cells from non viremic controllers.

TABLE 144

| |
|---|
| HABP4 |

Table 144 in an embodiment provides a signature of dendritic cells (e.g. cDC), and represents genes/proteins in particular DC subpopulations, preferably of which the expression (or activity) level is positively or negatively correlated with the quantitative phenotype CD4Count(Cells/mm3), preferably associated with HIV infection.

TABLE 145

| |
|---|
| HABP4 |

Table 145 in an embodiment provides a signature of dendritic cells (e.g. cDC), and represents genes/proteins in particular DC subpopulations, preferably of which the expression (or activity) level is positively correlated with the quantitative phenotype CD4Count(Cells/mm3), preferably associated with HIV infection.

TABLE 146

| |
|---|
| TM6SF1 |

Table 146 in an embodiment provides a signature of dendritic cells (e.g. cDC), and represents genes/proteins in particular DC subpopulations, preferably of which the expression (or activity) level is positively or negatively correlated with the quantitative phenotype T follicular helper cell-like defines as CXCR5+PD1+CD4+ T cells, preferably associated with HIV infection.

TABLE 147

| |
|---|
| TM6SF1 |

Table 147 in an embodiment provides a signature of dendritic cells (e.g. cDC), and represents genes/proteins in particular DC subpopulations, preferably of which the expression (or activity) level is negatively correlated with the quantitative phenotype T follicular helper cell-like defines as CXCR5+PD1+CD4+ T cells, preferably associated with HIV infection.

TABLE 148

| |
|---|
| RNF43, LMNA, EFHD2, ZNF473, ST6GALNAC6, TTC30A, GORAB, BCAR3, CIB1, WDR73, GTF2A1L, STON1, STON1-GTF2A1L, TNIP2, SRSF10, PHTF1, SLC9A8, LTN1, TUBB4B, MYO1C, ZFC3H1, MEF2A, BCL2A1, ASXL1, MICAL1, FARP2, RHBDD2, GABRB2, KIF9, TMEM160, MICB, ARMC10, STRN4, LAMP1, PDRG1, HDAC7, SEC61A2, EHD4, NTRK2, SNX11, RFWD3, PLEKHG2, GDPD5, INTS6, EGR1, LTA, ZEB2, CASZ1, GPATCH2, UBE2E1, MFSD5, DLST, SPATA2, CCDC144NL, FAM103A1, LHFPL3, GTF3C4, AHI1, DVL1, HSPA1A, RELB, RRP12, GFOD1, CLDN11, SERPINH1, CASC5, IL28RA, TMEM170A, CLK3, TFE3, KLC2, TUBB2A, ANAPC2, SIPA1L1, LENG8, CR2, SUCLG2, HMG20B, RAP1GDS1, ABCA10, RRBP1, SLC25A45, BRD3, TXLNA, GFM1, CUL4B, NCF1, RASA4, MTHFD1, SNX14, ERBB2, FAM195A, NDUFB11, NT5DC2, POLA1, SLC25A40, TMEM154, EIF2S3, CFDP1, BTK, SKAP2, PARVG, CCDC106, SIRPB1, IGJ, ANP32A, DECR1, MRPS34, GOPC, ROS1, ZGPAT, RNASE6, INTS10, DIS3L2, CYBB, PRPS2, PAPSS1, PQLC2, HADH, SELL, ZBTB7B, TNFSF12-TNFSF13, TNFSF12, TNFSF13, SLC9A9, TUBB4A, GMPPA, TTLL1, CNOT7, ANKIB1, HIST1H2AE, SERBP1, FUT10, GGH, ZNF93, F8A3, ZDHHC2, GADD45A, TPX2, ITGA4, LDHB, PPA1, C14orf159, PSMB10, HIST1H2BG, ATP6AP1, NNT, FRG1, PTGDR, CALR, CDCA3, CARD8, EIF1AY, CNOT3, HIST1H2AC, BCL11A, LOC100130301, HS2ST1, EID1, LIPA, ARHGEF6, CDC6, SET, PPBP, MED11. |

Table 148 in an embodiment provides a signature of dendritic cells (e.g. cDC), and represents genes/proteins in particular DC subpopulations, preferably of which the expression (or activity) level is positively or negatively correlated with the quantitative phenotype HIV-1-specific Neutralizing breadth defined by the proportions of HIV-1 strains tested (n=11) by the plasma of the study patients, preferably associated with HIV infection.

TABLE 149

| |
|---|
| RNF43, LMNA, EFHD2, ZNF473, ST6GALNAC6, TTC30A, GORAB, BCAR3, CIB1, WDR73, GTF2A1L, STON1, STON1-GTF2A1L, TNIP2, SRSF10, PHTF1, SLC9A8, LTN1, TUBB4B, MYO1C, ZFC3H1, MEF2A, BCL2A1, ASXL1, MICAL1, FARP2, RHBDD2, GABRB2, KIF9, TMEM160, MICB, ARMC10, STRN4, LAMP1, PDRG1, HDAC7, SEC61A2, EHD4, NTRK2, SNX11, RFWD3, PLEKHG2, GDPD5, INTS6, EGR1, LTA, ZEB2, CASZ1, GPATCH2, UBE2E1, MFSD5, DLST, SPATA2, CCDC144NL, FAM103A1, LHFPL3, GTF3C4, AHI1, DVL1, HSPA1A, RELB, RRP12, GFOD1, CLDN11, SERPINH1, CASC5, IL28RA, TMEM170A, CLK3, TFE3, KLC2, TUBB2A, ANAPC2, SIPA1L1, LENG8. |

Table 149 in an embodiment provides a signature of dendritic cells (e.g. cDC), and represents genes/proteins in particular DC subpopulations, preferably of which the expression (or activity) level is positively correlated with the quantitative phenotype HIV-1-specific Neutralizing breadth defined by the proportions of HIV-1 strains tested (n=11) by the plasma of the study patients, preferably associated with HIV infection.

TABLE 150

| |
|---|
| CR2, SUCLG2, HMG20B, RAP1GDS1, ABCA10, RRBP1, SLC25A45, BRD3, TXLNA, GFM1, CUL4B, NCF1, RASA4, MTHFD1, SNX14, ERBB2, FAM195A, NDUFB11, NT5DC2, POLA1, SLC25A40, TMEM154, EIF2S3, CFDP1, BTK, SKAP2, PARVG, CCDC106, SIRPB1, IGJ, ANP32A, DECR1, MRPS34, GOPC, ROS1, ZGPAT, RNASE6, INTS10, DIS3L2, CYBB, PRPS2, PAPSS1, PQLC2, HADH, SELL, ZBTB7B, TNFSF12-TNFSF13, TNFSF12, TNFSF13, SLC9A9, TUBB4A, GMPPA, TTLL1, CNOT7, ANKIB1, HIST1H2AE, SERBP1, FUT10, GGH, ZNF93, F8A3, ZDHHC2, GADD45A, TPX2, ITGA4, LDHB, PPA1, C14orf159, PSMB10, HIST1H2BG, ATP6AP1, NNT, FRG1, PTGDR, CALR, CDCA3, CARD8, EIF1AY, CNOT3, HIST1H2AC, BCL11A, LOC100130301, HS2ST1, EID1, LIPA, ARHGEF6, CDC6, SET, PPBP, MED11. |

Table 150 in an embodiment provides a signature of dendritic cells (e.g. cDC), and represents genes/proteins in particular DC subpopulations, preferably of which the expression (or activity) level is negatively correlated with the quantitative phenotype HIV-1-specific Neutralizing breadth defined by the proportions of HIV-1 strains tested (n=11) by the plasma of the study patients, preferably associated with HIV infection.

TABLE 151

| |
|---|
| RRAGB, TNPO3, TRIM68, PASK, BAIAP2L1, SERPINF1, UAP1L1, BOD1, ZNF85, C2orf42, RAB11FIP2, BCL2, RPA1, CAD, C16orf45, CELF6, FBXO9, IFT80, NCAPD3, CCDC78, SLC4A2, SNX15, NOMO1, HDAC6, CES4A, TMEM104, CRELD1, RIC8B, CNDP2, C15orf39. |

Table 151 in an embodiment provides a signature of dendritic cells (e.g. cDC), and represents genes/proteins in particular DC subpopulations, preferably of which the expression (or activity) level is positively or negatively correlated with the quantitative phenotype CD3− CD19+ CD38− CD27+ resting memory B cells (RestingMemory), preferably associated with HIV infection.

TABLE 152

| |
|---|
| RRAGB, TNPO3, TRIM68, PASK, SERPINF1, ZNF85, C2orf42, BCL2, RPA1, CAD, C16orf45, CELF6, FBXO9, IFT80, NCAPD3, CCDC78, SLC4A2, SNX15, HDAC6, CES4A, CRELD1, RIC8B, CNDP2. |

Table 152 in an embodiment provides a signature of dendritic cells (e.g. cDC), and represents genes/proteins in particular DC subpopulations, preferably of which the expression (or activity) level is positively correlated with the quantitative phenotype CD3− CD19+ CD38− CD27+ resting memory B cells (RestingMemory), preferably associated with HIV infection.

TABLE 153

| |
|---|
| C15orf39, TMEM104, NOMO1, RAB11FIP2, BOD1, UAP1L1, BAIAP2L1. |

Table 153 in an embodiment provides a signature of dendritic cells (e.g. cDC), and represents genes/proteins in particular DC subpopulations, preferably of which the expression (or activity) level is negatively correlated with the quantitative phenotype CD3− CD19+ CD38− CD27+ resting memory B cells (RestingMemory), preferably associated with HIV infection.

TABLE 154

| |
|---|
| UAP1L1, SERPINF1. |

Table 154 in an embodiment provides a signature of dendritic cells (e.g. cDC), and represents genes/proteins in particular DC subpopulations, preferably of which the expression (or activity) level is positively or negatively correlated with the quantitative phenotype CD3− CD19+ CD38Hi CD27− Transitional B cells (Transitional), preferably associated with HIV infection.

TABLE 155

| |
|---|
| UAP1L1 |

Table 155 in an embodiment provides a signature of dendritic cells (e.g. cDC), and represents genes/proteins in particular DC subpopulations, preferably of which the expression (or activity) level is positively correlated with the quantitative phenotype CD3− CD19+ CD38Hi CD27− Transitional B cells (Transitional), preferably associated with HIV infection.

TABLE 156

| |
|---|
| SERPINF1 |

Table 156 in an embodiment provides a signature of dendritic cells (e.g. cDC), and represents genes/proteins in particular DC subpopulations, preferably of which the expression (or activity) level is negatively correlated with the quantitative phenotype CD3− CD19+ CD38Hi CD27− Transitional B cells (Transitional), preferably associated with HIV infection.

Tables 1-156 associate in certain embodiments particular gene signatures with particular cell (sub)types or (sub) populations. The gene signatures and cell types/cell (sub) populations may be used in the various methods and compositions according to the invention are discussed herein.

Platforms for Profiling Single Cells

Cells may be considered processing units. Core constituents include skin cells, such as fibroblasts, adipocytes and epithelial cells; immune cells such as megakaryocytes, dendritic cells and T cells: brain cells such as neurons, ependymal cells and astrocytes and muscle cells such as smooth muscle, skeletal muscle and cardiac muscle. However, grouped cells are not identical (see, e.g., M D Slack et al. PNAS 105, (2008) and P. Dalerba et al. Nat. Biotech. 29, (2011)) and differences can underlie unique behaviors (see, e.g., A A Cohen et al. Science, 322 (2008), S Tay et al. Nature 466, (2010) and O. Feinerman et al. Mol. Sys. Bio. 437, (2010)).

Four fundamental questions may be asked: 1. How do cells respond to change? 2. Which differences influence those responses? 3. When is variability mitigated and when is it leveraged? 4. How does heterogeneity affect the interactions between functionally different cells? To address these questions, one must be able to precisely measure and manipulate large numbers of single mammalian cells in parallel.

For developing new platforms, Applicants leverage nano- and micro-fabrication to develop new platforms for thoroughly and controllably profiling single cells.

Conventional methods for studying single cells include optical microscopy and flow/mass cytometry. With optical microscopy, temporal and spatial information may be obtained, however there is limited depth due to spectral overlap between fluorophores. With flow/mass cytometry (see, e.g., S. C. Bendall et al., Single-Cell Mass Cytometry of Differential Immune and Drug Responses Across a Human Hematopoietic Continuum. *Science* 332, 677-678 (2011)), one can profile many observables (such as 6-10 for flow cytometry and 34+ for mass cytometry) and it is easy to achieve a large number of statistics. However, no spatial information may be obtained and it is extremely difficult to follow the same cell overtime.

Intercellular signaling is a compounding variable. Controlling a cellular microenvironment may be done by any device or microdevice—such as reverse emulsions, microwells and microfluidics—that can define and maintain a constant, known the extracellular milieu.

The present invention also involves utilizing nano- and micro-technology to complement current single cell studies. Using microinstructions, Applicants can restrain single cells or their components at concentrations similar to 10 million cells/ml.

Traditional population measurements involve lots of starting material and enable deep profiling of a particular molecular species. For instance, normally, upon activation, a naïve T cell will differentiate into one of several, functionally distinct T helper cell sub-types, depending upon the cytokine environment—some of these promote immune responses, whereas others 'shut down' immune activity. Each individual T helper also secretes lineage-dependent cytokines that can influence its own actions, as well as those of its peers. The correct balance between the sub-types is critical to normal immune function, and defects in the guiding molecular circuits can lead to autoimmune disorders, such as Multiple Sclerosis and Psoriasis, and allergies. Studying cellular decision making in populations of T cells on a single cell basis will reveal fundamental principles underlying cellular diversity, aid in developing diagnostics and therapeutic strategies for immune disorders, and provide a paradigm for similar studies in other mammalian cells.

To decouple single T cells from themselves and their peers, Applicants fabricate ordered capture pads for restraining cells during rapid solution perfusion. This enables examination of how cellular responses depend upon component heterogeneity in the absence of compounding external factors. By systematically controlling the levels of different cytokines in the perfusion media, Applicants also investigate how extracellular signaling affects intracellular circuits. Importantly, Applicants integrate optical and microfluidic controls so that optical interrogation and transcriptome analysis can be performed on the same cell.

Questions for TLR sensing in innate immune DCS include What are the functional subpopulations of DCs? How well do the ensemble network models describe individual DC behaviors? How is the population response encoded? Do different cells contribute different portions? What is the role of autocrine and paracrine signaling?

Questions in naïve T cell differential include What are the key cellular components? How uniform are conventional polarizing stimuli? How important is local cellular microenvironment? What roles do different cytokines and their timing play? How does intercellular communication normally affect the process? Do certain cells respond first and influence others? How important is autocrine signaling?

HIV

In one embodiment, the present invention relates to innate immunity against a pathogen HIV-1 and immune cells, such as functional cDC maturation, at the single-cell level analyzed by for example, RNAseq. Applicants identified a highly functional cDC subset present in EC that might provide critical information for future clinical approaches to induce highly-effective T cell responses in a larger number of patients and individuals.

B Cells/Monocytes

An objective of the B cell study was to identify patterns of differential expression (DE) between an elite controller and a non-neutralizer in cells tetramer-sorted for HIV protein (gp140) and non-sorted samples.

Expression study steps at the population level include a DE-analysis which involves projection (all genes) and a direct comparison (gene-by-gene). Expression study steps at the cell level involves clustering and DE-analysis.

Populations

One embodiment of the present invention is aimed at finding DE genes associated with neutralizing antibody (NA) breadth. NA Breadth has been defined as an integer in the phenotyping, and this integer has changed since the original phenotyping.

One embodiment of the invention involves identifying signatures of HIV-1 specific broadly neutralizing antibody (bnAb) ontogeny using a systems biology approach, specifically identification of leukocellular subset-specific signatures defining HIV-1 controllers with and without HIV-1-specific neutralizing breadth, identification of signatures during pre-infection or early infection that prospectively predict the development of neutralizing breadth during the ensuing disease process and generation of a comprehensive multidimensional database integrating all clinical, transcriptional, epigenetic and functional immunologic data.

Single-Cell RNAseq Analysis

One problem with RNA-seq analysis of bulk cell populations is that cell heterogeneity may confound results. Applicants therefore have started to use single-cell RNA-seq assays for further investigation of dendritic cells. In initial experiments LPS-stimulated bone marrow derived dendritic cells (BMDCs) were examined. While the gene expression levels of population replicates were tightly correlated with one another, there were substantial differences in gene expression between individual cells.

When Applicants compared dendritic cells with and without exposure to HIV on the population level, Applicants identify 26 genes that are differentially expressed between those two conditions. However, cells exposed to HIV could be classified in three different groups: Two groups that were grossly different from gene expression patterns from HIV-unexposed cells, and one group that appear to have transcriptional signatures similar to HIV-1 unexposed cells. This technology show single-cell RNA-seq of DC is technically possible, and allows to delineate distinct classes of DC with altered gene expression patterns. Applicants use this methodological approach in the future to better understand gene expression patterns associated with the development of neutralizing breadth.

Determining Genetic Interactions

In one aspect, the invention provides a method for determining genetic interactions. This method involves causing a set of P genetic perturbations in cells, wherein the method may comprise: determining, based upon random sampling, a subset of π genetic perturbations from the set of P genetic perturbations; performing said subset of π genetic perturbations in a population of cells; performing single-cell molecular profiling of the population of genetically perturbed cells of step; inferring single-cell molecular profiles for the set of P genetic perturbations in cells.

The perturbation methods as discussed herein may also be used to validate particular gene signatures or specific immunomodulators, such as for instance to identify relevant genes or pathways which are involved to obtain a particular gene signature, immune responder phenotype, or particular immune cell (sub)population, or cell state.

The population of cells with a plurality of genomic sequence or perturbation conditions involves a plurality of cells and perturbations to be tested and measurements sampled to obtain meaningful data and to infer appropriate circuits. The number of genes perturbed, and how many are perturbed simultaneously (the order of the perturbation, pairs, triplets, etc.) varies. In a tissue with n cell types, the rarest present in m %, how many cells X do you need to sequence so that you have at least Y of the rarest subtype.

For example, ~500 cells ensures ≥95% chance of including ≥10 of each type, based on the following calculation. Assume the most conservative scenario that of M cell subtypes (for example, 12), all but one having the lowest predicted proportion (for example, $p_{min}$=5%). Assuming that the Central Limit Theorem holds (a reasonable assumption when solving to detect at least 10 cells of each type) the number of cells of each type i, termed $T_i$, will distribute as $E[T_i]=N*p_{min}$, $STDV[T_i]=(N*p_{min}*(1-p_{min}))$. The minimal N (total number of cells to profile) can be solved such that all (m−1) subtypes have at least n cells (the last, majority, subtype easily clears this threshold since its proportion is much higher). Applicants confirmed with simulation that the strategy conservatively holds in practice even for n<10, and take a margin of additional (conservative) error, to allow for subsequent failed RNA-Seq experiments (<20-30%, depending on protocol).

Modelling Genetic Interactions

The method of the invention may be used for determining genetic interactions, including modelling and/or analyzing such interactions. Such genetic interactions form part of cellular circuitry, in that the interactions reflect connections of components within one or more cellular pathways. Such pathways may be intracellular pathways or intercellular pathways.

In some embodiments, the method of the invention may further comprise determining genetic interactions.

In some embodiments, the method of the invention may further comprise confirming genetic interactions with additional genetic manipulations.

The method may further comprise a validation step, wherein additional manipulations are performed in order to confirm previously identified genetic interactions. Such validation step may include in vivo or in vitro experiments, such as gene inactivation, gene deletion, gene activation or overexpression, and combinations thereof. Such genetic manipulations may be performed with any genetic tool available in the art, comprising but not limited to RNAi, CRISPR-Cas based gene editing, nucleic acid transfection, etc.

Genetic Perturbations

In one aspect, said set of P genetic perturbations or said subset of π genetic perturbations may comprise single-order genetic perturbations. Within the meaning of the present invention, single-order genetic perturbation means that a given cell undergoes a single genetic perturbation (one perturbation per cell).

In one aspect, said set of P genetic perturbations or said subset of π genetic perturbations may comprise combinatorial genetic perturbations. Within the meaning of the present invention, combinatorial or higher-order genetic perturbation means that a given cell undergoes a combination of k single-order genetic perturbations (k perturbations per cell), with k>1. In some embodiments, k is an integer ranging from 2 to 15. In some embodiments, k=2, 3, 4, 5, 6, 7, 8, 9 or 10.

Within the meaning of the present invention, said genetic perturbation may comprise gene knock-down (gene repression or gene inactivation), gene knock-out (gene deletion), gene activation, gene insertion, or regulatory element deletion.

Combinations of different types of genetic perturbations are also envisioned within the meaning of the present invention. For example, a combination of genetic perturbations may comprise a knock-down for a first gene, combined to an activation of a second gene, etc.

In one aspect, said set of P genetic perturbations or said subset of 71 genetic perturbations may comprise genome-wide perturbations. Genome-wide perturbations are genetic perturbations that affect loci across the entire genome. Genome-wide perturbation may include single perturbations of >100, >200, >500, >1,000, >2,500, >5,000, >10,000, >15,000 or >20,000 single genomic loci. The present invention encompasses k-order combinations of genome-wide perturbation.

In some embodiments, the method may comprise determining k-order genetic interactions.

In some embodiments, said set of P genetic perturbations may comprise combinatorial genetic perturbations, such as k-order combinations of single-order genetic perturbations, wherein k is an integer ranging from 2 to 15, and step (e) may comprise determining j-order genetic interactions, with j<k. Such embodiments rely on sampling higher-order interactions in order to more efficiently infer lower order ones. Given a limited number of possible assays, one is more powered to determine lower order interactions (e.g., 2-, 3-way) from measuring higher order interactions (e.g., 5-way) than from allotting all assays to the lower order, because any higher order interaction carries some information about all interaction terms up to that order (e.g., in compressed sensing, it informs in convolved form on additional Fourier coefficients). Thus, even if most interactions are low order (2- or 3-way) these embodiments are more powered to detect them.

CRISPR-Cas Systems

In some embodiments, RNAi- or CRISPR-Cas-based perturbation may be performed. Said perturbation may be performed (e.g. "delivered") in an array-format or pool-format. Some embodiments may comprise pooled single or combinatorial CRISPR-Cas-based perturbation with a genome-wide library of sgRNAs, wherein each sgRNA comprises a unique molecular identifier. In some embodiments, a step may comprise pooled combinatorial CRISPR-Cas-based perturbation with a genome-wide library of sgRNAs, wherein each sgRNA comprises a unique molecular identifier and is co-delivered with a reporter mRNA.

CRISPR-Cas systems, including CRISPR-Cas9 systems, as used herein, refer to non-naturally occurring systems derived from bacterial Clustered Regularly Interspaced Short Palindromic Repeats loci. These systems generally comprise an enzyme (Cas protein, such as Cas9 protein) and one or more RNAs. Said RNA is a CRISPR RNA and may be an sgRNA. Said RNA and/or said enzyme may be engineered, for example for optimal use in mammalian cells, for optimal delivery therein, for optimal activity therein, for specific uses in gene editing, etc.

sgRNA refers to a CRISPR single-guide RNA. This RNA is a component of a CRISPR-Cas system. The sequence of the sgRNA determines the target sequence for gene editing, knock-down, knock-out, insertion, etc. For genome-wide approaches, it is possible to design and construct suitable sgRNA libraries. Such sgRNAs may be delivered to cells using vector delivery such as viral vector delivery. Combination of CRISPR-Cas-mediated perturbations may be obtained by delivering multiple sgRNAs within a single cell. This may be achieved in pooled format. In the case of sgRNA viral vector delivery, combined perturbation may be obtained by delivering several sgRNA vectors to the same cell. This may also be achieved in pooled format, and number of combined perturbations in a cell then corresponds to the MOI (multiplicity of infection). Using CRISPR-Cas systems, one may generally implement MOI values of up to 10, 12 or 15.

The CRISPR-Cas system may be implemented in order to cause massively combinatorial molecular perturbations (MCMP), including single-order and combinatorial genome-wide genetic perturbations.

CRISPR-Cas-based gene editing allows to perform pooled genome-scale screens with expression readouts in primary cells (A Genome-wide CRISPR Screen in Primary Immune Cells to Dissect Regulatory Networks. Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi: 10.1016/j.cell.2015.06.059. Epub 2015 Jul. 16).

In some embodiments, the present invention involves combinatorial perturbations by way of CRISPR-Cas (such as CRISPR-Cas9) assays. In accordance with the present invention, sampling a far-from-exhaustive number of higher order perturbations, when coupled with complex genomic readouts, may suffice to resolve most non-linear relations. Accordingly, in some aspects, the present invention relies on pooled, combinatorial perturbations with genomic readout into Massively Combinatorial Perturbation Profiling (MCPP).

In some embodiments, the method of the invention may comprise one or more CRISPR-Cas-based assays. Such CRISPR-Cas assays are advantageous for implementing a precise perturbation of genes and their expression levels.

In some embodiments, CRISPR-Cas systems may be used to knockout protein-coding genes by frameshifts (indels). Embodiments include efficient and specific CRISPR-Cas9 mediated knockout (Gilbert, L. A., Horlbeck, M. A., Adamson, B., Villalta, J. E., Chen, Y., Whitehead, E. H., Guimaraes, C., Panning, B., Ploegh, H. L., Bassik, M. C., Qi, L. S., Kampmann, M. & Weissman, J. S. Genome-Scale CRISPR-Mediated Control of Gene Repression and Activation. Cell. 159, 647-661, doi:10.1016/j.cell.2014.09.029 (2014). PMCID:4253859; Ran, F. A., Cong, L., Yan, W. X., Scott, D. A., Gootenberg, J. S., Kriz, A. J., Zetsche, B., Shalem, O., Wu, X., Makarova, K. S., Koonin, E. V., Sharp, P. A. & Zhang, F. In vivo genome editing using *Staphylococcus aureus* Cas9. *Nature.* 520, 186-191, doi:10.1038/nature14299 (2015). PMCID:4393360), including a CRISPR mediated double-nicking to efficiently modify both alleles of a target gene or multiple target loci (Ran, F. A., Hsu, P. D., Lin, C. Y., Gootenberg, J. S., Konermann, S., Trevino, A. E., Scott, D. A., Inoue, A., Matoba, S., Zhang, Y. & Zhang, F. Double nicking by RNA-guided CRISPR Cas9 for enhanced genome editing specificity. *Cell.* 154, 1380-1389, doi:10.1016/j.cell.2013.08.021 (2013). PMCID: 3856256; Wang, H., Yang, H., Shivalila, C. S., Dawlaty, M. M., Cheng, A. W., Zhang, F. & Jaenisch, R. One-step generation of mice carrying mutations in multiple genes by CRISPR-Cas-mediated genome engineering. *Cell.* 153, 910-918, doi:10.1016/j.cell.2013.04.025 (2013). PMCID: 3969854) and implementation of a smaller Cas9 protein for delivery on smaller vectors (Ran, F. A., Cong, L., Yan, W. X., Scott, D. A., Gootenberg, J. S., Kriz, A. J., Zetsche, B., Shalem, O., Wu, X., Makarova, K. S., Koonin, E. V., Sharp, P. A. & Zhang, F. In vivo genome editing using *Staphylococcus aureus* Cas9. *Nature.* 520, 186-191, doi:10.1038/nature14299 (2015). PMCID:4393360).

CRISPR-mediated activation or inactivation (CRISPRa/i) systems may be used to activate or inactivate gene transcription. Briefly, a nuclease-dead (deactivated) Cas9 RNA-guided DNA binding domain (dCas9) (Qi, L. S., Larson, M. H., Gilbert, L. A., Doudna, J. A., Weissman, J. S., Arkin, A. P. & Lim, W. A. Repurposing CRISPR as an RNA-guided platform for sequence-specific control of gene expression. Cell. 152, 1173-1183, doi:10.1016/j.cell.2013.02.022 (2013). PMCID:3664290) tethered to transcriptional repressor domains that promote epigenetic silencing (e.g., KRAB) forms a "CRISPRi" (Gilbert, L. A., Larson, M. H., Morsut, L., Liu, Z., Brar, G. A., Torres, S. E., Stern-Ginossar, N., Brandman, O., Whitehead, E. H., Doudna, J. A., Lim, W. A., Weissman, J. S. & Qi, L. S. CRISPR-mediated modular RNA-guided regulation of transcription in eukaryotes. *Cell.* 154, 442-451, doi:10.1016/j.cell.2013.06.044 (2013). PMCID:3770145; Konermann, S., Brigham, M. D., Trevino, A. E., Hsu, P. D., Heidenreich, M., Cong, L., Platt, R. J., Scott, D. A., Church, G. M. & Zhang, F. Optical control of mammalian endogenous transcription and epigenetic states. *Nature.* 500, 472-476, doi:10.1038/nature12466 (2013). PMCID:3856241) that represses transcription. To use dCas9 as an activator (CRISPRa), a guide RNA may be engineered to carry RNA binding motifs (e.g., MS2) that recruit effector domains fused to RNA-motif binding proteins, increasing transcription (Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O. & Zhang, F. Genome-scale transcriptional activation by an engineered CRISPR-Cas9 complex. *Nature.* 517, 583-588, doi:10.1038/nature14136 (2015). PMCID:4420636).

CRISPR-Cas systems may also be used for the deletion of regulatory elements. To target non-coding elements, pairs of guides may be designed and used to delete regions of a defined size, and tile deletions covering sets of regions in pools. The delivery of two sgRNAs may mediate efficient excision of 500 bp genomic fragments.

CRISPR-Cas systems may also be used for gene editing, e.g. by RNA-templated homologous recombination. Keskin, H., Shen, Y., Huang, F., Patel, M., Yang, T., Ashley, K., Mazin, A. V. & Storici, F. Transcript-RNA-templated DNA recombination and repair. *Nature.* 515, 436-439, doi: 10.1038/nature13682 (2014).

CRISPR transgenic mice may be used to derive 'CRISPR-ready' cells. 'CRISPR-mice' are mice where the mouse germ line is engineered to harbor key elements of a CRISPR system, and cells require only the programmable (sgRNA) element to activate the CRISPR-Cas system. CRISPR mice include Cas9-transgenic mice (Platt, R. J., Chen, S., Zhou, Y., Yim, M. J., Swiech, L., Kempton, H. R., Dahlman, J. E., Parnas, O., Eisenhaure, T. M., Jovanovic, M., Graham, D. B., Jhunjhunwala, S., Heidenreich, M., Xavier, R. J., Langer, R., Anderson, D. G., Hacohen, N., Regev, A., Feng, G., Sharp, P. A. & Zhang, F. CRISPR-Cas9 knockin mice for genome editing and cancer modeling. *Cell.* 159, 440-455, doi:10.1016/j.cell.2014.09.014 (2014). PMCID:4265475; Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3): 675-86. doi: 10.1016/j.cell.2015.06.059. Epub 2015 Jul. 16).

CRISPR-Cas based perturbations, including single order or higher order perturbations, may be implemented in pooled format. The perturbation (screen) may be performed with expression readouts or reporter expression readout (genome-wide reporter-based pooled screens).

CRISPR-Cas functional genomics assays that may be used to cause sets of genetic perturbations are discussed in Shalem O., Sanjana N E., Zhang F. High-throughput functional genomics using CRISPR-Cas9. *Nat Rev Genet.* May; 16(5):299-311. (2015). doi: 10.1038/nrg3899. Epub 2015 Apr. 9.

sgRNA libraries, including genome-wide libraries, may be designed as discussed in Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi: 10.1016/j.cell.2015.06.059. Epub 2015 Jul. 16; Sanjana, N. E., Shalem, O. & Zhang, F. Improved vectors and genome-wide libraries for CRISPR screening. *Nat Methods.* 11, 783-784, doi:10.1038/nmeth.3047 (2014); Shalem, O., Sanjana, N. E., Hartenian, E., Shi, X., Scott, D. A., Mikkelsen, T. S., Heckl, D., Ebert, B. L., Root, D. E., Doench, J. G. & Zhang, F. Genome-scale CRISPR-Cas9 knockout screening in human cells. *Science.* 343, 84-87, doi:10.1126/science.1247005 (2014). PMCID:4089965; Shalem, O., Sanjana, N. E. & Zhang, F. High-throughput functional genomics using CRISPR-Cas9. Nat Rev Genet. 16, 299-311, doi:10.1038/nrg3899 (2015).

A pooled genome-wide screen for CRISPR-mediated KO (knock-out) may be performed as in Shalem, O., Sanjana, N. E., Hartenian, E., Shi, X., Scott, D. A., Mikkelsen, T. S., Heckl, D., Ebert, B. L., Root, D. E., Doench, J. G. & Zhang, F. Genome-scale CRISPR-Cas9 knockout screening in human cells. *Science.* 343, 84-87, doi:10.1126/science.1247005 (2014). PMCID:4089965.

An expression marker-based genome-wide CRISPR screen may be performed as in Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi: 10.1016/j.cell.2015.06.059. Epub 2015 Jul. 16.

A pooled, genome-scale, CRISPRa screen may be performed as in Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O. & Zhang, F. Genome-scale transcriptional activation by an engineered CRISPR-Cas9 complex. *Nature.* 517, 583-588, doi:10.1038/nature14136 (2015). PMCID:4420636.

Pooled combinatorial perturbations may be performed, where the delivered perturbations and impact (molecular profiling) are determined post hoc, in either a conventional readout (e.g., sorting followed by sequencing) or with high-content single cell genomics.

In some embodiment, the CRISPR-Cas screen is performed by co-delivering multiple sgRNA using viral vector delivery (eg, sgRNA encoding vectors at a relatively high MOI) into cells pre-expressing the Cas9 enzyme to obtain as many higher order combinations as possible. For small sets of ~5 genes one may generate a combinatorially complete ascertained set of all 32 perturbations.

To detect which perturbations were co-delivered in pooled bins, several strategies are envisioned: (1) Combining two or more guide barcodes using in situ PCR in PEG hydrogel that restricts the diffusion of double stranded DNA; (2) Split-pool tagging of guide barcodes in hydrogels, such that only guides from the same cell are tagged with the same sequence; (3) FISH of expressed guides for imaging readouts. In each case it is possible to use an error-correction scheme in the barcodes.

To detect which perturbations were co-delivered with a single cell genomics readout, it is possible to report the (combinatorial) perturbation in a manner compatible with the full genomic readout. For example one may use an sgRNA vector that also highly expresses a synthetic polyadenylated RNA reporter of the sgRNA barcode. This RNA will be captured along with the cellular mRNA in the transcriptome profiling, eg scRNA-seq (Drop-Seq, see below), or reported by FISH hybridization, such that the same assay ascertains the sgRNAs and their impact on expression (Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi: 10.1016/j.cell.2015.06.059. Epub 2015 Jul. 16).

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S.

application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 14, PROTECTED GUIDE RNAS (PGRNAS); U.S. application 62/096,708, 24 Dec. 14, PROTECTED GUIDE RNAS (PGRNAS); U.S. application 62/091,462, 12 Dec. 14, DEAD GUIDES FOR CRISPR TRANSCRIPTION FACTORS; U.S. application 62/096,324, 23 Dec. 14, DEAD GUIDES FOR CRISPR TRANSCRIPTION FACTORS; U.S. application 62/091,456, 12 Dec. 14, ESCORTED AND FUNCTIONALIZED GUIDES FOR CRISPR-CAS SYSTEMS; U.S. application 62/091,461, 12 Dec. 14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 14, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 14, RNA-TARGETING SYSTEM; U.S. application 62/096,656, 24 Dec. 14, CRISPR HAVING OR ASSOCIATED WITH DESTABILIZATION DOMAINS; U.S. application 62/096,697, 24 Dec. 14, CRISPR HAVING OR ASSOCIATED WITH AAV; U.S. application 62/098,158, 30 Dec. 14, ENGINEERED CRISPR COMPLEX INSERTIONAL TARGETING SYSTEMS; U.S. application 62/151,052, 22 Apr. 15, CELLULAR TARGETING FOR EXTRACELLULAR EXOSOMAL REPORTING; U.S. application 62/054,490, 24 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 14, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 14, DELIVERY, USE AND THERAPEUTIC APPLICATIONS OF THE CRISPR- CAS SYSTEMS AND COMPOSITIONS IN IMMUNE DISEASES OR DISORDERS; U.S. application 62/055,454, 25 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 14, MULTI-FUNCTIONAL-CRISPR COMPLEXES AND/OR OPTIMIZED ENZYME LINKED FUNCTIONAL-CRISPR COMPLEXES; U.S. application 62/087,475, 4 Dec. 14, FUNCTIONAL SCREENING WITH OPTIMIZED FUNCTIONAL CRISPR-CAS SYSTEMS; U.S. application 62/055,487, 25 Sep. 14, FUNCTIONAL SCREENING WITH OPTIMIZED FUNCTIONAL CRISPR-CAS SYSTEMS; U.S. application 62/087,546, 4 Dec. 14, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 14, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Naturel2466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol*. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) *Nat Biotechnol*. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) *Nat Biotechnol*. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) *Nat Biotechnol*. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91(2015).

Shalem et al., "High-throughput functional genomics using CRISPR-Cas9," *Nature Reviews Genetics* 16, 299-311 (May 2015).

Xu et al., "Sequence determinants of improved CRISPR sgRNA design," *Genome Research* 25, 1147-1157 (August 2015).

Parnas et al., "A Genome-wide CRISPR Screen in Primary Immune Cells to Dissect Regulatory Networks," *Cell* 162, 675-686 (Jul. 30, 2015).

Ramanan et al., CRISPR/Cas9 cleavage of viral DNA efficiently suppresses hepatitis B virus," *Scientific Reports* 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

Zetsche et al., "Cpf1 Is a Single RNA-Guided Endonuclease of a Class 2 CRISPR-Cas System," *Cell* 163, 1-13 (Oct. 22, 2015)

Shmakov et al., "Discovery and Functional Characterization of Diverse Class 2 CRISPR-Cas Systems," *Molecular Cell* 60, 1-13 (Available online Oct. 22, 2015)

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of TLR4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens the understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

Useful in the practice of the instant invention, reference is made to the article entitled BCL11A enhancer dissection by Cas9-mediated in situ saturating mutagenesis. Canver, M.C., Smith, E. C., Sher, F., Pinello, L., Sanjana, N. E., Shalem, O., Chen, D. D., Schupp, P. G., Vinjamur, D. S., Garcia, S. P., Luc, S., Kurita, R., Nakamura, Y., Fujiwara, Y., Maeda, T., Yuan, G., Zhang, F., Orkin, S. H., & Bauer, D. E. DOI:10.1038/nature15521, published online Sep. 16, 2015, the article is herein incorporated by reference and discussed briefly below:

Canver et al. describes novel pooled CRISPR-Cas9 guide RNA libraries to perform in situ saturating mutagenesis of the human and mouse BCL11A erythroid enhancers previously identified as an enhancer associated with fetal hemoglobin (HbF) level and whose mouse ortholog is necessary for erythroid BCL11A expression. This approach revealed critical minimal features and discrete vulnerabilities of these enhancers. Through editing of primary human progenitors and mouse transgenesis, the authors validated the BCL11A erythroid enhancer as a target for HbF reinduction. The authors generated a detailed enhancer map that informs therapeutic genome editing.

Reference is made to Zetsche et al., "Cpf1 Is a Single RNA-Guided Endonuclease of a Class 2 CRISPR-Cas System," Cell 163, 1-13 (Oct. 22, 2015) and Shmakov et al., "Discovery and Functional Characterization of Diverse Class 2 CRISPR-Cas Systems," Molecular Cell 60, 1-13 (Available online Oct. 22, 2015). Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens the understanding of CRISPR-Cas systems and advances their genome editing applications. Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains. Mentino is also made of "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), which relates to dimeric RNA-guided FokI Nucleases that recognize extended sequences and can edit endogenous genes with high efficiencies in human cells. In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30 C, e.g., 20-25 C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention). These and other CRISPR-Cas or CRISPR systems can be used in the practice of the invention.

Other Perturbations

The invention also involves perturbing by subjecting the cell to an increase or decrease in temperature. The temperature may range from about 0° C. to about 100° C., advantageously about 10° C., 15° C., 20° C., 25° C., 30° C., 35° C., 40° C., 45° C., 50° C., 55° C., 60° C., 65° C., 70° C., 75° C., 80° C., 85° C., 90° C., 95° C. or 100° C. In another embodiment, the temperature may be closer to a physiological temperature, e.g., about 30° C., 31° C., 32° C., 33° C., 34° C., 35° C., 36° C., 37° C., 38° C., 39° C. or 40° C.

The invention also involves perturbing by subjecting the cell to a chemical agent. Samples of chemical agents include, but are not limited to, an antibiotic, a small molecule, a hormone, a hormone derivative, a steroid or a steroid derivative.

In one aspect of the invention the perturbing may be with an energy source such as electromagnetic energy or ultrasound. The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 $mW/cm^2$, or more preferably at least 4 $mW/cm^2$. In another embodiment, the component of visible light may have a wavelength in the range of 620-700 nm and is red light.

The invention also involves perturbing by subjecting the cell to a chemical agent and/or temperature is across a gradient. A biomolecular gradient may be formed, for example, as reviewed in Keenan and Folch, Lab Chip. 2008 January; 8(1): doi:10.1039/b711887b. Biomolecule gradients have been shown to play roles in a wide range of biological processes including development, inflammation, wound healing, and cancer metastasis. Elucidation of these phenomena requires the ability to expose cells to biomolecule gradients that are quantifiable, controllable, and mimic those that are present in vivo.

A chemical gradient may be formed without requiring fluid flow (see, e.g., Abhyankar et al., Lab Chip, 2006, 6, 389-393). This device consists of a membrane-covered source region and a large volume sink region connected by a microfluidic channel. The high fluidic resistance of the membrane limits fluid flow caused by pressure differences in the system, but allows diffusive transport of a chemical species through the membrane and into the channel. The large volume sink region at the end of the microfluidic channel helps to maintain spatial and temporal stability of the gradient. The chemical gradient in a 0.5 mm region near the sink region experiences a maximum of 10 percent change between the 6 and 24 h data points. Abhyankar et al., *Lab Chip,* 2006, 6, 389-393 present the theory, design, and characterization of this device and provide an example of neutrophil chemotaxis as proof of concept for future quantitative cell-signaling applications.

In another embodiment, a gradient may also be introduced with nanowires. In this embodiment, the nanowires do not necessarily introduce a gradient but may introduce other things into the system. A generalized platform for introducing a diverse range of biomolecules into living cells in high-throughput could transform how complex cellular processes are probed and analyzed. Shalek et al., PNAS|Feb. 2, 2010 | vol. 107 | no. 5 demonstrate spatially localized, efficient, and universal delivery of biomolecules into immortalized and primary mammalian cells using surface-modified vertical silicon nanowires. The method relies on the ability of the silicon nanowires to penetrate a cell's membrane and subsequently release surface-bound molecules directly into the cell's cytosol, thus allowing highly efficient delivery of biomolecules without chemical modification or viral packaging. This modality enables one to assess the phenotypic consequences of introducing a broad range of biological effectors (DNAs, RNAs, peptides, proteins, and small molecules) into almost any cell type. Shalek et al., PNAS| Feb. 2, 2010 | vol. 107 | no. 5 show that this platform can be used to guide neuronal progenitor growth with small molecules, knock down transcript levels by delivering siRNAs, inhibit apoptosis using peptides, and introduce targeted proteins to specific organelles. Shalek et al., PNAS| Feb. 2, 2010 | vol. 107 | no. 5 further demonstrate codelivery of siRNAs and proteins on a single substrate in a microarray format, highlighting this technology's potential as a robust, monolithic platform for high-throughput, miniaturized bioassays.

A gradient may be established, for example, in a fluidic device, such as a microfluidic device (see, e.g., Tehranirokh et al., BIOMICROFLUIDICS 7, 051502 (2013)). Microfluidic technology allows dynamic cell culture in microperfusion systems to deliver continuous nutrient supplies for long term cell culture. It offers many opportunities to mimic the cell-cell and cell-extracellular matrix interactions of tissues by creating gradient concentrations of biochemical signals such as growth factors, chemokines, and hormones. Other applications of cell cultivation in microfluidic systems include high resolution cell patterning on a modified substrate with adhesive patterns and the reconstruction of complicated tissue architectures. In the review of Tehranirokh et al., BIOMICROFLUIDICS 7, 051502 (2013), recent advances in microfluidic platforms for cell culturing and proliferation, for both simple monolayer (2D) cell seeding processes and 3D configurations as accurate models of in vivo conditions, are examined.

Drop-Sequence Methods ("Drop-Seq")

Cells come in different types, sub-types and activity states, which are classify based on their shape, location, function, or molecular profiles, such as the set of RNAs that they express. RNA profiling is in principle particularly informative, as cells express thousands of different RNAs. Approaches that measure for example the level of every type of RNA have until recently been applied to "homogenized" samples—in which the contents of all the cells are mixed together. Methods to profile the RNA content of tens and hundreds of thousands of individual human cells have been recently developed, including from brain tissues, quickly and inexpensively. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. See, e.g., U.S. 62/048,227 filed Sep. 9, 2014.

Methods of Macosko et al., 2015*, Cell* 161, 1202-1214 and Klein et al., 2015*, Cell* 161, 1187-1201 are contemplated for the present invention.

Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets or microwells. The ability to conduct reactions in microdroplets depends on being able to merge different sample fluids and different microdroplets. See, e.g., US Patent Publication No. 20120219947. See also international patent application serial no. PCT/US2014/058637 for disclosure regarding a microfluidic laboratory on a chip.

Droplet/microwell microfluidics offers significant advantages for performing high-throughput screens and sensitive assays. Droplets allow sample volumes to be significantly reduced, leading to concomitant reductions in cost. Manipulation and measurement at kilohertz speeds enable up to 108 discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

Drop-Sequence methods and apparatus provides a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

The invention provides a method for creating a single-cell sequencing library comprising: merging one uniquely barcoded mRNA capture microbead with a single-cell in an emulsion droplet having a diameter of 75-125 μm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library.

The invention provides a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least two, and optimally more than twelve, such that, in the latter, there are more than 16 million unique barcodes on the surface of each bead in the pool. (See www.ncbi.nlm.nih.gov/pmc/articles/PMC206447).

Generally, the invention provides a method for preparing a large number of beads, particles, microbeads, nanoparticles, or the like with unique nucleic acid barcodes comprising performing polynucleotide synthesis on the surface of the beads in a pool-and-split fashion such that in each cycle of synthesis the beads are split into subsets that are subjected to different chemical reactions; and then repeating this split-pool process in two or more cycles, to produce a combinatorially large number of distinct nucleic acid barcodes. Invention further provides performing a polynucleotide synthesis wherein the synthesis may be any type of synthesis known to one of skill in the art for "building" polynucleotide sequences in a step-wise fashion. Examples include, but are not limited to, reverse direction synthesis with phosphoramidite chemistry or forward direction synthesis with phosphoramidite chemistry. Previous and well-known methods synthesize the oligonucleotides separately then "glue" the entire desired sequence onto the bead enzymatically. Applicants present a complexed bead and a novel process for producing these beads where nucleotides are chemically built onto the bead material in a high-throughput manner. Moreover, Applicants generally describe delivering a "packet" of beads which allows one to deliver millions of sequences into separate compartments and then screen all at once.

The invention further provides an apparatus for creating a single-cell sequencing library via a microfluidic system, comprising: a oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for mRNA capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

A mixture comprising a plurality of microbeads adorned with combinations of the following elements: bead-specific oligonucleotide barcodes created by the discussed methods; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). In an embodiment, the individual oligonucleotide molecules on the surface of any individual microbead contain all three of these elements, and the third element includes both oligo-dT and a primer sequence.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-(vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumaran 151); cyanine dyes; cyanosine; 4',6-diamidino-2-phenylindole (DAPI); 5'5"-dibromopyrogallol-sulfonephthalein (Bromopyrogallol Red); 7-diethylamino-3-(4'-isothiocyanatophenyl)-4-methylcoumarin;

diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride);

4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; TRD 700; IRD 800; La Jolla Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

The invention discussed herein enables high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect single cells or single organelles or single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 pL to 10 nL work as individual reactors. Disclosed embodiments provide $10^4$ to $10^5$ single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as discussed herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module discussed herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as discussed in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispensers. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries of the present invention may be contained within an immiscible oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays discussed herein. Fluids (e.g., aqueous fluids, immiscible oils, etc.) and other surfactants that may be utilized in the droplet libraries of the present invention are discussed in greater detail herein.

The present invention provides an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that 1011 or 1015 different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety.

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioinformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provides an ability to create a library of emulsion droplets on demand with the further capability of manipulating the droplets through the disclosed process(es). Disclosed embodiments may, thereby, provide dynamic tracking of the droplets and create a history of droplet deployment and application in a single cell based environment.

Droplet generation and deployment is produced via a dynamic indexing strategy and in a controlled fashion in accordance with disclosed embodiments of the present invention. Disclosed embodiments of the microfluidic device discussed herein provides the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

Undersampling—a Sampling Based Framework for Genetic Interactions

According to the invention, random sampling may comprise matrix completion, tensor completion, compressed sensing, or kernel learning.

In some aspects, where random sampling comprises matrix completion, tensor completion, or compressed sensing, $\pi$ may be of the order of log P.

The invention relies on a random sampling assumption, e.g. that the combinatorial space is sparse and/or of low rank. This assumption is generic and advantageously does not rely on the pre-determination of a (known) set of genetic interactions. This assumption constrains the range or complexity of models, and thus can be used to restrict sampling size (undersampling). Further, as detailed below, the invention relies on the following:: (1) Given a limited number of assays, if one wishes to infer interactions up to an order j, it is advantageous to randomly sample interactions at a higher order k>j, because higher order perturbations maximize the information that can be recovered; and (2) in such a method, one may use a model that accounts for higher order interactions when analyzing lower order ones. For example, it is possible to aim for each perturbation to target k~5-7 genes at once to estimate/model interactions at lower order j~3-5.

Although some experimental methods open the way to test non-linear interactions by high order combinatorial genetic perturbations, exhaustive combinatorial exploration is intractable for anything but 2- or 3-way interactions for a few genes.

According to the invention, random matrix theory and compressive sensing may be used to re-formulate this as a random sampling problem, developing a new framework from experimental design to model inference, testing and refinement.

To infer combinatorial models from a dramatic undersampling of the full high-order combinatorial space with massively combinatorial molecular perturbations (MCPP), one may rely on random matrix theory, compressive sensing and kernel learning.

According to the invention, it is made possible to model non-linear regulatory functions from genetic manipulations (perturbations).

One may learn models of higher-order genetic interactions from combinatorial perturbations with single cell profiling. Although the learning problem is underdetermined due to combinatorial explosion ($2^m$ possible interaction terms among m genes), it can become tractable in the presence of additional structure, including sparsity and smoothness, that constrains the range or complexity of models. One may thus rely on the following: (1) Given a limited number of assays, if one wishes to infer interactions up to an order j, it is advantageous to randomly sample interactions at a higher order k>j, because higher order perturbations maximize the information that can be recovered; and (2) in such a design, one can use a model that accounts for higher order interactions when analyzing lower order ones. One may for example aim for each perturbation to target k~5-7 genes at once to estimate interactions at j~3-5.

Thus the present invention relies on a learning approach that takes multiplex perturbations at a high order n and a complex readout data (e.g., RNA profile) and infers a model of genetic interactions at a lower order ($m<n$),as well as strategies for experimental design, model testing and refinement.

If one assumes that genetic interactions are low rank, sparse, or both, then the true number of degrees of freedom is small relative to the complete combinatorial expansion, so that one can infer the full nonlinear landscape with a relatively small random sampling of high-order perturbations, without specific knowledge of which genes are likely to interact. Analysis of prior studies supports the sparsity assumption in yeast (for fitness: Costanzo, M., Baryshnikova, A., Bellay, J., Kim, Y., Spear, E. D., Sevier, C. S., Ding, H., Koh, J. L., Toufighi, K., Mostafavi, S., Prinz, J., St Onge, R. P., VanderSluis, B., Makhnevych, T., Vizeacoumar, F. J., Alizadeh, S., Bahr, S., Brost, R. L., Chen, Y., Cokol, M., Deshpande, R., Li, Z., Lin, Z. Y., Liang, W., Marback, M., Paw, J., San Luis, B. J., Shuteriqi, E., Tong, A. H., van Dyk, N., Wallace, I. M., Whitney, J. A., Weirauch, M. T., Zhong, G., Zhu, H., Houry, W. A., Brudno, M., Ragibizadeh, S., Papp, B., Pal, C., Roth, F. P., Giaever, G., Nislow, C., Troyanskaya, O. G., Bussey, H., Bader, G. D., Gingras, A. C., Morris, Q. D., Kim, P. M., Kaiser, C. A., Myers, C. L., Andrews, B. J. & Boone, C. The genetic landscape of a cell. *Science.* 327, 425-431, doi:10.1126/science.1180823 (2010)), and fly (for 11 imaging phenotypes: Laufer, C., Fischer, B., Billmann, M., Huber, W. & Boutros, M. Mapping genetic interactions in human cancer cells with RNAi and multiparametric phenotyping. *Nat Methods.* 10, 427-431, doi:10.1038/nmeth.2436 (2013)), and to the limited tested extent, mammals (for 60 genes: Bassik, M. C., Kampmann, M., Lebbink, R. J., Wang, S., Hein, M. Y., Poser, I., Weibezahn, J., Horlbeck, M. A., Chen, S., Mann, M., Hyman, A. A., Leproust, E. M., McManus, M. T. & Weissman, J. S. A systematic mammalian genetic interaction map reveals pathways underlying ricin susceptibility. Cell. 152, 909-922, doi:10.1016/j.cell.2013.01.030 (2013). PMCID:3652613).

Matrix (Tensor) Completion.

All the values of a matrix (tensor) are filled in using a small collection of sampled entries. Applicants hypothesize that the rank of a tensor of higher-order interactions is a fraction of the number of tested genes which is tested by calculating the rank from a dense sampling of second or third order knockouts from a small collection of genes. If the rank of interactions is limited, then Applicants randomly sample sets of genes to knockout from a larger collection, and fill in the remaining values via nuclear norm regularized least-squares optimization (Candes, E. J. & Plan, Y. Matrix Completion With Noise. *Proceedings of the IEEE.* 98, 925-936, doi:Doi 10.1109/Jproc.2009.2035722 (2010)). Provable guarantees suggest that if the rank, r, is small relative to the number of genes, n, then $m \geq O(n^{6/5} r \log n)$ sampled entries are sufficient. However, since these guarantees assume rough uniformity in the loadings of interaction singular vectors, this assumption is unlikely to hold if the interaction matrix is very sparse. In this case, Applicants perform the same random sampling, and simultaneously regularize over both the nuclear norm and the L1 norm of the matrix (Richard, E., Savalle, P. & Vayatis, N. Estimation of Simultaneously Sparse and Low Rank Matrices. arXiv. doi:arXiv:1206.6474).

Compressed Sensing

Here, instead of working with a tensor of interaction terms, Applicants work with a basis that spans all higher order interactions. Each single quantitative phenotype is a real-valued function $f(g)$ on possible genotypes g (the $2^m$ possible allelic or knockout states), represented as binary strings of length m. Applicants analyze such Boolean functions using Fourier decomposition (O'Donnell, R. *Analysis of boolean functions.* (Cambridge University Press, 2014))

$$f(g) = \sum_{b \in \{0,1\}^m} \hat{f}_b (-1)^{b \cdot g}, \; \hat{f}_b = \frac{1}{2^m} \sum_{g \in \{0,1\}^m} f(g)(-1)^{g \cdot b},$$

$$f(g) = \sum_{b \in \{0,1\}^m} \hat{f}_b (-1)^{b \cdot g}, \; \hat{f}_b = \frac{1}{2^m} \sum_{g \in \{0,1\}^m} f(g)(-1)^{g \cdot b},$$

where f is an orthogonal basis indexed by binary strings b, and each Fourier coefficient $\hat{f}_b$ precisely quantifies the effect of one possible multi-gene interaction. For example with m=2, $\hat{f}_{00}$ is the average phenotype; $\hat{f}_{10}$ is the effect of the first gene KO, marginalized over the genetic background of the second; similarly for $\hat{f}_{01}$; and $\hat{f}_{11}$ quantifies the two-way interaction (the extent to which the double KO phenotype differs from that predicted by the sum of the effects of the single KOs). Applicants hypothesize that such genotype-phenotype maps are approximately sparse in the Fourier basis, such that there is a small number, s, of nonzero Fourier coefficients (not known a priori). With perturbations generated only up to a limited order, Applicants obtain a truncated Fourier model, which is a general linear model: the genetic interactions are in the basis functions (encoded into a design matrix), and the response is linear in the unknown Fourier coefficients. Applicants assume most truncated coefficients are negligible. Assuming that the genotype-phenotype maps are approximately sparse in the Fourier basis, Applicants use Li-penalized regression to learn the coefficients of the map from paired genotype-phenotype observations $g_i$, $f(g_i)$ (with uncertainty or noise in both).

Compressed sensing posits that if Applicants' perturbations are de-coherent under the given basis, then exact recovery is possible with dramatic under-sampling (in the noiseless case) (Candes, E. Compressive sampling. *Proceedings of the International Congress of Mathematicians Madrid*, Aug. 22-30, 2006. 3, 19, doi:10.4171/022 (2006)), such that a sample size n=C s log p will suffice, where s is the number of effectively nonzero coefficients, p is the magnitude of combinatorial expansion and C depends on noise and experimental design (how the $g_i$ are sampled) (Candes, E. Mathematics of sparsity (and few other things). *ICM* 2014 *Proceedings, to appear.* (2014)). By varying the penalization parameter, Applicants learn sparse structures at different levels of thresholding, and find the level below which the data become insufficient to capture the signal (Hastie, T., Friedman, J. & Tibshirani, R. *The elements of statistical learning.* Vol. 2 (Springer, 2009)). Applicants explore using a larger penalization parameter on the higher order interaction coefficients, and, with good estimates of single perturbations, even no penalty on the linear terms, or regressing those out first. If each experiment is a Poisson random sampling of KOs, Applicants expect the measurements to have good de-coherence under the Fourier basis, provided the mean number of KO experiments per gene is not too low. If Applicants' assumptions are correct, a soft phase transition in performance as the number of observations crosses a threshold should be observed. Applicants use a small complete dataset or downsampling of a larger more random dataset, to assess if the appropriate transition is observed.

Kernel Learning

If there is no strict sparsity in the rank or in the coefficients, Applicants build predictive functions of the effects of combinatorial perturbations, using a kernel of experimental similarity. Given m experiments, Applicants define an m x m polynomial kernel, for example, based on the overlap in knockouts between any pair of experiments. Applicants learn a weighted combination of kernel vectors that fits a collection of training data, and use the coefficients to predict the outcome of new experiments. Here, the density of nonlinear interaction terms can be much greater, since Applicants do not directly learn any particular interaction coefficient, but rather a kernelized version of the entire polynomial. Indeed, if the interaction terms are too sparse, kernel learning is unlikely to be successful with under-sampling.

Applicants analyzed 3-way interaction data measured by overexpression of every 3-way combination of 39 miRNAs and a phenotype of drug resistance, and confirmed substantial sparsity in the data. Applicants analyzed the 5-way interactions affecting expression profiles in response to salt in yeast between the MAPK Hog1 (p38 ortholog) and 4 TFs (1, 2, 3, 4, and 5 KO: 32 perturbations). Using a (non-regularized) linear model, Applicants quantified 1- and 2-way interactions, finding diverse non-linearities.

Analyzing a Cell Population at the Single Cell Level

The method according to the invention may comprise a step for single-cell molecular profiling. In some embodiments the step may comprise processing said cell population in order to physically separate cells. In some embodiments the step may comprise single-cell manipulation, e.g. using microfluidics based techniques. In some embodiments the step may comprise reverse emulsion droplet-based single-cell analysis or hydrogel droplet-based single-cell analysis.

The method of the invention may use microfluidics, e.g. to culture cells in specific combinations, control the spatiotemporal signals they receive, and/or trace and sample them as desired.

Molecular Profiling at the Single Cell Level

The method according to the invention may comprise a step for single-cell molecular profiling. This step may involve analyzing biomolecules quantitatively or semi-quantitatively. The biomolecules may include RNA, mRNA, pre-mRNA, proteins, chromatin or DNA. Said analysis may be performed genome-wide. Said analysis may be coupled (dual or sequential analysis of two or more types of biomolecules).

In some embodiments the step may comprise single-cell genomic profiling, single-cell RNA profiling, single-cell DNA profiling, single-cell epigenomic profiling, single-cell protein profiling, or single-cell reporter gene expression profiling. Proteins that may be used to alter genomic and epigenomic state are discussed in Shmakov et al., 2015, Molecular Cell 60, 1-13 and Zetsche et al., 2015, Cell 163, 759-771.

In some embodiments the step may comprise single-cell RNA abundance analysis, single-cell transcriptome analysis, single-cell exome analysis, single-cell transcription rate analysis, or single-cell RNA degradation rate analysis.

In some embodiments the step may comprise single-cell DNA abundance analysis, single-cell DNA methylation profiling, single-cell chromatin profiling, single-cell chromatin accessibility profiling, single-cell histone modification profiling, or single-cell chromatin indexing.

In some embodiments the step may comprise single-cell protein abundance analysis, single-cell post-translational protein modification analysis, or single-cell proteome analysis.

In some embodiments the step may comprise single-cell mRNA reporter analysis, detection or quantification.

In some embodiments the step may comprise single-cell dual molecular profiling, such any combination of two amongst single-cell RNA profiling, single-cell DNA profiling, single-cell protein profiling, mRNA reporter analysis.

The method of the invention may include at the step determining single cell RNA levels. For single cell RNA-Seq (scRNA-Seq), one may use Drop-Seq (Macosko, E. Z., Basu, A., Satija, R., Nemesh, J., Goldman, M., Tirosh, I., Bialas, A. R., Kamitaki, N., Sanes, J. R., Weitz, D. A., Shalek, A. K., Regev, A. & McCarroll, S. A. Highly Parallel Genome-wide Expression Profiling of Individual Cells Using Nanoliter Droplets. Cell. 2015 May 21; 161(5):1202-14. doi: 10.1016/j.cell.2015.05.002. PMCID:4481139) and variants thereof. This technique relies on reverse-emulsion, early barcoding for analyzing $10^4$-$10^6$ cells/experiment at very low cost. Drop-Seq enables to co-encapsulate individual cells with uniquely barcoded mRNA capture beads in reverse emulsion droplets. After lysis and mRNA capture, the emulsion is broken and all beads/cells are processed (RT, library prep) together, deconvolving each cell's profile from bead barcodes. In some embodiments, droplets can compartmentalize hundreds of cells/sec, are stable over time and to heat, and can serve as micro-vessels to add reagents; after RT, barcoded beads are stable and can be sorted or subselected. Sampling noise from shallow read depth is substantially lower than the technical variability between cells (Shalek, A. K., Satija, R., Shuga, J., Trombetta, J. J., Gennert, D., Lu, D., Chen, P., Gertner, R. S., Gaublomme, J. T., Yosef, N., Schwartz, S., Fowler, B., Weaver, S., Wang, J., Wang, X., Ding, R., Raychowdhury, R., Friedman, N., Hacohen, N., Park, H., May, A. P. & Regev, A. Single-cell RNA-seq reveals dynamic paracrine control of cellular variation. *Nature*. 510, 363-369, doi:10.1038/nature13437 (2014). PMCID:4193940.), so one may sufficiently estimate expression with ~100,000 reads per cell for many applications (especially with a 5' or 3'-end protocol, Satija, R., Farrell, J. A., Gennert, D., Schier, A. F. & Regev, A. Spatial reconstruction of single-cell gene expression data. Nature biotechnology. 33, 495-502, doi:10.1038/nbt.3192 (2015)).

Single cell RNA may also be analyzed as discussed in Klein, A. M., Mazutis, L., Akartuna, I., Tallapragada, N., Veres, A., Li, V., Peshkin, L., Weitz, D.A., Kirschner, M. W. Droplet barcoding for single-cell transcriptomics applied to embryonic stem cells. Cell. 2015 May 21; 161(5):1187-201. doi: 10.1016/j.cell.2015.04.044. PMCID: 4441768.

The method of the invention may include determining RNA transcription and degradation rates. One may use RNA metabolically labeled with 4-thiouridine, to measure RNA transcription and degradation rates (Rabani, M., Raychowdhury, R., Jovanovic, M., Rooney, M., Stumpo, D. J., Pauli, A., Hacohen, N., Schier, A. F., Blackshear, P. J., Friedman, N., Amit, I. & Regev, A. High-resolution sequencing and modeling identifies distinct dynamic RNA regulatory strategies. Cell. 159, 1698-1710, doi:10.1016/j.cell.2014.11.015 (2014). PMCID:4272607; Rabani, M., Levin, J. Z., Fan, L., Adiconis, X., Raychowdhury, R., Garber, M., Gnirke, A., Nusbaum, C., Hacohen, N., Friedman, N., Amit, I. & Regev, A. Metabolic labeling of RNA uncovers principles of RNA production and degradation dynamics in mammalian cells. Nature biotechnology. 29, 436-442, doi:10.1038/nbt.1861 (2011). PMCID:3114636).

The method of the invention may include a step of determining DNA methylation. One may apply methods for reduced representation (RRBS), targeted capture, and whole genome bisulfite sequencing of DNA methylation from bulk to ultra-low inputs (Chan, M. M., Smith, Z. D., Egli, D., Regev, A. & Meissner, A. Mouse ooplasm confers context-specific reprogramming capacity. Nature genetics. 44, 978-980, doi:10.1038/ng.2382 (2012). PMCID:3432711; Smith, Z. D., Chan, M. M., Humm, K. C., Karnik, R., Mekhoubad, S., Regev, A., Eggan, K. & Meissner, A. DNA methylation dynamics of the human preimplantation embryo. Nature. 511, 611-615, doi:10.1038/nature13581 (2014). PMCID: 4178976; Smith, Z. D., Chan, M. M., Mikkelsen, T. S., Gu, H., Gnirke, A., Regev, A. & Meissner, A. A unique regulatory phase of DNA methylation in the early mammalian embryo. Nature. 484, 339-344, doi:10.1038/nature10960 (2012). PMCID:3331945) to single cells.

The method of the invention may include a step determining Chromatin accessibility. This may be performed by ATAC-Seq. For massively parallel single cell ATAC-Seq one may implement a droplet-based assay. First, in-tube, one may use Tn5 transposase to fragment chromatin inside isolated intact nuclei and add universal primers at cutting sites. Next, in-drop, one may use a high diversity library of barcoded primers to uniquely tag all DNA that originated from the same single cell. Alternatively, one may perform all steps in drop. One may also use a strategy that relies on split pooled nuclei barcoding in plates (Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. *Science.* 2015 May 22; 348(6237): 910-4. doi: 10.1126/science.aab1601. Epub 2015 May 7). Applicants have optimized key steps in a mixture of human and mouse cells, with specificity that exceeds the initial performance of mRNA Drop-Seq. Applicants have also used a Fluidigm C1 protocol (see https://www.fluidigm.com/products/c1-system) to analyze ~100 single DCs, closely reproducing ensemble measures, high enrichment in TSSs, and nucleosome-like periodicity.

ATAC-seq (assay for transposase-accessible chromatin) identifies regions of open chromatin using a hyperactive prokaryotic Tn5-transposase, which preferentially inserts into accessible chromatin and tags the sites with sequencing adaptors [Pott and Lieb Genome Biology (2015) 16:172 DOI 10.1186/s13059-015-0737-7 and Buenrostro J D, Giresi P G, Zaba L C, Chang H Y, Greenleaf W J. Transposition of native chromatin for fast and sensitive epigenomic profiling of open chromatin, DNA-binding proteins and nucleosome position. Nat Methods. 2013; 10:1213-128]. Two very different approaches were used: one relied on physical isolation of single cells [Buenrostro J D, Wu B, Litzenburger U M, Ruff D, Gonzales M L, Snyder M P, et al. Single-cell chromatin accessibility reveals principles of regulatory variation. Nature. 2015; 523:486-90], and the other avoided single-cell reaction volumes by using a two-step combinatorial indexing strategy [Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4].

In the indexing scheme, Cusanovich et al. [Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4] lysed cells, and 2500 nuclei were placed into each well of a 96-well plate. Transposases loaded with unique adaptors were added to each well, creating 96 pools of approximately 2500 nuclei, each pool with distinct barcodes. Nuclei from all of the transposition reactions were mixed, and using a fluorescence-activated cell sorter (FACS) 15-25 nuclei were deposited into each well of a second 96-well plate. Nuclei in each well of this second plate were lysed, and the DNA was amplified using a primer containing a second barcode. The low number of nuclei per well ensured that about 90% of the resulting barcode combinations were unique to a single cell. This combinatorial indexing strategy enabled the recovery of 500-1500 cells with unique tags per experiment. Overall Cusanovich et al. obtained scATAC-seq data from over 15,000 individual cells from mixtures of GM12878 lymphoblastoid cells with HEK293, HL-60, or mouse Patski cells. The number of reads associated with any single cell was very low, varying from 500 to about 70,000 with a median of fewer than 3000 reads per cell.

Buenrostro et al. [Buenrostro J D, Wu B, Litzenburger U M, Ruff D, Gonzales M L, Snyder M P, et al. Single-cell chromatin accessibility reveals principles of regulatory variation. Nature. 2015; 523:486-90] used a programmable microfluidic device (Cl, Fluidigm) to isolate single cells and perform ATAC-seq on them in nanoliter reaction chambers. Each nanochamber was analyzed under a microscope to ensure that a single viable cell had been captured. This approach is simple and has the significant advantage of a carefully monitored reaction environment for each individual cell, although the throughput was limited to processing 96 cells in parallel. Buenrostro et al. sampled 1632 cells from eight different cell lines, including GM12878, K562, and H1 cells, and obtained an average of 73,000 reads per cell, about 20 times the number of reads per cell obtained using the barcoding strategy.

The method of the invention may include a step of determining histone modifications and protein-DNA interactions. One may apply tools that use genomic barcoding to index chromatin prior to immunoprecipitation to enable multiplexed analysis of limited samples and individual cells in a single reaction. For single-cell chromatin profiling, one may use Drop-ChTP where the chromatin of individual cells is barcoded in droplets. Based on the Drop-Seq technique, one may encapsulate single cells, lyse and MNase-digest chromatin, then fuse a second droplet with barcoded oligos, ligate them to the fragmented chromatin, break the emulsion, add carrier chromatin, and carry out ChIP-Seq. this may be performed using a protocol with split-pool barcoding to collect $10^4$-$10^5$ single cells/assay.

ChIP-sequencing, also known as ChIP-seq, is a method used to analyze protein interactions with DNA which may be used with perturbation. ChIP-seq combines chromatin immunoprecipitation (ChTP) with massively parallel DNA sequencing to identify the binding sites of DNA-associated proteins. It can be used to map global binding sites precisely for any protein of interest. ChIP-seq is used primarily to determine how transcription factors and other chromatin-associated proteins influence phenotype-affecting mechanisms. Determining how proteins interact with DNA to regulate gene expression is for understanding many biological processes and disease states. This epigenetic information is complementary to genotype and expression analysis. ChIP-seq technology is as an alternative to ChIP-chip which requires a hybridization array. Specific DNA sites in direct physical interaction with transcription factors and other proteins can be isolated by chromatin immunoprecipitation. ChIP produces a library of target DNA sites bound to a protein of interest in vivo. Massively parallel sequence analyses are used in conjunction with whole-genome sequence databases to analyze the interaction pattern of any protein with DNA, see, e.g., Johnson D S, Mortazavi A et al. (2007) Genome-wide mapping of in vivo protein-DNA interactions. Science 316: 1497-1502, or the pattern of any epigenetic chromatin modifications. This can be applied to the set of ChIP-able proteins and modifications, such as transcription factors, polymerases and transcriptional machinery, structural proteins, protein modifications, and DNA modifications. See, e.g., "Whole Genome Chromatin IP Sequencing," Illumina, Inc (2010), available at www.illumina.com/Documents/products/datasheets/datasheet chip_sequence.pdf (Chromatin Immunoprecipitation with massively parallel sequencing).

For multiplex analysis of (limited) bulk samples, one may rely on chromatin indexing (MINT-ChIP; iChIP), where MNase-fragmented chromatin is indexed by ligation to a uniquely barcoded adaptor and then pooled and processed in multiplex through all subsequent phases, either with (MINT-ChIP) or without (iChIP: Lara-Astiaso, D., Weiner, A., Lorenzo-Vivas, E., Zaretsky, I., Jaitin, D. A., David, E., Keren-Shaul, H., Mildner, A., Winter, D., Jung, S., Friedman, N. & Amit, I. Immunogenetics. Chromatin state dynamics during blood formation. *Science.* 345, 943-949, doi:10.1126/science.1256271 (2014). PMCID:4412442) carrier chromatin (without adaptors).

The method of the invention may include a step of determining proteins. Recently developed assays (e.g., CyTOF: Bendall, S. C., Simonds, E. F., Qiu, P., Amir el, A. D., Krutzik, P. O., Finck, R., Bruggner, R. V., Melamed, R., Trejo, A., Ornatsky, O. I., Balderas, R. S., Plevritis, S. K., Sachs, K., Pe'er, D., Tanner, S. D. & Nolan, G. P. Single-cell mass cytometry of differential immune and drug responses across a human hematopoietic continuum. *Science.* 332, 687-696, doi:10.1126/science.1198704 (2011). PMCID: 3273988), allow multiplexed, single cell detection of dozens of proteins in millions of cells, but rely on antibodies and cannot yet be combined with DNA readout. Conversely, mass spectrometry (LC-MS/MS) allows quantitative analysis of entire proteomes, but deep analysis requires large amounts of protein/cells. To measure single cell protein levels and post-translational modifications (PTMs), one may use one of three complementary antibody-based assays: (1) standard flow cytometry with a few proteins/PTMs, >$10^6$ single cells; (2) CyTOF (Bendall, S. C., Simonds, E. F., Qiu, P., Amir el, A. D., Krutzik, P. O., Finck, R., Bruggner, R. V., Melamed, R., Trejo, A., Ornatsky, O. I., Balderas, R. S., Plevritis, S. K., Sachs, K., Pe'er, D., Tanner, S. D. & Nolan, G. P. Single-cell mass cytometry of differential immune and drug responses across a human hematopoietic continuum. *Science.* 332, 687-696, doi:10.1126/science.1198704 (2011). PMCID:3273988) (heavy metal labeling with multiplex barcoding; ~30-50 proteins/PTMs, $10^5$-$10^6$ single cells); and (3) novel, highly multiplexed, DNA sequencing-based readouts of protein levels (100s proteins/PTMs; $10^6$ cells). For sequencing based readouts, one may use one of two approaches, geared at detecting hundreds of proteins in single cells: Immuno-Seq (when antibodies can be washed out: Niemeyer, C. M., Adler, M. & Wacker, R. Detecting antigens by quantitative immuno-PCR. *Nat Protoc.* 2, 1918-1930, doi:10.1038/nprot.2007.267 (2007)) and proximity extension assays (PEA, when antibodies cannot be washed away: Hammond, M., Nong, R. Y., Ericsson, O., Pardali, K. & Landegren, U. Profiling cellular protein complexes by proximity ligation with dual tag microarray readout. *PLoS One.* 7, e40405, doi:10.1371/journal.pone.0040405 (2012). PMCID:3393744; Nong, R. Y., Wu, D., Yan, J., Hammond, M., Gu, G. J., Kamali-Moghaddam, M., Landegren, U. & Darmanis, S. Solid-phase proximity ligation assays for individual or parallel protein analyses with readout via real-time PCR or sequencing. *Nat Protoc.* 8, 1234-1248, doi:10.1038/nprot.2013.070 (2013); Stahlberg, A., Thomsen, C., Ruff, D. & Aman, P. Quantitative PCR analysis of DNA, RNAs, and proteins in the same single cell. *Clin Chem.* 58, 1682-1691, doi:10.1373/clinchem.2012.191445 (2012).) These use DNA-sequence based encoding, and are compatible with other genomic readouts (e.g., sgRNA barcodes). DNA-sequence tags can be conjugated to antibodies (Janssen, K. P., Knez, K., Spasic, D. & Lammertyn, J. Nucleic acids for ultra-sensitive protein detection. *Sensors* (Basel). 13, 1353-1384, doi:10.3390/s130101353 (2013). PMCID:3574740), nanobodies (Pardon, E., Laeremans, T., Triest, S., Rasmussen, S. G., Wohlkonig, A., Ruf, A., Muyldermans, S., Hol, W. G., Kobilka, B. K. & Steyaert, J. A general protocol for the generation of Nanobodies for structural biology. *Nat Protoc.* 9, 674-693, doi:10.1038/nprot.2014.039 (2014). PMCID:4297639; Theile, C. S., Witte, M. D., Blom, A. E., Kundrat, L., Ploegh, H. L. & Guimaraes, C. P. Site-specific N-terminal labeling of proteins using sortase-mediated reactions. *Nat Protoc.* 8, 1800-1807, doi:10.1038/nprot.2013.102 (2013). PMCID:3941705) or aptamers (Janssen, K. P., Knez, K., Spasic, D. & Lammertyn, J. Nucleic acids for ultra-sensitive protein detection. *Sensors* (Basel). 13, 1353-1384, doi:10.3390/s130101353 (2013). PMCID:3574740.).

The present invention will be further illustrated in the following Examples which are given for illustration purposes only and are not intended to limit the invention in any way.

EXAMPLES

Example 1: Single-Cell RNA-Seq Identifies a Unique Subset of Conventional Dendritic Cells with Distinct IFN Signature and Superior AntigenHIV-1-Presentioning Properties after Exposure to HIV-1

Introduction

DCs are critical for the priming of effective adaptive immunity against pathogens. In contrast to MDDCs, primary cDC can support HIV-1 replication in vitro and induce cell-intrinsic responses against the virus. Higher susceptibility of cDC from EC to induce innate responses against HIV-1. Such potent cell-intrinsic responses in cDC from EC are caused by sensing of accumulated cytoplasmic HIV-1 DNA. Leads to enhanced maturation and antigen presenting cell function of DC after exposure to HIV-1.

Materials and Methods

Study Participants

HIV-1 controllers who had maintained <2000 copies/ml HIV-1 VL for a median of 5 years (range 2-14) in the absence of antiretroviral therapy; median CD4 T cell counts: 885.5 cells/ml, range 1453-515 cells/ml; n=8 patients, untreated chronic progressors (CP, median VL: 8173 copies/ml, range 24031-643 copies/ml; median CD4 T cell counts: 396.5 cells/ml, range 623-102 cells/ml; n=8 patients), and HIV-1 seronegative healthy persons (Neg, n=7), were recruited for this study. All subjects gave written informed consent and the study was approved by the Institutional Review Board of Massachusetts General Hospital/Partners Healthcare.

Infection and Isolation of cDC for RNAseq Analysis and Functional Assays.

PBMC without prior in vitro culture with activating agents, were infected with GFP-encoding VSV-G pseudotyped HIV-1 virus (MOI=2.4) for 2 hours at 37° C. At 24 and 48 h post-infection CD14− CD11c+ HLADR+ cDC were sorted from total PBMC into 96 well plates at one cell per well for single-cell RNA-seq. In some experiments, bulk cDCs from the same individual were sorted at 6 and 12 h post-infection with HIV-1.

For subsequent functional validation of cDC subsets, viable CD14− CD11c+ HLADR+ cDC were sorted into three subpopulations expressing High, intermediate and Low levels of CD64 and PDL-1.

For additional functional assays and inhibition of innate immune sensing of HIV-1 experiments, total BDCA1$^+$ cDCs were purified from total PBMC by MACS as previously described (Martin-Gayo et al., 2015) using anti-human BDCA-1 Kit and MS and LD columns and/or AutoMACS (Miltenyi Biotec) (purity >90%). In some experiments, magnetically isolated cDCs were treated with HIV-1 alone or in combination with 2 ug/ml of TLR2, TLR3, TLR4, TLR8 ligands.

Flow Cytometry and DC Phenotype

PBMC or isolated cDCs were stained with LIVE/DEAD cell blue viability dye (Invitrogen, Carlsbad, CA) and monoclonal antibodies directed against CD11c (Biolegend), CD14 (BD), HLA-DR, CD64, PDL-1, ICAM1, CD16, SLAMF8 (Biolegend) and subsequently analyzed on a Fortessa cytometer (BD Biosciences, San Jose, CA). For intracellular cytokine staining, cells were treated with a commercial fixation/permeabilization kit (BioLegend) according to the manufacturer's protocol. Data were analyzed with FlowJo software (Tree Star). cDCs were identified from bulk PBMCs as a population of viable CD14− lymphocytes expressing high levels of CD11c and HLA-DR.

Mixed Leukocyte Reaction Assays cDC expressing high, intermediate and low levels of CD64 and PD-L1 were purified by sorting and mixed with allogeneic total peripheral blood T lymphocytes previously stained with 5 μM carboxyfluorescein succinimidyl ester (CFSE; Invitrogen) at a T:DC ratio of 4:1. As a control, T cells were also cultured in the presence of media only or 2.5 mg/ml PHA and 501 U/ml IL-2. After incubation for 6 days, cells were washed, stained with viability dye and anti-CD4 and anti-CD8 antibodies (Biolegend, San Diego, CA), and CFSE dilution on CD4 and CD8 T cell subpopulations was analyzed by flow cytometry using a Fortessa flow cytometer.

siRNA knock down and inhibitory drug assays cDC from were infected with VSV-G pseudotyped HIV-1 after 16 hours, in the absence or the presence of drugs antagonizing either TLR3 (60 nM of CU CPT 4a, R&D), TBK1 (1 uM BX795, Invivogen) activation or HIV-1 retrotranscription (50 nM AZT or 100 nM Efavirenz). Phenotypical analysis was performed at 24 hours p.i. by flow cytometry. Efficiency of siRNA-mediated knockdown was confirmed at the mRNA levels by qPCR.

Whole Transcriptome Amplification

Following sorting, 96-well plates of single cells were whole transcriptome amplified as described in Trombetta et al. Lysed cell samples were cleaned with 2.2× volume AMPure XP SPRI beads (Beckman Coulter). Reverse transcription and PCR were then performed on the samples. For population samples total RNa was isolated using a column (RNeasy plus Micro RNA kit; Qiagen) following manufacturer's instructions. Two L of extracted RNA were added to 8 μL of water and cleaned with 2.2× volume beads. While transcriptome amplification was performed on these samples analogous to the amplification of the single cell samples.

Following whole transcriptome amplification, PCR products were cleaned with 0.9× volume SPRI beads and eluted in water. Concentration of cDNA in the resulting solution was determined using a Qubit 3.0 Fluorimeter (Thermo Fisher) and analyzed using a high sensitivity DNA chip for BioAnalyzer (Agilent).

Library Prep

WTA products were diluted to a concentration of 0.1 to 0.4 ng/μL and tagmented and amplified using Nextera XT DNA Sample preparation reagents (Illumina). Tagmentation was performed according to manufacturer's instructions, modified to use 14 the recommended volume of reagents, extended tagmentation time to 10 minutes and extended PCR time to 60s. PCR primers were ordered form Integrated DNA Technologies. Nextera products were then cleaned twice with at 0.9× volume of SPRI beads and eluted in water. The library was quantified using Qubit and analyzed using a high sensitivity DNA chip. The library was diluted to 2.2 μM and sequenced on a NextSeq 500 (Illumina).

Results

Figure 2A:
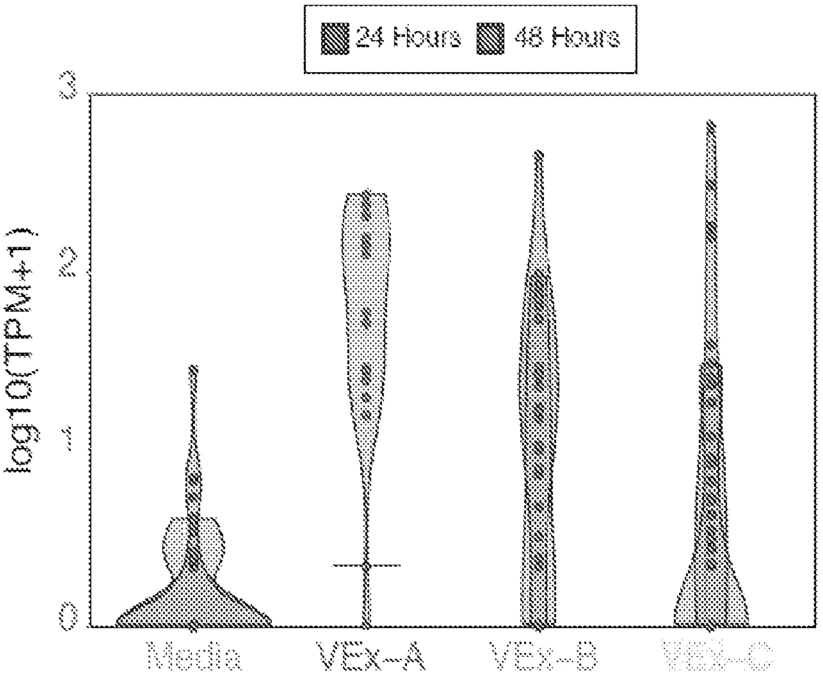
FIG. 2A-2C. (2A) Violin plot of viral TPM in each media control and each VEx subset at 24 and 48 hours. (2B) Alignment of viral reads (grey) from media and VEx samples at 24 and 48 hours to pseudo-typed viral plasmid (bar at top, colored by gene) in Integrated Genomics Viewer. Viral reads align to the plasmid with few mutations. (2C) PCA from 1B colored by mean RNA half-life. High RNA turnover is shown in blue, low turnover in green.
Figure 2B:
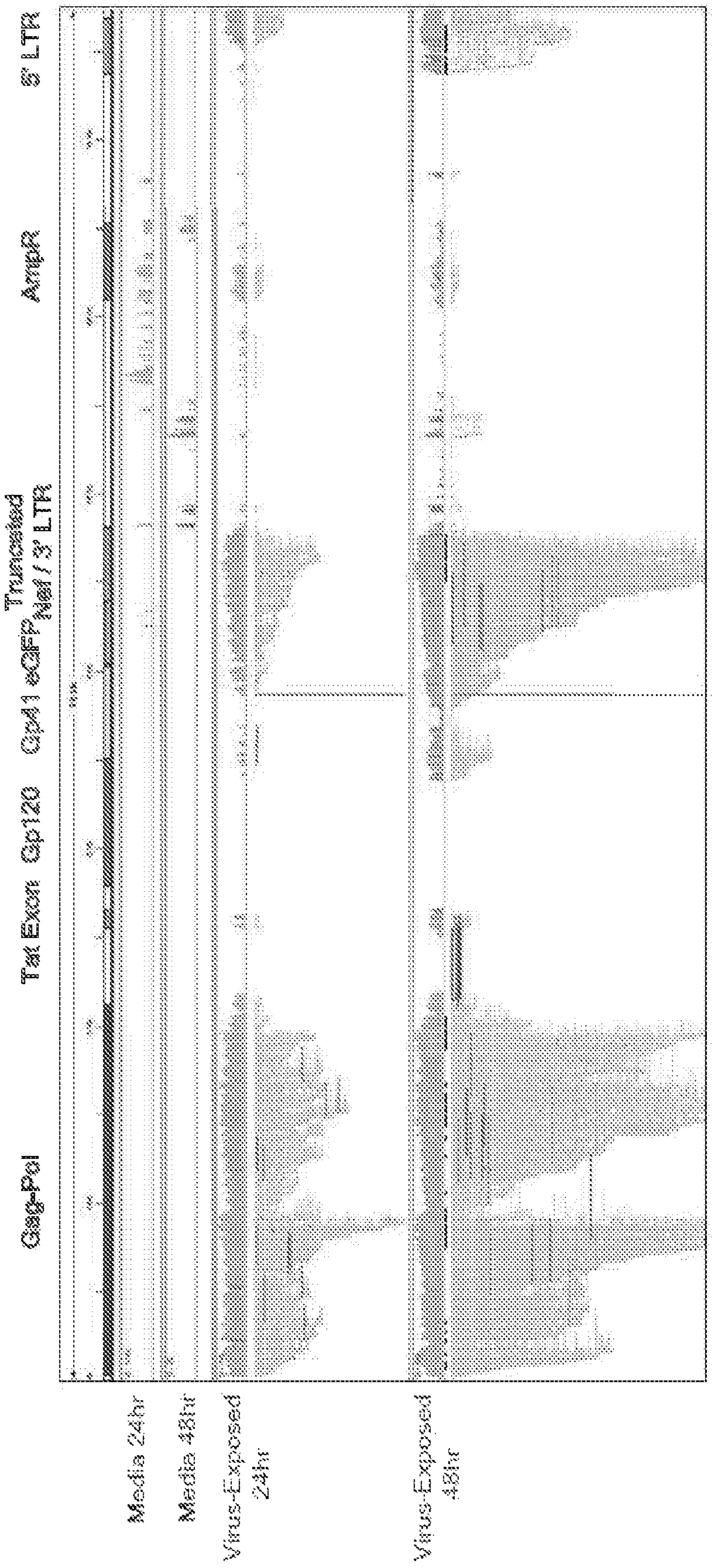
Figure 2C:
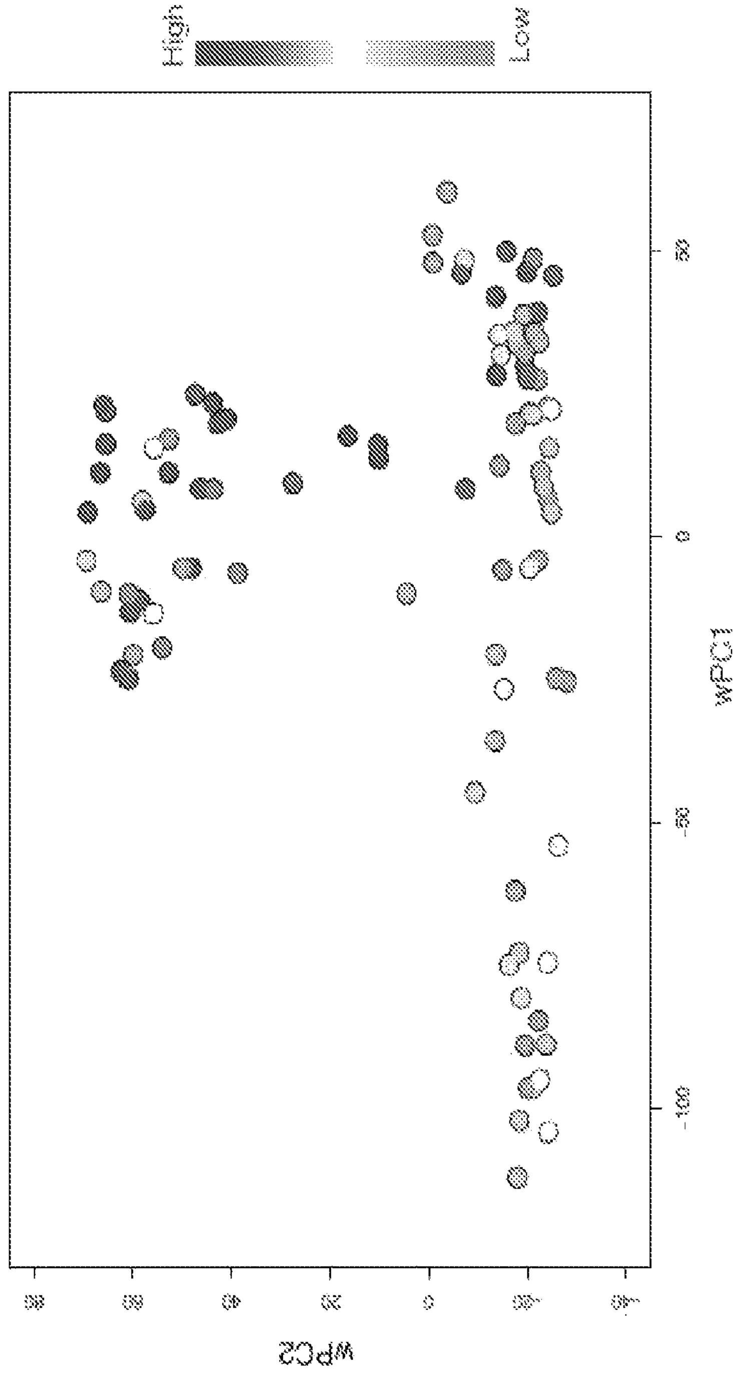
Figure 3A:
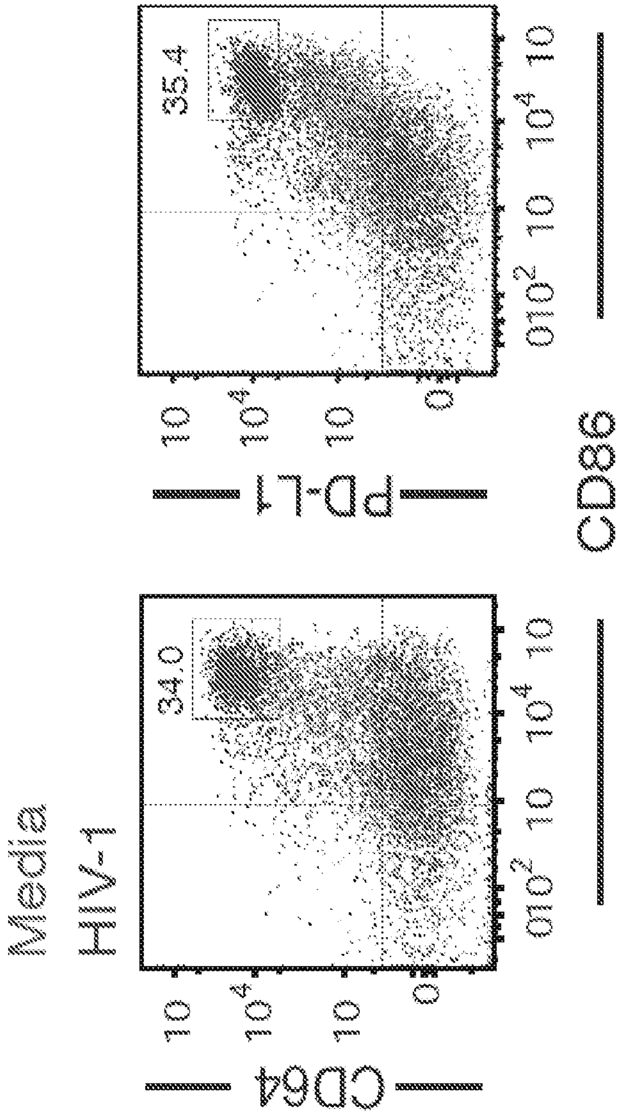
FIG. 3A-3F. (3A) Flow cytometry overlayed dot plots of CD14-PBMCs from the original patient used for Sc-RNA analysis cultured in media (grey) or media and pseudo-typed HIV virus (blue). Flow plots analyze expression of CD64 (y-axis, left panel) and PD-L1 (y-axis, right plots) vs CD86 (x-axis). (3B) Flow cytometry analysis of CD64 vs PD-L1 expression on CD14−, CD11c+, HLADR+ PBMCs defining 3 populations CD64 high, PD-L1 high (blue); CD64 intermediate, PD-L1 intermediate (orange); and CD64 low, PD-L1 low (green) populations. (3C) Spider plot depicting estimated proportions of sorted PD-L1, CD64 high (blue) medium (orange) and low (green) for VEx subset, given exposure (solid line) or control (dashed line). Gene signatures for the PD-L1, CD64 populations were generated from sequencing data on the sorted populations from A. (3D) Concentration of HIV-1 reverse transcripts present on sorted $CD64^{Hi}$ $PD\text{-}L1^{Hi}$ (Hi; blue), CD64Int PD-L1Int (Int; orange) and $CD64^{Lo}$ $PD\text{-}L1^{Lo}$(Lo; green) at 24 h after exposure to VSV-G pseudotyped HIV-1 virus. (3E) Representative flow cytometry histograms showing overlay of CFSE dilution of CD4 (left panel) and CD8 (right panel) cultured for 7 days in the presence of sorted PD-L1, CD64 high (blue), CD64Int PD-L1Int (orange), and $CD64^{Lo}$ $PD\text{-}L1^{Lo}$ (green) to allogeneic HIV-1 exposed cDCs. Numbers on histograms represent percentage of CFSELo proliferating cells. (3F) Proportion of proliferating CD4 (left) and CD8 (right) from n=5 patients cultured with sorted allogeneic Hi, Int and Lo HIV-1 exposed cDC populations defined as in (E). PD-L1, CD64 high populations have significantly greater ability to stimulate proliferation in both $CD4^+$ and $CD8^+$ T cells. **=$p<0.05$ Kruskal Wallis and post hoc dunn's test #=$p<0.05$ Wilcoxon matched-pairs signed rank test.
Figure 3B:
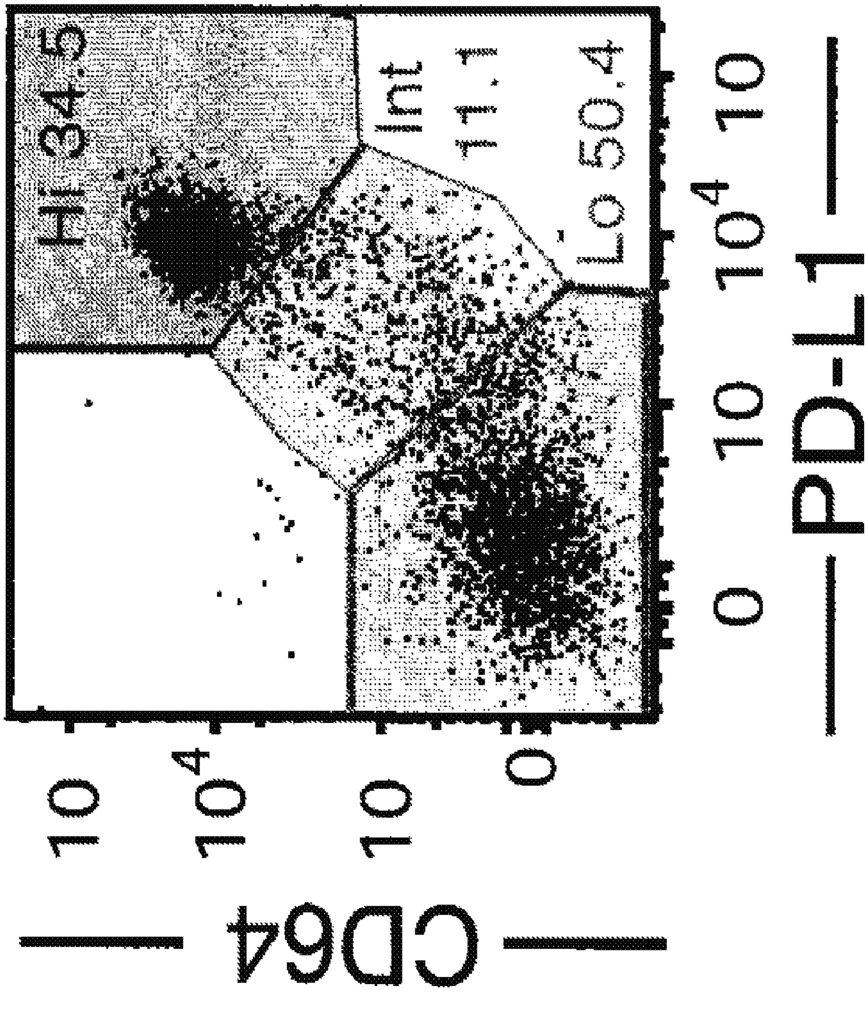
Figure 3C:
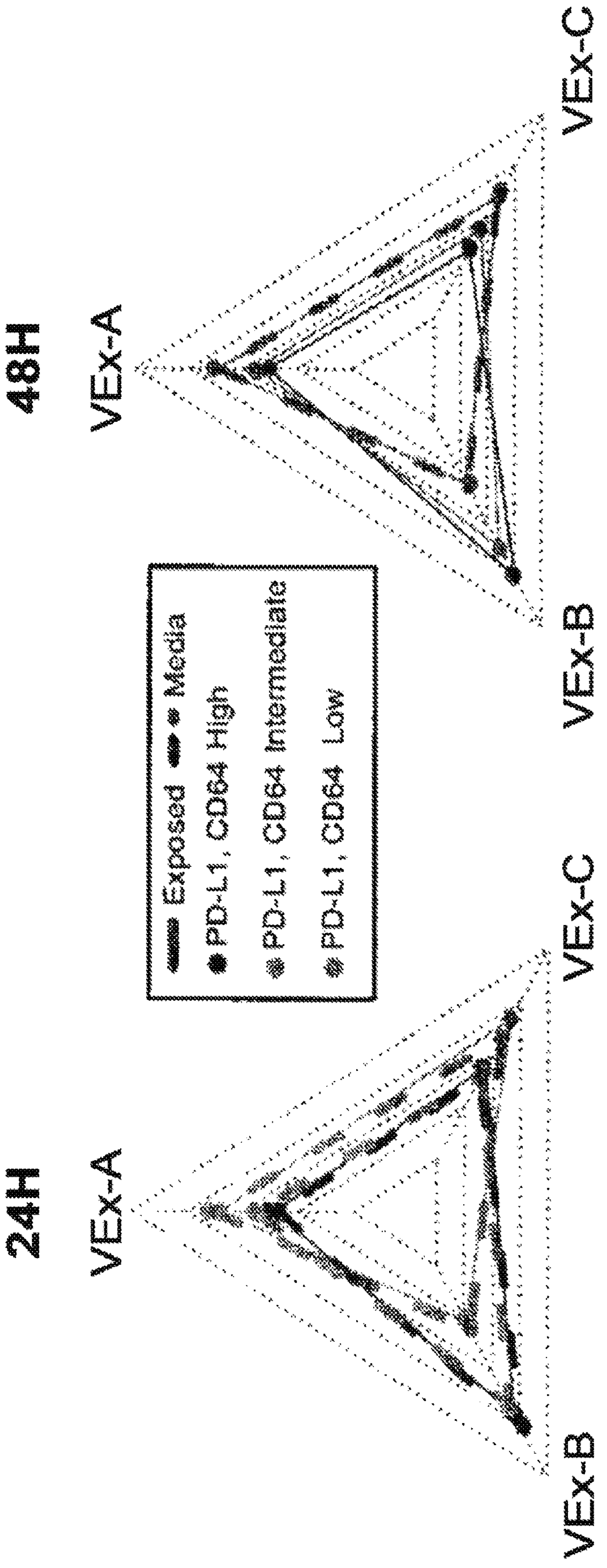
Figure 3D:
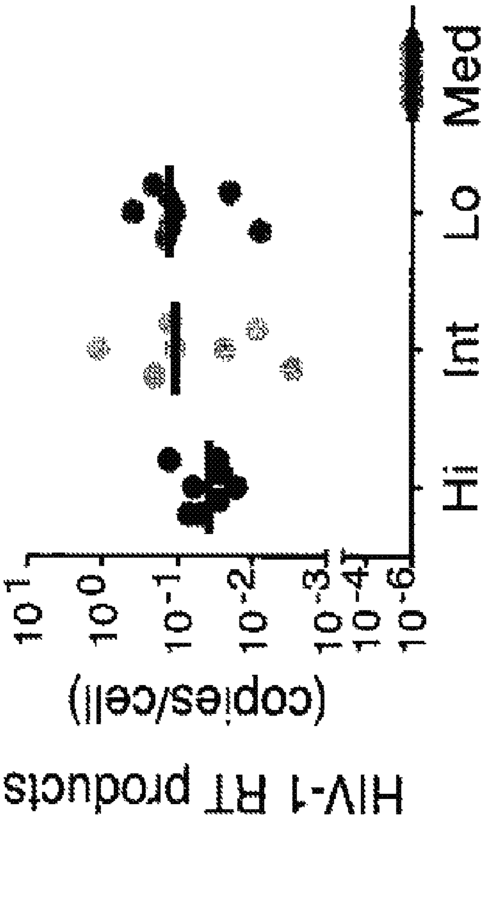
Figure 3E:
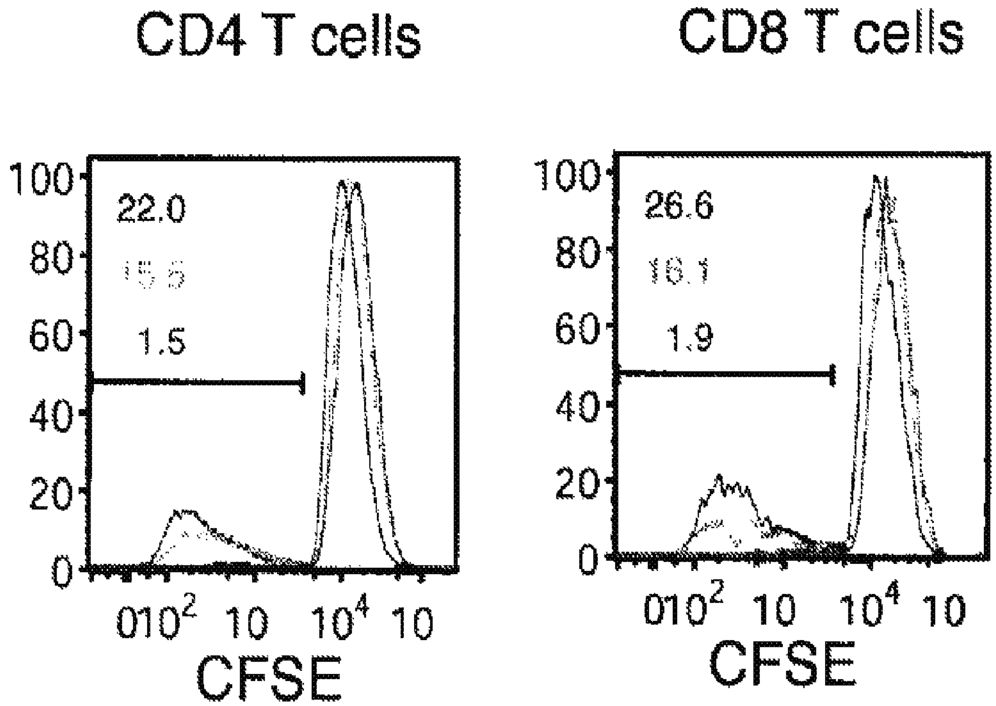
Figure 3F:
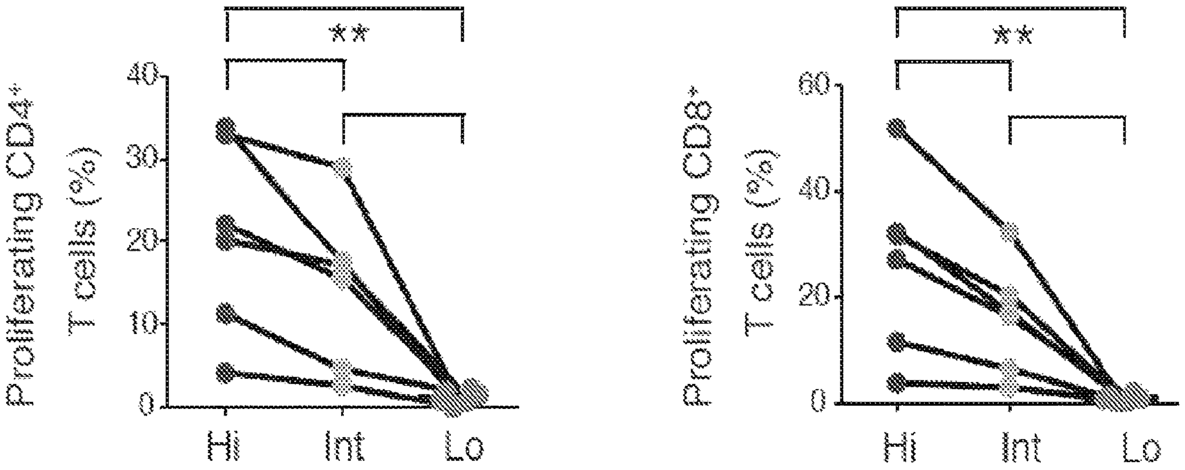

Single-cell transcriptional profiling identifies subgroups of dendritic cells with diverse gene expression patterns after HIV-1 exposure (FIG. 1; FIG. 2).

Phenotypic and functional characterizations of a subgroup of dendritic cells with enhanced type I IFN expression after exposure to HIV-1 (FIG. 3).

Inducing dendritic cells with superior antigen-presenting properties after exposure to HIV-1 by vaccine adjuvants (FIG. 4).

Discussion

Applicants Identified single-cell clusters and transcriptional signatures within DCs from EC exposed to HIV-1 using single-cell RNAseq technology and the relationship between transcriptional signatures of each single-cell cluster and type I IFN responses. Vex-B cluster is highly enriched in cells that display high levels of expression of type I IFN stimulated genes such that are correlated with cellular activation markers such as proinflammatory cytokines (TNF-alpha, IL-1), costimulatory molecules and increased levels of proteins involved in antigen processing.

Applicants show biological/functional implications of dendritic cell subsets characterized by specific transcriptional patterns observed by RNAseq. Applicants identified that Vex-B like cells represent a group of highly activated DCs that acquire effective antigen presenting cell functionality as a result of potent anti-viral responses against HIV-1.

Applicants identified that adjuvants trigger highly functional DC phenotype in HIV negative individuals. Among different TLR ligands tested (TLR2, TLR3, TLR4, TLR8), Applicants have identified TLR3 ligands as unique modulator of DC functional phenotype in combination with HIV-1 particles or ss/dsDNA.

Applicants identified the kinetics of activation and possible earlier events of activation identified by projection of transcriptional patterns at different time points leading to the identification of novel proteins/sensors contributing to the CD64$^{HI}$ PD-L1$^{HI}$ DC phenotype.

Conclusions

1—Single cell level RNAseq analysis revealed 3 different transcriptional patterns in cDCs from EC exposed to HIV (ie Vex-A, -B, -C).

2—Vex-B transcriptional pattern is characterized by high expression of interferon stimulated genes, proinflammatory cytokines, and costimulatory molecules, suggesting enhanced maturation and APC function.

3—CD64$^{Hi}$ PD-L1$^{Hi}$ cDCs are induced more efficiently in EC after exposure to HIV-1 and define a highly functional subset of cDCs with improved abilities to induce T cell.

4—Combination of TLR3 ligand and HIV-1 or HIV-1 DNA can be used as an adjuvant cocktail to induce CD64$^{Hi}$ PD-L1$^{Hi}$ DCs from healthy individuals.

Example 2

Single-Cell RNA-Seq Analysis of in cDCs from 3 HIV-1 Elite Controllers

Figure 5A:
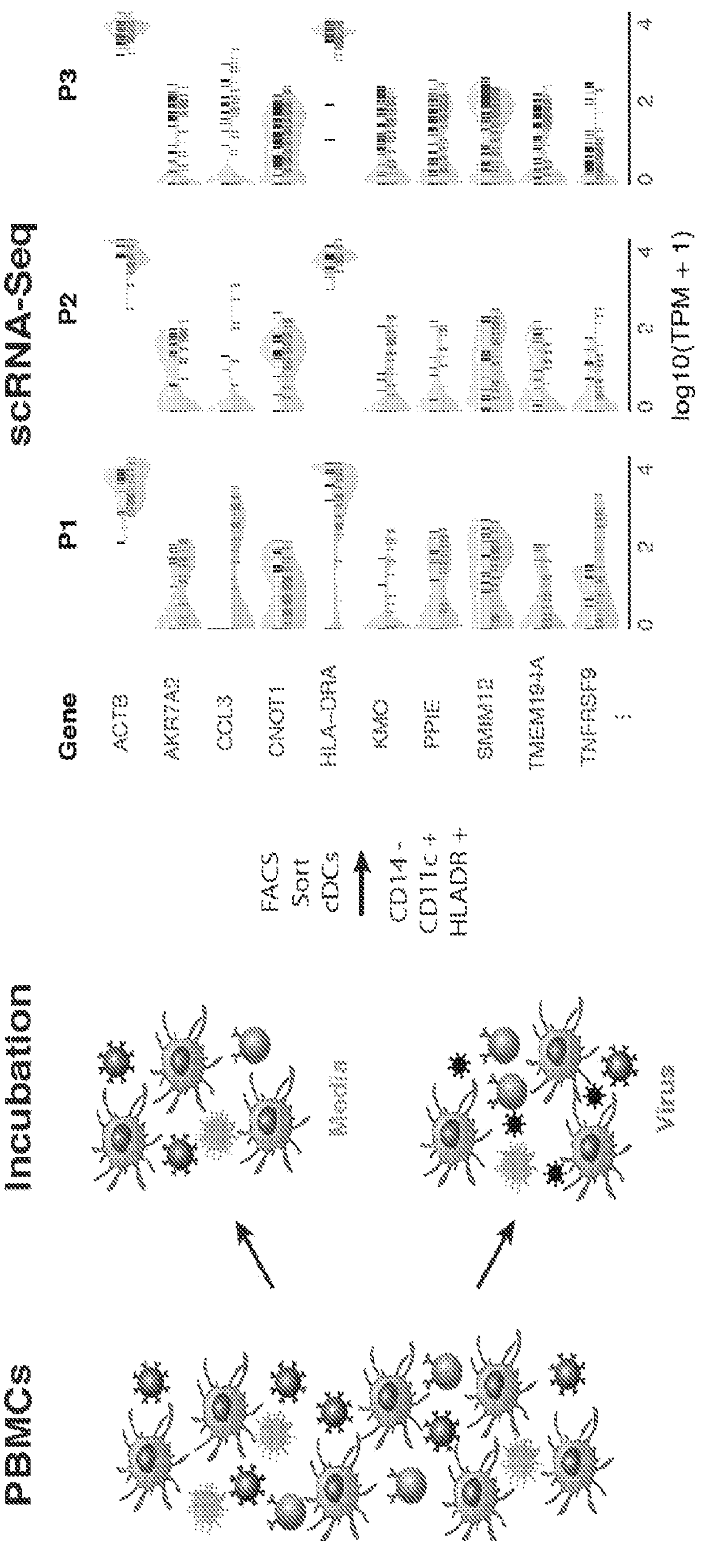
FIGS. 5A-5C illustrate scRNA-Seq of the response of elite controller (EC) conventional dendritic cells (cDCs) to viral infection. (5A) Left: Schematic representation of experimental system. After incubation with or without virus for 48 hours, conventional dendritic cells (cDCs) were isolated from PBMCs by FACS and profiled by scRNA-Seq. Right: Violin plots of single-cell expression levels for ten select genes for each EC donor (p1, p2, p3). Vertical lines represent individual cellular values; the upper (grey) half of the violin shows the distribution of values for a media control and the bottom (red) shows the same for virus-exposed cells. (5B) t-Distributed Stochastic Neighbor Embedding (t-SNE) of all FACS sorted DCs across three EC subjects (p1 circles, p2 triangles and p3 squares). Virus exposed cells are outlined in red; media exposed have no outline. Cells separate into five distinct clusters. (5C) Bar-plot depicting percentage of total cDCs in each cluster for each patient under media and viral exposure conditions.

To globally characterize cDC (defined as CD14$^-$, CD11c$^{Hi}$, HLA-DR$^+$) innate responses to HIV-1 in ECs, Applicants performed single-cell RNA-Seq (scRNA-Seq)(F. Paul et al., Transcriptional Heterogeneity and Lineage Commitment in Myeloid Progenitors. *Cell,* 1-16 (2015); A. K. Shalek et al., Single-cell transcriptomics reveals bimodality in expression and splicing in immune cells. *Nature* 498, 236-240 (2013); A. K. Shalek et al., Single-cell RNA-seq reveals dynamic paracrine control of cellular variation. *Nature* 510, 363-369 (2014), D. Grin et al., Single-cell messenger RNA sequencing reveals rare intestinal cell types. *Nature,* 1-23 (2015); E. Z. Macosko et al., Highly Parallel Genome-wide Expression Profiling of Individual Cells Using Nanoliter Droplets. *Cell* 161, 1202-1214 (2015)) on peripheral blood mononuclear cells (PBMCs) from three ECs (p1, p2, p3) that had been exposed to either a VSV-G pseudotyped HIV-1 or media alone for 48 hours in vitro (FIG. 5A, Methods) (H. Chen et al., CD4+ T cells from elite controllers resist HIV-1 infection by selective upregulation of p21. *The Journal of clinical investigation* 121, 1549-1560 (2011)). Stimulating PBMCs as an ensemble mimics critical physiological interactions between cDCs and other immune cell types, while the use of a VSV-G pseudotyped HIV-1 enhances infection efficiency (N. Manel et al., A cryptic sensor for HIV-1 activates antiviral innate immunity in dendritic cells. *Nature* 467, 214-217 (2010)). Following incubation, Applicants sorted single cDCs and performed SMART-Seq2-based scRNA-Seq (S. Picelli et al., Smart-seq2 for sensitive full-length transcriptome profiling in single cells. *Nature methods,* 1-5 (2013)). We subsequently estimated gene expression levels, filtering genes and cells according to alignment characteristics (FIG. 10).

Transcriptional Profiles of Single cDCs Separate into Five Distinct Clusters

Figure 5C:
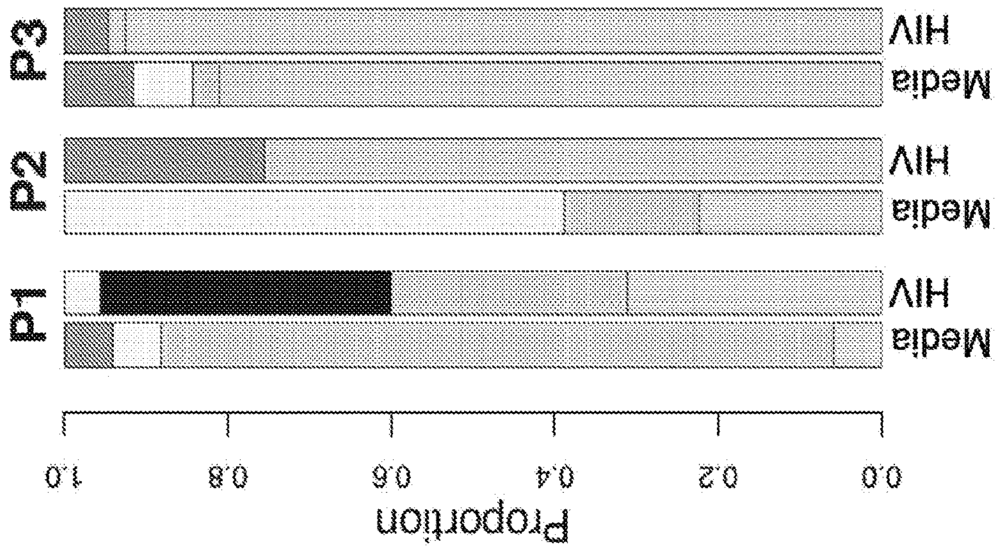
Figure 5B:
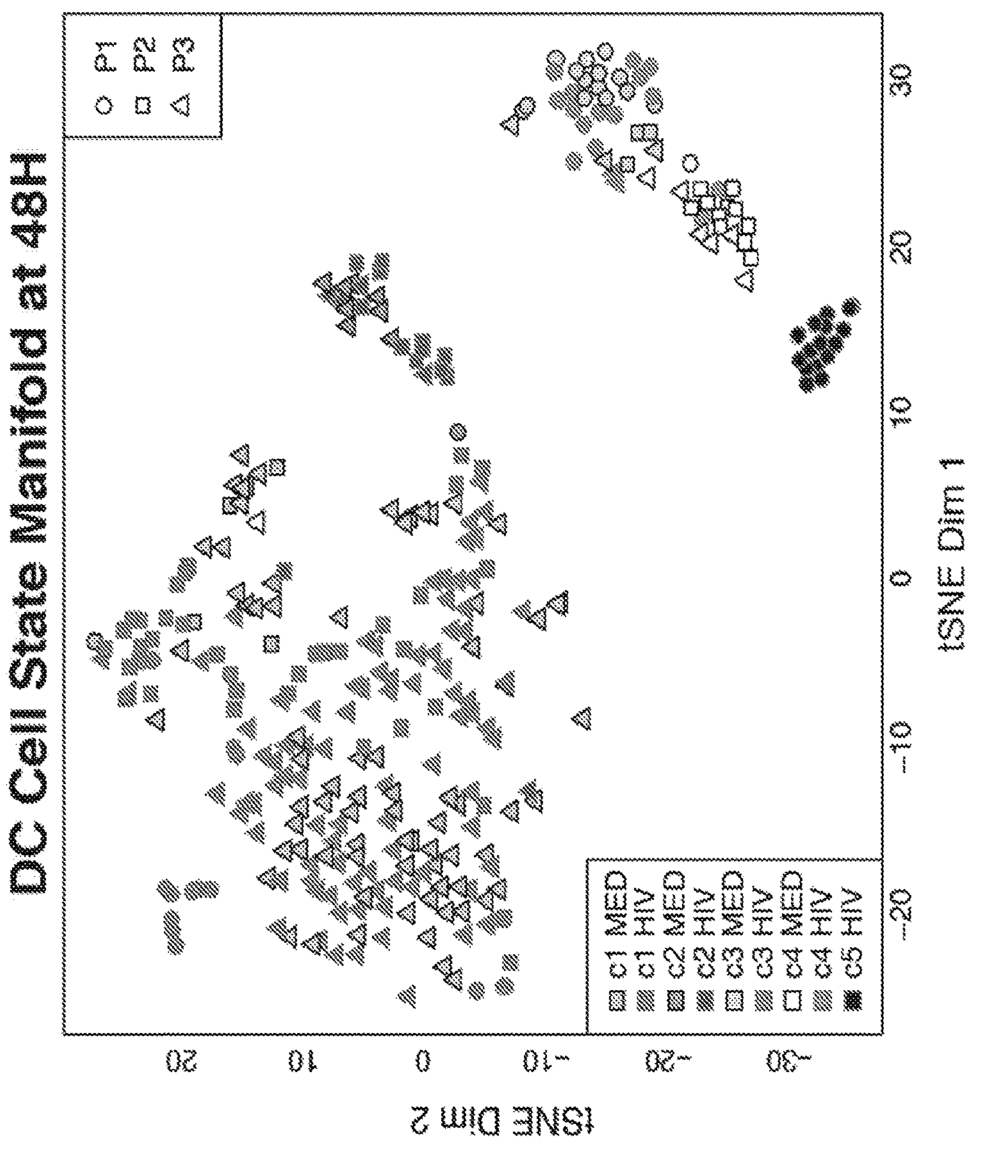

Unsupervised k-medoids-based clustering of the libraries over all patients and experimental conditions revealed five (cluster 1-5;c1-5) distinct response groups among cDCs (FIG. 5B). Single cells from both the media control and viral exposure conditions could be found in most (c1-c4) single-cell groups (FIG. 5B, FIG. 5C). Despite heterogeneity in cluster distribution across the tested EC patients, c1 was consistently enriched following viral exposure in all ECs individuals, while the c3 and c4 were relatively enriched in media-exposed single cells (FIG. 5C).

Figure 6A:
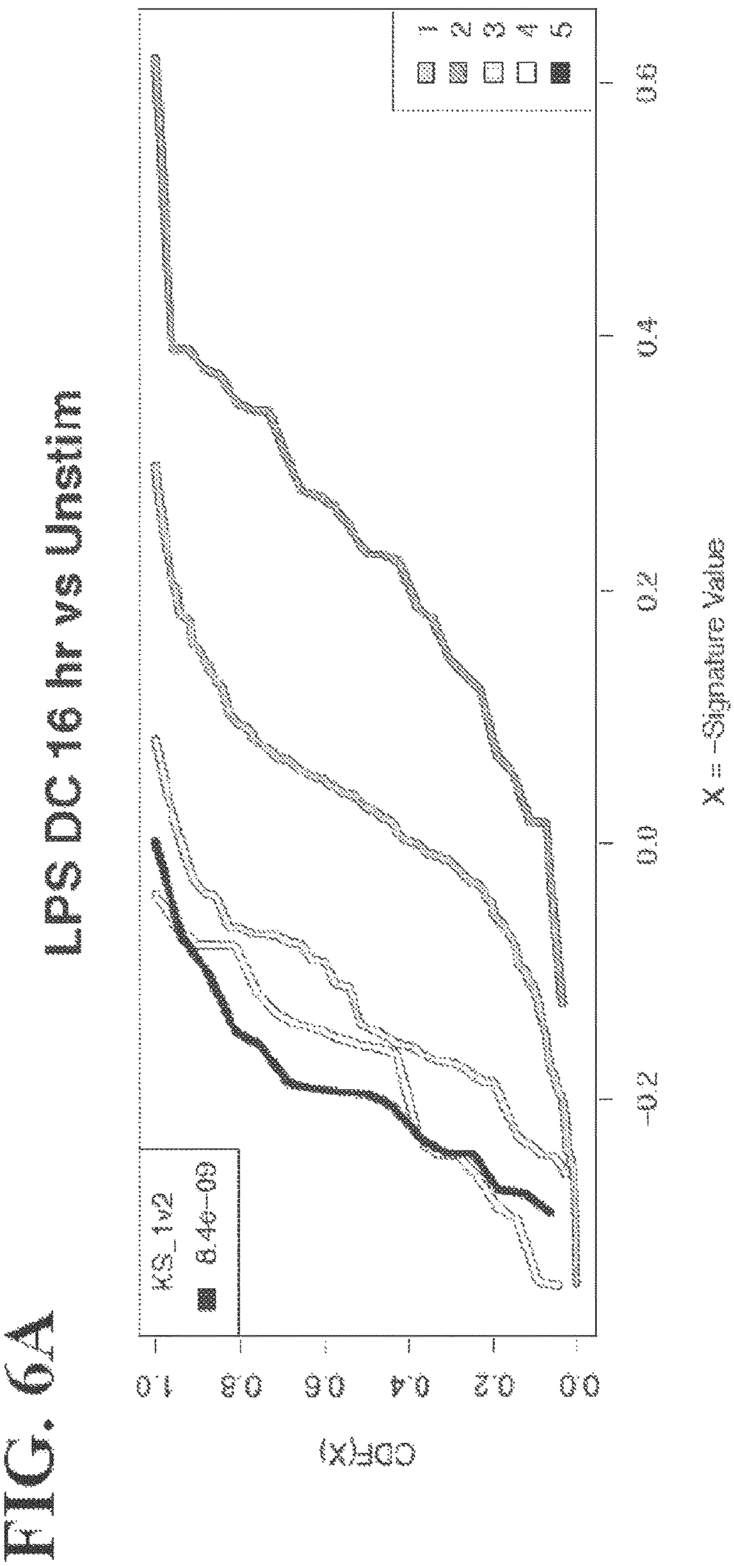
FIGS. 6A-6J illustrate the identification of a potentially functional response group. (6A-6D) CDF comparisons for single cells from each cluster identified in FIG. 1 with gene signatures from GSE. (6E) Potential surface markers specific for cluster 1 (cyan), cluster 2 (orange), shared cluster 1/2 (white). (6F) Adjusted negative log-fold-change p-value for regulatory pathways in cluster 1 vs 3/4/5 and cluster 2 vs 3/4/5, enriched in cluster 1 (cyan) and common to cluster 1 and 2 (white). (6G) Upstream regulator pathways significantly deactivated (blue), neutral (white) or activated (orange) in cluster 1 vs combined cluster 3/4/5. (6H) Canonical pathways significantly deactivated (blue), neutral (white) or activated (orange) in cluster 1 vs combined cluster 3/4/5. (6I) Volcano plot of negative log IDR vs mean differential log-expression between cluster 1 and cluster 3/4/5. Selected potential marker genes are labeled in red. (6J) Selection of cluster one-specific genes encoding surface proteins for validation as cluster 1 markers. Thirty-one genes (listed in box) were significantly differentially expressed in cluster 1, reproducible across all three ECs profiled, and markers of cell differentiation. Candidate markers shown in green were selected for validation by FACS.
Figure 6B:
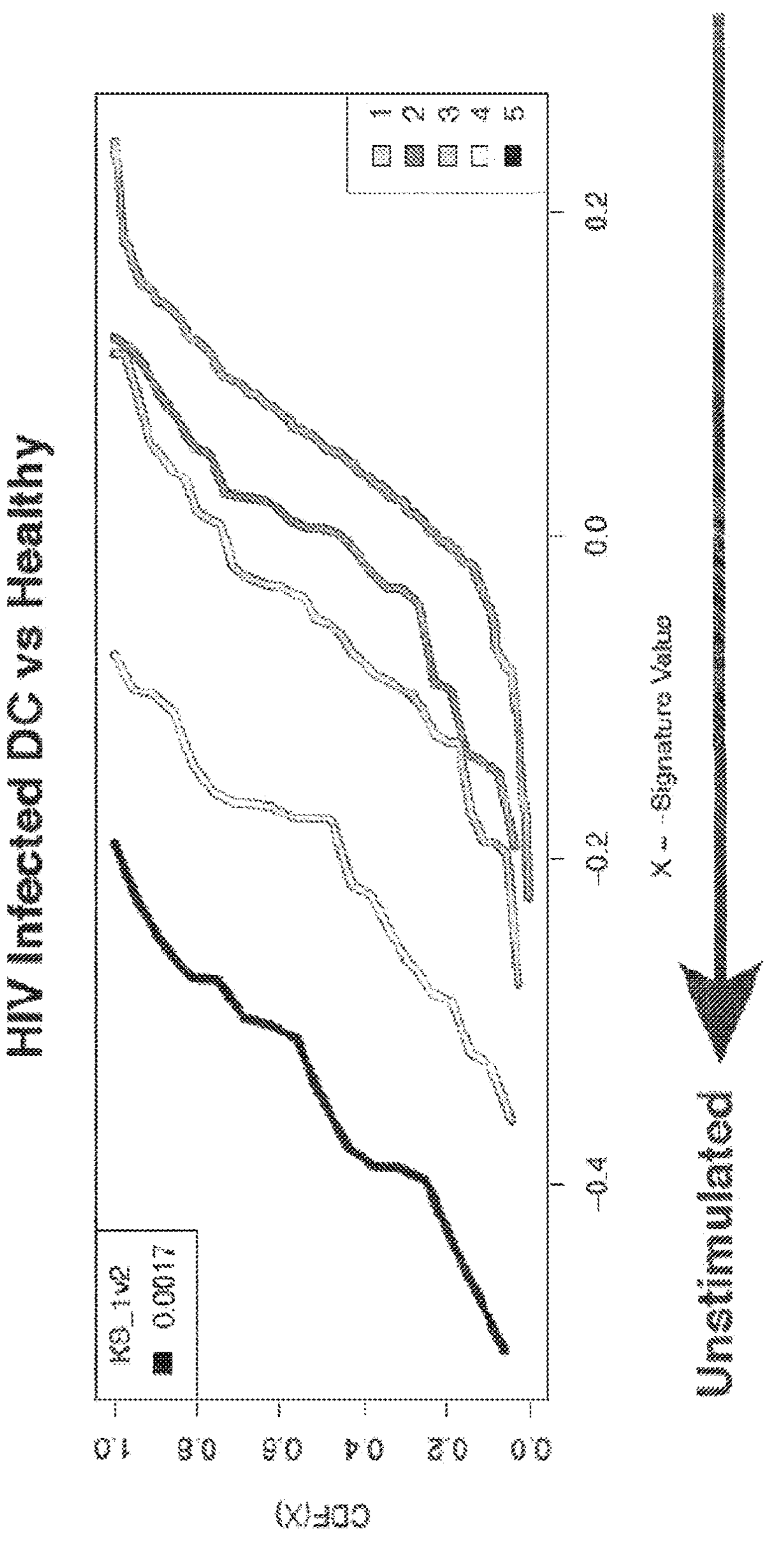
Figure 6C:
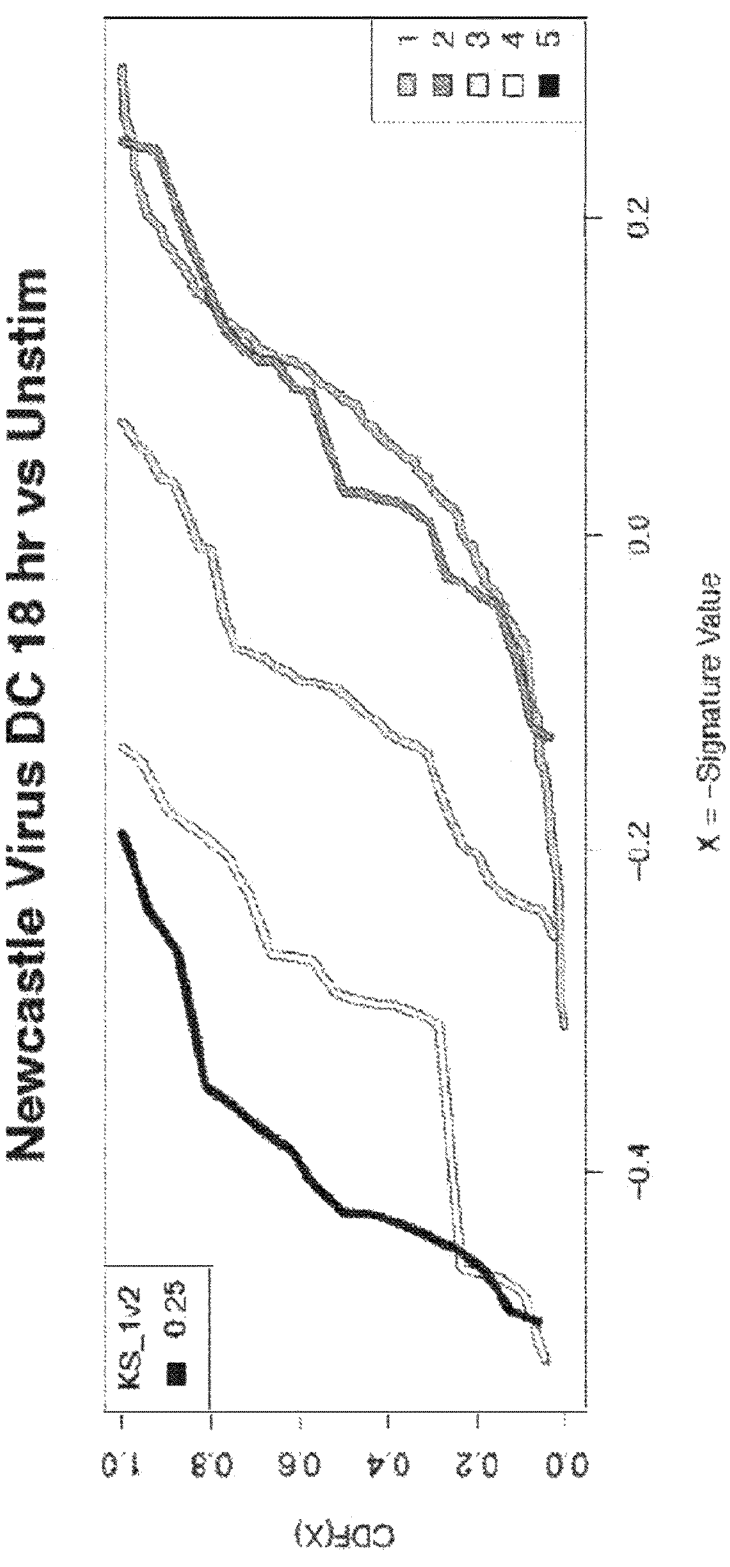
Figure 6D:
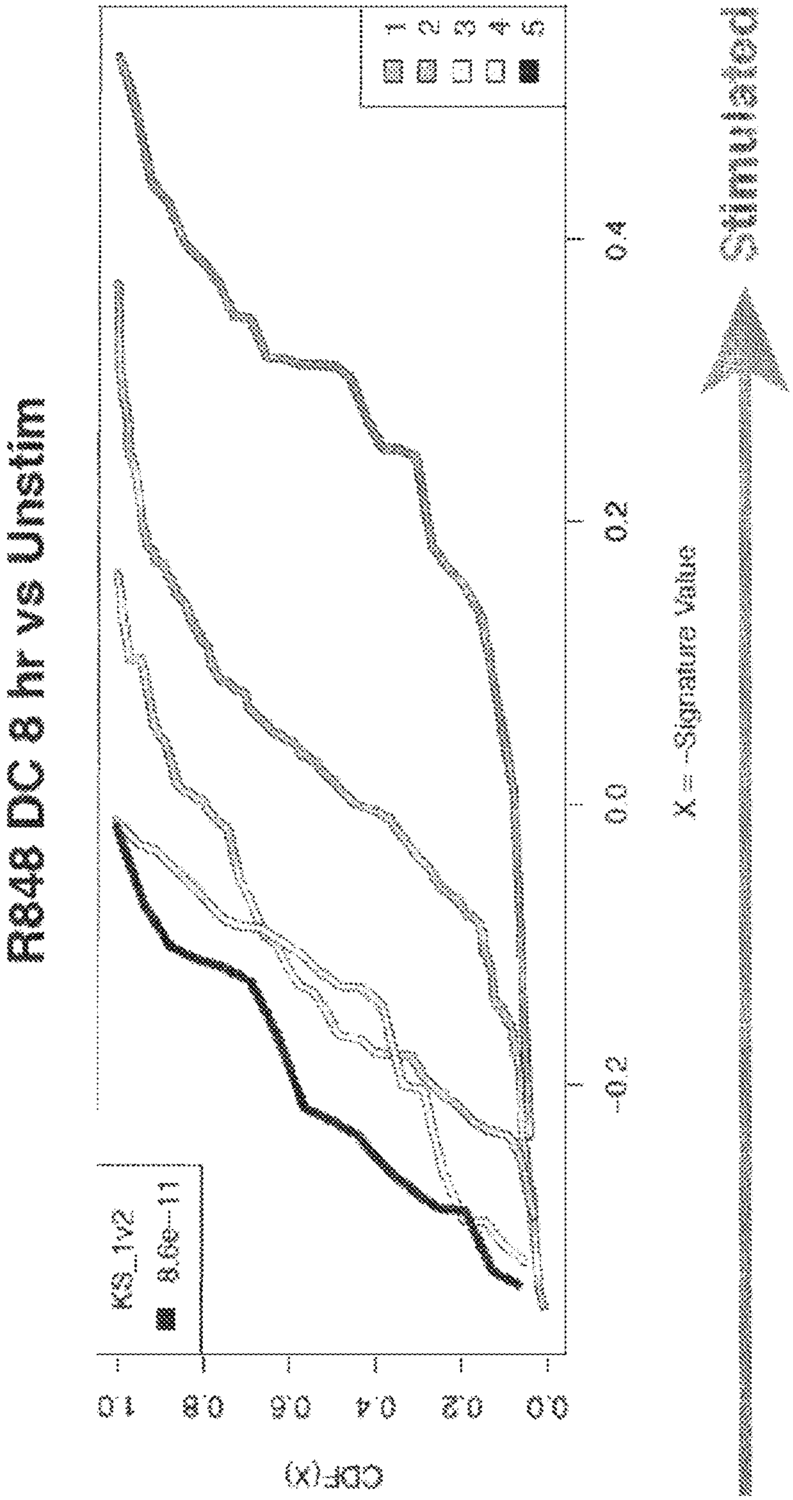
Figure 6E:
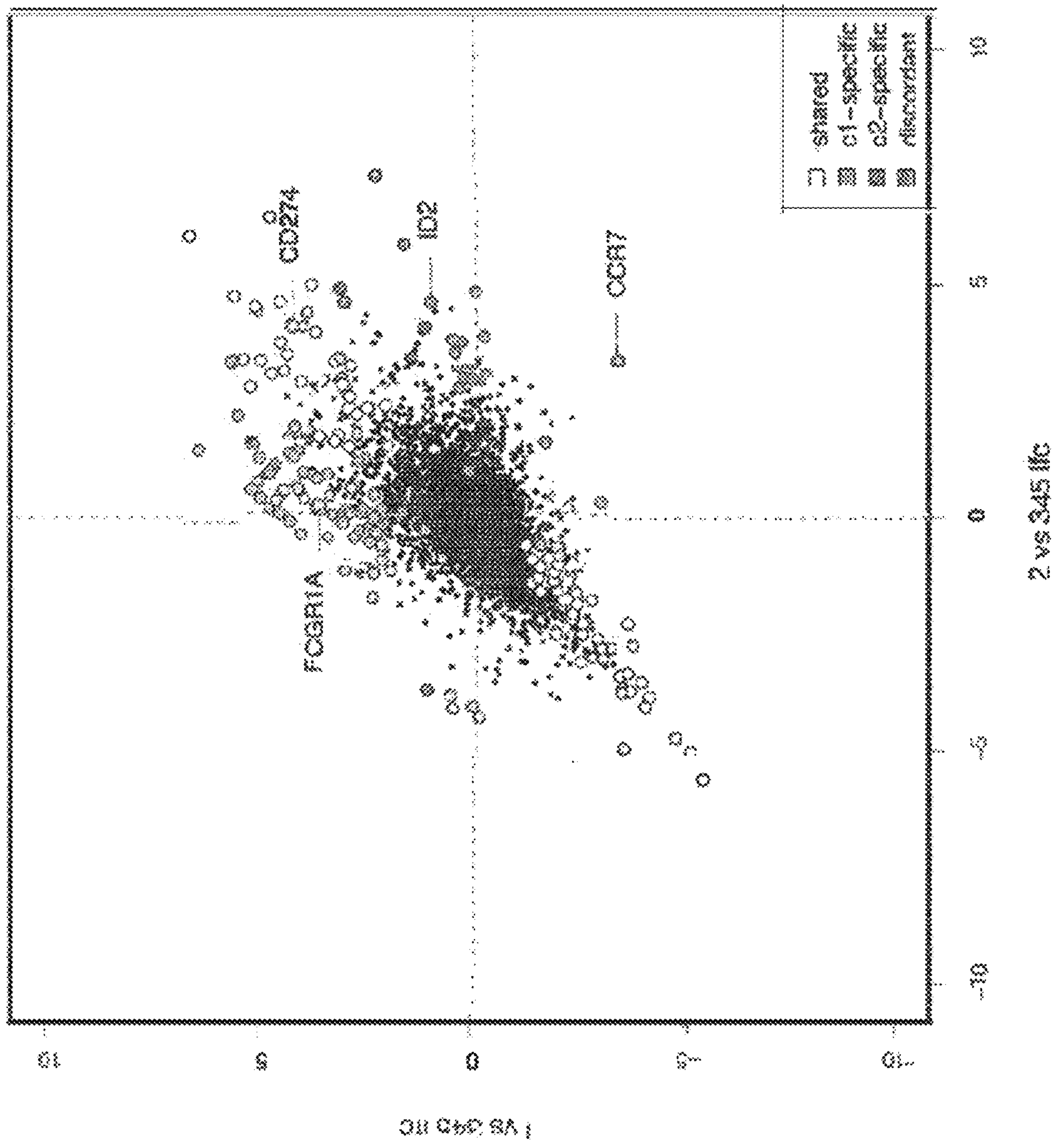
Figure 6F:
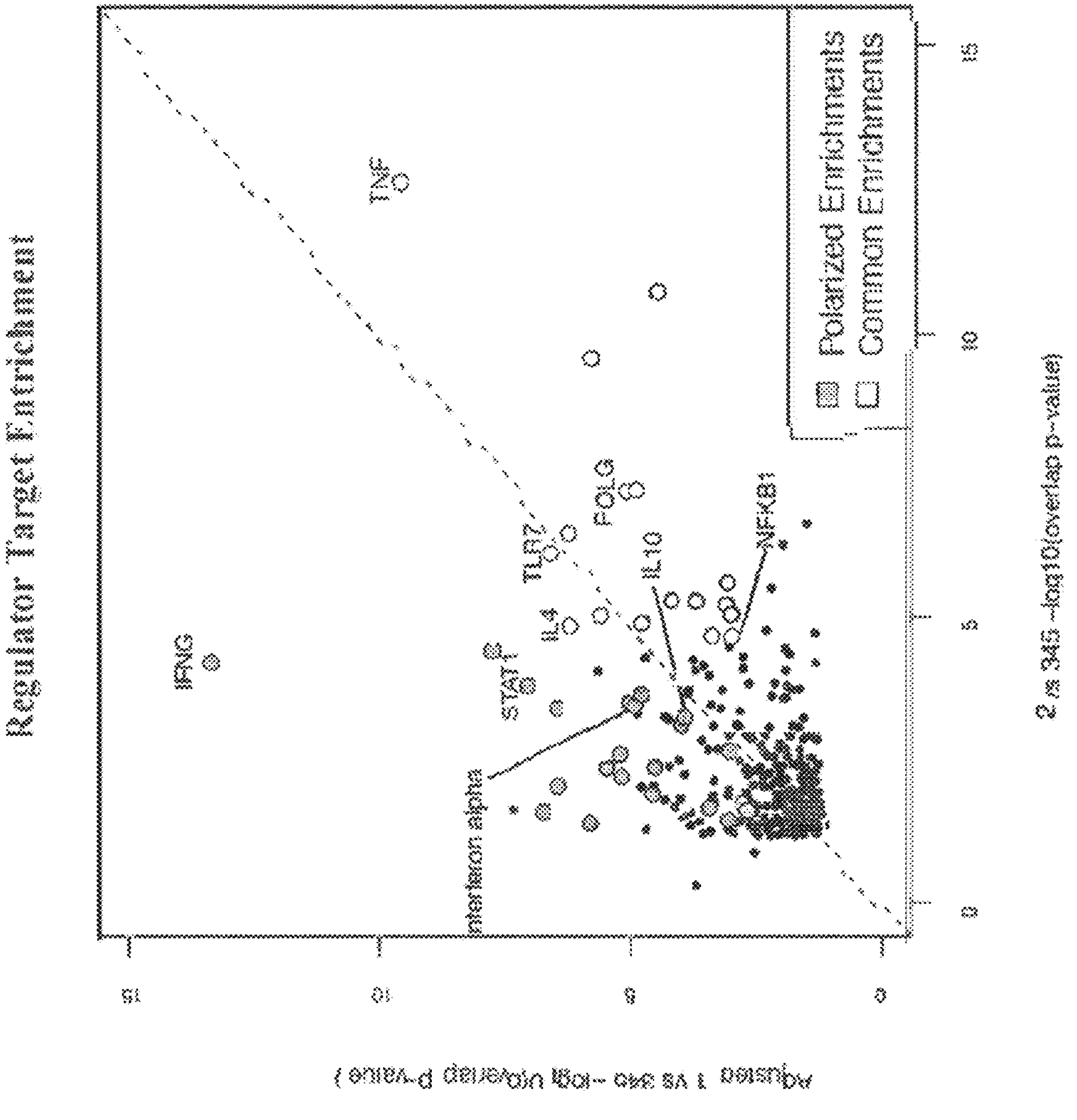
Figure 13A:
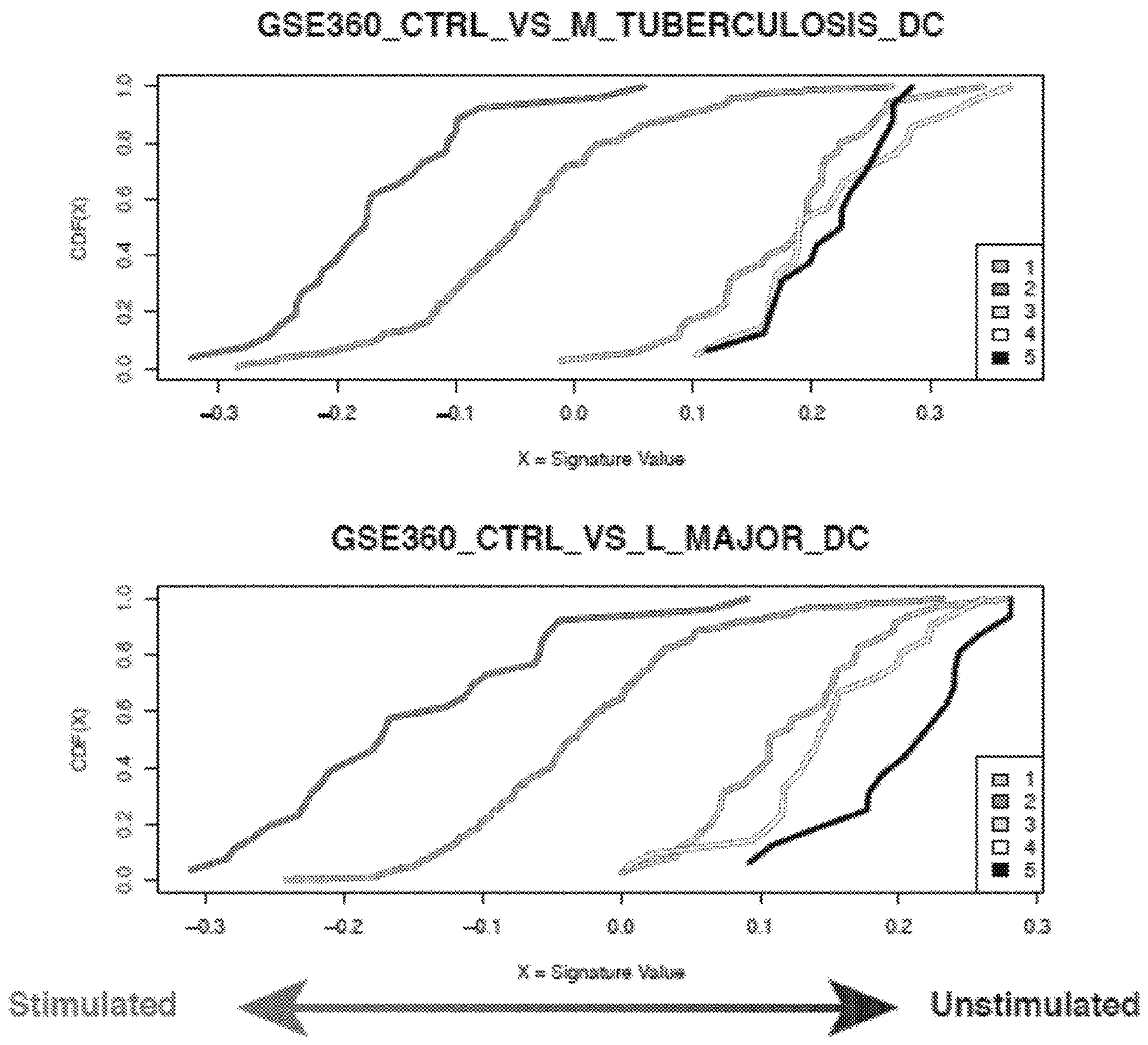
FIGS. 13A and 13B illustrate the identification of a potentially functional response group. (13A) CDF comparisons for single cells from each cluster identified in FIG. 1 with gene signatures from GSE. Cumulative distribution function (y axis) of the overlap between single cell cluster data (colored lines) and gene expression signatures from stimulated vs unstimulated data in GSE. Cluster data with gene expression signatures more closely mapping GSE data from the stimulated condition shift left, unstimulated shift right. (13B) CDF plot showing overlaps with a gene set of interferon stimulated genes. Clusters with stronger interferon stimulated gene signatures shift right.
Figure 13B:
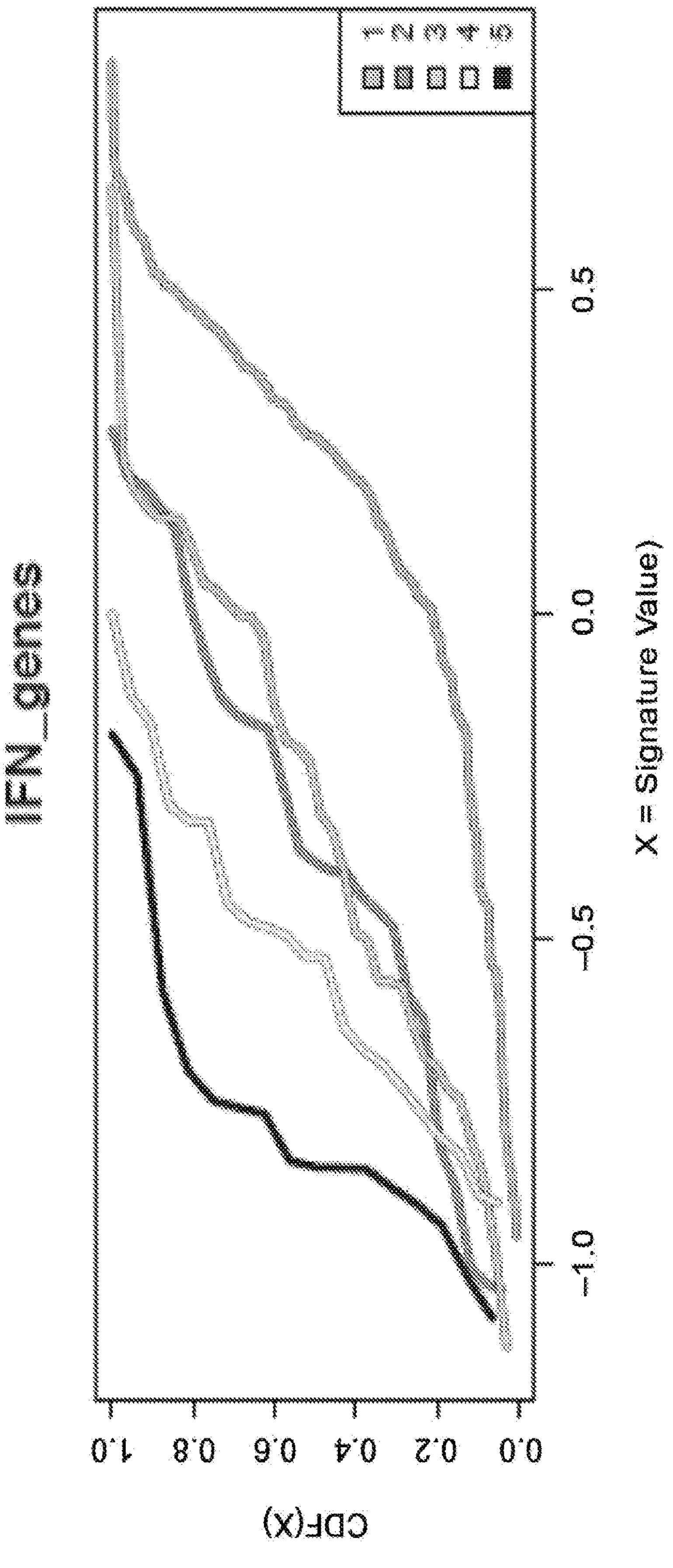

To better understand the relationships among each single-cell cluster and how it relates to their functional state, Applicants first performed a gene set enrichment analysis comparing the expression profiles of each single-cell cluster with publicly available transcriptional signatures from previously published studies. Interestingly, in gene sets significantly matching with the single cell transcriptional data cluster 1 and 2 response group signatures consistently associated with DC activation (FIG. 6A-6D and FIG. 13A). However, cluster 1 cDCs appear to be more consistent with antiviral innate responses, displaying the highest level of overlap with expression patterns from DC exposed to HIV and Newcastle virus (FIG. 6A-6D), while cluster 2 cDC appears to be more similar to signatures from DCs stimulated via TLR ligands such as LPS and R484 (FIG. 6A-6D) or with bacterial or parasitic infections (FIG. 13A). Despite high level of overlap between cluster 1 and cluster 2 signatures due to shared DC activation pathways between antiviral and bacterial/parasitic responses (FIG. 6E-6F), differential expressed gene analysis between these two response groups identified genes which separate these response groups by direction of activation (FIG. 6E). Genes preferentially expressed by cluster 1 encode for molecules associated with activation (CD83), endocytosis and antigen presentation (LAMP3, CD63, CD86, CST7) and migration (CCR7, CCR1) (FIG. 6E), suggesting different levels of activation or polarization between clusters 1 and 2. In fact, genes differentially expressed between cluster 1 and 2 seemed to be mainly associated with DC maturation (FIG. 13B). Data from p 1 showed higher numbers of c2-like cells at 24 hours and relatively more c1-like cells after a 48 hour incubation, suggesting that c2-like cells may shift to a more c1-like modality over time (FIG. 12).

Figure 6G:
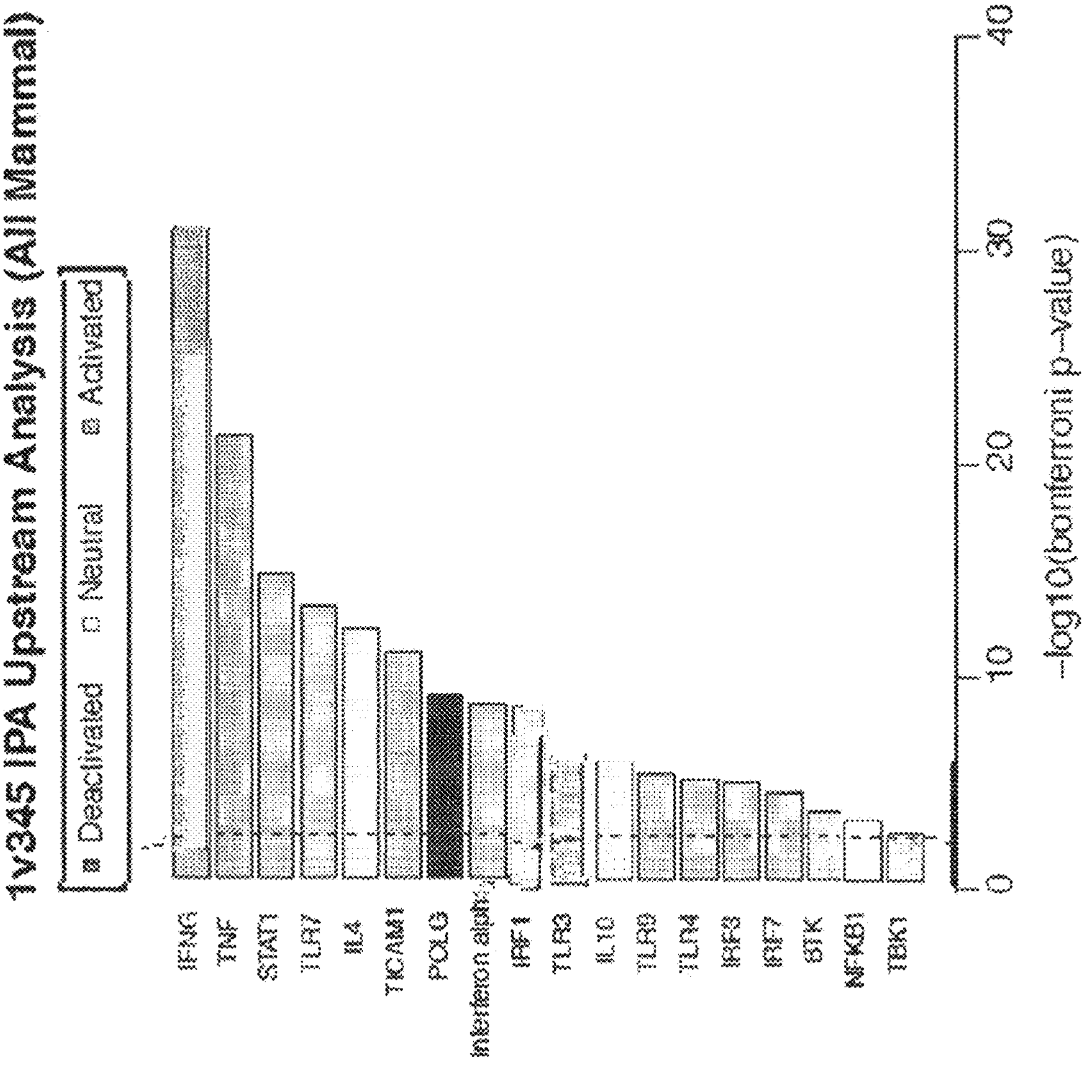

Analysis of upstream regulators in the c1 vs c2 response revealed several regulatory pathways associated with antiviral response (IFNG, TLR3, STAT1, IRF1) and TLR activation significantly associated with the c1 response (FIG. 6G).

Figure 6H:
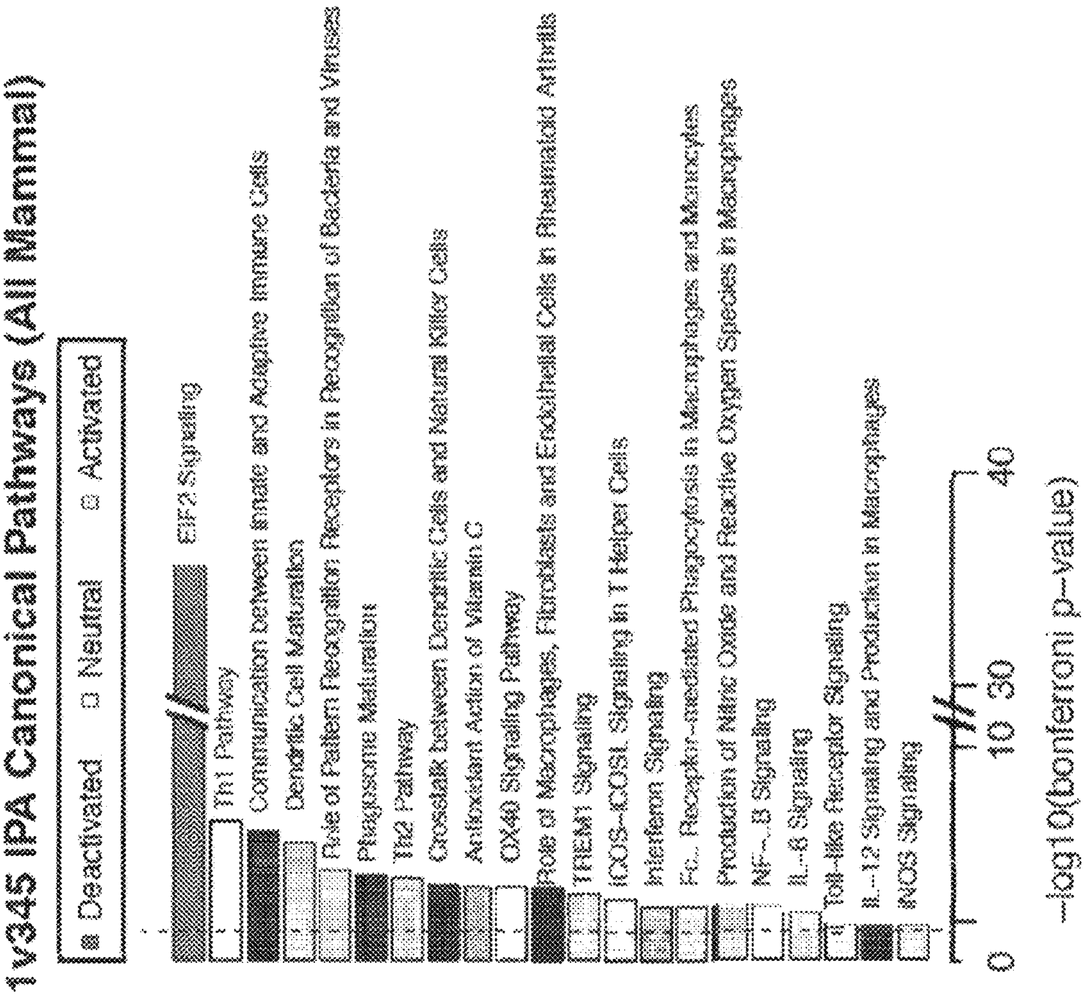
Figure 6I:
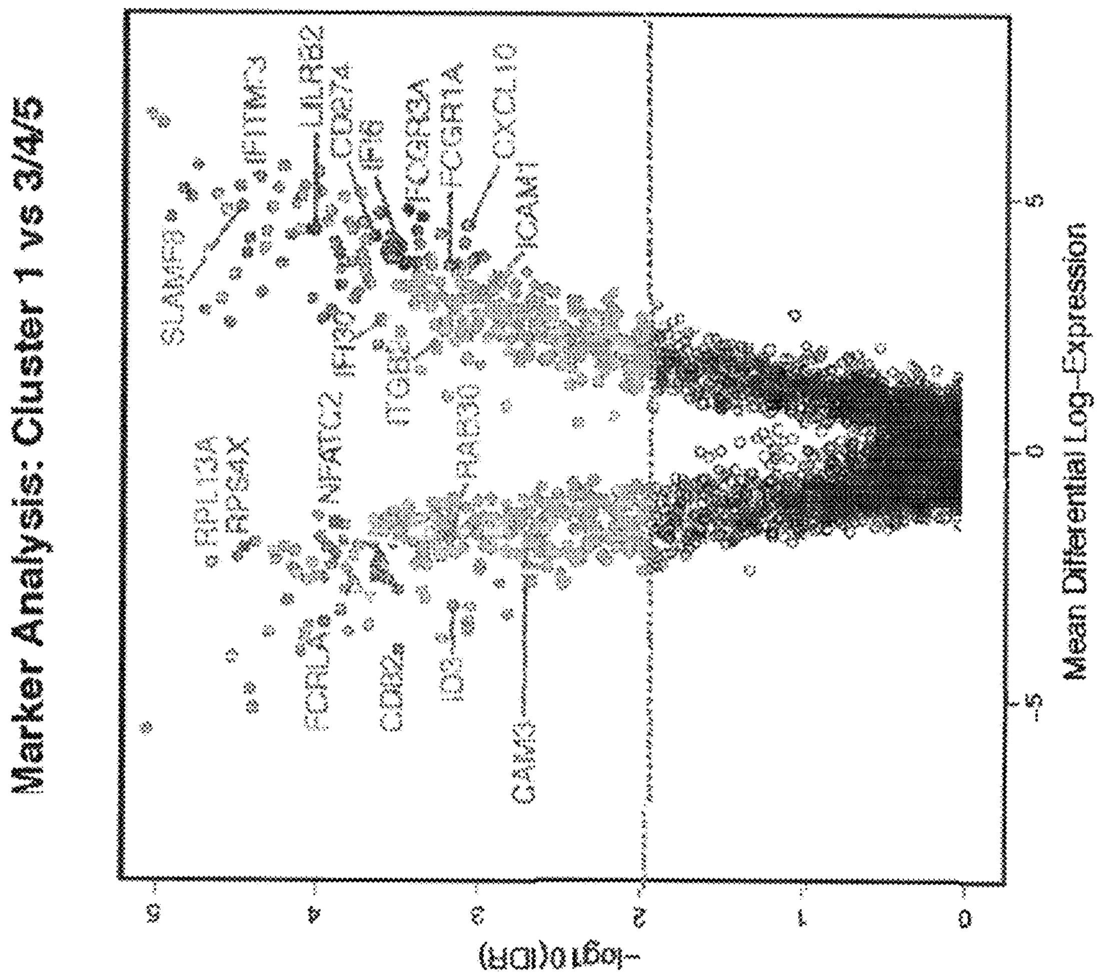
Figure 6J:
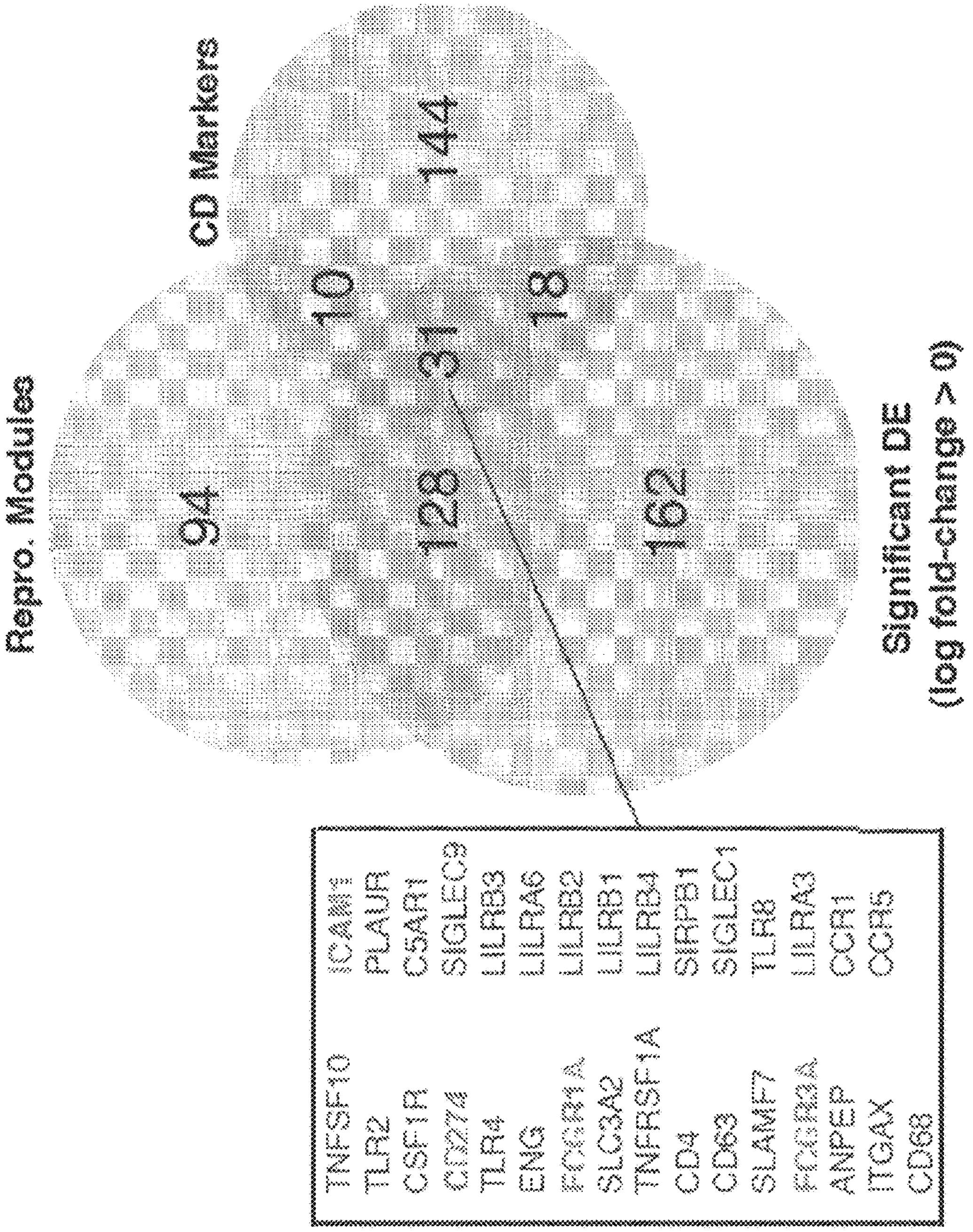
Figure 13C:
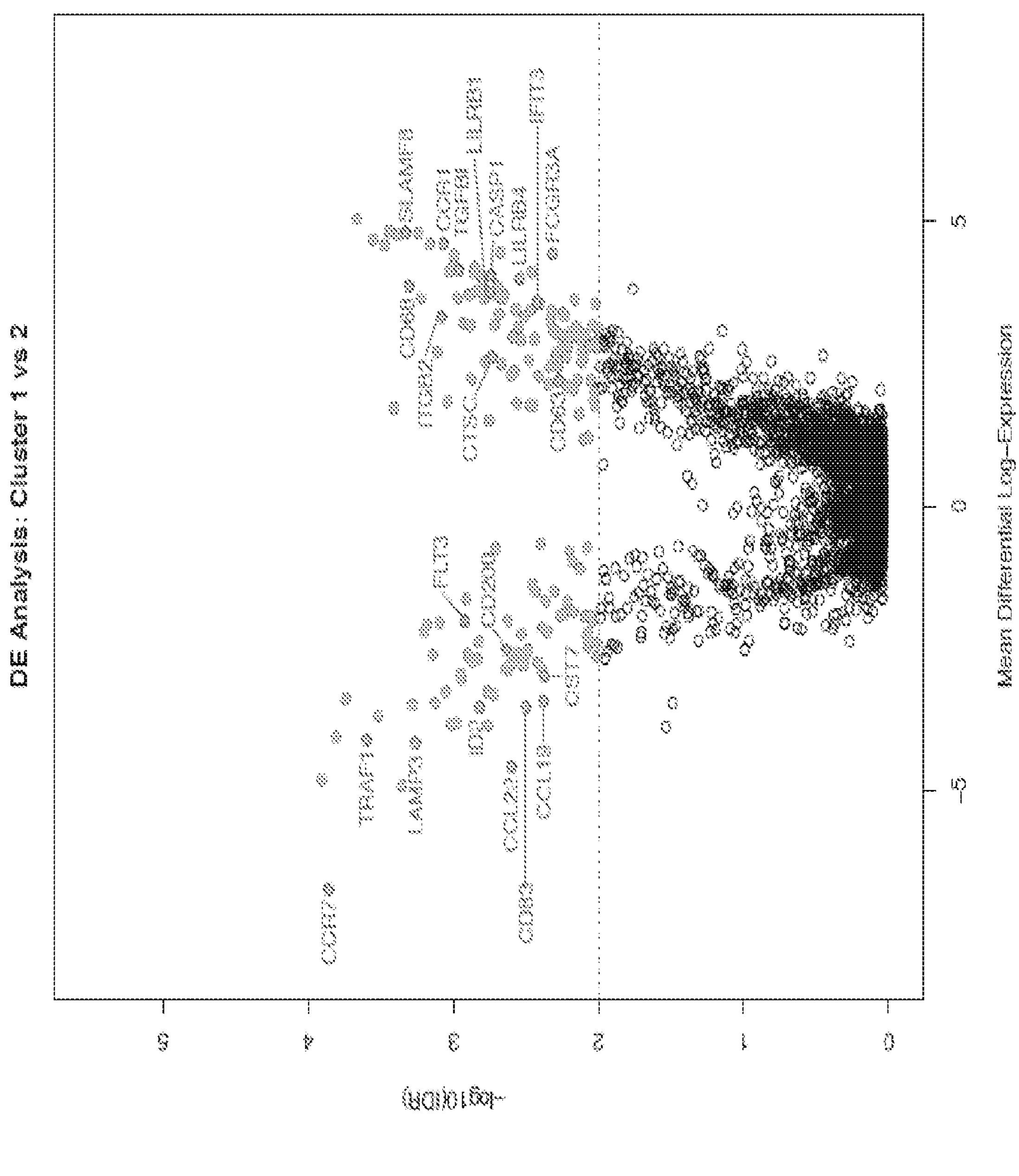
FIG. 13C illustrates a volcano plot of negative log IDR vs mean differential log-expression between cluster 1 and cluster 2. Selected potential marker genes are labeled in red.
Figure 13D:
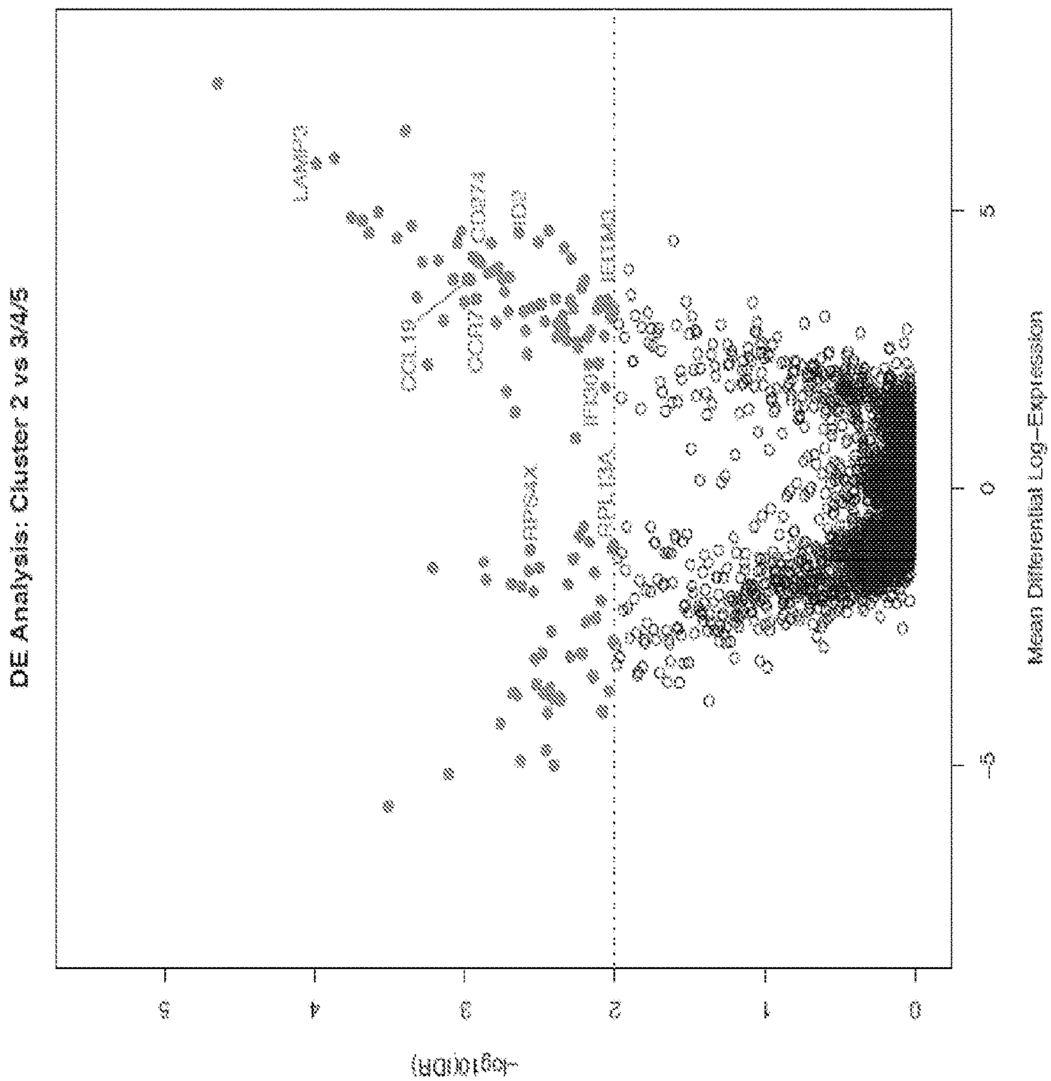
FIG. 13D illustrates a volcano plot of negative log IDR vs mean differential log-expression between cluster 2 and combined cluster 3/4/5. Selected potential marker genes are labeled in red.
Figure 13E:
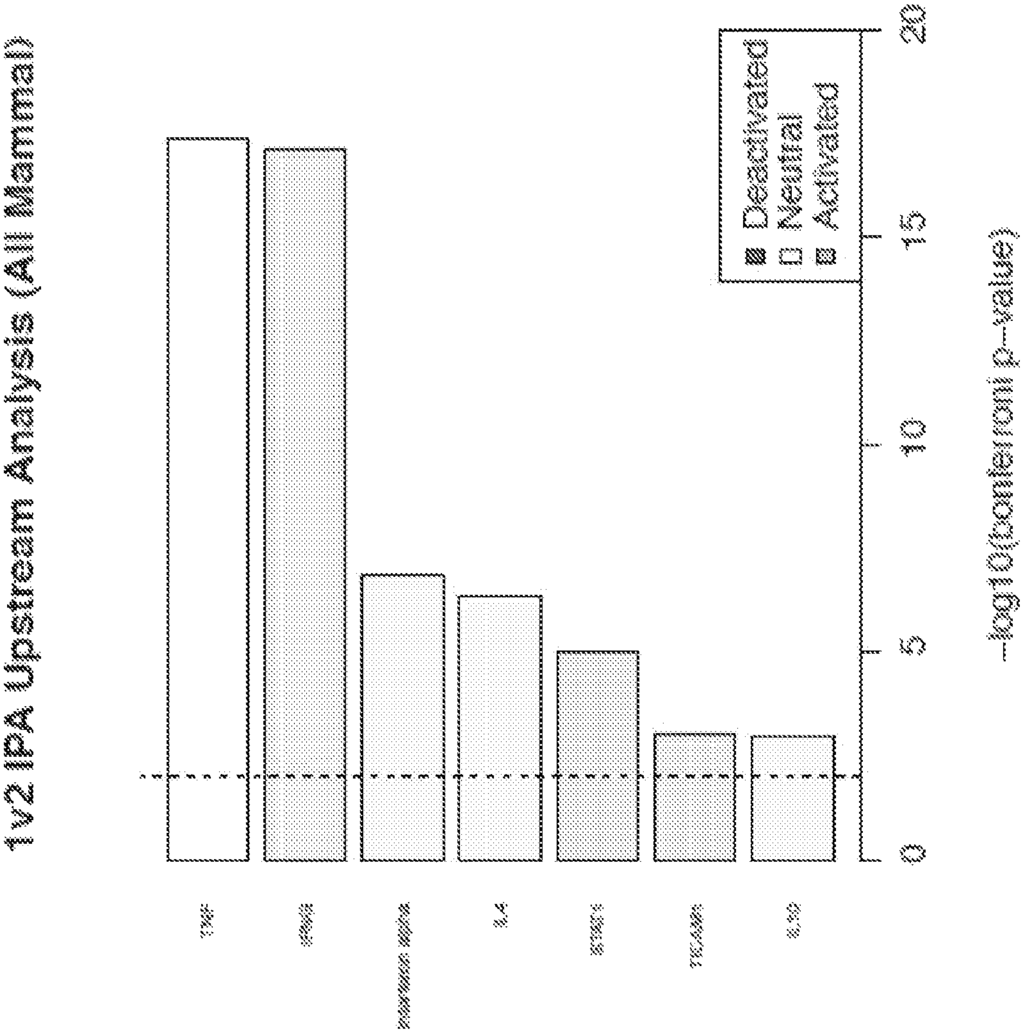
FIGS. 13E and 13F illustrate an analysis of immune activation across clusters. (13E) Upstream regulator pathways significantly deactivated (blue), neutral (white) or activated (orange) in cluster 1 vs cluster 2. (13F) Canonical pathways significantly deactivated (blue), neutral (white) or activated (orange) in cluster 1 vs cluster 2.
Figure 13F:
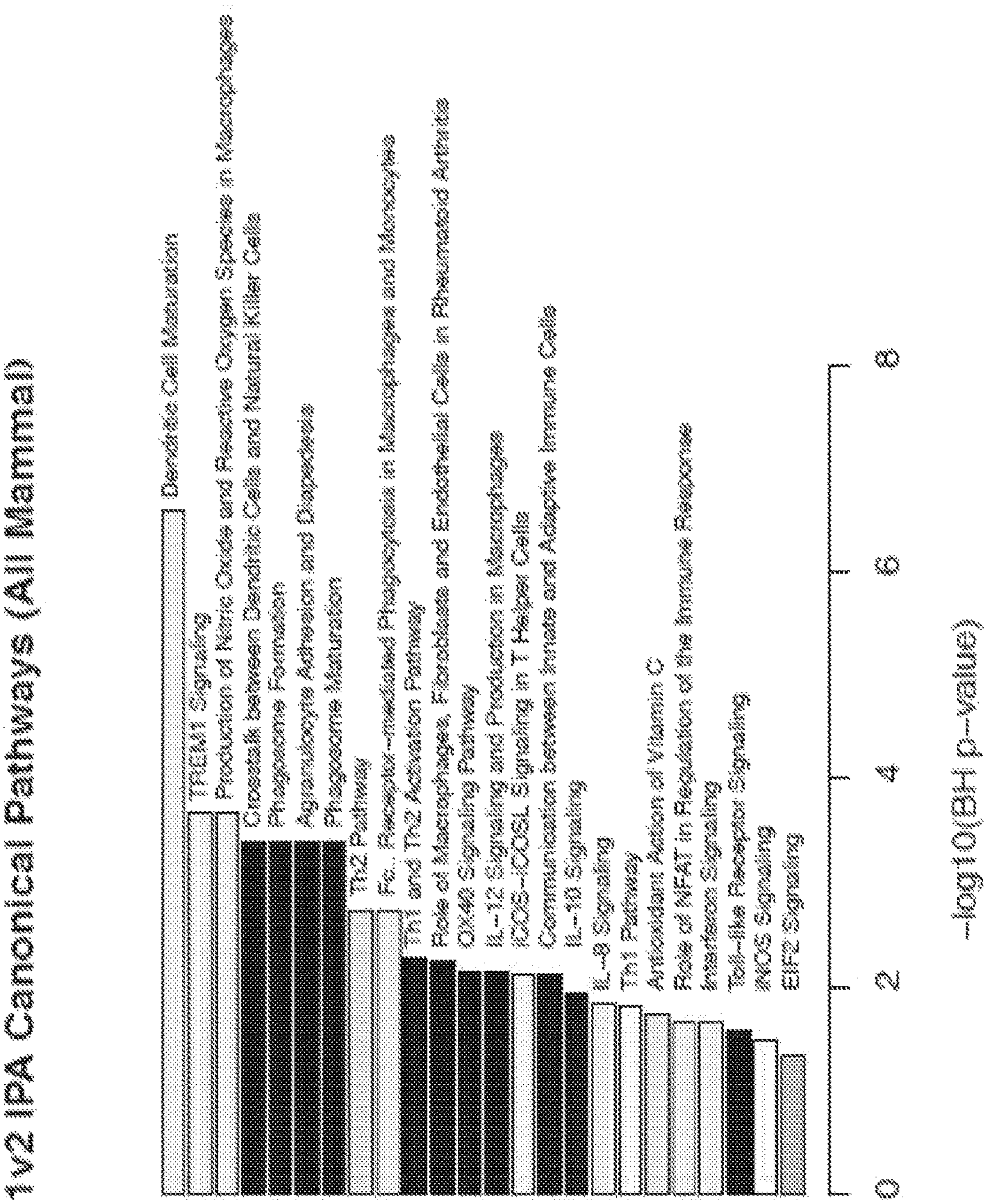
Figure 13G:
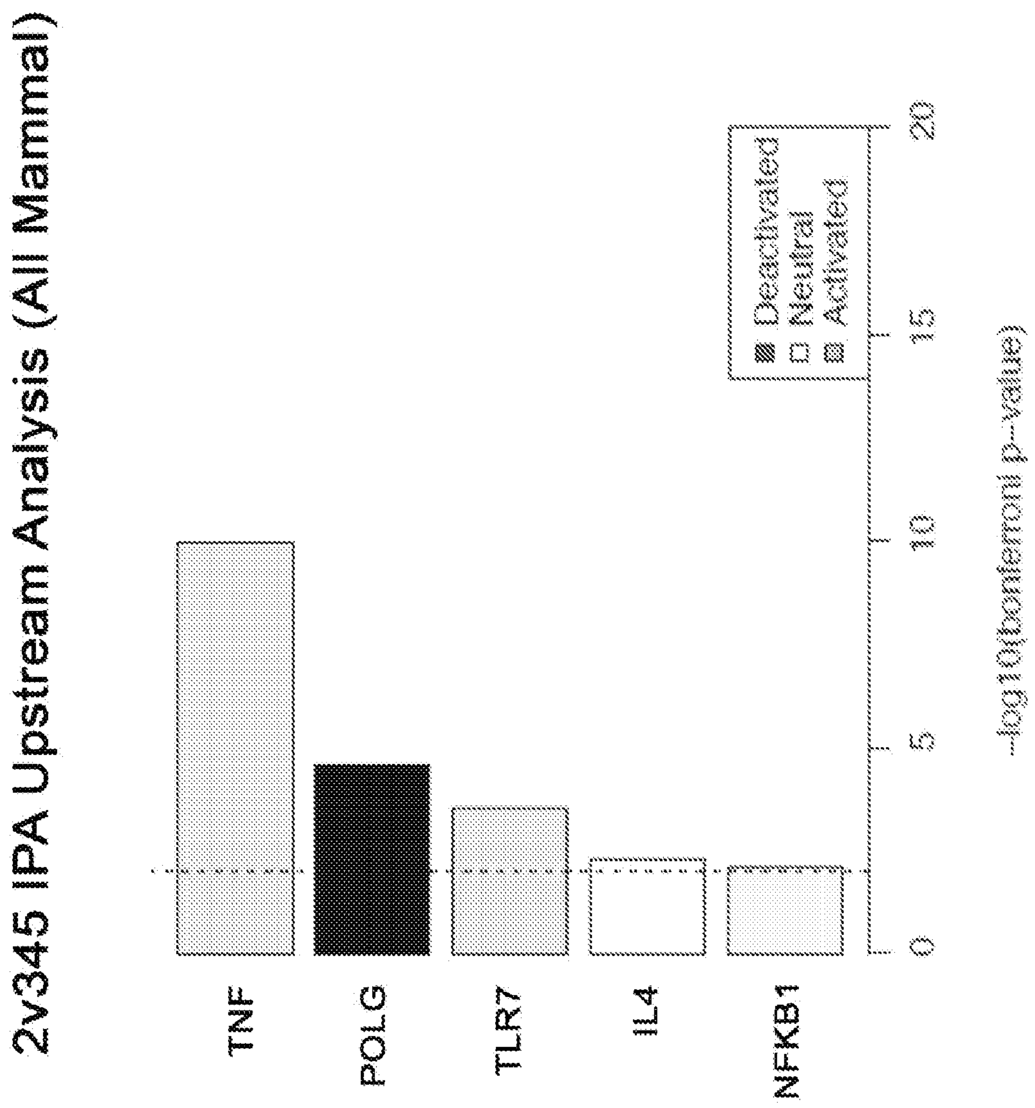
FIGS. 13G and 13H illustrate an analysis of immune activation across clusters. (13G) Upstream regulator pathways significantly deactivated (blue), neutral (white) or activated (orange) in cluster 2 vs combined cluster 3/4/5. (13H) Canonical pathways significantly deactivated (blue), neutral (white) or activated (orange) in cluster 2 vs combined cluster 3/4/5.
Figure 13H:
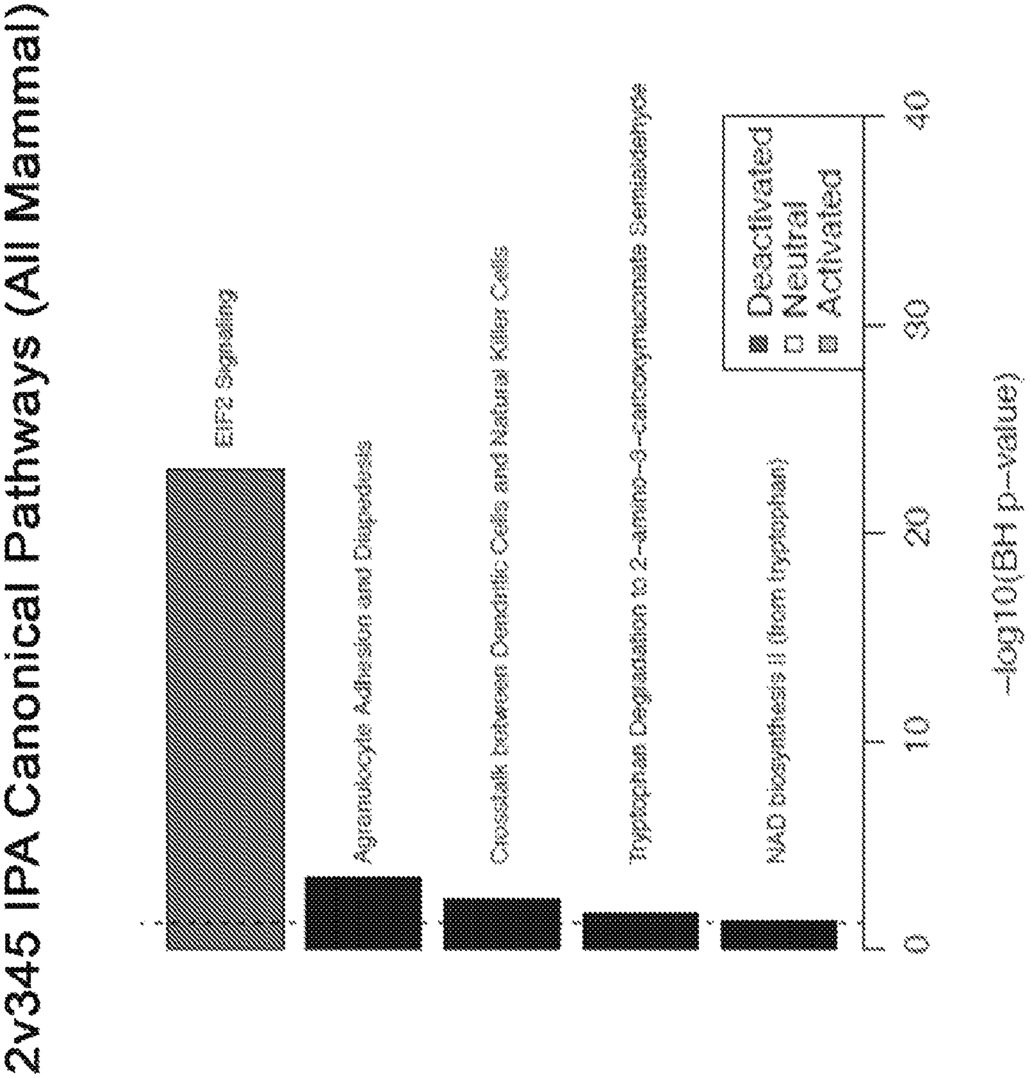
Figure 14:
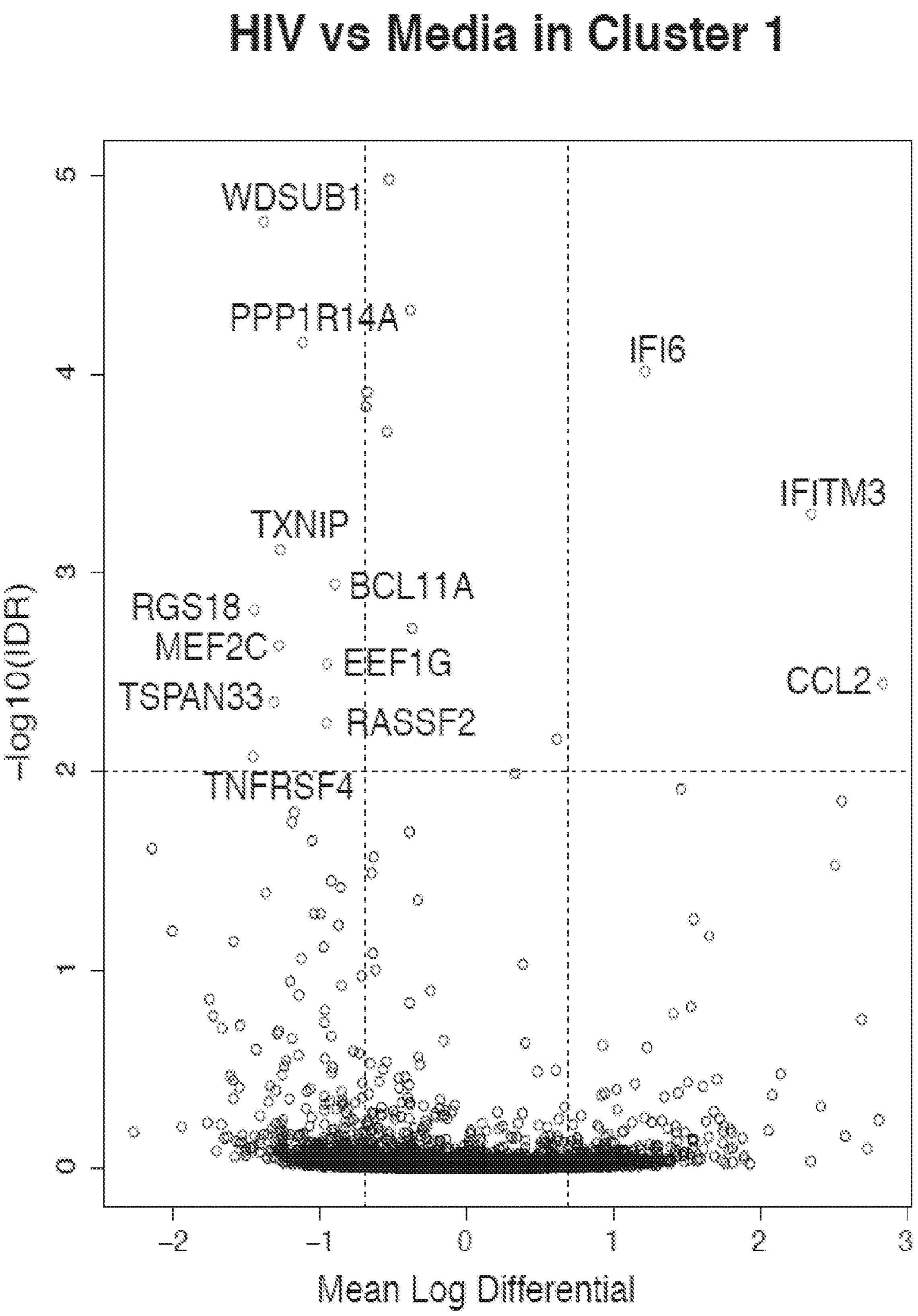
FIG. 14 illustrates the identification of genes enriched in Media vs HIV exposure conditions for cluster 1. Specifically, Negative log 10 (Irreproducible Discovery Rate) vs mean log differential of genes expressed in cluster 1 single cells in media and virus exposure conditions. Genes significantly differentially expressed in HIV (right) or Media (left) are highlighted in red and labeled.
Figure 15A:
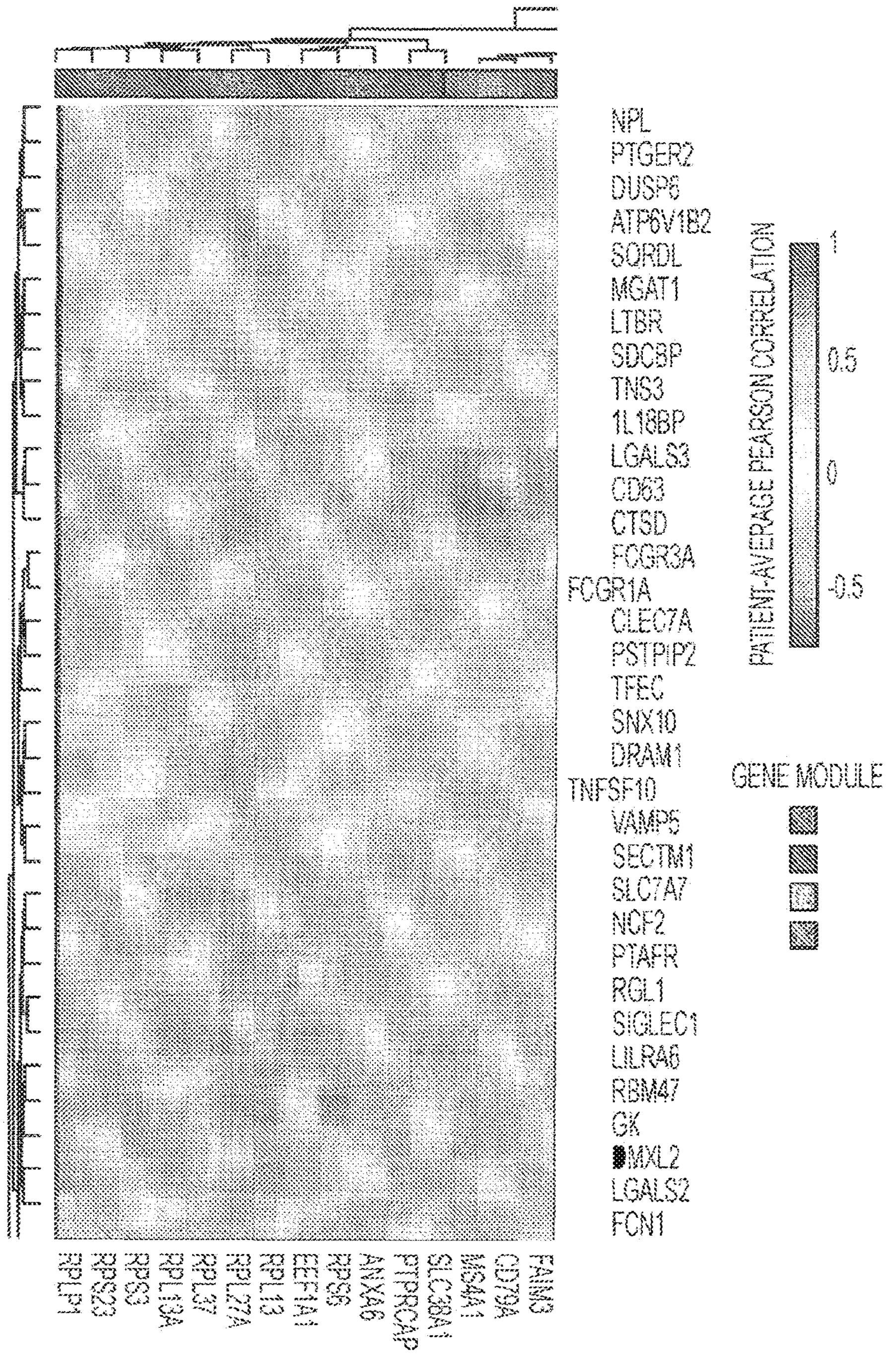
FIG. 15A-15X illustrate hierarchical clustering of a genes cross genes correlation matrix for genes reproducibly expressed across all three EC patients. Reproducible genes cluster into four modules (m1-m4).
Figure 15B:
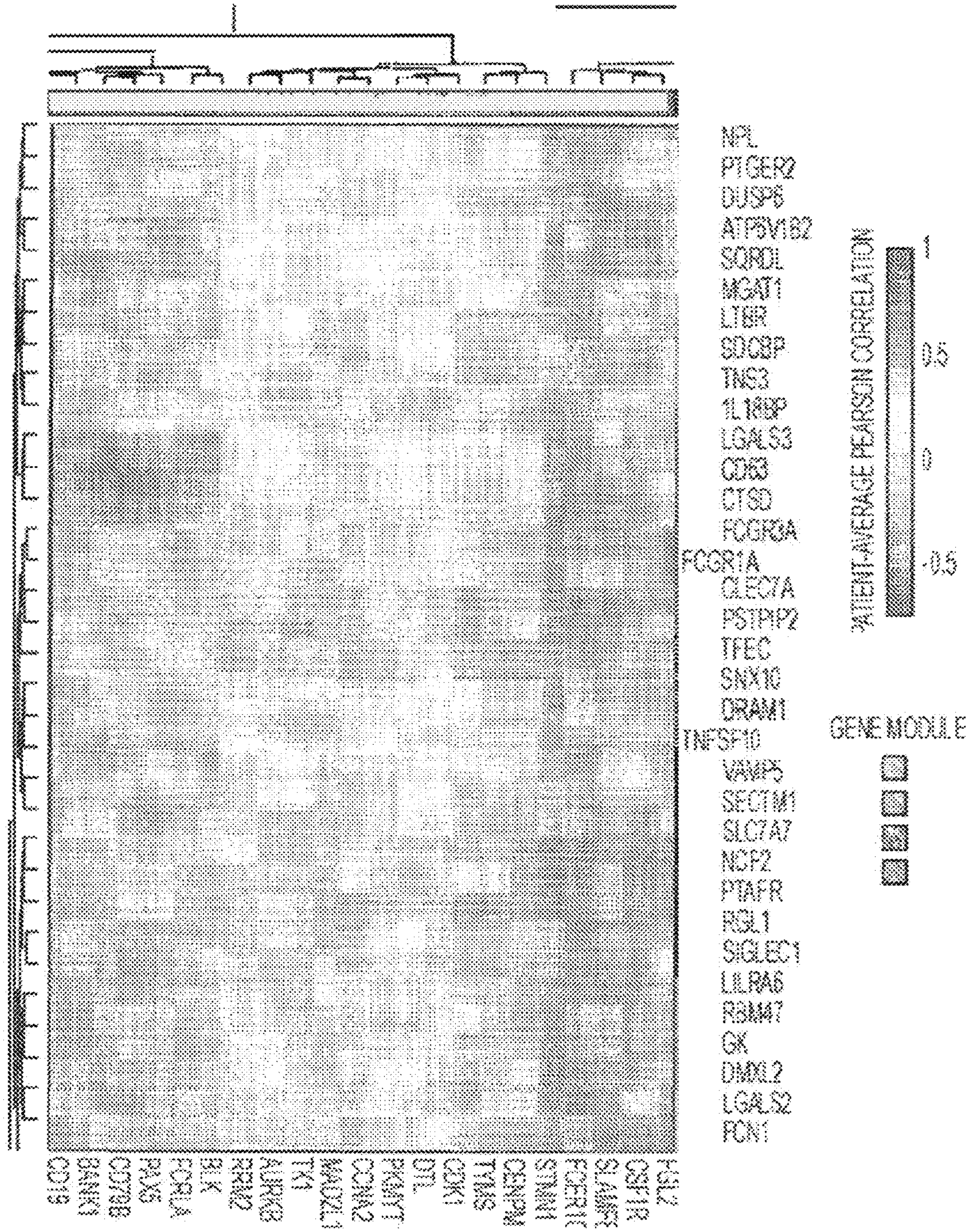
FIGS. 15Y-15LLL illustrate hierarchical clustering of genes (from reproducible modules in a) cross cells (48 hour single cell data from p1, p2, p3) heatmap.
Figure 15C:
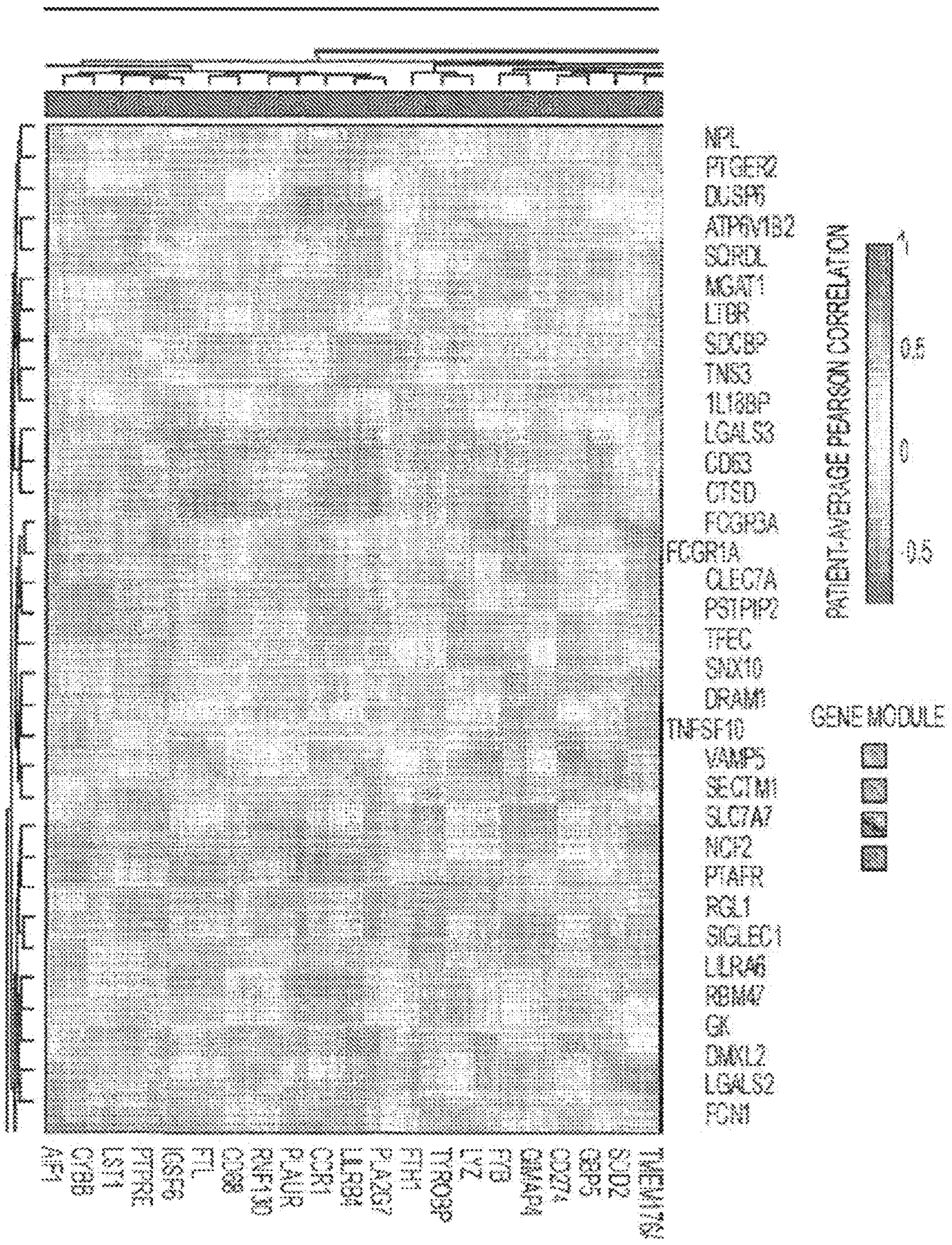
Figure 15D:
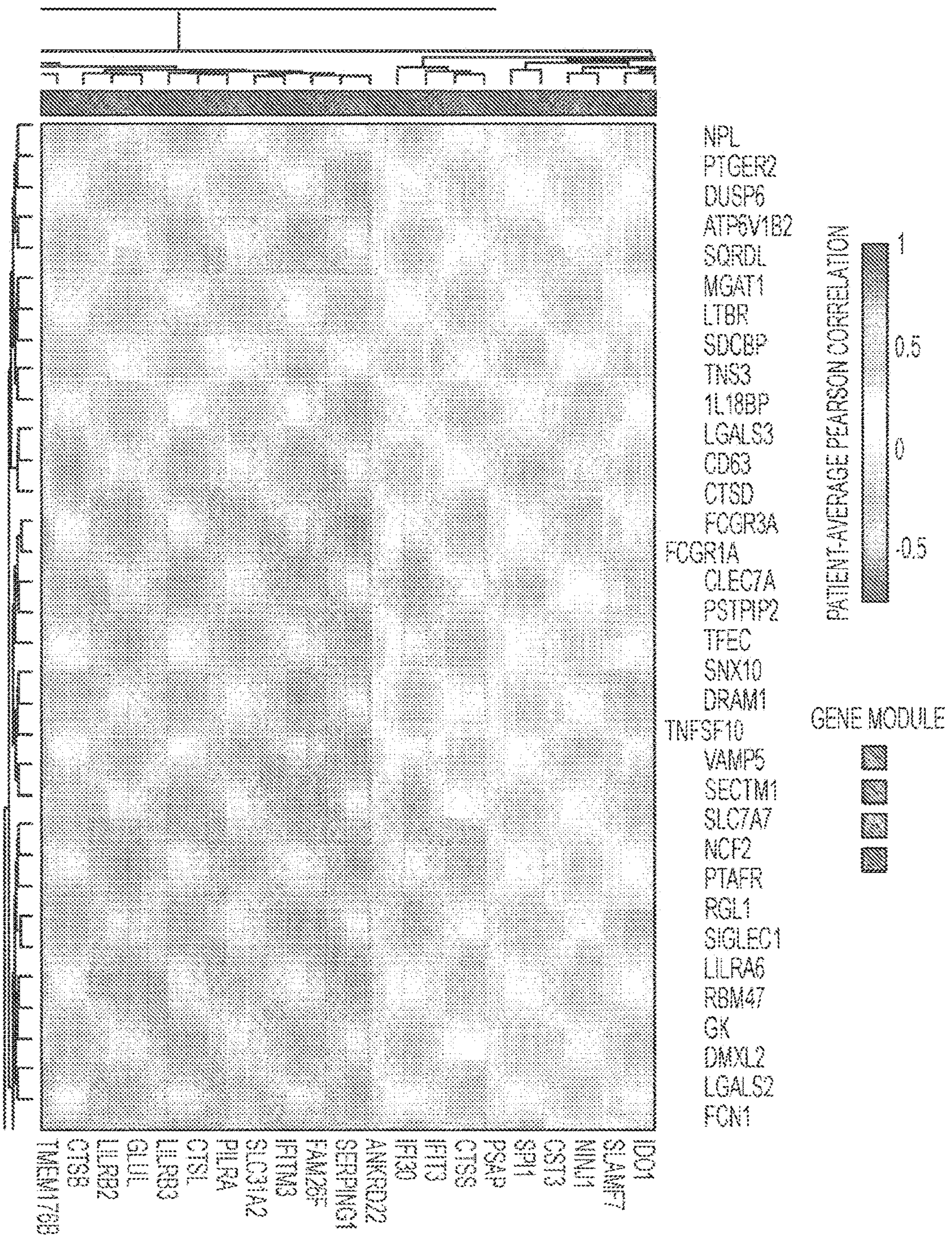
Figure 15E:
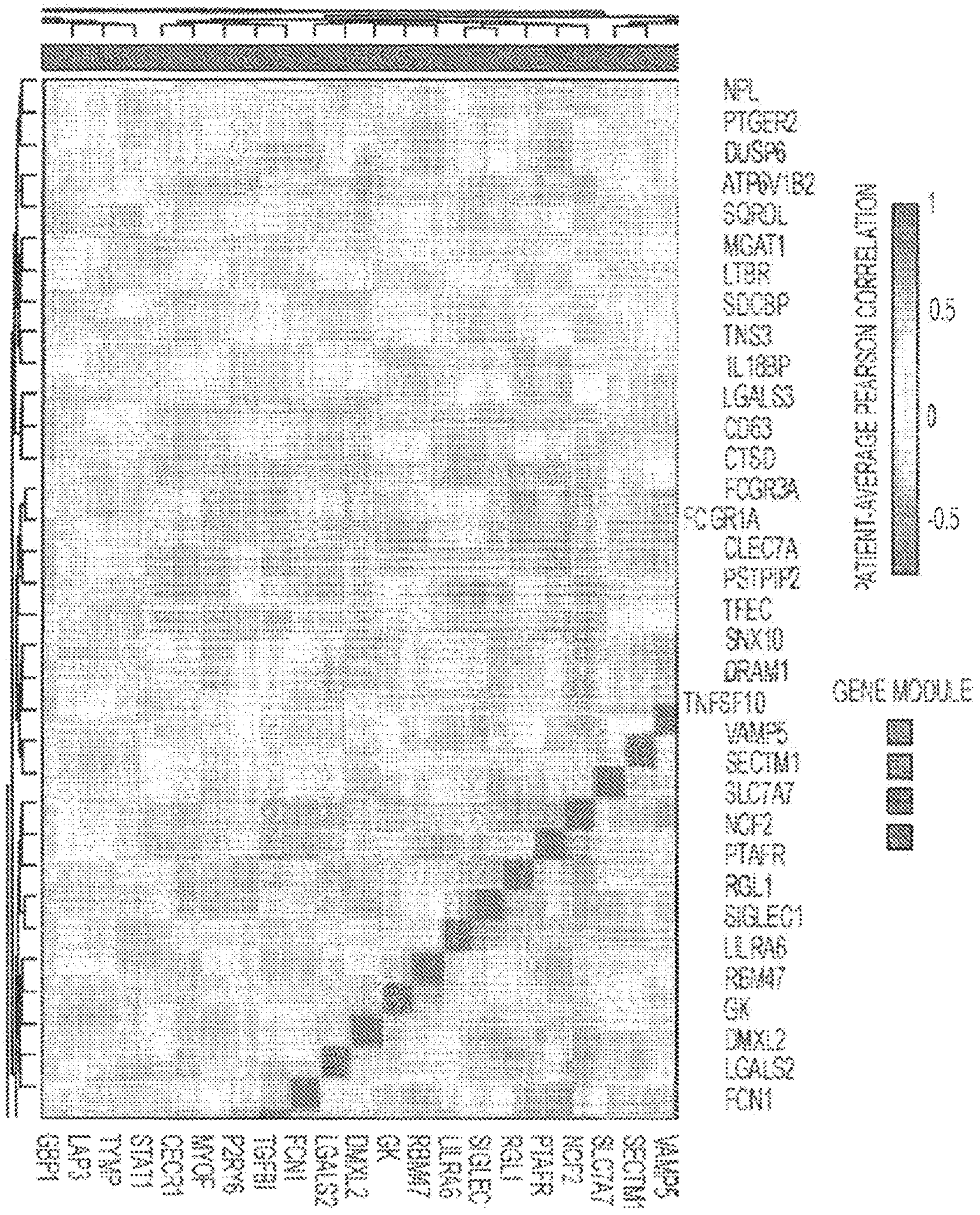
Figure 15F:
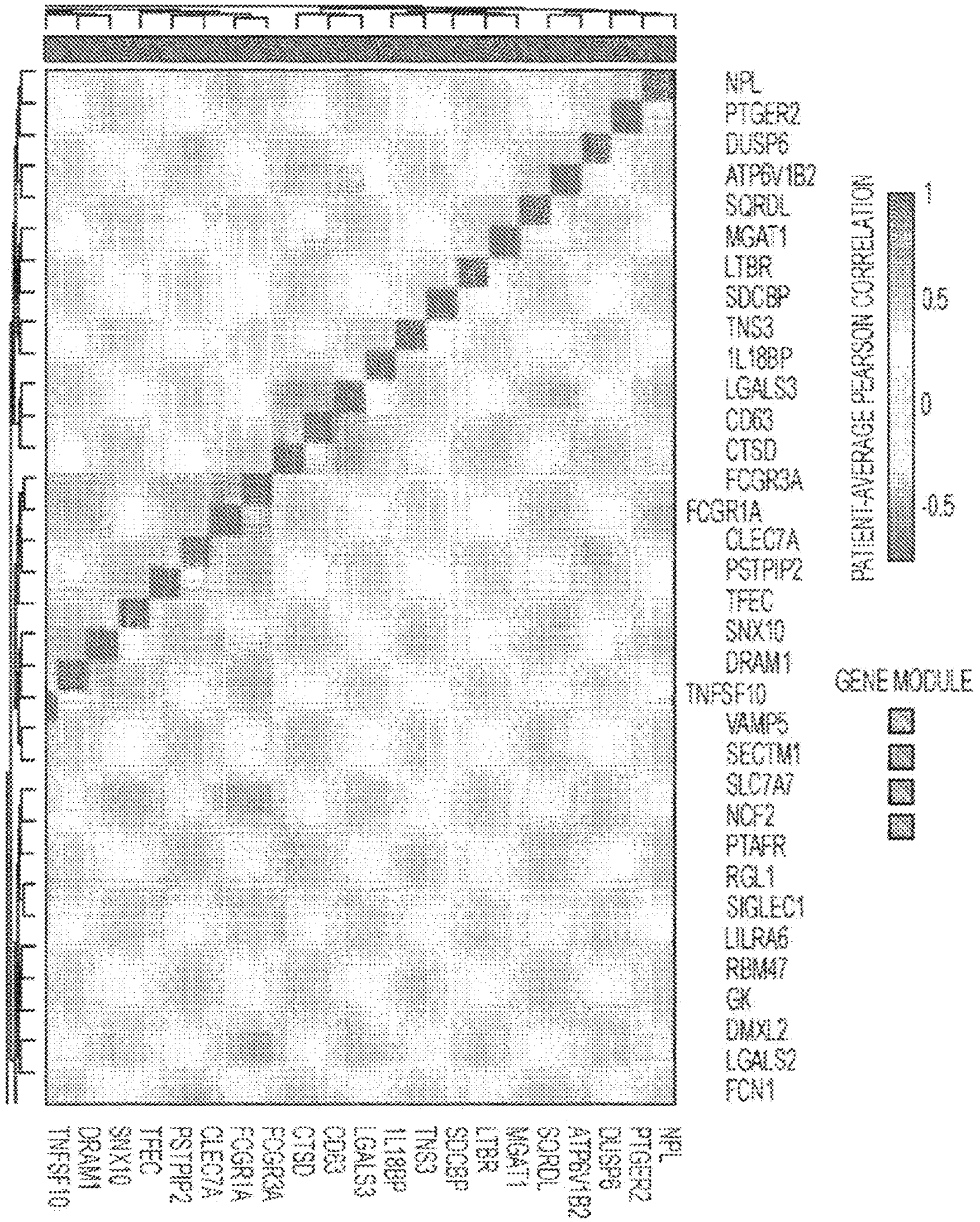
Figure 15G:
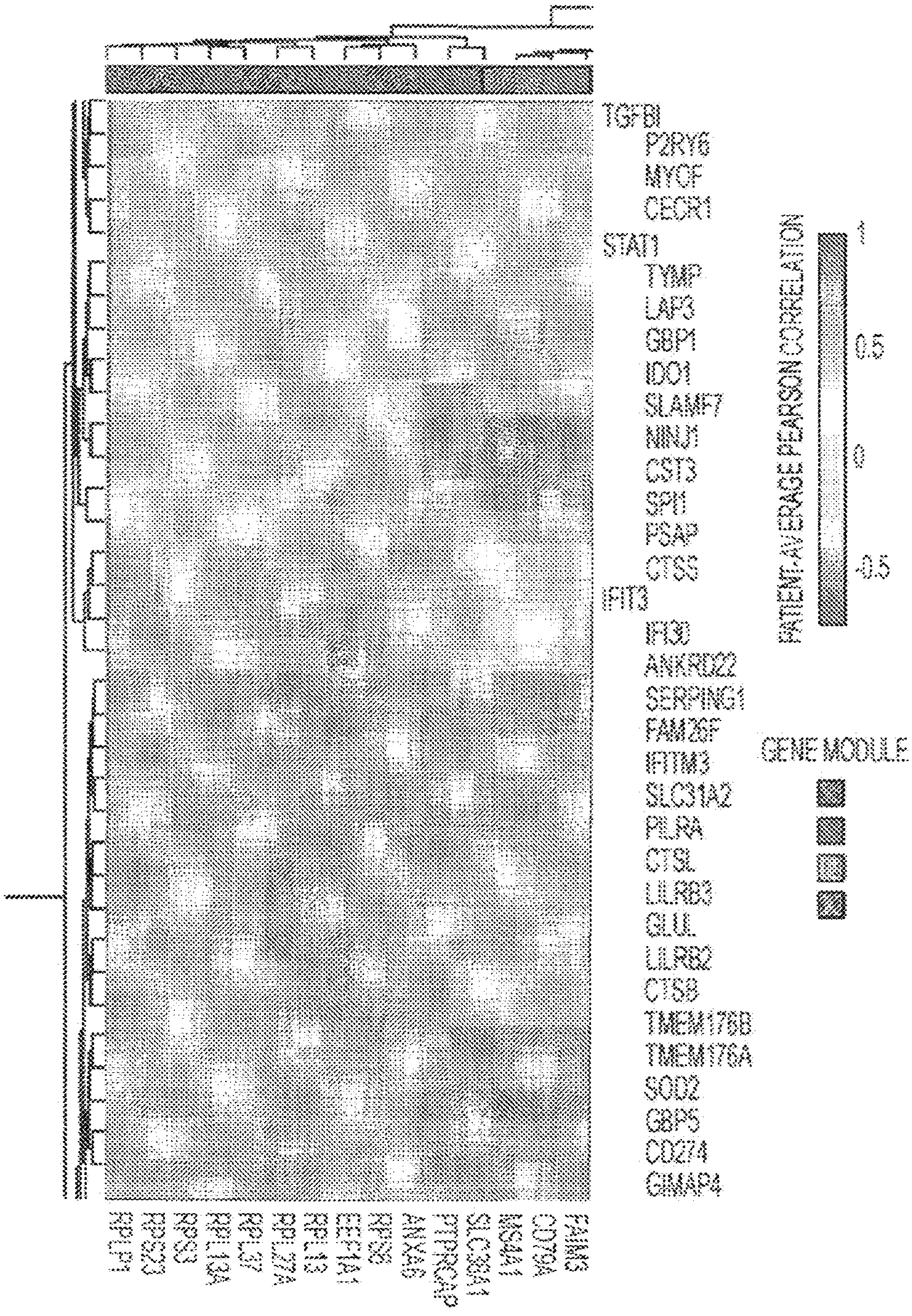
Figure 15H:
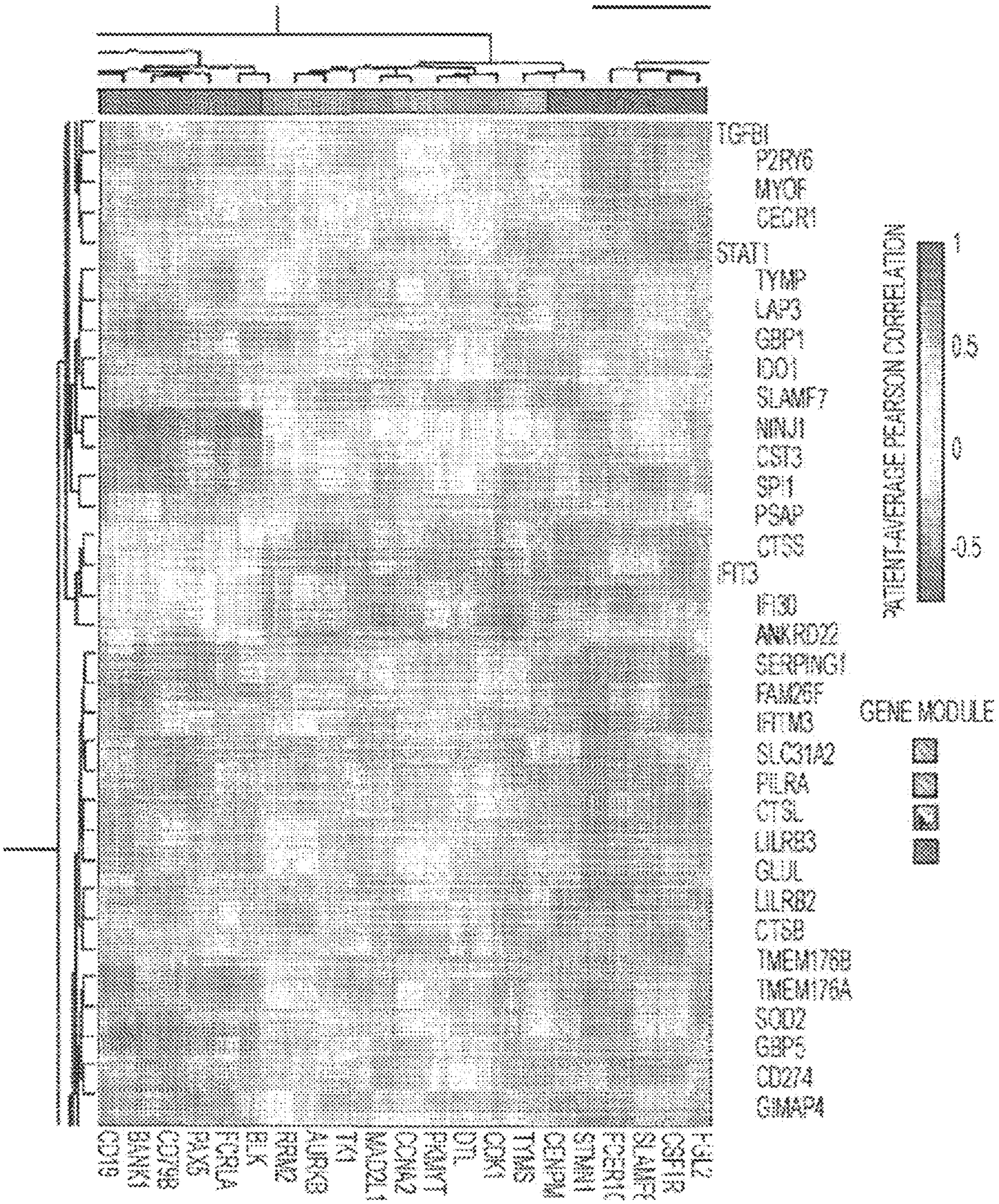
Figure 15I:
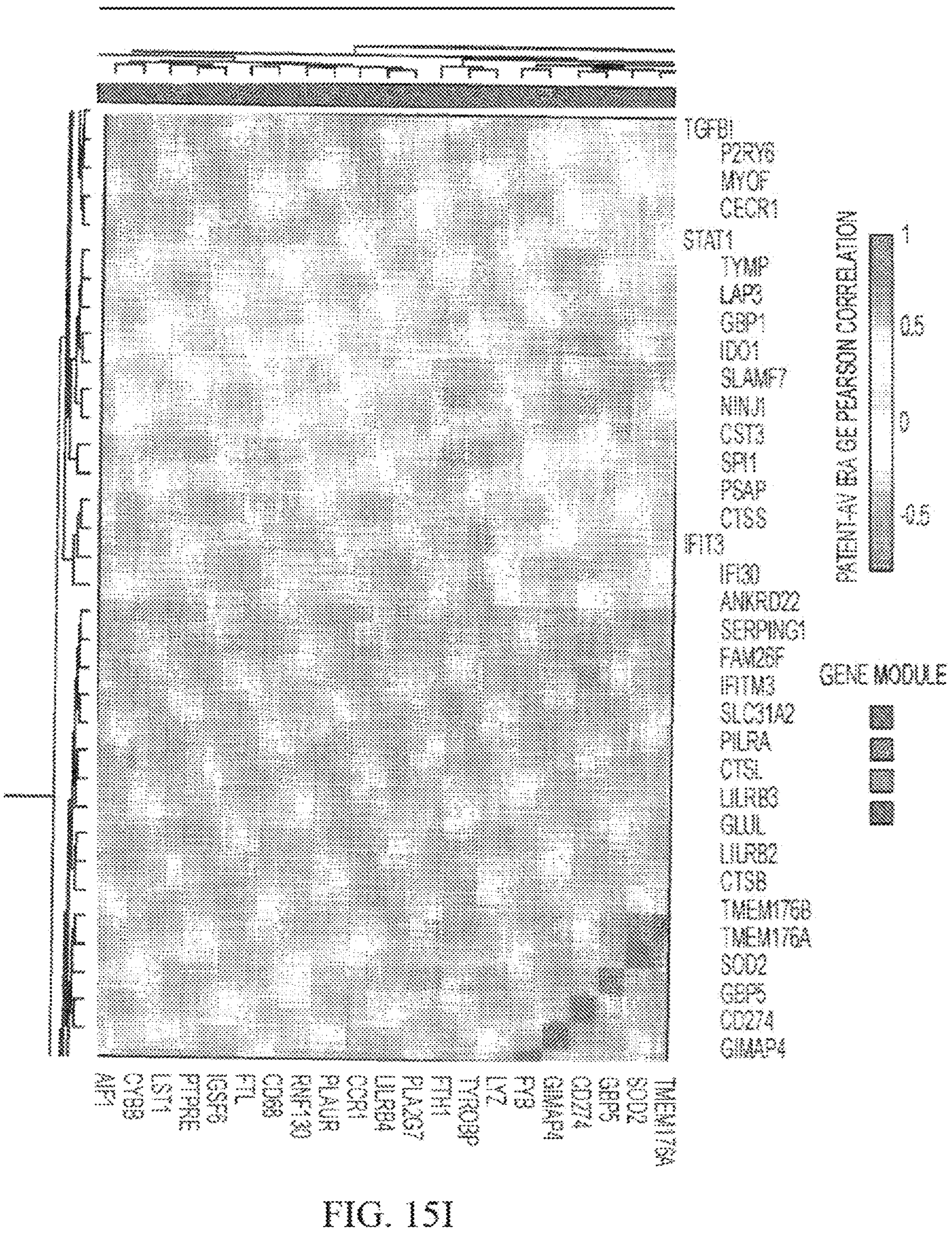
Figure 15J:
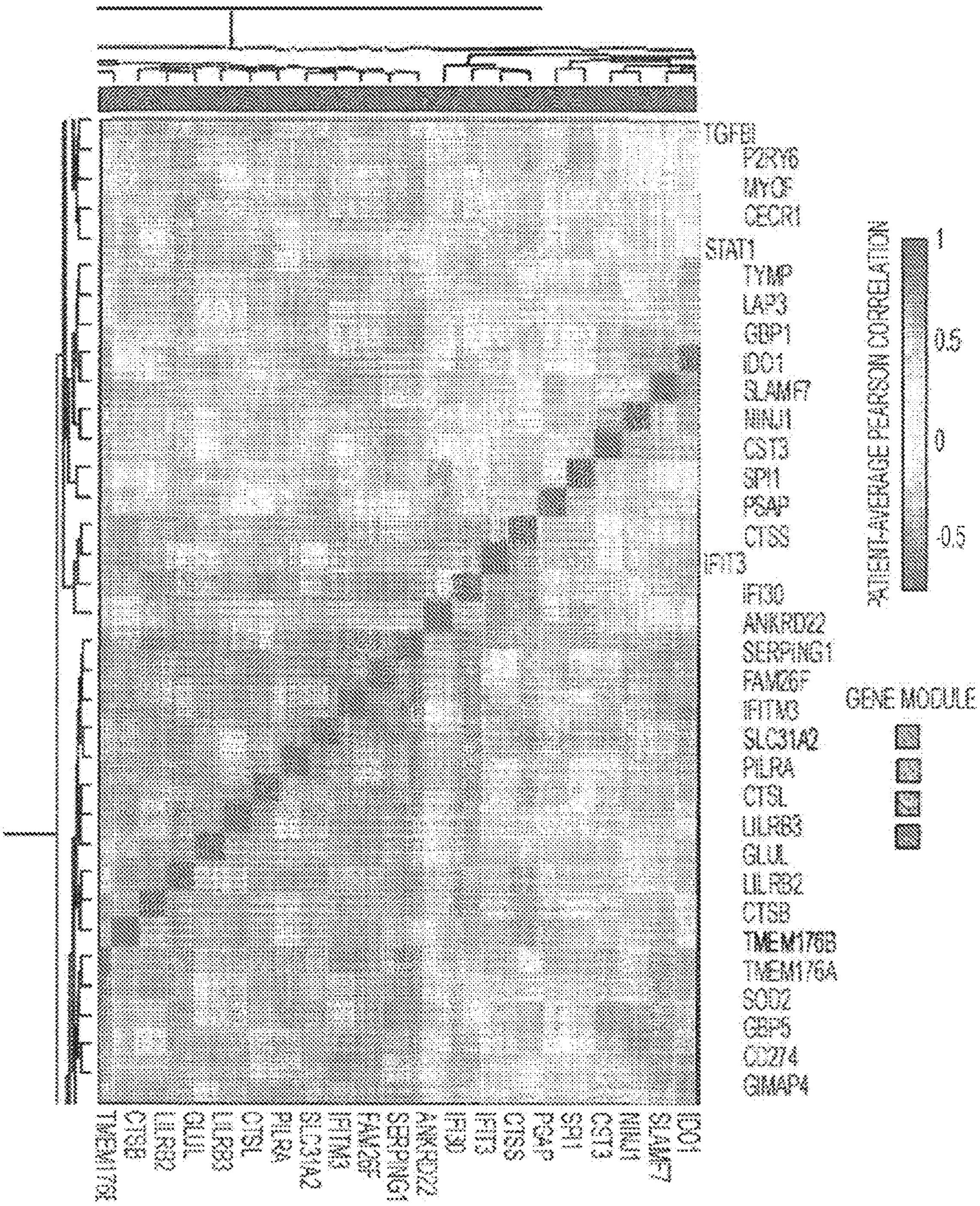
Figure 15K:
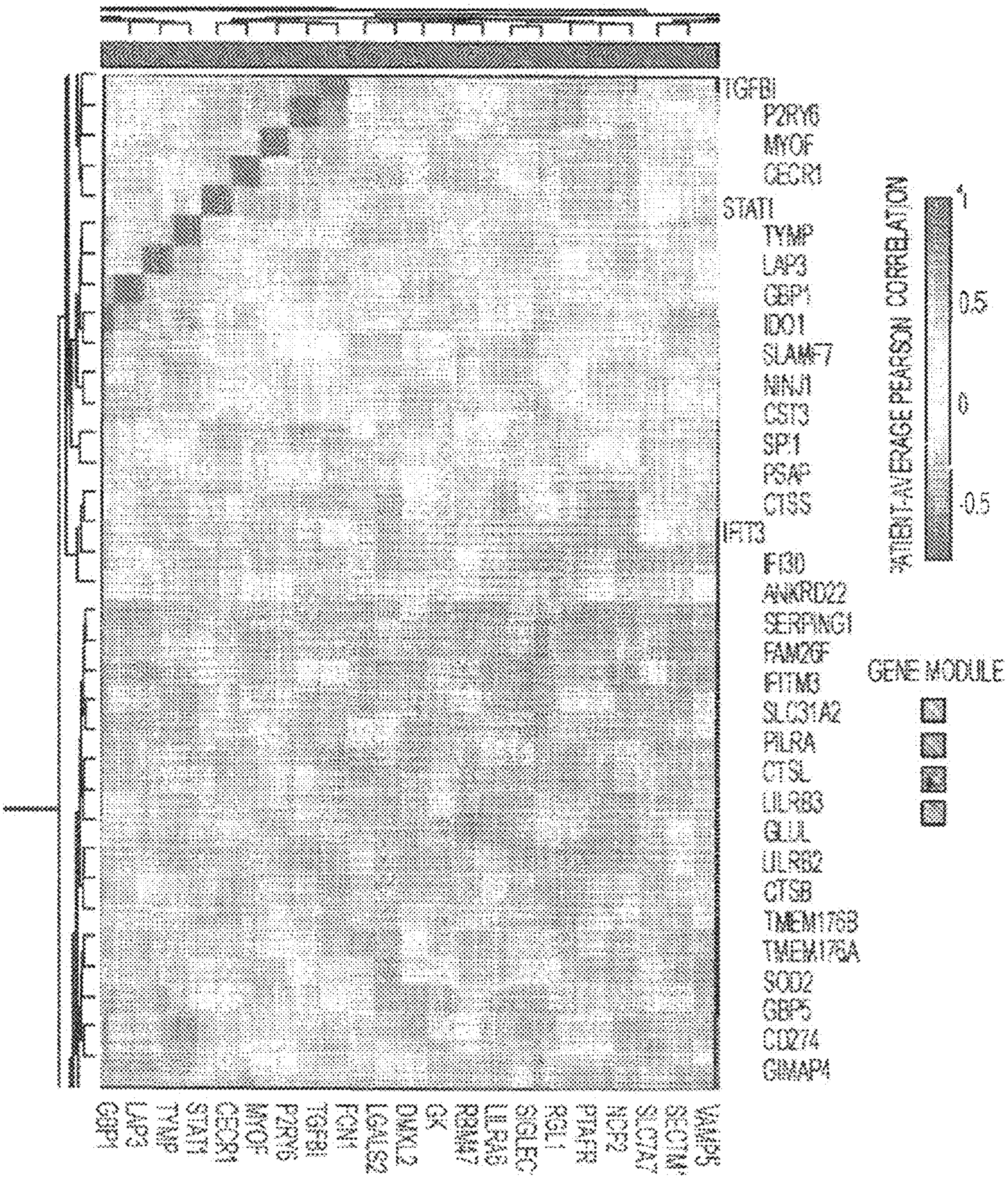
Figure 15L:
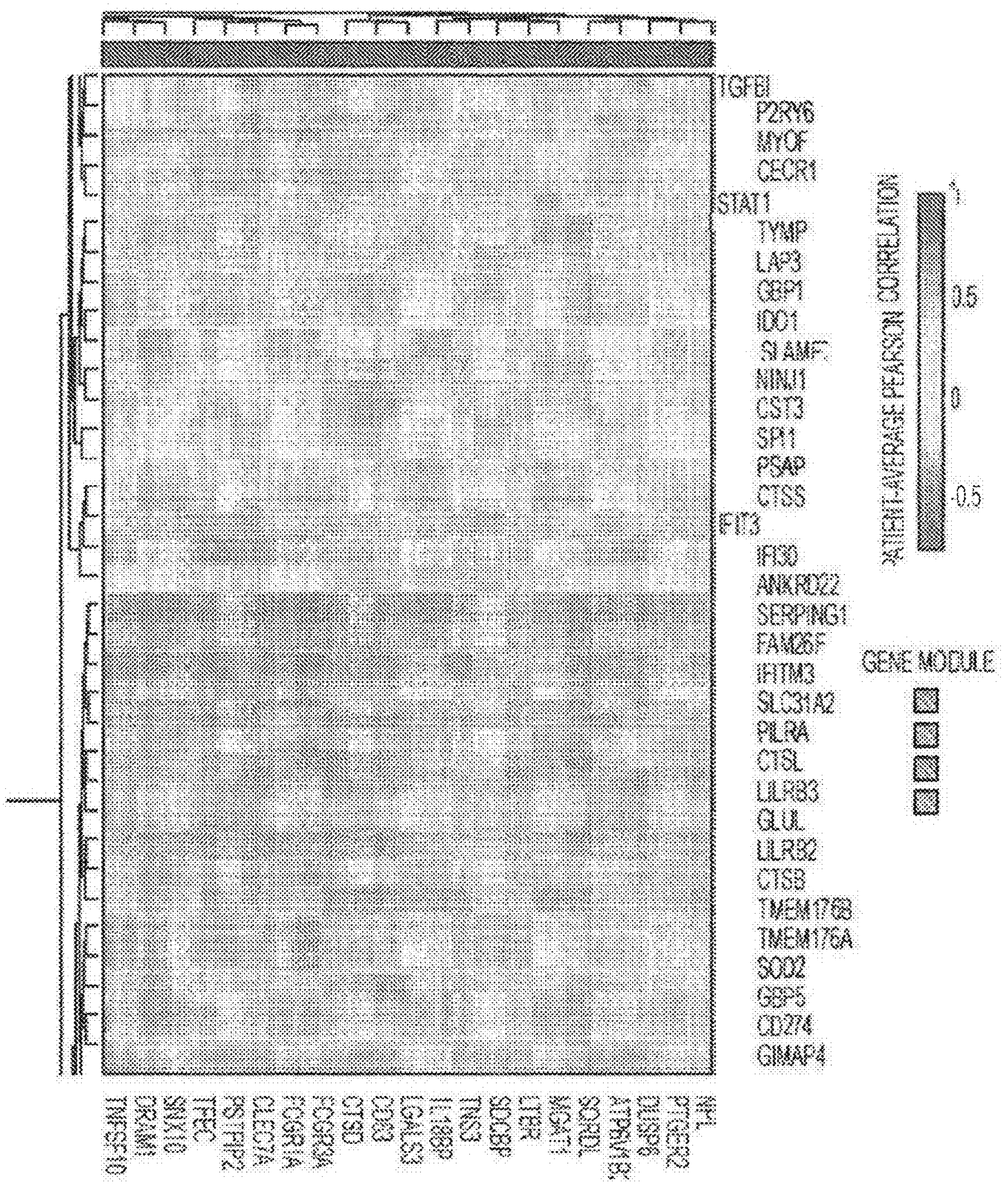
Figure 15M:
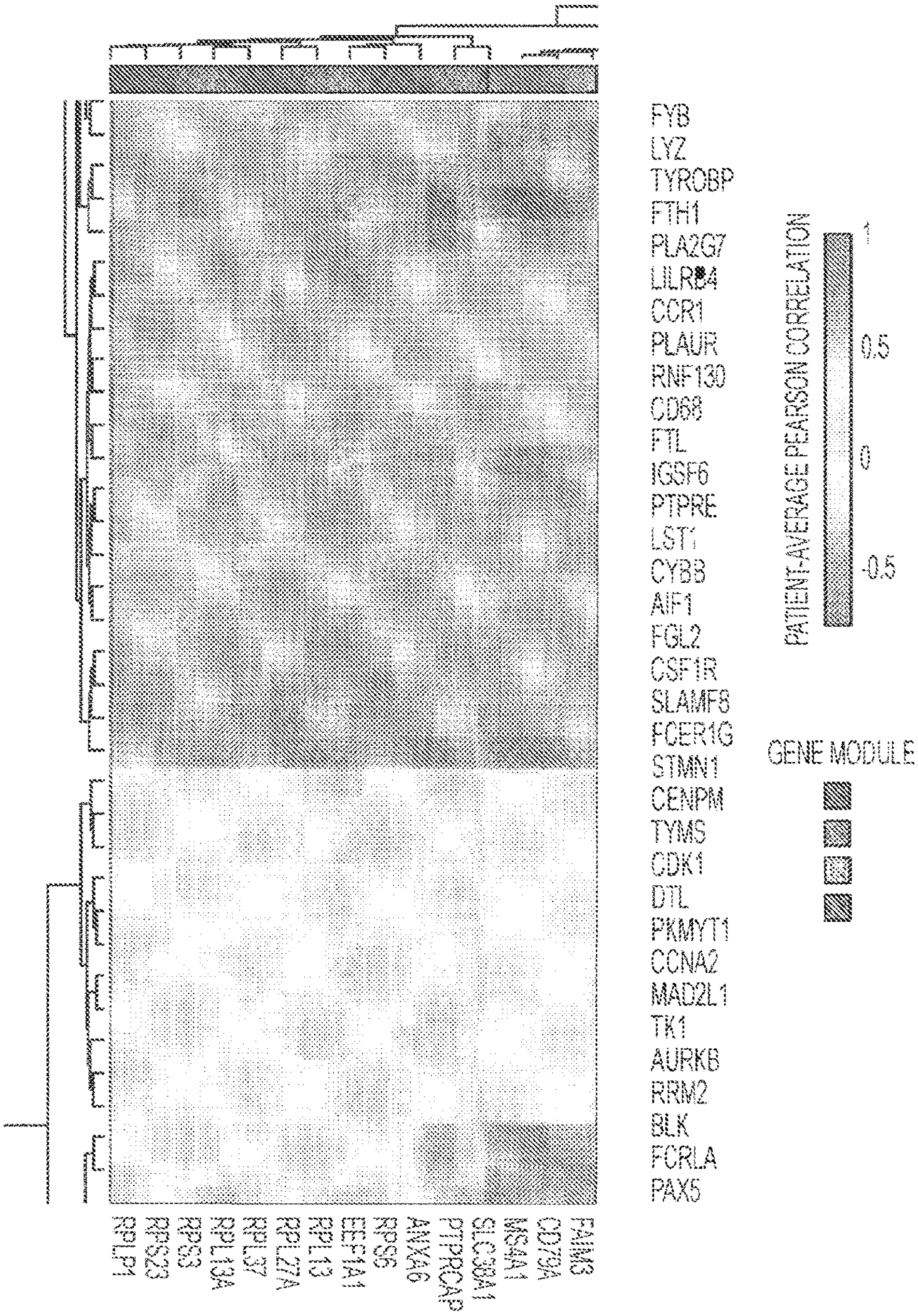
Figure 15N:
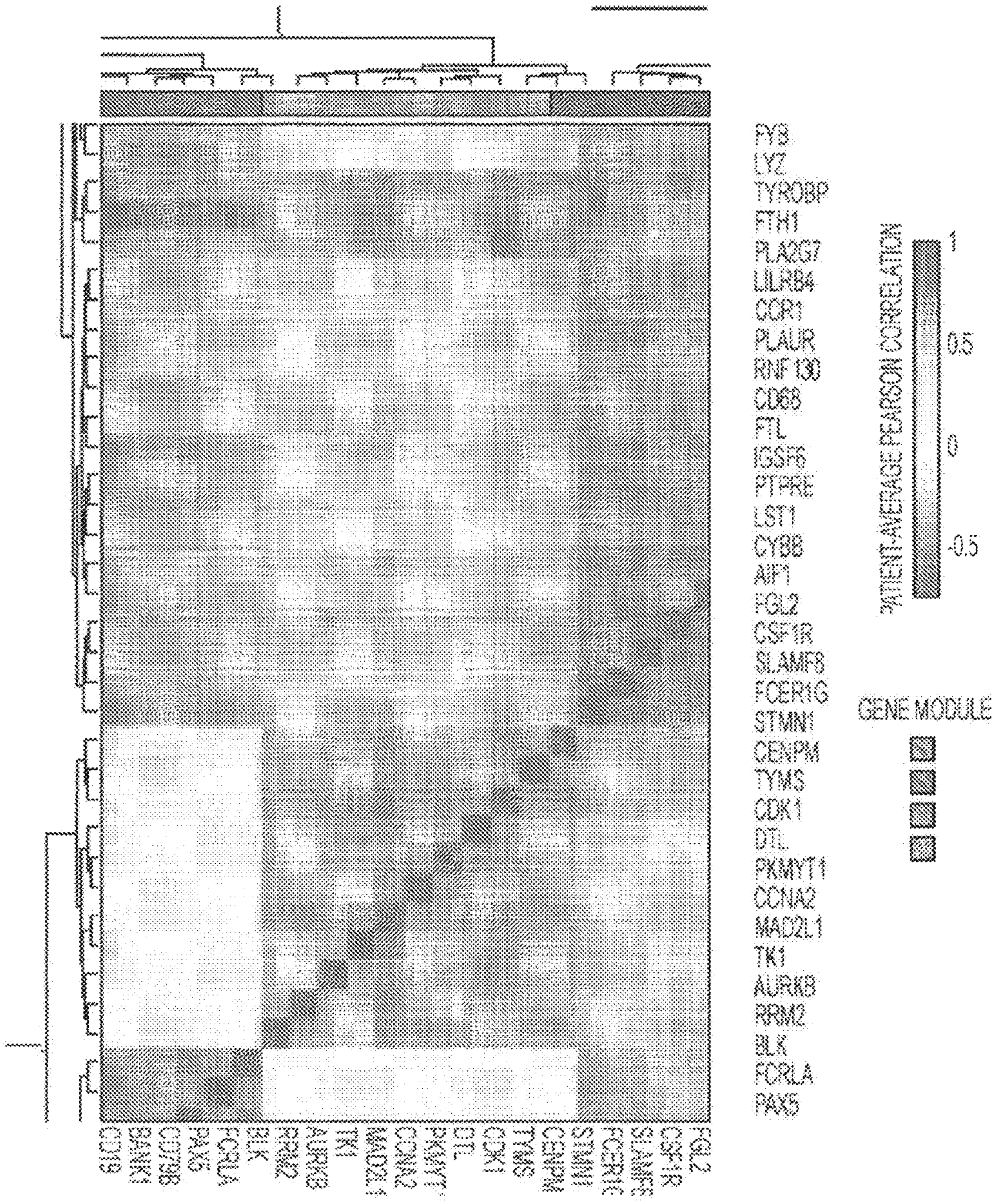
Figure 15O:
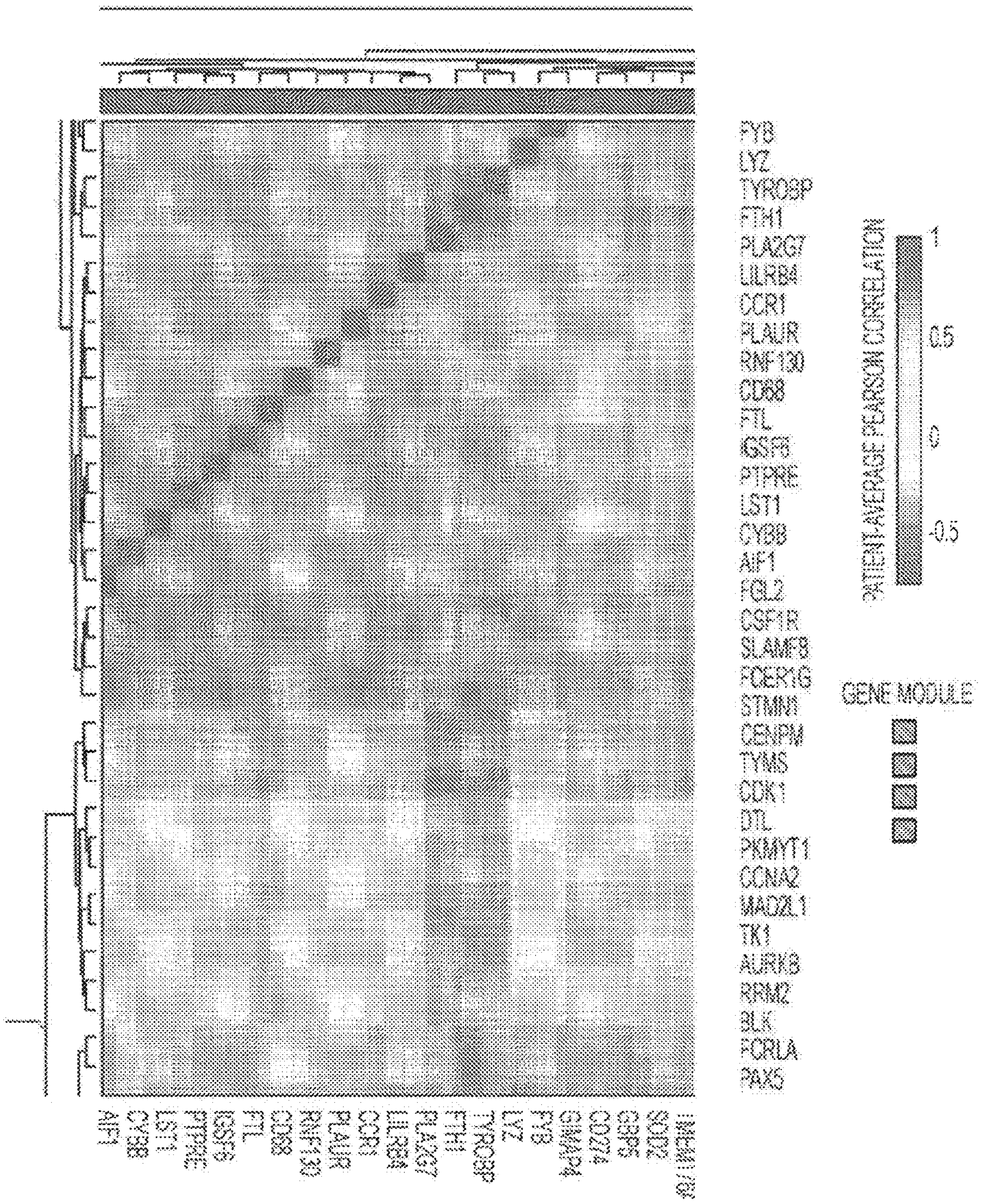
Figure 15P:
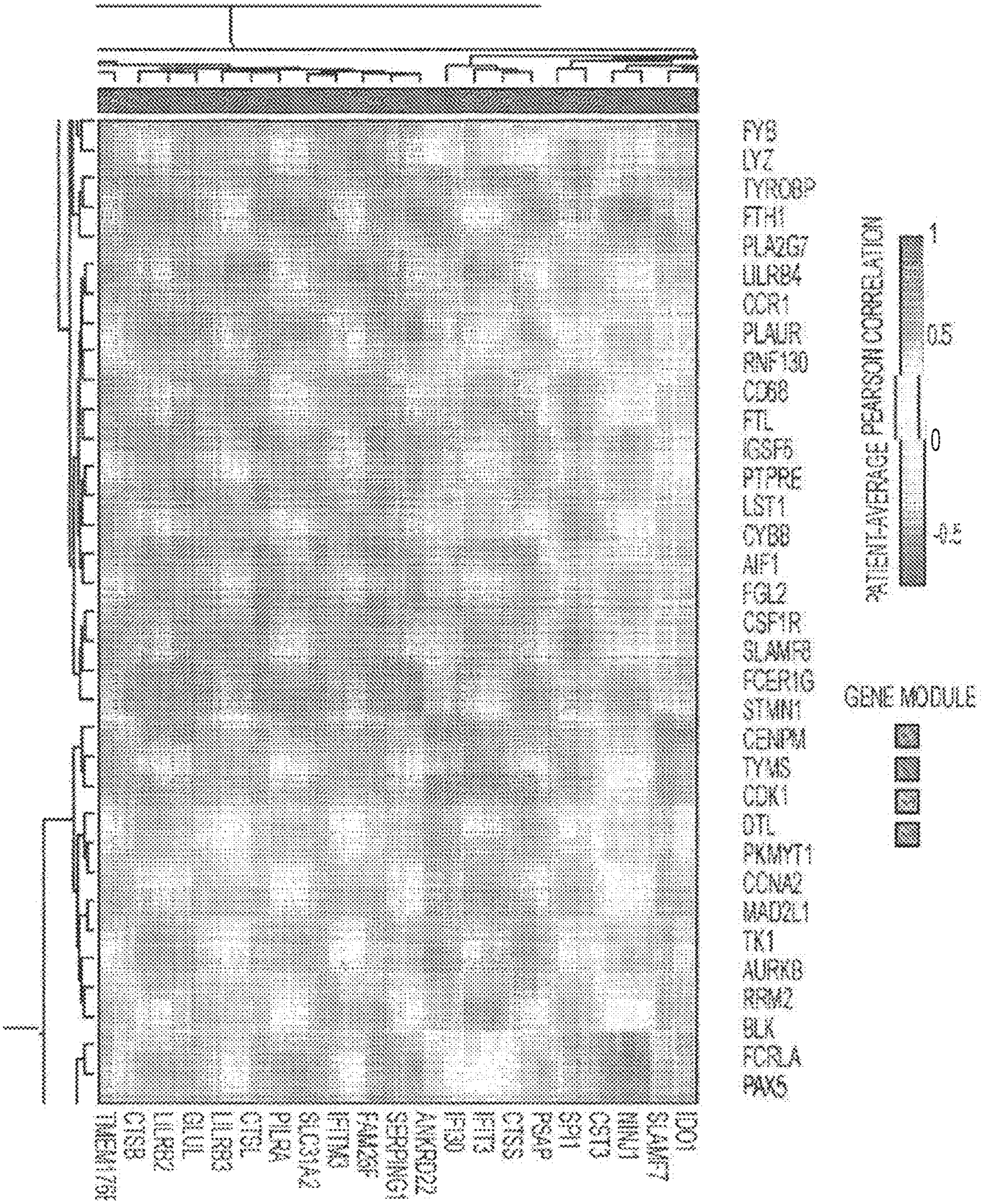
Figure 15Q:
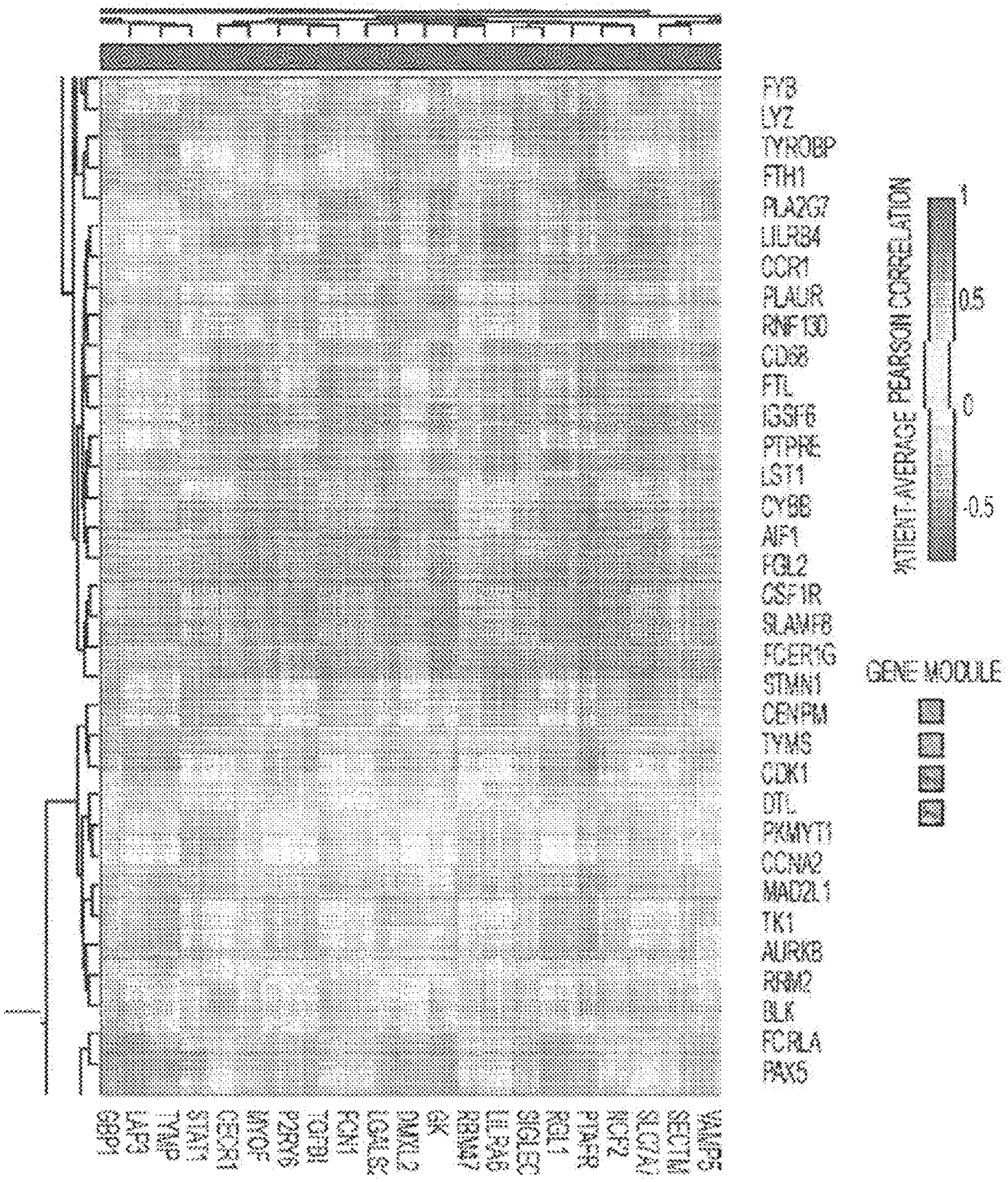
Figure 15R:
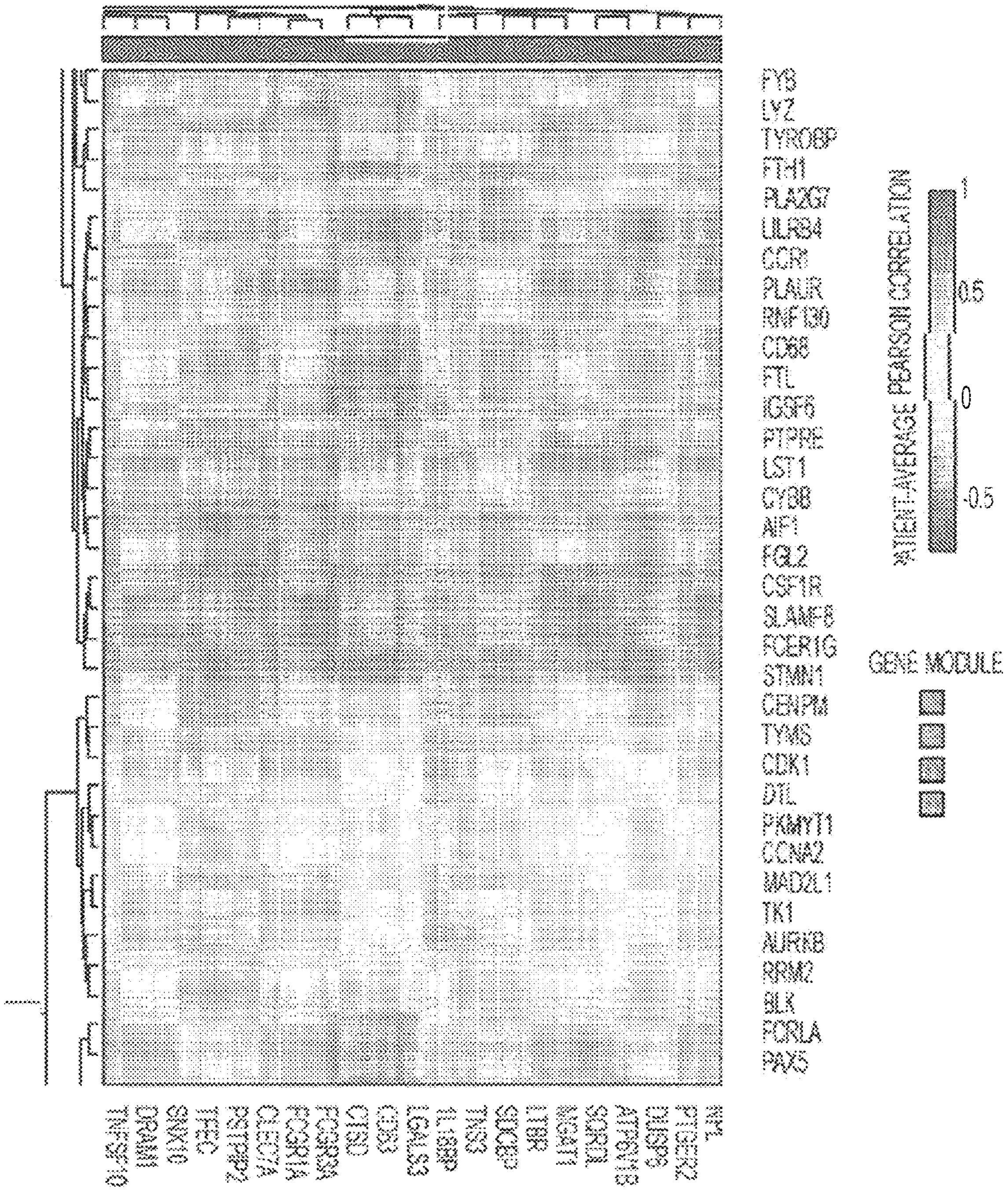
Figure 15S:
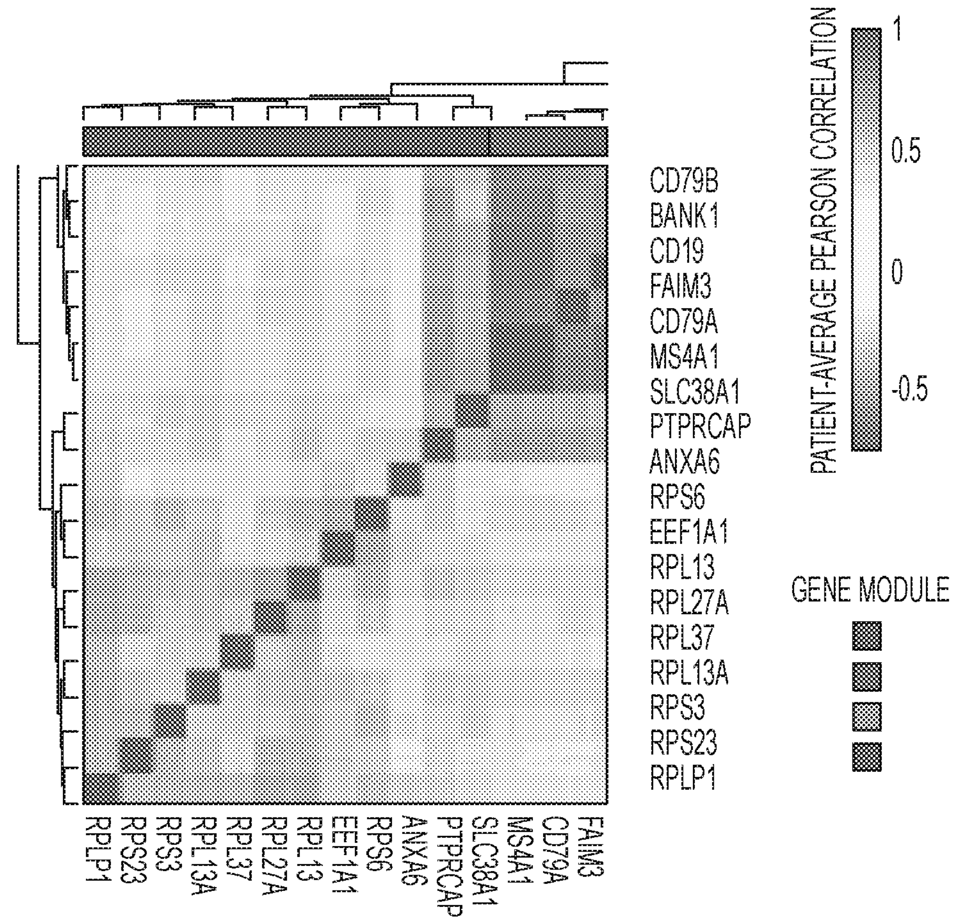
Figure 15T:
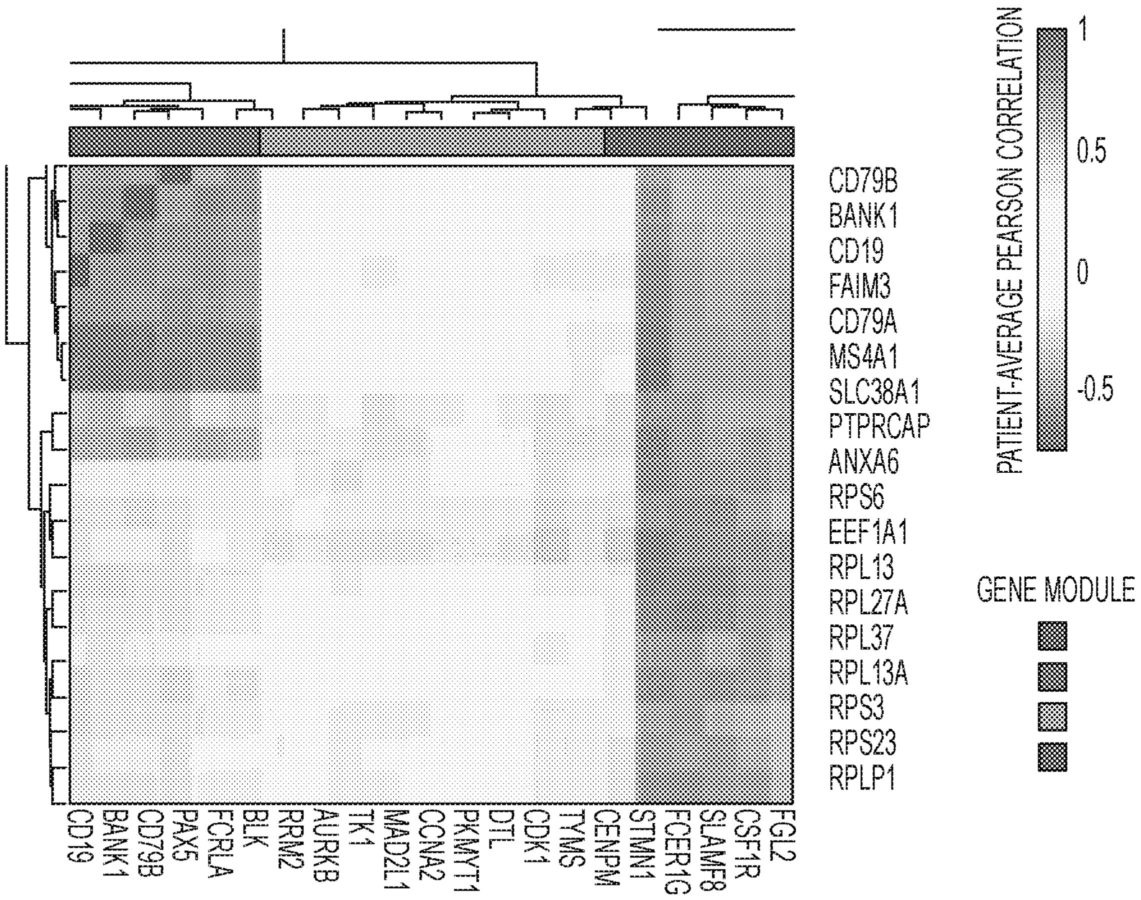
Figure 15U:
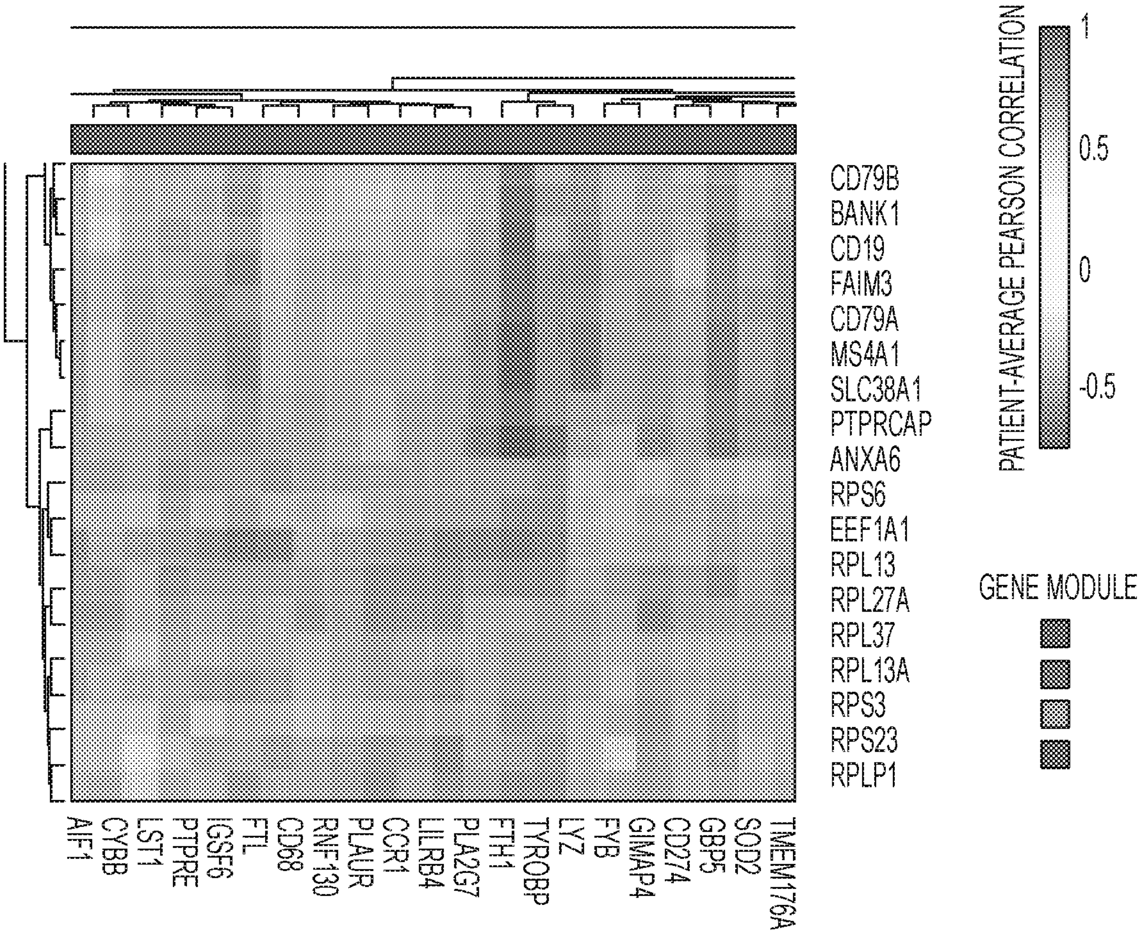
Figure 15V:
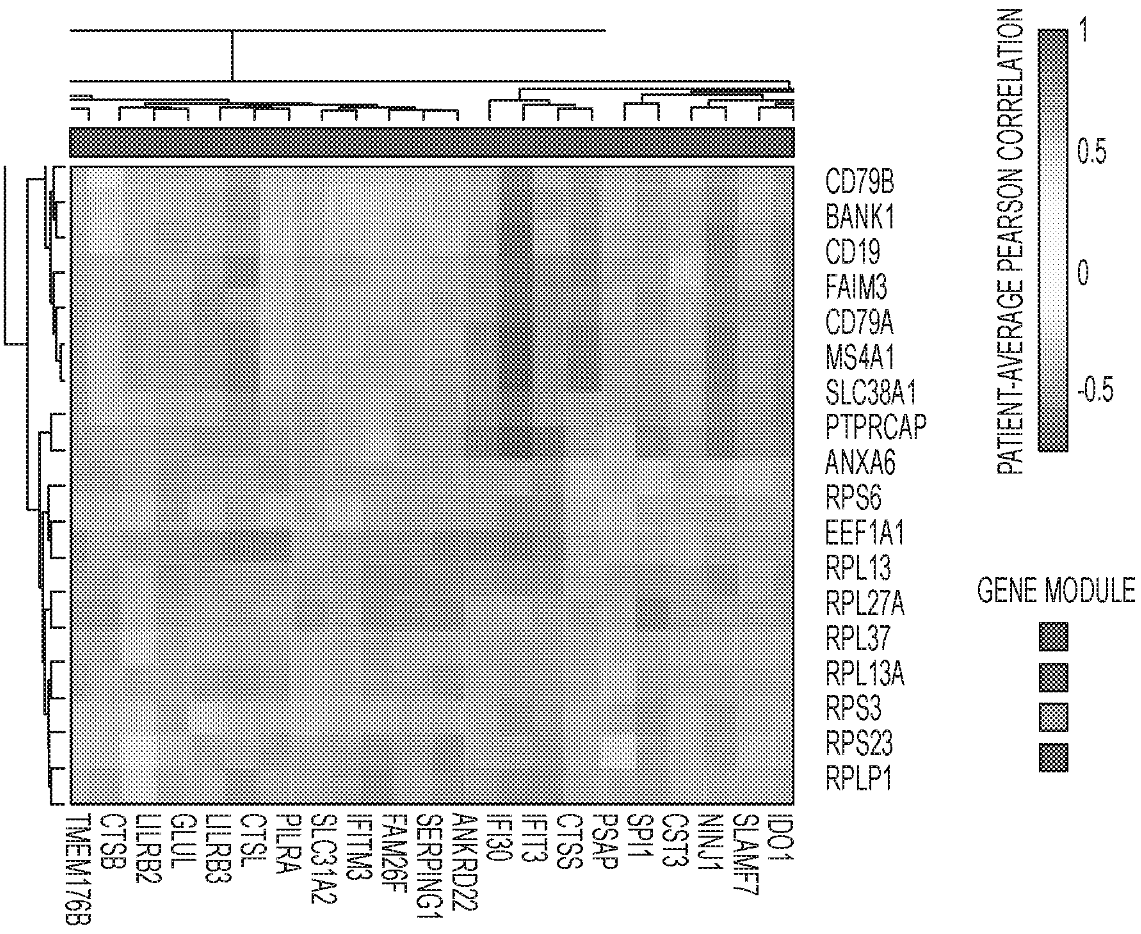
Figure 15W:
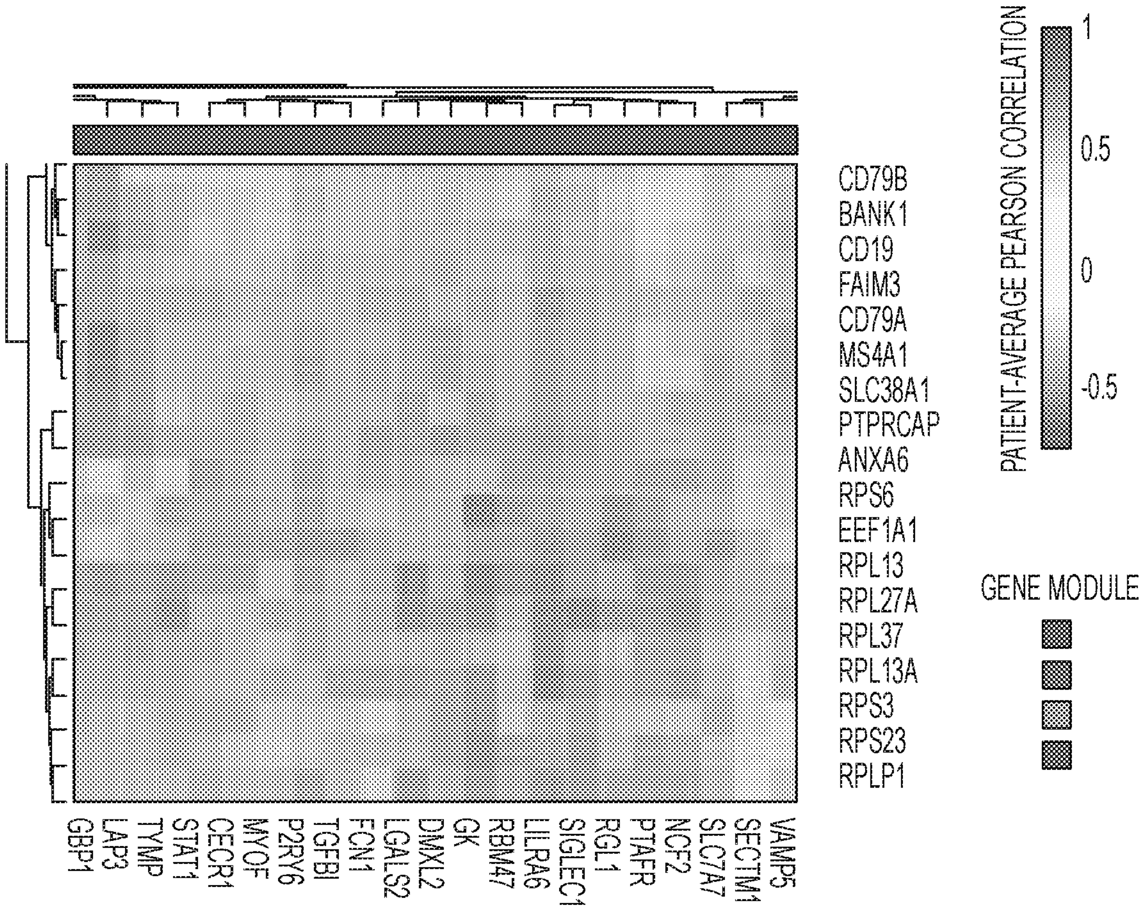
Figure 15X:
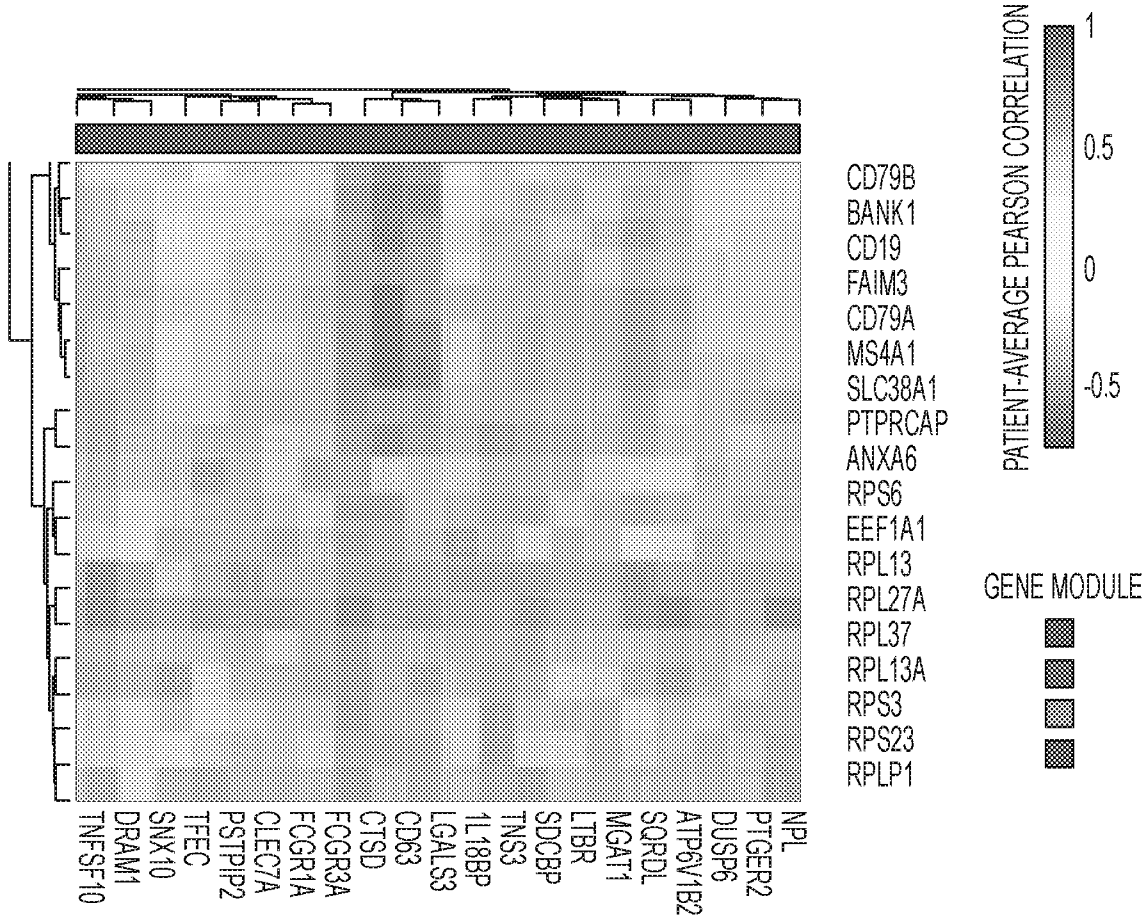
Figure 15Y:
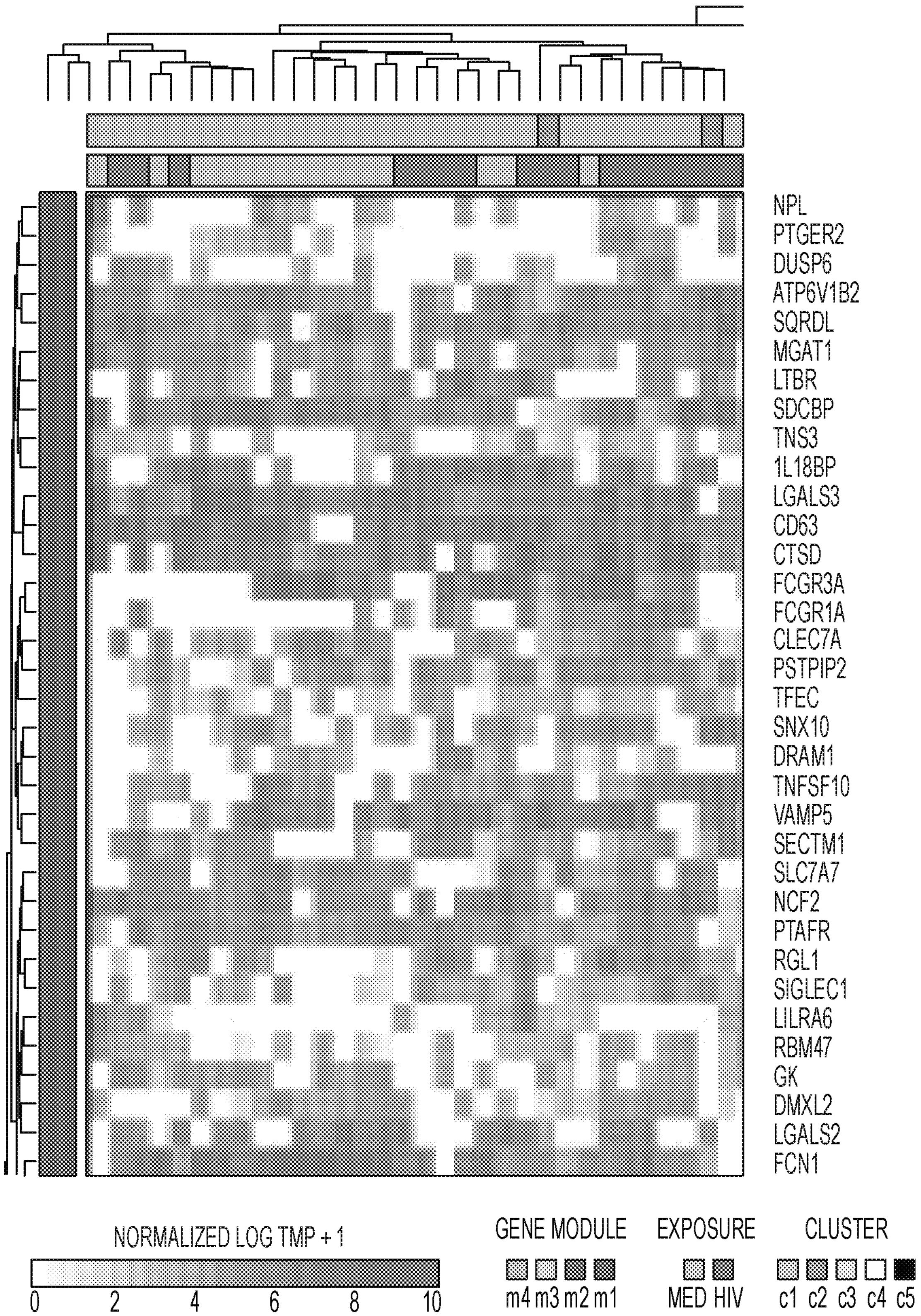
Figure 15Z:
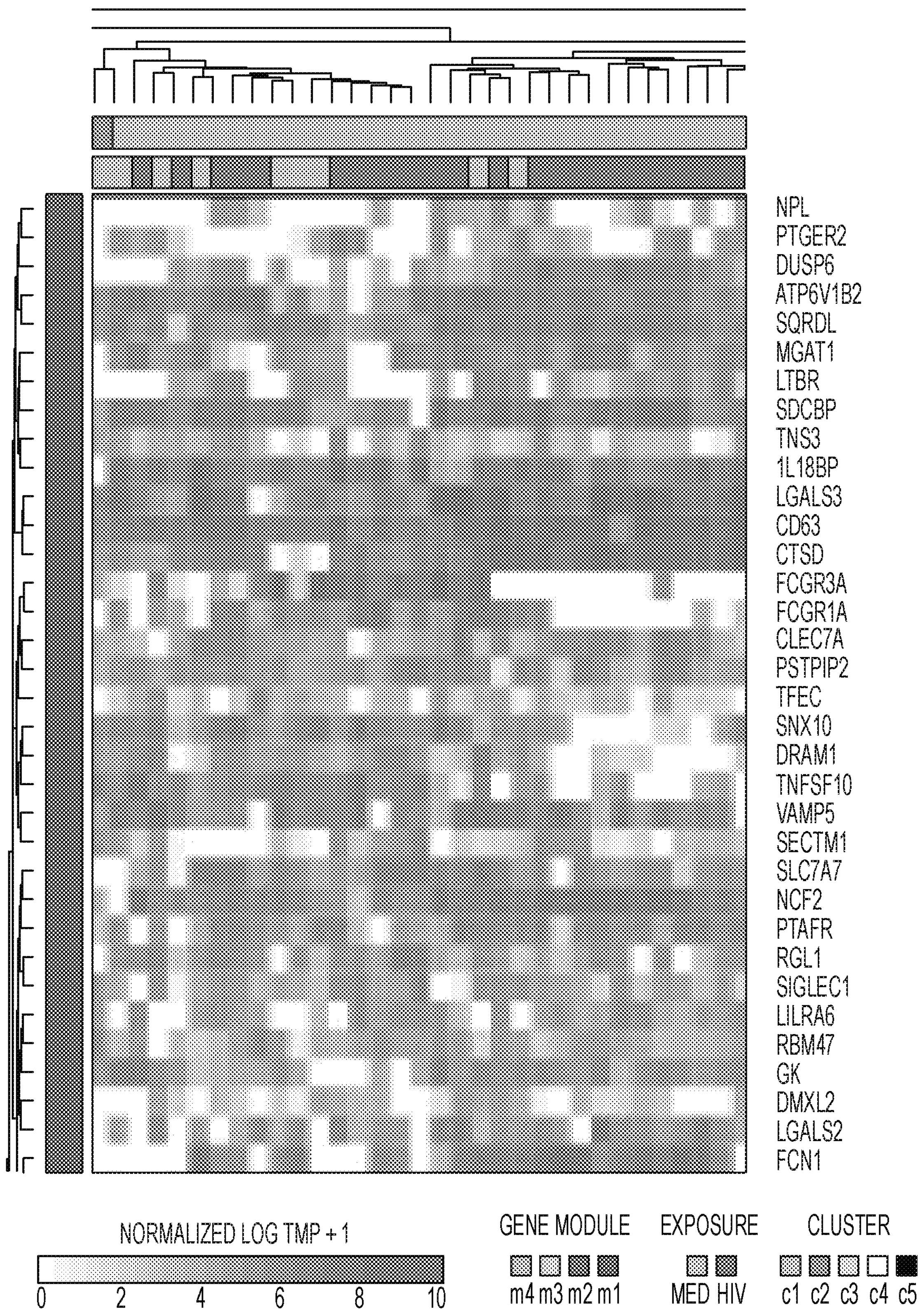
Figure 15A:
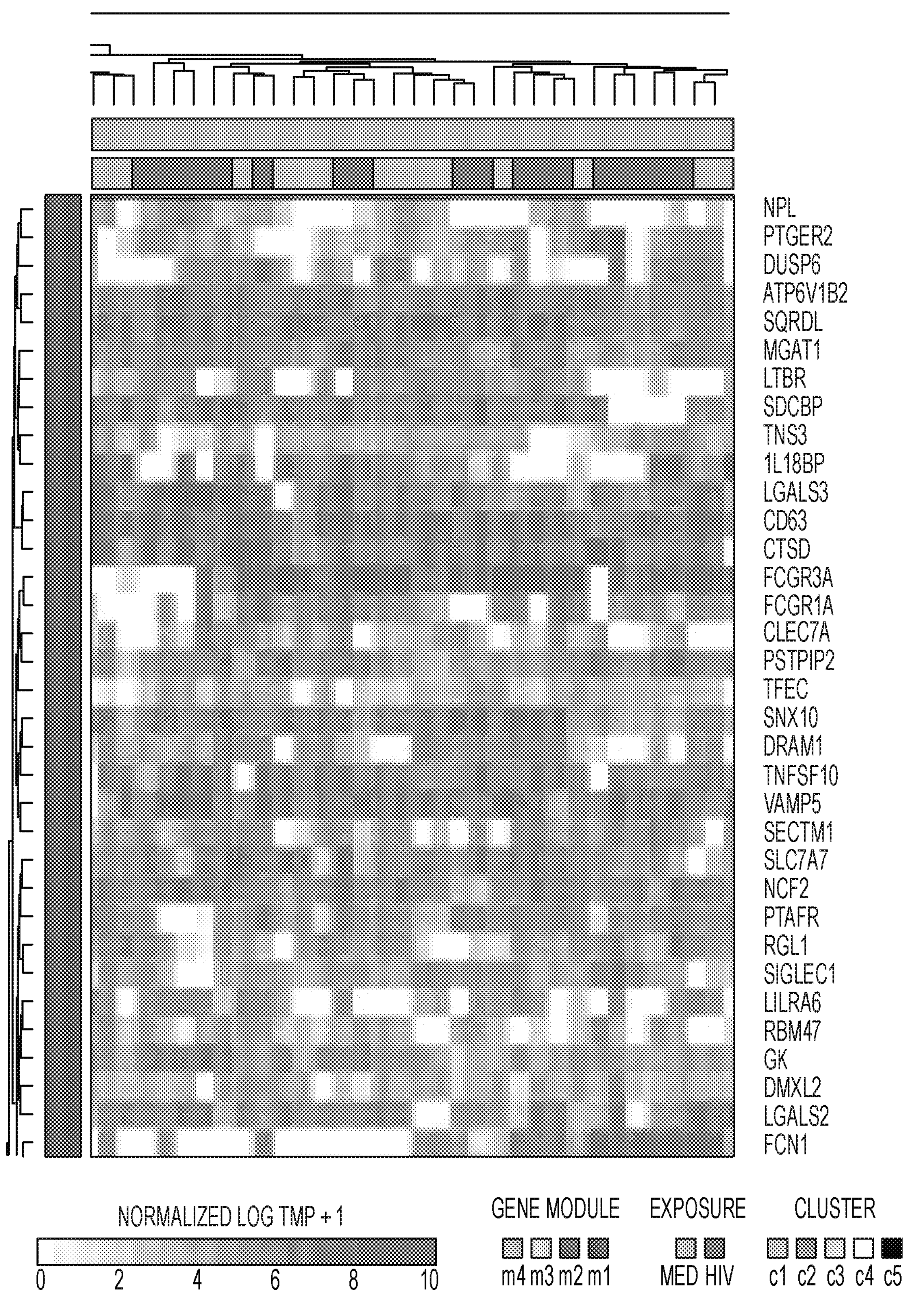
Figure 15B:
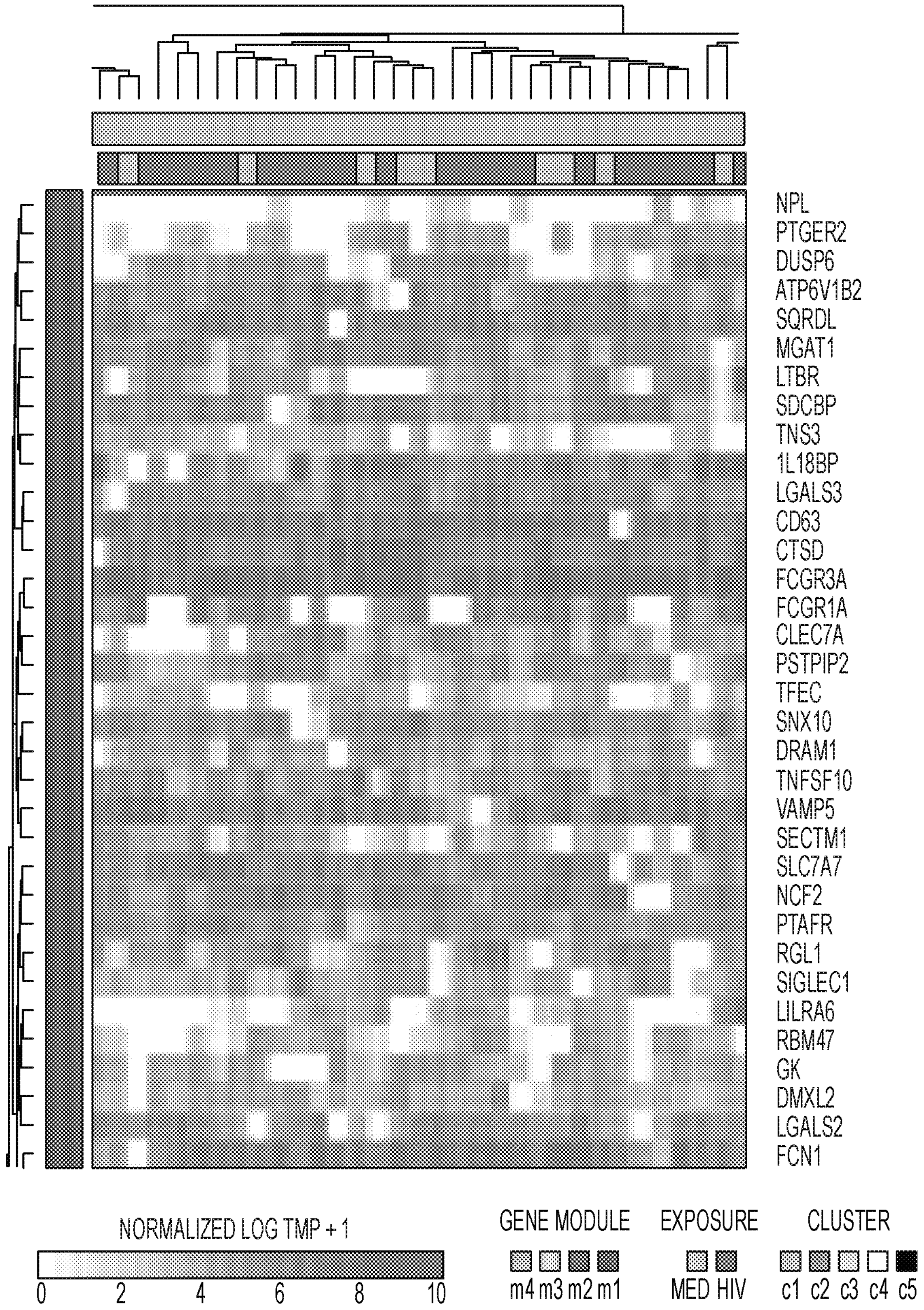
Figure 15C:
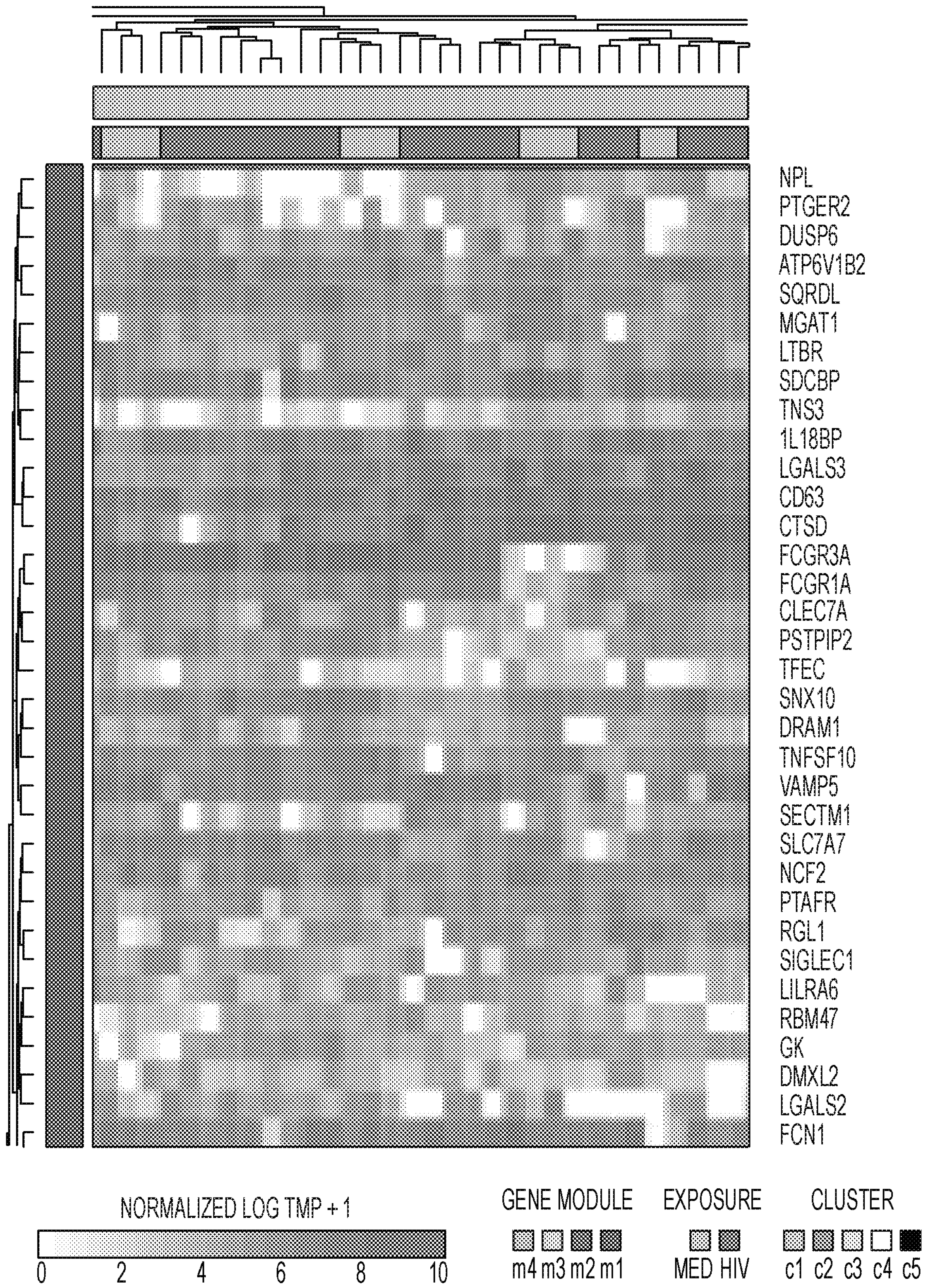
Figure 15D:
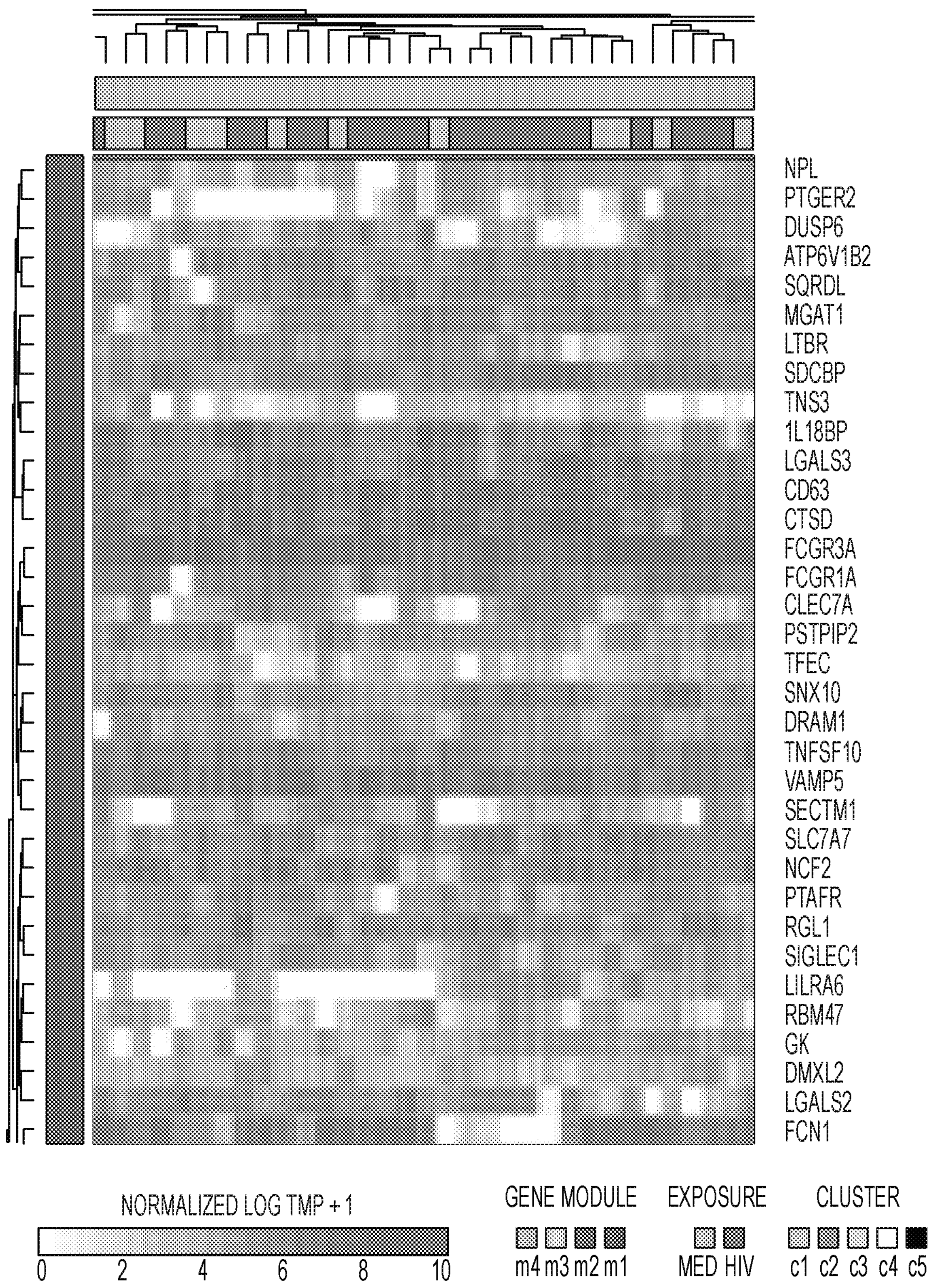
Figure 15E:
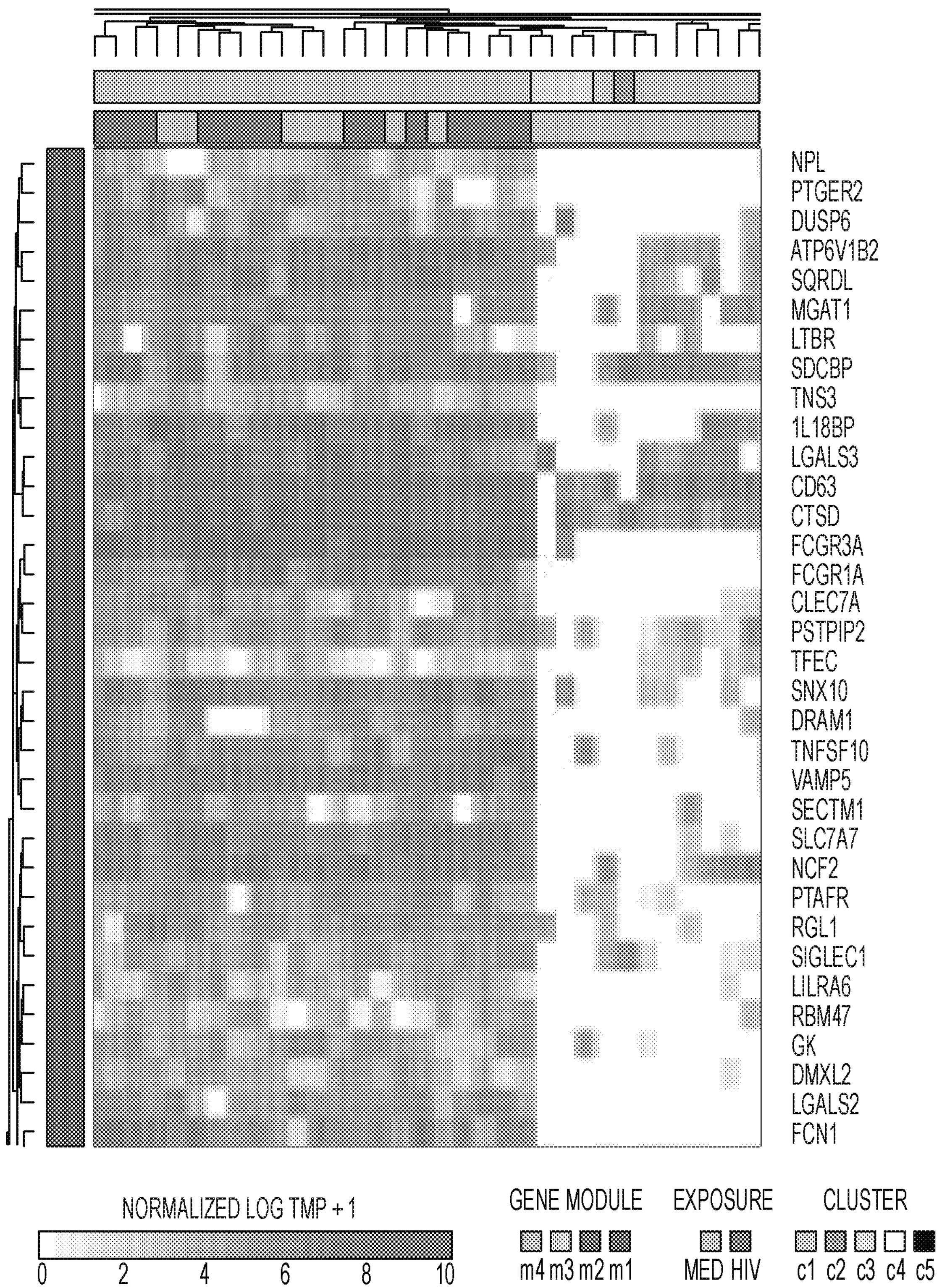
Figure 15F:
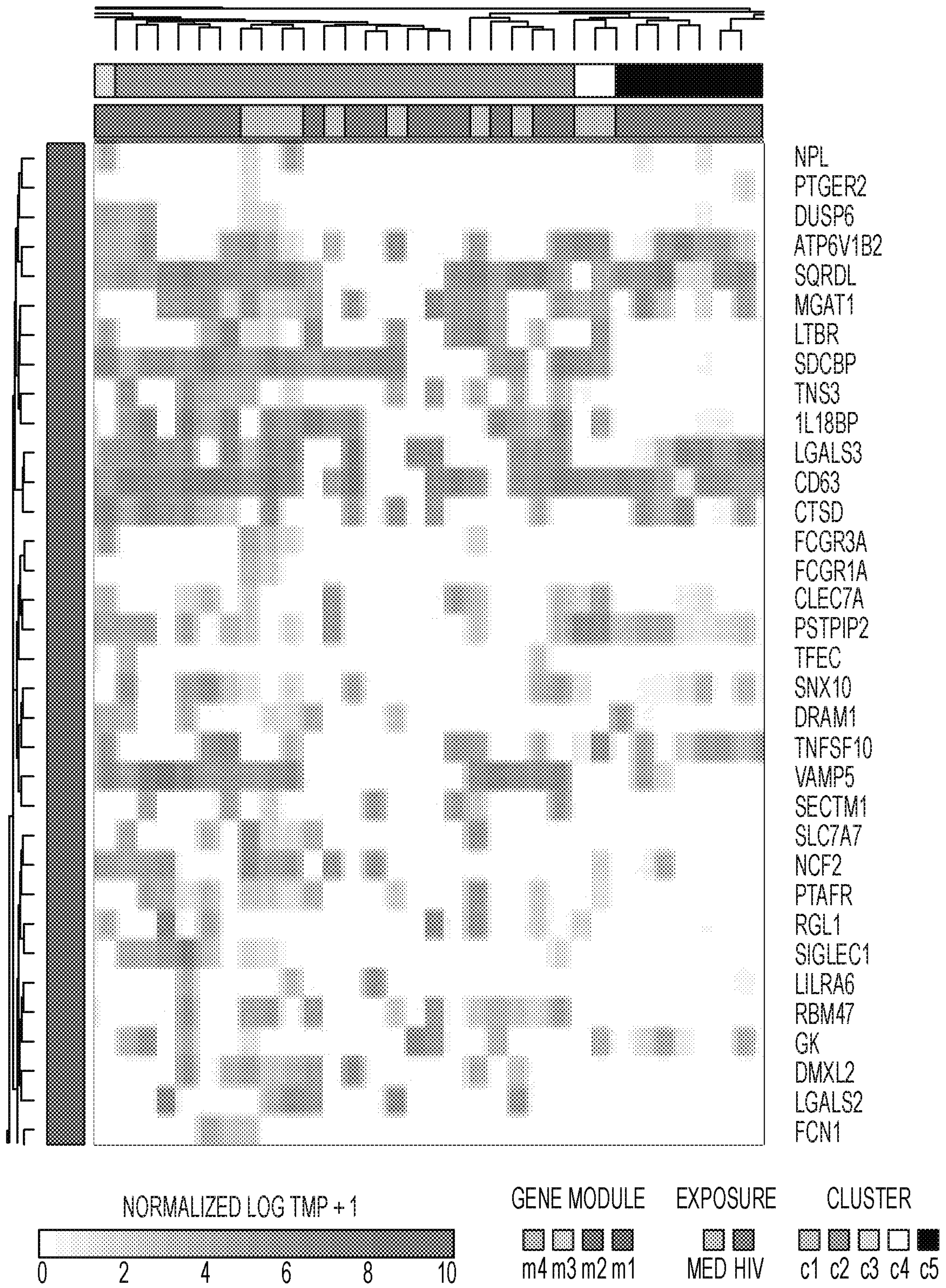
Figure 15G:
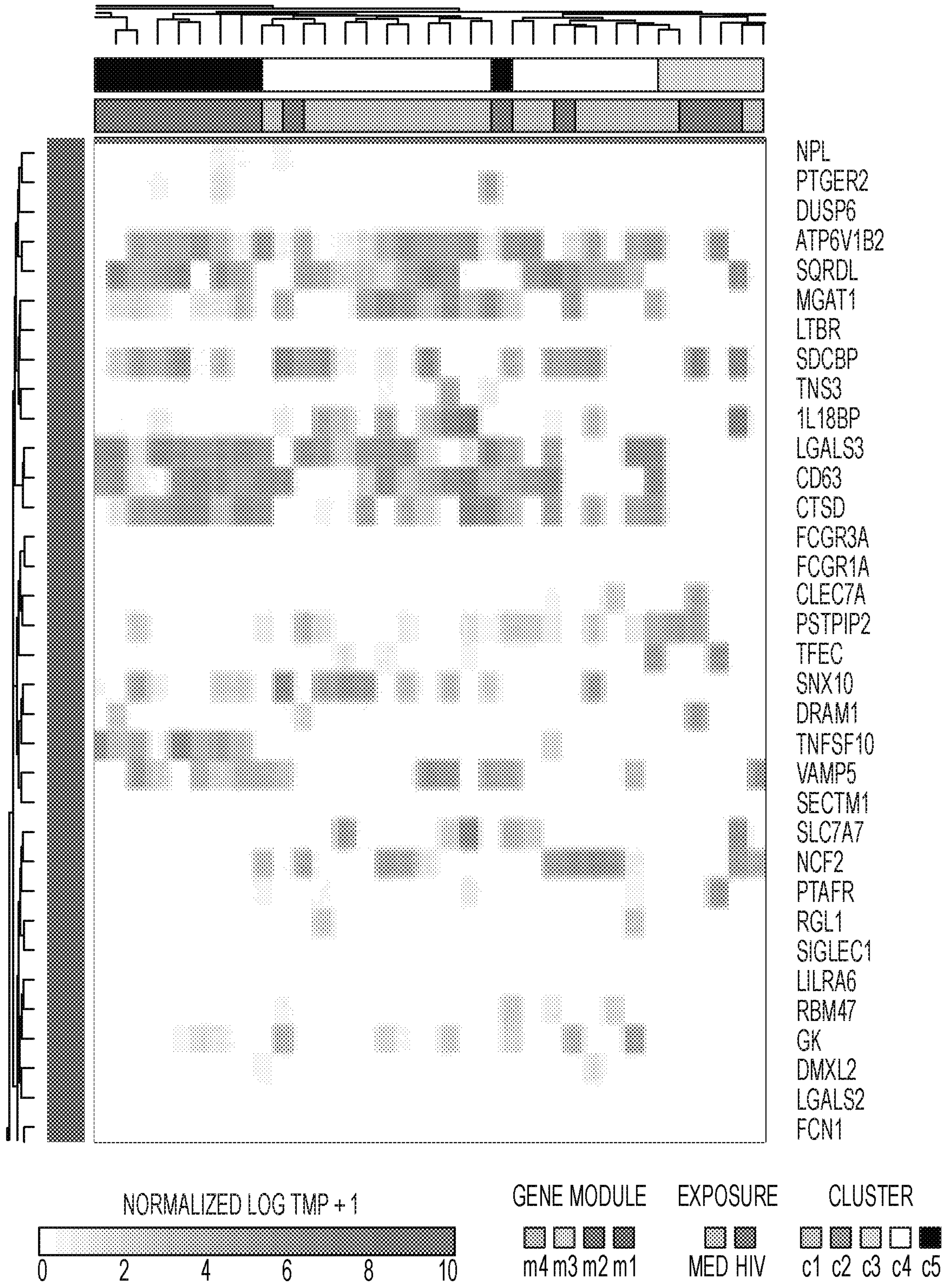
Figure 15H:
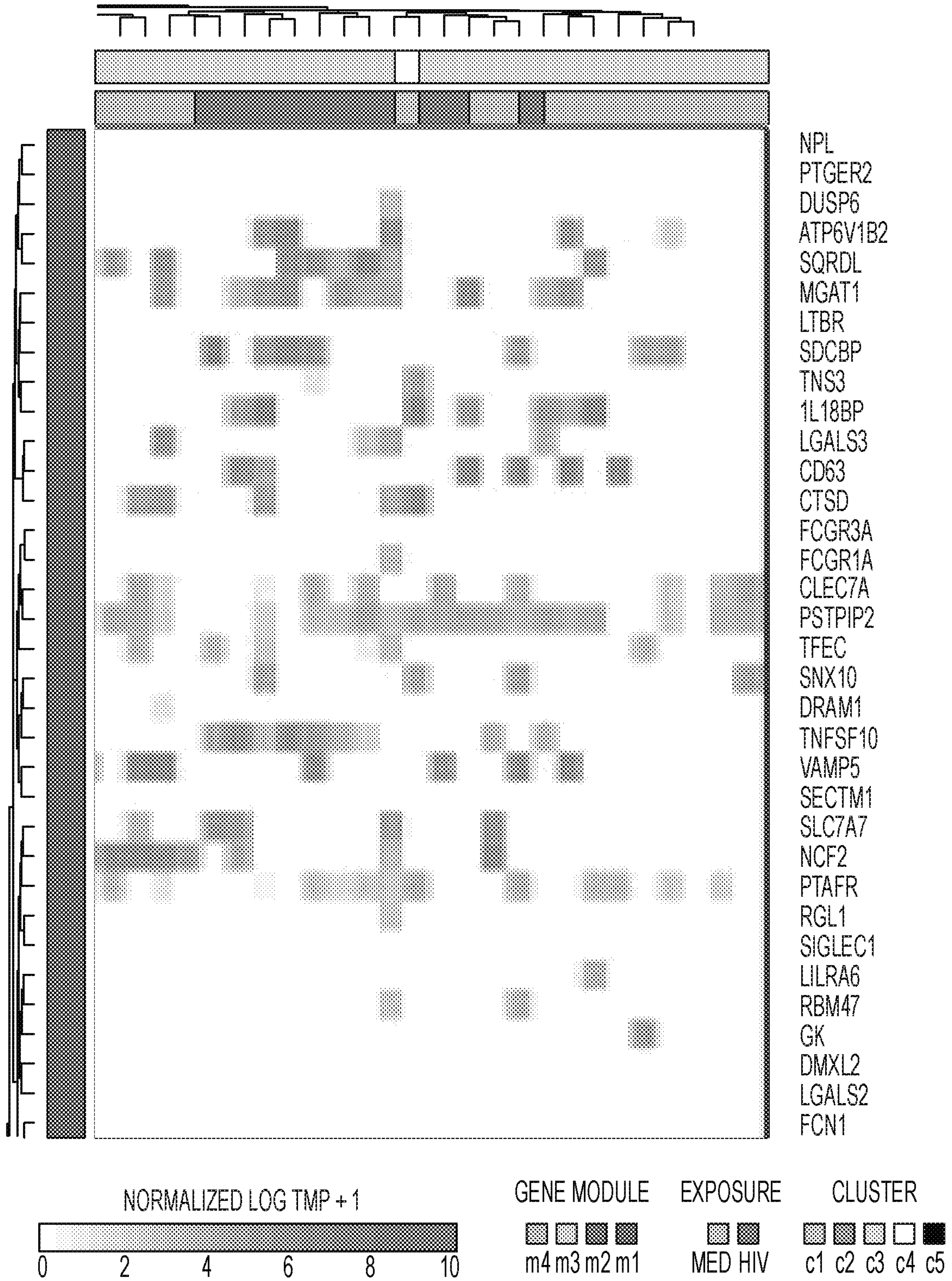
Figure 15I:
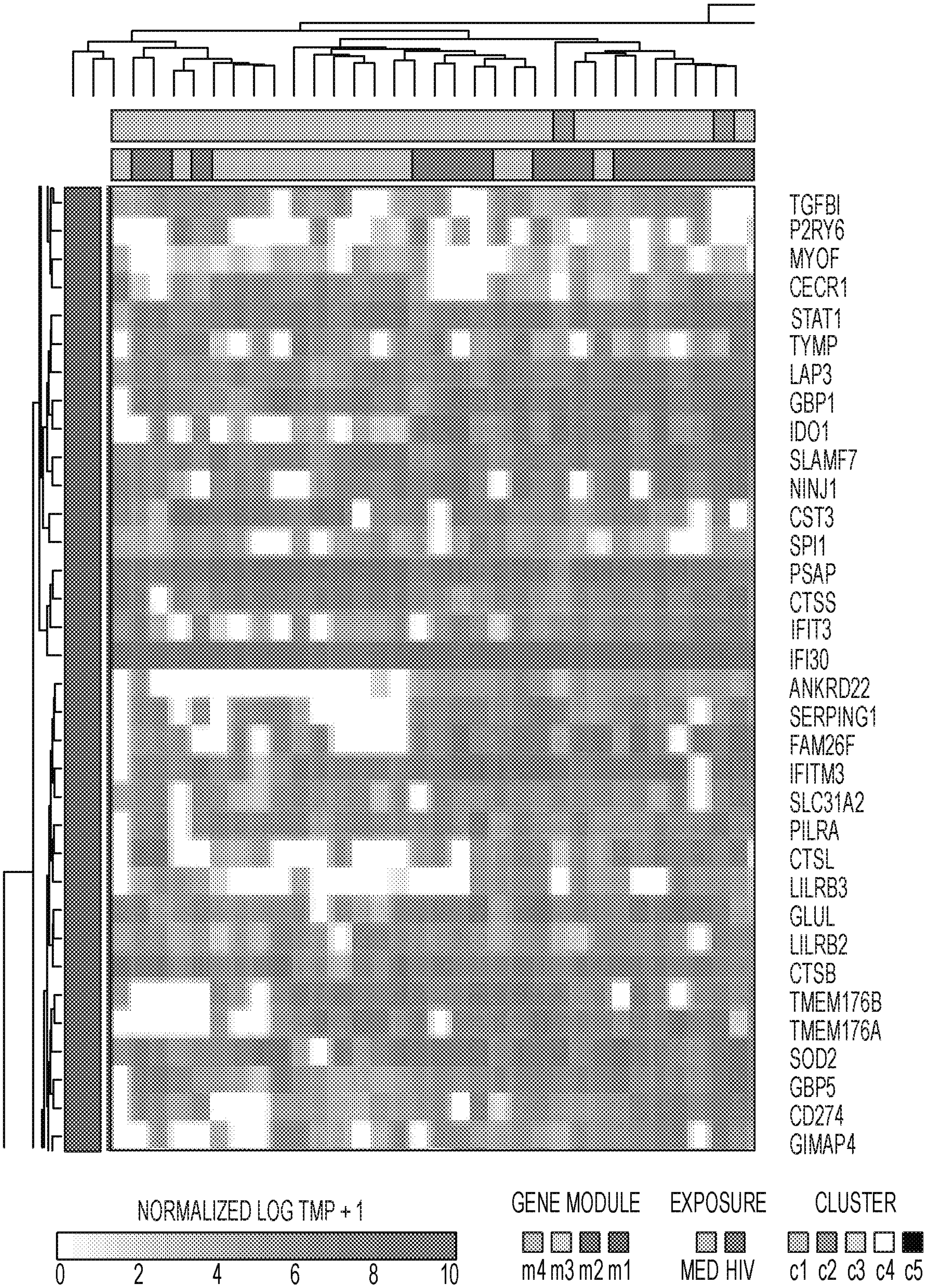
Figure 15J:
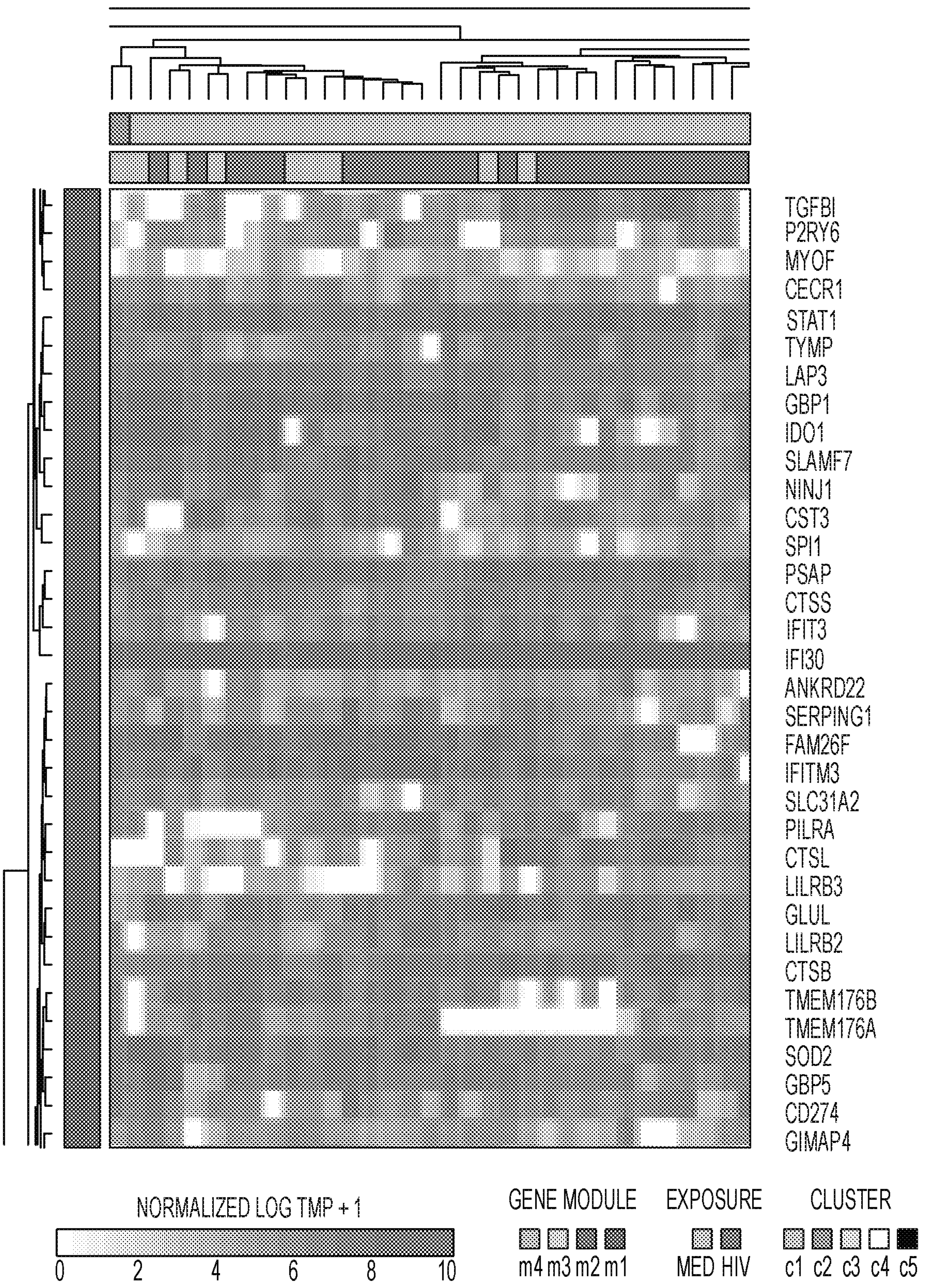
Figure 15K:
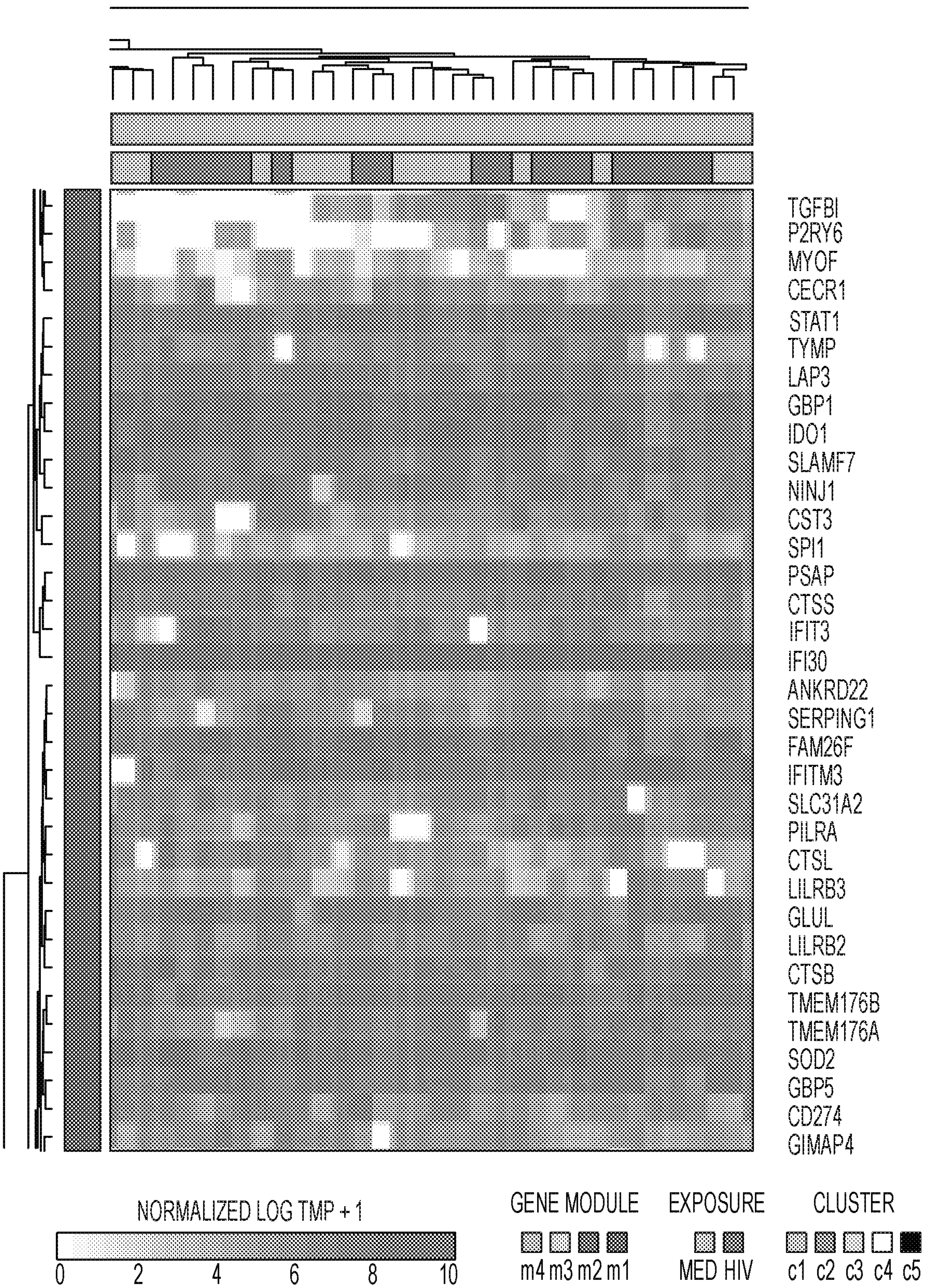
Figure 15L:
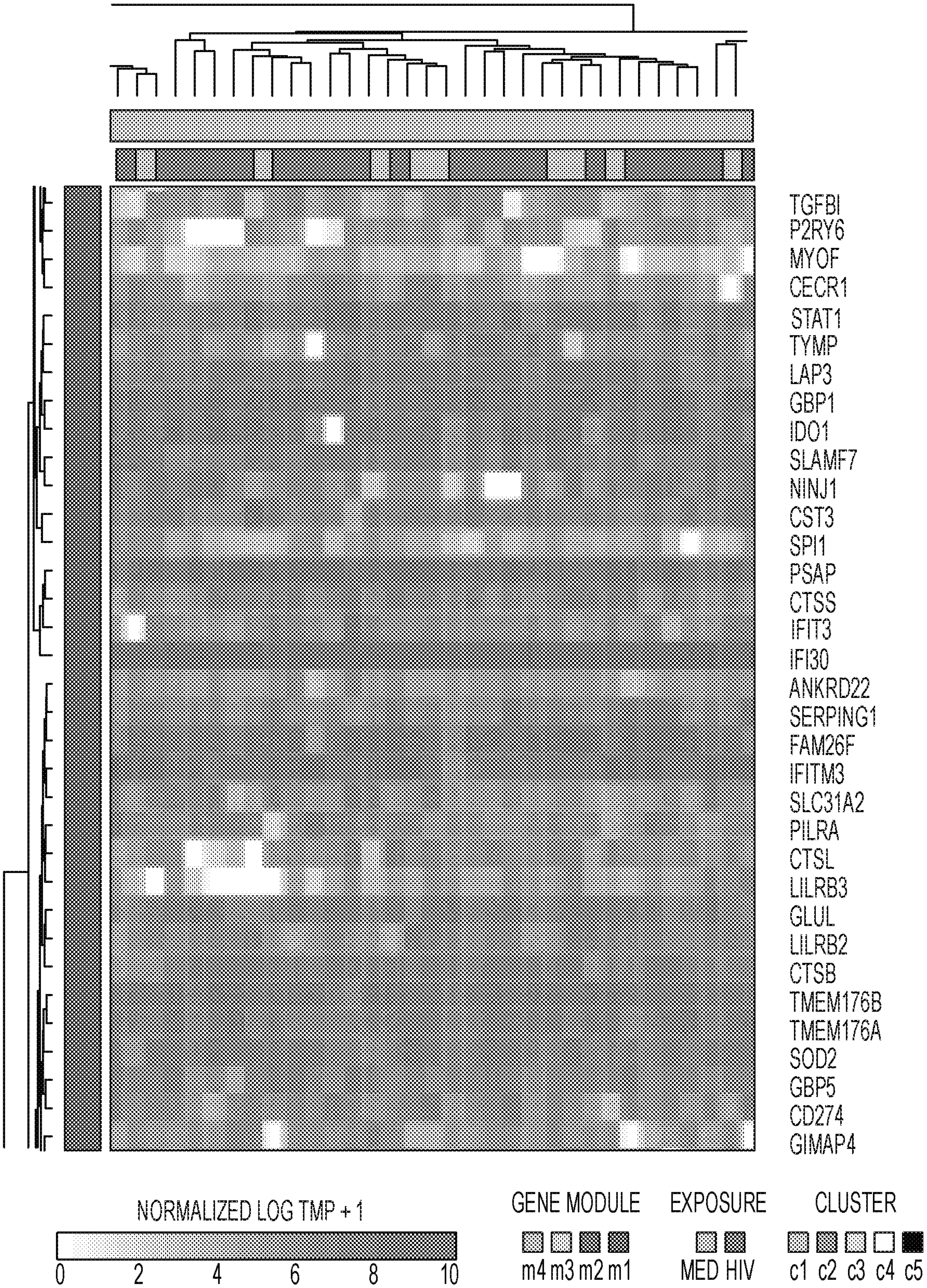
Figure 15M:
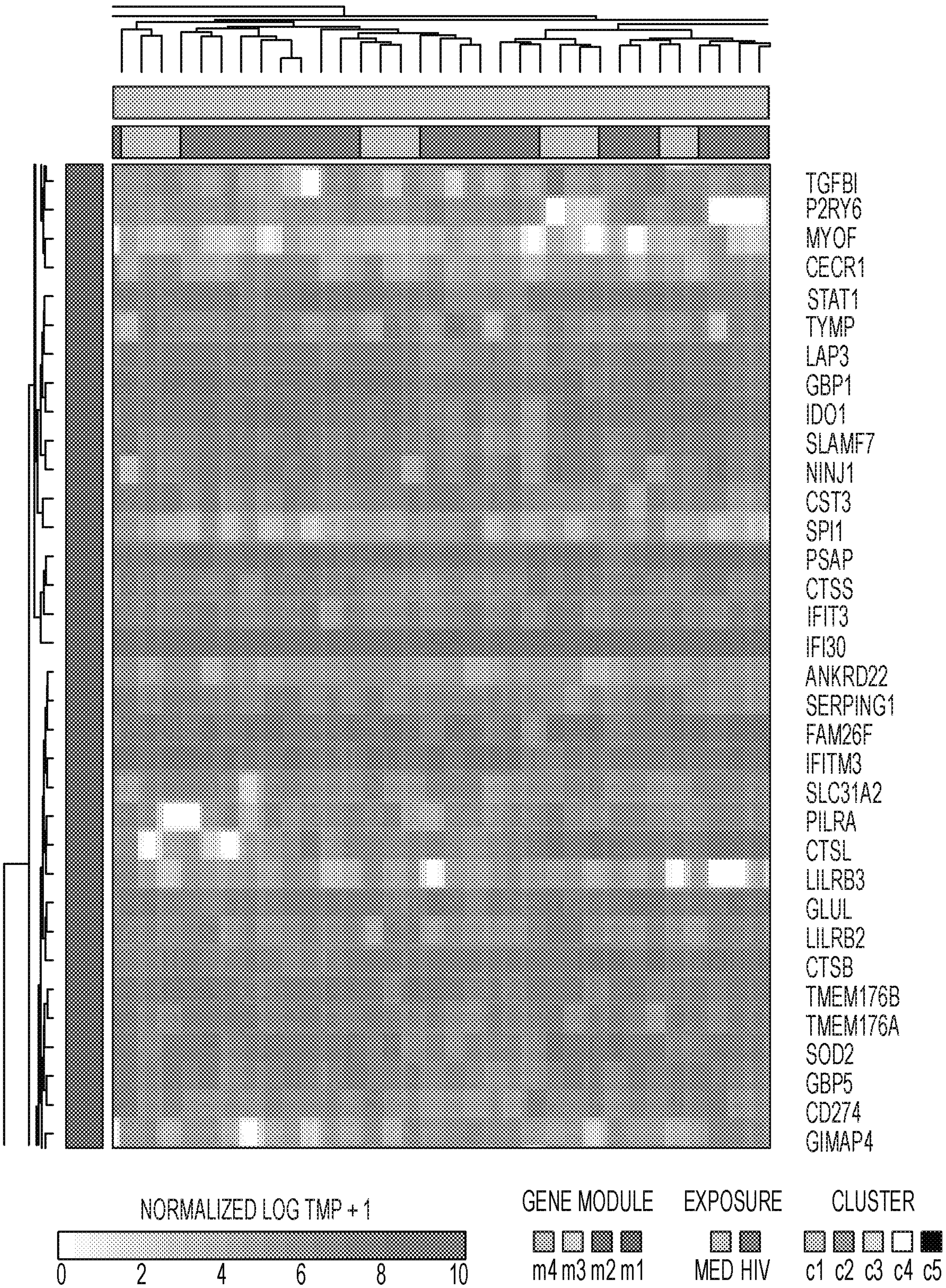
Figure 15N:
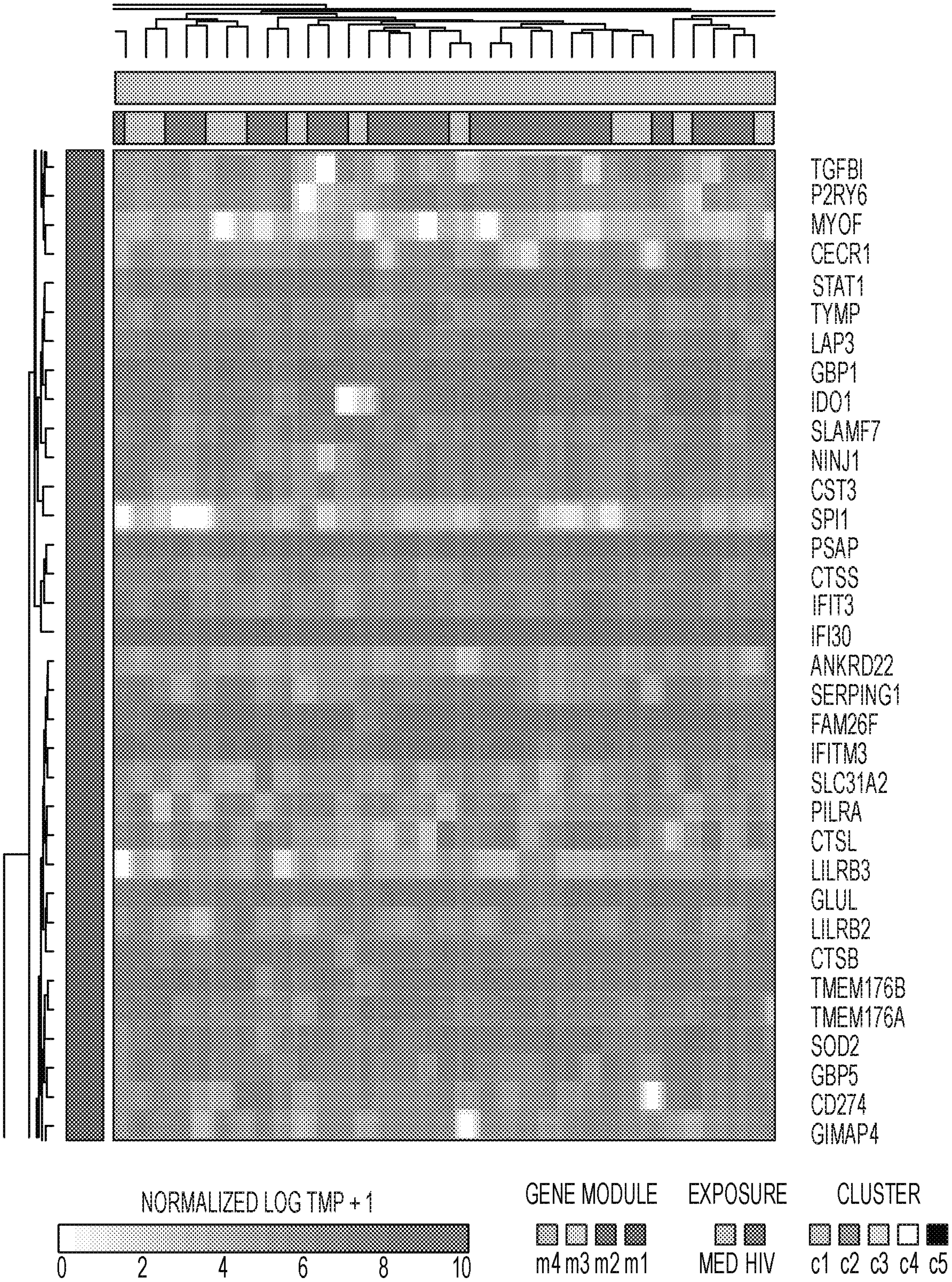
Figure 15O:
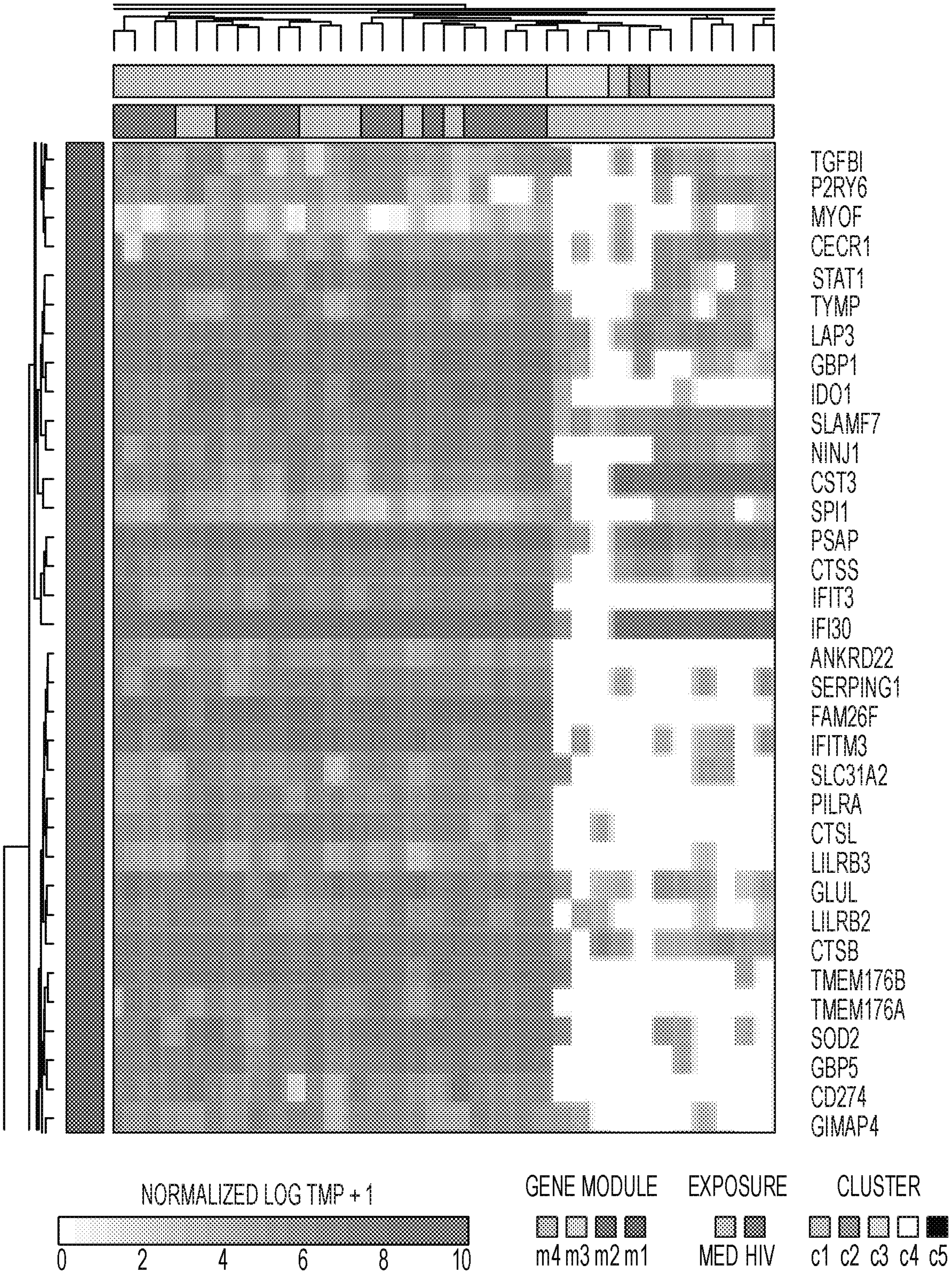
Figure 15P:
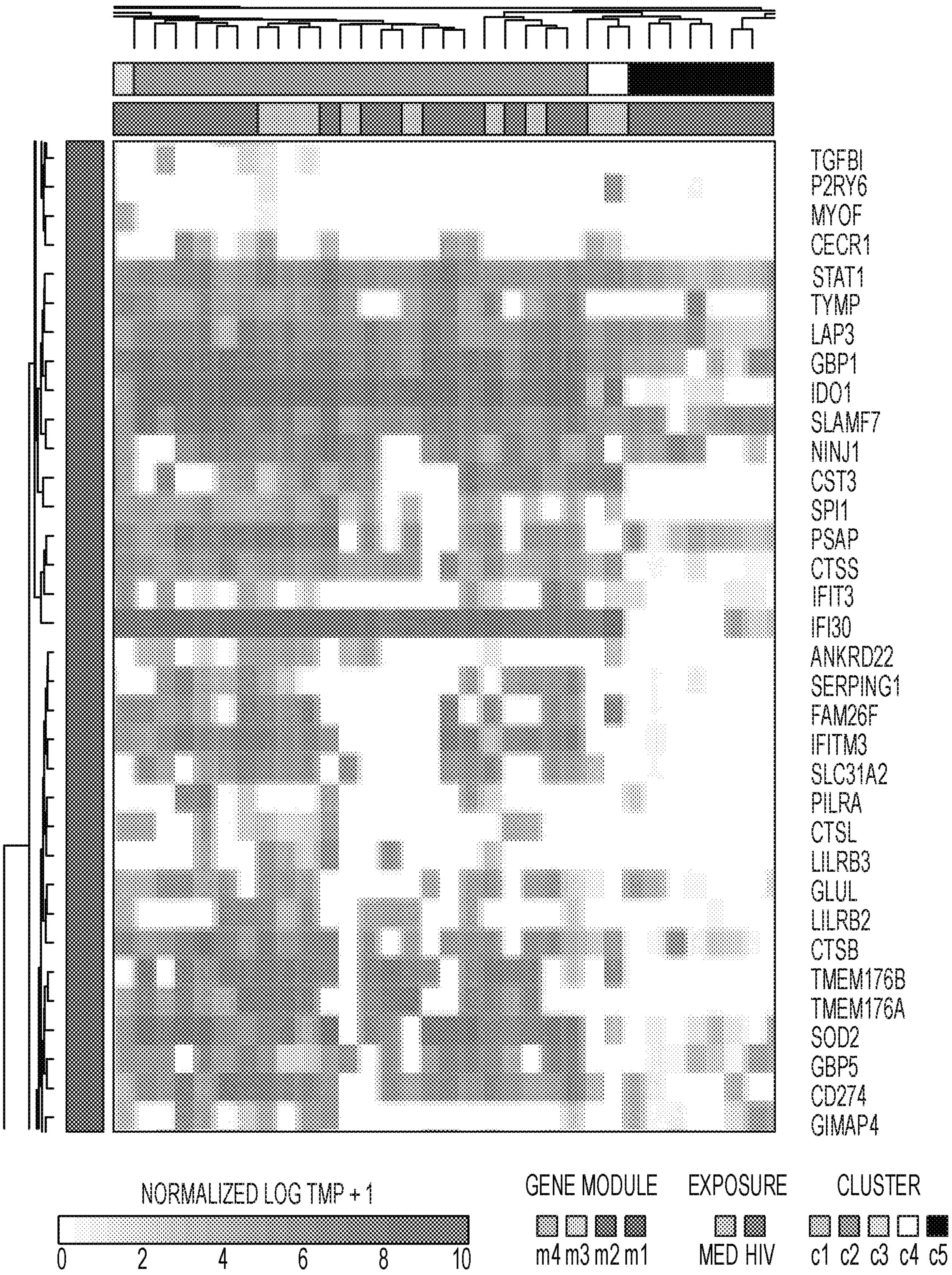
Figure 15Q:
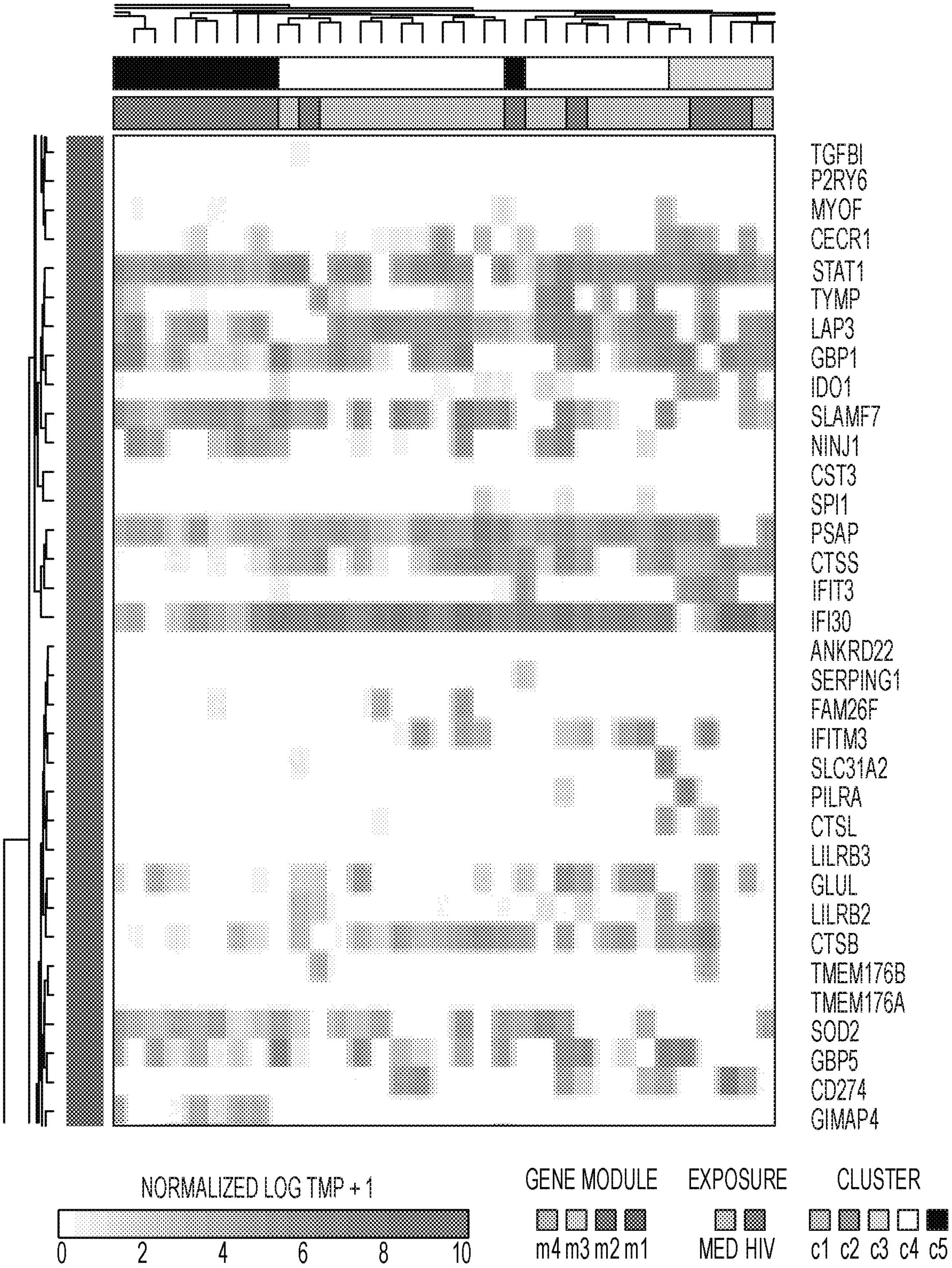
Figure 15R:
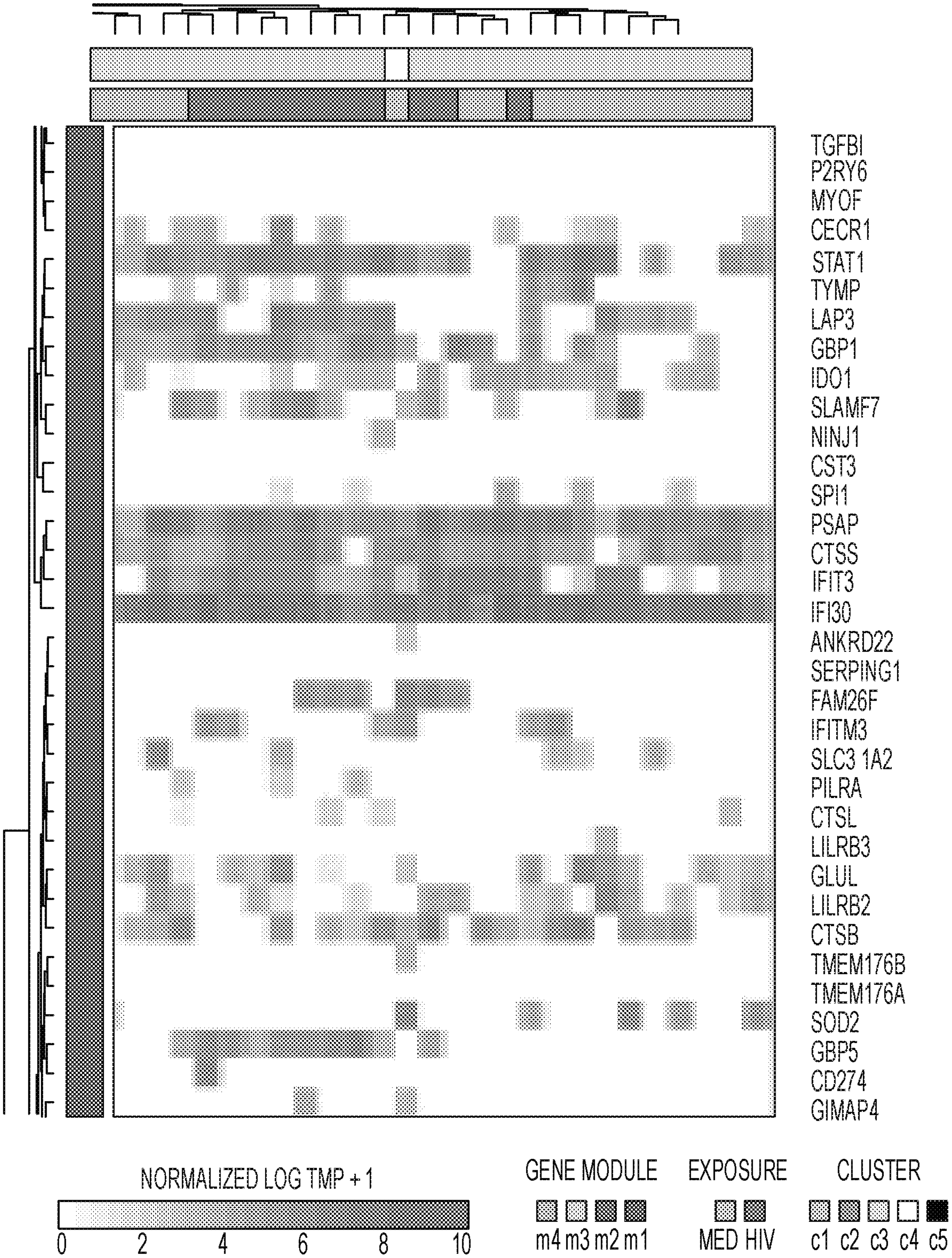
Figure 15S:
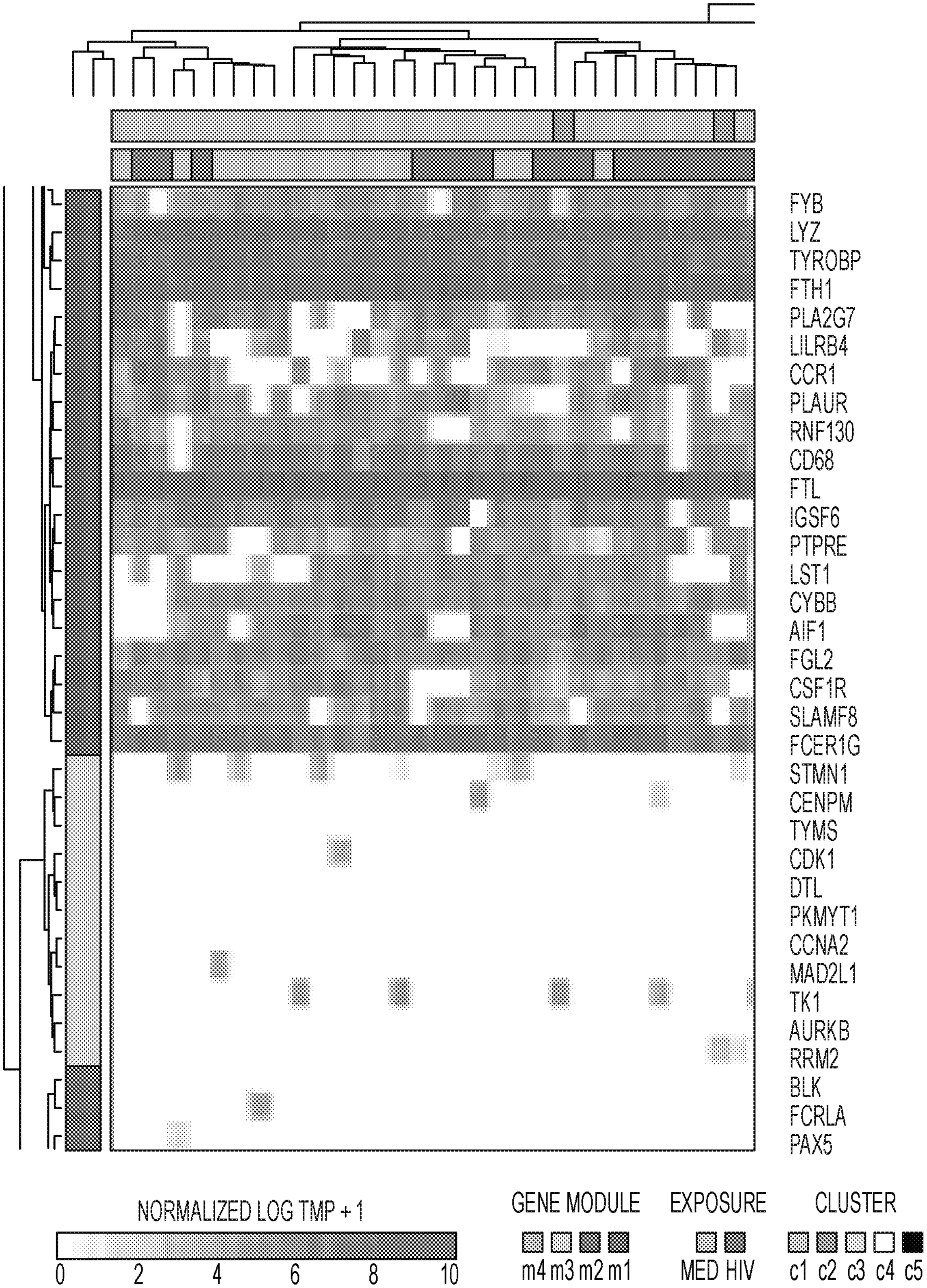
Figure 15T:
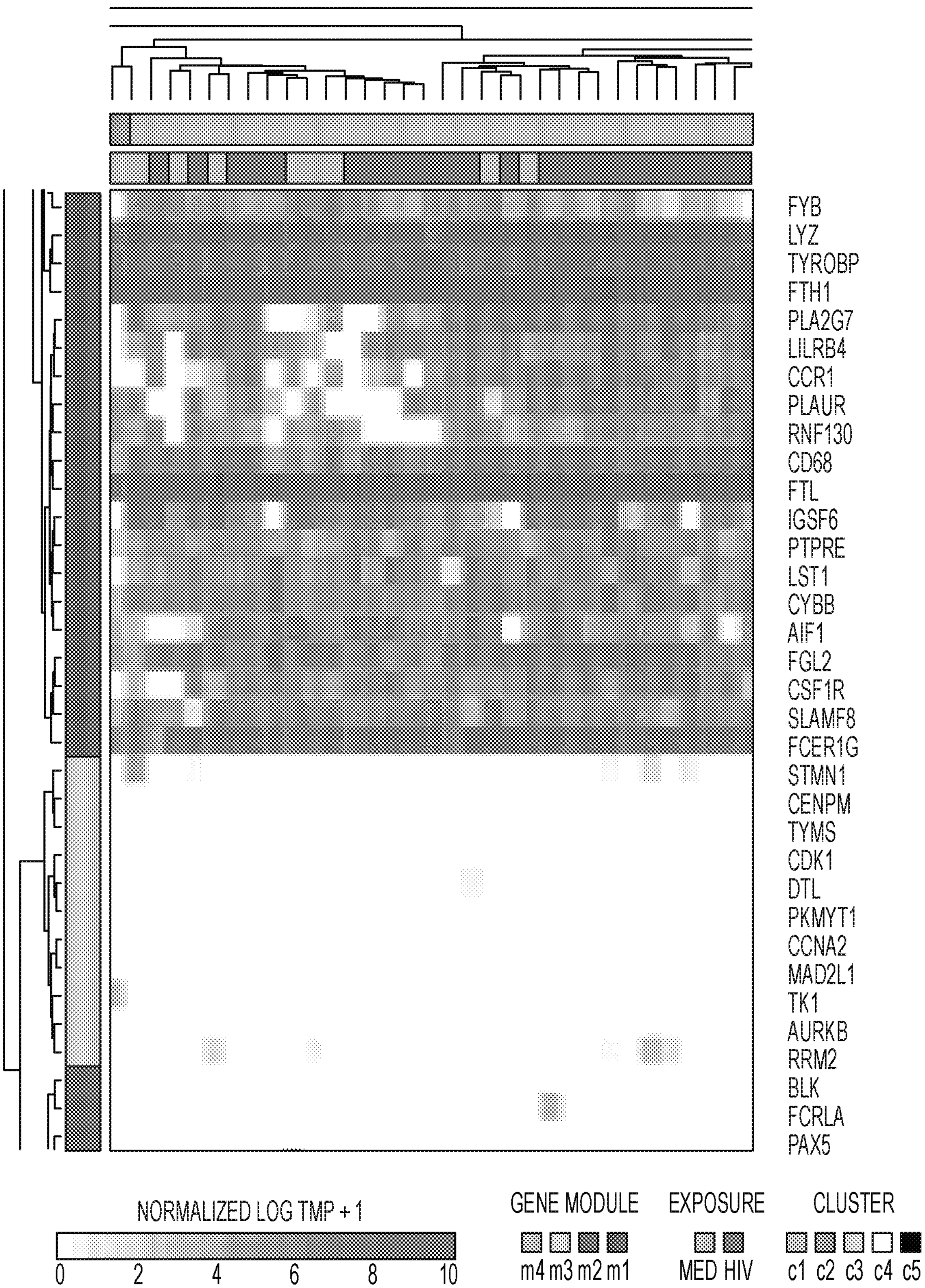
Figure 15U:
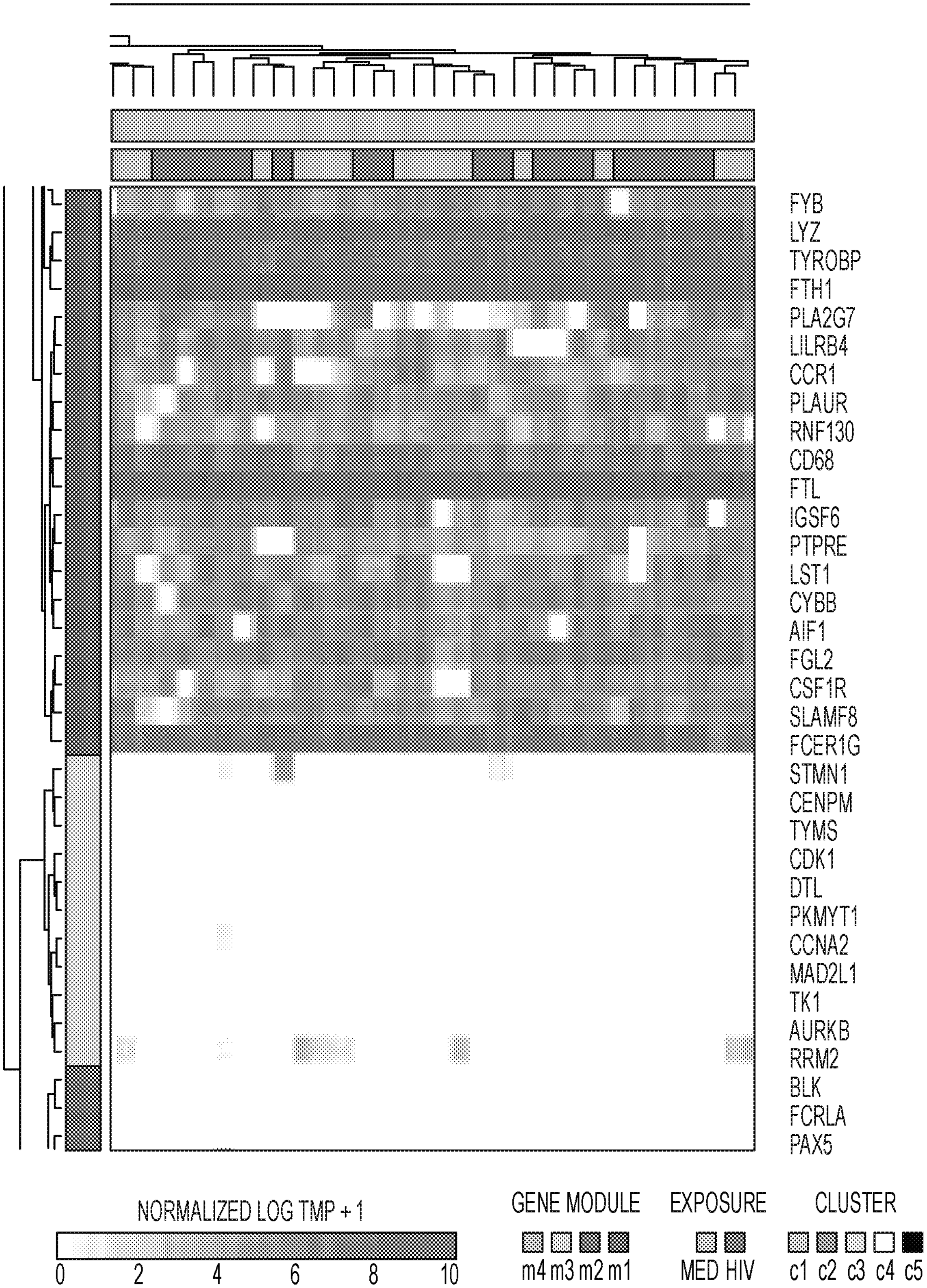
Figure 15V:
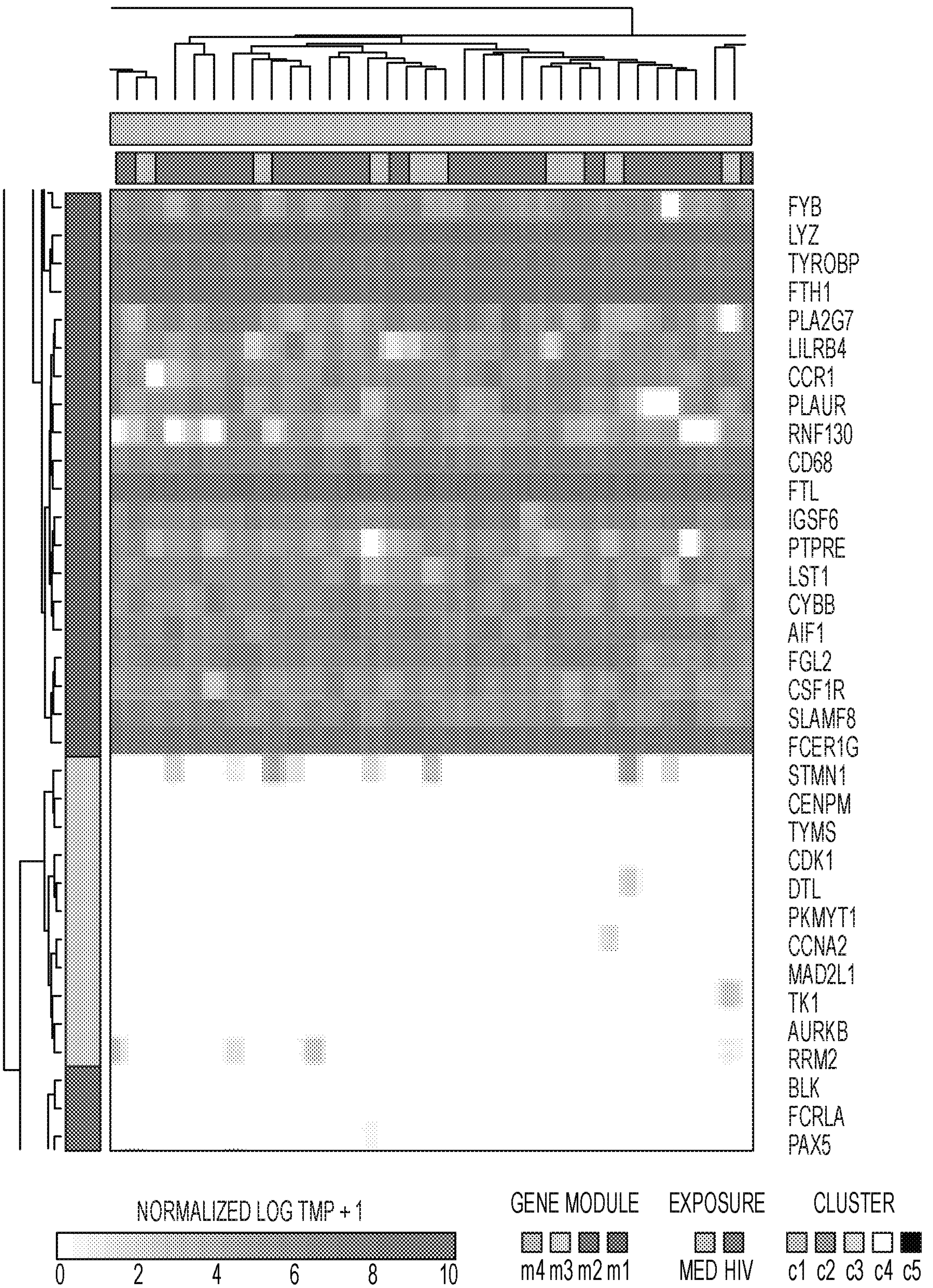
Figure 15W:
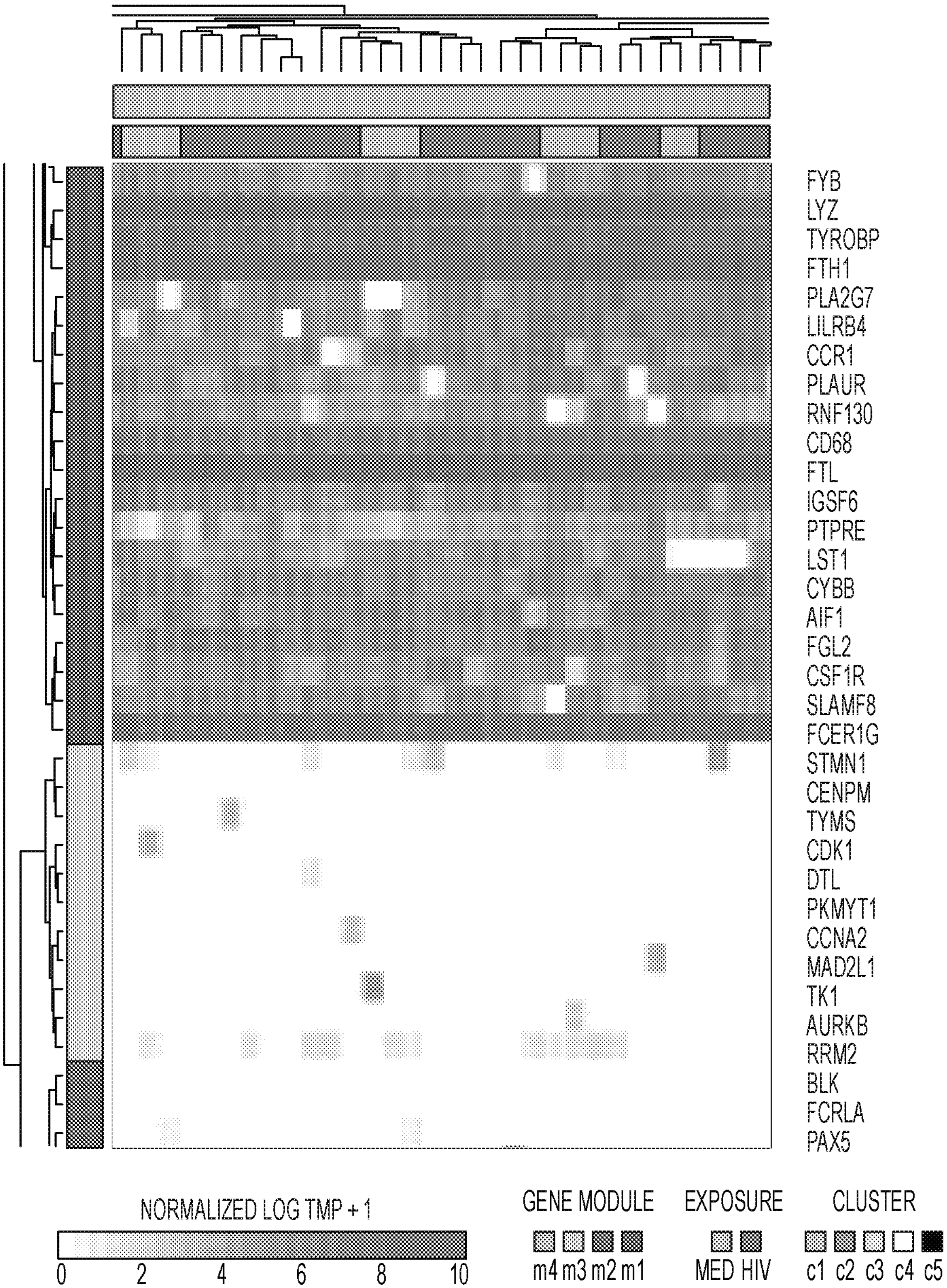
Figure 15X:
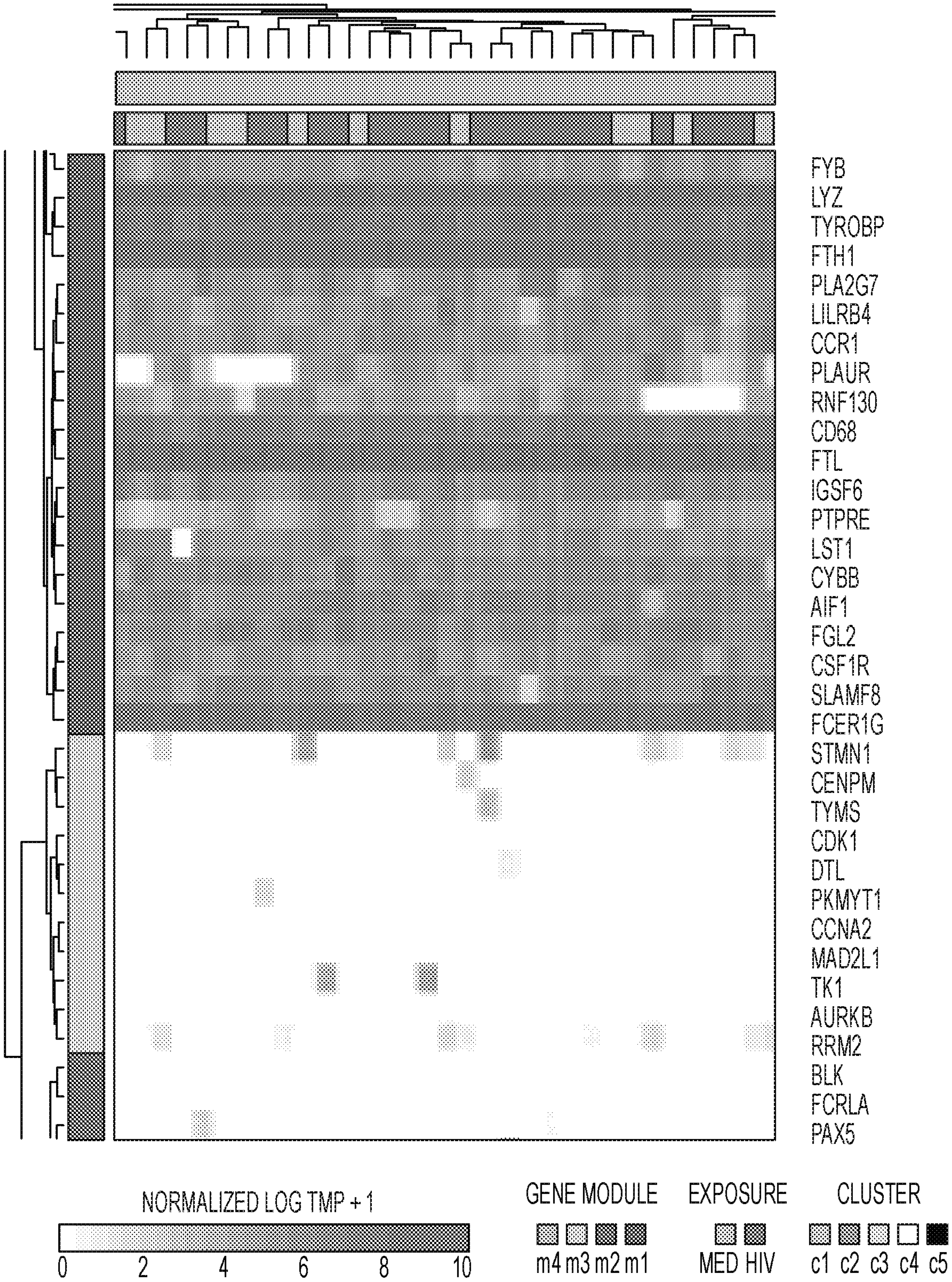
Figure 15Y:
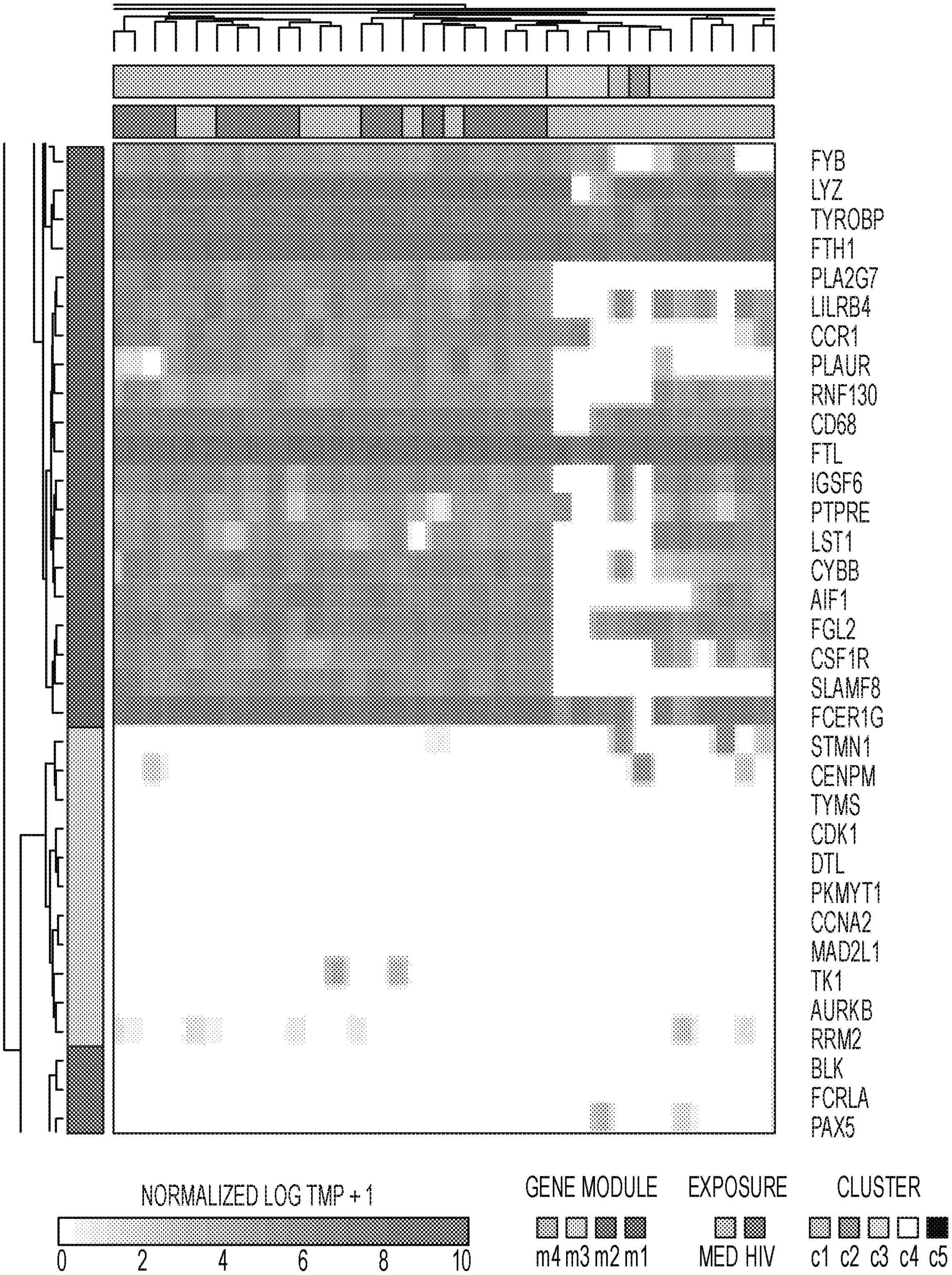
Figure 15Z:
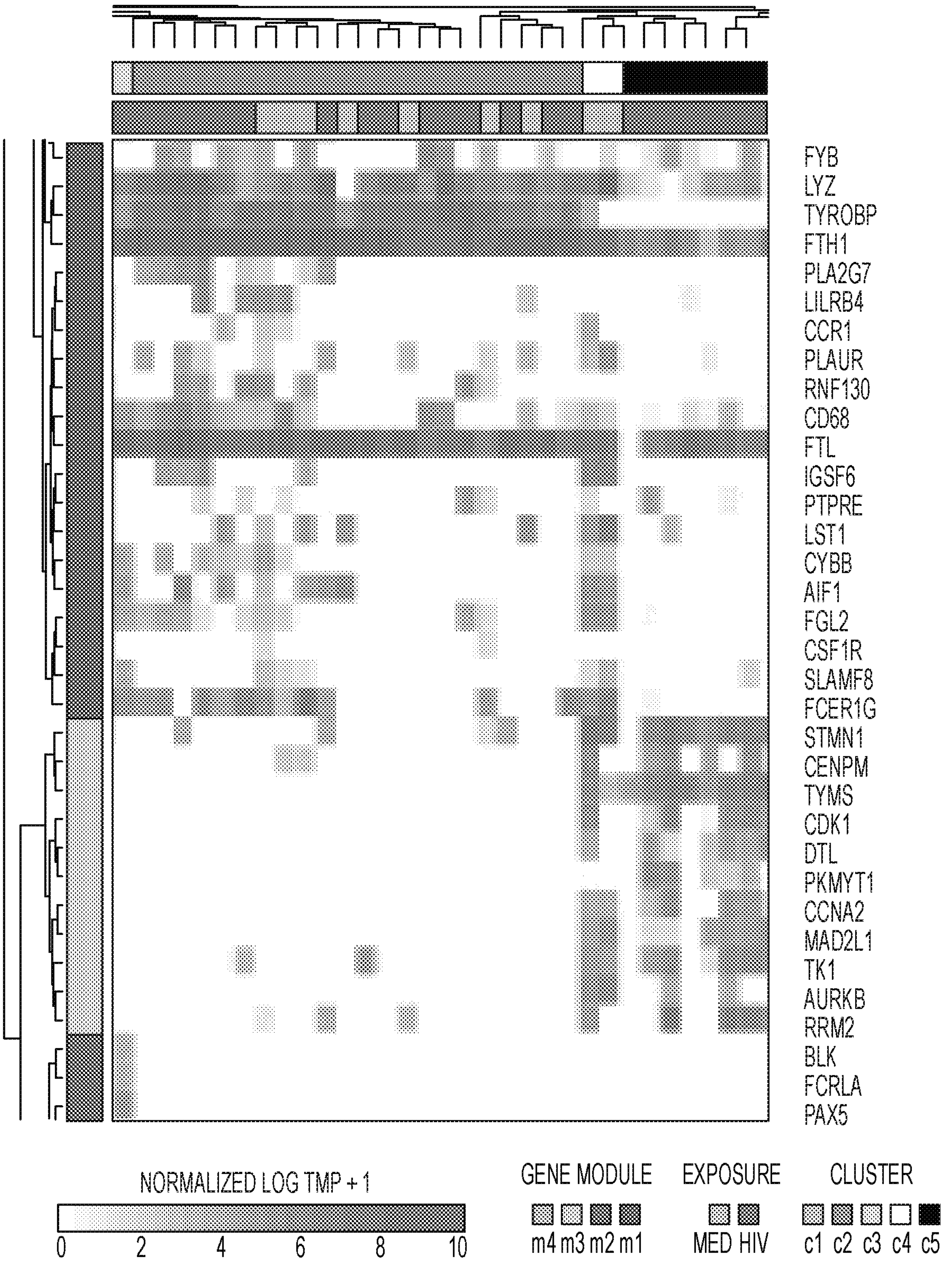
Figure 16A:
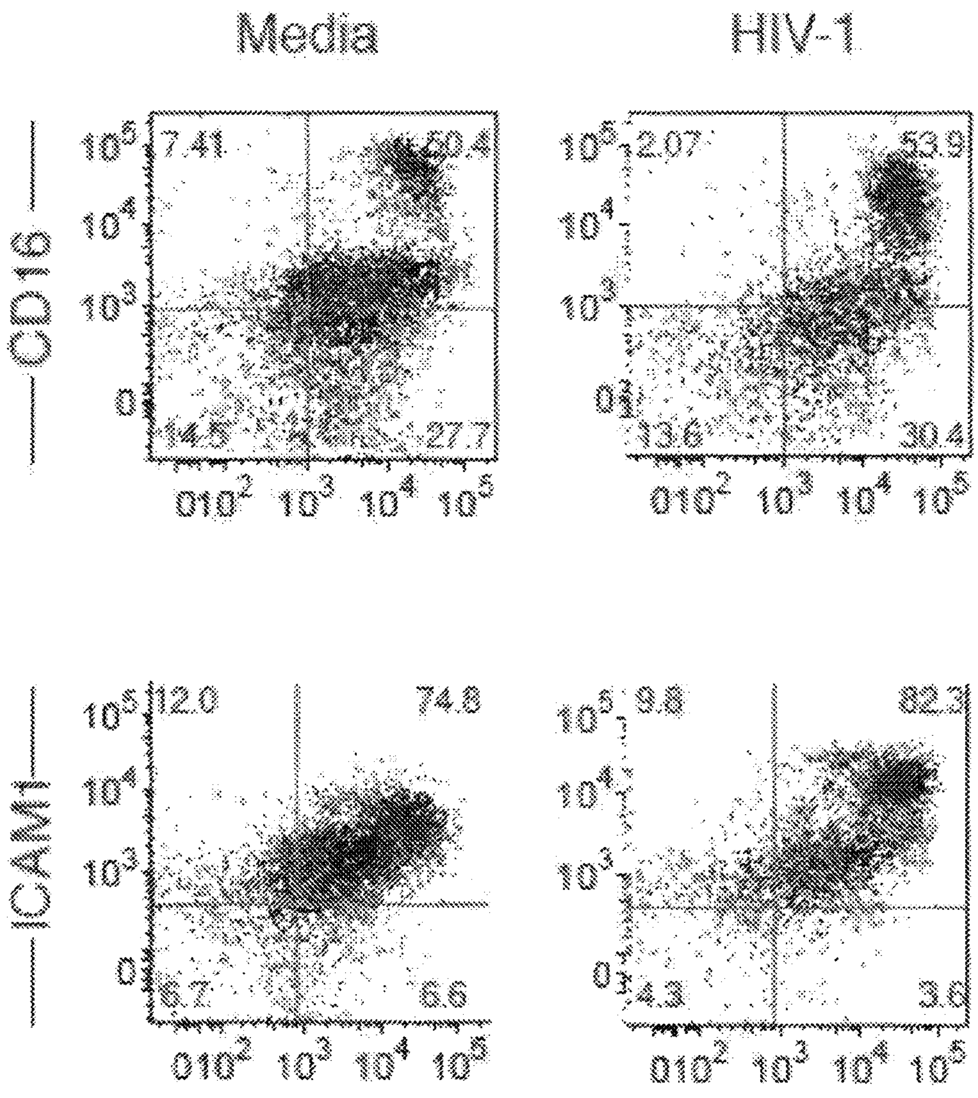
FIG. 16A illustrates representative flow cytometry analysis of CD86 (X) versus either CD16 or ICAM1 or SLAMF8 or CLEC12A (Y) in gated CD14− CD11cHi HLADR+ DCs from our p1 EC patient cultured for 24 h in the presence of Media (left) or HIV-1 (right).
Figure 16B:
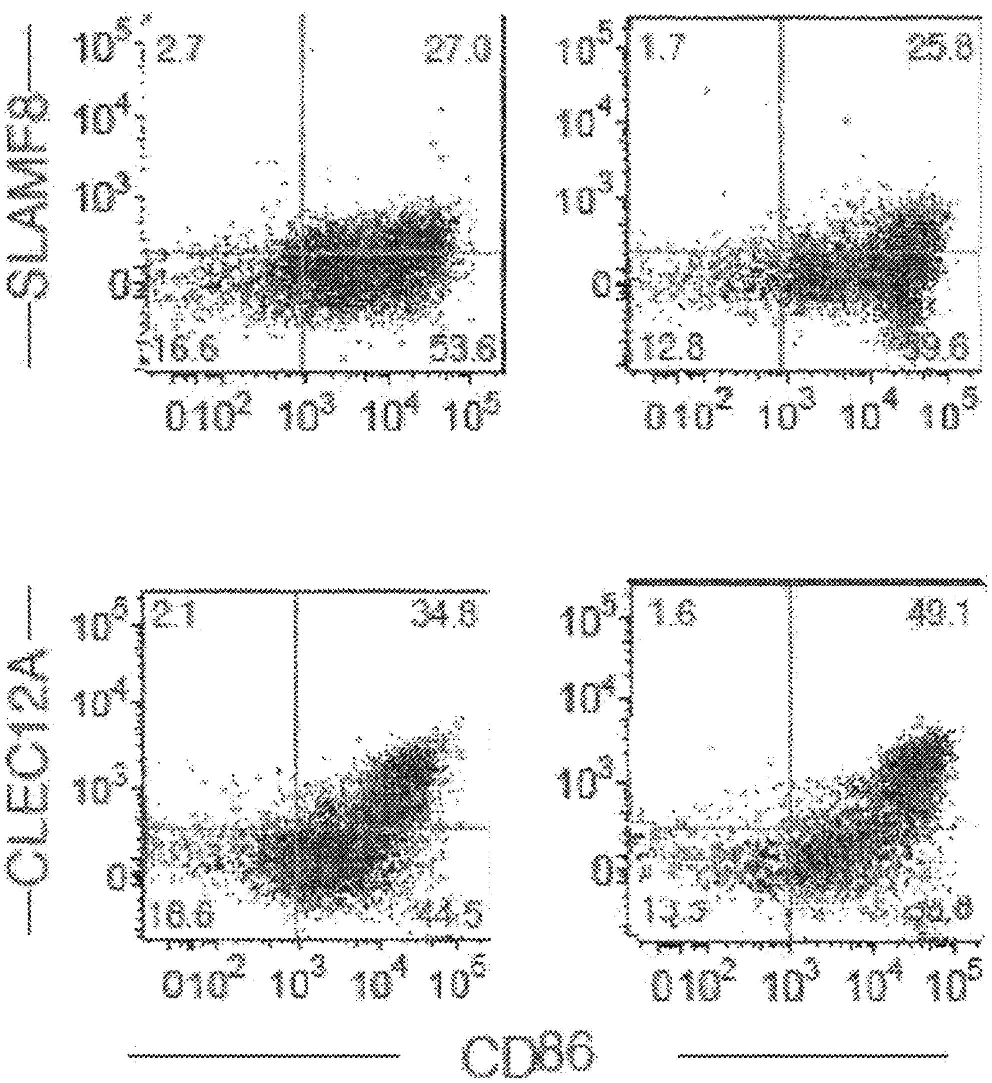
FIGS. 16B and 16C illustrate the summary of proportions of CD86Hi DCs from HIV-1 EC (green), chronic progressors (pink) and healthy individuals (blue) expressing high levels of each of the markers analyzed in FIG. 16A. Statistical significance was calculated using a Wilcoxon matched pairs rank test (*p<0.05).
Figure 16C:
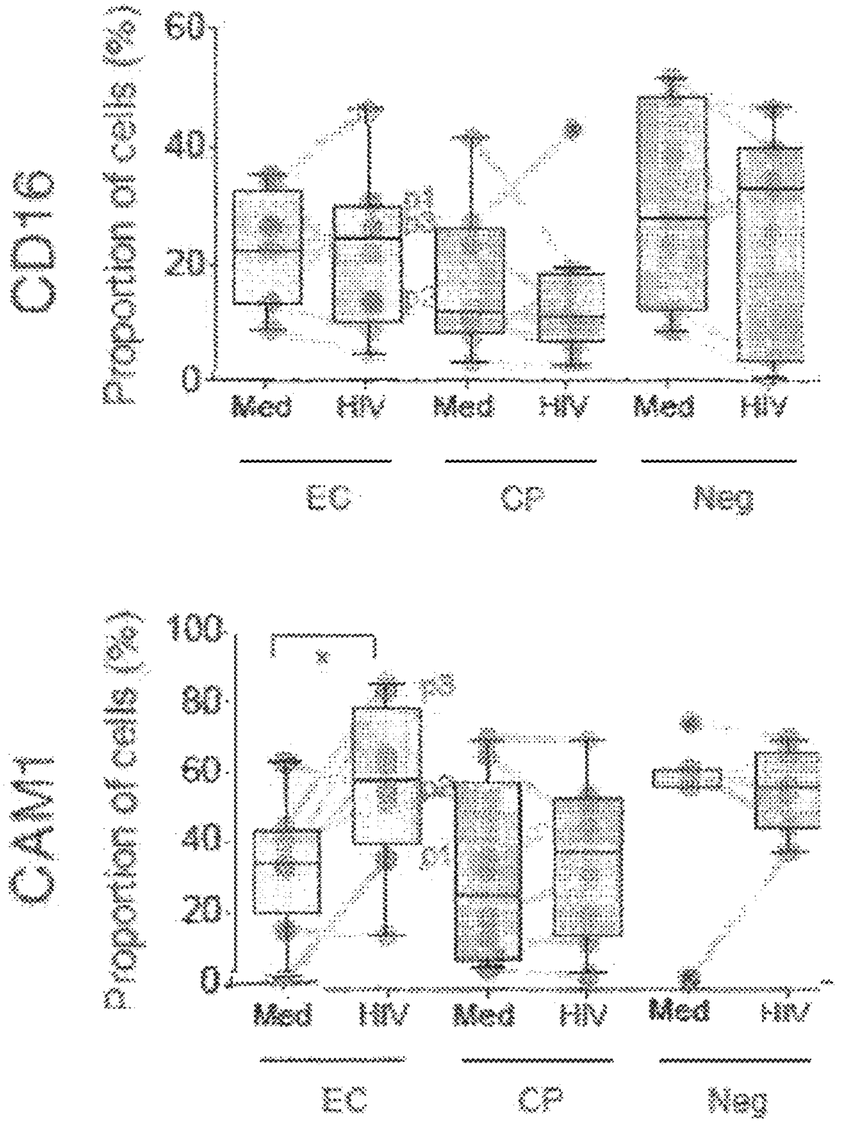
Figure 16D:
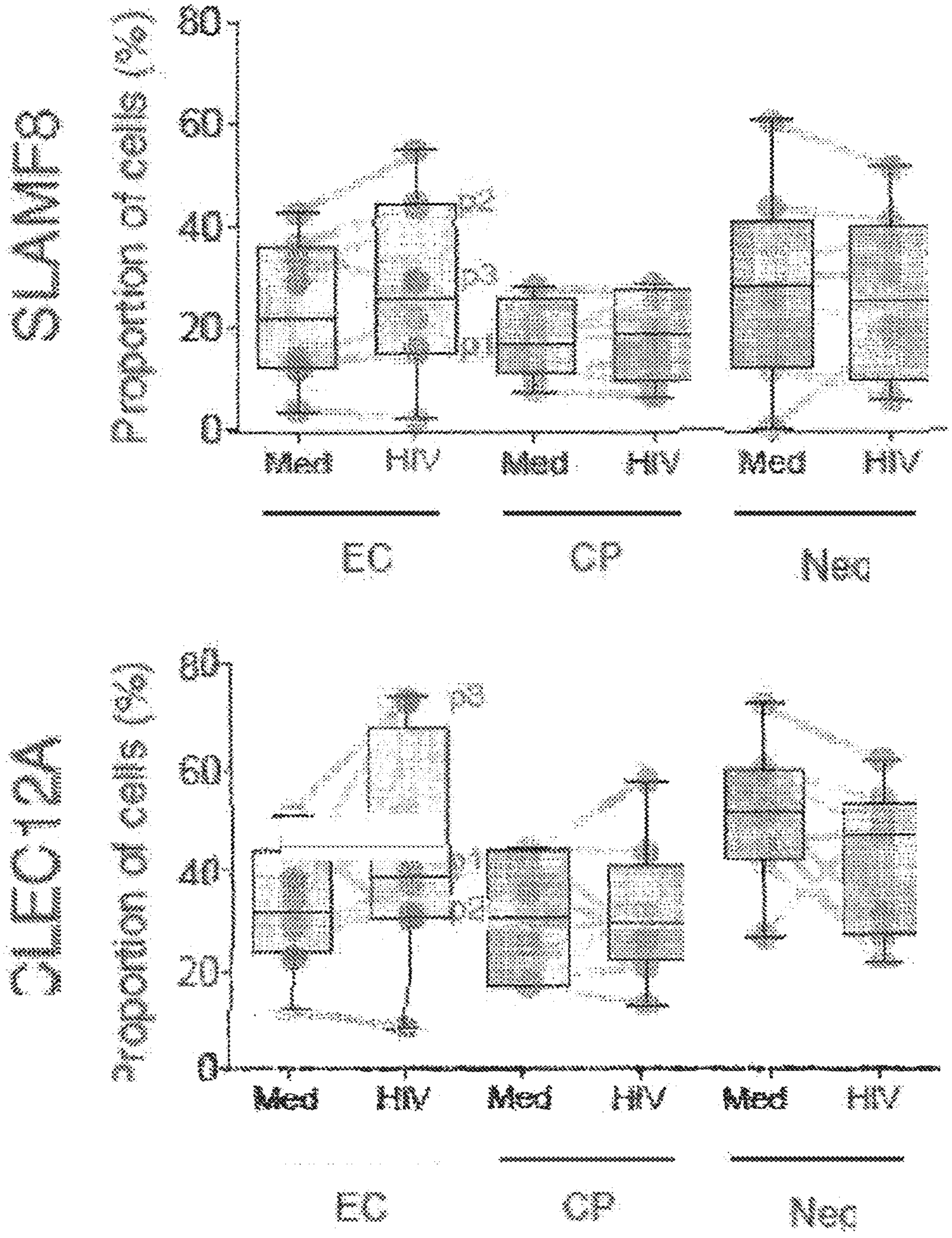
FIGS. 16D and 16D illustrate quantification of HIV-1 Reverse transcript amounts by qPCR present in cDCs exposed in vitro for 24 h to a VSV-G pseudotyped HIV-1 virus and sorted on high (Hi; Blue; n=8) and low (Lo; green; n=8) expression levels of CD64 and PD-L1. As a control, cDCs treated in media only were included in the analysis as a control in some experiments (Orange; n=5). Data indicates values of HIV-1 gag DNA amplification relative to endogenous CCR5 levels present in each DNA sample.
Figure 16E:
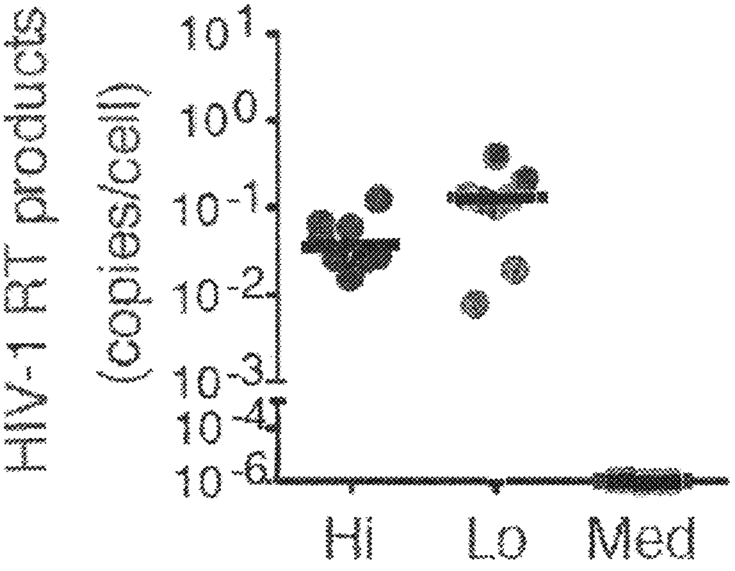

Applicants next sought to identify genes and pathways differentially expressed between the more (c1 or c2) and less activated (c3/4/5) single-cell groups. Pathway enrichment analysis of these transcriptional signatures revealed that cluster 1 was characterized by a highly significant association with pathways related to DC maturation, innate recognition of microbes by PRR and interferon, inflammatory cytokine and TLR signaling (FIG. 6G). Moreover, analyses of putative upstream regulators for cluster 1 highlighted several innate pathways capable of inducing antiviral responses such as TLR, MAVS, STAT and TBK1 pathways (FIG. 6H). While similar association with inflammatory and innate activation of TLR was also observed for cluster 2 when compared to clusters 3, 4 and 5, they were less significant (FIG. 13C). Finally, to better understand the antiviral identity of c1 and c2 responses, Applicants specifically analyzed expression patterns of interferon stimulated genes (ISG) in all single cell clusters. As shown in FIG. 13A, significantly higher levels of ISGs were present in ci, therefore indicating that this cluster represents indeed a highly antiviral activation state. Overall, these observations suggest that the cluster 1 represents a population of cDCs that are highly activated in response to viral exposure and maybe be highly functional in priming adaptive immunity.

Figure 11A:
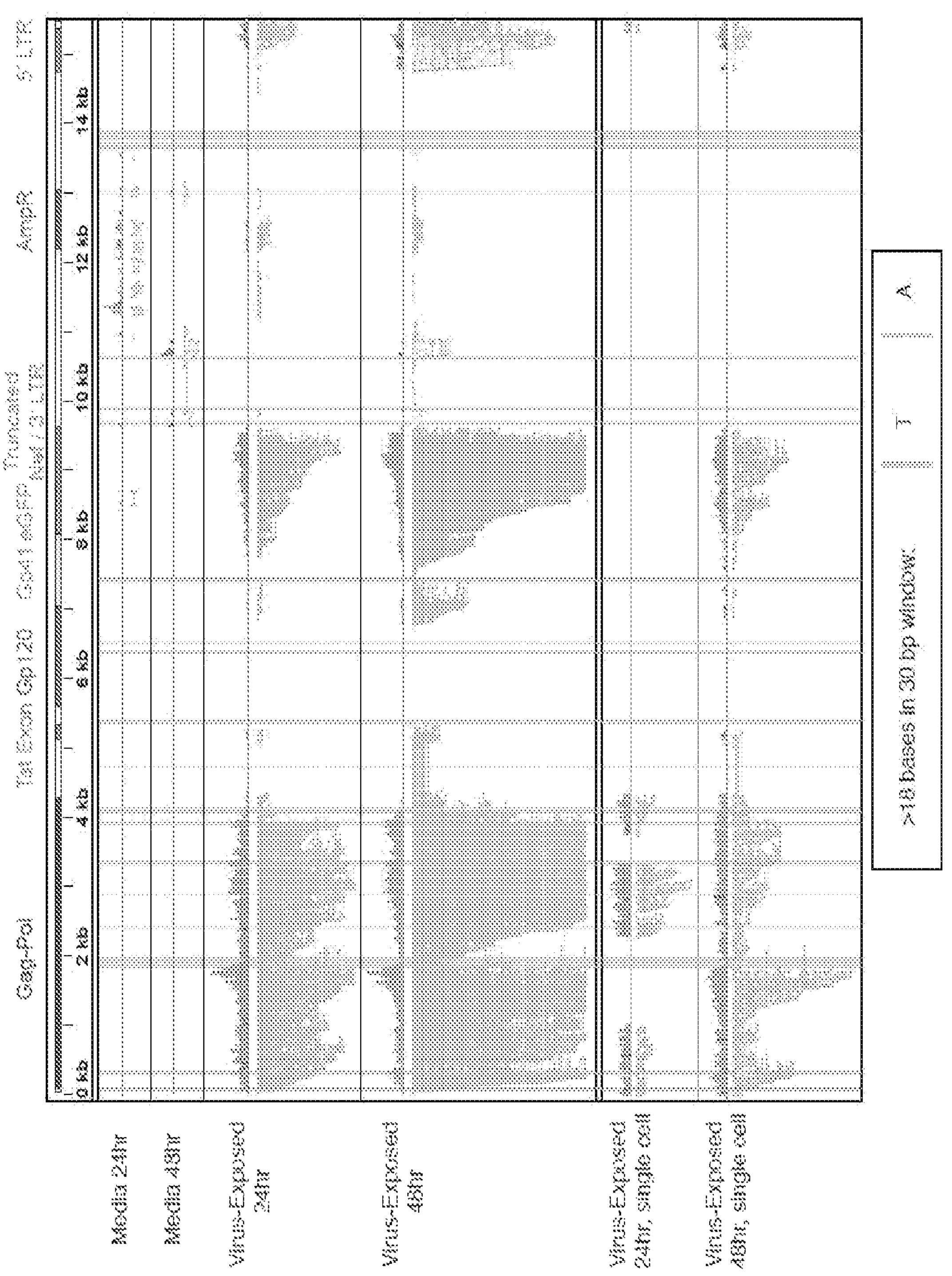
FIG. 11A illustrates alignment of viral reads (reads in grey; histogram of reads in green) from pooled media or virus-exposed cells at 24 and 48 hours (top) to the viral sequence between the 5' LTR and 3' LTR of our pseudotyped viral plasmid (bar at top, colored by gene). Representative single cells are shown at bottom. Vertical bars mark positions in the plasmid sequence where there are at least 18 Adenines in a 30 base pair window.
Figure 11B:
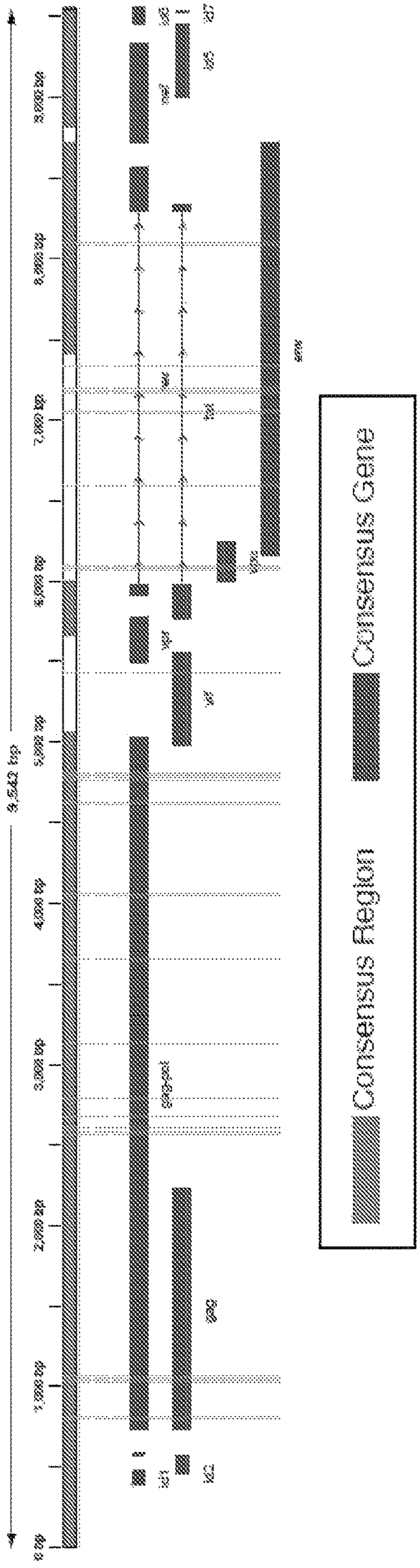
FIG. 11B illustrates HIV-1 B consensus genome www.hiv.lanl.gov/) with regions homologous to pseudotyped virus highlighted in red (BLAST). Bottom: consensus genes shown in blue. Adenine-rich regions (>18 A in 30 bp window) could potentially anneal primers used in SMART-Seq2 and are marked with vertical bars.
Figure 12A:
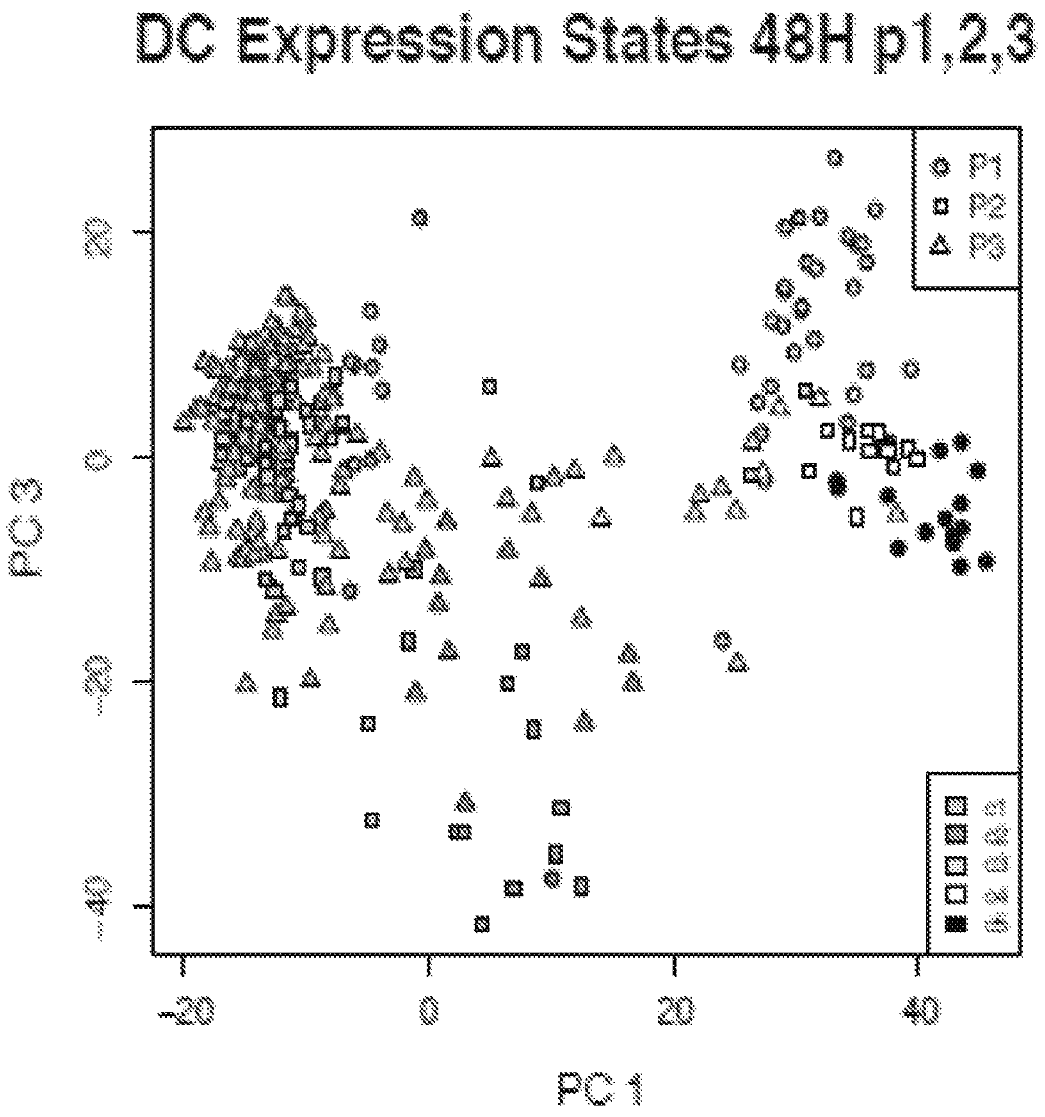
FIGS. 12A-12D illustrates single cell data structure at 24 hours in patient 1. (12A) illustrates PCA of single cell sequencing data from p1, p2 and p3 after 48 hour incubation (same data presented in t-SNE in FIG. 5B). (12B) illustrates cDCs from p1 incubated for 24 (FIGS. 12A-12B) and 48 (FIGS. 12C-12D) in Media (left) or HIV (right), plotted in the same PCA space as in a. Data points at 24 hours are colored by nearest neighbor from 48 hour clustering.
Figure 12B:
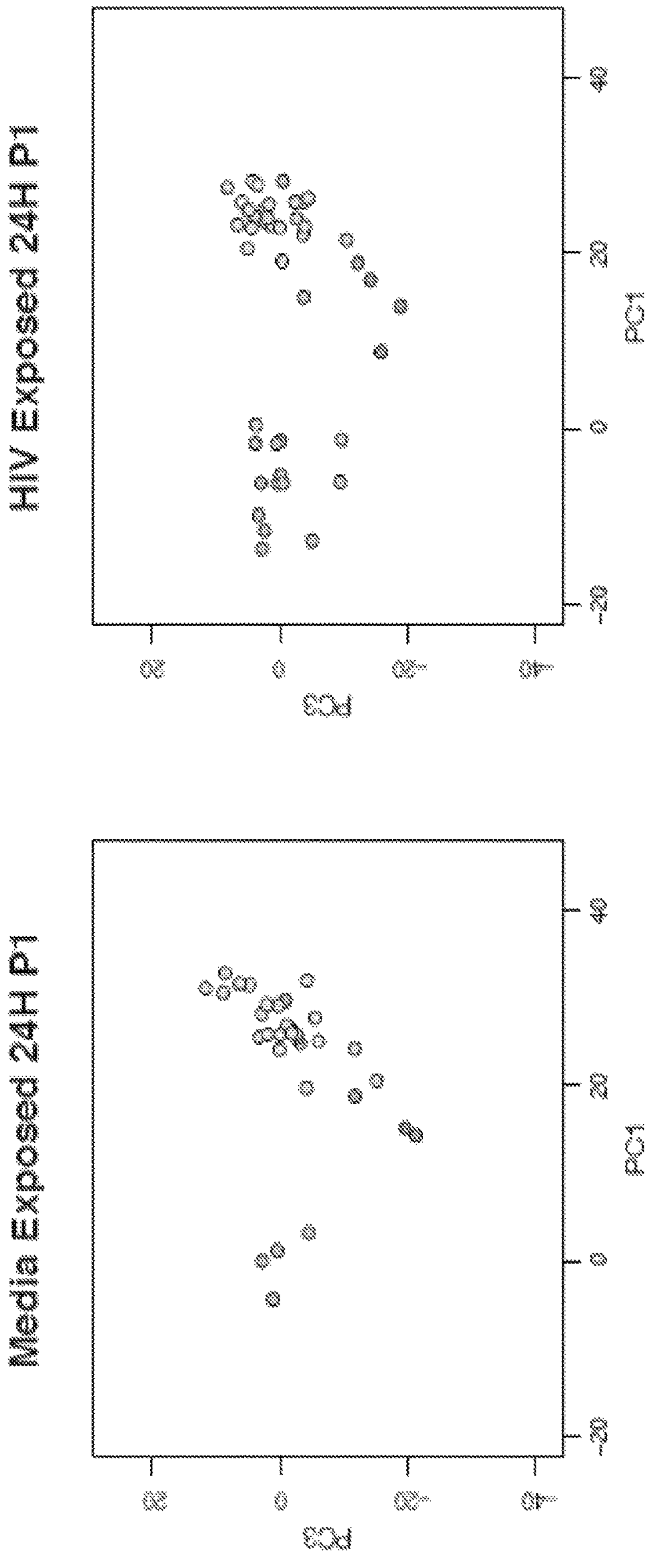
Figure 12C:
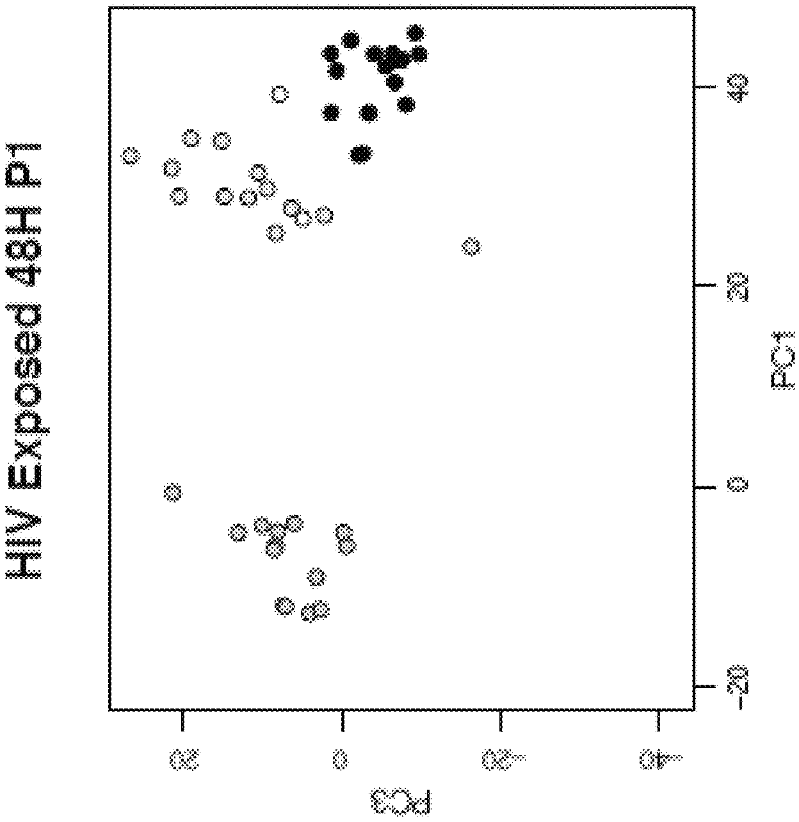
Figure 12D:
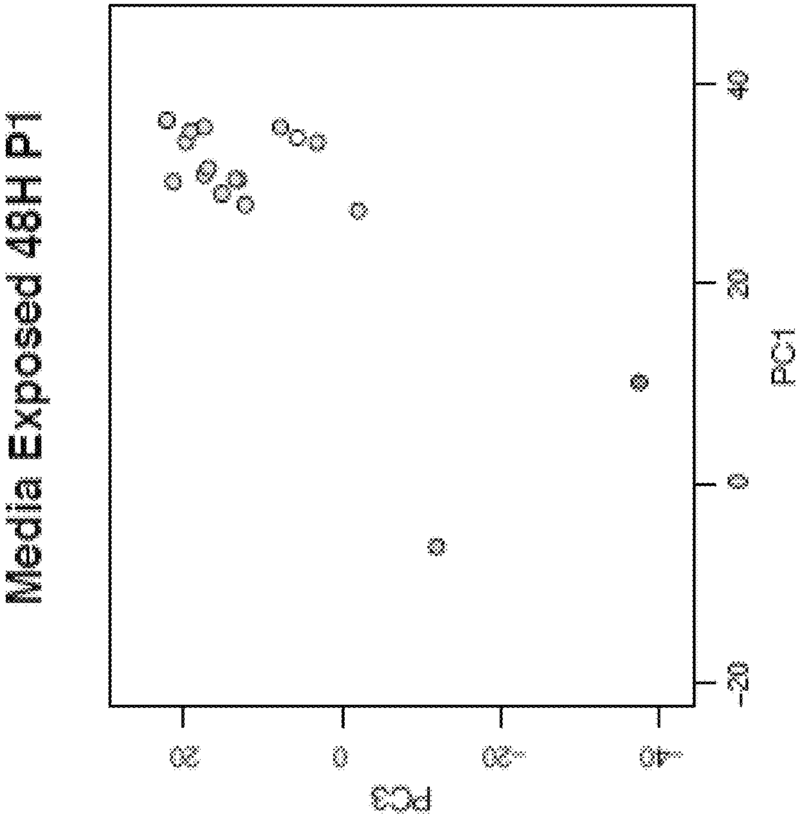

Before further characterizing the cluster 1 response, Applicants first considered whether the distinct cDC responses were simply driven by differences in viral burden. Adenine-rich regions in pseudotyped HIV-1 enabled us to efficiently prime viral RNA and reverse transcription (RT) products using SMART-Seq2, and thereby explore genome-wide associations between viral activity and host intracellular response patterns (Picelli et al. 2013) (FIG. 11). Importantly, the detection of HIV-1 transcripts was restricted to virus-exposed cells (>0 transcripts per million (TPM) in 1/56 media-exposed cell vs 52/95 virus-exposed cells; $p=6.6\times10^{13}$; Fisher's Exact Test) and included GFP-specific reads, confirming that HIV-1 transcripts reflected exogenous pseudotyped virus rather than autologous HIV-1, which also contains adenine-rich regions (FIG. 11).

Coexpression of CD64 & PD-L1 at the Surface defines Cluster 1-like cDCs

Figure 7A:
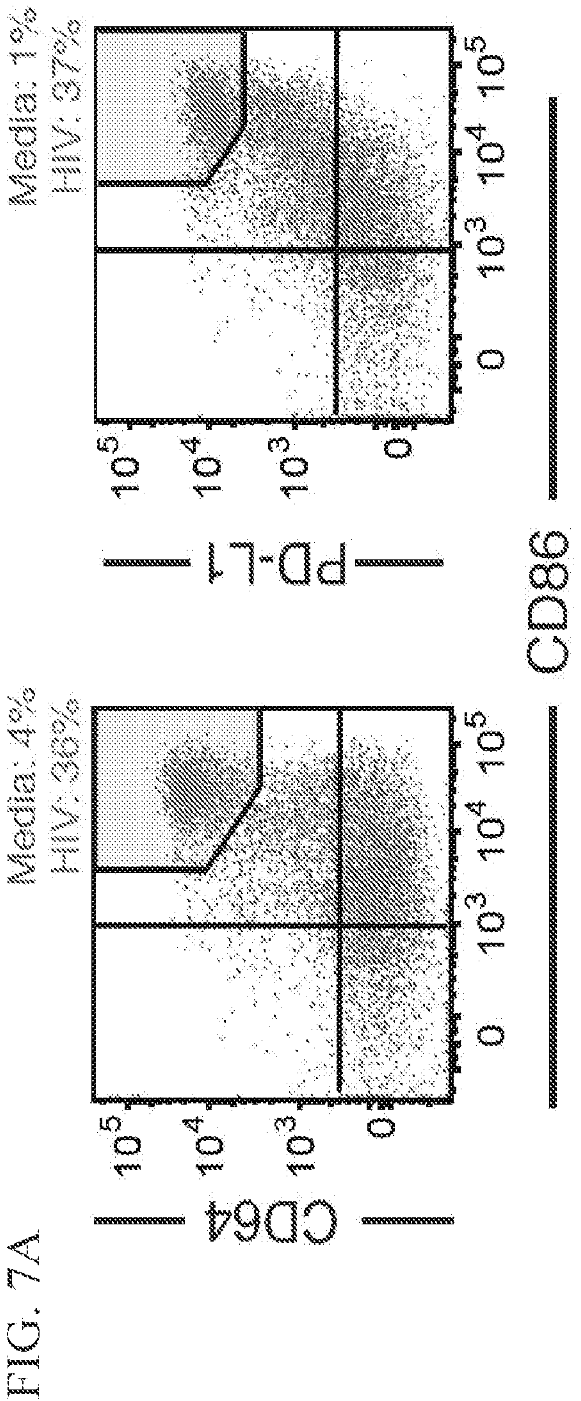
FIGS. 7A-7G illustrate that high levels of CD64 and PD-L1 definice highly functional cluster 1-like cDCs. (7A) Flow cytometry analysis of either CD64 (y-axis, left panel) or PD-L1 (y-axis, right panel) vs CD86 (x-axis) expression in cDCs from p1 in FIG. 5. Numbers above represent the percentage of $CD64^{Hi}$/PD-$L1^{Hi}$ cells (top right gate; light blue) at 24 hours in media (grey) and pseudotyped virus exposure (red) conditions. (7B) Flow cytometry plots showing analysis of CD64 vs PD-L1 expression on cDCs exposed to pseudotyped HIV-1 for 24h, defining 2 populations: $CD64^{Hi}$,PD-$L1^{Hi}$ (Hi; blue) and $CD64^{Lo}$,PD-$L1^{Lo}$ (Lo; green). Percentage in each gate listed above. (7C) Spider plot depicting the contribution of each subset (c1-c5) to population-level RNA-Seq data from cells in the Hi and Lo PD-L1, CD64 gates (as in 7C), 48 h after viral (solid line) or media exposure (dashed line). (7D) Proportion of proliferating $CD4^+$ (left) and $CD8^+$ (right) T cells co-cultured with the Hi and Lo sorted virus-exposed cDCs populations (n=5 patients). (7E) proportion of total $IFN\gamma^+$ $CD8^+$ T cells cultured with the Hi and Lo sorted virus-exposed cDCs populations (n=5 patients). (7F) Pie chart showing CD107a and $TNF\alpha$ expression on $CD8^+$ T cells cultured with Hi (left) or Lo (right) cDCs. (7G) Dot plots of proportions of $CD107a^+$, $TNF\alpha^+$ (left) and $CD107a^+$, $TNF\alpha^-$ (right) $CD8^+$ T cells cultured with Hi and Lo cDCs. Statistical significance was evaluated using Wilcoxon matched pairs signed-rank test (*, p<0.05).
Figure 8A:
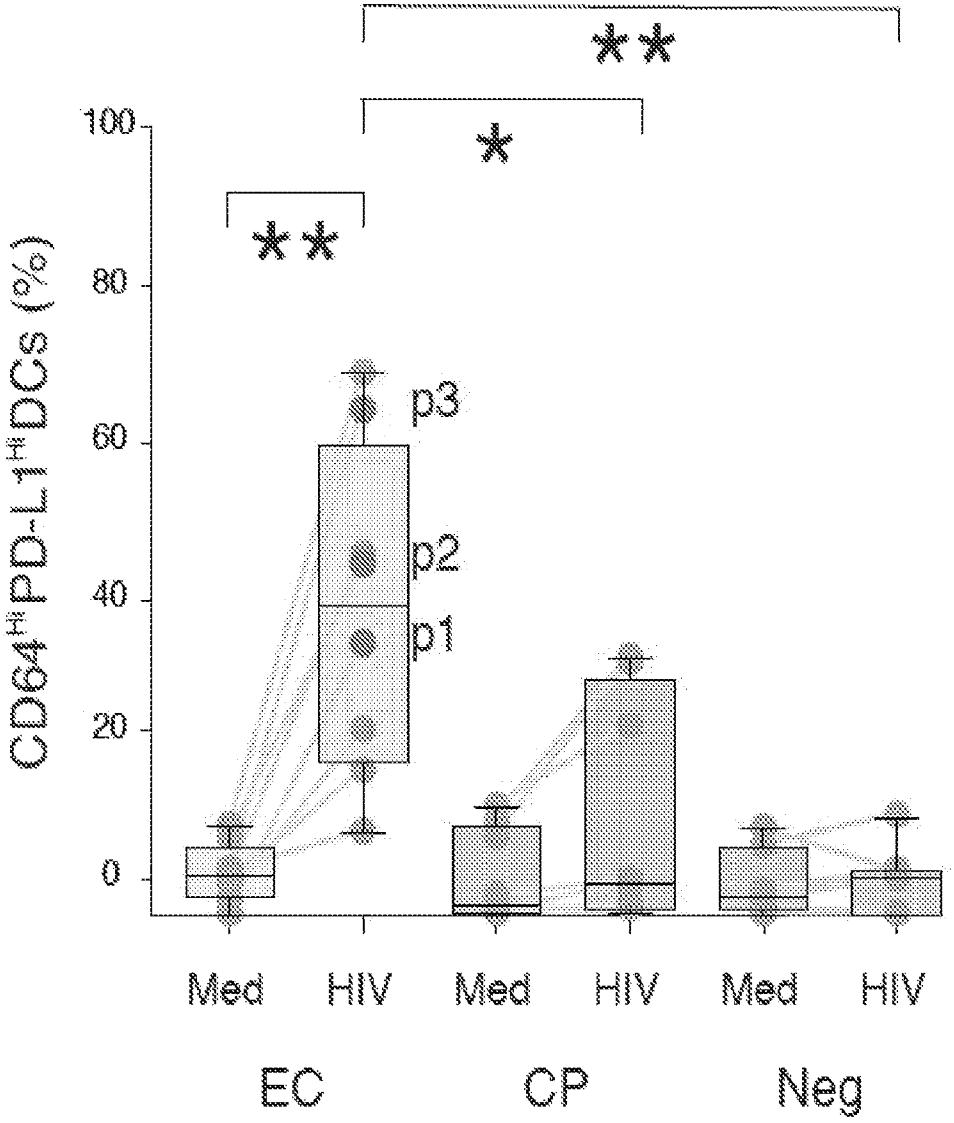
FIGS. 8A-8G illustrate adjuvant based modulation of innate immune activation in cDCs alters maturation towards a cluster 1 phenotype. (8A) Proportions of $CD64^{Hi}$, PD-$L1^{Hi}$ cDCs induced from multiple elite controllers (n=8), untreated chronic progressors (n=8) and HIV-negative individuals (n=7) after 24 h of culture in media or VSV-G pseudotyped HIV-1 (, p<0.01; Wilcoxon signed-rank test). (8B) Heatmap of weighted correlations between scRNA-Seq cluster medians and microarray data from mouse BMDC populations that were either unstimulated or stimulated with different TLR ligands for 24h (adapted from Amit et al, Science 2009 (Amit et al. 2009); see Methods). (8C) Proportion of $CD64^{Hi}$,PD-$L1^{Hi}$ cells among cDCs from PBMCs isolated from HIV-negative individuals cultured in the absence or the presence of VSV-G pseudotyped HIV-1, alone or in combination with TLR ligands (TLRL: TLR2L, PGNA, n=11; TLR3L, PolyI:C, n=11; TLR4L, LPS, n=8; TLR8L, CLO97, n=11; Methods). Statistical significance was calculated using Dunn's test (, p<0.01). (8D) Volcano plot of negative log un-adjusted p-value (Wilcoxon Rank-Sum) vs mean difference in upstream regulatory score between cluster 1 and cluster 3/4/5 based on single-cell correlations with shRNA-perturbation profiles from mouse BMDCs stimulated with LPS for 6h (adapted from N. Chevrier et al., Systematic Discovery of TLR Signaling Components Delineates Viral-Sensing Circuits. *Cell* 147, 853-867 (2011); see Methods). The net effect (activate, inhibit, both) of each perturbation is denoted by color (red, blue, grey; respectively), as is its breadth (size). (8E) Proportions of $CD64^{Hi}$,PD-$L1^{Hi}$ cells among EC cDCs cultured in the presence or absence of virus and DMSO (control) or 1 μM of BX795 TBK1 inhibitor (cyan; n=10). Statistical significance was calculated using a Wilcoxon signed-rank test (*, p<0.05). (8F) Proportions of $CD64^{Hi}$, PD-$L1^{Hi}$ cells among cDCs from healthy individuals (indigo) and elite controllers (olive) cultured in the absence or the presence of 2 μg/ml Poly I.C and polymer nanoparticles loaded with single-stranded (ss) or double stranded (ds) 100 nucleotide HIV-1 DNA (n=8), HIV negative individuals; n=6, ECs; **, p<0.01; *, p<0.05, Wilcoxon signed-rank test (black) or Mann-Whiney test (red). (8G) Proportion of proliferating $CD4^+$ or $CD8^+$ cultured with Hi or Lo cDC from a healthy donor stimulated with TLRL3 and nanoparticles containing gag ssDNA.

We next sought to functionally characterize cluster 1 due to its potential link to the effective innate immune responses observed in EC (Martin-Gayo et al. 2015). To identify putative markers for prospectively isolating c1-like cells after exposure to HIV-1, Applicants mined the scRNA-Seq profiles for surface protein encoding transcripts that were reproducibly differentially expressed in c1 vs c3/4/5 (log fold-change greater than zero) across all three ECs. (FIG. 6H and FIG. 15). Overall, Applicants obtained a list of 31 candidate markers (FIG. 6H) from which Applicants selected six (FCGR3, FCGR1, CD274, CLEC12A, ICAM1, SLAMF8) to profile at the protein-level by flow cytometry on cDCs 24 h after infection with pseudotyped HIV-1 (FIG. 16 and FIG. 7A). Among these, CD64 (FCGRIA) and PD-L1 (CD274) (FIG. 7A) exhibited the most dramatic virus-induced upregulation in the 3 patients previously characterized by RNAseq, as well as multiple other ECs (FIGS. 7A, 8A). CD64 is an Fc-receptor for IgG (C. E. van der Poel, R. M. Spaapen, J. G. van de Winkel, J. H. Leusen, Functional characteristics of the high affinity IgG receptor, FcgammaRI. *Journal of immunology* 186, 2699-2704 (2011)), while PD-L1 has been implicated in mediating the balance between T cell activation and immunopathology, as well as immediate effector differentiation and long-term memory formation in T cells (P. M. Odorizzi, K. E. Pauken, M. A. Paley, A. Sharpe, E. J. Wherry, Genetic absence of PD-1 promotes accumulation of terminally differentiated exhausted CD8+ T cells. The Journal of experimental medicine 212, 1125-1137 (2015)).

Figure 7B:
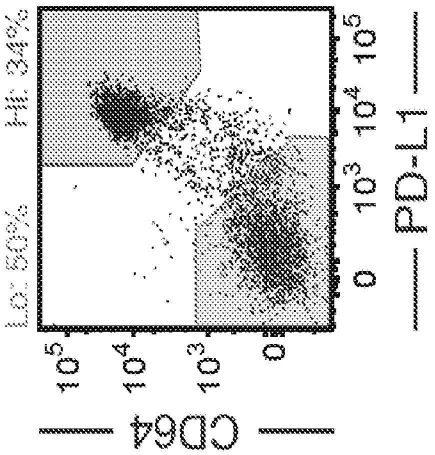
Figure 7C:
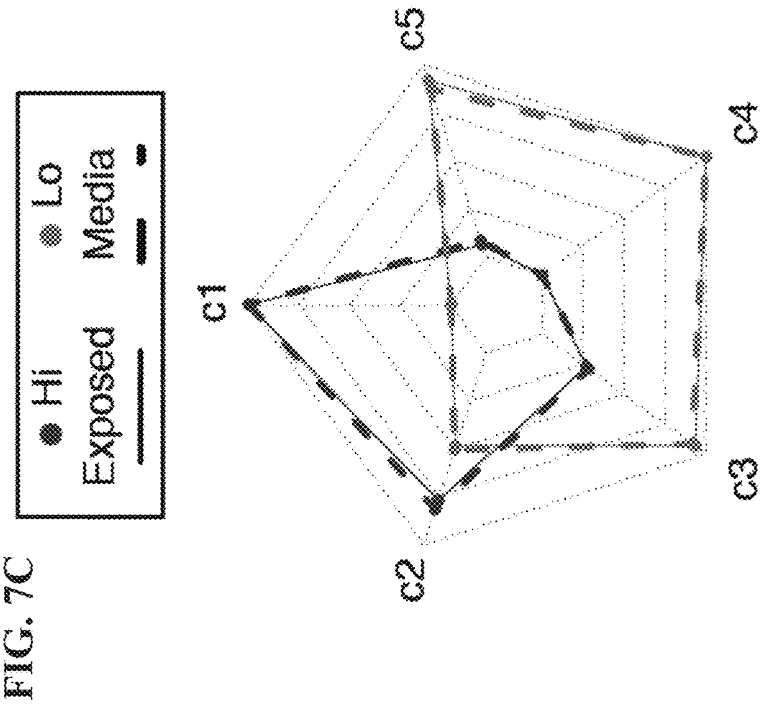

When Applicants sorted cDCs based on surface expression of CD64 and PD-L1, Applicants observed two dominant populations: one $CD64^{Hi}$, PD-L1Hi and the other $CD64^{L}$o, $PD\text{-}Li^{Lo}$ (FIG. 7B). Population-level transcriptional profiling of cDCs sorted on $CD64^{Hi}$, $PD\text{-}L1^{Hi}$ at 24 and 48 h post-viral stimulation gave gene expression profiles dominated by the c1, and to a lesser extent c2, signatures, while those sorted on $CD64^{Lo}$, $PD\text{-}L1^{Lo}$ matched a mixture of c3, 4, 5 (FIG. 7C), suggesting that CD64 and PD-L1 co-expression do indeed mark cluster 1-like cells. Importantly, Applicants highlight that while these markers are correlated with cluster 1 and cluster 2 responses, they are not necessarily involved in inducing either phenotype. Notably, all three sorted cDC subsets exhibited similar levels of HIV-1 reverse transcription at early time points after ex-vivo infection (FIG. 16C), suggesting differences in microbial sensing pathways, rather than viral replication dynamics, as the underlying cause of the differential viral responses observed among the cDC subsets.

Figure 7D:
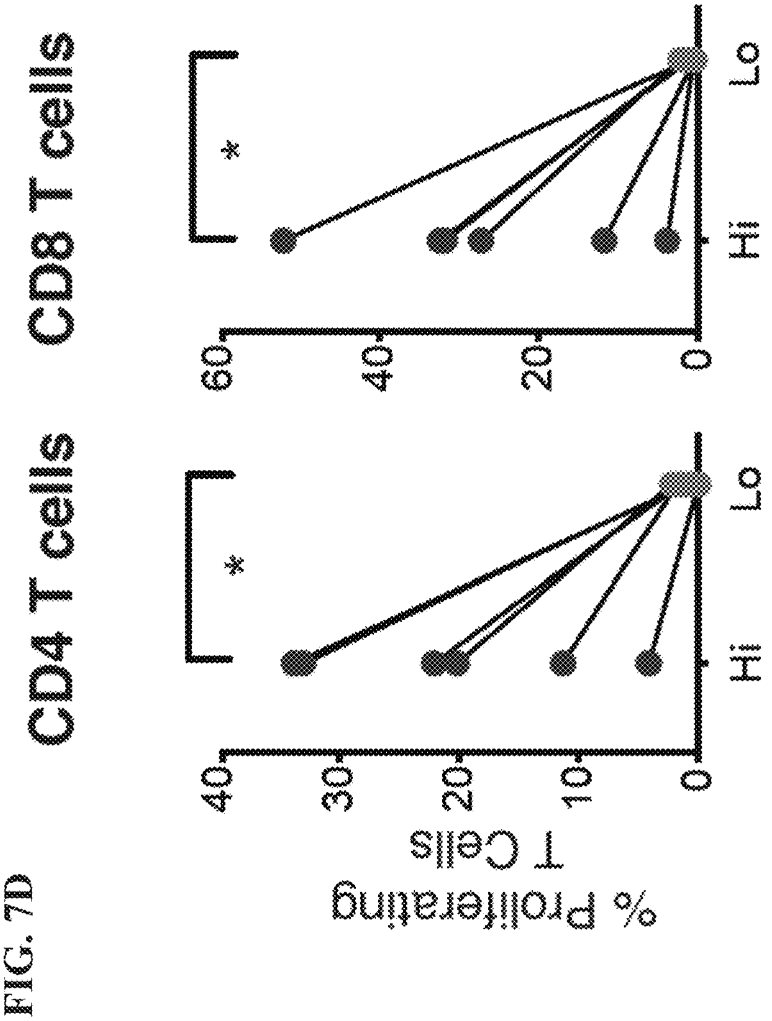
Figure 7E:
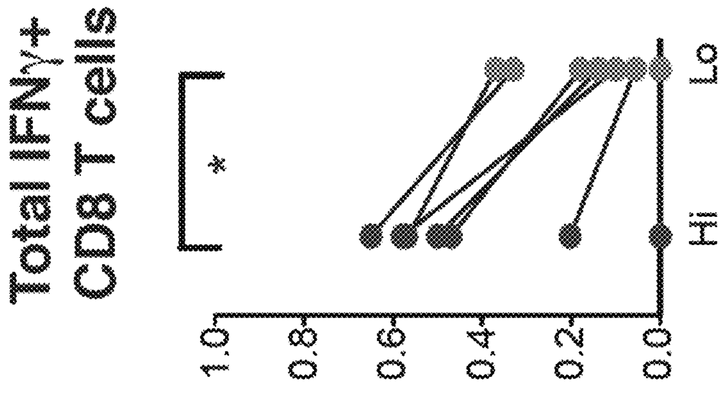
Figure 7F:
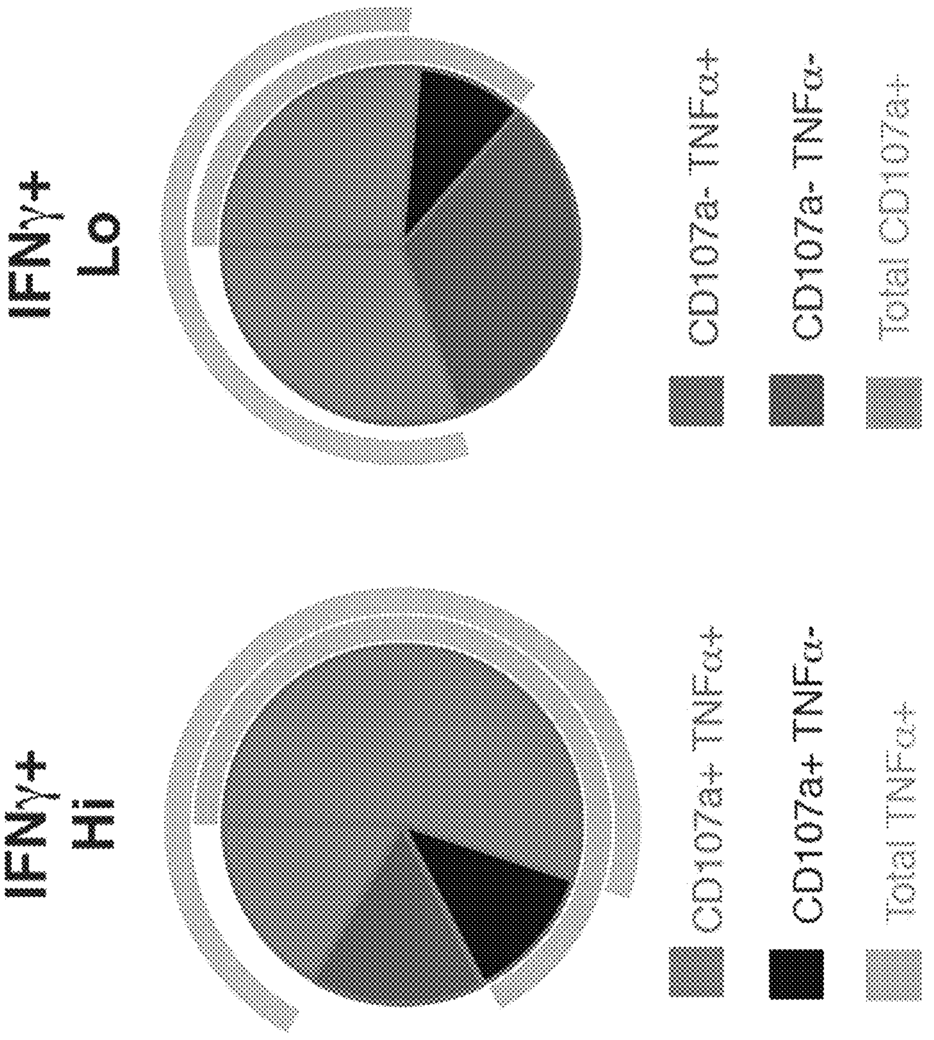
Figure 7G:
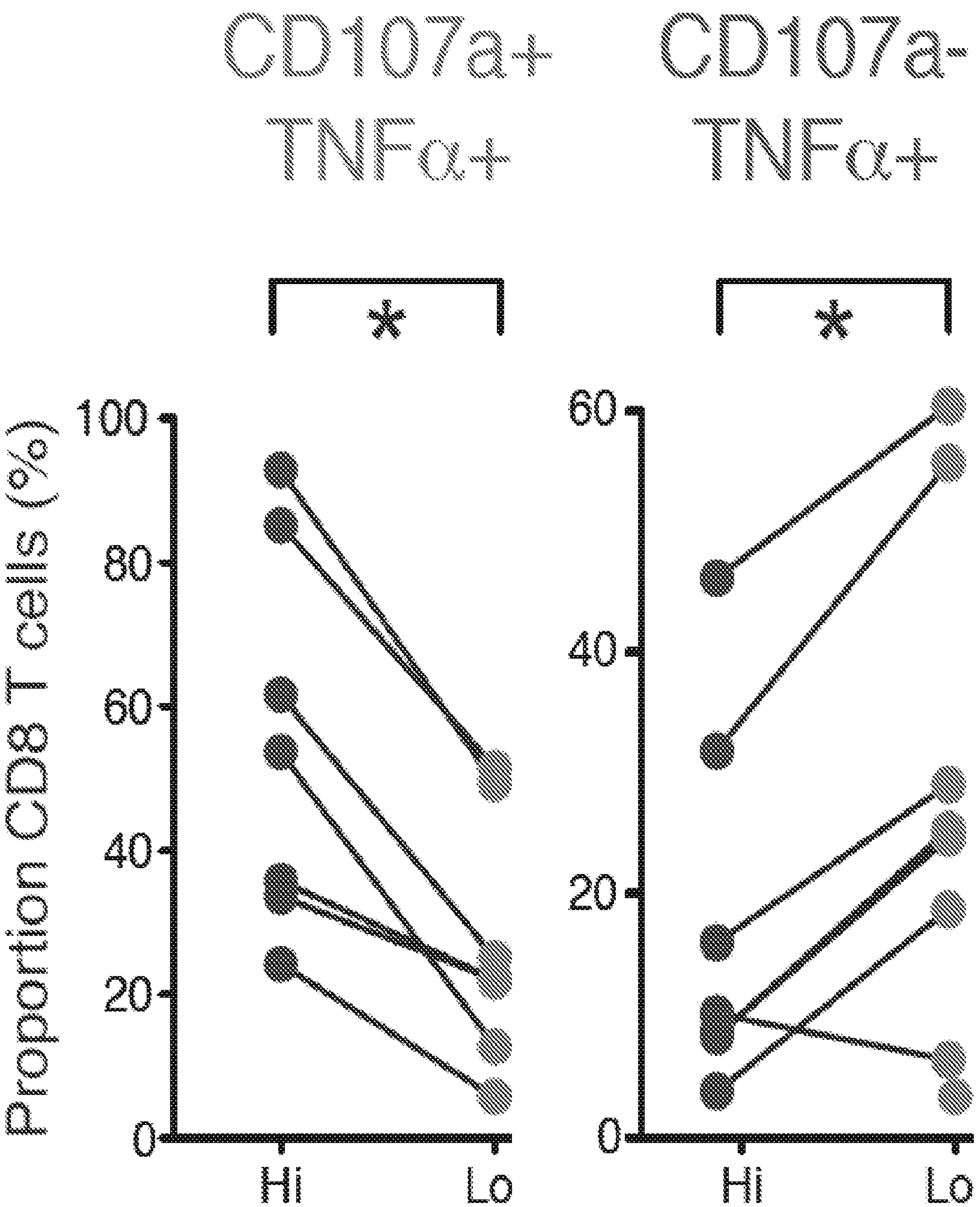

$CD64^{Hi}PD\text{-}L1^{HI}$ cDCs Display Superior Antigen Presenting Cell Properties Applicants next examined the antigen presenting abilities of the CD64, PD-L1 cDC subpopulations using mixed leukocyte reactions. In these experiments, the cluster 1-like/$CD64^{Hi}$ $PD\text{-}L1^{Hi}$ DC population demonstrated superior ability to stimulate $CD4^{+}$ and $CD8^{+}$ T cell proliferation relative to $CD64^{L}$o, $PD\text{-}L1^{Lo}$ populations across multiple ECs (FIG. 7D). Similar results were obtained under more physiological culture conditions, where $CD64^{Hi}$, $PD\text{-}L1^{Hi}$ cDC were capable of efficiently stimulating the production of IFN in a significantly higher proportion of autologous $CD8^{+}$ T cells as compared to $CD64^{Lo}$,$PD\text{-}L1^{Lo}$ DCs (FIG. 7E). Further, IFNγ+ $CD8^{+}$ T cells primed in the presence of cluster 1-like $CD64^{Hi}$, $PD\text{-}L1^{Hi}$ DC expressed significantly higher levels of the degranulation markers CD107a and TNF (FIG. 7F, 7G) Collectively, these data indicate that cluster 1-like $CD64^{Hi}$, $PD\text{-}L1^{Hi}$ DC most likely have superior abilities to induce HIV-1 specific cytotoxic $CD8^{+}$ T cells.

Figure 17A:
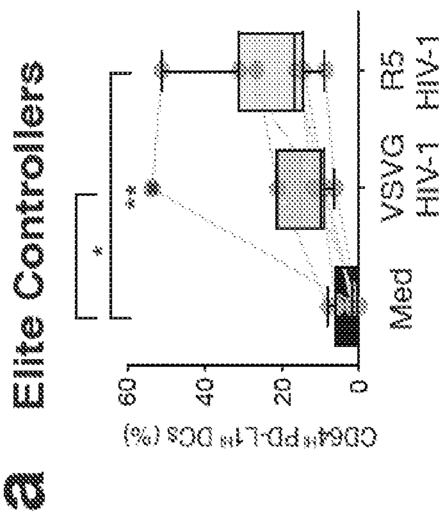
FIGS. 17A-17C illustrate the Proportions of $CD64^{Hi}$ $PD\text{-}L1^{Hi}$ cells included within CD14− CD11 cHi HLADR+ cDC from elite controllers (a, n=7) and HIV negative donors (b, n=7) after 24 h of culture in the presence of Media or either VSV-G pseudotyped or CCR5 (R5) tropic HIV-1 virus. Statistical significance was calculated using a Kruskal-wallis test followed by a Dunn's test. *p<0.05; **p<0.01. Also, the proportions of $CD64^{Hi}$ $PD\text{-}L1^{Hi}$ cells detected in cDCs sorted prior to culture in the presence of media and VSV-G pseudotyped virus. Statistical significance was calculated using a wilcoxon test (*p<0.05).
Figure 17B:
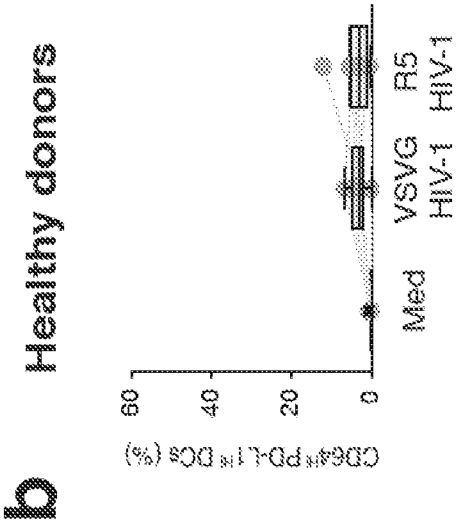
Figure 17C:
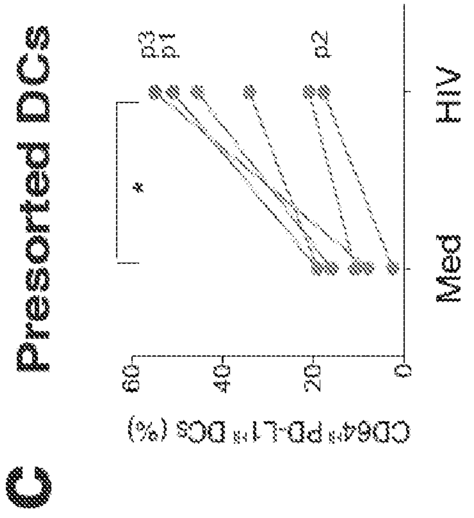
Figure 18A:
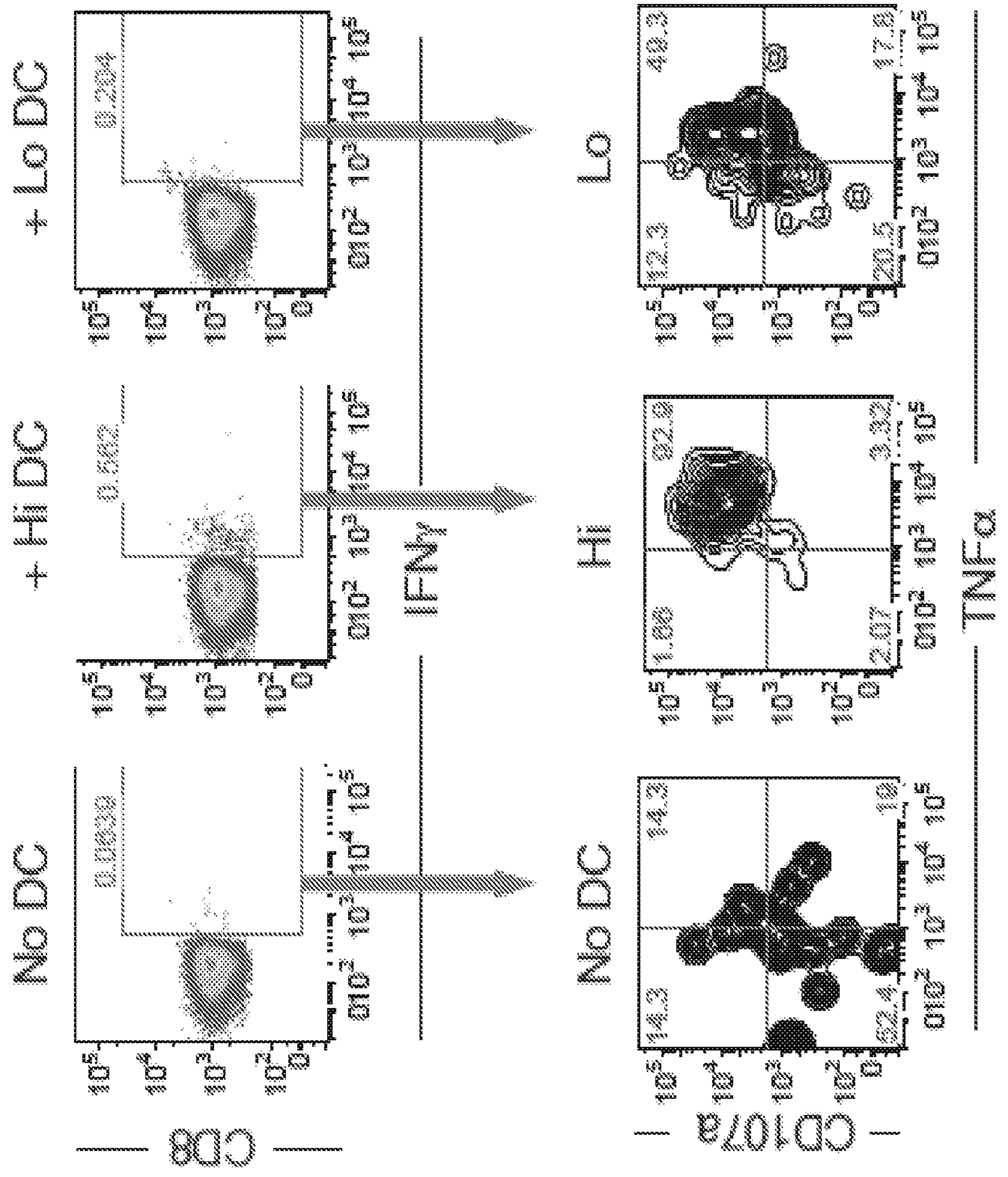
FIG. 18A illustrates the flow cytometry analysis of CD8 vs intracellular levels of IFNgamma present in gated CD8 T cells cultured in the absence or the presence of autologous cDC exposed to HIV-1 and expressing either high or low levels of CD64 and PD-L1. Expression of CD107a and intracellular TNFalpha was analyzed on gated IFNgamma positive cells in each condition (lower panels). Numbers in quadrants represent proportions of positive cells.
Figure 18B:
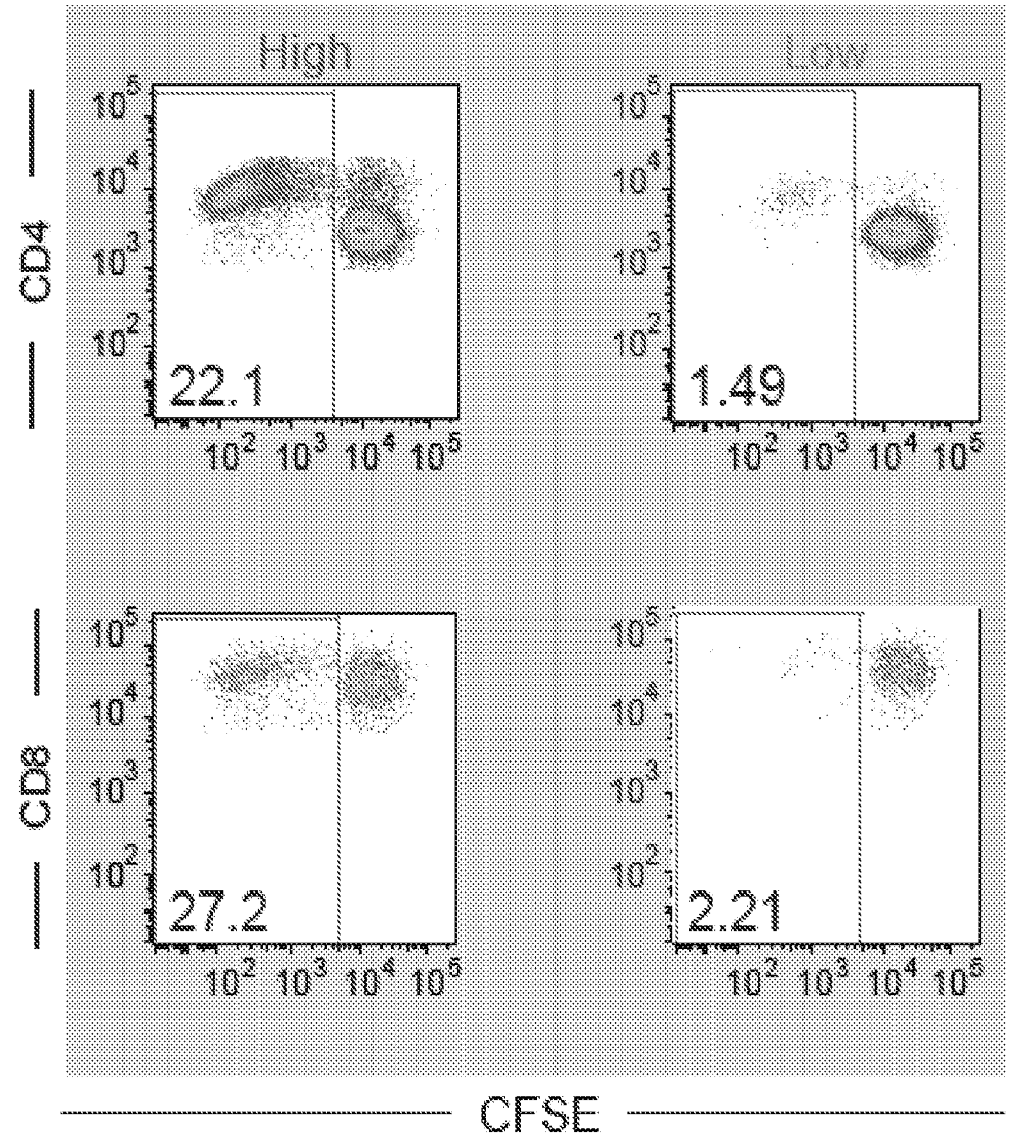
FIG. 18B illustrates the flow cytometry analysis of CFSE levels present in CD4 (upper panels) and CD8 (lower panels) co-cultured in the presence of allogeneic cDC exposed to HIV-1 and expressing high or low levels of CD64 and PD-L1. Numbers on plots represent proportions of CFSE low proliferating T cells.

Consistent with the previous findings (E. Martin-Gayo et al., Potent Cell-Intrinsic Immune Responses in Dendritic Cells Facilitate HIV-1-Specific T Cell Immunity in HIV-1 Elite Controllers. *PLoS pathogens* 11, e1004930 (2015)), highly functional antigen-presenting cDCs with a c1-like/$CD64^{Hi}$, $PD\text{-}L1^{Hi}$ phenotype were more frequent in, but not unique to, ECs after viral exposure (p=0.0078; Wilcoxon matched-pairs signed rank test), potentially explaining improved CTL responses in ECs (X. Gao et al., AIDS restriction HLA allotypes target distinct intervals of HIV-1 pathogenesis. *Nature medicine* 11, 1290-1292 (2005); P. Kiepiela et al., Dominant influence of HLA-B in mediating the potential co-evolution of HIV and HLA. *Nature* 432, 769-775 (2004)). Lower proportions of cDCs with this phenotype were also detected in HIV-1 chronic progressors (CP) and healthy individuals (Neg) (FIG. 8A). These cohort-intrinsic differences were also observed when cDCs were exposed to CCR5-tropic HIV-1 viruses (FIGS. 17A and 17B), suggesting that this phenomenon is not restricted to the VSV-G pseudotyped HIV-1 constructs. Finally, the c1-like/$CD64^{Hi}$, $PD\text{-}L1^{Hi}$ cDC phenotype observed in EC could be effectively induced in cDCs sorted prior to stimulation with VSV-G pseudotyped HIV-1 virus, suggesting that the propensity to respond thusly is driven by properties intrinsic to the cDCs rather than a paracrine signals from neighboring cells (FIG. 17C).

Figure 8B:
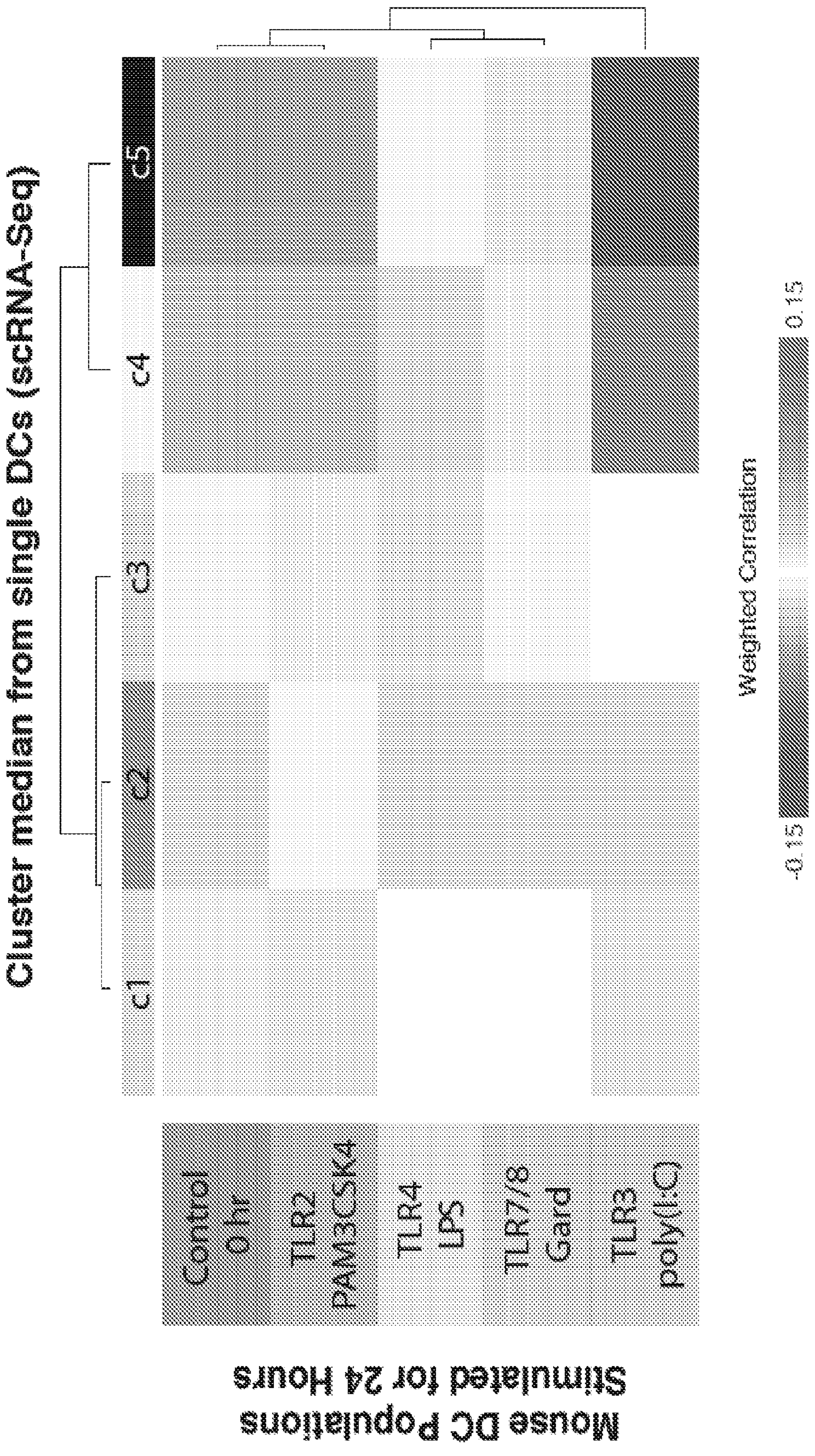
Figure 9A:
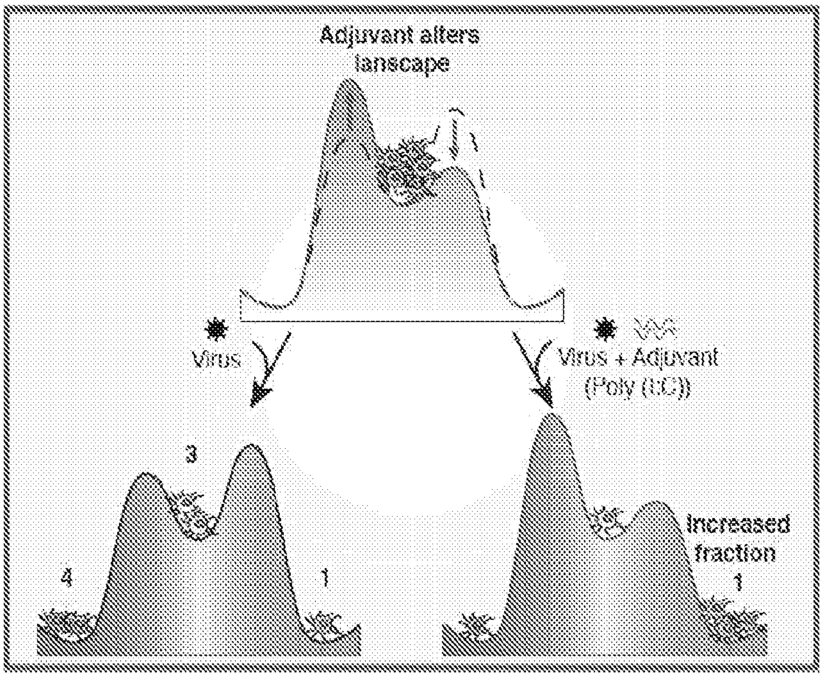
FIGS. 9A-9B illustrate a unifying model of results. (9A) Potential-energy diagram conceptualizing how adjuvants and perturbations alter the percentage of cDCs generating each response profile, cluster 1-5. (9B) Network diagram depicting tested nodes implicated in the cluster 1 cDC response.

A Computational Framework for Modulating the Fraction of $CD64^{Hi}$ $PD\text{-}L1^{Hi}$ cDC Responses with Adjuvants Given their potential therapeutic and prophylactic importance for non-EC populations, Applicants next sought to uncover the molecular mechanisms responsible for the acquisition of the c1-like/$CD64^{Hi}$, $PD\text{-}L1^{Hi}$ cDC phenotype. The upstream regulator analysis and gene set enrichments for cluster 1 highlighted several signatures of human DC stimulation, including multiple components of TLR pathways (FIG. 6A-6D, FIG. 13), suggesting that differences in TLR activation might contribute to shaping the antiviral response of this cDC subset and that Applicants might be able to select TLR adjuvants that would favor it. To identify which TLR pathway is more compatible with the c1 signature, due to limited public availability of human perturbation data, Applicants chose to utilize microarray data from mouse bone-marrow derived DCs (BMDCs) stimulated with a comprehensive panel of TLR ligands (I. Amit et al., Unbiased reconstruction of a mammalian transcriptional network mediating pathogen responses. *Science* 326, 257-263 (2009)). For each single-cell cluster average, Applicants calculated weighted correlations between the scRNA-Seq profiles and the BMDC microarray data (FIG. 8B). The analysis showed that cluster 1 positively correlated only with TLR3 stimulation with Poly(I:C). Cluster 2, while mildly tied with TLR3 stimulation, was significantly more correlated with the gene expression of mouse BMDCs stimulated with a TLR4 agonist (LPS). Clusters 3, 4 and 5, meanwhile, correlated more positively with unstimulated and TLR2 treated cells. Collectively, these analyses generate the actionable hypothesis that triggering the endosomal dsRNA sensor TLR3 might selectively activate downstream pathways that synergize with cytosolic viral sensing mechanisms to increase the fraction of cDCs maturing towards a cluster 1-like/$CD64^{Hi}$, $PD\text{-}L1^{Hi}$ phenotype (FIG. 9).

Figure 8C:
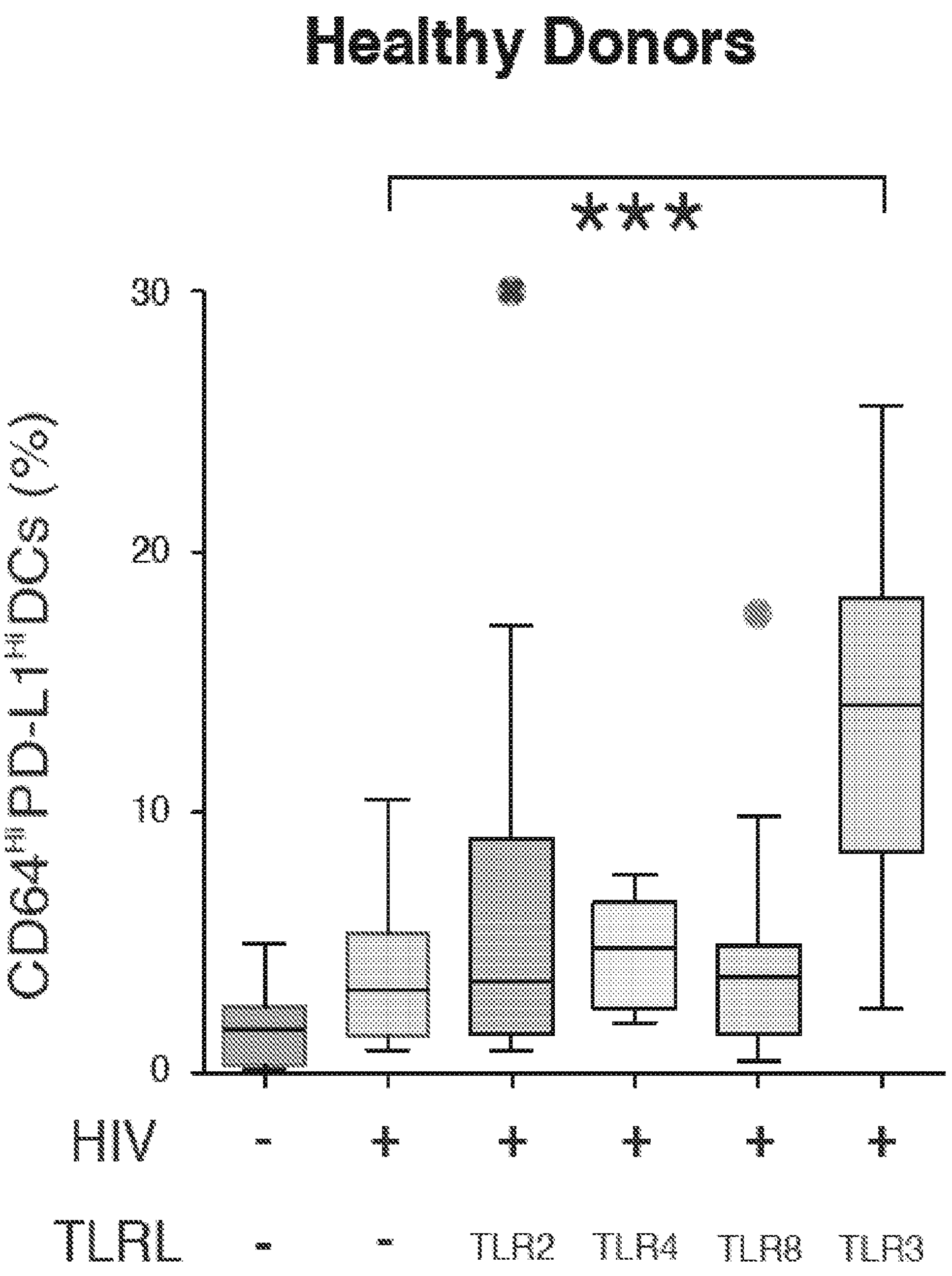
Figure 19A:
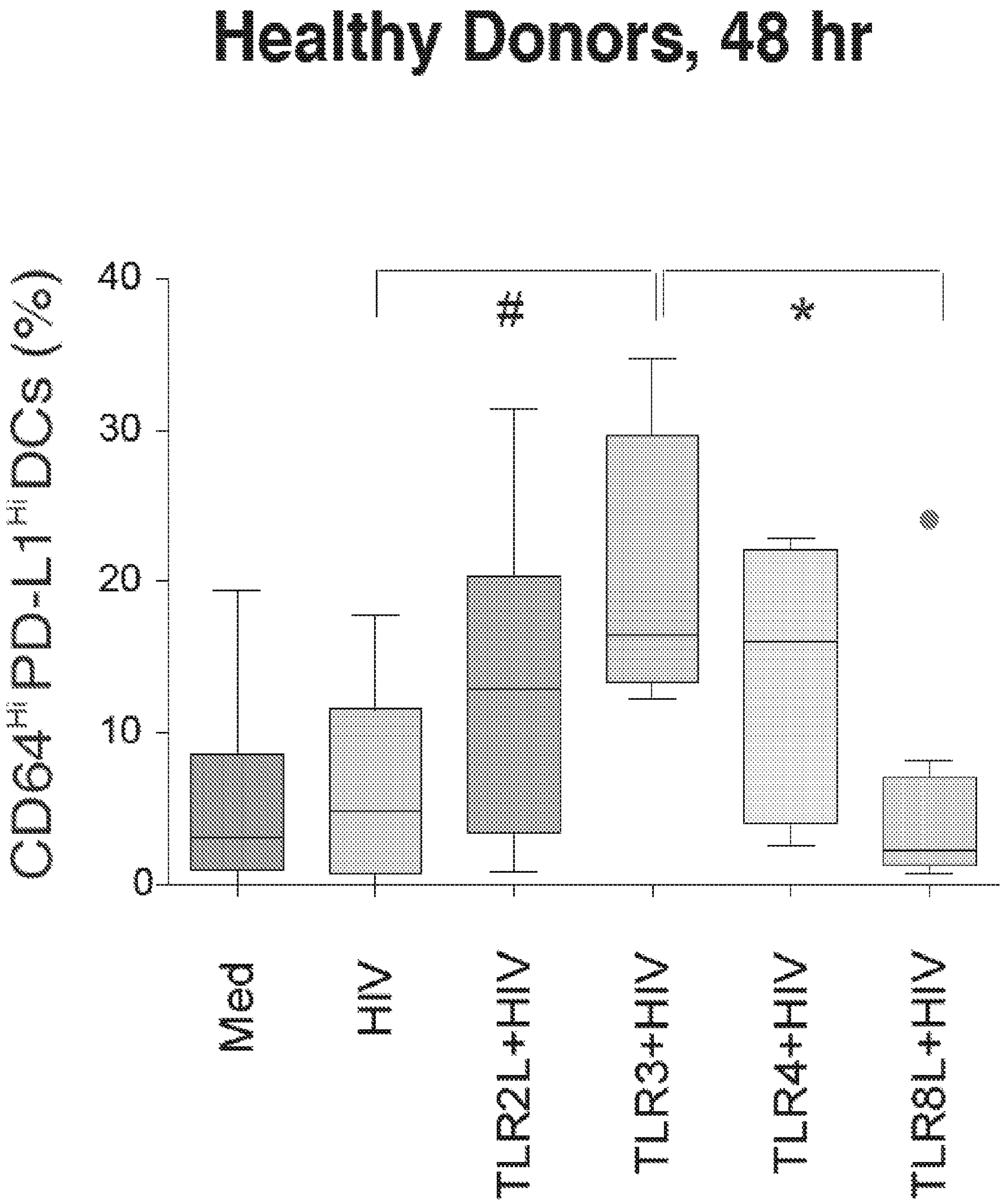
FIG. 19A illustrates the proportion of $CD64^{Hi}$ $PD\text{-}L1^{Hi}$ cells present on CD14− CD11cHi HLADR+ cDCs from healthy individuals cultured in the absence or the presence of VSV-G pseudotyped HIV-1 alone or in combination with TLR ligands (TLRL)(TLR4L,LPS; TLR3L Poly:IC; TLR2L, PGNA; TLR8L, CL097). Combination of HIV-1 plus TLR3L significantly induce the CD64, PD-L1 high pop in non-elite controllers. ***, p<0.001 Wilcoxon matched pairs signed rank test.
Figure 19B:
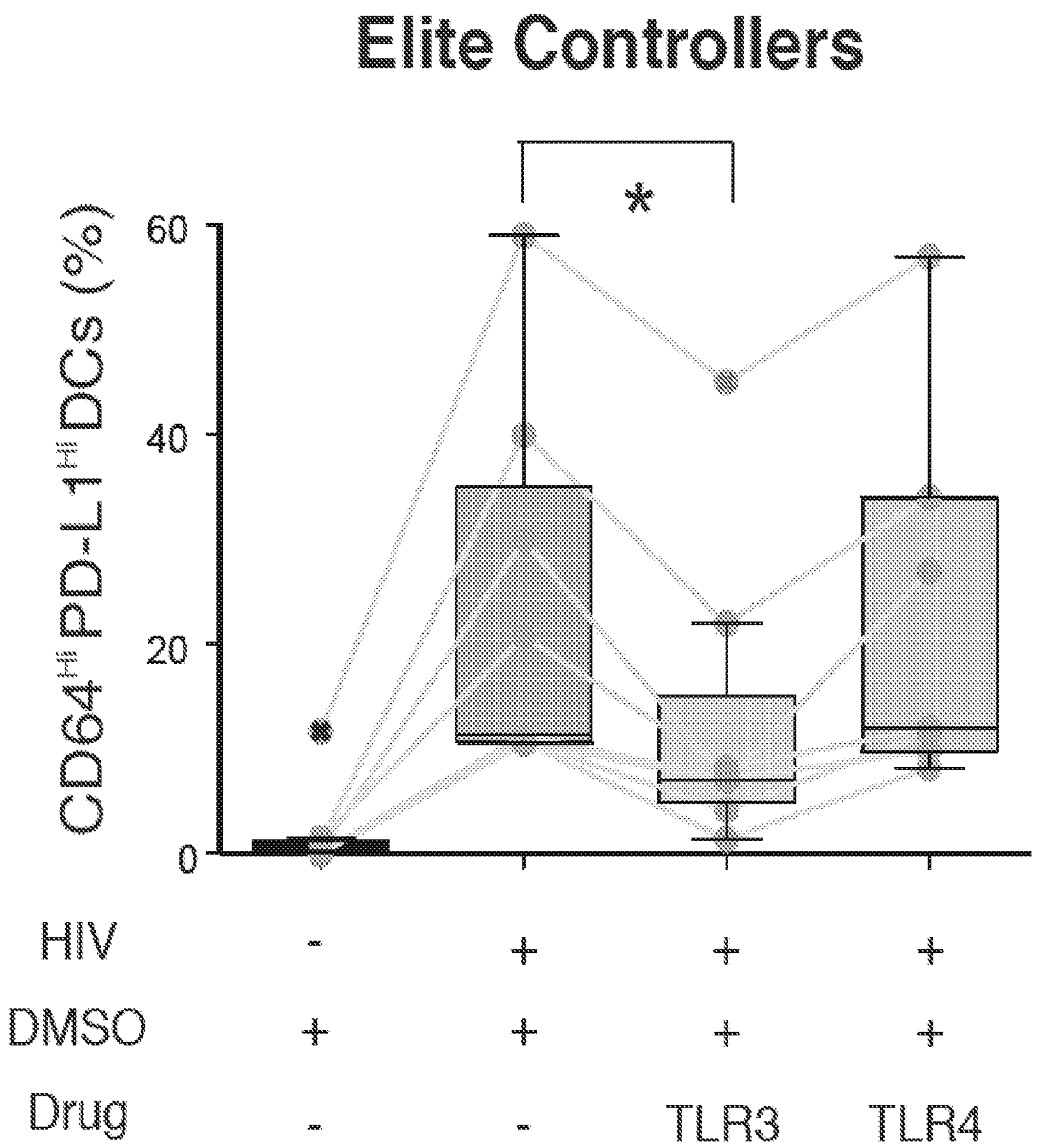
FIG. 19B illustrates the proportions of $CD64^{Hi}$, $PD\text{-}L1^{Hi}$ cells among cDCs ($CD14^-$, $CD11c^+$, $HLADR^+$) cultured in the presence or absence of virus and DMSO (control) or either TLR3 or TLR4 antagonists (SOM). Statistical significance was calculated using a Wilcoxon signed-rank test (*, p<0.05).

To test this hypothesis, Applicants incubated PBMCs from several HIV-negative persons (n=7)—that do not spontaneously generate significant numbers of cluster 1-like/$CD64^{H}$i $PD\text{-}L1^{Hi}$ cells in vitro in the presence of VSV-G pseudotyped HIV-1 (FIG. 8A)—with virus and different TLR agonists, including Poly(I:C) as a TLR3 ligand, for 24 hours. In contrast to the other TLR ligands tested, Applicants observed that co-incubation of cDCs with virus and Poly(I: C) led to a significant increase in the proportion of cluster 1-like/CD64$^{Hi}$, PD-L1$^{Hi}$ cDCs in PBMCs from healthy individuals (p=0.0091, Kruskal-Wallis and post hoc Dunn's test) (FIG. 8C). Similar results were observed after a 48 h incubation (FIG. 19A). Meanwhile, in ECs, a TLR3, but not a TLR4, inhibitor had a modest, but significant, effect on the acquisition of the cluster 1/CD64$^{Hi}$, PD-L1$^{Hi}$ cDC phenotype (p=0.02; Wilcoxon matched-pairs signed-rank test; FIG. 19B).

Figure 8D:
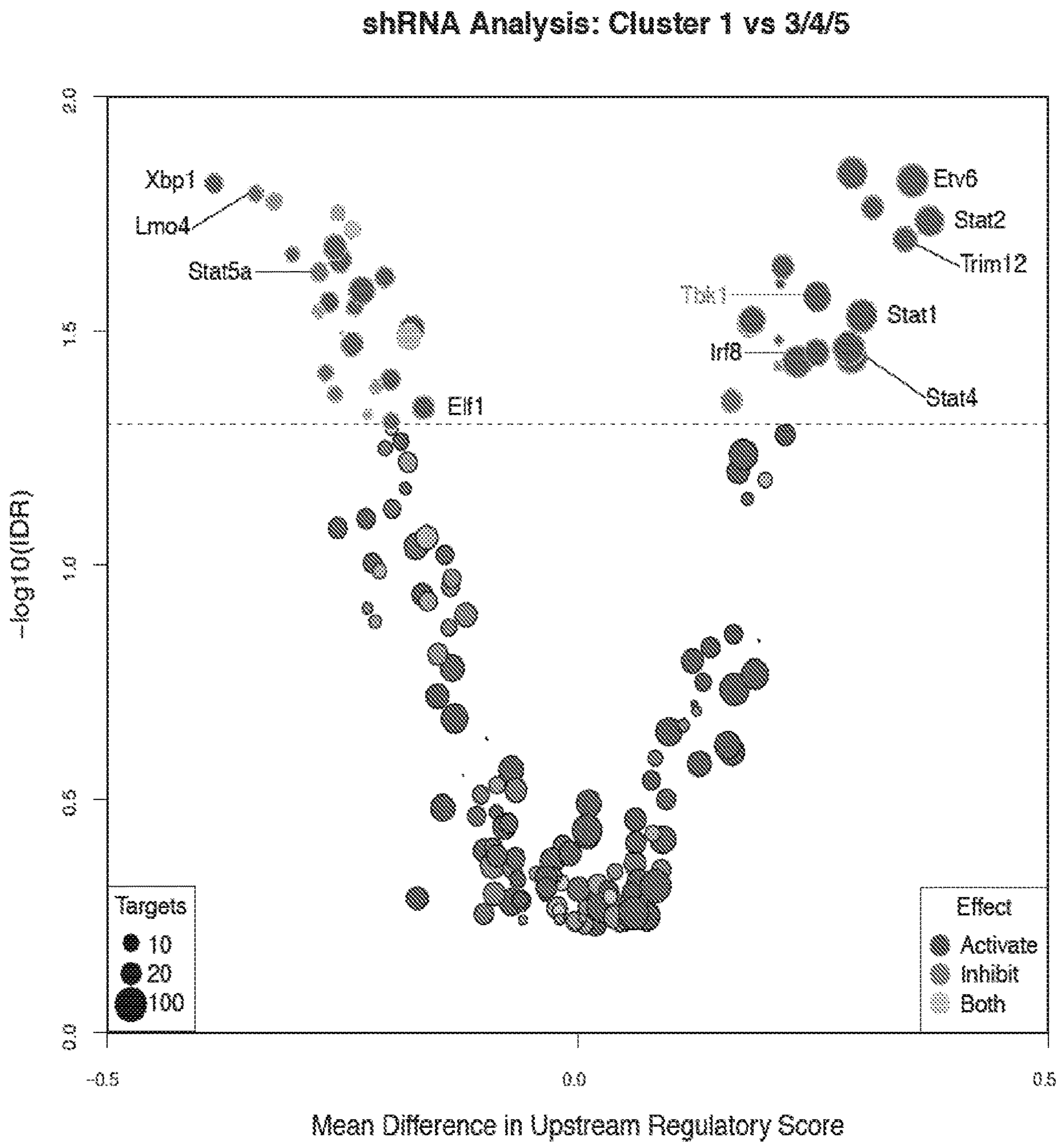
Figure 8E:
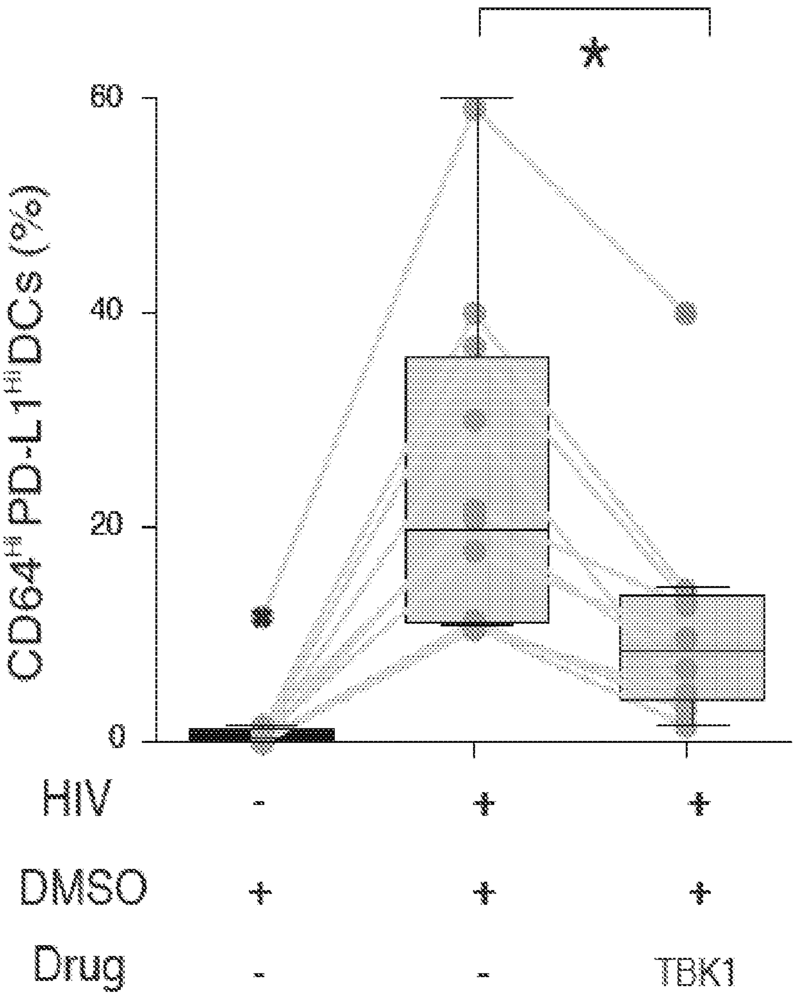

Computational Identification of Master Regulators of CD64$^{Hi}$PD-L1$^{HI}$ cDC Generation To more thoroughly understand the signaling cascades responsible for cluster-1 induction and identify additional nodes for modulating its abundance, Applicants next examined downstream regulators that could integrate signals from TLR3 and other innate immune viral sensing pathways to generate the cluster-1-like phenotype. For this purpose, Applicants developed a second computational approach to identify the potential importance of transcription factors and signaling molecules previously perturbed in mouse BMDCs (N. Chevrier et al., Systematic Discovery of TLR Signaling Components Delineates Viral-Sensing Circuits. *Cell* 147, 853-867 (2011)) for generating cluster 1 over cluster 3,4,5 signatures (FIGS. 8D, FIG. 13C). Among the top positive regulators of cluster 1 was TBK1, a recognized signal mediator that is activated in multiple innate immune sensing pathways at the convergence of the organelle-associated adaptors MAVS, TRIF (downstream effector of TLR3, TLR4), and STING (effector of the intracellular DNA sensor cGAS) (M. Habjan, A. Pichlmair, Cytoplasmic sensing of viral nucleic acids. *Current opinion in virology* 11, 31-37 (2015); Y. M. Loo, M. Gale, Jr., Immune signaling by RIG-I-like receptors. Immunity 34, 680-692 (2011); Z. Ma, B. Damania, The cGAS-STING Defense Pathway and Its Counteraction by Viruses. *Cell host & microbe* 19, 150-158 (2016)), previously detected in the upstream regulator analysis (FIG. 2D). To evaluate whether signaling through TBK1 contributes to the maturation of cDCs into the cluster 1-like/CD64$^{Hi}$, PD-L1$^{Hi}$ subset in ECs, Applicants added BX795, a TBK-1 antagonist, to EC PBMCs at the time of viral addition. As shown in FIG. 8E, inhibition of TBK1 during viral exposure led to a dramatic and significant abrogation of the induction of the cluster 1-like/CD64$^{Hi}$, PD-L1$^{Hi}$ population in ECs (p=0.0020; Wilcoxon signed-rank test), suggesting that stimulation of TBK1 is a critical driver of the acquisition of a cluster 1 phenotype by cDCs.

Figure 4A:
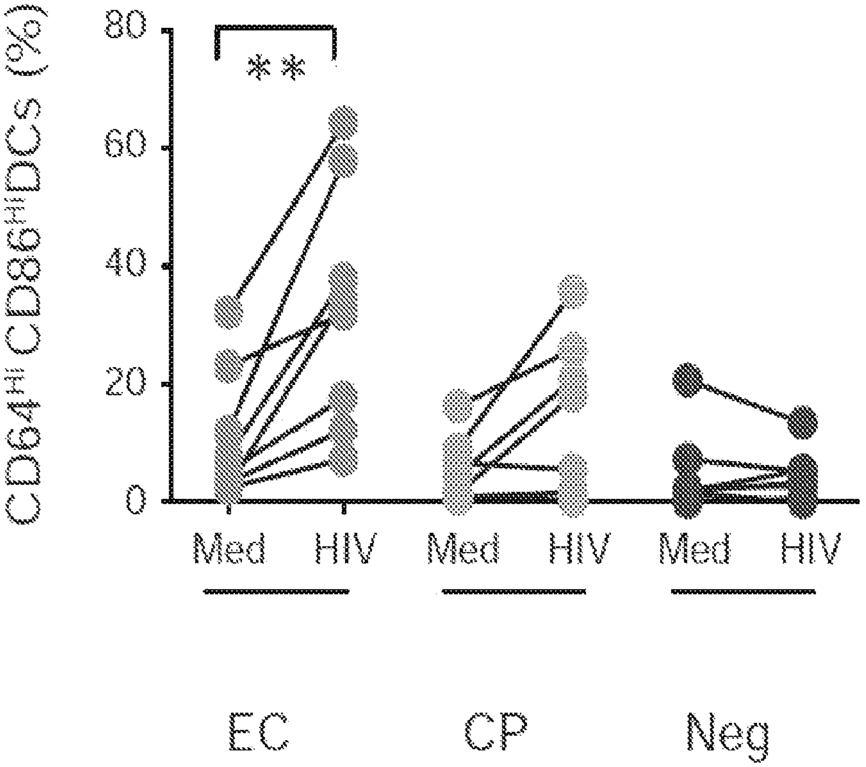
FIG. 4A-4F. (4A) Percentage of $CD64^{Hi}$ $CD86^{Hi}$ (top) and $PD\text{-}L1^{Hi}$ $CD86^{Hi}$ (lower) cells in CD14− CD11cHi HLADR+ PBMCs from elite controllers (EC), untreated chronic progressors (CP) and HIV-negative (Neg) after 24 h of culture in media or VSV-G pseudotyped HIV-1. PD-L1 high, CD64 high cells are observed in all patients, but are only significantly induced by virus in cultures of EC cells. ; $p<0.01$ Wilcoxon matched pairs signed rank test. (4B) Heatmap of correlations between scRNA-Seq (single cells colored by PCA cluster in 1B) and publically available mouse DC populations microarray or nCounter data. Mouse DCs were stimulated for 0 hours (control) or 24 hours with one of five TLR adjuvants. Dotted lines separate cells in different clusters. VEx-B appears most characteristic of TLR3-agonist induction (POLY I.C). (4C) Proportion of $CD64^{Hi}$ $PD\text{-}L1^{Hi}$ cells present on CD14− CD11cHi HLADR+ cDCs from healthy individuals cultured in the absence or the presence of VSV-G pseudotyped HIV-1 alone or in combination with TLR ligands (TLRL)(TLR4L,LPS; TLR3L Poly:IC; TLR2L, PGNA; TLR8L, CL097). Combination of HIV-1 plus TLR3L significantly induce the CD64, PD-L1 high pop in non-elite controllers. *, $p<0.001$ Wilcoxon matched pairs signed rank test (4D) Volcano plot of shRNA signatures, colored by effect and sized according to impact on TLR4 in mouse at 6 hours. Highly significant genes are named in the plot. (4E) Proportions of CD64, PD-L1 high cells included in CD14− CD11cHi HLADR+ cDCs cultured in the presence or absence of virus and DMSO (control) or a drug inhibiting TBK1 (cyan). TBK1 was chosen from the volcano plot in D. PBMCs from ECs were incubated with the indicated combination of virus, DMSO and drug and analyzed by FACS. Drugs targeting TBK1 *$p<0.05$; Wilcoxon matched pairs signed rank test. (4F) Proportions of $CD64^{Hi}$ $PD\text{-}L1^{Hi}$ cells from cells from healthy individuals (Left) and elite controllers (right) cultured in the absence or the presence of TLR3 ligands and nano-particle loaded HIV-1 ss/ds DNA (100 nt Gag). Single controls of cells exposed to TLR3L, ss/dsDNA and nanoparticles are also included. *P<0.05; **P<0.01 Wilcoxon signed rank test n=8 HIV negative patients and n=6 elite controllers.
Figure 4A:
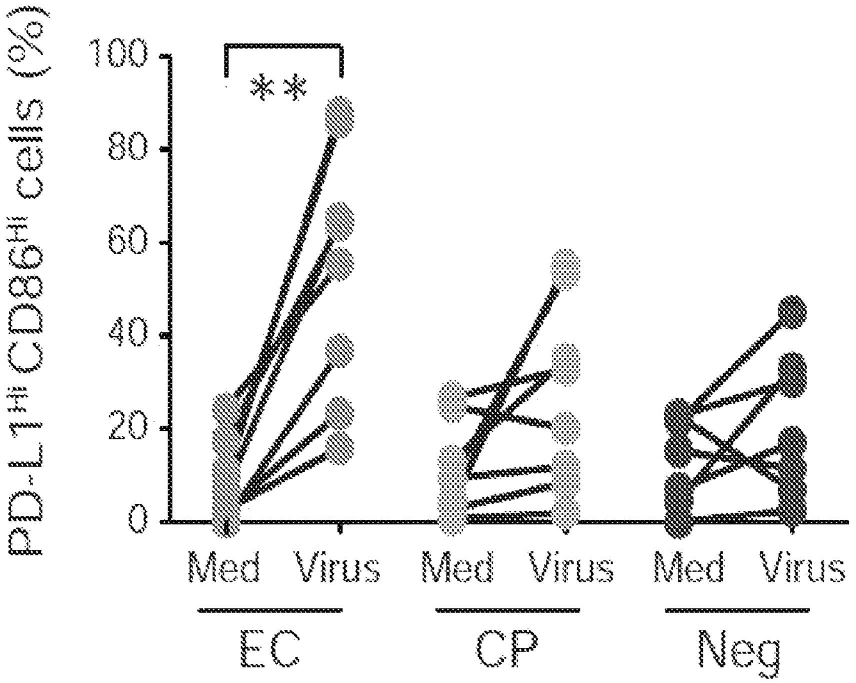
Figure 4B:
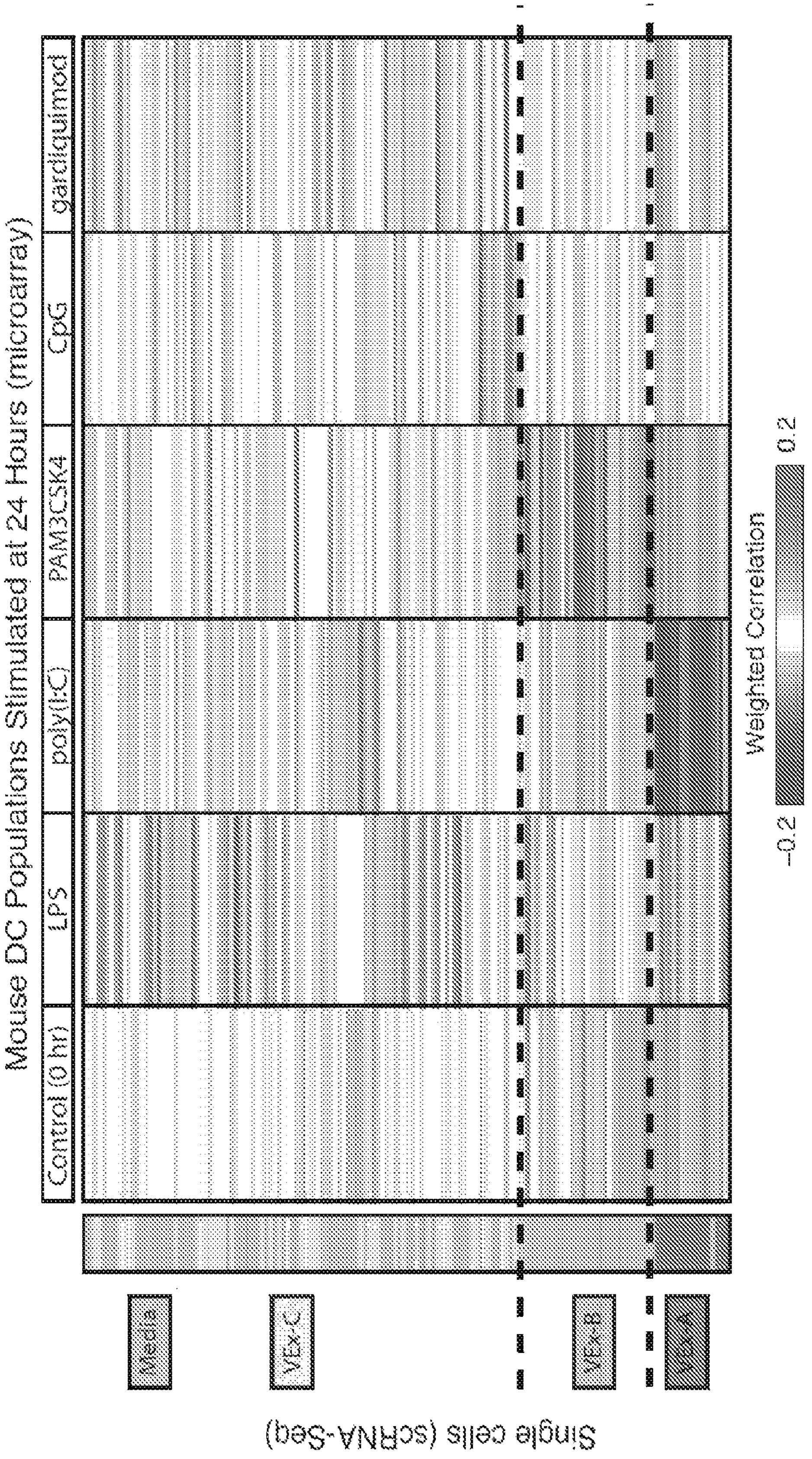
Figure 4C:
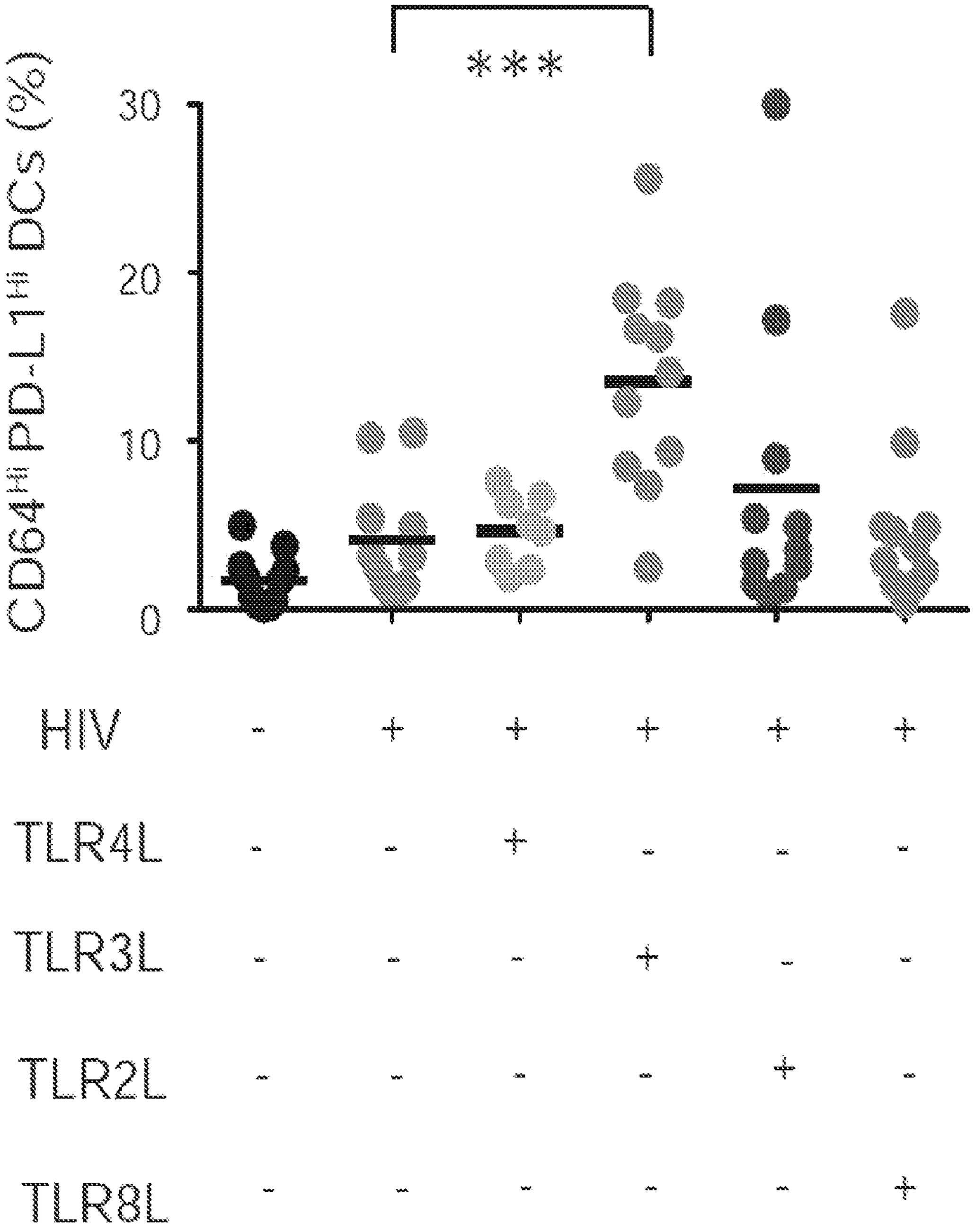
Figure 4D:
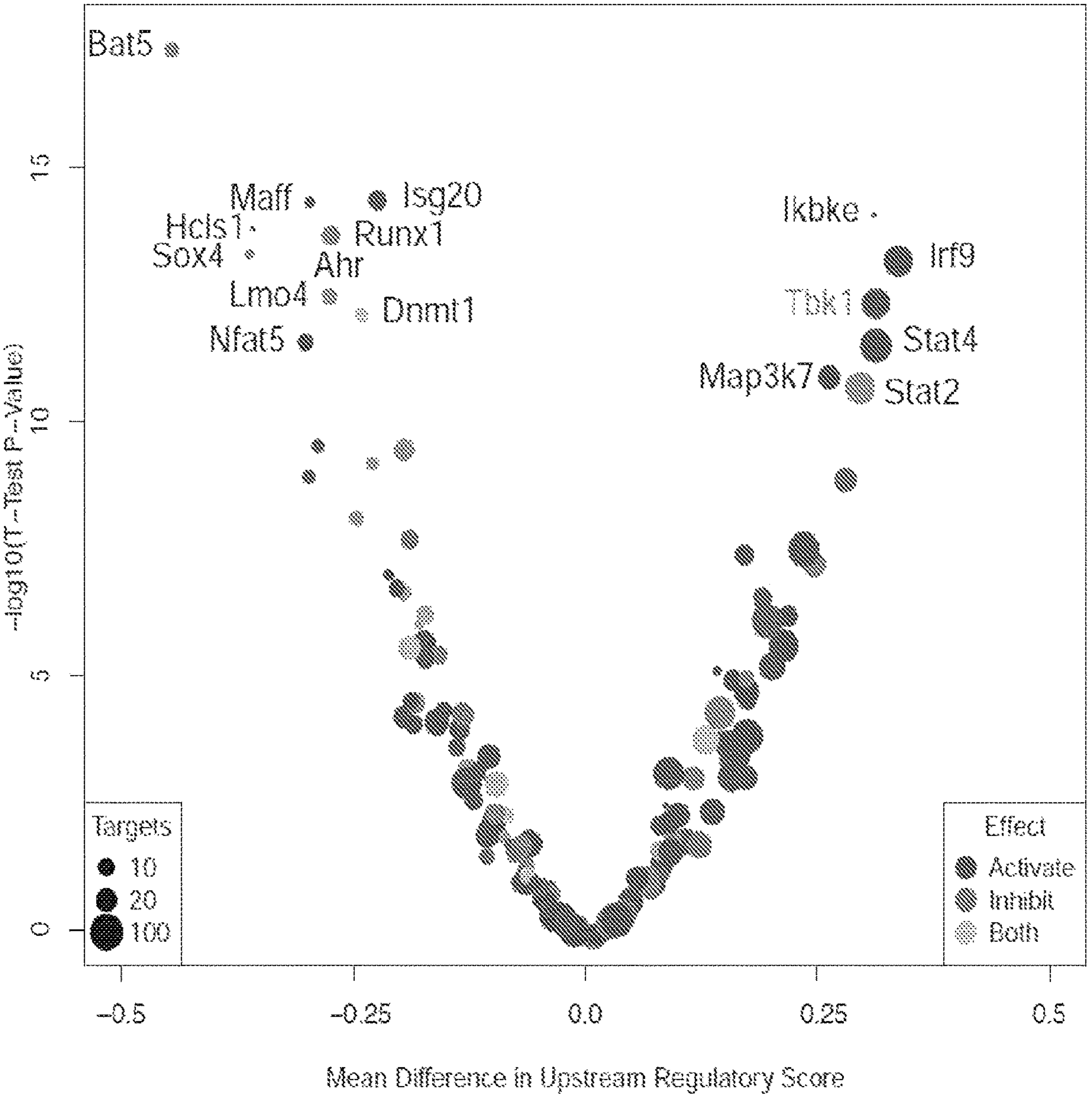
Figure 4E:
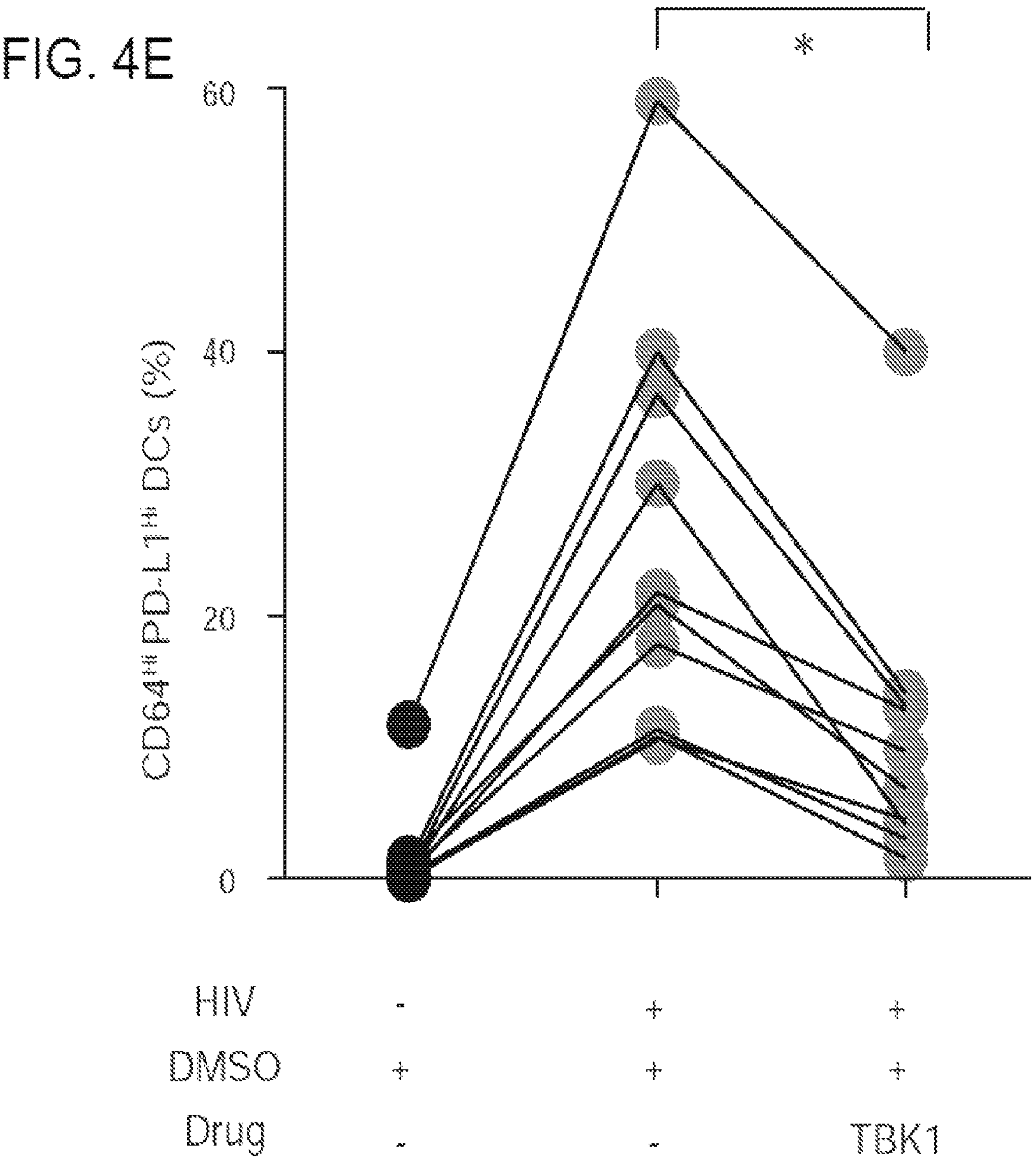
Figure 4F:
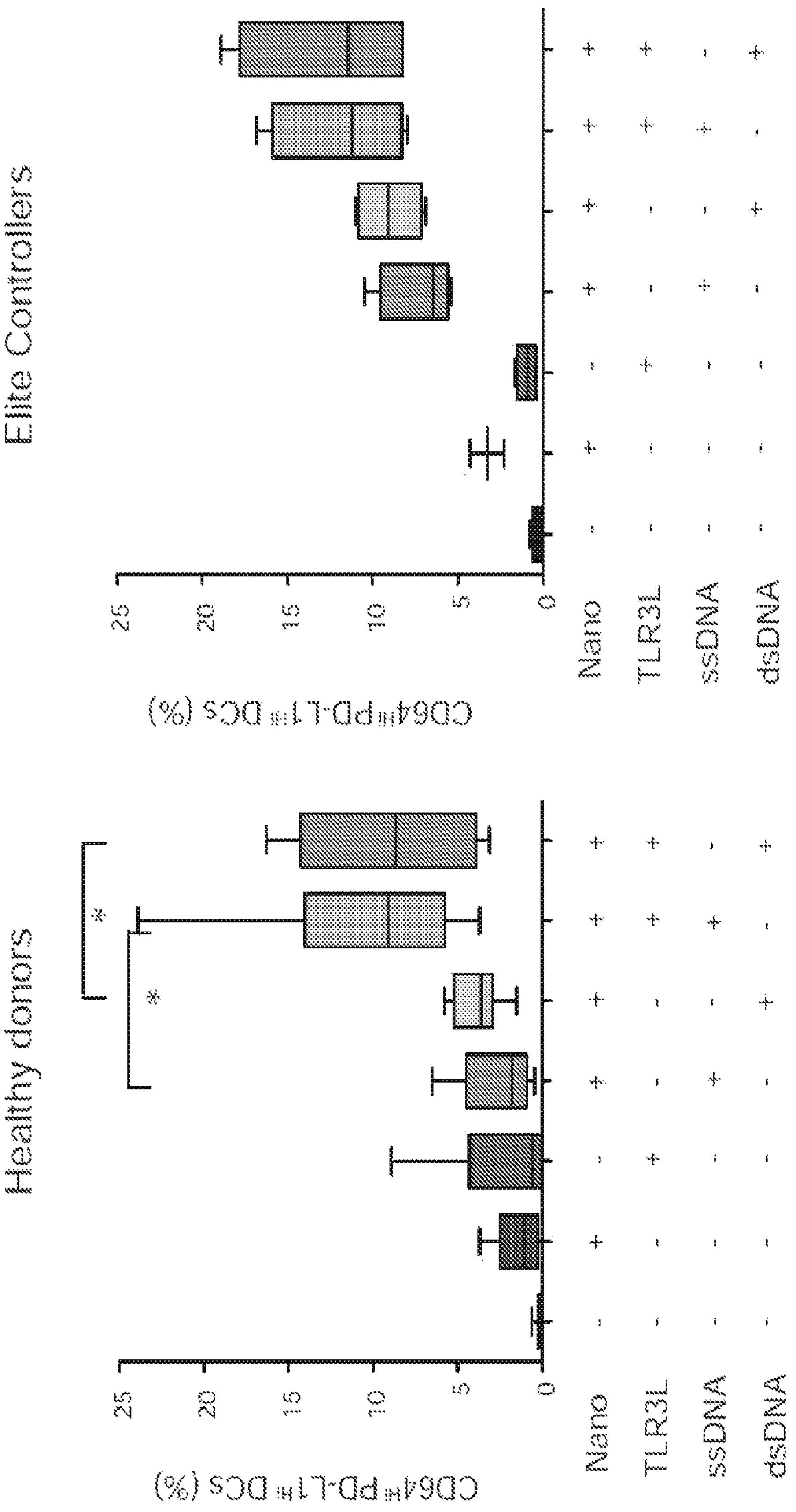
Figure 8F:
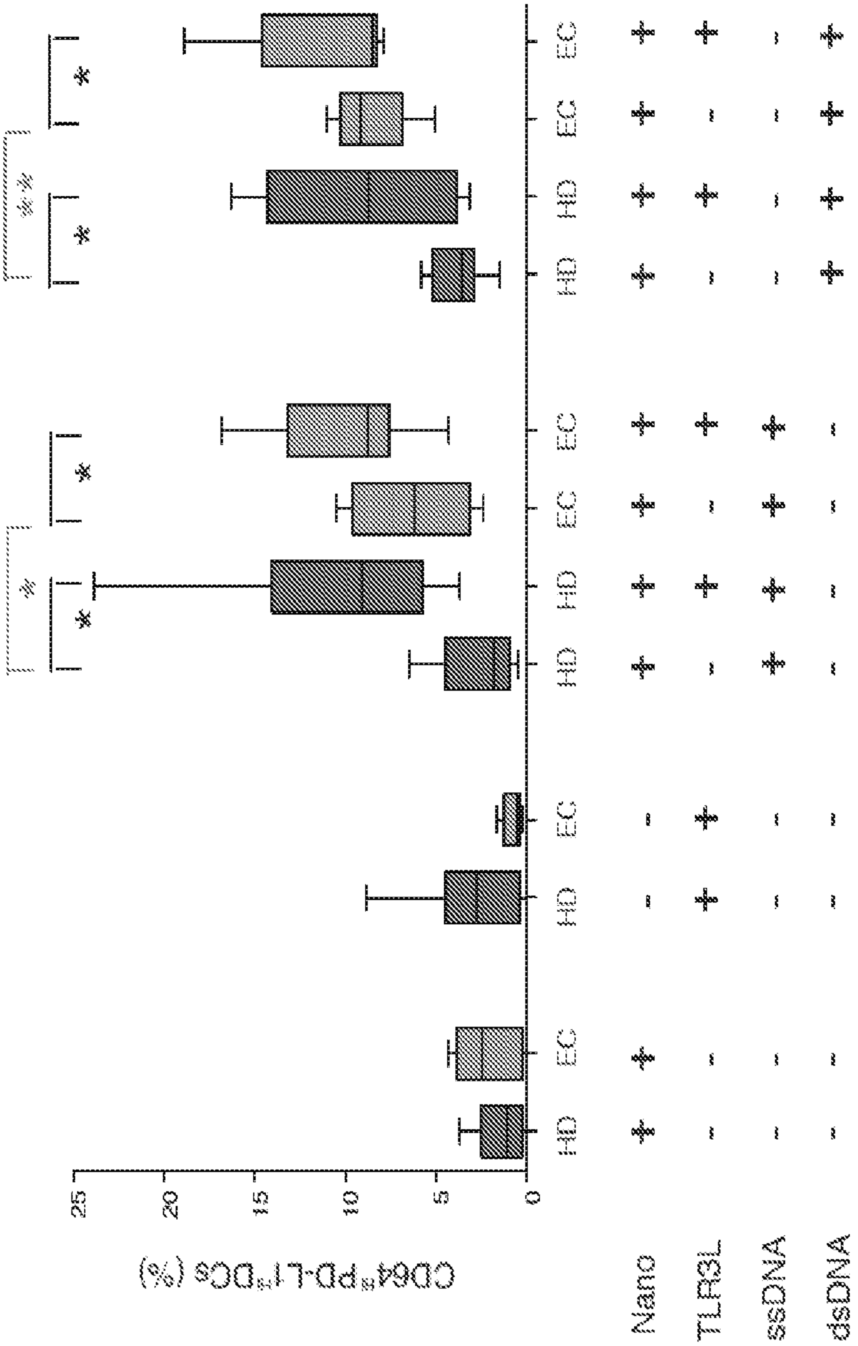
Figure 8G:
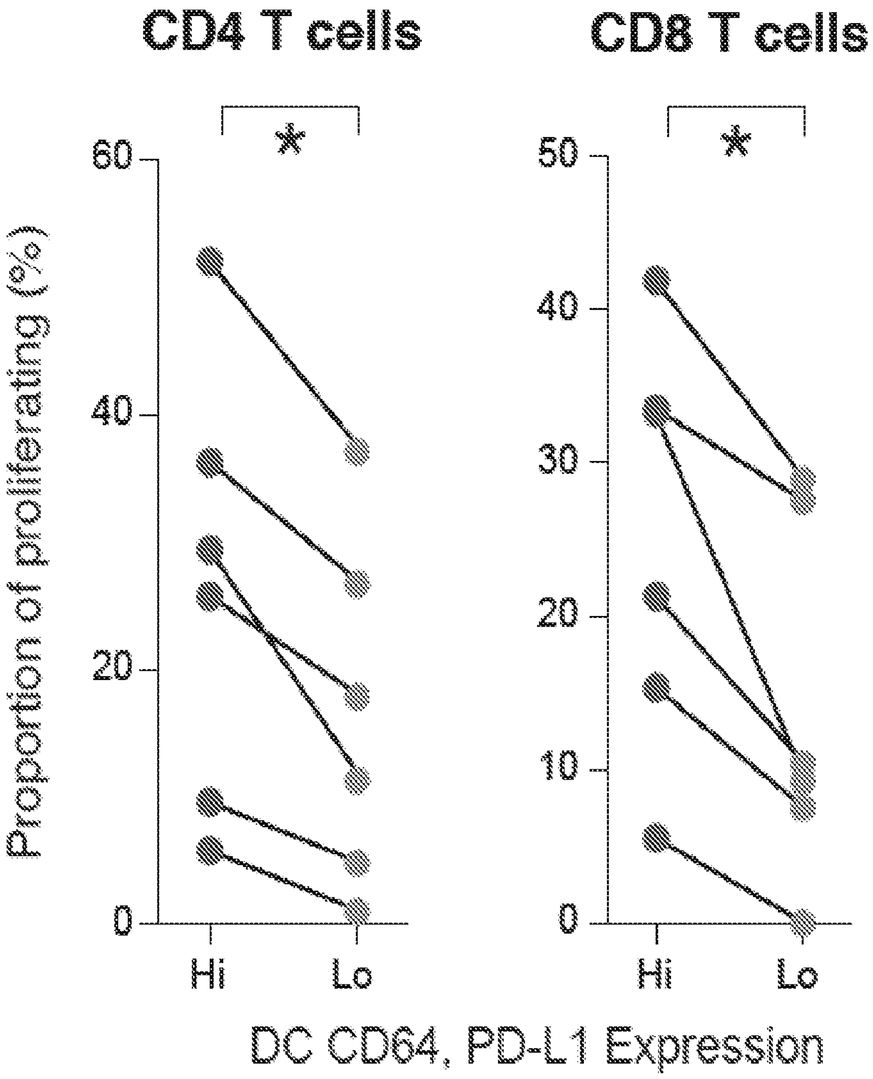
Figure 9B:
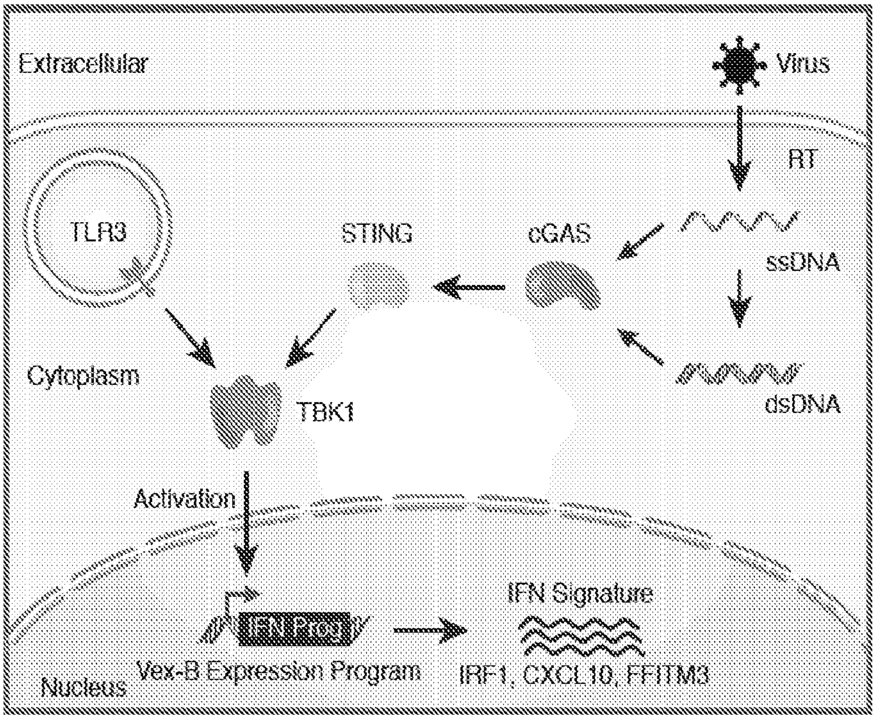
Figure 10A:
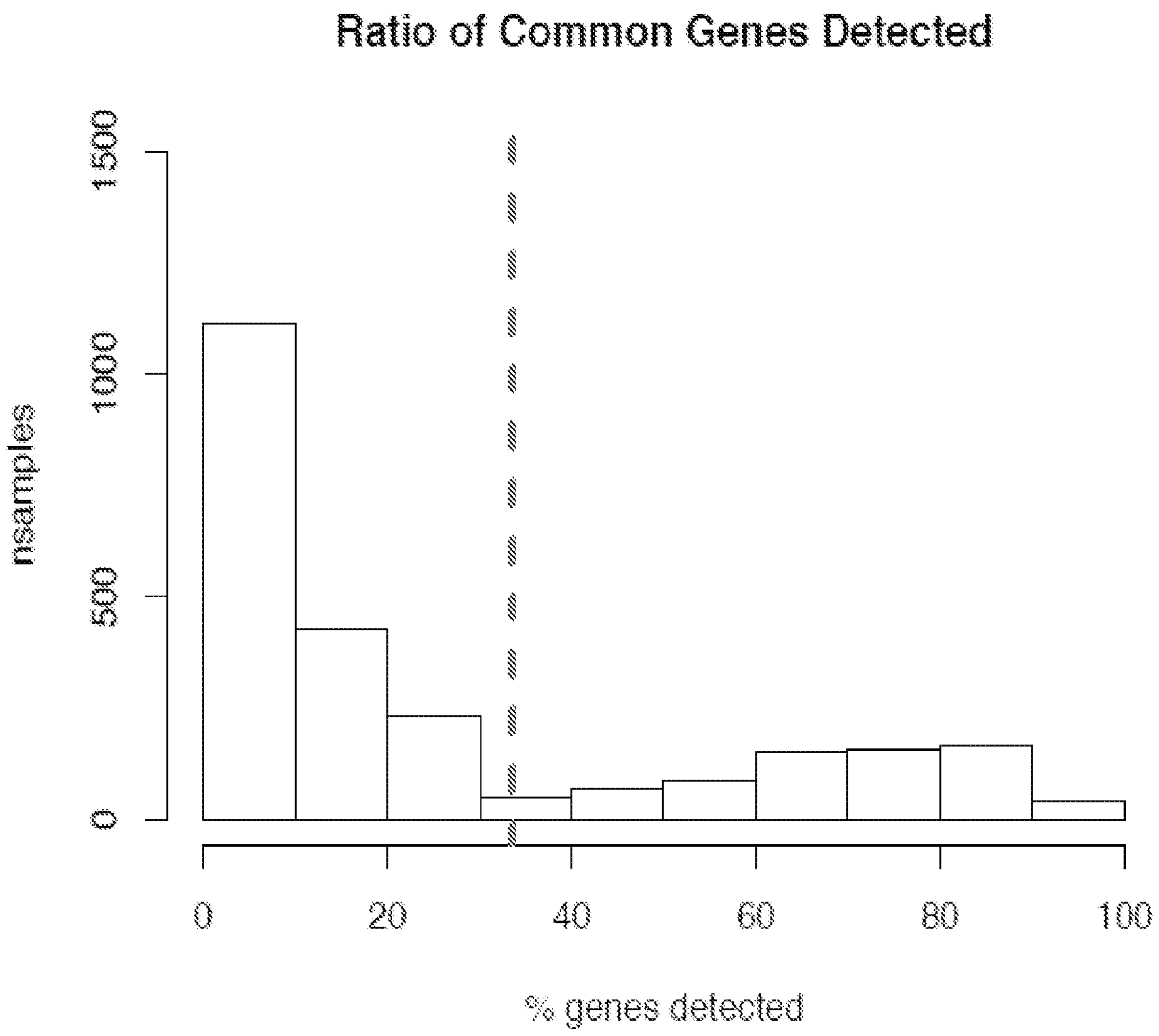
FIG. 10A illustrates the distribution of "common genes" detected per library (see Methods). Red line represents adaptive threshold below which all samples were removed from further analysis.
Figure 10B:
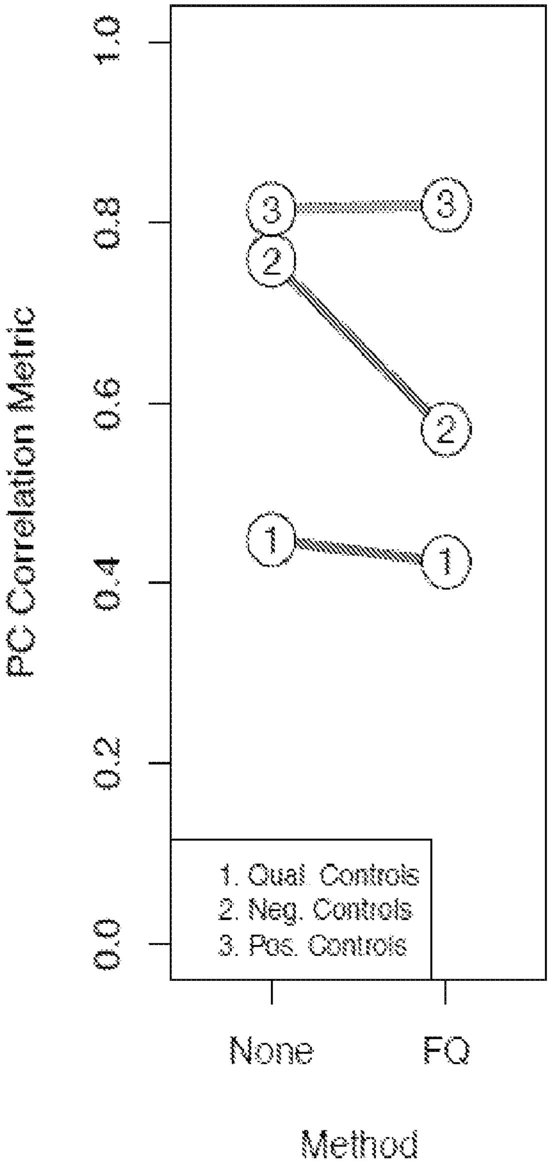
FIG. 10B illustrates the difference in scone correlation normalization metrics before and after full-quantile normalization. While the correlation between the first 3 expression PCs and the first 3 PCs computed across negative controls (1. Picard Tools Metrics and 2. Housekeeping Genes) tend to decrease, correlations with the first 3 PCs across positive controls (3. Innate Immune System genes) tends to increase.
Figure 10C:
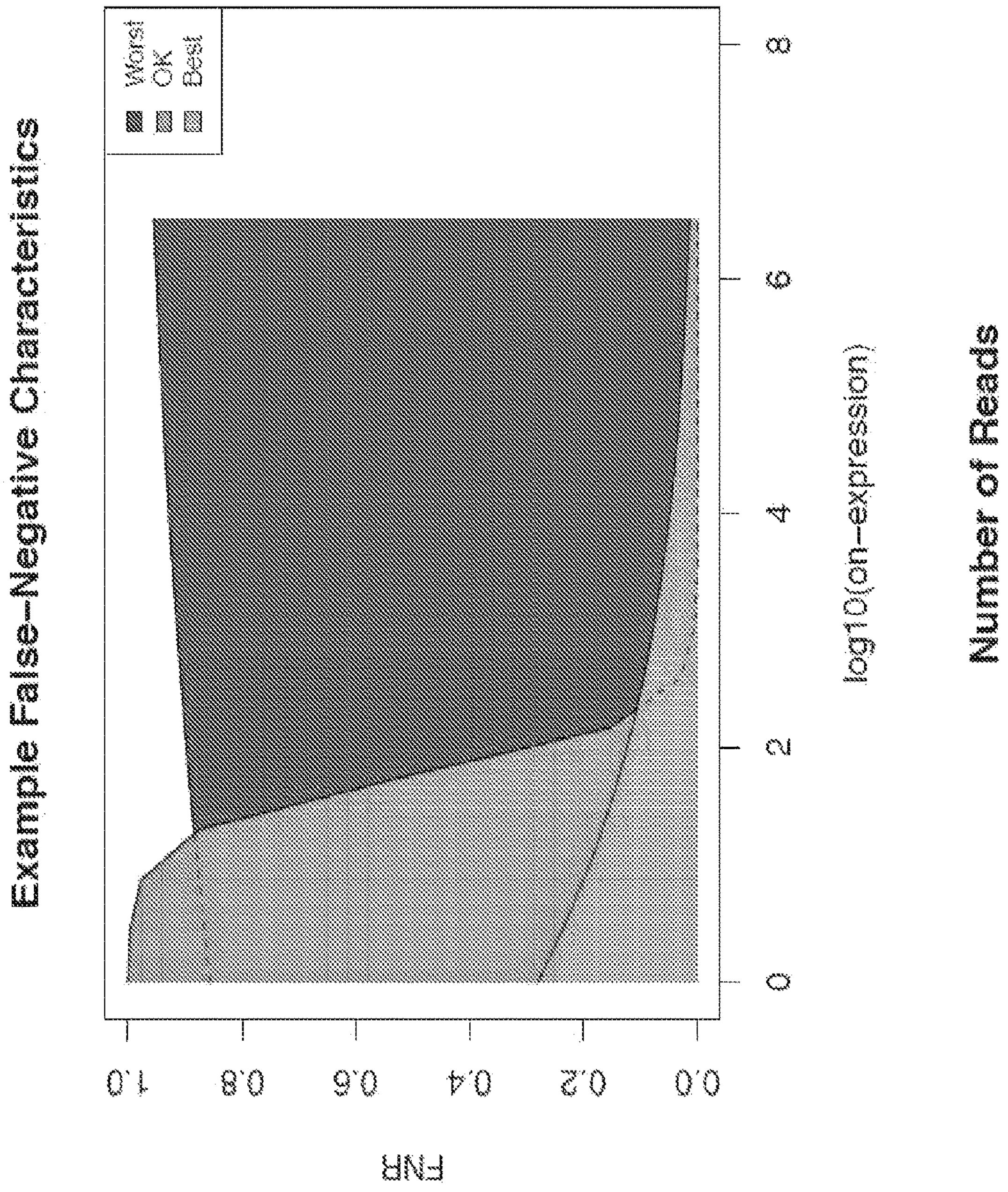
FIG. 10C illustrates three examples of False-Negative Characteristic fits, exhibiting three different relationships between the mean expression of a housekeeping gene and rate of "drop-out." Colors represent the overall quality of the AUC.
Figure 10D:
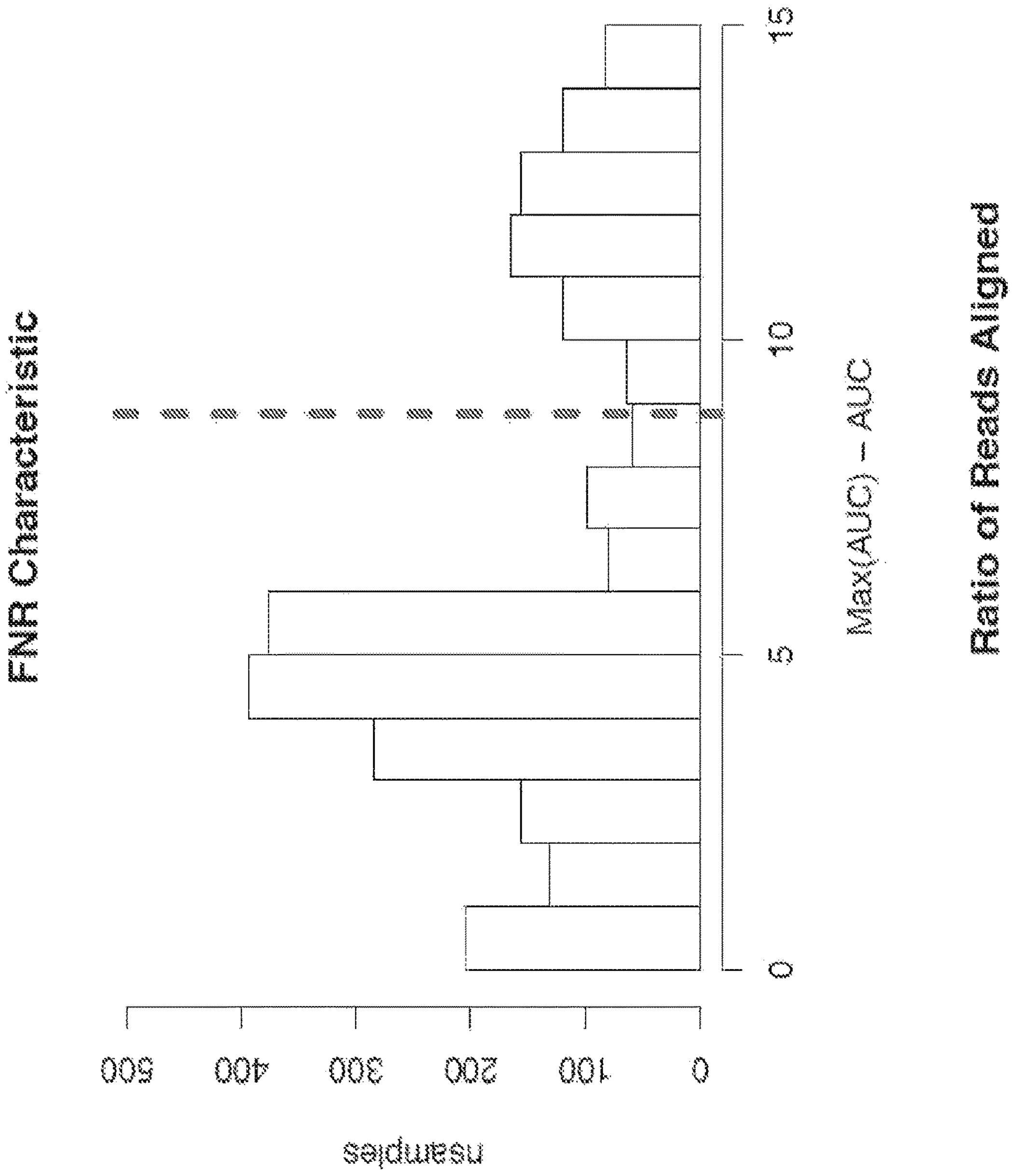
FIG. 10D illustrates the distribution of fit FNR AUC per library. Red line represents adaptive threshold above which all samples were removed from further analysis.
Figures 10E, 10F:
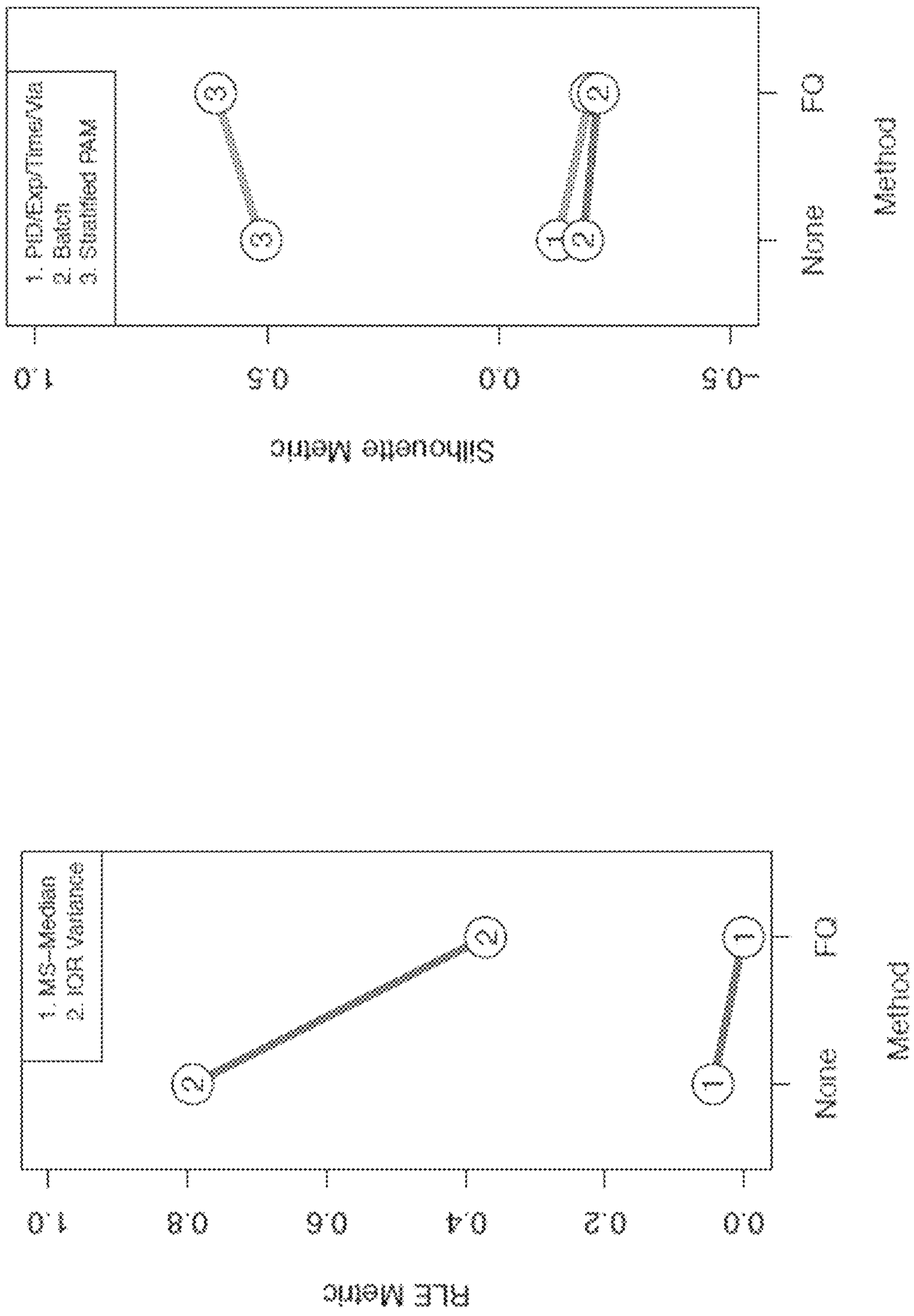
FIG. 10E illustrates the difference in scone RLE metrics before and after full-quantile normalization. The mean sample-median RLE decreases, as does the variance of the sample-IQR RLE decrease: both global differential expression and differential expression variability is reduced.
FIG. 10F illustrates the difference in scone average silhouette width metrics before and after full-quantile normalization. The average silhouette width of biological exposure group (patient×exposure×timepoint×viability sort) as well as that of the batch decrease. However, the average silhouette width of PAM clustering tends to increase.
Figure 10G:
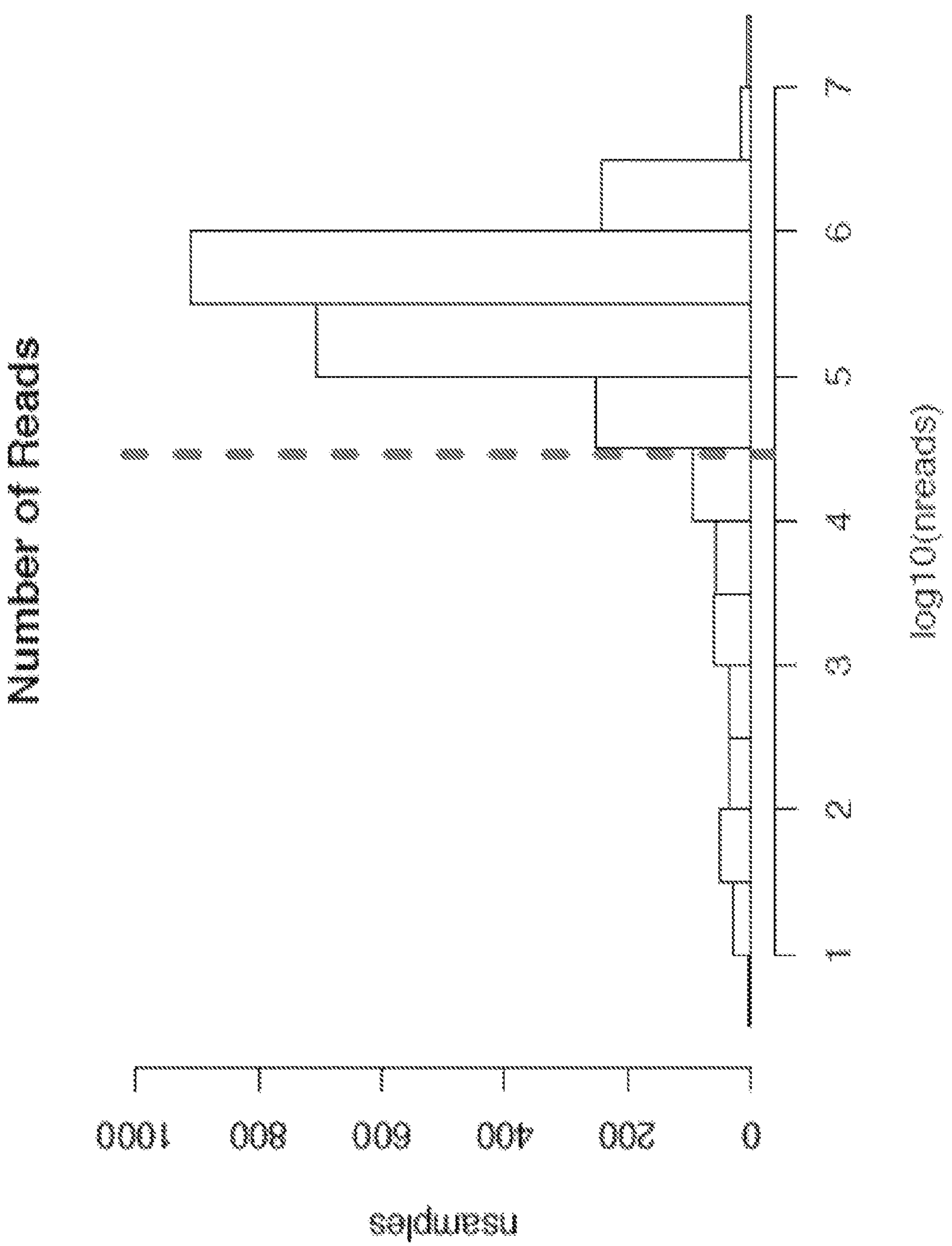
FIG. 10G illustrates the distribution of number of reads per library. Red line represents adaptive threshold below which all samples were removed from further analysis.
Figure 10H:
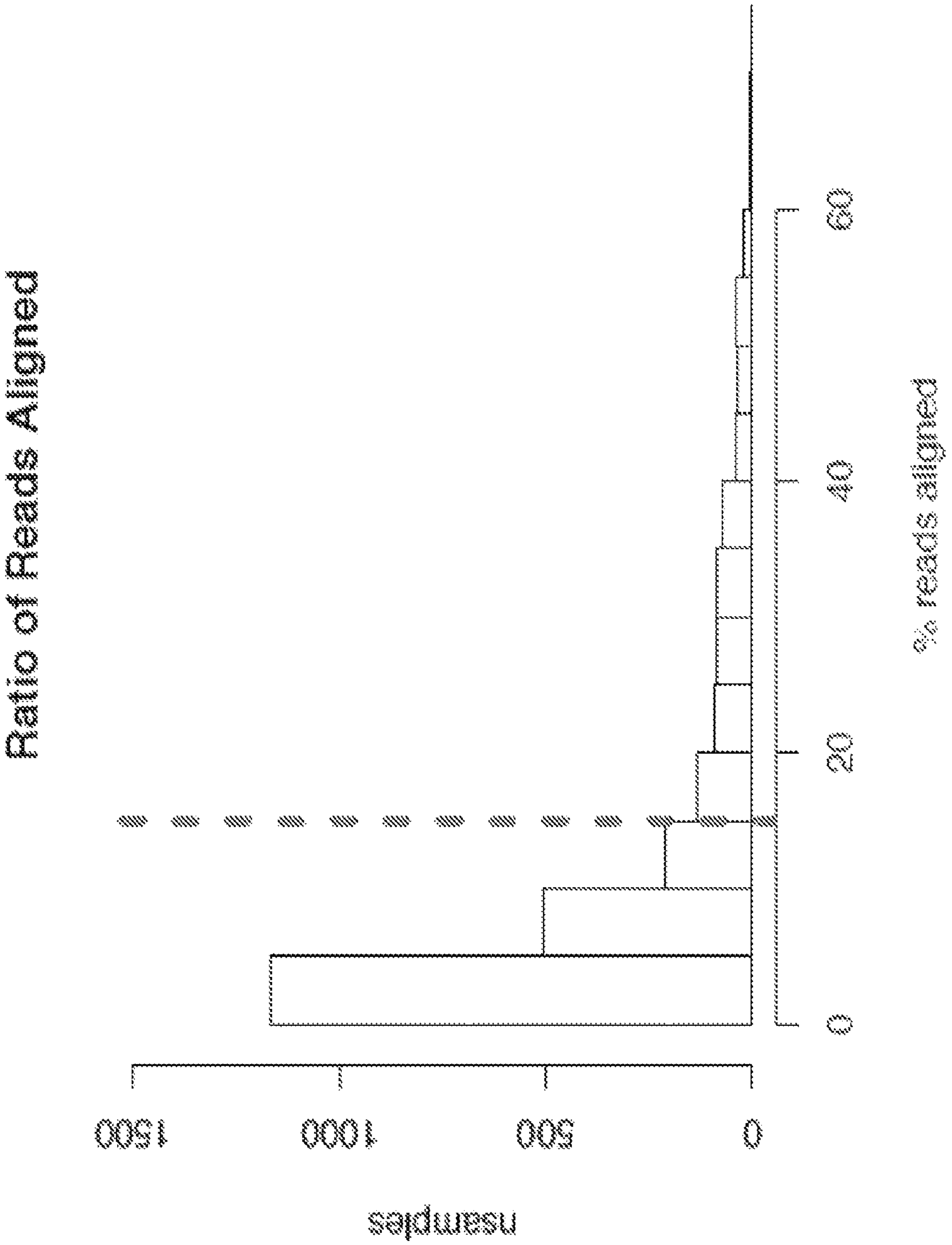
FIG. 10H illustrates the distribution of alignment ratio per library. Red line represents adaptive threshold below which all samples were removed from further analysis.

Toward Prophylactic Application: Enhanced Induction of CD64$^{Hi}$ PD-L1$^{HI}$ cDCs with Combined Stimulation of Intracellular DNA and TLR3 Sensing Pathways Finally, Applicants explored how Applicants might further exploit this TBK1-dependent innate immune sensing pathway to boost the fraction of cDCs acquiring the cluster 1 phenotype without exposure to live virus. For this purpose, Applicants incubated PBMCs from healthy individuals or ECs simultaneously with a TLR3 agonist (Poly(I.C)) and single- or double-stranded HIV-1 Gag DNA (ssDNA or dsDNA, respectively) encapsulated in polymeric nanoparticles. A similar delivery vehicle has been previously shown to selectively activate cGAS- and STING-dependent immune recognition pathways, recapitulating HIV-1 immune sensing during natural infection (N. Yan, A. D. Regalado-Magdos, B. Stiggelbout, M. A. Lee-Kirsch, J. Lieberman, The cytosolic exonuclease TREX1 inhibits the innate immune response to human immunodeficiency virus type 1. *Nature immunology* 11, 1005-1013 (2010)). When Applicants analyzed the fraction of cDCs differentiating into cluster-1-like/CD64$^{Hi}$, PD-L1$^{Hi}$ cells, Applicants found that activation of either DNA (HIV-1) or RNA (TLR3 agonist) sensing alone in PBMCs from healthy persons was insufficient to fully induce a substantial fraction of cluster 1-like responses (FIG. 8F; p=0.05; Wilcoxon matched-pairs signed rank test). Combining both stimuli, however, significantly increased the proportion of cluster 1-like/CD64$^{Hi}$, PD-L1$^{Hi}$ cDCs in PBMCs isolated from healthy individuals (p=0.0156 and p=0.0313 for ss- and dsDNA, respectively; Wilcoxon matched-pairs signed rank test). Similar results were obtained with cells from ECs (p=0.0469 both ss and dsDNA; Wilcoxon matched-pairs signed rank test), with the notable exception that, in ECs, exposure to ssDNA and dsDNA alone led to significantly higher levels of cluster 1-like/CD64$^{Hi}$, PD-L1$^{Hi}$ cDCs relative to cells cultured only in media, suggesting a heightened baseline ability of EC to respond to intracellular DNA. In mixed leukocyte reactions the CD64$^{Hi}$, PD-L1$^{Hi}$ cDCs generated from HIV-negative donors incubated with TLRL3 and nanoparticles containing gag ssDNA demonstrated a superior ability to stimulate proliferation in CD4+ and CD8$^{+}$ T cells compared to CD64$^{Lo}$, PD-L1$^{Lo}$ cDCs, suggesting these cDCs may function similarly to the CD64$^{Hi}$, PD-L1$^{Hi}$ cDCs generated by ECs in response to virus (FIG. 4G). Based on these results, Applicants propose that simultaneous induction of DNA and dsRNA sensing through the cGAS-STING (16, 34) and TLR3 pathways can potentiate (FIG. 9A) the maturation of cluster 1-like/CD64$^{Hi}$, PD-L1$^{Hi}$ cells in healthy individuals by converging on TBK1 (FIG. 9B). Thus, co-stimulation of TLR and DNA sensor agonists, and potentially TBK1 directly, might be a promising strategy for inducing the highly functional Cluster-1-like/CD64$^{Hi}$, PD-L1$^{Hi}$ cDCs that occur naturally in EC.

In summary, by examining elite control, a phenotypic extreme of the human response to HIV-1 infection, Applicants have identified a uniquely enriched CD64$^{Hi}$, PD-L Hi cDC cell state that is primed to drive adaptive immunity, and seems to represent a previously unrecognized correlate of effective antiviral response against HIV-1. By developing novel computational approaches that treat the five observed gene expression response profiles (cluster 1,2,3,4,5) as "basis vectors" for deconvolving previously measured ensemble datasets, Applicants have realized a rational, extendable framework for modulating their relative abundance. The experimental validations of select hypotheses support an inferred role for TLR3 in synergizing with cytosolic viral recognition machinery to induce a TBK1-dependent cluster 1-like/CD64$^{Hi}$, PD-L1$^{Hi}$ response. Together, this suggests the utility, and potential generality, of the experimental and computational approaches for identifying relevant immunomodulators that can rebalance the composition of the immune system for potential therapeutic and prophylactic use. Collectively, the work demonstrates the potential of scRNA-Seq to discover, genome-wide, functional cellular immune response states, associated markers, and shifts in abundance that can inform the overall efficacy of immune responses.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of identifying an agent for treating HIV infection or suppressing HIV replication comprising:

incubating peripheral blood mononuclear cells (PBMCs) in the presence and in the absence of a test compound, measuring the proportion of cells that are $CD64^{Hi}$, PD-$L1^{Hi}$ dendritic cells (DCs) compared to the proportion that are $CD64^{Lo}$, PD-$L1^{Lo}$ DCs, in the presence and in the absence of the test compound, and identifying the agent as treating HIV infection or suppressing HIV replication if the proportion of $CD64^{Hi}$, PD-$L1^{Hi}$ DCs is increased in the presence of the test compound relative to the proportion of $CD64^{Hi}$, PD-$L1^{Hi}$ DCs in the absence of the test compound.

2. The method of claim 1, which comprises measuring expression of one or more of FCGR3A, CLEC12A, SLAMF8, and ICAM1 in the PBMCs in the presence and absence of the test compound, wherein the agent treats the HIV infection or suppresses HIV replication if the expression of one or more of FCGR3A, CLEC12A, SLAMF8, and ICAM1 is increased in the presence of the test compound relative to the expression in the absence of the test compound.

3. The method according to claim 1, wherein the method comprises inducing a population of $CD64^{Hi}$, PD-$L1^{Hi}$ dendritic cells (DCs) for treating HIV infection, prophylactically treating HIV infection, or suppressing HIV replication in a subject in need thereof, which comprises:

contacting PBMCs with an agent that activates TBK1; and/or contacting PBMCs with an agent that activates a pathway selected from: IFNG, TLR3, STAT1, MAVS, and IRF1; and/or incubating PBMCs with an agent that increases the proportion of $CD64^{Hi}$, PD-$L1^{Hi}$ DCs.

4. The method of claim 3, further comprising isolating a population of dendritic cells based on a $CD64^{Hi}$, PD-$L1^{Hi}$ signature.

5. The method of claim 3, further comprising measuring the proportion of cells that are $CD64^{Hi}$, PD-$L1^{Hi}$ dendritic cells (DCs) compared to the proportion that are $CD64^{Lo}$, PD-$L1^{Lo}$ DCs, in the presence and absence of the agent, and identifying the agent as treating HIV infection or suppressing HIV replication if the proportion of $CD64^{Hi}$, PD-$L1^{Hi}$ DCs is increased in the presence of the agent.

6. The method of claim 3, wherein the PBMCs are contacted in vivo or ex vivo.

7. The method of claim 3, which comprises, either contacting the PBMCs with one or more of a toll-like receptor 3 (TLR3) agonist, a cGAS agonist, or a STING agonist, or, contacting the PBMCs with a TLR3 agonist and a cGAS-STING agonist.

8. The method of claim 3, wherein cells of the population of $CD64^{Hi}$, PD-$L1^{Hi}$ dendritic cells comprise:

one or more of the following markers differentially expressed as compared to conventional dendritic cells (cDCs): TNFSF10, TLR2, CSF1R, TLR4, ENG, SLC3A2, TNFRSF1A, CD4, CD63, SLAMF7, FCGR3A, ANPEP, ITGAX, CD68, ICAM1, PLAUR, C5AR1, SIGLEC9, LILRB3, LILRA6, LILRB2, LILRB1, LILRB4, SIRPB1, SIGLEC1, TLR8, LILRA3, CCR1, and CCR5; and/or one or more of the following markers upregulated as compared to conventional dendritic cells (cDCs): CD83, LAMP3, CD63, CD86, and CST7; and/or one or more of the following markers upregulated as compared to cDCs: TNFSF10, TLR2, TLR4, TNFRSF1A, CD63, SLAMF7, FCGR3A, ITGAX, CD68, ICAM1, PLAUR, C5AR1, SIGLEC9, LILRB3, LILRA6; LILRB2, LILRB1, LILRB1, SIRPB1, SIGLEC1, TLR8, LILRA3, CCR1, and CCR5; and/or or more of the following markers upregulated as compared to cDCs: CD274, FCGR1A, FCGR3A, CLEC12A, SLAMF8, and ICAM1; and/or one or more of the following markers downregulated as compared to cDCs: CSF1R, SLC3A2, CD4, ANPEP.

9. The method of claim 1, wherein the identified agent induces a population of dendritic cells having an HIV elite controller phenotype.

10. A therapeutically effective amount of an isolated TLR3L and HIV ss/dsDNA-induced dendritic cell population effective at treating or preventing an HIV infection in a subject, wherein said dendritic cell population comprises at least 5%, at least 10% or at least 20% more $CD64^{Hi}$, PD-$L1^{Hi}$ cells than a dendritic cell population induced by either TLR3L or HIV ss/dsDNA alone.

11. A method of treating or preventing an HIV infection in a subject comprising administering to the subject the isolated TLR3L and HIV ss/dsDNA-induced dendritic cell population of claim 10.

12. The method of claim 11, wherein the dendritic cell population exhibits enhanced T cell activation capabilities compared to a dendritic cell population induced by either TLR3L or HIV ss/dsDNA alone.

13. The method of claim 11, wherein the dendritic cell population exhibits superior antigen presentation capabilities compared to a dendritic cell population induced by either TLR3L or HIV ss/dsDNA alone.

14. The method of claim 11, further comprising monitoring the subject's immune response to HIV.

* * * * *